(12) United States Patent
Beaudoin et al.

(10) Patent No.: US 8,153,814 B2
(45) Date of Patent: Apr. 10, 2012

(54) SULFONAMIDE DERIVATIVES

(75) Inventors: Serge Beaudoin, Durham, NC (US); Michael Christopher Laufersweiler, Durham, NC (US); Christopher John Markworth, Durham, NC (US); Brian Edward Marron, Durham, NC (US); David Simon Millan, Sandwich (GB); David James Rawson, Sandwich (GB); Steven Michael Reister, Durham, NC (US); Kosuke Sasaki, Sandwich (GB); Robert Ian Storer, Sandwich (GB); Paul Anthony Stupple, Sandwich (GB); Nigel Alan Swain, Sandwich (GB); Christopher William West, Durham, NC (US); Shulan Zhou, Durham, NC (US)

(73) Assignees: Pfizer Limited, Sandwich (GB); Icagen, Inc., Durham, NC (US)

( * ) Notice: Subject to any disclaimer, the term of this patent is extended or adjusted under 35 U.S.C. 154(b) by 234 days.

(21) Appl. No.: 12/685,913

(22) Filed: Jan. 12, 2010

(65) Prior Publication Data
US 2010/0197655 A1 Aug. 5, 2010

Related U.S. Application Data

(60) Provisional application No. 61/143,920, filed on Jan. 12, 2009, provisional application No. 61/245,726, filed on Sep. 25, 2009, provisional application No. 61/258,760, filed on Nov. 6, 2009.

(51) Int. Cl.
*C07D 277/00* (2006.01)
*A61K 31/425* (2006.01)
(52) U.S. Cl. ........................ 548/190; 514/371
(58) Field of Classification Search ............................ None
See application file for complete search history.

(56) References Cited

U.S. PATENT DOCUMENTS

| | | | |
|---|---|---|---|
| 4,945,090 A | 7/1990 | Schmiechen et al. | 514/232.8 |
| 5,389,635 A | 2/1995 | Olson | 514/255 |
| 6,087,392 A | 7/2000 | Reiter | 514/459 |
| 6,110,964 A | 8/2000 | Robinson | 514/456 |
| 6,197,810 B1 | 3/2001 | Reiter | 514/459 |
| 6,214,870 B1 | 4/2001 | McClure et al. | 514/466 |
| 6,342,521 B1 | 1/2002 | Reiter | 514/472 |
| 2001/0046989 A1 | 11/2001 | Levin et al. | 514/228.8 |
| 2003/0158186 A1 | 8/2003 | Malik et al. | 514/227.5 |
| 2004/0110743 A1 | 6/2004 | Miyamato et al. | 514/212.01 |
| 2005/0009871 A1 | 1/2005 | Ramesh et al. | 514/316 |
| 2005/0107364 A1 | 5/2005 | Hutchinson et al. | 514/223.2 |
| 2005/0282818 A1 | 12/2005 | Ramesh et al. | 514/254.03 |
| 2006/0183745 A1 | 8/2006 | Bo et al. | 514/214 |
| 2007/0135431 A1 | 6/2007 | Smith et al. | 514/235.2 |
| 2007/0167497 A1 | 7/2007 | Nambu et al. | 514/352 |
| 2008/0103129 A1 | 5/2008 | Zhang et al. | 514/212.08 |
| 2008/0242656 A1 | 10/2008 | Fryer et al. | 514/211.09 |
| 2008/0293706 A1 | 11/2008 | Chaudhari et al. | 514/228.2 |
| 2010/0056528 A1 | 3/2010 | Yacovan et al. | 514/238.2 |
| 2011/0077269 A1 | 3/2011 | Martinborough | 514/312 |

FOREIGN PATENT DOCUMENTS

| | | |
|---|---|---|
| EP | 0532239 | 3/1993 |
| EP | 0569193 | 11/1993 |
| EP | 1088819 | 4/2001 |
| EP | 1201238 | 5/2002 |
| GB | 2263635 | 8/1993 |
| WO | WO 9746556 | 12/1997 |
| WO | WO 9942462 | 8/1999 |
| WO | WO 03048159 | 6/2003 |
| WO | WO 2004014370 | 2/2004 |
| WO | WO 2004103980 | 12/2004 |
| WO | WO 2005000309 | 1/2005 |
| WO | WO 2005007621 | 1/2005 |
| WO | WO 2005013914 | 2/2005 |
| WO | WO 2005054176 | 6/2005 |
| WO | WO 2005116026 | 12/2005 |
| WO | WO 2006030925 | 3/2006 |
| WO | WO 2006051270 | 5/2006 |
| WO | WO 2006060762 | 6/2006 |
| WO | WO 2006076644 | 7/2006 |
| WO | WO 2007076034 | 7/2007 |
| WO | WO 2007118859 | 10/2007 |
| WO | WO 2007125351 | 11/2007 |
| WO | WO 2008002490 | 1/2008 |
| WO | WO 2008050200 | 5/2008 |
| WO | WO 2008057280 | 5/2008 |
| WO | WO 2008118758 | 10/2008 |
| WO | WO 2008137027 | 11/2008 |
| WO | WO 2009011850 | 1/2009 |
| WO | WO 2009012242 | 1/2009 |
| WO | WO 2009017719 | 2/2009 |
| WO | WO 2009065131 | 5/2009 |

OTHER PUBLICATIONS

Payne, J. et al., "Identification of KD5170: A novel mercaptoketone-based histone deacetylase inhibitor", Bioorganic and Medicinal Chemistry Letters, vol. 18, No. 23, 2008, p. 6093-6096.

(Continued)

*Primary Examiner* — Janet Andres
*Assistant Examiner* — Heidi Reese
(74) *Attorney, Agent, or Firm* — J. Michael Dixon; Gregg C. Benson

(57) ABSTRACT

The present invention relates to compounds of the formula

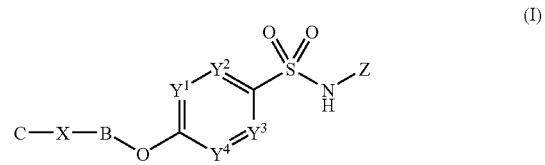

(I)

and pharmaceutically acceptable salts, solvates or tautomers thereof, to processes for the preparation of, intermediates used in the preparation of, and compositions containing such compounds, and the uses of such compounds, in particular for the treatment of pain.

6 Claims, No Drawings

OTHER PUBLICATIONS

RN 1031058-98-6 Chemical Abstracts Registry database, Jun. 26, 2008, Aurora Fine Chemicals.

Kharul, Rajendra K. et al. "Efficient Synthesis of Structurally Novel Diaryl Ethers by Regioselective Functionalization", Synthetic Communications (2008), 38(23), pp. 4282-4294.

Ohta, B. "Studies on Chemotherapeutics, XVII. Intramolecular Rearrangement of p-Hydroxy-benzenesulfonamide Derivatives", Yakugaku Zasshi—(Series) vol. 71, 1951, p. 315-318.

Reiter, L, et al., "Pyran-containing sulfonamide hydroxamic acids: potent MMP inhibitors that spare MMP-1", Journal Bioorganic and Medicinal Chemistry Letters, vol. 14, No. 13, 2004, p. 3389-3395.

SULFONAMIDE DERIVATIVES

This application claims benefit under 35 USC 119(e) of U.S. Provisional Application 61/143,920, filed Jan. 12, 2009; U.S. Provisional Application 61/245,726, filed Sep. 25, 2009; and U.S. Provisional Application 61/258,760, filed Nov. 6, 2009.

This invention relates to sulfonamide derivatives. More particularly, this invention relates to heteroaryl substituted sulphonamide derivatives and to processes for the preparation of, intermediates used in the preparation of, compositions containing, and the uses of, such derivatives.

The sulfonamide derivatives of the present invention are sodium channel modulators and have a number of therapeutic applications, particularly in the treatment of pain.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)). See Table A, below.

TABLE A

| Type | Gene Symbol | Primary tissue | TTX IC-50 nM | Disease association | Indications |
|---|---|---|---|---|---|
| $Na_v1.1$ | SCN1A | CNS/PNS | 10 | Epilepsy | Pain, seizures, neurodegeneration |
| $Na_v1.2$ | SCN2A | CNS | 10 | Epilepsy | Epilepsy, neurodegeneration |
| $Na_v1.3$ | SCN3A | CNS | 15 | — | Pain |
| $Na_v1.4$ | SCN4A | Sk. muscle | 25 | Myotonia | Myotonia |
| $Na_v1.5$ | SCN5A | Heart | 2000 | Arrhythmia | Arrhythmia |
| $Na_v1.6$ | SCN8A | CNS/PNS | 6 | — | Pain, movement disorders |
| $Na_v1.7$ | SCN9A | PNS | 25 | Erythermalgia | Pain |
| $Na_v1.8$ | SCN10A | PNS | 50000 | — | Pain |
| $Na_v1.9$ | SCN11A | PNS | 1000 | — | Pain |

There are currently at least nine known members of the family of voltage-gated sodium channel (VGSC) alpha subunits. Names for this family include SCNx, SCNAx, and $Na_vx.x$. The VGSC family has been phylogenetically divided into two subfamilies $Na_v1.x$ (all but SCN6A) and $Na_v2.x$ (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v1.5$, H1) is almost exclusively expressed in cardiac tissue, is thought to play a central role in the generation of the cardia action potential and propagation of electrical impulses in the heart, and has also been shown to underlie a variety of cardiac arrhythmias and conduction disorders (Liu H, et al., *Am. J. Pharmacogenomics*, 3(3): 173-9 (2003)). Consequently, blockers of Nav1.5 have found clinical utility in treatment of such disorders (Srivatsa U, et al., *Curr. Cardiol. Rep.*, 4(5): 401-10 (2002)), but binding of drugs to Nav1.5 may also result in abnormal cardiac rhythms. The remaining TTX-resistant sodium channels, Nav1.8 (SCN10A, PN3, SNS) and Nav1.9 (SCN11A, NaN, SNS2) are expressed in the peripheral nervous system and show preferential expression in primary nociceptive neurons. Human genetic variants of these channels have not been associated with any inherited clinical disorder. However, aberrant expression of Nav1.8 has been found in the CNS of human multiple sclerosis (MS) patients and also in a rodent model of MS (Black, J A, et al., *Proc. Natl. Acad. Sci. USA*, 97(21): 11598-602 (2000)). Evidence for involvement in nociception is both associative (preferential expression in nociceptive neurons) and direct (genetic knockout). Nav1.8-null mice exhibited typical nociceptive behavior in response to acute noxious stimulation but had significant deficits in referred pain and hyperalgesia (Laird J M, et al., *J. Neurosci.*, 22(19):8352-6 (2002)).

The TTX-sensitive subset of voltage-gated sodium channels is expressed in a broader range of tissues than the TTX-resistant channels and has been associated with a variety of human disorders. The $Na_v1.1$ channel well exemplifies this general pattern, as it is expressed in both the central and peripheral nervous system and has been associated with several seizure disorders including Generalized Epilepsy with Febrile Seizures Plus, types 1 and 2 (GEFS+1, GEFS+2), Severe Myoclonic Epilepsy of Infancy (SMEI), and others (Claes, L, et al., *Am. J. Hum. Genet.*, 68: 1327-1332 (2001); Escayg, A., *Am. J. Hum. Genet.*, 68: 866-873 (2001); Lossin, C, *Neuron*, 34: 877-884 (2002)). The Nav1.2 channel is largely, if not exclusively, expressed in the central nervous system and quantitative studies indicate it is the most abundant VGSC of the CNS. Mutations of Nav1.2 are also associated with seizure disorders (Berkovic, S. F., et al., *Ann. Neurol.*, 55: 550-557 (2004)) and Nav1.2-null "knockout" mice exhibit perinatal lethality (Planells-Cases R et al., *Biophys. J.*, 78(6):2878-91 (2000)). Expression of the Nav1.4 gene is largely restricted to skeletal muscle and, accordingly, mutations of this gene are associated with a variety of movement disorders (Ptacek, L. J., *Am. J. Hum. Genet.*, 49: 851-854 (1991); Hudson A J, *Brain*, 118(2): 547-63 (1995)). The majority of these disorders are related to hyperactivity or "gain-of-function" and have been found to respond to treatment with sodium channel blockers (Desaphy J F, et al., *J. Physiol.*, 554(2): 321-34 (2004)).

Neither the SCN3A nor the SCN8A VGSC genes have been conclusively linked to heritable disorders in humans. Loss-of-function mutations of the SCN8A gene are known in mice and yield increasingly debilitating phenotypes, dependent upon the remaining functionality of the gene products (Meister M H, *Genetica*, 122(1): 37-45 (2004)). Homozygous null mutations cause progressive motor neuron failure leading to paralysis and death, while heterozygous null animals are asymptomatic. Homozygous $med^J$ mice have nearly 90% reduction in functional Nav1.6 current and exhibit dystonia and muscle weakness but are still viable. Evidence for Nav1.6 being important for nociception is largely associative as Nav1.6 is expressed at high levels in dorsal root ganglia and can be found in spinal sensory tracts (Tzoumaka E, *J. Neurosci. Res.*, 60(1): 37-44 (2000)). It should be noted however that expression of Nav1.6 is not restricted to sensory neurons of the periphery. Like the Nav1.6 channel, expression of the Nav1.3 VGSC can also be detected in both the central and peripheral nervous system, though levels in the adult CNS are generally much higher than PNS. During development and the early postnatal period, Nav1.3 is expressed in peripheral neurons but this expression wanes as the animal matures (Shah B S, *J. Physiol.*, 534(3): 763-76 (2001); Schaller K L, *Cerebellum*, 2(1): 2-9 (2003)). Following neuronal insult, Nav1.3 expression is upregulated, more closely mimicking the developmental expression patterns (Hains B C, *J. Neurosci.*, 23(26): 8881-92 (2003)). Coincident with the recurrence of Nav1.3 expression is the emergence of a rapidly re-priming sodium current in the injured axons with a biophysical profile similar to Nav1.3 (Leffler A, et al., *J. Neurophysiol.*, 88(2): 650-8 (2002)). Treatment of injured axons with high levels of GDNF has been shown to diminish the rapidly repriming sodium current and reverse thermal and mechanical pain-related behaviors in a rat model of nerve injury, presumably by down-regulating the expression of Nav1.3 (Boucher T J, *Curr. Opin. Pharmacol.*, 1(1): 66-72 (2001)). Specific down-regulation of Nav1.3 via treatment with antisense oligonucleotides has also been shown to reverse pain-related behaviors following spinal cord injury (Hains B C, *J. Neurosci.*, 23(26): 8881-92 (2003)).

The $Na_v1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that $Na_v1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_v1.7$ protein has been shown to accumulate in neuromas, particularly painful neuromas (Kretschmer et al., *Acta. Neurochir. (Wien)*, 144(8): 803-10 (2002)). Gain of function mutations of $Na_v1.7$, both familial and sporadic, have been linked to primary erythermalgia, a disease characterized by burning pain and inflammation of the extremities (Yang et al., *J. Med. Genet.*, 41(3): 171-4 (2004), and paroxysmal extreme pain disorder (Waxman, S G *Neurology.* 7;69(6): 505-7(2007)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433) and carbamazepine is effective in reducing the number and severity of attacks in PEPD (Fertleman et al, *Neuron.*; 52(5):767-74 (2006). Further evidence of the role of Nav1.7 in pain is found in the phenotype of loss of function mutations of the SCN9A gene. Cox and colleagues (*Nature*, 444(7121):894-8 (2006)) were the first to report an association between loss-of-function mutations of SNC9A and congenital indifference to pain (CIP), a rare autosomal recessive disorder characterized by a complete indifference or insensitivity to painful stimuli. Subsequent studies have revealed a number of different mutations that result in a loss of function of the SCN9A gene and the CIP phenotype (Goldberg et al, *Clin Genet.*; 71(4): 311-9 (2007), Ahmad et al, *Hum Mol Genet.* 1; 16(17): 2114-21 (2007)).

Sodium channel-blocking agents have been reported to be effective in the treatment of various disease states, and have found particular use as local anesthetics and in the treatment of cardiac arrhythmias. It has also been reported that sodium channel-blocking agents may be useful in the treatment of pain, including acute, chronic, inflammatory and/or neuropathic pain; see, for example, Wood, J N et al., *J. Neurobiol.*, 61(1): 55-71 (2004). Preclinical evidence demonstrates that sodium channel-blocking agents can suppress neuronal firing in peripheral and central sensory neurons, and, it is via this mechanism, that they may be useful for relieving pain. In some instances, abnormal or ectopic firing can originate from injured or otherwise sensitized neurons. For example, it has been shown that sodium channels can accumulate in peripheral nerves at sites of axonal injury and may function as generators of ectopic firing (Devor et al. *J. Neurosci.*, 132: 1976 (1993)). Changes in sodium channel expression and excitability have also been shown in animal models of inflammatory pain where treatment with proinflammatory materials (CFA, Carrageenan) promoted pain-related behaviors and correlated with increased expression of sodium channel subunits (Gould et al., *Brain Res.*, 824(2): 296-9 (1999); Black et al., *Pain*, 108(3): 237-47 (2004)). Alterations in either the level of, expression of, or distribution of sodium channels, therefore, may have a major influence on neuronal excitability and pain-related behaviors. As such there is a desire to seek new sodium channel modulators.

WO-A-2005/054176 discusses peroxisome proliferator activated receptor modulators.

EP-A-1088819 discusses 6-azauracil derivatives, which are stated to be thyroid receptor ligands.

International patent application WO-A-2005/013914 (publication date 17 Feb. 2005) discloses compounds, in particular heteroarylamino sulfonylphenyl derivatives, which are useful as inhibitors of voltage gated sodium channels with a number of therapeutic uses, including the treatment of pain.

International patent application WO-A-2008/118758 (publication date 2 Oct. 2008) discloses compounds, in particular aryl sulphonamides, which are sodium channel modulators with a number of therapeutic uses, particularly for the treatment of pain.

International patent application WO-A-2009/012242 (publication date 22 Jan. 2009) discloses compounds, in particular N-thiazolyl benzenesulfonamides, which are sodium channel modulators with a number of therapeutic uses, particularly for the treatment of pain.

However, there remains a need for still further new sodium channel modulators, including modulators which are potentially able to block activity at a given sodium channel. The compounds of the present invention described herein are selective Nav1.7 channel modulators. In particular, they show an affinity for the Nav1.7 channel which is greater than their affinity for Nav1.5 channels. Preferred compounds of the invention show selectivity for the Nav1.7 channel as compared with the Nav1.5. Advantageously, the compounds of the invention show little or no affinity for the Nav1.5 channel.

The compounds of the present invention, being Nav1.7 modulators, are therefore potentially useful in the treatment of a wide range of disorders, particularly pain. The treatment of pain is a preferred use. All forms of pain are potentially treatable with the compounds of the present invention including acute pain; chronic pain; neuropathic pain; inflammatory pain; visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

Other conditions that may be treated with the compounds of the present invention include anal fissure, neuronal injury, spinal injury and epilepsy.

It is an objective of the invention to provide new Nav1.7 channel modulators and that, preferably, such new modulators are suitable for further development as drug candidates. Preferred compounds should bind potently to the Nav1.7 channel, show functional activity as Nav1.7 channel modulators, and preferably show little affinity for other sodium channels, particularly Nav1.5. Furthermore, the preferred compounds should have one or more of the following improved properties: be well absorbed from the gastrointestinal tract; be metabolically stable; have an improved metabolic profile, in particular with respect to the toxicity or allergenicity of any metabolites formed; or possess favourable pharmacokinetic properties whilst still retaining their activity profile as Nav1.7 channel modulators. It is further preferred that they should also be non-toxic and demonstrate few side-effects. Furthermore, such preferred drug candidates should preferably exist in a physical form that is stable, non-hygroscopic and easily formulated. Preferred compounds of the present invention are selective for the Nav1.7 channel over Nav1.5, which may potentially lead to one or more improvements in the side-effect profile. Without wishing to be bound by theory, such selectivity, is thought to advantageously reduce any cardiovascular side effects which may be associated with affinity for the Nav1.5 channel. Preferably compounds of the present invention demonstrate a selectivity of 10-fold, more preferably 30-fold, most preferably 100-fold, for the Nav1.7 channel when compared to their selectivity for the Nav1.5 channel whilst maintaining good potency for the Nav1.7 channel. In addition, the most preferred compounds of the present invention may optionally also show selectivity for the Nav1.7 channel over Nav1.3, whilst maintaining good potency for the Nav1.7 channel.

SUMMARY OF THE INVENTION

The invention therefore provides as Embodiment 1 a compound of the formula (I):

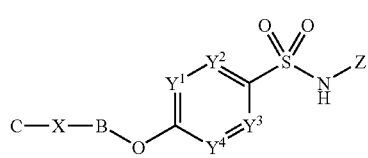

wherein

Z is $Het^2$, optionally substituted on a ring carbon atom with one or more substituents selected from the group consisting of halo, cyano, $(C_1$-$C_4)$alkyl, halo$(C_1$-$C_4)$alkyl, $(C_1$-$C_4)$alkoxy, halo$(C_1$-$C_4)$alkoxy, $(C_3$-$C_8)$cycloalkyl, $(C_3$-$C_8)$cycloalkyl$(C_1$-$C_4)$alkyl, $(C_1$-$C_4)$alkyl-S—, amino, $(C_1$-$C_4)$alkylamino, di$(C_1$-$C_4)$alkylamino, amino$(C_1$-C4)alkyl, $(C_1$-$C_4)$alkylamino$(C_1$-$C_4)$alkyl, and di[$(C_1$-$C_4)$alkyl]amino$(C_1$-$C_4)$alkyl; and/or $Het^2$ is optionally substituted on a ring nitrogen atom with $(C_1$-$C_4)$alkyl, halo$(C_1$-$C_4)$alkyl and $(C_3$-$C_8)$cycloalkyl; with the proviso that Z is not tetrazolyl;

$Y^1$, $Y^2$, $Y^3$ and $Y^4$ are each independently CH, $CR^1$ or N, provided that no more than two of $Y^1$, $Y^2$, $Y^3$ and $Y^4$ are N;

each $R^1$ is independently selected from the group consisting of halo, cyano, amino, hydroxy, $(C_1$-$C_4)$alkyl, halo$(C_1$-$C_4)$alkyl, hydroxy$(C_1$-$C_4)$alkyl, $(C_1$-$C_4)$alkoxy, halo$(C_1$-$C_4)$alkoxy, $(C_1$-$C_4)$alkoxy$(C_1$-$C_4)$alkyl, —C(O)H, —C(O)$(C_1$-$C_4)$alkyl, and —C(O)N$(R^2)_2$;

each $R^2$ is independently hydrogen, $(C_1$-$C_4)$alkyl, halo$(C_1$-$C_4)$alkyl, hydroxy$(C_1$-$C_4)$alkyl, or $(C_3$-$C_6)$cycloalkyl; or, where a nitrogen is substituted with two $R^2$ groups, each independently selected from $(C_1$-$C_4)$alkyl, halo$(C_1$-$C_4)$alkyl, or hydroxy$(C_1$-$C_4)$alkyl, they may be taken together with the N atom to which they are attached to form a 4- to 6-membered ring which, when so formed, may therefore optionally be substituted with hydrogen, alkyl, halo, hydroxy, hydroxyalkyl or haloalkyl;

B is phenyl or $Het^2$, wherein, when B is $Het^2$ it is attached to the oxy linker at a ring carbon atom, and wherein B is optionally further substituted on a ring carbon atom with one or more substituents selected from the group consisting of halo, cyano, hydroxy, $(C_1$-$C_4)$alkyl, halo$(C_1$-$C_4)$alkyl, $(C_1$-$C_4)$alkoxy, halo$(C_1$-$C_4)$alkoxy, cyano$(C_1$-$C_4)$alkyl, amino, $(C_1$-$C_4)$alkylamino, di$(C_1$-$C_4)$alkylamino, amino$(C_1$-$C_4)$alkyl, $(C_1$-$C_4)$alkylamino$(C_1$-$C_4)$alkyl, di[$(C_1$-$C_4)$alkyl]amino$(C_1$-C4)alkyl, trifluoromethylthio, hydroxy$(C_1$-$C_4)$alkyl, $(C_1$-$C_4)$alkoxy$(C_1$-$C_4)$alkyl, —C(O)$R^2$, —C(O)O$R^2$, —OC(O)$R^2$, —C(O)—N$(R^2)_2$, —CH$_2$—C(O)$R^2$, —CH$_2$—C(O)O$R^2$, —CH$_2$—OC(O)$R^2$, —CH$_2$—C(O)—N$(R^2)_2$, S(O)$_2R_2$, S(O)$_2$N$(R^2)_2$, $(C_3$-$C_8)$cycloalkyl, and $(C_3$-$C_8)$cycloalkyl$(C_1$-$C_4)$alkyl; and/or $Het^2$ is optionally substituted on a ring nitrogen atom with a substituent selected from the group consisting of $(C_1$-$C_4)$alkyl, halo$(C_1$-$C_4)$alkyl, hydroxy$(C_1$-$C_4)$alkyl, $(C_1$-$C_4)$alkoxy$(C_1$-$C_4)$alkyl, amino$(C_1$-$C_4)$alkyl, $(C_1$-$C_4)$alkylamino$(C_1$-$C_4)$alkyl, di[$(C_1$-$C_4)$alkyl]amino$(C_1$-$C_4)$alkyl, —CH$_2$—C(O)$R^2$, —CH$_2$—C(O)O$R^2$, —CH$_2$—C(O)—N$(R^2)_2$, S(O)$_2R^2$, and S(O)$_2$N$(R^2)_2$;

X is absent, —O—, methylene, ethylene, methylene-O—, or —O-methylene;

C is $(C_3$-$C_8)$cycloalkyl, $Het^1$, phenyl, or $Het^2$, each optionally substituted on a ring carbon atom with one or more substituents selected from the group consisting of halo, cyano, hydroxy, $(C_1$-$C_4)$alkyl, halo$(C_1$-$C_4)$alkyl, $(C_1$-$C_4)$alkoxy, halo$(C_1$-$C_4)$alkoxy, N$(R^2)_2$, $(R^2)_2$N$(C_1$-$C_4)$alkyl, trifluoromethylthio, hydroxy$(C_1$-$C_4)$alkyl, $(C_1$-$C_4)$alkoxy$(C_1$-$C_4)$alkyl, —C(O)$R^2$, —C(O)O$R^2$, —OC(O)$R^2$, —C(O)—N$(R^2)_2$, —CH$_2$—C(O)$R^2$, —CH$_2$—C(O)O$R^2$, —CH$_2$—OC(O)$R^2$, —CH$_2$—C(O)—N$(R^2)_2$, S(O)$_2R^2$, S(O)$_2$N$(R^2)_2$, $(C_3$-$C_8)$cycloalkyl$(C_1$-$C_4)$alkyl, $(C_3$-$C_8)$cycloalkoxy, $(C_3$-$C_8)$cycloalkylamino, $(C_3$-$C_8)$cycloalkylamino$(C_1$-$C_4)$alkyl, $(C_3$-$C_8)$cycloalkyl$(C_1$-$C_4)$alkylamino, $(C_3$-$C_8)$cycloalkyl$(C_1$-$C_4)$alkylamino$(C_1$-$C_4)$alkyl, $(C_3$-$C_8)$cycloalkyl$(C_1$-$C_4)$alkoxy and D; and/or $Het^2$ is optionally substituted on a ring nitrogen atom with a substituent selected from the group consisting of hydroxy, $(C_1$-$C_4)$alkyl, halo$(C_1$-$C_4)$alkyl, amino$(C_1$-$C_4)$alkyl, $(C_1$-$C_4)$alkylamino$(C_1$-$C_4)$alkyl, di[$(C_1$-$C_4)$alkyl]amino$(C_1$-$C_4)$alkyl, hydroxy$(C_1$-$C_4)$alkyl, $(C_1$-$C_4)$alkoxy$(C_1$-$C_4)$alkyl, —C(O)$R^2$, —C(O)O$R^2$, —CH$_2$—C(O)$R^2$, —CH$_2$—C(O)O$R^2$, —CH$_2$—C(O)—N$(R^2)_2$, S(O)$_2R^2$, and S(O)$_2$N$(R^2)_2$ and D;

with the proviso that C is not 3,5-dioxo-4,5-dihydro-3H-[1,2,4]triazin-2-yl;

D is phenyl, benzyl, $(C_3$-$C_8)$cycloalkyl, or $Het^1$, each optionally substituted on a carbon atom with one or more substituents independently selected from the group consisting of halo, cyano, hydroxy, $(C_1$-$C_4)$alkyl, halo$(C_1$-$C_4)$alkyl, $(C_1$-$C_4)$alkoxy, halo$(C_1$-$C_4)$alkoxy, amino, $(C_1$-$C_4)$alkylamino, di$(C_1$-$C_4)$alkylamino, amino$(C_1$-$C_4)$alkyl, $(C_1$-$C_4)$alkylamino$(C_1$-C4)alkyl, di[$(C_1$-$C_4)$alkyl]amino$(C_1$-$C_4)$alkyl, trifluoromethylthio, hydroxy$(C_1$-$C_4)$alkyl, $(C_1$-$C_4)$alkoxy$(C_1$-$C_4)$alkyl, —C(O)$R^2$, —C(O)O$R^2$, —OC(O)$R^2$, —C(O)—N$(R^2)_2$, —CH$_2$—C(O)$R^2$, —CH$_2$—C(O)O$R^2$, —CH$_2$—OC(O)$R^2$, —CH$_2$—C(O)—N$(R^2)_2$, S(O)$_2R^2$, and S(O)$_2$N$(R_2)_2$;

Het[1] is a 3- to 8-membered, saturated or partially unsaturated monocyclic heterocyclic group comprising one or two or three ring members selected from —NR[3]—, —O—, —C(O)— and —S(O)$_p$—;

R[3] is either the point of attachment to X or C to give

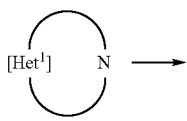

or R[3] is selected from the group consisting of hydrogen, $(C_1-C_4)$alkyl, halo$(C_1-C_4)$alkyl, hydroxy$(C_1-C_4)$alkyl, $(C_1-C_4)$alkoxy$(C_1-C_4)$alkyl, —C(O)$(C_1-C_4)$alkyl, —C(O)O$(C_1-C_4)$alkyl, —CH$_2$—C(O)O$(C_1-C_4)$alkyl, —CH$_2$—C(O)—N$((C_1-C_4)$alkyl$)_2$, S(O)$_2$R[2], S(O)$_2$N(R[2])$_2$ and $(C_3-C_8)$ cycloalkyl;

p is 0, 1 or 2; and

Het[2] is a 5- or 6-membered aromatic heterocyclic group comprising either (a) 1 to 4 nitrogen atoms, (b) one oxygen or one sulphur atom or (c) 1 oxygen atom or 1 sulphur atom and 1 or 2 nitrogen atoms;

or a tautomer thereof, or a pharmaceutically acceptable salt or solvate of the compound of formula (I), or its tautomer;

with the proviso that the compound of formula (I) is not the following specific compound:

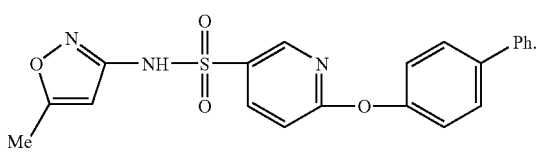

As used herein the term alkyl means an alicyclic, saturated hydrocarbon chain of the formula $C_nH_{2n+1}$ containing the requisite number of carbon atoms, which may be linear or branched. Examples of such groups include methyl, ethyl, n-propyl, isopropyl, n-butyl, isobutyl, sec-butyl, tert-butyl, pentyl, isoamyl and hexyl. Unless other wise specified the alkyl group contains from 1 to 6 carbon atoms.

As used herein the term alkylene means a bivalent acyclic, saturated hydrocarbon group of the formula $C_nH_{2n}$ containing the requisite number of carbon atoms, which may be linear or branched. Examples of alkylene include methylene, 1,1-ethylene, 1,2-ethylene, 1,1-propylene, 1,2-propylene, 1,3-propylene and 2,2-propylene. Unless otherwise specified the alkylene group contains from 1 to 6 carbon atoms.

As used herein the term aryl means a phenyl ring or a 5- or 6-membered aromatic heterocyclic group both of which can be optionally substituted with one or more substituents selected from the group consisting of halo, CN, halo$(C_1-C_4)$ alkyl, halo$(C_1-C_4)$alkoxy, and NO$_2$.

As used herein the term halo means fluoro, chloro, bromo or iodo.

As used herein the term alkoxy means an alicyclic, saturated hydrocarbon chain of the formula OC$_n$H$_{2n+1}$ containing the requisite number of carbon atoms, which may be linear or branched. Examples of alkoxy include methoxy, ethoxy, n-propoxy, i-propoxy, n-butoxy, i-butoxy, sec-butoxy and t-butoxy.

Haloalkyl and haloalkoxy mean an alkyl or alkoxy group, containing the requisite number of carbon atoms, substituted with one or more halo atoms as hereinbefore defined.

The term "hydroxy" as used herein means an OH group.

Specific examples of cycloalkyl include cyclopropyl, cyclobutyl, cyclopentyl, cyclohexyl and cycloheptyl, preferably cyclopropyl, cyclobutyl, cyclopentyl or cyclohexyl each of which may be optionally substituted as specified.

Specific examples of Het[1] include oxiranyl, aziridinyl, oxetanyl, azetidinyl, tetrahydrofuranyl, pyrrolidinyl, tetrahydropyranyl, piperidinyl, morpholinyl, thiomorpholinyl, piperazinyl, azepinyl, oxapinyl, oxazepinyl and diazepinyl (each optionally substituted as specified above).

Specific examples of Het[2] include pyrrolyl, furanyl, thiophenyl, pyrazolyl, imidazolyl, isoxazolyl, oxazolyl, isothiazolyl, thiazolyl, triazolyl oxadiazolyl, thiadiazolyl, tetrazolyl, pyridinyl, pyridazinyl, pyrimidinyl, and pyrazinyl (optionally substituted as specified above). The structures of these groups are depicted below:

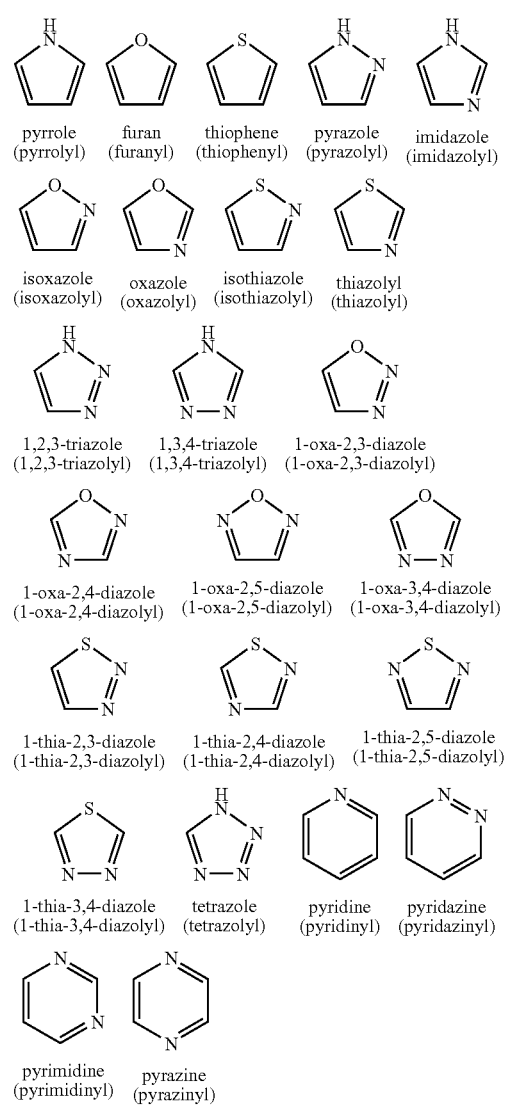

In the following embodiments of the invention, any group not specifically defined has the same meaning as given for formula (I) above. In each case, where an embodiment covers a compound where:

Z is tetrazolyl;
C is 3,5-dioxo-4,5-dihydro-3H-[1,2,4]triazin-2-yl; or
a compound of formula

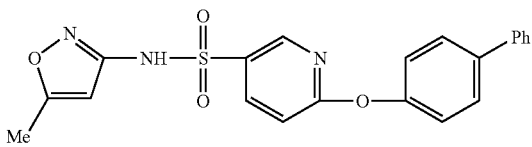

such compounds are excluded.

In Embodiment (2), the invention provides a compound of formula (I), or a pharmaceutically acceptable salt, solvate or tautomer thereof, according to Embodiment 1, wherein Z is Het², optionally substituted as defined in Embodiment 1, with the proviso that Z is not tetrazolyl.

In Embodiment (2a), the invention provides a compound of formula (I), or a pharmaceutically acceptable salt, solvate or tautomer thereof, according to Embodiment 1, wherein Z is Het², optionally substituted as defined in Embodiment 1, with the proviso that Z is not tetrazolyl or isoxazoyl.

In Embodiment (2.1), the invention provides a compound of formula (I), or a pharmaceutically acceptable salt, solvate or tautomer thereof, according to Embodiment 1, wherein Z is a 5-membered aromatic heterocyclic group comprising either thiophenyl, or comprises either (a) 1 to 3 nitrogen atoms or (c) 1 oxygen atom or 1 sulphur atom and 1 or 2 nitrogen atoms, and Z is optionally substituted as defined in Embodiment 1.

In Embodiment (2.2), the invention provides a compound of formula (I), or a pharmaceutically acceptable salt, solvate or tautomer thereof, according to Embodiment 1, wherein Z is thiophenyl, imidazolyl, isothiazolyl, 2-thiazolyl, 4-thiazolyl, 5-thiazolyl, 1-thia-3,4-diazolyl, 1-thia-2,5-diazolyl, 1-thia-2,4-diazolyl, 1-thia-2,3-diazolyl, 1,3,4-triazolyl, oxazolyl, pyrazolyl, 1-oxa-2,5-diazolyl, or isoxazolyl, and Z is optionally substituted as defined in Embodiment 1.

In Embodiment (2.2a), the invention provides a compound of formula (I), or a pharmaceutically acceptable salt, solvate or tautomer thereof, according to Embodiment 1, wherein Z is imidazolyl, isothiazolyl, 2-thiazolyl, 4-thiazolyl, 5-thiazolyl, 1-thia-3,4-diazolyl, 1-thia-2,5-diazolyl, 1-thia-2,4-diazolyl, 1-thia-2,3-diazolyl, 1,3,4-triazolyl, oxazolyl and Z is optionally substituted as defined in Embodiment 1.

In Embodiment (2.2b), the invention provides a compound of formula (I), or a pharmaceutically acceptable salt, solvate or tautomer thereof, according to Embodiment 1, wherein Z is 2-thiazolyl, 4-thiazolyl, 1-thia-3,4-diazolyl or 1-thia-2,4-diazolyl and Z is optionally substituted as defined in Embodiment 1.

In Embodiment (2.2c), the invention provides a compound of formula (I), or a pharmaceutically acceptable salt, solvate or tautomer thereof, according to Embodiment 1, wherein Z is thiophenyl, imidazolyl, isothiazolyl, 2-thiazolyl, 4-thiazolyl, 5-thiazolyl, 1-thia-3,4-diazolyl, 1-thia-2,5-diazolyl, 1-thia-2,4-diazolyl, 1-thia-2,3-diazolyl, 1,3,4-triazolyl, oxazolyl, pyrazolyl, 1-oxa-2,5-diazolyl, or isoxazolyl, and Z is either unsubstituted or optionally substituted on a ring carbon atom with halo, for example bromo, chloro, fluoro or iodo; ($C_1$-$C_4$)alkyl, for example methyl, ethyl or isopropyl; ($C_1$-$C_4$) alkoxy, for example methoxy or ethoxy; ($C_1$-$C_4$)alkyl-S—, for example $CH_3S$—; or cyano; or optionally substituted on a ring nitrogen atom with ($C_1$-$C_4$)alkyl, for example methyl.

In Embodiment (2.3), the invention provides a compound of formula (I), or a pharmaceutically acceptable salt, solvate or tautomer thereof, according to Embodiment 1, wherein Z is either 2-thiazolyl or 4-thiazolyl each of which are either unsubstituted or monosubstituted on a ring carbon atom with halo, for example chloro; or Z is 1-thia-3,4-diazolyl which is unsubstituted; or Z is 1-thia-2,4-diazolyl which is unsubstituted.

In an alternative Embodiment (2.4), the invention provides a compound of formula (I), or a pharmaceutically acceptable salt, solvate or tautomer thereof, according to Embodiment 1, wherein Z is 6-membered aromatic heterocyclic group comprising 1 to 4 nitrogen atoms, and Z is optionally substituted as defined in Embodiment 1.

In Embodiment (2.5), the invention provides a compound of formula (I), or a pharmaceutically acceptable salt, solvate or tautomer thereof, according to Embodiment 1, wherein Z is pyridinyl, pyrazinyl, pyridazinyl, or pyrimidinyl, more preferably pyridinyl, pyridazinyl, or pyrimidinyl and Z is optionally substituted as defined in Embodiment 1.

In Embodiment (2.5a), the invention provides a compound of formula (I), or a pharmaceutically acceptable salt, solvate or tautomer thereof, according to Embodiment 1, wherein Z is pyridinyl, pyrazinyl, pyridazinyl, or pyrimidinyl and Z is optionally substituted on a ring carbon atom with halo, for example chloro, or fluoro; ($C_1$-$C_4$)alkyl, for example methyl; halo($C_1$-$C_4$)alkyl, for example trifluoromethyl; ($C_1$-$C_4$) alkoxy, for example methoxy; or cyano.

In Embodiment (2.6) the invention provides a compound of formula (I), or a pharmaceutically acceptable salt, solvate or tautomer thereof, according to Embodiment 1, wherein Z is pyrimidinyl, which is unsubstituted; or Z is pyridinyl which is substituted on a ring carbon with halo, for example fluoro; or Z is pyridazinyl, which is unsubstituted.

In another Embodiment (2.7), the invention provides a compound of formula (I), or a pharmaceutically acceptable salt, solvate or tautomer thereof, according to Embodiment 1, wherein Z is Het² substituted on a ring nitrogen as defined in Embodiment 1. Preferably Z is imidazolyl substituted on a ring nitrogen, more preferably substituted on a ring nitrogen with ($C_1$-$C_4$)alkyl, for example methyl.

In Embodiment (3), the invention provides a compound of formula (I), or a pharmaceutically acceptable salt, solvate or tautomer thereof, according to any preceding Embodiment, wherein $Y^2$ and $Y^3$ cannot both be N; more preferably, no more than one of $Y^1$, $Y^2$, $Y^3$ and $Y^4$ is N.

In Embodiment (3.1), the invention provides a compound of formula (I), or a pharmaceutically acceptable salt, solvate or tautomer thereof, according to any preceding Embodiment, wherein
$Y^1$ is N, $Y^2$ is $CR^1$, and $Y^3$ and $Y^4$ are each CH; or
$Y^1$ is N, $Y^4$ is $CR^1$, and $Y^2$ and $Y^3$ are each CH; or
$Y^1$, $Y^2$, $Y^3$ and $Y^4$ are each independently CH or $CR^1$, where preferably no more than two of $Y^1$, $Y^2$, $Y^3$ and $Y^4$ are $CR^1$.

In Embodiment (3.2), the invention provides a compound of formula (I), or a pharmaceutically acceptable salt, solvate or tautomer thereof, according to any preceding Embodiment, wherein
$Y^1$, $Y^2$, $Y^3$ and $Y^4$ are each CH; or
$Y^1$ is $CR^1$, and $Y^2$, $Y^3$ and $Y^4$ are each CH; or
$Y^2$ is $CR^1$ and $Y^1$, $Y^3$ and $Y^4$ are each CH; or
$Y^1$ and $Y^4$ are $CR^1$ and $Y^2$ and $Y^3$ are CH; or
$Y^1$ and $Y^3$ are $CR^1$ and $Y^2$ and $Y^4$ are CH; or
$Y^1$ and $Y^2$ are $CR^1$ and $Y^3$ and $Y^4$ are CH.

In Embodiment (3.3), the invention provides a compound of formula (I), or a pharmaceutically acceptable salt, solvate or tautomer thereof, according to any preceding Embodiment, wherein $Y^1$ is $CR^1$, and $Y^2$, $Y^3$ and $Y^4$ are each CH; or $Y^1$ and $Y^3$ are $CR^1$ and $Y^2$ and $Y^4$ are CH.

In Embodiment (4), the invention provides a compound of formula (I), or a pharmaceutically acceptable salt, solvate or tautomer thereof, according to any preceding Embodiment, wherein each $R^1$ is independently selected from the group consisting of halo, cyano, ($C_1$-$C_4$)alkyl, halo($C_1$-$C_4$)alkyl, ($C_1$-$C_4$)alkoxy, —C(O)H, $NH_2$ and —C(O)$NH_2$; more preferably, each $R^1$ is independently selected from the group consisting of fluoro, chloro, bromo, iodo, cyano, methyl, ethyl, trifluoromethyl, methoxy, —C(O)H, $NH_2$ and —C(O)$NH_2$.

In Embodiment (4.1), the invention provides a compound of formula (I), or a pharmaceutically acceptable salt, solvate or tautomer thereof, according to any preceding Embodiment, wherein $Y^1$ is N, $Y^4$ is $CR^1$, and $Y^2$ and $Y^3$ are each CH and $R^1$ is independently selected from halo, for example chloro; or cyano.

In Embodiment (4.2), the invention provides a compound of formula (I), or a pharmaceutically acceptable salt, solvate or tautomer thereof, according to any preceding Embodiment, wherein one of $Y^1$, $Y^2$, $Y^3$ or $Y^4$ are $CR^1$, and the others are each CH, and $R^1$ is independently selected from halo, for example fluoro, chloro or iodo; cyano; ($C_1$-$C_4$)alkyl, for example methyl or ethyl; halo($C_1$-$C_4$)alkyl, for example trifluoromethyl; ($C_1$-$C_4$)alkoxy, for example methoxy; and —C(O)$NH_2$.

In yet another alternative preferred embodiment (4.3), the invention provides a compound of formula (I), or a pharmaceutically acceptable salt, solvate or tautomer thereof, according to any preceding Embodiment, wherein $Y^1$ is $CR^1$, and $Y^2$, $Y^3$ and $Y^4$ are each CH and $R^1$ is cyano.

In yet another alternative preferred embodiment (4.4), the invention provides a compound of formula (I), or a pharmaceutically acceptable salt, solvate or tautomer thereof, according to any preceding Embodiment, wherein two of $Y^1$ $Y^2$, $Y^3$ and $Y^4$ are $CR^1$ and the other two are CH and each $R^1$ is independently selected from halo, for example fluoro, chloro or bromo; cyano; and ($C_1$-$C_4$)alkyl, for example methyl.

In Embodiment (4.5), the invention provides a compound of formula (I), or a pharmaceutically acceptable salt, solvate or tautomer thereof, according to any preceding Embodiment, wherein $Y^1$ and $Y^3$ are $CR^1$ and $Y^2$ and $Y^4$ are CH and each $R^1$ is independently selected from halo, for example fluoro or chloro; or ($C_1$-$C_4$)alkyl, for example methyl. For example, both $R^1$ groups are fluoro. Alternatively one is fluoro and the other chloro. Yet another alternative is where one $R^1$ group is fluoro and the other $R^1$ group is methyl.

In Embodiment (5), the invention provides a compound of formula (I), or a pharmaceutically acceptable salt, solvate or tautomer thereof, according to any preceding Embodiment, wherein B is selected from the group consisting of:

(i) phenyl;

(ii) 5-membered aromatic heterocyclic group comprising either (a) 1 to 3 nitrogen atoms, or (c) 1 oxygen atom or 1 sulphur atom and 1 or 2 nitrogen atoms;

(iii) 6-membered aromatic heterocyclic group comprising 1 or 2 nitrogen atoms;

and wherein B is optionally substituted as defined in Embodiment 1.

In Embodiment (5a), the invention provides a compound of formula (I), or a pharmaceutically acceptable salt, solvate or tautomer thereof, according to any preceding Embodiment, wherein B is phenyl optionally substituted as defined in Embodiment 1.

In Embodiment (5b), the invention provides a compound of formula (I), or a pharmaceutically acceptable salt, solvate or tautomer thereof, according to any preceding Embodiment, wherein B is a 5-membered aromatic heterocyclic group comprising either (a) 1 to 3 nitrogen atoms, or (c) 1 oxygen atom or 1 sulphur atom and 1 or 2 nitrogen atoms, more preferably where B is a 5-membered aromatic heterocyclic group comprising either (a) 1 to 3 nitrogen atoms, or (c) 1 oxygen atom or 1 sulphur atom and 1 or 2 nitrogen atoms but is not pyrazolyl, optionally substituted as defined in Embodiment 1.

In Embodiment (5c), the invention provides a compound of formula (I), or a pharmaceutically acceptable salt, solvate or tautomer thereof, according to any preceding Embodiment, wherein B is a 6-membered aromatic heterocyclic group comprising 1 or 2 nitrogen atoms optionally substituted as defined in Embodiment 1.

In Embodiment (5.1), the invention provides a compound of the formula (I), or a pharmaceutically acceptable salt, solvate or tautomer thereof, according to any preceding Embodiment, wherein B is phenyl, thiazolyl, thiadiazolyl, pyrazolyl, triazolyl, pyridinyl, pyrimidinyl, pyridazinyl or pyrazinyl, and wherein B is optionally substituted as defined in Embodiment 1.

In Embodiment (5.1a), the invention provides a compound of the formula (I), or a pharmaceutically acceptable salt, solvate or tautomer thereof, according to any preceding Embodiment, wherein B is phenyl, thiazolyl, thiadiazolyl, triazolyl, pyridinyl, pyrimidinyl, pyridazinyl or pyrazinyl, and wherein B is optionally substituted as defined in Embodiment 1.

In a most preferred Embodiment (5.2), the invention provides a compound of the formula (I), or a pharmaceutically acceptable salt, solvate or tautomer thereof, according to any preceding Embodiment, wherein B is phenyl, optionally substituted as defined in Embodiment 1.

In Embodiment (5.3); the invention provides a compound of formula (I), or a pharmaceutically acceptable salt, solvate or tautomer thereof, according to any preceding Embodiment, wherein B is unsubstituted; or is substituted on a ring carbon atom with one or two substituents independently selected from the group consisting of halo, cyano, ($C_1$-$C_4$)alkyl, halo($C_1$-C4)alkyl, ($C_1$-$C_4$)alkoxy, halo($C_1$-$C_4$)alkoxy, cyano($C_1$-$C_4$)alkyl, amino, ($C_1$-$C_4$)alkylamino, di($C_1$-$C_4$)alkylamino, hydroxy($C_1$-$C_4$)alkyl, ($C_1$-$C_4$)alkoxy($C_1$-$C_4$)alkyl, —C(O)$OR^2$, —C(O)—N($R^2$)$_2$, —$CH_2$—C(O)—N($R^2$)$_2$ and ($C_3$-$C_8$)cycloalkyl; and/or is substituted on a ring nitrogen atom with one or two substituents independently selected from the group consisting of ($C_1$-$C_4$)alkyl, halo($C_1$-$C_4$)alkyl, hydroxy($C_1$-$C_4$)alkyl, $CH_2$—C(O)$R^2$, or —$CH_2$C(O)$OR^2$.

In Embodiment (5.4), the invention provides a compound of formula (I), or a pharmaceutically acceptable salt, solvate or tautomer thereof, according to any preceding Embodiment, wherein B is unsubstituted; or is substituted on a ring carbon atom with one or two substituents selected from cyano, methyl, ethyl, i-propyl, i-butyl, t-butyl, trifluoromethyl, 2,2,2-trifluoroethyl, C($CH_3$)$_2$CN, methoxy, difluoromethoxy, trifluoromethoxy, hydroxymethyl, hydroxyethyl, hydroxypropyl, hydroxybutyl, methoxymethyl, bromo, chloro, fluoro, iodo, —$NH_2$, —NH($CH_3$), —N($CH_3$)$_2$, —$CH_2$—C(O)—$NH_2$, —C(O)—N($CH_3$)$_2$, —C(O)$OCH_3$ and cyclopropyl; and/or is substituted on a ring nitrogen atom with one or two substituents selected from methyl, t-butyl, hydroxyethyl, —CH$_2$C(O)H, —CH$_2$—C(O)O—CH$_2$CH$_3$ or 2,2,2-trifluoroethyl.

In Embodiment (5.5), the invention provides a compound of formula (I), or a pharmaceutically acceptable salt, solvate or tautomer thereof, according to any preceding Embodiment, wherein B is phenyl, which is unsubstituted; or is substituted on a ring carbon with one substituent selected from halo, for example fluoro, chloro, bromo, or iodo; cyano; (C$_1$-C$_4$)alkyl, for example methyl, ethyl, i-propyl, or i-butyl; halo(C$_1$-C$_4$)alkyl, for example trifluoromethyl; (C$_1$-C$_4$)alkoxy, for example methoxy; cyano(C$_1$-C$_4$)alkyl, for example C(CH$_3$)$_2$CN; halo(C$_1$-C$_4$)alkoxy, for example difluoromethoxy, or trifluoromethoxy; hydroxy(C$_1$-C$_4$)alkyl, for example hydroxymethyl, hydroxyethyl, hydroxypropyl, or hydroxybutyl; (C$_1$-C$_4$)alkoxy(C$_1$-C$_4$)alkyl, for example methoxymethyl; —C(O)OR$^2$, for example when R$^2$ is (C$_1$-C$_4$)alkyl, for example methyl, to form —C(O)OCH$_3$; —C(O)—N(R$^2$)$_2$ for example when R$^2$ is (C$_1$-C$_4$)alkyl, for example methyl, to form —C(O)—N(CH$_3$)$_2$; and (C$_3$-C$_8$)cycloalkyl, for example cyclopropyl; or is substituted on a ring carbon with two substituents independently selected from halo, for example fluoro, chloro or bromo; and (C$_1$-C$_4$)alkyl, for example methyl, to form, for example difluoro; dichloro; dibromo; fluoro, chloro; or chloro, methyl.

In Embodiment (5.6) the invention provides a compound of formula (I), or a pharmaceutically acceptable salt, solvate or tautomer thereof, according to any preceding Embodiment, wherein B is phenyl, which is substituted on a ring carbon with one substituent selected from halo, for example fluoro, or chloro; halo(C$_1$-C$_4$)alkyl, for example trifluoromethyl; or halo(C$_1$-C$_4$)alkoxy, trifluoromethoxy; or is substituted on a ring carbon with two substituents, selected from halo, for example fluoro, or chloro; halo(C$_1$-C$_4$)alkyl, for example trifluoromethyl; or halo(C$_1$-C$_4$)alkoxy, trifluoromethoxy. For example one substituent is fluoro and the other chloro. Alternatively one substituent is fluoro and the other is trifluoromethyl.

In a preferred Embodiment (6), the invention provides a compound of formula (I), or a pharmaceutically acceptable salt, solvate or tautomer thereof, according to any preceding Embodiment, wherein C is (C$_3$-C$_8$)cycloalkyl, for example cyclopropyl or cyclohexyl, optionally substituted as defined in Embodiment 1.

In Embodiment (6a), the invention provides a compound of formula (I), or a pharmaceutically acceptable salt, solvate or tautomer thereof, according to any preceding Embodiment, wherein the C ring, at the atom where it attaches to X, or directly to ring B if X is absent, is not further substituted except that such an atom may be substituted by hydrogen if chemically possible.

In Embodiment (6b), the invention provides a compound of formula (I), or a pharmaceutically acceptable salt, solvate or tautomer thereof, according to any preceding Embodiment, wherein C is phenyl, optionally substituted as defined in Embodiment 1.

In Embodiment (6c), the invention provides a compound of formula (I), or a pharmaceutically acceptable salt, solvate or tautomer thereof, according to any preceding Embodiment, wherein C is Het$^1$, optionally substituted as defined in Embodiment 1.

In Embodiment (6d), the invention provides a compound of formula (I), or a pharmaceutically acceptable salt, solvate or tautomer thereof, according to any preceding Embodiment, wherein C is Het$^2$, optionally substituted as defined in Embodiment 1.

In Embodiment (6.1), the invention provides a compound of formula (I), or a pharmaceutically acceptable salt, solvate or tautomer thereof, according to any preceding Embodiment, wherein C is Het$^2$, attached to X, or directly to ring B if X is absent, at a carbon atom and optionally substituted as defined in Embodiment 1.

In Embodiment (6.1a), the invention provides a compound of formula (I), or a pharmaceutically acceptable salt, solvate or tautomer thereof, according to any preceding Embodiment, wherein C is Het$^1$, attached to X, or directly to ring B if X is absent, at a carbon atom and optionally substituted as defined in Embodiment 1.

In Embodiment (6.2), the invention provides a compound of the formula (I), or a pharmaceutically acceptable salt, solvate or tautomer thereof, according to any preceding Embodiment, wherein C is a 5-membered aromatic heterocyclic group comprising either (a) 1 to 4 nitrogen atoms, (b) one oxygen or one sulphur atom or (c) 1 oxygen atom or 1 sulphur atom and 1 or 2 nitrogen atoms, for example furanyl, pyrazolyl; imidazolyl; 1,2,3-triazolyl; 1,3,4-triazolyl; tetrazolyl; thiazolyl; isothiazolyl; oxazolyl; isoxazolyl; or 1-oxa-2,4-diazolyl, each optionally substituted as defined in Embodiment 1.

In another even more preferred Embodiment (6.2a), the invention provides a compound of the formula (I), or a pharmaceutically acceptable salt, solvate or tautomer thereof, according to any preceding Embodiment, wherein C is a 6-membered aromatic heterocyclic group comprising either (a) 1 to 4 nitrogen atoms, (b) one oxygen or one sulphur atom or (c) 1 oxygen atom or 1 sulphur atom and 1 or 2 nitrogen atoms, for example pyridinyl, pyrazinyl, pyridazinyl, or pyrimidinyl, each optionally substituted as defined in Embodiment 1.

In yet another even more preferred Embodiment (6.2b), the invention provides a compound of the formula (I), or a pharmaceutically acceptable salt, solvate or tautomer thereof, according to any preceding Embodiment, wherein C is a 3- to 8-membered, saturated or partially unsaturated monocyclic heterocyclic group comprising one or two ring members selected from —NR$^3$—, —O—, —C(O)—, for example azetidinyl; pyrrolidinyl; piperidinyl; oxetanyl; tetrahydropyranyl; pyrrolidonyl; imidazolidonyl; or morpholinyl, each optionally substituted as defined in Embodiment 1.

In yet further preferred Embodiment (6.3) the invention provides a compound of the formula (I), or a pharmaceutically acceptable salt, solvate or tautomer thereof, according to any preceding Embodiment, wherein C is phenyl; cyclopropyl; cyclohexyl; pyrazolyl; furanyl, imidazolyl; 1,2,3-triazolyl; 1,2,4-triazolyl; 1,3,4-triazolyl; tetrazolyl; thiazolyl; isothiazolyl; oxazolyl; isoxazolyl; 1-oxa-2,4-diazolyl; pyridinyl; pyrazinyl; pyridazinyl; pyrimidinyl; azetidinyl; pyrrolidinyl; piperidinyl; oxetanyl; tetrahydropyranyl; pyrrolidonyl; imidazolidonyl; or morpholinyl, each optionally substituted as defined in Embodiment 1.

In Embodiment (6.3a), the invention provides a compound of the formula (I), or a pharmaceutically acceptable salt, solvate or tautomer thereof, according to any preceding Embodiment, wherein C is pyrazolyl; pyridinyl; pyridazinyl; pyrimidinyl; azetidinyl; piperidinyl; or tetrahydropyranyl; each optionally substituted as defined in Embodiment 1.

In Embodiment (6.4) the invention provides a compound of the formula (I), or a pharmaceutically acceptable salt, solvate or tautomer thereof, according to any preceding Embodiment, wherein C is unsubstituted; or C is substituted on a ring carbon atom with one or two substituents selected from the group consisting of halo, cyano, hydroxy, $(C_1-C_4)$alkyl, halo$(C_1-C_4)$alkyl, $(C_1-C_4)$alkoxy, halo$(C_1-C_4)$alkoxy, $(R^2)_2$amino, $(R^2)_2$amino$(C_1-C_4)$alkyl, hydroxy$(C_1-C_4)$alkyl, $(C_1-C_4)$alkoxy$(C_1-C_4)$alkyl, —C(O)R$^2$, —CH$_2$—O—C(O)R$^2$, —C(O)—NH$_2$, —C(O)—N(R$^2$)$_2$, $(C_3-C_8)$cycloalkoxy, and D; and/or when C is Het$^2$ it is substituted on a ring nitrogen atom with one substituent selected from the group consisting of $(C_1-C_4)$alkyl, halo$(C_1-C_4)$alkyl, di[$(C_1-C_4)$alkyl]amino$(C_1-C_4)$alkyl, hydroxy$(C_1-C_4)$alkyl, $(C_1-C_4)$alkoxy$(C_1-C_4)$alkyl, —C(O)R$^2$, —CH$_2$—C(O)O—R$_2$, —CH$_2$—C(O)—NR$_2$; and D; and/or when C is Het$^1$, R$^3$ is optionally selected from the group of substituents consisting of hydrogen, $(C_1-C_4)$alkyl, or —C(O)$(C_1-C_4)$alkyl.

In Embodiment (6.5) the invention provides a compound of the formula (I), or a pharmaceutically acceptable salt, solvate or tautomer thereof, according to any preceding Embodiment, wherein C is unsubstituted; or C is substituted on a ring carbon atom with one or two substituents selected from the group consisting of chloro, fluoro, cyano, hydroxy, methyl, ethyl, i-proyl, t-butyl, difluoromethyl, trifluoromethyl, methoxy, ethoxy, i-propoxy, trifluoromethoxy, NH$_2$, —N(CH$_3$)$_2$, —CH$_2$NH$_2$, —NH(cyclobutyl), —CH$_2$N-azetidinyl, —CH$_2$N-3,3-difluoroazetidinyl, —CH$_2$N-3,3-dihydroxymethylazetidinyl, —CH$_2$N-3-hydroxypyrrolidinyl hydroxymethyl, hydroxyethyl, methoxymethyl, -methoxyethyl, —C(O)CH$_3$, —C(O)OH, —CH$_2$C(O)OCH$_3$, —CH$_2$OC(O)CF$_3$, —C(O)—NH$_2$, —C(O)—N(CH$_3$)$_2$, —C(O)—NH(t-butyl), C(O)—NH(cyclopropyl), —C(O)N-azetidinyl, —C(O)N-3-methylazetidinyl cyclobutyloxy, and D, wherein D is cyclopropyl, cyclohexyl, azetidinyl, morpholinyl and piperazinyl; and/or when C is Het$^2$, it is substituted on a ring nitrogen atom with one substituent selected from the group consisting of hydroxy, methyl, ethyl, t-butyl, difluoromethyl, trifluoromethyl, 2,2,2-trifluoroethyl, 3-fluoropropyl, (CH$_2$)$_2$N(CH$_3$)$_2$, hydroxyethyl, methoxyethyl, —C(O)CH$_3$, —CH$_2$—C(O)O—CH$_2$CH$_3$, —CH$_2$—C(O)OH, —CH$_2$—C(O)—N(CH$_3$)$_2$ and D, wherein D is phenyl, benzyl, cyclopropyl, cyclobutyl, dioxidotetrahydro-3-thienyl, azetidinyl, N-methylazetidinyl, N-ethylazetidinyl, N-isopropylazetidinyl, tetrahydrafuranyl, piperidinyl, N-methylpiperidinyl; and/or when C is Het$^1$, R$^3$ is either the point of attachment to X; hydrogen, methyl or C(O)CH$_3$, C(O)OCH$_3$, C(O)OC(CH$_3$)$_3$.

In an even more preferred Embodiment (6.6), invention provides a compound of formula (I), or a pharmaceutically acceptable salt, solvate or tautomer thereof, according to any preceding Embodiment, wherein C is pyrazolyl, which is preferably attached to X, or directly to ring B if X is absent, via a carbon atom, more preferably via the carbon at the 3 position or the carbon at the 4 position and most preferably via the carbon at the 3 position.

In Embodiment (6.6a), invention provides a compound of formula (I), or a pharmaceutically acceptable salt, solvate or tautomer thereof, according to any preceding Embodiment, wherein C is pyrazolyl, which is unsubstituted, or which is substituted on a ring carbon atom with one or two substituents independently selected from halo, for example fluoro, chloro; cyano; hydroxy; $(C_1-C_4)$alkyl, for example methyl; halo$(C_1-C_4)$alkyl, for example difluoromethyl or trifluoromethyl; $(C_1-C_4)$alkoxy, for example methoxy, ethoxy, i-propoxy, methoxymethyl, or methoxyethyl; amino; di(C$_1$-C$_4$)alkylamino, for example N(CH$_3$)$_2$; hydroxy$(C_1-C_4)$alkyl, for example hydroxymethyl; —C(O)OR$^2$, wherein R$^2$ is (C$_1$-C$_4$)alkyl, for example ethyl; —CH$_2$—O—C(O)R$^2$ wherein R$^2$ is independently selected from halo(C$_1$-C$_4$)alkyl, for example trifluoromethyl; —C(O)—N(R$^2$)$_2$ wherein R$^2$ is independently selected from hydrogen, or (C$_1$-C$_4$)alkyl, for example methyl or t-butyl; and D, wherein D is (C$_3$-C$_8$) cycloalkyl, for example cyclopropyl, which is unsubstituted; and/or which is substituted on a ring nitrogen atom with one substituent selected from (C$_1$-C$_4$)alkyl, for example methyl, ethyl or t-butyl; halo(C$_1$-C$_4$)alkyl, for example difluoromethyl, trifluoromethyl, 2,2,2-trifluoroethyl, or 3,3,3-trifluoropropyl; (C$_1$-C$_4$)alkoxy(C$_1$-C$_4$)alkyl, for example methoxyethyl; di[(C$_1$-C$_4$)alkyl]amino(C$_1$-C$_4$)alkyl, for example (CH$_2$)$_2$N(CH$_3$)$_2$; —C(O)R$^2$, wherein R$^2$ is (C$_1$-C$_4$)alkyl, for example t-butyl; —CH$_2$—C(O)OR$^2$ wherein R$^2$ is independently selected from hydrogen, or (C$_1$-C$_4$)alkyl, for example ethyl; —CH$_2$—C(O)—N(R$^2$)$_2$, wherein both R$^2$ are selected from hydrogen, or (C$_1$-C$_4$)alkyl, for example methyl; and D, for example phenyl, which is unsubstituted; benzyl, which is unsubstituted; (C$_3$-C$_8$)cycloalkyl, for example cyclopropyl or cyclobutyl; Het$^1$, for example azetidinyl which is attached to the C ring via a carbon atom, more preferably via a carbon atom at the 3 position and which azetidinyl is unsubstituted, or which is substituted on the N atom with (C$_1$-C$_4$)alkyl, for example methyl, ethyl or isopropyl, or C(O)(C$_1$-C$_4$)alkyl, for example C(O)CH$_3$; or piperidinyl which is unsubstituted, or which is substituted on the N atom with (C$_1$-C$_4$)alkyl, for example methyl; or dioxidotetrahydro-3-thienyl which is unsubstituted; or tetrahydrofuranyl, which is unsubstituted.

In Embodiment (6.7), the invention provides a compound of formula (I), or a pharmaceutically acceptable salt, solvate or tautomer thereof, according to any preceding Embodiment, wherein C is pyrazolyl, which is unsubstituted, or which is substituted on a ring carbon atom with one substituent selected from (C$_1$-C$_4$)alkyl, for example methyl; or amino; or which is substituted on a ring nitrogen atom with one substituent selected from (C$_1$-C$_4$)alkyl, for example methyl; or D, for example azetidinyl wherein R$^3$ is hydrogen or (C$_1$-C$_4$)alkyl, for example methyl or ethyl. Preferably the pyrazolyl is attached to X, or directly to ring B if X is absent, via a carbon atom, more preferably via a carbon atom at the 3 position.

In Embodiment (6.8), the invention provides a compound of formula (I), or a pharmaceutically acceptable salt, solvate or tautomer thereof, according to any preceding Embodiment, wherein C is pyridinyl, which is unsubstituted, or which is substituted on a ring carbon atom with one substituent selected from hydroxy; halo, for example fluoro or chloro; cyano; (C$_1$-C$_4$)alkyl, for example methyl; halo(C$_1$-C$_4$)alkyl, for example trifluoromethyl; (C$_1$-C$_4$)alkoxy, for example methoxy; N(R$^2$)$_2$, wherein R$^2$ is selected from hydrogen, or (C$_1$-C$_4$)alkyl, for example methyl, or (C$_3$-C$_6$)cycloalkyl, for example cyclobutyl, to give for example amino, N(CH$_3$)$_2$, NH(cyclobutyl); N(R$^2$)$_2$(C$_1$-C$_4$)alkyl, for example N-azetidinylmethyl, 3,3-difluoro-N-azetidinylmethyl; hydroxy(C$_1$-C$_4$)alkyl, for example hydroxymethyl; C(O)N(R$^2$)$_2$, for example C(O)N-azetidinyl; (C$_3$-C$_8$)cycloalkoxy, for example cyclobutoxy; and D, wherein D is Het$^1$, for example azetidinyl, morpholinyl, or piperazinyl, all of which are unsubstituted; or D is pyridinyl is substituted on a ring nitrogen with hydroxy.

In Embodiment (6.9), the invention provides a compound of formula (I), or a pharmaceutically acceptable salt, solvate or tautomer thereof, according to any preceding Embodiment, wherein C is pyridinyl, which is substituted on a ring carbon atom with one substituent selected from N(R$^2$)$_2$, wherein R$^2$ is selected from hydrogen, or (C$_1$-C$_4$)alkyl, for example methyl, to give, for example amino, or N(CH$_3$)$_2$;

N(R²)₂(C₁-C₄)alkyl, wherein R² is selected from hydrogen to give, for example aminomethyl, or both R² groups are selected from (C₁-C₄)alkyl and are taken together with the N to which they are attached to form a 4 memebered ring to give, for example, N-azetidinylmethyl; (C₃-C₈)cycloalkoxy, for example cyclobutoxy; or D where D is Het¹, for example piperazinyl.

In Embodiment (6.10), invention provides a compound of formula (I), or a pharmaceutically acceptable salt, solvate or tautomer thereof, according to any preceding Embodiment, wherein C is pyridazinyl, which is unsubstituted; or substituted on a ring carbon with halo, for example chloro.

In Embodiment (6.11), invention provides a compound of formula (I), or a pharmaceutically acceptable salt, solvate or tautomer thereof, according to any preceding Embodiment, wherein C is azetidinyl, which is preferably attached to X via a carbon atom, more preferably the carbon at the 3 position and R³ is selected from H or C(O)(C₁-C₄)alkyl, for example —C(O)—CH₃, C(O)O(C₁-C₄)alkyl, for example —C(O)O—CH₃.

In Embodiment (6.12), the invention provides a compound of formula (I), or a pharmaceutically acceptable salt, solvate or tautomer thereof, according to any preceding Embodiment, wherein C is azetidinyl which is attached to X, or directly to ring B if X is absent, via a carbon atom, more preferably the carbon at the 3 position and where R³ is selected from H.

In Embodiment (6.13), the invention provides a compound of formula (I), or a pharmaceutically acceptable salt, solvate or tautomer thereof, according to any preceding Embodiment, wherein C is piperidinyl, which is preferably attached to X, or directly to ring B if X is absent, via a carbon atom, more preferably the carbon at the 4 position, and which piperidinyl is unsubstituted, or which is substituted on a ring carbon with two substituents selected from halo, for example fluoro; or where R³ is selected from H, (C₁-C₄)alkyl, for example methyl, or C(O)O(C₁-C₄)alkyl, for example —C(O)O—C(CH₃)₂.

In Embodiment (6.14), the invention provides a compound of formula (I), or a pharmaceutically acceptable salt, solvate or tautomer thereof, according to any preceding Embodiment, wherein C is piperidinyl, which is attached to X, or directly to ring B if X is absent, via a carbon atom at the 4 position and which is unsubstituted.

In Embodiment (6.15), invention provides a compound of formula (I), or a pharmaceutically acceptable salt, solvate or tautomer thereof, according to any preceding Embodiment, wherein C is tetrahydropyranyl, which is preferably attached to X, or directly to ring B if X is absent, via a carbon atom, more preferably the carbon at the 4 position, and which tetrahydropyranyl is unsubstituted.

In Embodiment (6.16), the invention provides a compound of formula (I), or a pharmaceutically acceptable salt, solvate or tautomer thereof, according to any preceding Embodiment, wherein C is pyrimidinyl, which is substituted on a ring carbon atom with one substituent selected from N(R²)₂, for example amino; or D where D is Het¹, for example N-azetidinyl, N-morpholinyl or N-piperazinyl, most preferably piperazinyl wherein R₃ is hydrogen.

In Embodiment (7) the invention provides a compound of formula (I), or a pharmaceutically acceptable salt, solvate or tautomer thereof, according to any preceding Embodiment, wherein X is absent, —O—, methylene, or —O-methylene.

In Embodiment (7.1), the invention provides a compound of formula (I), or a pharmaceutically acceptable salt, solvate or tautomer thereof, according to any preceding Embodiment, wherein X is absent.

In Embodiment (7.2), the invention provides a compound of formula (I), or a pharmaceutically acceptable salt, solvate or tautomer thereof, according to any preceding Embodiment, wherein when B is phenyl, X is absent, and C is phenyl; (C₃-C₈)cycloalkyl, for example cyclopropyl; Het¹, for example, azetidinyl, piperidinyl, oxetanyl, tetrahydropyranyl, pyrrolidonyl, imidazolidonyl; phenyl; or Het², for example furanyl, pyrazolyl, imidazolyl, 1,2,3-triazolyl, 1,2,4-triazolyl, 1,3,4-triazolyl, tetrazolyl, thiazolyl, isothiazolyl, oxazolyl, isoxazolyl, 1-oxa-2,4-diazolyl, pyridinyl, pyrazinyl, pyridazinyl, or pyrimidinyl.

In Embodiment (7.3), the invention provides a compound of formula (I), or a pharmaceutically acceptable salt, solvate or tautomer thereof, according to any preceding Embodiment, wherein when B is phenyl, X is absent, and C is azetidinyl, piperidinyl, tetrahydropyranyl pyrazolyl, pyridinyl, pyridazinyl or pyrimidinyl.

In Embodiment (7.4), the invention provides a compound of formula (I), or a pharmaceutically acceptable salt, solvate or tautomer thereof, according to any preceding Embodiment, wherein when B is phenyl, X is O, and C is phenyl; or Het², for example, pyridinyl.

In Embodiment (7.5), the invention provides a compound of formula (I), or a pharmaceutically acceptable salt, solvate or tautomer thereof, according to any preceding Embodiment, wherein when B is phenyl, X is CH₂, and C is (C₃-C₈)cycloalkyl, for example cyclopropyl; Het¹, for example, azetidinyl, morpholinyl, pyrrolidonyl, piperidinyl; or Het², for example, pyrazolyl, 1,3,4-triazolyl, imidazolyl, isoxazolyl, or pyridinyl.

In Embodiment (7.6), the invention provides a compound of formula (I), or a pharmaceutically acceptable salt, solvate or tautomer thereof, according to any preceding Embodiment, wherein when B is phenyl, X is OCH₂, and C phenyl.

In Embodiment (7.7), the invention provides a compound of formula (I), or a pharmaceutically acceptable salt, solvate or tautomer thereof, according to any preceding Embodiment, wherein when B is pyrazolyl, X is absent, and C phenyl; (C₃-C₈)cycloalkyl, for example cyclohexyl; or Het², for example, pyridinyl.

In Embodiment (7.8), the invention provides a compound of formula (I), or a pharmaceutically acceptable salt, solvate or tautomer thereof, according to any preceding Embodiment, wherein when B is pyrazolyl, X is CH₂, and C is phenyl.

In Embodiment (7.9), the invention provides a compound of formula (I), or a pharmaceutically acceptable salt, solvate or tautomer thereof, according to any preceding Embodiment, wherein when B is thiazolyl, X is CH₂, and C is phenyl.

In Embodiment (7.10), the invention provides a compound of formula (I), or a pharmaceutically acceptable salt, solvate or tautomer thereof, according to any preceding Embodiment, wherein when B is pyridinyl, X is absent, and C is phenyl or Het², for example, pyrazolyl.

In Embodiment (7.11), the invention provides a compound of formula (I), or a pharmaceutically acceptable salt, solvate or tautomer thereof, according to any preceding Embodiment, wherein when B is pyridinyl, X is O, and C is phenyl.

In Embodiment (7.12), the invention provides a compound of formula (I), or a pharmaceutically acceptable salt, solvate or tautomer thereof, according to any preceding Embodiment, wherein when B is pyrimidnyl, X is absent, and C is phenyl.

In Embodiment (7.13), the invention provides a compound of formula (I), or a pharmaceutically acceptable salt, solvate or tautomer thereof, according to any preceding Embodiment, wherein when B is pyridazinyl, X is absent, and C is phenyl.

In Embodiment (7.14), the invention provides a compound of formula (I), or a pharmaceutically acceptable salt, solvate or tautomer thereof, according to any preceding Embodiment, wherein when B is pyrazinyl, X is absent, and C is phenyl.

In Embodiment (8), the invention provides a compound of the formula (Ia)

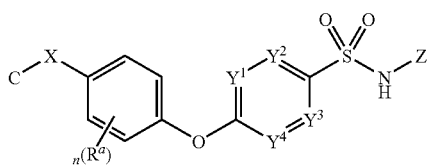

or a pharmaceutically acceptable salt, solvate or tautomer thereof,
wherein Z, $Y^1$, $Y^2$, $Y^3$, $Y^4$, X and C are as defined in any of the preceding Embodiments;
each $R^a$ is independently selected from the group consisting of halo, cyano, hydroxy, ($C_1$-$C_4$)alkyl, halo($C_1$-$C_4$)alkyl, ($C_1$-$C_4$)alkoxy, halo($C_1$-$C_4$)alkoxy, cyano($C_1$-$C_4$)alkyl, amino, ($C_1$-$C_4$)alkylamino, di($C_1$-$C_4$)alkylamino, amino ($C_1$-$C_4$)alkyl, ($C_1$-$C_4$)alkylamino($C_1$-C4)alkyl, di[($C_1$-$C_4$) alkyl]amino($C_1$-$C_4$)alkyl, trifluoromethylthio, hydroxy ($C_1$-$C_4$)alkyl, ($C_1$-$C_4$)alkoxy($C_1$-$C_4$)alkyl, —C(O)$R^2$, —C(O)O$R^2$, —OC(O)$R^2$, —C(O)—N($R^2$)$_2$, —CH$_2$—C (O)$R^2$, —CH$_2$—C(O)O$R^2$, —CH$_2$—OC(O)$R^2$, —CH$_2$—C(O)—N($R^2$)$_2$, S(O)$_2$$R^2$, S(O)$_2$N($R^2$)$_2$, ($C_3$-$C_8$)cycloalkyl, and ($C_3$-$C_8$)cycloalkyl($C_1$-$C_4$)alkyl; and
n is 0, 1 or 2.

It will be appreciated that compounds of the formula (Ia) are also embraced by formula (I) and that formula (Ia) is a preferred, sub group of the formula (I).

In Embodiment (8.1), the invention provides a compound of the formula (Ia) according to Embodiment 8, and C is a 5-membered aromatic heterocyclic group comprising either (a) 1 to 4 nitrogen atoms, (b) one oxygen or one sulphur atom or (c) 1 oxygen atom or 1 sulphur atom and 1 or 2 nitrogen atoms; optionally substituted as defined in Embodiment 1.

In Embodiment (8.2), the invention provides for a compound of formula (Ia) according to Embodiment 8, and each $R^a$ is independently selected from the group consisting of halo, cyano, ($C_1$-$C_4$)alkyl, halo($C_1$-$C_4$)alkyl, ($C_1$-$C_4$)alkoxy, halo($C_1$-$C_4$)alkoxy, amino, ($C_1$-$C_4$)alkylamino, di($C_1$-$C_4$) alkylamino, hydroxy($C_1$-$C_4$)alkyl, ($C_1$-$C_4$)alkoxy($C_1$-$C_4$) alkyl, —C(O)O$R^2$, —C(O)—N($R^2$)$_2$, —CH$_2$—C(O)—N ($R^2$)$_2$ and ($C_3$-$C_8$)cycloalkyl.

In Embodiment (9), the invention provides a compound of the formula (Ib)

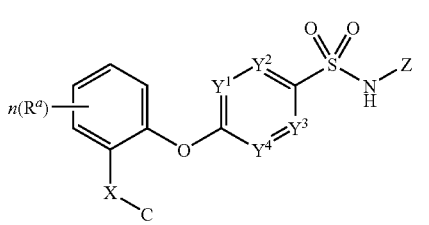

or a pharmaceutically acceptable salt, solvate or tautomer thereof,
wherein Z, $Y^1$, $Y^2$, $Y^3$, $Y^4$, X and C are as defined in any of the preceding Embodiments;
each $R^a$ is independently selected from the group consisting of halo, cyano, hydroxy, ($C_1$-$C_4$)alkyl, halo($C_1$-$C_4$)alkyl, ($C_1$-$C_4$)alkoxy, halo($C_1$-$C_4$)alkoxy, cyano($C_1$-$C_4$)alkyl, amino, ($C_1$-$C_4$)alkylamino, di($C_1$-$C_4$)alkylamino, amino($C_1$-$C_4$)alkyl, ($C_1$-$C_4$)alkylamino($C_1$-$C_4$)alkyl, di[($C_1$-$C_4$)alkyl] amino($C_1$-$C_4$)alkyl, trifluoromethylthio, hydroxy($C_1$-$C_4$) alkyl, ($C_1$-$C_4$)alkoxy($C_1$-$C_4$)alkyl, —C(O)$R^2$, —C(O)O$R^2$, —OC(O)$R^2$, —C(O)—N($R^2$)$_2$, —CH$_2$—C(O)$R^2$, —CH$_2$—C(O)O$R^2$, —CH$_2$—OC(O)$R^2$, —CH$_2$—C(O)—N($R^2$)$_2$, S(O)$_2$$R^2$, S(O)$_2$N($R^2$)$_2$, ($C_3$-$C_8$)cycloalkyl, and ($C_3$-$C_8$)cycloalkyl($C_1$-$C_4$)alkyl;
and
n is 0, 1 or 2.

It will be appreciated that compounds of the formula (Ib) are also embraced by formula (I) and that formula (Ib) is a preferred, sub group of the formula (I).

In Embodiment (9.1), the invention provides a compound of the formula (Ib) according to Embodiment 9, and C is a 5-membered aromatic heterocyclic group comprising either (a) 1 to 4 nitrogen atoms, (b) one oxygen or one sulphur atom or (c) 1 oxygen atom or 1 sulphur atom and 1 or 2 nitrogen atoms; optionally substituted as defined in Embodiment 1.

In Embodiment (9.2), the invention provides a compound of the formula (Ib) according to Embodiment 9, and each $R^a$ is independently selected from the group consisting of halo, cyano, ($C_1$-$C_4$)alkyl, halo($C_1$-$C_4$)alkyl, ($C_1$-$C_4$)alkoxy, halo ($C_1$-$C_4$)alkoxy, amino, ($C_1$-$C_4$)alkylamino, di($C_1$-$C_4$)alkylamino, hydroxy($C_1$-$C_4$)alkyl, ($C_1$-$C_4$)alkoxy($C_1$-$C_4$)alkyl, —C(O)O$R^2$, —C(O)—N($R^2$)$_2$, —CH$_2$—C(O)—N($R^2$)$_2$ and ($C_3$-$C_8$)cycloalkyl.

Specific preferred compounds according to the invention are those listed in the Examples section below and the pharmaceutically acceptable salts and solvates thereof.

DETAILED DESCRIPTION

As used herein the term compounds of the invention means, unless otherwise stated, compounds of formula (I), formula (Ia), formula (Ib), and compounds of Embodiment 1, Embodiment 2, Embodiment 2a, Embodiment 2.1, Embodiment 2.2, Embodiment 2.2a, Embodiment 2.2b, Embodiment 2.2c, Embodiment 2.3, Embodiment 2.4, Embodiment 2.5, Embodiment 2.5a, Embodiment 2.6, Embodiment 2.7, Embodiment 3, Embodiment 3.1, Embodiment 3.2, Embodiment 3.3, Embodiment 4, Embodiment 4.1, Embodiment 4.2, Embodiment 4.3, Embodiment 4.4, Embodiment 4.5, Embodiment 5, Embodiment 5a, Embodiment 5b, Embodiment 5c, Embodiment 5.1, Embodiment 5.1a, Embodiment 5.2, Embodiment 5.3, Embodiment 5.4, Embodiment 5.5, Embodiment 5.6, Embodiment 6, Embodiment 6a, Embodiment 6b, Embodiment 6c, Embodiment 6d, Embodiment 6.1, Embodiment 6.1a, Embodiment 6.2, Embodiment 6.2a, Embodiment 6.2b, Embodiment 6.3, Embodiment 6.3a, Embodiment 6.4, Embodiment 6.5, Embodiment 6.6, Embodiment 6.6a, Embodiment 6.7, Embodiment 6.8, Embodiment 6.9, Embodiment 6.10, Embodiment 6.11, Embodiment 6.12, Embodiment 6.13, Embodiment 6.14, Embodiment 6.15, Embodiment 6.16, Embodiment 7, Embodiment 7.1, Embodiment 7.2, Embodiment 7.3, Embodiment 7.4, Embodiment 7.5, Embodiment 7.6, Embodiment 7.7, Embodiment 7.8, Embodiment 7.9, Embodiment 7.10, Embodiment 7.11, Embodiment 7.12, Embodiment 7.13, Embodiment 7.14, Embodiment 8, Embodiment 8.1, Embodiment 8.2, Embodiment 9, Embodiment 9.1, and Embodiment 9.2. In each case, where the embodiment covers the compound according to the formula below:

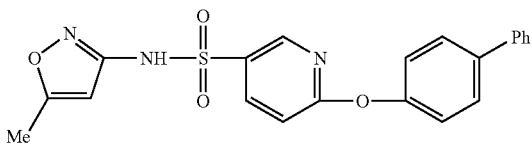

it is excluded.

Some compounds of the formula (I), (Ia) or (Ib), according to any one of the preceding Embodiments, may exist in several different tautomeric forms. Tautomerism, or tautomeric isomerism, occurs where structural isomers are interconvertible via a low energy barrier. It can take the form of proton tautomerism, so called valence tautomerism in compounds which contain an aromatic moiety. In some compounds different tautomeric isomers may exist with respect to the position of certain protecting groups or prodrug moieties. Illustrative examples of such tautomeric forms are provided below but one of ordinary skill in the art would understand that many different tautomeric forms of such compounds may be possible and that the examples provided below are not exhaustive. Therefore, all references to compound of formula (I), (Ia) or (Ib), according to any one of the preceding Embodiments, should be taken to include tautomers thereof, whether illustrated or not. Furthermore, the illustrative examples provided below indicate situations where certain atoms are substituted with hydrogen. However, one of ordinary skill in the art would also understand that such tautomeric forms may also exist when such atoms are substituted by certain protecting groups or with prodrug substitutents. As such the disclosure herein is intended to also describe such alternative tautomeric forms. Furthermore, one of ordinary skill would understand that certain intermediates used in the preparation of compounds capable of tautomerising are themselves capable of existing in different tautomeric forms.

One such illustrative example is when the compound of formula (I), (Ia) or (Ib), according to any one of the preceding Embodiments, is a compound of the formula (Ic):

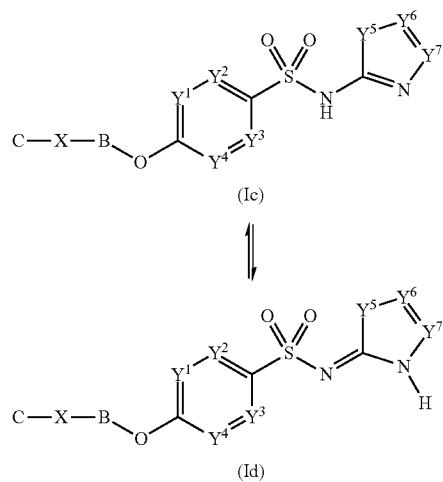

or a pharmaceutically acceptable salt or solvate thereof, wherein:

$Y^1, Y^2, Y^3, Y^4$, B, X and C are as defined in any one of the Embodiments above;

$Y^5$ is $NR^4$, oxygen or sulphur atom;

$Y^6$ and $Y^7$ are each independently selected from $CR^4$ or nitrogen atoms;

provided that $Y^5$, $Y^6$ and $Y^7$ cannot all be nitrogen; and each $R^4$ is independently selected from the group consisting of hydrogen, halo, cyano, $(C_1-C_4)$alkyl, halo$(C_1-C_4)$alkyl, $(C_1-C_4)$alkoxy, halo$(C_1-C_4)$alkoxy, $(C_3-C_8)$cycloalkyl, amino, $(C_1-C_4)$alkylamino and di$(C_1-C_4)$alkylamino;

tautomerism may occur to provide for example, a compound of the formula (Id).

Illustratively, when compounds of formula (Ic) comprise a nitrogen atom at $Y^6$ a third tautomer, may also exist which is represented below by formula (Ie) below:

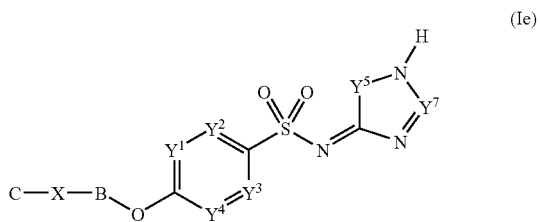

Furthermore, when the compound of formula (I), (Ia) or (Ib), according to any one of the preceding Embodiments, is a compound of the formula (If), as shown below, or a pharmaceutically acceptable salt or solvate thereof, wherein:

$Y^1, Y^2, Y^3, Y^4$, B, X and C are as defined in any one of the Embodiments above;

$Y^8, Y^9, Y^{10}$ and $Y^{11}$ are selected from $CR^4$, or a nitrogen atom in accordance with the definition of Z in Embodiment 1 above; and each $R^4$ is independently selected from the group consisting of hydrogen, halo, cyano, $(C_1-C_4)$alkyl, halo$(C_1-C_4)$alkyl, $(C_1-C_4)$alkoxy, halo$(C_1-C_4)$alkoxy, $(C_3-C_8)$cycloalkyl, amino, $(C_1-C_4)$alkylamino and di$(C_1-C_4)$alkylamino; tautomerism may occur to provide for example, a compound of the formula (Ig). Additionally, two other tautomers are possible represented by formulae (Ih) and (Ii). If $Y^{10}$ is a nitrogen atom then a compound of the formula (Ih) is possible and if $Y^8$ is a nitrogen atom then a compound of formula (Ii) is possible.

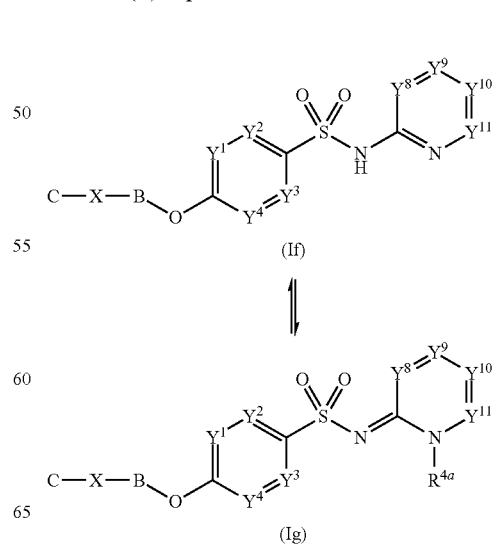

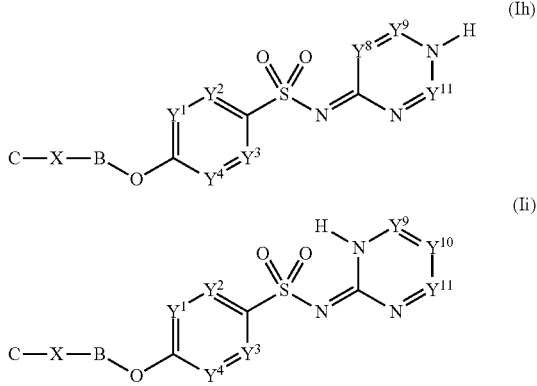

All references to compounds of the invention, or to compounds of formulae (I), (Ia), and (Ib), should therefore be taken to include, where appropriate, the tautomeric isomers of the compounds, as exemplified by formulae (Ic), (Id), (Ie), (If), (Ig), (Ih), and (Ii) above.

Pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isothionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised.

For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, polymorphs, prodrugs (including tautomeric forms of such prodrugs), and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

One skilled in the art would recognise that many different pro-drug forms of compounds of the present invention are possible. However, some illustrative examples of prodrugs in accordance with the invention include:

(i) where the compound of formula (I) contains a carboxylic acid functionality (—COOH), an ester thereof, for example, replacement of the hydrogen with $(C_1-C_8)$alkyl;

(ii) where the compound of formula (I) contains an alcohol functionality (—OH), an ether thereof, for example, replacement of the hydrogen with $(C_1-C_6)$alkanoyloxymethyl; and (iii) where the compound of formula (I) contains a primary or secondary amino functionality (—$NH_2$ or —NHR where R≠H), an amide thereof, for example, replacement of one or both hydrogens with $(C_1-C_{10})$alkanoyl.

A particularly useful prodrug of compounds of formula (I) which have a general formula (Ic), is formed by replacement of the hydrogen of the —NH-group of the sulphonamide moiety or the hydrogen of the —NH-group of the 1,3-thiazolyl ring of such compounds is replaced by a prodrug moiety (Prodrug) which is either —$CH_2OP(=O)(OR')_2$ or —$CH_2OC(=O)R'$ wherein R' is selected from the group consisting of hydrogen or $(C_1-C_6)$alkyl, for example —$C(CH_3)_3$. Such compounds are prepared by reaction of the —NH-group of the sulphonamide moiety or the —NH-group of the 1,3-thiazolyl ring of the compounds of formula (Ic) with either an alkyl linked phosphate, such as an alkyl linked phosphoric acid or an alkyl linked phosphate ester, or with an alkyl linked carboxylic acid group, such as an alkyl linked carboxylic acid or an alkyl linked carboxylic ester. Such prodrug compounds can generally be schematically represented as shown below by formula (Ic') or its tautomeric form (Id'):

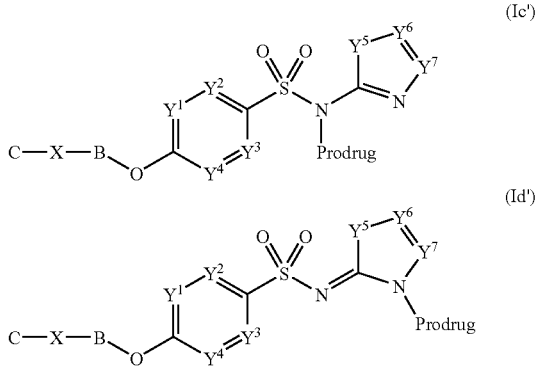

wherein C, X, B, $Y^1$, $Y^2$, $Y^3$, $Y^4$, $Y^5$, $Y^6$, $Y^7$ are as defined above for compounds of formula (Ic) and Prodrug is a pro-drug moiety as defined above. Phosphate prodrugs have been generally described in, for example, Rautio, J.; Kumpulainen, H.; Heimbach, T.; Oliyai, R.; Oh, D.; Järvinen, T.; Savolainen, J. *Nat. Rev. Drug Discovery* 2008, 7, 255. Carboxylic acid and related ester prodrugs have been generally described in Calheiros, T.; Iley, J.; Lopes, F.; Moreira, R. *Bioorg. Med. Chem. Lett.* 1995, 5, 937 and in Lopes, F.; Moreira, R.; Iley, J. *Bioorg. Med. Chem.* 2000, 8, 707.

When forming such prodrugs it is preferred that the hydrogen of the —NH-group of the sulphonamide moiety or the hydrogen of the —NH-group of the 1,3-thiazolyl ring of such compounds is replaced by —CH$_2$OP(=O)(OR')$_2$, in particular wherein R' is hydrogen to give —CH$_2$OP(=O)(OH)$_2$, or where R' is —C(CH$_3$)$_3$ to give —CH$_2$OP(=O)(OC(CH$_3$)$_3$)$_2$.

As such, in yet another embodiment, Embodiment 10, the invention provides for a prodrug of compounds of formula (Ic') wherein the hydrogen of the —NH-group of the sulphonamide moiety or the hydrogen of the —NH-group of the 1,3-thiazolyl ring of such compounds is replaced by either —CH$_2$OP(=O)(OR')$_2$ or —CH$_2$OC(=O)R' wherein R' is selected from the group consisting of hydrogen or (C$_1$-C$_6$) alkyl, for example —C(CH$_3$)$_3$, or a pharmaceutically acceptable salt, solvate or tautomer thereof.

Further examples of replacement groups in accordance with the foregoing examples and examples of other prodrug types may be found in the aforementioned references.

As used herein, unless otherwise specified, references to formula (I) also encompass references to prodrugs, and salts, solvates or tautomers thereof, such as those of Embodiment (10).

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC)

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, and $^{125}$I are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

The compounds of formula (I), being Nav1.7 channel modulators, are potentially useful in the treatment of a range of disorders. The treatment of pain, particularly neuropathic, nociceptive and inflammatory pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-

395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders;
erythermalgia; and
orofacial pain, including dental pain, otic pain, burning mouth syndrome and temporomandibular myofascial pain.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parental Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing the compound of formula (I). The overall daily dose may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention depends, of course, on the mode of administration. For example, oral administration may require a higher total daily dose, than an intravenous dose. The total daily dose may be administered in single or divided doses.

For the avoidance of doubt, references herein to "treatment" include references to curative, palliative and prophylactic treatment.

Combinations

A Nav1.7 channel modulator may be usefully combined with another pharmacologically active compound, or with two or more other pharmacologically active compounds, particularly in the treatment of pain. For example, a Nav1.7 channel modulator, particularly a compound of formula (I), or a pharmaceutically acceptable salt, solvate or tautomer thereof, as defined above, may be administered simultaneously, sequentially or separately in combination with one or more agents selected from:

an alternative Nav1.7 channel modulator, for example one or more alternative compounds of the present invention, or alternatively those compounds disclosed in WO 2009/012242;

an alternative sodium channel modulator, such as a Nav1.3 modulator, for example those disclosed in WO 2008/118758; or a Nav1.8 modulator, for example those disclosed in WO 2008/135826, more particularly N-[6-Amino-5-(2-chloro-5-methoxyphenyl)pyridin-2-yl]-1-methyl-1H-pyrazole-5-carboxamide;

a compound which increases the levels of endocannabinoid such as compounds with fatty acid amid hydrolase inhibitory (FAAH) activity, in particular those disclosed in WO 2008/047229, more particularly N-pyridazin-3-yl-4-(3-{[5-(trifluoromethyl)pyridine-2-yl]oxy}benzylidene)piperidine-1-carboxamide;

a compound which is an inhibitor of mPGEs-1;

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and, ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a $5-HT_{1B/1D}$ agonist such as eletriptan, sumatriptan, naratriptan, zolmitriptan or rizatriptan;

a $5-HT_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)butyl]thio]-5-chloro-3-pyridinecarbonitrile; 2-[[(1 R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine;

a 5-HT3 antagonist, such as ondansetron;

and the pharmaceutically acceptable salts and solvates thereof.

Such combinations offer significant advantages, including synergistic activity, in therapy.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

It will be appreciated that the invention exists in a number of different embodiments including:

(i) a compound of formula (I) or a pharmaceutically acceptable salt, solvate or tautomer thereof;

(ii) a process for the preparation of a compound of formula (I) or a pharmaceutically acceptable salt, solvate or tautomer thereof;

(iii) a pharmaceutical composition including a compound of formula (I) or a pharmaceutically acceptable salt, solvate or tautomer thereof, together with a pharmaceutically acceptable excipient;

(iv) a pharmaceutical composition including a compound of formula (I) or a pharmaceutically acceptable salt, solvate or tautomer thereof, together with a pharmaceutically acceptable excipient, for use in the treatment of a disease or condition for which a Nav1.7 channel modulator is indicated, particularly for the treatment of pain;

(v) a compound of formula (I) or a pharmaceutically acceptable salt, solvate or composition thereof, for use as a medicament;

(vi) the use of a compound of formula (I) or of a pharmaceutically acceptable salt, solvate or composition thereof, for the manufacture of a medicament to treat a disease or condition for which a Nav1.7 channel modulator is indicated, particularly for the treatment of pain;

(vii) a compound of formula (I) or of a pharmaceutically acceptable salt, solvate or composition thereof, for use in the treatment of a disease or condition for which a Nav1.7 channel modulator is indicated, particularly for use in the treatment of pain;

(viii) a method of treating a disease or condition for which a Nav1.7 channel modulator is indicated in a mammal, including a human being, including administering to said mammal an effective amount of a compound of formula (I) or a pharmaceutically acceptable salt, solvate or composition thereof.

All of the compounds of the formula (I) can be prepared by the procedures described in the general methods presented below or by the specific methods described in the Examples section and the Preparations section, or by routine modifications thereof which can be made by employing the common general knowledge of one skilled in the art (see, for example, Comprehensive Organic Chemistry, Ed Barton and Ollis, Elsevier; Comprehensive Organic Transformations: A guide to Functional Group preparations, Larock, John Wiley & Sons). The present invention also encompasses any one or more of these processes for preparing the compounds of formula (I), in addition to any novel intermediates used therein.

In the following general methods, Z, $Y^1$, $Y^2$, $Y^3$, $Y^4$, B, X, C and D are as previously defined for a compound of the formula (I) unless otherwise stated.

Compounds of the present invention can be prepared using readily available starting materials or known intermediates. The synthetic schemes set forth below provide exemplary synthetic pathways for the preparation of compounds of the invention.

When preparing derivatives of formula (I) in accordance with the invention, it is open to a person skilled in the art to routinely select the best order of steps with which to synthesise the intermediates, and to choose the form of the intermediate compounds which provides the best combination of features for this purpose. Such features include the melting point, solubility, processability and yield of the intermediate form and the resulting ease with which the product may be purified on isolation.

The skilled person may undertake the synthetic steps described below in any suitable order in order to arrive at the compounds of formula (I).

According to a first process, compounds of formula (I) may be prepared from compounds of formula (VI) by the process illustrated in Scheme 1.

cyclo(2.2.2)octane, triethylamine, NaOH or pyridine. Preferred conditions comprise NaOH in 1,4-dioxane or pyridine in dichloromethane at room temperature.

Compounds of formula (II) can be prepared from compounds of formula (IV) according to reaction step (iv) by nucleophilic aromatic substitution reaction with a phenol (III)

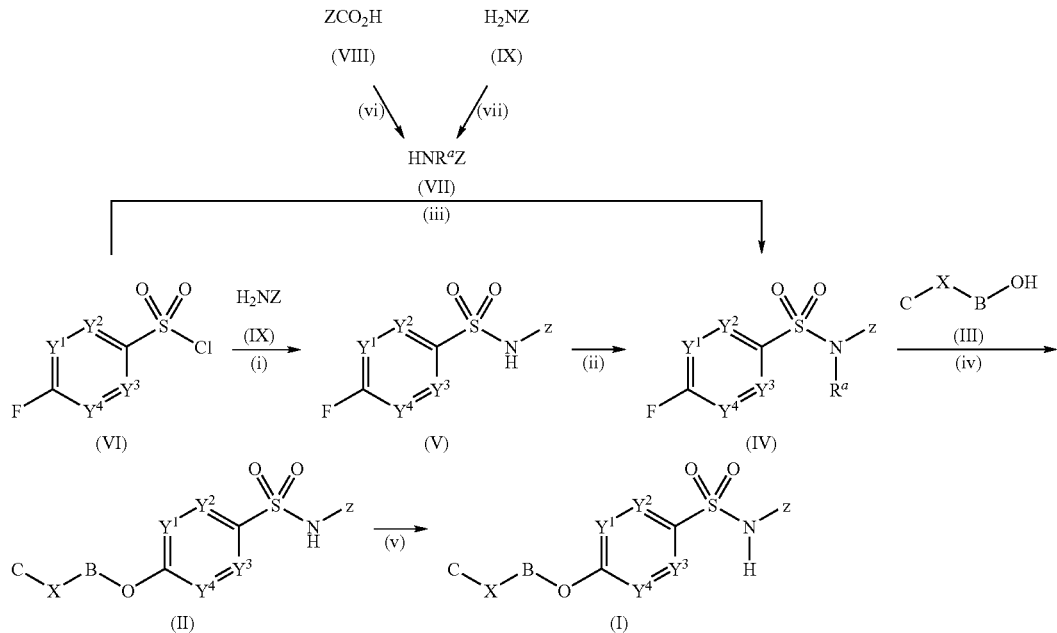

Wherein $R^a$ is a suitable protecting group, preferably dimethoxybenzyl, tert-butyloxycarbonyl, tert-butyl, methoxymethyl or ethoxyethyl.

Compounds of formula (VI) are either commercially available or can be prepared according to Scheme 8.

Compounds of formula (III) are either commercially available or can be prepared according to Scheme 11.

Compounds of formula (VIII) and (IX) are commercially available.

Compounds of formula (IV) can be prepared from compounds of formula (VI) and (VII) according to reaction step (iii) by displacement of a sulfonyl chloride with $HNR^aZ$ under basic reaction conditions. Typical conditions comprise lithium hexamethyldisilazane in THF from −78° C. to ambient temperature.

Alternatively, compounds of formula (IV) can be prepared from compounds of formula (V) according to reaction step (ii) by introduction of a suitable protecting group such as tert-butyl or methoxymethyl or ethoxyethyl dimethoxybenzyl under basic reaction conditions or Mitsunobu conditions. Typical conditions comprise di-tert-butyldicarbonate and triethylamine in THF or chloromethyl methyl ether and diisopropylethylamine in methylene chloride or chloromethyl ethyl ether and diisopropylethylamine in methylene chloride or dimethoxybenzylalcohol, diisopropylazodicarboxylate and triphenylphosphine in THF.

Compounds of formula (V) can be prepared from compounds of formula (VI) according to reaction step (i) by displacement of a sulfonyl chloride under basic reaction conditions, for example lithium hexamethyldisilazane, diazabiunder basic reaction conditions, for example potassium carbonate in DMF or DMSO, sodium hydride in NMP or DMF, sodium hydroxide or potassium hydroxide in 1,4-dioxane and water or DMSO or potassium tert-butoxide in THF at from room temperature to 150° C. Preferred conditions comprise 2 equivalents of potassium carbonate in DMF at 90° C.

Compounds of formula (I) can be prepared from compounds of formula (II) according to reaction step (v) by suitable deprotection methods under acidic conditions for example HCl, formic acid or trifluoroacetic acid. Preferred methods comprise trifluoroacetic acid in dichloromethane or neat trifluoroacetic acid at a temperature of room temperature to 55° C. Alternatively, if the protecting group is dimethoxybenzyl, compounds of formula (I) can be prepared from compounds of formula (II) under basic conditions such as sodium bicarbonate in ethanol/water at 80° C. or heating in an appropriate solvent such as ethanol or toluene at temperatures exceeding 70° C.

Compounds of formula (VII) can be prepared from compounds of formula (VIII) according to reaction step (vi) by Curtius rearrangement through generation of an acyl azide using diphenylphosphoryl azide. Preferred conditions comprise diphenylphosphoryl azide and triethylamine with tert-butanol in toluene at 90° C.

Alternatively compounds of formula (VII) may be prepared from compounds of formula (IX) according to reaction step (vii) through the processes outlined for reaction step (ii) or by reductive amination with an aldehyde. Typical reaction conditions comprise dimethoxybenzaldehyde in toluene at 110° C. followed by reduction with sodium borohydride.

According to a second process, compounds of formula (I) may also be prepared from compounds of formula (V) by the process illustrated in Scheme 2.

Scheme 2

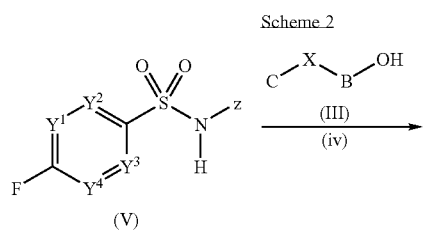

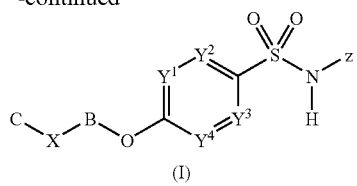

Compounds of formula (I) can be prepared from compounds of formula (V) by nucleophilic aromatic substitution reaction according to process step (iv) as described above for Scheme 1.

According to a third process, compounds of formula (I) may also be prepared from compounds of formula (XIII) by the process illustrated in Scheme 3.

Scheme 3

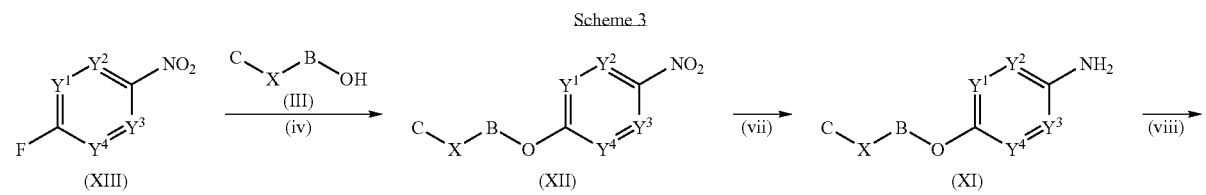

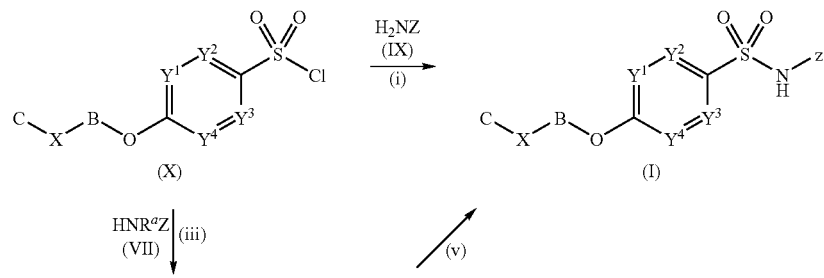

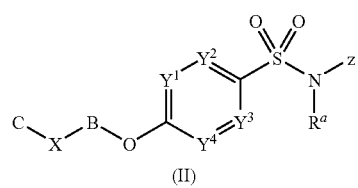

Compounds of formula (XIII) are commercially available.

Compounds of formula (XII) can be prepared from compounds of formula (XIII) by nucleophilic aromatic substitution reaction according to process step (iv) as described above for Scheme 1. Preferred conditions comprise NaH in NMP at 0° C.

Compounds of formula (XI) can be prepared from compounds of formula (XII) by a reduction reaction according to process step (vii) for example hydrogenation, a suitable metal reduction or use of sodium dithionite. Preferred conditions comprise calcium chloride or ammonium chloride in the presence of iron in ethanol/water.

Compounds of formula (X) can be prepared from compounds of formula (XI) according to process step (viii) by a Sandmeyer reaction. Typical conditions comprise sodium nitrite in HCl, acetic acid and water, followed by sulfur dioxide in acetic acid with copper chloride at 0° C.

Compounds of formula (I) can be prepared from compounds of formula (X) by reaction according to process step (i) by displacement of a sulfonyl chloride under basic reaction conditions with compounds of formula (IX) as described above for Scheme 1.

Alternatively compounds of formula (I) can be prepared from compounds of formula (X) by reaction according to process steps (iii) and (v) by displacement of a sulfonyl chloride under basic reaction conditions with compounds of formula (VII) followed by a suitable deprotection step as described above for Scheme 1.

According to a fourth process, compounds of formula (I) may also be prepared from compounds of formula (X) by the process illustrated in Scheme 4.

Scheme 4

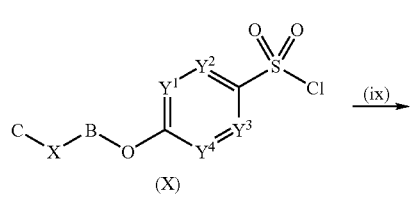

(X)

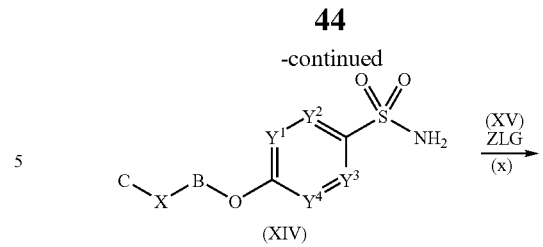

(XIV)

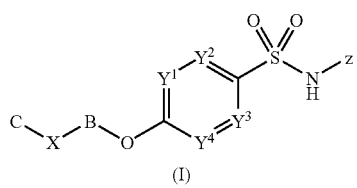

(I)

Wherein LG is a suitable leaving group such as Cl, Br, I, F.

Compounds of formula (XV) are commercially available.

Compounds of formula (XIV) can be prepared from compounds of formula (X) according to process step (ix) by displacement of a sulfonyl chloride with ammonia or a protected ammonium species such as dimethoxybenzylamine (that can be deprotected at a later stage under suitable conditions to those skilled in the art). Typical conditions comprise 7N $NH_3$ in methanol and THF at room temperature.

Compounds of formula (I) can be prepared from compounds of formula (XIV) according to reaction step (x) by displacement of a suitable leaving group on a heterocycle as described by Z under basic reaction conditions. Typical conditions comprise potassium carbonate in DMF.

According to a fifth process, compounds of formula (I) may also be prepared from compounds of formula (X) by the process illustrated in Scheme 5.

Scheme 5

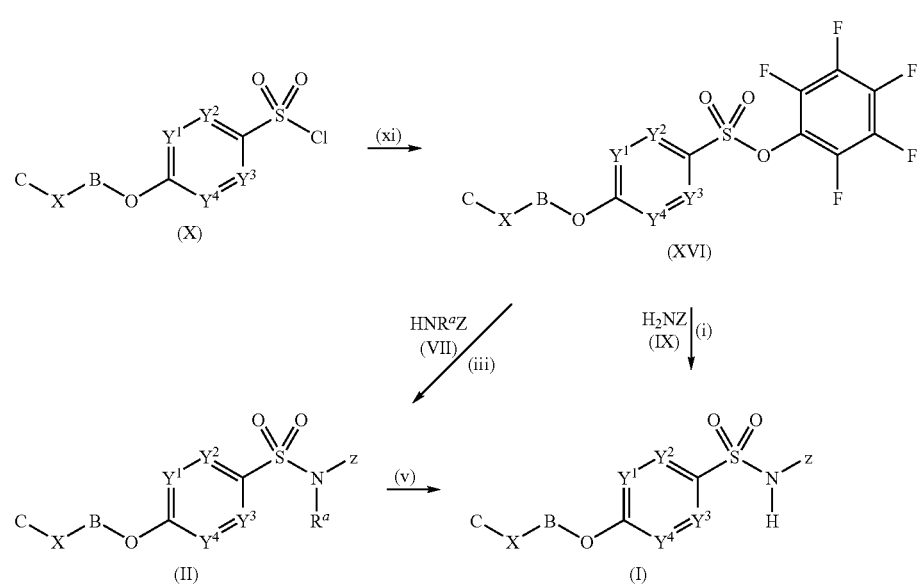

Compounds of formula (XVI) can be prepared from compounds of formula (X) according to process step (xi) by displacement of a sulfonyl chloride with pentafluorophenol. Typical conditions comprise pentafluorophenol, or optionally a trichlorophenol intermediate, and triethylamine in dichloromethane at room temperature.

Compounds of formula (I) can be prepared from compounds of formula (XVI) by reaction according to process step (i) by displacement of a pentafluorophenyl ester under basic reaction conditions with compounds of formula (IX) as described above for Scheme 1.

Alternatively compound of formula (I) can be prepared from compounds of formula (XVI) by reaction according to process steps (iii) and (v) by displacement of a pentafluorophenyl ester under basic reaction conditions with compounds of formula (VII) followed by a suitable deprotection step as described above for Scheme 1.

According to a sixth process, compounds of formula (I) may also be prepared from compounds of formula (IV) by the process illustrated in Scheme 6.

DMF at 0° C., followed by nucleophilic aromatic substitution reaction with compounds of formula (XX) as described in Scheme 1.

Compounds of formula (I) may be prepared from compounds of formula (XVII) according to process step (xii) and (v) by a cross-coupling reaction, with compounds of formula (XXI), in the presence of a suitable catalyst system, (e.g. palladium or nickel), and base. Typically 'Suzuki' conditions are used, comprising 1.2-3 equivalents of boronic acid, base and 0.01-0.25 equivalents of a palladium catalyst with phosphine based ligands in an organic solvent at a temperature of from 50° C. to 100° C. Preferred conditions comprise boronic acid, $Na_2CO_3$ and $Pd(PPh_3)_4$ in DMF/water or DME/water at 80° C. followed by a suitable deprotection step as described in Scheme 1.

According to a seventh process, compounds of formula (I) may also be prepared from compounds of formula (V) by the process illustrated in Scheme 7.

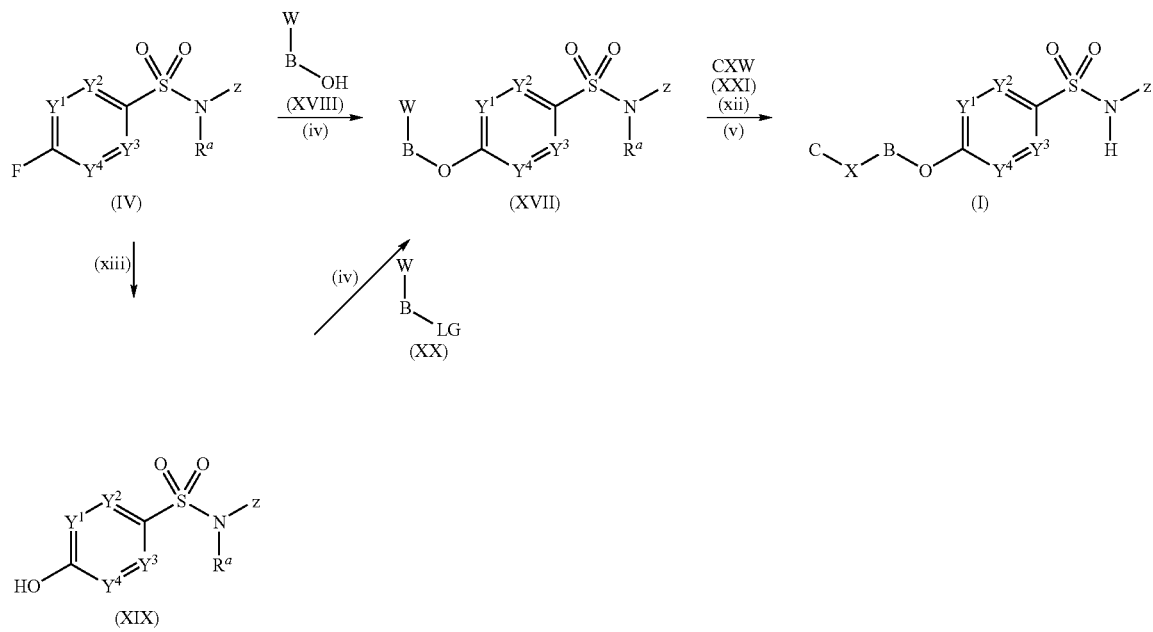

Scheme 6

Wherein

LG is a suitable leaving group as described in Scheme 4.

W can be an optionally substituted/ligated metal or boron group suitable for cross-coupling reactions such as a trialkylstannane, dihydroxyborane, dialkoxyborane or halozinc or a suitable group for cross-coupling reactions, typically Br or I.

Compounds of formula (XVIII), (XXI) and (XX) are commercially available or can be prepared according to Scheme 11.

Compounds of formula (XVII) can be prepared from compounds of formula (IV) according to process step (iv) by nucleophilic aromatic substitution reaction with compounds of formula (XVIII) as described in Scheme 1.

Alternatively compounds of formula (XVII) can be prepared from compounds of formula (IV) according to process steps (xiii) and (iv) by nucleophilic aromatic substitution with TMS-ethanol, typical conditions comprise sodium hydride in

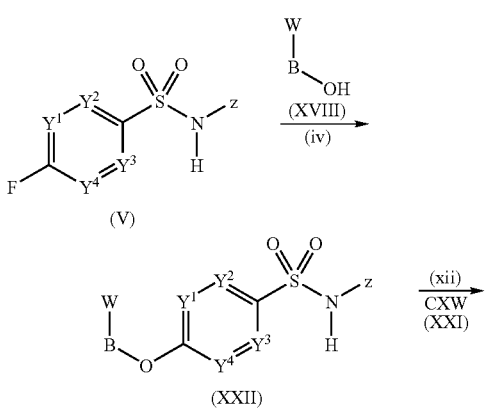

Scheme 7

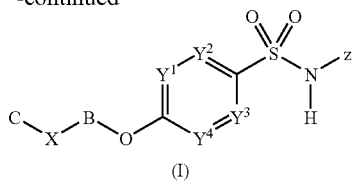

(I)

Wherein

W can be an optionally substituted/ligated metal or boron group or a suitable group for cross-coupling reactions, typically Br or I as described for Scheme 6.

Compounds of formula (XXII) can be prepared from compounds of formula (V) according to process step (iv) by nucleophilic aromatic displacement reaction as described in Scheme 1.

Compounds of formula (I) can be prepared from compounds of formula (XXII) according to process step (xii) by a cross-coupling reaction, with compounds of formula (XXI), in the presence of a suitable catalyst system as described in Scheme 6.

According to an eighth process, compounds of formula (VI) may also be prepared from compounds of formula (XXIII) by the process illustrated in Scheme 8.

Scheme 8

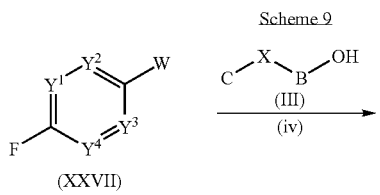

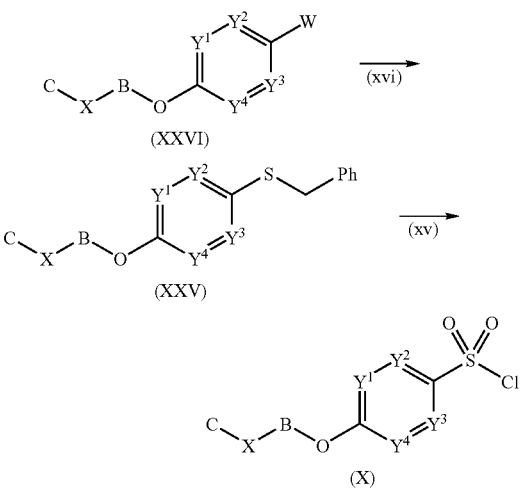

Compounds of formula (XXIII) are commercially available.

Compounds of formula (XXIV) can be prepared from compounds of formula (XXIII) according to process step (xiv) by nucleophilic aromatic substitution reaction with benzylmercaptan. Typical conditions comprise benzylmercaptan and cesium carbonate in DMSO at room temperature.

Compounds of formula (VI) can be prepared from compounds of formula (XXIV) according to reaction step (xv), an oxidation process in the presence of bleach. Preferred conditions comprise bleach and 4M HCl (aqueous) in dichloromethane at 0° C.

According to a ninth process, compounds of formula (X) may also be prepared from compounds of formula (XXVII) by the process illustrated in Scheme 9.

Wherein

W can be an optionally substituted/ligated metal or boron group or a suitable group for cross-coupling reactions, typically Br or I as described for Scheme 6.

Compounds of formula (XXVII) are commercially available.

Compounds of formula (XXVI) can be prepared from compounds of formula (XXVII) by nucleophilic aromatic substitution reaction according to process step (iv) as described above for Scheme 1.

Compounds of formula (XXV) can be prepared from compounds of formula (XXVI) by a palladium catalysed cross-coupling reaction with benzylmercaptan according to process step (xvi). Typical conditions comprise benzylmercaptan, palladium dibenzylideneacetone and xantphos in 1,4-dioxane and diisopropyl ether at reflux.

Compounds of formula (X) can be prepared from compounds of formula (XXV) by an oxidation reaction according to process step (xv) as described for Scheme 8.

According to a tenth process, compounds of formula (I) may also be prepared from compounds of formula (X) by the process illustrated in Scheme 10.

Scheme 10

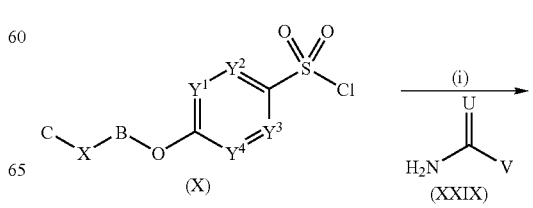

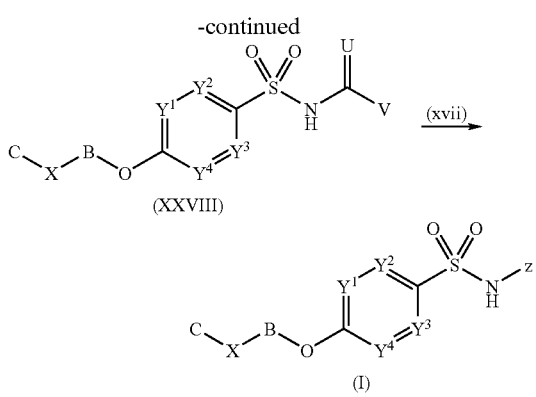

Wherein

U and V are any suitable ring precursors such as N, NH, S, O etc.

Compounds of formula (XXIX) are commercially available.

Compounds of formula (XXVIII) can be prepared according to reaction step (i) by displacement of a sulfonyl chloride with compounds of formula (XXIX) under basic reaction conditions as described in Scheme 1. Typical conditions comprise sodium hydroxide in acetone and water at room temperature.

Compounds of formula (I) can be prepared from compounds of formula (XXVIII), a cyclisation reaction according to process step (xvii). Typical conditions comprise heating at 120° C. in the presence of a suitable electrophile such as DMFDMA, trimethylorthoformate or glycoaldehyde.

According to an eleventh process, compounds of formula (III) may also be prepared from compounds of formula (XXX) by the process illustrated in Scheme 11.

Scheme 11

Compounds of formula (XXX) are commercially available or can be synthesized from methods known to one skilled in the art.

Compounds of formula (III) may be prepared from compounds of formula (XXX) by the process illustrated in Scheme 11. Where C is an aromatic heterocyclic group, compounds of formula (III) can be formed from compounds of formula (XXX) with R1 being a group such as a carboxylic acid, ester, aldehyde, primary carboxamide, amine, hydrazine, oxime, nitrile, hydroxylamine, acetyl, furan, dialkylaminoprop-2-ene-1-one, semicarbazone, diimine, alkyne or acid chloride using methods decribed in the literature. Such literature is described and cited in text books such as: *Heterocyclic Chemistry*, J. A. Joule and K. Mills (Blackwell Science); *Handbook of Heterocyclic Chemistry*, A. R. Katritzky and A. F. Pozharskii (Pergamon); *The Chemistry of Heterocycles: Structure, Reactions, Syntheses and Applications*, T. Eicher and S. Hauptmann (Wiley-VCH); *Heterocyclic Chemistry*, T. L. Gilchrist (Addison Wesley Longman).

Alternatively R1 can be an optionally substituted metal or a boron group suitable for cross-coupling reactions such as a trialkylstannane, dihydroxyborane, dialkoxyborane or halozinc or a suitable group for cross-coupling reactions, typically Br, I or Cl. Typical 'Suzuki' conditions comprise of 1.2-3 equivalents of boronic acid, base and 0.01-0.25 equivalents of a palladium catalyst with phosphine based ligands in an organic solvent at a temperature of from 50° C. to 100° C. Typical 'Stifle' conditions are 1-1.5 eq stannane, 2-3 eq caesium fluoride, 0.01-0.25 eq of a palladium catalyst and 0.1-0.25 eq copper (I) iodide.

Scheme 12

According to a twelfth process, compounds of formula (II) may also be prepared from compounds of formula (IV) by the process illustrated in Scheme 12.

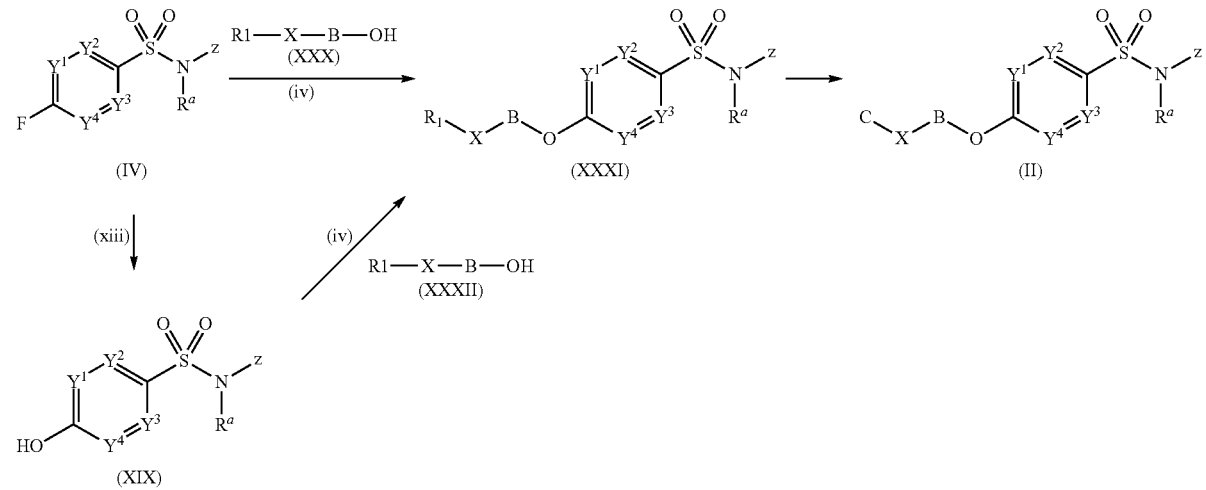

Wherein

LG is a suitable leaving group as described in Scheme 4.

R¹ is described in Scheme 11

Compounds of formula (XXXI) can be prepared from compounds of formula (IV) according to process step (iv) by nucleophilic aromatic substitution reaction with compounds of formula (XXX) as described in Scheme 1.

Alternatively compounds of formula (XXXI) can be prepared from compounds of formula (IV) according to process steps (xiii) and (iv) by nucleophilic aromatic substitution with TMS-ethanol, typical conditions comprise sodium hydride in DMF at 0° C., followed by nucleophilic aromatic substitution reaction with compounds of formula (XXXII) as described in Scheme 1.

Compounds of formula (II) may be prepared from compounds of formula (XXXI) according to standard processes described in Scheme 11.

According to a thirteenth process, compounds of formula (I) may also be prepared from compounds of formula (V) by the process illustrated in Scheme 13.

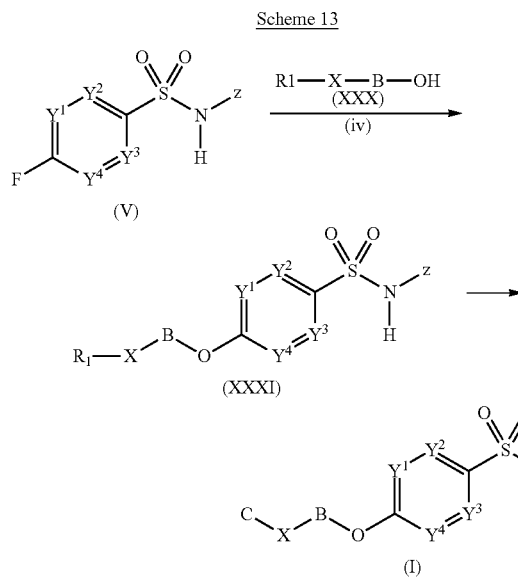

Scheme 13

Compounds of formula (XXXI) can be prepared from compounds of formula (V) according to process step (iv) by nucleophilic aromatic displacement reaction as described in Scheme 1.

Compounds of formula (I) can be prepared from compounds of formula (XXXI) according to processes described in Scheme 11.

The methods described in Schemes 12 and 13 using R1-X—B—OH in a nucleophilic aromatic substitution reaction can also be used in place of C—X—B—OH to synthesise (I) by the methods described in Schemes 3, 4 and 5.

According to a fourteenth process compounds of formula (I) and (II) can be modified through further reaction of C to change the substitution on C when C is Het1, Het2 or Ar. As an example, when C contains a primary or secondary amino functionality, further substitution can be made through a simple alkyaltion or reductive alkylation procedure. Preferred conditions for the reductive alkylation include an alkyl aldehyde, sodium triacetoxyborohydride and acetic acid in tetrahydrofuran at room temperature. As a further example, when C is chloropyridyl, further substitution is possible through nucleophilic displacement by an amino or alkoxy functionality.

According to a fifteenth process compounds of formula (III) when C is Het2 may be further modified to convert C into a different Het2. As an example when C is furan, a Diels Alder with a reaction with an azadicarboxylate ester in the presence of a Lewis acid catalyst such as zinc triflate yields a bicyclic adduct. Ester hydrolysis with for example an acid (such as acetic acid) or a base (such as sodium hydroxide) results in decarboxylation and dehydration to yield a pyridazine.

According to a sixteenth process:

Scheme 16

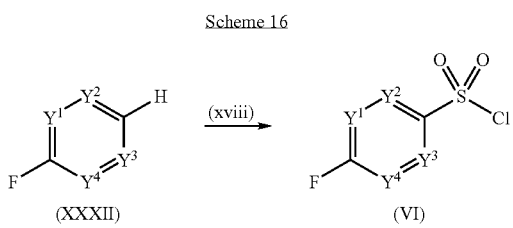

compounds of formula (XXXII), which are commercially available or known in the literature, are typically treated with chlorosulfonic acid in chloroform at 0° C. with warming to ambient temperature to provide compounds of formula (VI).

Referring to the general methods above, it will be readily understood to the skilled person that where protecting groups are present, these will be generally interchangeable with other protecting groups of a similar nature, e.g. where a sulfonamide is described as being protected with a tert-butyl or dimethoxybenzyl group, this may be readily interchanged with any suitable sulfonamide protecting group. Suitable protecting groups are described in 'Protective Groups in Organic Synthesis' by T. Greene and P. Wuts (3$^{rd}$ edition, 1999, John Wiley and Sons).

The present invention also relates to novel intermediate compounds as defined above, all salts, solvates and complexes thereof and all solvates and complexes of salts thereof as defined hereinbefore for compounds of formula (I). The invention includes all polymorphs of the aforementioned species and crystal habits thereof.

EXAMPLES & PREPARATIONS

The following experimental details illustrate specifically how certain compounds of formula (I) may be prepared. All examples, unless indicated as a reference example, are compounds of formula (I). Preparations are intermediates useful in the synthesis of compounds of formula (I).

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad.

The mass spectra (m/z) were recorded using either electrospray ionisation (ESI) or atmospheric pressure chemical ionisation (APCI). When relevant, and unless stated otherwise, the m/z data provided are for isotopes $^{19}$F, $^{35}$Cl and $^{79}$Br.

The following abbreviations have been used for common solvents: CDCl$_3$, deuterochloroform; d$_5$-DMSO, deuterodimethylsulphoxide; CD$_3$OD, deuteromethanol; THF, tetrahydrofuran. 'Ammonia' refers to a concentrated solution of ammonia in water possessing a specific gravity of 0.88.

Where thin layer chromatography (TLC) has been used it refers to silica gel TLC using silica gel 60 $F_{254}$ plates, $R_f$ is the distance travelled by a compound divided by the distance travelled by the solvent front on a TLC plate.

Where compounds are purified by HPLC the following methods are used:

Preparative Reverse Phase HPLC Methods:

a) Phenomenex 250×30 mm 15 micron C18 column. 40 mL/minutes. Gradient 85% A to 100% B over 25 minutes. Solvent A: 7800 water/200 acetonitrile/8 trifluoroacetic acid. Solvent B: 7200 acetonitrile/800 water/8 trifluoroacetic acid, 254 nM UV detection.

b) Phenomenex 100×21.2 mm 10 micron C18 column. 20 mL/minutes. Gradient 85% A to 100% B over 25 minutes. Solvent A: 7800 water/200 acetonitrile/8 trifluoroacetic acid. Solvent B: 7200 acetonitrile/800 water/8 trifluoroacetic acid, 254 nM UV detection.

Certain compounds of the Examples and Preparations were purified using Automated Preparative High Performance Liquid Chromatography (HPLC). Reversed-phase HPLC conditions were on FractionLynx systems. Samples were submitted dissolved in 1mL of DMSO. Depending on the nature of the compounds and the results of a pre-analysis, the purification was performed under either acidic conditions or basic conditions at ambient temperature. Acidic runs were carried out on a Sunfire Prep C18 OBD column (19×50 mm, 5 μm), basic runs were carried out on a Xterra Prep MS C18 (19×50 mm, 5 μm), both from Waters. A flow rate of 18 mL/minutes was used with mobile phase A: water+0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 minute then ran from 5% to 98% B over 6 minutes followed by a 2 minutes hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/minutes supply of Nitrogen. The Waters ZQ MS was tuned with the following parameters:

| | |
|---|---|
| ES+ Cone voltage: 30 v | Capillary: 3.20 kv |
| ES– Cone voltage: –30 v | Capillary: –3.00 kv |
| Desolvation gas: 600 L/hour | |
| Source Temp: 120° C. | |
| Scan range 150-900 Da | |

The fraction collection was triggered by both MS and ELSD.

Quality control analysis was performed using a LCMS method orthogonal to the preparative method. Acidic runs were carried out on a Sunfire C18 (4.6×50 mm, 5 μm), basic runs were carried out on a Xterra C18 (4.6×50 mm, 5 μm), both from Waters. A flow rate of 1.5 mL/minutes was used with mobile phase A: water+0.1% modifier (v/v) and B: acetonitrile+0.1% modifier (v/v). For acidic runs the modifier was formic acid, for basic run the modifier was diethylamine. A Waters 1525 binary LC pump ran a gradient elution from 5% to 95% B over 3 minutes followed by a 1 minute hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/minutes supply of Nitrogen. The Waters ZQ MS was tuned with the following parameters:

| | |
|---|---|
| ES+ Cone voltage: 25 v | Capillary: 3.30 kv |
| ES– Cone voltage: –30 v | Capillary: –2.50 kv |
| Desolvation gas: 800 L/hour | |
| Source Temp: 150° C. | |
| Scan range 160-900 Da | |

Unless otherwise noted, LCMS conditions were run according to one of the conditions given below:

6 Minute LC-MS Gradient and Instrument Conditions
Acid run:
A: 0.1% formic acid in water
B: 0.1% formic acid in acetonitrile
Column: C18 phase Phenomenex Gemini 50×4.6 mm with 5 micron particle size
Gradient: 95-5% A over 3 min, 1 minute hold, 1 ml/minute
UV: 210 nm-450 nm DAD
Temperature: 50 C 2 Minute LC-MS Gradient and Instrument Conditions
Acid run:
A: 0.1% formic acid in water
B: 0.1% formic acid in acetonitrile
Column: C18 phase Fortis Pace 20×2.1 mm with 3 micron particle size
Gradient: 70-2% A over 1.8 min, 0.2 minutes hold, 1.8 ml/minutes
UV: 210 nm-450 nm DAD
Temperature: 75 C C18 30 Minute Method LC-MS Gradient and Instrument Conditions
A: 0.1% formic acid in H2O
B: 0.1% formic acid in MeCN
Column: Phenomenex C18 phase Gemini 150×4.6 mm with 5 micron particle size
Gradient: 98-2% A over 18 min, 2 minutes hold, 1 ml/minutes
UV: 210 nm-450 nm DAD
Temperature: 50 C Phenyl Hexyl 30 Minute Method LC-MS Gradient and Instrument Conditions
A: 10 mM ammonium acetate in H2O
B: 10 mM ammonium acetate in methanol
Column: Phenomenex Phenyl Hexyl 150×4.6 mm with 5 micron particle size
Gradient: 98-2% A over 18 min, 2 minutes hold, 1 ml/minute
UV: 210 nm-450 nm DAD
Temperature: 50 C Unless otherwise provided herein:
AcOH means acetic acid,
Boc means tert-butoxycarbonyl; (tert-butyloxycarbonyl)
WSCDI means 1-(3-dimethylaminopropyl)-3-ethylcarbodiimide hydrochloride;
CBz means benzyloxycarbonyl;
CDI means N,N'-carbonyldiimidazole;
DABCO means 1,4-diazabicyclo[2.2.2]octane
DCC means N,N'-dicyclohexylcarbodiimide;
DCM means dichloromethane; methylene chloride;
DMAP means 4-dimethylaminopyridine;
DMB means dimethoxybenzyl;
DME means dimethoxyethane;
DMF means N,N-dimethylformamide;
DMFDMA means N,N-dimethylformamide dimethylacetal
DMSO means dimethyl sulphoxide;

Et₃N means triethylamine;
EtOH means ethanol
HBTU means O-benzotriazol-1-yl-N,N,N',N'-tetramethyluronium hexafluorophosphate;
HCl means hydrochloric acid;
HOAT means 1-hydroxy-7-azabenzotriazole;
HOBT means 1-hydroxybenzotriazole hydrate;
Hünig's base means N-ethyldiisopropylamine;
K₂CO₃ means potassium carbonate;
KOH means potassium hydroxide;
LiHMDS means lithium bis(trimethylsilyl)amide;
Me means methyl;
NaH means sodium hydride;
Na₂CO₃ means sodium carbonate;
NaOH means sodium hydroxide;
NH₃ means ammonia;
NMP means N-methylpyrrolidinone;
Pd(PPh₃)₄ means palladium tetrakis;
Pd₂(dba)₃ means Tris(dibenzylideneacetone)dipalladium;
TBTU means O-(Benzotriazol-1-yl)-N,N,N',N'-tetramethyluronium tetrafluoroborate;
TFA means trifluoroacetic acid;
THF means tetrahydrofuran; and
TMS means trimethylsilyl.

Example 1

3-cyano-4-(4-fluoro-2-(1-methyl-1H-pyrazol-5-yl)phenoxy)-N-(1,2,4-thiadiazol-5-yl)benzenesulfonamide

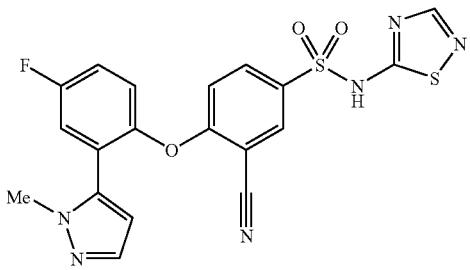

Method A

To a suspension of sodium hydride (60% dispersion in oil, 0.062 g) in N,N-dimethylformamide (5 mL) was added 4-fluoro-2-(1-methyl-1H-pyrazol-5-yl)phenol (Preparation 88A, 0.072 g, 0.00037 mol). This was stirred at room temperature for 10 minutes. To this mixture was added 3-cyano-4-fluoro-N-(1,2,4-thiadiazol-5-yl)benzenesulfonamide (Preparation 65, 0.103 g, 0.000362 mol) and the resulting mixture was stirred for 3 hours. The reaction was quenched with 1N HCl (aq) and extracted twice with ethyl acetate. The combined organic layers were dried over sodium sulfate, filtered, and concentrated in vacuo. The resulting residue was purified by flash column chromatography using a gradient of 0-10% methanol in CH₂Cl₂ to give the title compound as a white solid. LCMS Rt=1.50 minutes MS m/z 457.0 [MH]+

Example 2

2-fluoro-4-(2-(2-methylthiazol-4-yl)phenoxy)-N-(thiazol-2-yl)benzenesulfonamide)

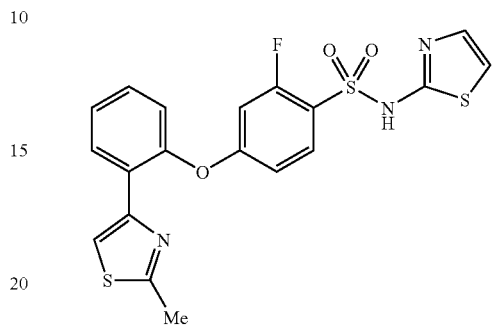

Method B

To a suspension of sodium hydride (60% dispersion in oil, 0.0260 g) in N,N-dimethylformamide (5 mL) was added 2-(2-methylthiazol-4-yl)phenol (0.0830 g, 0.000434 mol). This was stirred at 20° C. for 10 minutes and then cooled to 5° C. in an ice water bath. To this mixture was added N-tert-butyl-2,4-difluoro-N-(thiazol-2-yl)benzenesulfonamide (Preparation 62, 0.151 g, 0.000454 mol) and the reaction was allowed to slowly warm to room temperature. After stirring for 16 hours, the reaction was quenched with water and extracted twice with ethyl acetate. The combined organic layers were dried over sodium sulphate, filtered, and concentrated in vacuo. The resulting residue was purified by flash column chromatography. The purified product was dissolved in methylene chloride (15 mL) and treated with trifluoroacetic acid (5 mL, 0.06 mol). After stirring for 30 minutes, the reaction was concentrated in vacuo and the residue purified by flash column chromatography using a gradient of 0-5% methanol in CH₂Cl₂, providing the title compound as a white solid. LCMS Rt=1.54 minutes MS m/z 447.8 [MH]+

Example 3

3-fluoro-4-(2-(1-methyl-1H-pyrazol-5-yl)phenoxy)-N-(thiazol-2-yl)benzenesulfonamide

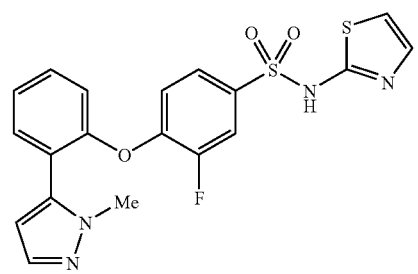

Method C

To a suspension of sodium hydride (60% dispersion in oil, 52 mg, 0.0013 mol) in DMF (1 mL) was added 2-(1-methyl-1H-pyrazol-5-yl)phenol (Preparation 92A, 176 mg, 0.00101 mol) as a solution in DMF (1 mL) and the mixture was stirred for 15 minutes. To this was added N-tert-butyl-3,4-difluoro-N-thiazol-2-yl-benzenesulfonamide (Preparation 60, 350 mg, 0.00105 mol) as a solution in DMF (1 mL). The resulting orange solution was heated at 80° C. for 3 days. After cooling the reaction was diluted with ethyl acetate and washed with saturated aqueous NaHCO$_3$, water, and brine. The organic layer was dried over MgSO$_4$, filtered, and concentrated in vacuo. The crude product was purified by flash column chromatography using a 0-100% ethyl acetate in hexanes gradient to give a clear oil. This was dissolved in trifluoroacetic acid (3 mL, 0.04 mol) and heated to 50° C. for 24 h. After cooling, the reaction was concentrated in vacuo and purified by flash column chromatography using a 0-10% methanol in CH$_2$Cl$_2$ gradient to give the title compound as a white solid. LCMS Rt=1.49 minutes MS m/z 430.9 [MH]+

Example 4

3-cyano-4-[(4'-isopropoxy-2'-methylbiphenyl-2-yl)oxy]-N-1,2,4-thiadiazol-5-ylbenzenesulfonamide

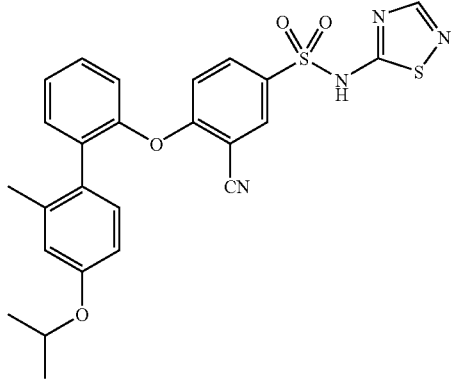

Method D

To a solution of 4'-isopropoxy-2'-methyl-biphenyl-2-ol (Preparation 37, 51 mg, 0.212 mmol) and KOH (17.8 mg, 0.318 mmol) in DMSO (1 mL) was added 3-cyano-4-fluoro-N-(1,2,4-thiadiazol-5-yl)benzenesulfonamide (Preparation 65, 30 mg, 0.11 mmol). The mixture was stirred at room temperature overnight followed by stirring at 60° C. for 24 h. 2N HCl (aq) (5 ml) was added to the reaction mixture followed by extraction into tert-butyl methyal ether (10 ml). The organic layer was collected, dried (MgSO4) and concentrated in vacuo to afford the crude compound which was purified using silica gel column chromatography (dichloromethane:methanol 95:5) to furnish the title compound. LCMS Rt=3.38 minutes MS m/z 507 [MH]+

Example 5

3-cyano-4-[(5-fluoro-3'-isopropoxybiphenyl-2-yl)oxy]-N-1,2,4-thiadiazol-5-ylbenzenesulfonamide

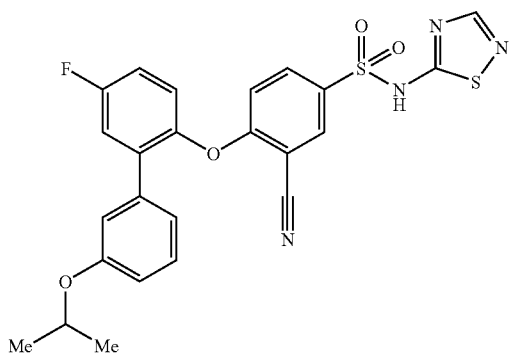

Method E

To a solution of 4-(2-bromo-4-fluoro-phenoxy)-3-cyano-N-[1,2,4]thiadiazol-5-ylbenzenesulfonamide (Preparation 44, 72.6 mg, 0.15 mmol) in DMF (0.8 mL) was added 3-isopropoxyphenylboronic acid (40 mg, 0.225 mmol), palladium tetrakis triphenylphosphine (8.10 mg, 0.007 mmol) and a 2M aqueous solution of sodium carbonate (0.225 mL, 0.45 mmol). The reaction was heated to 100° C. overnight. After cooling to room temperature, saturated aqueous ammonium chloride (3 mL) and dichloromethane (3 mL) was added and the organic extracted into dichloromethane (3×3 mL). The organic layer was concentrated in vacuo and the title compound purified by preparative HPLC. LCMS Rt=2.46 minutes MS m/z 511 [MH]+

Example 6

3-cyano-4-(2-cyclopropyl-4-fluorophenoxy)-N-1,2,4-thiadiazol-5-ylbenzenesulfonamide

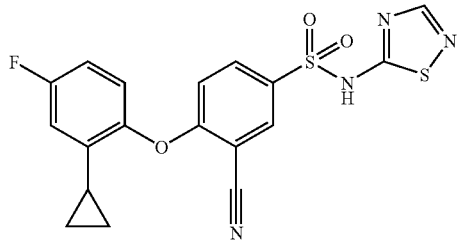

Method F

To a solution of 2-cyclopropyl-4-fluorophenol (US2005245519, 60 mg, 0.4 mmol) and potassium carbonate (82.9 mg, 0.6 mmol) in DMF (1 ml) was added 3-cyano-4-fluoro-N-(1,2,4-thiadiazol-5-yl)benzenesulfonamide (Preparation 65, 57 mg, 0.2 mmol). The reaction was heated to 80-100° C. overnight. Saturated aqueous ammonium chloride and dichloromethane were added to the cooled reaction and the organics extracted into dichloromethane (3×3 ml). The organic layer was dried (MgSO4) and concentrated in vacuo to furnish the crude residue that was purified using preparative HPLC. LCMS Rt=2.29 minutes MS m/z 417 [MH]+

Example 95

4-(biphenyl-2-yloxy)-3-cyano-N-1,3-oxazol-2-ylbenzenesulfonamide

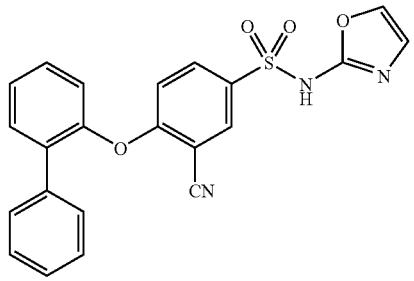

Method G

Triethylamine (38 ul, 0.27 mmol) was added to oxazol-2-ylamine (14 mg, 0.169 mmol) in THF (0.5 ml) and stirred for 5 minutes. 4-(biphenyl-2-yloxy)-3-cyano-benzenesulfonyl chloride (Preparation 55, 50 mg, 0.14 mmol) in THF (0.5 ml) was then added slowly and the reaction stirred at room temperature overnight. Aqueous 2N HCl was added and the reaction extracted into ethyl acetate three times, the organic layer collected, dried (MgSO4), and concentrated in vacuo to furnish a crude residue that was purified using preparative HPLC. LCMS Rt=3.17 minutes MS m/z 418 [MH]+

Example 96

4-(biphenyl-2-yloxy)-3-cyano-N-(3-methoxy-1,2,4-thiadiazol-5-yl)benzenesulfonamide

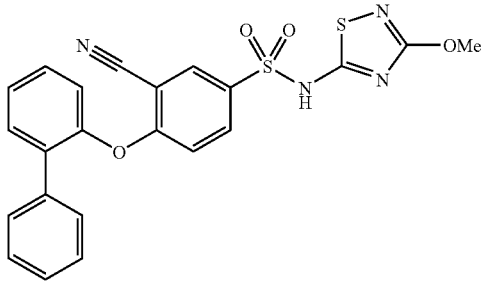

Method H

NaOH (8 mg, 0.203 mmol) in water (0.25 ml) was added to 3-methoxy-[1,2,4]-thiadiazol-5-ylamine (27 mg, 0.203 mmol) in 1,4-dioxane (1.0 ml) and stirred at ambient temperature for 5 minutes. 4-(Biphenyl-2-yloxy)-3-cyano-benzenesulfonyl chloride (Preparation 55, 50 mg, 0.14 mmol) in 1,4-dioxane (0.5 ml) was added slowly and stirring continued at ambient temperature overnight. Aqueous HCl solution (2M, 0.2 ml) was added, then saturated brine (2 ml), and the mixture extracted with ethyl acetate (3×2 ml). The combined organic layers were collected, dried (MgSO4), and concentrated in vacuo to furnish a crude residue that was purified using preparative HPLC.

LCMS Rt=2.49 min MS m/z 464.9 [MH]+

Example 97

4-(biphenyl-2-yloxy)-3-cyano-N-1,3-thiazol-4-yl-benzenesulfonamide

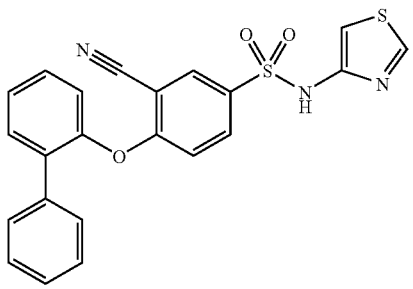

Method I 4-(Biphenyl-2-yloxy)-3-cyano-benzenesulfonyl chloride (Preparation 55, 50 mg, 0.14 mmol) in MeCN (0.5 ml) was added dropwise to thiazol-4-ylamine (20 mg, 0.15 mmol) and DABCO (34 mg, 0.297 mmol) in MeCN (0.5 ml) and the heterogeneous mixture stirred together at 70° C. for 24 h. The reaction was concentrated in vacuo and the residue was taken up in methanol (5 ml), passed through pad of charcoal and Celite™, and washed with methanol. The filtrate was concentrated in vacuo to afford a crude residue that was purified using preparative HPLC. LCMS Rt=3.72 min MS m/z 433.9 [MH]+

Example 98

4-(biphenyl-2-yloxy)-3-cyano-N-(3-isopropyl-1,2,4-thiadiazol-5-yl)benzenesulfonamide

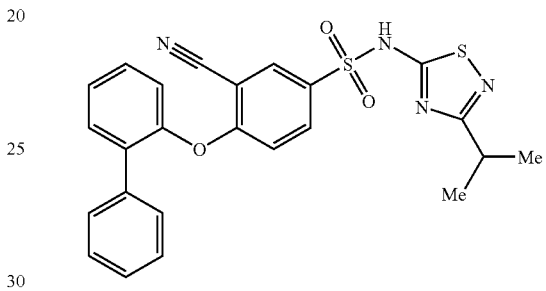

Method J

LiHMDS (1M solution in THF, 194 ul, 0.194 mmol) was added to a stirred solution of 3-isopropyl-[1,2,4]thiadiazol-5-ylamine (28 mg, 0.194 mmol) in THF (0.5 ml). 4-(biphenyl-2-yloxy)-3-cyano-benzenesulfonic acid pentafluorophenyl ester (Preparation 58, 50 mg, 0.097 mmol) was added and the reaction was heated to 50° C. overnight. The reaction was cooled and concentrated in vacuo before being purified using preparative HPLC.

LCMS Rt=3.88 min MS m/z 477 [MH]+

Example 99

4-(biphenyl-2-yloxy)-3-cyano-N-isothiazol-4-ylbenzenesulfonamide

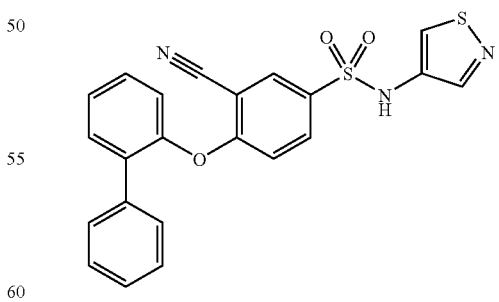

Method K

To a solution of isothiazol-4-ylamine (40 mg, 0.293 mmol) in pyridine (0.5 ml) and dichloromethane (0.5 ml) was added 4-(biphenyl-2-yloxy)-3-cyano-benzenesulfonyl chloride (Preparation 55, 60 mg, 0.16 mmol) and the reaction stirred at room temperature overnight. 2N HCl was added and the reaction extracted into dichloromethane. The organic layer was collected, dried (MgSO$_4$) and concentrated in vacuo to furnish a crude residue that was purified using preparative HPLC.

LCMS Rt=3.75 minutes MS m/z 434 [MH]+

Example 134

N-(5-chloro-1,3-thiazol-2-yl)-3-cyano-4-(2-phenoxyphenoxy)benzenesulfonamide

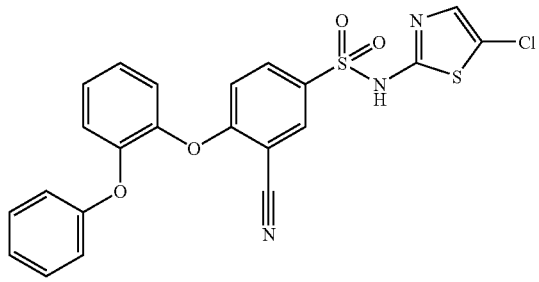

Method L

To a solution of N-(5-chloro-thiazol-2-yl)-3-cyano-4-fluorobenzenesulfonamide (Preparation 52, 0.2 mmol, 63.5 mg) and 2-phenoxyphenol (74 mg, 0.4 mmol) in THF (1 mL) was added t-BuOK in THF (1 M, 0.6 mL). The reaction was heated at 50° C. overnight. The reaction was cooled to room temperature and poured into saturated aqueous NH$_4$Cl. The mixture was extracted thrice with CH$_2$Cl$_2$ and the combined organic layer was dried over MgSO$_4$ followed by evaporation in vacuo to obtain the crude residue which was purified using preparative HPLC to afford the title compound.

LCMS Rt=3.66 minutes MS m/z 484 [M$^{35}$ClH]+, 486 [M$^{37}$ClH]+

Example 170

4-[4-Chloro-2-(1-methyl-1H-pyrazol-5-yl)phenoxy]-3-cyano-N-1,3-thiazol-2-ylbenzenesulfonamide

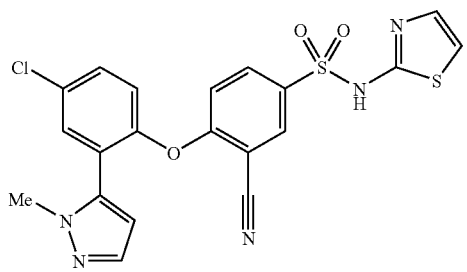

3-Cyano-4-fluoro-N-1,3-thiazol-2-ylbenzenesulfonamide, (Preparation 46, 500 mg, 0.00176 mol), 4-chloro-2-(1-methyl-1H-pyrazol-5-yl)phenol, (Preparation 89, 370 mg, 0.00177 mol) and potassium carbonate (700 mg, 0.00287 mol) were stirred in dimethylformamide (5 mL) at 80° C. for 24 hours. The reaction mixture was cooled and partitioned between ethyl acetate (150 mL) and aqueous hydrochloric acid (80 mL of 2 molar), the organic layer was dried over anhydrous sodium sulphate, filtered and the solvents removed in vacuo to give an orange solid. The solid was triturated with diethyl ether (20 mL) to give the title compound as an orange powder, (680 mg).

LCMS=1.40 minutes, MS m/z =472 [M$^{35}$ClH]+

$^1$HNMR (d$_6$-DMSO): δ 3.73 (s, 3H), 6.20 (d, 1H), 6.88 (d, 1H), 6.93 (d, 1H), 7.29 (d, 1H), 7.33 (d, 1H), 7.49 (d, 1H), 7.66-7.71 (m, 2H), 7.87-7.91 (m, 1H), 8.10 (d, 1H).

Example 279

4-[4-(2-tertbutyl-5-trifluoromethyl-2H-pyrazol-3-yl)-phenoxy]-3-cyano-N-thiazol-2-yl-benzenesulfonamide

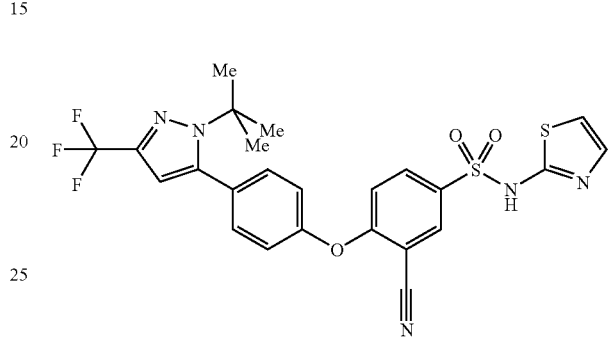

Method M

3-Cyano-4-fluoro-N-(thiazol-2-yl)benzenesulfonamide (Preparation 46, 89 mg, 0.31 mmol) was added to a mixture of 4-(2-tert-butyl-5-trifluoromethyl-2H-pyrazol-3-yl)-phenol (Preparation 190, 89 mg, 0.31 mmol) and potassium carbonate (130 mg, 0.94 mmol) in N,N-dimethylformamide (2 mL, 30 mmol). The reaction mixture was heated at 150° C. in the microwave for 2 hours. The reaction mixture was diluted with ethyl acetate, washed with water and brine, dried over anhydrous sodium sulfate, filtered and was concentrated to give the crude product that was purified via automated flash chromatography (silica gel, 0% to 80% ethyl acetate in hexanes). 114 mg (66%) of the product was obtained as a white solid.

LCMS Rt=1.80 minutes; MS m/z 548 [MH]+

$^1$H NMR (300 MHz, d$_6$-DMSO): δ 1.46 (s, 9H), 6.73 (s, 1H), 6.92 (d, J=4.6 Hz, 1H), 7.14 (d, J=8.9 Hz, 1H), 7.34 (d, J=4.6 Hz, 1H), 7.38 (m, 2H), 7.61 (m, 2H), 8.10 (dd, J=8.9 & 2.2 Hz, 1H), 8.28 (d, J =2.2 Hz, 1H), 12.95 (s, br, 1H).

Library Protocol 1

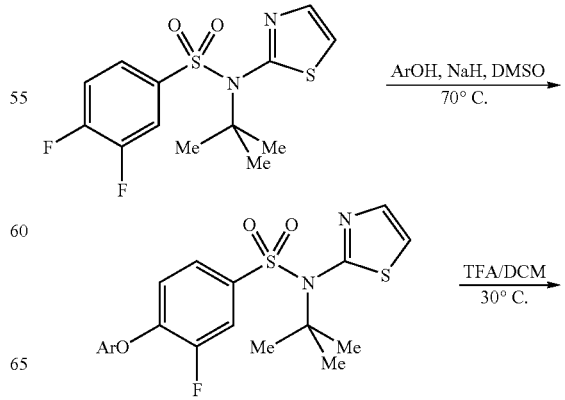

-continued

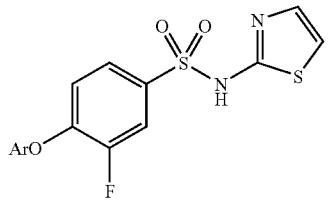

To a solution of the phenol (100 μmol) in dimethylsulphoxide (1 ml) was added NaH (60% dispersion in oil, 8 mg, 200 μmol) and the reaction shaken at 30° C. for 1 hour. The reaction mixture was cooled to 5° C. and a solution of N-tert-butyl-3,4-difluoro-N-(thiazol-2-yl)benzenesulfonamide (Preparation 60, 100 μmol) in dimethylsulphoxide (100 μl) was added followed by continued shaking at 70° C. for 16 hours. The crude product was purified by preparative HPLC to yield pure intermediate. 1 ml of a trifluoroacetic acid/dichloromethane solution (1:7) was added to the intermediate and the reaction shaken at 30° C. for 1 hour. The reaction was concentrated in vacuo to yield the desired product.

The following further examples can be prepared analogously to the General Methods (as described above), and Methods A-M, as described for Examples 1-6, 95-99, 134, and 279, and Library protocol 1, substituting appropriate starting materials where necessary and making appropriate changes to experimental conditions informed by common general knowledge. Purification was performed either by silica gel column chromatography, trituration or preparative HPLC.

| Eg No | Name | MS m/z (unless otherwise indicated) |
|---|---|---|
| 7 | 3-cyano-4-{[2-(4-ethylphenyl)pyridin-3-yl]oxy}-N-1,2,4-thiadiazol-5-ylbenzenesulfonamide | 464 [MH]+ |
| 8 | 3-cyano-4-{[2-(dimethylamino)-4-(4-fluorophenyl)pyrimidin-5-yl]oxy}-N-1,2,4-thiadiazol-5-ylbenzenesulfonamide | 498 [MH]+ |
| 9 | 3-cyano-4-{[2-(dimethylamino)-4-(4-methylphenyl)pyrimidin-5-yl]oxy}-N-1,2,4-thiadiazol-5-ylbenzenesulfonamide | 494 [MH]+ |
| 10 | 3-cyano-4-[(4'-methoxy-2'-methylbiphenyl-2-yl)oxy]-N-1,2,4-thiadiazol-5-ylbenzenesulfonamide | 479 [MH]+ |
| 11 | 3-cyano-4-[(4'-cyanobiphenyl-2-yl)oxy]-N-1,2,4-thiadiazol-5-ylbenzenesulfonamide | 460 [MH]+ |
| 12 | 3-cyano-4-[(6-methyl-2-phenylpyridin-3-yl)oxy]-N-1,2,4-thiadiazol-5-ylbenzenesulfonamide | 450 [MH]+ |
| 13 | 3-cyano-4-[(4'-cyano-3'-methoxybiphenyl-2-yl)oxy]-N-1,2,4-thiadiazol-5-ylbenzenesulfonamide | 490 [MH]+ |
| 14 | 3-cyano-4-{[2-(dimethylamino)-4-(2-fluorophenyl)pyrimidin-5-yl]oxy}-N-1,2,4-thiadiazol-5-ylbenzenesulfonamide | 498 [MH]+ |
| 15 | 3-cyano-4-[(4'-isopropoxy-3-methylbiphenyl-2-yl)oxy]-N-1,2,4-thiadiazol-5-ylbenzenesulfonamide | 505 [MH]− |
| 16 | 3-cyano-4-{[4-(4-fluorophenyl)-2-(methylamino)pyrimidin-5-yl]oxy}-N-1,2,4-thiadiazol-5-ylbenzenesulfonamide | 482 [MH]− |
| 17 | 3-cyano-4-{[2-(4-methylphenyl)pyridin-3-yl]oxy}-N-1,2,4-thiadiazol-5-ylbenzenesulfonamide | 450 [MH]+ |
| 18 | 4-{[2-amino-4-(4-chlorophenyl)pyrimidin-5-yl]oxy}-3-cyano-N-1,2,4-thiadiazol-5-ylbenzenesulfonamide | 484 [MH]− |
| 19 | 3-cyano-4-[(6-ethyl-2-phenylpyridin-3-yl)oxy]-N-1,2,4-thiadiazol-5-ylbenzenesulfonamide | 464 [MH]+ |
| 20 | 3-cyano-4-[(3-phenylpyrazin-2-yl)oxy]-N-1,2,4-thiadiazol-5-ylbenzenesulfonamide | 437 [MH]+ |
| 21 | 3-cyano-4-[(4-phenylpyridazin-3-yl)oxy]-N-1,2,4-thiadiazol-5-ylbenzenesulfonamide | 437 [MH]+ |
| 22 | 3-cyano-4-[(2-phenylpyridin-3-yl)oxy]-N-1,2,4-thiadiazol-5-ylbenzenesulfonamide | 436 [MH]+ |
| 23 | 4-[(2-amino-4-phenylpyrimidin-5-yl)oxy]-3-cyano-N-1,2,4-thiadiazol-5-ylbenzenesulfonamide | 452 [MH]+ |
| 24 | 4-(biphenyl-2-yloxy)-3-cyano-N-(1,2,4-thiadiazol-5-yl)benzenesulfonamide | 435 [MH]+ |
| 25 | 4-(4-chloro-2-(1-methyl-1H-pyrazol-5-yl)phenoxy)-3-cyano-N-(1,2,4-thiadiazol-5-yl)benzenesulfonamide | 473 [M$^{35}$ClH]+ |
| 26 | 3-cyano-4-(4-fluoro-2-(1-(2,2,2-trifluoroethyl)-1H-pyrazol-5-yl)phenoxy)-N-(1,2,4-thiadiazol-5-yl)benzenesulfonamide | 525 [MH]+ |
| 27 | 3-cyano-4-(2-(1,4-dimethyl-1H-pyrazol-5-yl)-4-methylphenoxy)-N-(1,2,4-thiadiazol-5-yl)benzenesulfonamide | 467 [MH]+ |
| 28 | 3-cyano-4-(2-(1,4-dimethyl-1H-pyrazol-3-yl)-4-methylphenoxy)-N-(1,2,4-thiadiazol-5-yl)benzenesulfonamide | 467 [MH]+ |
| 29 | ethyl 2-(5-(2-(4-(N-1,2,4-thiadiazol-5-ylsulfamoyl)-2-cyanophenoxy)-5-chlorophenyl)-1H-pyrazol-1-yl)acetate | 545 [M$^{35}$ClH]+ |
| 30 | methyl 4-(4-(N-1,2,4-thiadiazol-5-ylsulfamoyl)-2-cyanophenoxy)-3-(1-methyl-1H-pyrazol-5-yl)benzoate | 497.2 [MH]+ |
| 31 | 3-cyano-4-[(2',5'-difluoro-3-methylbiphenyl-2-yl)oxy]-N-1,2,4-thiadiazol-5-ylbenzenesulfonamide | 485 [MH]+ |
| 32 | 3-cyano-4-[(3'-isopropoxy-3-methylbiphenyl-2-yl)oxy]-N-1,2,4-thiadiazol-5-ylbenzenesulfonamide | 507 [MH]+ |
| 33 | 3-cyano-N-1,2,4-thiadiazol-5-yl-4-[(2',5,5'-trifluorobiphenyl-2-yl)oxy]benzenesulfonamide | 489 [MH]+ |
| 34 | 3-cyano-4-[(3'-isopropoxybiphenyl-2-yl)oxy]-N-1,2,4-thiadiazol-5-ylbenzenesulfonamide | 493 [MH]+ |
| 35 | 3-cyano-4-[(2',4'-difluoro-3-methylbiphenyl-2-yl)oxy]-N-1,2,4-thiadiazol-5-ylbenzenesulfonamide | 485 [MH]+ |
| 36 | 3-cyano-4-[(2',5'-difluorobiphenyl-2-yl)oxy]-N-1,2,4-thiadiazol-5-ylbenzenesulfonamide | 471 [MH]+ |
| 37 | 3-cyano-4-{[3-methyl-3'-(trifluoromethoxy)biphenyl-2-yl]oxy}-N-1,2,4-thiadiazol-5-ylbenzenesulfonamide | 533 [MH]+ |
| 38 | 3-cyano-4-[(3'-fluoro-3-methylbiphenyl-2-yl)oxy]-N-1,2,4-thiadiazol-5-ylbenzenesulfonamide | 467 [MH]+ |
| 39 | 3-cyano-4-[(4'-fluoro-3-methylbiphenyl-2-yl)oxy]-N-1,2,4-thiadiazol-5-ylbenzenesulfonamide | 467 [MH]+ |
| 40 | 3-cyano-4-{[3-methyl-4'-(trifluoromethoxy)biphenyl-2-yl]oxy}-N-1,2,4-thiadiazol-5-ylbenzenesulfonamide | 533 [MH]+ |
| 41 | 3-cyano-4-[(3'-fluoro-4'-methoxy-3-methylbiphenyl-2-yl)oxy]-N-1,2,4-thiadiazol-5-ylbenzenesulfonamide | 497 [MH]+ |
| 42 | 3-cyano-4-[(4'-methoxy-3-methylbiphenyl-2-yl)oxy]-N-1,2,4-thiadiazol-5-ylbenzenesulfonamide | 479 [MH]+ |
| 43 | 3-cyano-4-[(2'-fluoro-3-methylbiphenyl-2-yl)oxy]-N-1,2,4-thiadiazol-5-ylbenzenesulfonamide | 467 [MH]+ |
| 44 | 3-cyano-4-[(3',4'-difluoro-3-methylbiphenyl-2-yl)oxy]-N-1,2,4-thiadiazol-5-ylbenzenesulfonamide | 485 [MH]+ |
| 45 | 3-cyano-4-[(3',5'-difluoro-3-methylbiphenyl-2-yl)oxy]-N-1,2,4-thiadiazol-5-ylbenzenesulfonamide | 485 [MH]+ |

| Eg No | Name | MS m/z (unless otherwise indicated) |
|---|---|---|
| 46 | 3-cyano-N-1,2,4-thiadiazol-5-yl-4-[(2',4',5'-trifluorobiphenyl-2-yl)oxy]benzenesulfonamide | 489 [MH]+ |
| 47 | 3-cyano-4-[(3'-fluorobiphenyl-2-yl)oxy]-N-1,2,4-thiadiazol-5-ylbenzenesulfonamide | 451 [MH]– |
| 48 | 3-cyano-4-[(3'-fluoro-4'-methoxybiphenyl-2-yl)oxy]-N-1,2,4-thiadiazol-5-ylbenzenesulfonamide | 483 [MH]+ |
| 49 | 3-cyano-4-[(4'-fluorobiphenyl-2-yl)oxy]-N-1,2,4-thiadiazol-5-ylbenzenesulfonamide | 453 [MH]+ |
| 50 | 3-cyano-4-[(2'-fluorobiphenyl-2-yl)oxy]-N-1,2,4-thiadiazol-5-ylbenzenesulfonamide | 453 [MH]+ |
| 51 | 3-cyano-4-[(4'-methoxybiphenyl-2-yl)oxy]-N-1,2,4-thiadiazol-5-ylbenzenesulfonamide | 465 [MH]+ |
| 52 | 3-cyano-4-[(3',4'-difluorobiphenyl-2-yl)oxy]-N-1,2,4-thiadiazol-5-ylbenzenesulfonamide | 471 [MH]+ |
| 53 | 3-cyano-4-[(3',5'-difluorobiphenyl-2-yl)oxy]-N-1,2,4-thiadiazol-5-ylbenzenesulfonamide | 471 [MH]+ |
| 54 | 3-cyano-4-[(4'-isopropoxybiphenyl-2-yl)oxy]-N-1,2,4-thiadiazol-5-ylbenzenesulfonamide | 493 [MH]+ |
| 55 | 3-cyano-N-1,2,4-thiadiazol-5-yl-4-{[3'-(trifluoromethoxy)biphenyl-2-yl]oxy}benzenesulfonamide | 519 [MH]+ |
| 56 | 3-cyano-4-[(2',4'-difluorobiphenyl-2-yl)oxy]-N-1,2,4-thiadiazol-5-ylbenzenesulfonamide | 471 [MH]+ |
| 57 | 3-cyano-N-1,2,4-thiadiazol-5-yl-4-{[4'-(trifluoromethoxy)biphenyl-2-yl]oxy}benzenesulfonamide | 519 [MH]+ |
| 58 | 3-cyano-4-{[1-(2,4-difluorophenyl)-3-(trifluoromethyl)-1H-pyrazol-5-yl]oxy}-N-1,2,4-thiadiazol-5-ylbenzenesulfonamide | 529 [MH]+ |
| 59 | 3-cyano-4-{[1-(3,4-difluorophenyl)-3-(trifluoromethyl)-1H-pyrazol-5-yl]oxy}-N-1,2,4-thiadiazol-5-ylbenzenesulfonamide | 529 [MH]+ |
| 60 | 3-cyano-4-[4-(cyclopropylmethyl)phenoxy]-N-1,2,4-thiadiazol-5-ylbenzenesulfonamide | 413 [MH]+ |
| 61 | 4-[4-(azetidin-1-ylmethyl)-2-fluorophenoxy]-3-cyano-N-1,2,4-thiadiazol-5-ylbenzenesulfonamide | 446 [MH]+ |
| 62 | 3-cyano-4-[2-(3,5-dimethyl-1H-pyrazol-4-yl)phenoxy]-N-1,2,4-thiadiazol-5-ylbenzenesulfonamide | NMR Data was: $^1$HNMR (d$_6$-DMSO): δ 2.05 (s, 6H), 6.59 (d, 1H), 7.33-7.55 (m, 4H), 7.84-7.94 (m, 1H), 8.06-8.15 (m, 1H), 8.47 (s, 1H). |
| 63 | 3-cyano-4-[2-(pyridin-4-yloxy)phenoxy]-N-1,2,4-thiadiazol-5-ylbenzenesulfonamide | 452 [MH]+ |
| 64 | 4-{[4-(4-chlorophenyl)-1-methyl-1H-pyrazol-3-yl]oxy}-3-cyano-N-1,2,4-thiadiazol-5-ylbenzenesulfonamide | 473 [M$^{35}$ClH]+<br>475 [M$^{37}$ClH]+ |
| 65 | 3-cyano-4-{[3-isopropyl-1-(4-methoxyphenyl)-1H-pyrazol-4-yl]oxy}-N-1,2,4-thiadiazol-5-ylbenzenesulfonamide | 497 [MH]+ |
| 66 | 4-[(1-benzyl-4-methyl-1H-pyrazol-3-yl)oxy]-3-cyano-N-1,2,4-thiadiazol-5-ylbenzenesulfonamide | 453 [MH]+ |
| 67 | 4-{[1-(2-chlorophenyl)-3-isopropyl-1H-pyrazol-4-yl]oxy}-3-cyano-N-1,2,4-thiadiazol-5-ylbenzenesulfonamide | 501 [M$^{35}$ClH]+<br>503 [M$^{37}$ClH]+ |
| 68 | 3-cyano-4-(2-phenoxyphenoxy)-N-1,2,4-thiadiazol-5-ylbenzenesulfonamide | 451 [MH]+ |
| 69 | 3-cyano-4-[2-(1-methyl-5-oxopyrrolidin-2-yl)phenoxy]-N-1,2,4-thiadiazol-5-ylbenzenesulfonamide | 456 [MH]+ |
| 70 | 3-cyano-4-[2-(1-methyl-1H-pyrazol-5-yl)phenoxy]-N-1,2,4-thiadiazol-5-ylbenzenesulfonamide | 439 [MH]+ |
| 71 | 3-cyano-4-[2,4-dichloro-6-(1-methyl-1H-pyrazol-5-yl)phenoxy]-N-1,2,4-thiadiazol-5-ylbenzenesulfonamide | 507 [M$^{35}$ClH]+ |
| 72 | 3-cyano-4-[2-(1-ethyl-3,5-dimethyl-1H-pyrazol-4-yl)phenoxy]-N-1,2,4-thiadiazol-5-ylbenzenesulfonamide | 481 [MH]+ |
| 73 | 3-cyano-4-[2,4-difluoro-6-(1-methyl-1H-pyrazol-5-yl)phenoxy]-N-1,2,4-thiadiazol-5-ylbenzenesulfonamide | 475 [MH]+ |
| 74 | 3-cyano-4-(5-fluoro-2-phenoxyphenoxy)-N-1,2,4-thiadiazol-5-ylbenzenesulfonamide | 469 [MH]+ |
| 75 | 3-cyano-4-[2-fluoro-6-(2-methoxy-4-methylphenoxy)phenoxy]-N-1,2,4-thiadiazol-5-ylbenzenesulfonamide | 513 [MH]+ |
| 76 | 2-(2-{2-cyano-4-[(1,2,4-thiadiazol-5-ylamino)sulfonyl]phenoxy}phenoxy)benzamide | 494 [MH]+ |
| 77 | 3-cyano-4-[2-(4-fluorophenoxy)phenoxy]-N-1,2,4-thiadiazol-5-ylbenzenesulfonamide | 469 [MH]+ |
| 78 | 3-cyano-4-[2-(4-cyanophenoxy)-5-methylphenoxy]-N-1,2,4-thiadiazol-5-ylbenzenesulfonamide | 490 [MH]+ |
| 79 | 4-(4-chloro-2-phenoxyphenoxy)-3-cyano-N-1,2,4-thiadiazol-5-ylbenzenesulfonamide | 485 [M$^{35}$ClH]+<br>487 [M$^{37}$ClH]+ |
| 80 | 4-{[1-benzyl-3-(trifluoromethyl)-1H-pyrazol-5-yl]oxy}-3-cyano-N-1,2,4-thiadiazol-5-ylbenzenesulfonamide | 507 [MH]+ |
| 81 | 3-cyano-4-{[1-phenyl-3-(trifluoromethyl)-1H-pyrazol-5-yl]oxy}-N-1,2,4-thiadiazol-5-ylbenzenesulfonamide | 493 [MH]+ |
| 82 | 3-cyano-4-[(1-methyl-3-phenyl-1H-pyrazol-5-yl)oxy]-N-1,2,4-thiadiazol-5-ylbenzenesulfonamide | 439 [MH]+ |
| 83 | 4-[2-(1-tert-butyl-1H-pyrazol-5-yl)-3-fluorophenoxy]-3-cyano-N-1,2,4-thiadiazol-5-ylbenzenesulfonamide | 499 [MH]+ |
| 84 | 4-[2-(1-tert-Butyl-1H-pyrazol-3-yl)-3-fluoro-phenoxy]-3-cyano-N-[1,2,4]thiadiazol-5-yl-benzene-sulfonamide | 499 [MH]+ |
| 85 | 3-Cyano-4-[3-fluoro-2-(1-methyl-1H-pyrazol-3-yl)-phenoxy]-N-[1,2,4]thiadiazol-5-yl-benzene-sulfonamide | 457 [MH]+ |
| 86 | 3-cyano-4-[3-fluoro-2-(1-methyl-1H-pyrazol-5-yl)phenoxy]-N-1,2,4-thiadiazol-5-ylbenzenesulfonamide | 457 [MH]+ |
| 87 | 3-cyano-4-{[3-cyclopropyl-1-(2,5-difluorophenyl)-1H-pyrazol-5-yl]oxy}-N-1,2,4-thiadiazol-5-ylbenzenesulfonamide | 501 [MH]+ |
| 88 | 3-cyano-4-{[1-(2-fluorophenyl)-3-(trifluoromethyl)-1H-pyrazol-5-yl]oxy}-N-1,2,4-thiadiazol-5-ylbenzenesulfonamide | 511 [MH]+ |
| 89 | 3-cyano-4-[3-fluoro-2-(2H-pyrazol-3-yl)phenoxy]-N-[1,2,4]thiadiazol-5-yl-benzenesulfonamide | 443 [MH]+ |
| 90 | 4-(4-chloro-2-(1-(2-hydroxyethyl)-1H-pyrazol-5-yl)phenoxy)-3-cyano-N-(1,2,4-thiadiazol-5-yl)benzenesulfonamide | 503 [M$^{35}$ClH]+ |
| 91 | 3-cyano-4-(4-(hydroxymethyl)-2-(1-methyl-1H-pyrazol-5-yl)phenoxy)-N-(1,2,4-thiadiazol-5-yl)benzenesulfonamide | 469 [MH]+ |
| 92 | 3-(4-chloro-benzyl)-5-{2-cyano-4-(1,2,4-thiadiazol-5-ylsulfamoyl)-phenoxy}-pyrazol-1-yl-acetic acid ethyl ester | 559 [M$^{35}$ClH]+ |
| 93 | 2-[3-(4-chlorobenzyl)-5-{2-cyano-4-[(1,2,4-thiadiazol-5-ylamino)sulfonyl]phenoxy}-1H-pyrazol-1-yl]acetamide | 530 [M$^{35}$ClH]+ |
| 94 | 4-{[3-(4-chlorobenzyl)-1-(2-hydroxyethyl)-1H-pyrazol-5-yl]oxy}-3-cyano-N-1,2,4-thiadiazol-5-ylbenzenesulfonamide | 517 [M$^{35}$ClH]+ |
| 100 | 4-(biphenyl-2-yloxy)-3-cyano-N-(5-methyl-1,3-thiazol-2-yl)benzenesulfonamide | 448 [MH]+ |
| 101 | 4-(biphenyl-2-yloxy)-3-cyano-N-(4-methyl-1,3-thiazol-2-yl)benzenesulfonamide | 448 [MH]+ |
| 102 | 4-(biphenyl-2-yloxy)-3-cyano-N-(3-ethyl-1,2,4-thiadiazol-5-yl)benzenesulfonamide | 463 [MH]+ |
| 103 | 4-(biphenyl-2-yloxy)-3-cyano-N-(3-methyl-1,2,4-thiadiazol-5-yl)benzenesulfonamide | 449 [MH]+ |
| 104 | 4-(biphenyl-2-yloxy)-3-cyano-N-1,3,4-thiadiazol-2-ylbenzenesulfonamide | 435 [MH]+ |

| Eg No | Name | MS m/z (unless otherwise indicated) |
|---|---|---|
| 105 | 4-(biphenyl-2-yloxy)-3-cyano-N-1,3-thiazol-5-ylbenzenesulfonamide | 434 [MH]+ |
| 106 | 4-(biphenyl-2-yloxy)-3-cyano-N-pyrimidin-4-ylbenzenesulfonamide | 429 [MH]+ |
| 107 | 4-(biphenyl-2-yloxy)-3-cyano-N-(5-cyano-1,3-thiazol-2-yl)benzenesulfonamide | 457 [MH]– |
| 108 | 4-(biphenyl-2-yloxy)-3-cyano-N-isoxazol-4-ylbenzenesulfonamide | 435 [MNH$_4$]+ |
| 109 | 4-(biphenyl-2-yloxy)-3-cyano-N-1,2,5-thiadiazol-3-ylbenzenesulfonamide | 433 [MH]– |
| 110 | 4-(biphenyl-2-yloxy)-3-cyano-N-isoxazol-3-ylbenzenesulfonamide | 418 [MH]+ |
| 111 | REFERENCE EXAMPLE 4-(biphenyl-2-yloxy)-3-cyano-N-[2-(trifluoromethyl)phenyl]benzenesulfonamide | 512 [MNH$_4$]+ |
| 112 | 4-(biphenyl-2-yloxy)-3-cyano-N-(5-methyl-1,2,3-thiadiazol-4-yl)benzenesulfonamide | 449 [MH]+ |
| 113 | 4-(biphenyl-2-yloxy)-3-cyano-N-(1-methyl-1H-imidazol-2-yl)benzenesulfonamide | 431 [MH]+ |
| 114 | REFERENCE EXAMPLE 4-(biphenyl-2-yloxy)-3-cyano-N-phenylbenzenesulfonamide | 444 [MNH$_4$]+ |
| 115 | 4-(biphenyl-2-yloxy)-3-cyano-N-[6-(trifluoromethyl)pyrimidin-4-yl]benzenesulfonamide | 497 [MH]+ |
| 116 | 4-(biphenyl-2-yloxy)-3-cyano-N-[2-(trifluoromethyl)pyrimidin-4-yl]benzenesulfonamide | 497 [MH]+ |
| 117 | 4-(biphenyl-2-yloxy)-3-cyano-N-1H-imidazol-2-ylbenzenesulfonamide | 417 [MH]+ |
| 118 | 3-fluoro-N-1,3-thiazol-2-yl-4-{4-[(1,3,5-trimethyl-1H-pyrazol-4-yl)methyl]phenoxy}benzenesulfonamide | 473 [MH]+ |
| 119 | 4-[3-(benzyloxy)phenoxy]-3-fluoro-N-1,3-thiazol-2-ylbenzenesulfonamide | 457 [MH]+ |
| 120 | 4-[4-(benzyloxy)-3-fluorophenoxy]-3-fluoro-N-1,3-thiazol-2-ylbenzenesulfonamide | 475 [MH]+ |
| 121 | 3-fluoro-4-[4-(1,3-oxazol-4-yl)phenoxy]-N-1,3-thiazol-2-ylbenzenesulfonamide | 418 [MH]+ |
| 122 | 4-{4-[(3,5-dimethylisoxazol-4-yl)methyl]phenoxy}-3-fluoro-N-1,3-thiazol-2-ylbenzenesulfonamide | 460 [MH]+ |
| 123 | 4-[2,6-dimethyl-4-(pyrrolidin-1-ylmethyl)phenoxy]-3-fluoro-N-1,3-thiazol-2-ylbenzenesulfonamide | 462 [MH]+ |
| 124 | 3-fluoro-4-[4-(4-fluorophenoxy)phenoxy]-N-1,3-thiazol-2-ylbenzenesulfonamide | 461 [MH]+ |
| 125 | 4-[4-(azetidin-1-ylmethyl)-3-fluorophenoxy]-3-fluoro-N-1,3-thiazol-2-ylbenzenesulfonamide | 438 [MH]+ |
| 126 | 3-fluoro-4-(3-phenoxyphenoxy)-N-1,3-thiazol-2-ylbenzenesulfonamide | 443 [MH]+ |
| 127 | 3-fluoro-4-(4-phenoxyphenoxy)-N-1,3-thiazol-2-ylbenzenesulfonamide | 443 [MH]+ |
| 128 | 3-fluoro-4-[2-(3-methylisothiazol-5-yl)phenoxy]-N-1,3-thiazol-2-ylbenzenesulfonamide | 448 [MH]+ |
| 129 | 3-fluoro-4-[2-(4-methylisothiazol-5-yl)phenoxy]-N-1,3-thiazol-2-ylbenzenesulfonamide | 448 [MH]+ |
| 130 | 3-fluoro-4-[2-(2-methyl-1,3-thiazol-4-yl)phenoxy]-N-1,3-thiazol-2-ylbenzenesulfonamide | 448 [MH]+ |
| 131 | 3-fluoro-4-(2-pyridin-2-ylphenoxy)-N-1,3-thiazol-2-ylbenzenesulfonamide | 428 [MH]+ |
| 132 | 4-[4-(3-ethyl-5-methyl-4H-1,2,4-triazol-4-yl)phenoxy]-3-fluoro-N-1,3-thiazol-2-ylbenzenesulfonamide | 460 [MH]+ |
| 133 | 3-fluoro-4-[2-(tetrahydro-2H-pyran-2-yl)phenoxy]-N-1,3-thiazol-2-ylbenzenesulfonamide | 435 [MH]+ |
| 135 | N-(5-chloro-1,3-thiazol-2-yl)-3-cyano-4-[2-(pyridin-4-yloxy)phenoxy]benzenesulfonamide | 485 [M$^{35}$ClH]+ 487 [M$^{37}$C)H]+ |
| 136 | 4-[2-(benzyloxy)phenoxy]-N-(5-chloro-1,3-thiazol-2-yl)-3-cyanobenzenesulfonamide | 498 [M$^{35}$ClH]+ 500 [M$^{37}$ClH]+ |
| 137 | 4-{[4-(4-chlorophenyl)-1-methyl-1H-pyrazol-3-yl]oxy}-N-(5-chloro-1,3-thiazol-2-yl)-3-cyanobenzenesulfonamide | 506 [M$^{35}$ClH]+ 508 [M$^{37}$ClH]+ |
| 138 | N-(5-chloro-1,3-thiazol-2-yl)-3-cyano-4-[(1-methyl-4-phenyl-1H-pyrazol-5-yl)oxy]benzenesulfonamide | 472 [M$^{35}$ClH]+ 474 [M$^{37}$ClH]+ |
| 139 | 4-[(1-benzyl-4-methyl-1H-pyrazol-3-yl)oxy]-N-(5-chloro-1,3-thiazol-2-yl)-3-cyanobenzenesulfonamide | 486 [M$^{35}$ClH]+ 488 [M$^{37}$ClH]+ |
| 140 | 4-{[1-(2-chlorophenyl)-3-isopropyl-1H-pyrazol-4-yl]oxy}-N-(5-chloro-1,3-thiazol-2-yl)-3-cyanobenzenesulfonamide | NMR Data was: $^1$HNMR (d$_6$-DMSO): δ 1.20 (d, 6H), 2.83-2.96 (m, 1H), 7.23 (d, 1H), 7.47-7.56 (m, 2H), 7.58 (s, 1H), 7.64-7.71 (m, 2H), 8.09 (dd, 1H), 8.27 (d, 1H), 8.39 (s, 1H). |
| 141 | N-(5-chloro-1,3-thiazol-2-yl)-3-cyano-4-{[1-phenyl-3-(trifluoromethyl)-1H-pyrazol-5-yl]oxy}benzenesulfonamide | 526 [M$^{35}$ClH]+ 528 [M$^{37}$ClH]+ |
| 142 | 4-{[1-benzyl-3-(trifluoromethyl)-1H-pyrazol-5-yl]oxy}-N-(5-chloro-1,3-thiazol-2-yl)-3-cyanobenzenesulfonamide | 540 [M$^{35}$ClH]+ 542 [M$^{37}$ClH]+ |
| 143 | N-(5-chloro-1,3-thiazol-2-yl)-3-cyano-4-[(1-cyclohexyl-3-methyl-1H-pyrazol-5-yl)oxy]benzenesulfonamide | 478 [M$^{35}$ClH]+ 480 [M$^{37}$ClH]+ |
| 144 | N-(5-chloro-1,3-thiazol-2-yl)-3-cyano-4-(2-cyclopropylphenoxy)benzenesulfonamide | 432 [M$^{35}$ClH]+ 434 [M$^{37}$ClH]+ |
| 145 | N-(5-chloro-1,3-thiazol-2-yl)-3-cyano-4-{[3-isopropyl-1-(4-methoxyphenyl)-1H-pyrazol-4-yl]oxy}benzenesulfonamide | NMR Data was: $^1$HNMR (d$_6$-DMSO): δ 1.2 (d, 6H), 2.85 (m, 1H), 3.8 (s, 3H), 7.0 (m, 2H), 7.25 (m, 1H), 7.6 (m, 1H), 7.75 (m, 2H), 8.0 (m, 1H), 8.25 (m, 1H), 8.6 (s, 1H). |
| 146 | 4-(biphenyl-2-yloxy)-N-(5-chloro-1,3-thiazol-2-yl)-3-cyanobenzenesulfonamide | 468 [MH]+ |
| 147 | 4-(Biphenyl-2-yloxy)-N-(5-chloro-thiazol-2-yl)-3-fluoro-benzenesulfonamide | 461 [M$^{35}$ClH]+ |
| 148 | 3-chloro-4-[4-(cyclopropylmethyl)phenoxy]-N-1,2,4-thiadiazol-5-ylbenzenesulfonamide | 422 [M$^{35}$ClH]+ |
| 149 | 4-(biphenyl-2-yloxy)-3-chloro-N-1,2,4-thiadiazol-5-ylbenzenesulfonamide | 444 [M$^{35}$ClH]+ 446 [M$^{37}$ClH]+ |
| 150 | 4-(biphenyl-2-yloxy)-3-chloro-N-1,2,4-thiadiazol-5-ylbenzenesulfonamide | 444 [M$^{35}$ClH]+ 446 [M$^{37}$ClH]+ |
| 151 | 3-cyano-4-[4-fluoro-2-(6-methoxypyridin-3-yl)phenoxy]-N-1,3-thiazol-2-ylbenzenesulfonamide | 483 [MH]+ |
| 152 | 3-cyano-4-[(4',5-difluorobiphenyl-2-yl)oxy]-N-1,3-thiazol-2-ylbenzenesulfonamide | 470 [MH]+ |
| 153 | 3-cyano-4-{[5-fluoro-3'-(2-hydroxyethyl)biphenyl-2-yl]oxy}-N-1,3-thiazol-2-ylbenzenesulfonamide | 496 [MH]+ |
| 154 | 3-cyano-4-[(5-fluoro-3'-methoxybiphenyl-2-yl)oxy]-N-1,3-thiazol-2-ylbenzenesulfonamide | 482 [MH]+ |
| 155 | 4-[(5-chloro-4'-isopropoxybiphenyl-2-yl)oxy]-3-cyano-N-1,3-thiazol-2-ylbenzenesulfonamide | 526 [M$^{35}$ClH]+ |
| 156 | 4-[(5-chlorobiphenyl-2-yl)oxy]-3-cyano-N-1,3-thiazol-2-ylbenzenesulfonamide | 468 [M$^{35}$ClH]+ |
| 157 | 3-cyano-4-[(5-fluoro-4'-isopropoxybiphenyl-2-yl)oxy]-N-1,3-thiazol-2-ylbenzenesulfonamide | 510 [MH]+ |
| 158 | 3-cyano-N-1,3-thiazol-2-yl-4-[(3',4',5-trifluorobiphenyl-2-yl)oxy]benzenesulfonamide | 488 [MH]+ |
| 159 | 4-[4-chloro-2-(2-methyl-1H-imidazol-1-yl)phenoxy]-3-cyano-N-1,3-thiazol-2-ylbenzenesulfonamide | 472 [M$^{35}$ClH]+ 474 [M$^{37}$ClH]+ |

| Eg No | Name | MS m/z (unless otherwise indicated) |
|---|---|---|
| 160 | 3-cyano-4-{[5-fluoro-3'-(methoxymethyl)biphenyl-2-yl]oxy}-N-1,3-thiazol-2-ylbenzenesulfonamide | 496 [MH]+ |
| 161 | 3-cyano-4-{[5-fluoro-3'-(hydroxymethyl)biphenyl-2-yl]oxy}-N-1,3-thiazol-2-ylbenzenesulfonamide | 482 [MH]+ |
| 162 | 3-cyano-4-{[5-fluoro-4'-(hydroxymethyl)biphenyl-2-yl]oxy}-N-1,3-thiazol-2-ylbenzenesulfonamide | 482 [MH]+ |
| 163 | 3-cyano-4-{[5-fluoro-4'-(methoxymethyl)biphenyl-2-yl]oxy}-N-1,3-thiazol-2-ylbenzenesulfonamide | 496 [MH]+ |
| 164 | 4-(4-chloro-2-pyridin-2-ylphenoxy)-3-cyano-N-1,3-thiazol-2-ylbenzenesulfonamide | 470 [M$^{35}$ClH]+ |
| 165 | 4-(biphenyl-2-yloxy)-3-cyano-N-(thiazol-2-yl)benzenesulfonamide | 434 [MH]+ |
| 166 | 3-cyano-4-(2-(2-methylthiazol-4-yl)phenoxy)-N-(thiazol-2-yl)benzenesulfonamide | 455 [MH]+ |
| 167 | 4-(1-(4-chlorobenzyl)-1H-pyrazol-4-yloxy)-3-cyano-N-(thiazol-2-yl)benzenesulfonamide | 472 [M$^{35}$ClH]+ |
| 168 | 3-cyano-4-(1-phenyl-3-(trifluoromethyl)-1H-pyrazol-5-yloxy)-N-(thiazol-2-yl)benzenesulfonamide | 492 [MH]+ |
| 169 | 3-cyano-4-(4-fluoro-2-(1-methyl-1H-pyrazol-5-yl)phenoxy)-N-(thiazol-2-yl)benzenesulfonamide | 456 [MH]+ |
| 170 | 4-(4-fluoro-2-(1-methyl-1H-pyrazol-5-yl)phenoxy)-3-cyano-N-(thiazol-2-yl)benzenesulfonamide | 472 [M$^{35}$ClH]+ |
| 171 | 4-(4-chloro-2-(1-phenyl-1H-pyrazol-5-yl)phenoxy)-3-cyano-N-(thiazol-2-yl)benzenesulfonamide | 534 [M$^{35}$ClH]+ |
| 172 | 3-cyano-4-(2-(1-methyl-1H-pyrazol-5-yl)phenoxy)-N-(thiazol-2-yl)benzenesulfonamide | 438 [MH]+ |
| 173 | 4-(2-(1,3,4-oxadiazol-2-yl)phenoxy)-3-cyano-N-(thiazol-2-yl)benzenesulfonamide | 426 [MH]+ |
| 174 | 3-cyano-4-(2-(isoxazol-5-yl)phenoxy)-N-(thiazol-2-yl)benzenesulfonamide | 425 [MH]+ |
| 175 | 3-cyano-4-(4-fluoro-2-(1-(2,2,2-trifluoroethyl)-1H-pyrazol-5-yl)phenoxy)-N-(thiazol-2-yl)benzenesulfonamide | 524 [MH]+ |
| 176 | 3-cyano-4-(4-fluoro-2-(5-methyl-1H-pyrazol-1-yl)phenoxy)-N-(thiazol-2-yl)benzenesulfonamide | 456 [MH]+ |
| 177 | 4-(4-chloro-2-(1-(2,2,2-trifluoroethyl)-1H-pyrazol-5-yl)phenoxy)-3-cyano-N-(thiazol-2-yl)benzenesulfonamide | 540 [M$^{35}$ClH]+ |
| 178 | 4-(2-chloro-4-(1-methyl-1H-pyrazol-3-yl)phenoxy)-3-cyano-N-(thiazol-2-yl)benzenesulfonamide | 472 [M$^{35}$ClH]+ |
| 179 | 4-(2-chloro-4-(1-methyl-1H-pyrazol-5-yl)phenoxy)-3-cyano-N-(thiazol-2-yl)benzenesulfonamide | 472 [M$^{35}$ClH]+ |
| 180 | 3-cyano-4-(2-(1-ethyl-1H-pyrazol-5-yl)-4-fluorophenoxy)-N-(thiazol-2-yl)benzenesulfonamide | 471 [MH]+ |
| 181 | 3-cyano-4-(2-(4-phenyl-4H-1,2,4-triazol-3-yl)phenoxy)-N-(thiazol-2-yl)benzenesulfonamide | 501 [MH]+ |
| 182 | 4-(2-chloro-4-(4-methyl-4H-1,2,4-triazol-3-yl)phenoxy)-3-cyano-N-(thiazol-2-yl)benzenesulfonamide | 473 [M$^{35}$ClH]+ |
| 183 | 3-cyano-N-thiazol-2-yl-4-[4-(3-trifluoromethyl-pyrazol-1-yl)-phenoxy]-benzenesulfonamide | 492 [MH]+ |
| 184 | 4-[4-(1-tert-butyl-1H-pyrazol-3-yl)-2-fluoro-phenoxy]-3-cyano-N-thiazol-2-yl-benzenesulfonamide | 498 [MH]+ |
| 185 | 3-cyano-4-[2-fluoro-4-(1H-pyrazol-3-yl)-phenoxy]-N-thiazol-2-yl-benzenesulfonamide | 442 [MH]+ |
| 186 | 3-cyano-4-[4-(3,5-dimethyl-pyrazol-1-yl)-phenoxy]-N-thiazol-2-yl-benzenesulfonamide | 452 [MH]+ |
| 187 | 4-(biphenyl-4-yloxy)-3-cyano-N-thiazol-2-yl-benzenesulfonamide | 434 [MH]+ |
| 188 | 3-cyano-4-[5-(2-fluoro-phenyl)-2-(2,2,2-trifluoro-ethyl)-2H-pyrazol-3-yloxy]-N-thiazol-2-yl-benzenesulfonamide | 524 [MH]+ |
| 189 | 4-[5-(4-chloro-phenyl)-2-(2,2,2-trifluoro-ethyl)-2H-pyrazol-3-yloxy]-3-cyano-N-thiazol-2-yl-benzenesulfonamide | 540 [M$^{35}$ClH]+ |
| 190 | 3-cyano-4-[5-phenyl-2-(2,2,2-trifluoro-ethyl)-2H-pyrazol-3-yloxy]-N-thiazol-2-yl-benzenesulfonamide | 506 [MH]+ |
| 191 | 3-cyano-4-(5-cyclopropyl-2-pyridin-2-yl-2H-pyrazol-3-yloxy)-N-thiazol-2-yl-benzenesulfonamide | 465 [MH]+ |
| 192 | 3-Cyano-4-(2-cyclohexyl-5-cyclopropyl-2H-pyrazol-3-yloxy)-N-thiazol-2-yl-benzenesulfonamide | 470 [MH]+ |
| 193 | 3-cyano-4-[5-cyclopropyl-2-(2-fluoro-phenyl)-2H-pyrazol-3-yloxy]-N-thiazol-2-yl-benzenesulfonamide | 482 [MH]+ |
| 194 | 3-Cyano-4-[5-cyclopropyl-2-(2,2,2-trifluoro-ethyl)-2H-pyrazol-3-yloxy]-N-thiazol-2-yl-benzenesulfonamide | 470 [MH]+ |
| 195 | 3-Cyano-4-[5-cyclopropyl-2-(2,5-difluoro-phenyl)-2H-pyrazol-3-yloxy]-N-thiazol-2-yl-benzenesulfonamide | 500 [MH]+ |
| 196 | 4-[4-Chloro-2-(4-fluoro-2-methyl-2H-pyrazol-3-yl)-phenoxy]-3-cyano-N-thiazol-2-yl-benzenesulfonamide | 490 [M$^{35}$ClH]+ |
| 197 | 4-(4-chloro-3-methyl-2-[1,3,4]oxadiazol-2-yl-phenoxy)-3-cyano-N-thiazol-2-yl-benzenesulfonamide | 474 [M$^{35}$ClH]+ |
| 198 | 4-[2-(2-tert-butyl-2H-pyrazol-3-yl)-3-chloro-phenoxy]-3-cyano-N-thiazol-2-yl-benzenesulfonamide | 514 [M$^{35}$ClH]+ |
| 199 | 4-[3-chloro-2-(2H-pyrazol-3-yl)-phenoxy]-3-cyano-N-thiazol-2-yl-benzenesulfonamide | 458 [M$^{35}$ClH]+ |
| 200 | 3-cyano-4-(2-(3-methyl-1H-pyrazol-4-yl)phenoxy)-N-(thiazol-2-yl)benzenesulfonamide | 438 [MH]+ |
| 201 | 3-cyano-4-{[5-fluoro-4'-(2-hydroxyethyl)biphenyl-2-yl]oxy}-N-1,3-thiazol-2-ylbenzenesulfonamide | 496 [MH]+ |
| 202 | 3-cyano-N-thiazol-2-yl-4-[4-(5-trifluoromethyl-2H-pyrazol-3-yl)-phenoxy]-benzenesulfonamide | 492 [MH]+ |
| 203 | 5-(N-thiazol-2-ylsulfamoyl)-2-(4-(3-(trifluoromethyl)-1H-pyrazol-5-yl)phenoxy)benzamide | 510 [MH]+ |
| 204 | 4-{[1-(4-chlorobenzyl)-1H-pyrazol-3-yl]oxy}-N-1,2,4-thiadiazol-5-yl-3-(trifluoromethyl)benzenesulfonamide | NMR Data was: $^1$HNMR (d$_6$-DMSO): δ 5.2 (s, 2H), 6.1 (m, 1H), 7.25 (m, 3H), 7.4 (m, 2H), 7.9 (m, 1H), 8.0 (m, 2H), 8.45 (s, 1H). |
| 205 | 4-(biphenyl-2-yloxy)-N-1,2,4-thiadiazol-5-yl-3-(trifluoromethyl)benzenesulfonamide | NMR Data was: $^1$HNMR (d$_6$-DMSO): δ 6.86 (d, 1H, J = 8.4 Hz), 7.23-7.49 (m, 8H), 7.58 (d, 1H, J = 7.6 Hz), 7.89-7.92 (m, 2H), 8.39 (s, 1H). |
| 206 | 4-(1-(4-chlorobenzyl)-1H-pyrazol-4-yloxy)-2-fluoro-N-(thiazol-2-yl)benzenesulfonamide | 465 [M$^{35}$ClH]+ |
| 207 | 2-fluoro-4-(2'-methoxybiphenyl-2-yloxy)-N-(thiazol-2-yl)benzenesulfonamide | 457 [MH]+ |
| 208 | 2-fluoro-4-(2'-methoxybiphenyl-3-yloxy)-N-(thiazol-2-yl)benzenesulfonamide | 427 [MH]+ |
| 209 | 4-(biphenyl-4-yloxy)-2-fluoro-N-(thiazol-2-yl)benzenesulfonamide | 427 [MH]+ |
| 210 | 4-(biphenyl-3-yloxy)-2-fluoro-N-(thiazol-2-yl)benzenesulfonamide | 427 [MH]+ |

| Eg No | Name | MS m/z (unless otherwise indicated) |
|---|---|---|
| 211 | 4-(4-chloro-2-(1-phenyl-1H-pyrazol-5-yl)phenoxy)-2-fluoro-N-(thiazol-2-yl)benzenesulfonamide | 527 [M$^{35}$ClH]+ |
| 212 | 4-(2-(1-tert-butyl-1H-pyrazol-3-yl)-4-fluorophenoxy)-2-fluoro-N-(thiazol-2-yl)benzenesulfonamide | 491 [MH]+ |
| 213 | 2-fluoro-4-(4-fluoro-2-(1H-pyrazol-5-yl)phenoxy)-N-(thiazol-2-yl)benzenesulfonamide | 435 [MH]+ |
| 214 | 4-[2-(4-chloro-benzyl)-thiazol-2-yloxy]-2-fluoro-N-thiazol-2-yl-benzenesulfonamide | 482 [M$^{35}$ClH]+ |
| 215 | 3-fluoro-4-(4-methyl-2-(1-methyl-1H-pyrazol-3-yl)phenoxy)-N-(thiazol-2-yl)benzenesulfonamide | 431 [MH]+ |
| 216 | 4-(4-chloro-2-(1-methyl-1H-pyrazol-3-yl)phenoxy)-3-fluoro-N-(thiazol-2-yl)benzenesulfonamide | 465 [M$^{35}$ClH]+ |
| 217 | 4-(2-(1-tert-butyl-1H-pyrazol-5-yl)-4-fluorophenoxy)-3-fluoro-N-(thiazol-2-yl)benzenesulfonamide | 491 [MH]+ |
| 218 | 3-fluoro-4-(4-fluoro-2-(1H-pyrazol-5-yl)phenoxy)-N-(thiazol-2-yl)benzenesulfonamide | 435 [MH]+ |
| 219 | 4-(4-chloro-2-(1-methyl-1H-pyrazol-5-yl)phenoxy)-3-fluoro-N-(thiazol-2-yl)benzenesulfonamide | 465 [M$^{35}$ClH]+ |
| 220 | 4-(2-(1-benzyl-1H-pyrazol-5-yl)-4-chlorophenoxy)-3-fluoro-N-(thiazol-2-yl)benzenesulfonamide | 541 [M$^{35}$ClH]+ |
| 221 | ethyl 2-(5-(5-fluoro-2-(2-fluoro-4-(N-thiazol-2-ylsulfamoyl)phenoxy)phenyl)-1H-pyrazol-1-yl)acetate | 521 [MH]+ |
| 222 | 3-fluoro-4-(4-methyl-2-(1-methyl-1H-pyrazol-5-yl)phenoxy)-N-(thiazol-2-yl)benzenesulfonamide | 445 [MH]+ |
| 223 | 4-(2-(1-tert-butyl-4-methyl-1H-pyrazol-5-yl)-4-methylphenoxy)-3-fluoro-N-(thiazol-2-yl)benzenesulfonamide | 501 [MH]+ |
| 224 | 3-fluoro-4-(4-methyl-2-(1H-pyrazol-5-yl)phenoxy)-N-(thiazol-2-yl)benzenesulfonamide | 445 [MH]+ |
| 225 | 3-fluoro-4-(4-fluoro-2-(1-(2,2,2-trifluoroethyl)-1H-pyrazol-5-yl)phenoxy)-N-(thiazol-2-yl)benzenesulfonamide | 517 [MH]+ |
| 226 | 4-(4-bromo-2-(1-methyl-1H-pyrazol-5-yl)phenoxy)-3-fluoro-N-(thiazol-2-yl)benzenesulfonamide | 511 [M$^{81}$BrH]+ |
| 227 | 4-(4-chloro-2-(1-phenyl-1H-pyrazol-5-yl)phenoxy)-3-fluoro-N-(thiazol-2-yl)benzenesulfonamide | 527 [M$^{35}$ClH]+ |
| 228 | 4-[2-(2,5-difluoro-phenyl)-5-trifluoromethyl-2H-pyrazol-3-yloxy]-3-fluoro-N-thiazol-2-yl-benzenesulfonamide | 521 [MH]+ |
| 229 | 3-fluoro-4-(2-phenyl-5-trifluoromethyl-2H-pyrazol-3-yloxy)-N-thiazol-2-yl-benzenesulfonamide | 485 [MH]+ |
| 230 | 3-fluoro-4-[2-(2-fluoro-phenyl)-5-trifluoromethyl-2H-pyrazol-3-yloxy)-N-thiazol-2-yl-benzenesulfonamide | 503 [MH]+ |
| 231 | 3-fluoro-4-(5-methyl-2-phenyl-2H-pyrazol-3-yloxy)-N-thiazol-2-yl-benzenesulfonamide | 431 [MH]+ |
| 232 | 4-[1-(4-chloro-benzyl)-1H-pyrazol-3-yloxy]-3-fluoro-N-thiazol-2-yl-benzenesulfonamide | 465 [M$^{35}$ClH]+ |
| 233 | 3-fluoro-4-(1-methyl-4-phenyl-1H-pyrazol-3-yloxy)-N-(thiazol-2-yl)benzenesulfonamide | 431 [MH]+ |
| 234 | 3-fluoro-4-(4-(methoxymethyl)-2-(1-methyl-1H-pyrazol-5-yl)phenoxy)-N-(thiazol-2-yl)benzenesulfonamide | 475 [MH]+ |
| 235 | 4-(1-(4-chlorobenzyl)-1H-pyrazol-4-yloxy)-3-fluoro-N-(thiazol-2-yl)benzenesulfonamide | 465 [M$^{35}$ClH]+ |
| 236 | 3-fluoro-4-(5-phenylpyrimidin-4-yloxy)-N-(thiazol-2-yl)benzenesulfonamide | 429 [MH]+ |
| 237 | 3-fluoro-4-{4-fluoro-2-[1-(2-hydroxyethyl)-1H-pyrazol-5-yl]phenoxy}-N-1,3-thiazol-2-ylbenzenesulfonamide | 479 [MH]+ |
| 238 | 2-(5-(5-fluoro-2-(2-fluoro-4-(N-thiazol-2-ylsulfamoyl)phenoxy)phenyl)-1H-pyrazol-1-yl)acetic acid | 493 [MH]+ |
| 239 | 2-(5-(5-fluoro-2-(2-fluoro-4-(N-thiazol-2-ylsulfamoyl)phenoxy)phenyl)-1H-pyrazol-1-yl)-N,N-dimethylacetamide | 520 [MH]+ |
| 240 | 4-[2-tert-butyl-5-(4-chloro-benzyl)-2H-pyrazol-3-yloxy]-3-fluoro-N-thiazol-2-yl-benzenesulfonamide | 521 [M$^{35}$ClH]+ |
| 241 | 4-[5-(4-chloro-benzyl)-2-methyl-2H-pyrazol-3-yloxy]-3-fluoro-N-thiazol-2-yl-benzenesulfonamide | 479 [M$^{35}$ClH]+ |
| 242 | 4-(biphenyl-2-yloxy)-3-fluoro-N-thiazol-2-yl-benzenesulfonamide | 427 [MH]+ |
| 243 | 4-(3-(4-chlorobenzyl)-1H-pyrazol-5-yloxy)-3-fluoro-N-(thiazol-2-yl)benzenesulfonamide | 465 [M$^{35}$ClH]+ |
| 244 | 4-(4-chloro-3-methyl-2-[1,3,4]oxadiazol-2-yl-phenoxy)-3-fluoro-N-thiazol-2-yl-benzenesulfonamide | 467 [M$^{35}$ClH]+ |
| 245 | 4-[4-(2-tert-butyl-5-trifluoromethyl-2H-pyrazol-3-yl)-phenoxy]-3-fluoro-N-thiazol-2-yl-benzenesulfonamide | 541 [MH]+ |
| 246 | 3-fluoro-N-(thiazol-2-yl)-4-(4-(3-(trifluoromethyl)-1H-pyrazol-5-yl)phenoxy)benzenesulfonamide | 485 [MH]+ |
| 247 | 4-(biphenyl-4-yloxy)-3-fluoro-N-thiazol-2-yl-benzenesulfonamide | 427 [MH]+ |
| 248 | 4-[4-(3,5-dimethyl-pyrazol-1-yl)-phenoxy]-3-fluoro-N-thiazol-2-yl-benzenesulfonamide | 445 [MH]+ |
| 249 | 2-(1-(4-chlorobenzyl)-1H-pyrazol-4-yloxy)-5-(N-thiazol-2-ylsulfamoyl)benzamide | 490 [M$^{35}$ClH]+ |
| 250 | 2-(biphenyl-2-yloxy)-5-(N-thiazol-2-ylsulfamoyl)benzamide | 452 [MH]+ |
| 251 | 4-(biphenyl-2-yloxy)-3-fluoro-N-(1,3,4-thiadiazol-2-yl)benzenesulfonamide | 428 [MH]+ |
| 252 | 4-(2-(1-benzyl-3-methyl-1H-pyrazol-4-yl)phenoxy)-3-fluoro-N-(1,2,4-thiadiazol-5-yl)benzenesulfonamide | 522 [MH]+ |
| 253 | 4-[2-(2,5-difluoro-phenyl)-5-trifluoromethyl-2H-pyrazol-3-yloxy]-3-fluoro-N-1,2,4-thiadiazol-5-yl-benzenesulfonamide | 522 [MH]+ |
| 254 | 3-fluoro-4-(2-phenyl-5-trifluoromethyl-2H-pyrazol-3-yloxy)-N-1,2,4-thiadiazol-5-yl-benzenesulfonamide | 486 [MH]+ |
| 255 | 3-fluoro-4-[2-(2-fluoro-phenyl)-5-trifluoromethyl-2H-pyrazol-3-yloxy]-N-1,2,4-thiadiazol-5-yl-benzenesulfonamide | 504 [MH]+ |
| 256 | 4-(biphenyl-2-yloxy)-3-methyl-N-1,2,4-thiadiazol-5-ylbenzenesulfonamide | NMR Data was: $^1$HNMR (d$_6$-DMSO): δ 2.24 (s, 3H), 6.65 (m, 1H), 7.09 (m, 1H), 7.25-7.53 (m, 9H), 7.62 (m, 1H), 8.44 (s, 1H). |
| 257 | 4-{[1-(4-chlorobenzyl)-1H-pyrazol-3-yl]oxy}-3-methyl-N-1,2,4-thiadiazol-5-ylbenzenesulfonamide | NMR Data was: $^1$H NMR (400 MHz, d$_6$-DMSO): δ 2.3 (s, 3H), 5.22 (s, 2H), 5.9 (m, 1H), 7.0 (m, 1H), 7.2 (m, 2H), 7.4 (m, 2H), 7.6 (m, 1H), 7.8 (m, 1H), 8.45 (s, 1H). |
| 258 | 4-(biphenyl-2-yloxy)-3-methyl-N-1,3-thiazol-2-ylbenzenesulfonamide | 423 [MH]+ |
| 259 | 4-{[1-(4-chlorobenzyl)-1H-pyrazol-3-yl]oxy}-3-methoxy-N-1,2,4-thiadiazol-5-ylbenzenesulfonamide | NMR Data was: $^1$HNMR (d$_6$-DMSO): δ 3.8 (s, 3H), 5.2 (s, 2H), 5.9 (m, 1H), 7.1 (m, 1H), 7.2 (m, 2H), 7.4 (m, 3H), 7.8 (m, 1H), 8.45 (s, 1H |

| Eg No | Name | MS m/z (unless otherwise indicated) |
|---|---|---|
| 260 | 4-(biphenyl-2-yloxy)-N-1,2,4-thiadiazol-5-yl-2-(trifluoromethyl)benzenesulfonamide | NMR Data was: $^1$HNMR (d$_6$-DMSO): δ 7.15 (m, 1H), 7.25-7.36 (m, 5H), 7.42-7.44 (m, 3H), 7.49 (m, 1H), 7.56 (m, 1H), 8.05 (m, 1H), 8.46 (s, 1H) |
| 261 | 4-(biphenyl-2-yloxy)-2-methyl-N-1,2,4-thiadiazol-5-ylbenzenesulfonamide | NMR Data was: $^1$HNMR (d$_6$-DMSO): δ 2.4 (s, 3H), 6.7 (m, 1H), 6.9 (m, 1H), 7.1 (m, 1H), 7.2-7.5 (m, 8H), 7.8 (m, 1H), 8.4 (s, 1H) |
| 262 | 4-(biphenyl-2-yloxy)-3-methoxy-N-1,2,4-thiadiazol-5-ylbenzenesulfonamide | NMR Data was: $^1$HNMR (d$_6$-DMSO): δ 3.8 (s, 3H), 6.9 (m, 2H), 7.2-7.4 (m, 7H), 7.45-7.5 (m, 3H), 8.44 (s, 1H) |
| 263 | 4-(biphenyl-2-yloxy)-2-chloro-N-1,2,4-thiadiazol-5-ylbenzenesulfonamide | NMR Data was: $^1$HNMR (d$_6$-DMSO): δ 6.89 (dd, 1H, J = 2.4 & 8.8 Hz), 7.07 (d, 1H, J = 2.4 Hz), 7.24-7.50 (m, 8H), 7.55 (dd, 1H, J = 2.0 & 7.6 Hz), 7.94 (d, 1H, J = 8.8 Hz), 8.48 (s, 1H) |
| 264 | 4-(biphenyl-2-yloxy)-3,5-difluoro-N-1,2,4-thiadiazol-5-ylbenzenesulfonamide | NMR Data was: $^1$HNMR (d$_6$-DMSO): δ 6.90 (m, 1H), 7.16-7.70 (m, 10H), 8.48 (s, 1H) |
| 265 | 4-{[1-(4-chlorobenzyl)-1H-pyrazol-3-yl]oxy}-3,5-difluoro-N-1,2,4-thiadiazol-5-ylbenzenesulfonamide | NMR Data was: $^1$HNMR (d$_6$-DMSO): δ 5.15 (s, 2H), 5.97 (d, 1H, J = 2.0 Hz), 7.15 (d, 2H, J = 8.0 Hz), 7.39 (d, 2H, J = 8.0 Hz), 7.67 (d, 2H, J = 6.8 Hz), 7.76 (d, 1H, J = 2.0 Hz), 8.46 (s, 1H) |
| 266 | 4-(biphenyl-2-yloxy)-2,5-difluoro-N-1,2,4-thiadiazol-5-ylbenzenesulfonamide | NMR Data was: $^1$HNMR (d$_6$-DMSO): δ 6.89-6.90 (m, 1H), 7.22 (m, 1H), 7.29-7.53 (m, 8H), 7.68-7.70 (m, 1H), 8.47 (s, 1H) |
| 267 | 4-(biphenyl-2-yloxy)-2-chloro-5-fluoro-N-1,2,4-thiadiazol-5-ylbenzenesulfonamide | NMR Data was: $^1$HNMR (d$_6$-DMSO): δ 7.01 (m, 1H), 7.24 (m, 1H), 7.28-7.48 (m, 7H), 7.53 (m, 1H), 7.88 (d, 1H) 8.49 (s, 1H) |
| 268 | 4-(biphenyl-2-yloxy)-2-cyano-N-1,2,4-thiadiazol-5-ylbenzenesulfonamide | 435 [MH]+ |
| 269 | 4-(biphenyl-2-yloxy)-2,3-difluoro-N-1,2,4-thiadiazol-5-ylbenzenesulfonamide | NMR Data was: $^1$HNMR (d$_6$-DMSO): δ 6.70-6.74 (m, 1H), 7.26-7.55 (m, 10H), 8.43 (s, 1H) |
| 270 | 4-(biphenyl-2-yloxy)-5-chloro-2-fluoro-N-1,2,4-thiadiazol-5-ylbenzenesulfonamide | NMR Data was: $^1$HNMR (d$_6$-DMSO): δ 6.72 (m, 1H), 7.22 (m, 1H), 7.27 (m, 1H), 7.36 (m, 2H), 7.39-7.48 (m, 4H), 7.54 (m, 1H), 7.79 (m, 1H), 8.41 (s, 1H) |
| 271 | 4-(biphenyl-2-yloxy)-3-fluoro-N-thiazol-4-yl-benzenesulfonamide | 427 [MH]+ |
| 272 | 4-[4-chloro-2-(2-methyl-2H-pyrazol-3-yl)-phenoxy]-3-fluoro-N-thiazol-4-yl-benzenesulfonamide | 465 [M$^{35}$ClH]+ |
| 273 | 4-(biphenyl-4-yloxy)-3-fluoro-N-thiazol-4-yl-benzenesulfonamide | 427 [MH]+ |
| 274 | 3-fluoro-4-(2-phenyl-5-trifluoromethyl-2H-pyrazol-3-yloxy)-N-thiazol-4-yl-benzenesulfonamide | 485 [MH]+ |
| 275 | 4-[4-chloro-2-(2-methyl-2H-pyrazol-3-yl)-phenoxy]-3-fluoro-N-(5-fluoro-thiazol-2-yl)-benzenesulfonamide | 483 [M$^{35}$ClH]+ |
| 276 | 4-(biphenyl-2-yloxy)-N-thiazol-2-yl-benzenesulfonamide | 409 [MH]+ |
| 277 | 4-(5-methyl-2-phenyl-2H-pyrazol-3-yloxy)-N-thiazol-2-yl-benzenesulfonamide | 413 [MH]+ |
| 278 | 6-(biphenyl-2-yloxy)-pyridine-3-sulfonic acid thiazol-2-ylamide | 410 [MH]+ |
| 280 | 3-cyano-4-[4-(2-ethyl-5-trifluoromethyl-2H-pyrazol-3-yl)-phenoxy]-N-thiazol-2-yl-benzenesulfonamide | 520 [MH]+ |
| 281 | 4-(4-(1-tert-butyl-3-(trifluoromethyl)-1H-pyrazol-5-yl)phenoxy)-3-cyano-N-(5-fluorothiazol-2-yl)benzenesulfonamide | 566 [MH]+ |
| 282 | 3-cyano-4-[4-(2-methyl-5-trifluoromethyl-2H-pyrazol-3-yl)-phenoxy]-N-thiazol-2-yl-benzenesulfonamide | 506 [MH]+ |

The following further examples can be prepared analogously to the General Schemes described above, Library Protocols 1 and 2 (as described above and below) and Methods A-M as described for Examples 1-6, 95-99, 134, 170, and 279 above, or any of the other fully written up experimental conditions provided, substituting appropriate starting materials where necessary and making appropriate changes to experimental conditions informed by the schemes and conditions provided and common general knowledge. Purification was performed either by silica gel column chromatography, trituration or preparative HPLC.

Library Protocol 2

To the phenol (60 μmol) was added 600 μL of a prepared dimethyl sulphoxide solution of 3-cyano-4-fluoro-N-(5-fluoropyridin-2-yl)benzenesulfonamide (Preparation 301, 40 μmol per 600 μL). Potassium carbonate (16.6 mg, 120 μmol) was added and the mixture was stirred at 90° C. for 60 hours. The reaction mixture was cooled to room temperature and filtered. The filtrate was purified by preparative HPLC to afford the title compound.

| Eg No | Name | MS m/z (unless otherwise incidated) |
|---|---|---|
| 283 | 4-[4-chloro-2-(1-isopropyl-1H-pyrazol-4-yl)phenoxy]-3-cyano-N-1,2,4-thiadiazol-5-ylbenzenesulfonamide | 501 [M$^{35}$ClH]+ |
| 284 | 3-cyano-4-[2-(5-cyanopyridin-3-yl)-4-(trifluoromethyl)phenoxy]-N-1,2,4-thiadiazol-5-ylbenzenesulfonamide | 529 [MH]+ |
| 285 | 4-[2-(1-tert-butyl-1H-pyrazol-5-yl)-4-fluorophenoxy]-3-cyano-N-1,2,4-thiadiazol-5-ylbenzenesulfonamide | 499 [MH]+ |
| 286 | 4-[4-chloro-2-(1-methyl-1H-pyrazol-3-yl)phenoxy]-3-cyano-N-1,2,4-thiadiazol-5-ylbenzenesulfonamide | 473 [M$^{35}$ClH]+ |
| 287 | [1-(4-{2-cyano-4-[(1,2,4-thiadiazol-5-ylamino)sulfonyl]phenoxy}phenyl)-1H-pyrazol-4-yl]methyl trifluoroacetate | 551 [MH]+ |

| Eg No | Name | MS m/z (unless otherwise incidated) |
|---|---|---|
| 288 | 3-cyano-4-{4-[4-(hydroxymethyl)-1H-pyrazol-1-yl]phenoxy}-N-1,2,4-thiadiazol-5-ylbenzenesulfonamide | 455 [MH]+ |
| 289 | 3-cyano-4-[4-iodo-2-(1H-pyrazol-4-yl)phenoxy]-N-1,2,4-thiadiazol-5-ylbenzenesulfonamide | 551 [MH]+ |
| 290 | 3-cyano-4-{3-[1-ethyl-3-(trifluoromethyl)-1H-pyrazol-5-yl]phenoxy}-N-(3-methyl-1,2,4-thiadiazol-5-yl)benzenesulfonamide | 535 [MH]+ |
| 291 | 3-cyano-4-{4-[1-ethyl-3-(trifluoromethyl)-1H-pyrazol-5-yl]phenoxy}-N-(3-methyl-1,2,4-thiadiazol-5-yl)benzenesulfonamide | 535 [MH]+ |
| 292 | 3-cyano-4-{2-cyano-4-[1-methyl-3-(trifluoromethyl)-1H-pyrazol-5-yl]phenoxy}-N-1,3-thiazol-2-ylbenzenesulfonamide | 531 [MH]+ |
| 293 | 3-cyano-4-{2-cyano-4-[1-methyl-3-(trifluoromethyl)-1H-pyrazol-5-yl]phenoxy}-N-1,2,4-thiadiazol-5-ylbenzenesulfonamide | 532 [MH]+ |
| 294 | 5-chloro-4-[4-chloro-2-(1-methyl-1H-pyrazol-5-yl)phenoxy]-2-fluoro-N-(3-methyl-1,2,4-thiadiazol-5-yl)benzenesulfonamide | 514 [M$^{35}$ClH]+ 516 [M$^{37}$ClH]+ |
| 295 | 5-chloro-2-fluoro-4-[4-fluoro-2-(1-methyl-1H-pyrazol-5-yl)phenoxy]-N-pyrimidin-4-ylbenzenesulfonamide | 478 [M$^{35}$ClH]+ 480 [M$^{37}$ClH]+ |
| 296 | 5-chloro-4-{2-cyano-4-[1-methyl-3-(trifluoromethyl)-1H-pyrazol-5-yl]phenoxy}-2-fluoro-N-1,3-thiazol-2-ylbenzenesulfonamide | 558 [M$^{35}$ClH]+ 560 [M$^{37}$ClH]+ |
| 297 | 5-chloro-4-{2-cyano-4-[1-methyl-3-(trifluoromethyl)-1H-pyrazol-5-yl]phenoxy}-2-fluoro-N-1,3,4-thiadiazol-2-ylbenzenesulfonamide | 559 [M$^{35}$ClH]+ |
| 298 | 5-chloro-2-fluoro-4-[4-fluoro-2-(1-methyl-1H-pyrazol-5-yl)phenoxy]-N-1,3,4-thiadiazol-2-ylbenzenesulfonamide | 484 [M$^{35}$ClH]+ |
| 299 | 5-chloro-4-[4-chloro-2-(1-methyl-1H-pyrazol-5-yl)phenoxy]-2-fluoro-N-1,3,4-thiadiazol-2-ylbenzenesulfonamide | 500 [M$^{35}$ClH]+ |
| 300 | 5-chloro-4-[4-chloro-2-(1H-pyrazol-5-yl)phenoxy]-2-fluoro-N-1,3,4-thiadiazol-2-ylbenzenesulfonamide | 486 [M$^{35}$ClH]+ |
| 301 | 4-[4-chloro-2-(1-methyl-1H-pyrazol-5-yl)phenoxy]-2,5-difluoro-N-1,3,4-thiadiazol-2-ylbenzenesulfonamide | 484 [M$^{35}$ClH]+ |
| 302 | 4-[4-chloro-2-(1H-pyrazol-5-yl)phenoxy]-2,5-difluoro-N-1,3,4-thiadiazol-2-ylbenzenesulfonamide | 470 [M$^{35}$ClH]+ |
| 303 | 4-{4-[1-tert-Butyl-3-(trifluoromethyl)-1H-pyrazol-5-yl]phenoxy}-2-fluoro-N-1,3-thiazol-2-ylbenzenesulfonamide | 541 [MH]+ |
| 304 | 5-chloro-4-[4-chloro-2-(1-methyl-1H-pyrazol-5-yl)phenoxy]-2-fluoro-N-1,3-thiazol-2-ylbenzenesulfonamide | 499 [M$^{35}$ClH]+ |
| 305 | 5-chloro-4-{4-[1-ethyl-3-(trifluoromethyl)-1H-pyrazol-5-yl]phenoxy}-2-fluoro-N-1,3-thiazol-2-ylbenzenesulfonamide | 547 [M$^{35}$ClH]+ |
| 306 | 4-[4-chloro-2-(4-methyl-4H-1,2,4-triazol-3-yl)phenoxy]-3-fluoro-N-1,3-thiazol-2-ylbenzenesulfonamide | 466 [M$^{35}$ClH]+ |
| 307 | 4-[4-Chloro-2-(4-fluoro-1-methyl-1H-pyrazol-5-yl)phenoxy]-3-fluoro-N-1,3-thiazol-2-ylbenzenesulfonamide | 483 [M$^{35}$ClH]+ |
| 308 | 4-[4-Chloro-2-(1H-pyrazol-5-yl)phenoxy]-3-fluoro-N-1,3-thiazol-2-ylbenzenesulfonamide | 451 [M$^{35}$ClH]+ |
| 309 | 4-[4-Cyclopropyl-2-(1-methyl-1H-pyrazol-5-yl)phenoxy]-3-fluoro-N-1,3-thiazol-2-ylbenzenesulfonamide | 471 [MH]+ |
| 310 | 3-cyano-4-[4-fluoro-2-(3-isopropoxy-1-methyl-1H-pyrazol-5-yl)phenoxy]-N-1,3-thiazol-2-ylbenzenesulfonamide | 514 [MH]+ |
| 311 | 3-cyano-N-(3,5-difluoropyridin-2-yl)-4-{4-[1-ethyl-3-(trifluoromethyl)-1H-pyrazol-5-yl]phenoxy}benzenesulfonamide | 550 [MH]+ |
| 312 | 3-cyano-4-[4-iodo-2-(1-methyl-1H-pyrazol-5-yl)phenoxy]-N-1,3-thiazol-2-ylbenzenesulfonamide | 564 [MH]+ |
| 313 | 4-[4-chloro-2-(1-methyl-1H-pyrazol-5-yl)phenoxy]-3-cyano-N-1,3-thiazol-4-ylbenzenesulfonamide | 472 [M$^{35}$ClH]+ |
| 314 | 4-[4-chloro-2-(1H-pyrazol-4-yl)phenoxy]-3-cyano-N-(5-fluoropyridin-2-yl)benzenesulfonamide | 470 [M$^{35}$ClH]+ |
| 315 | 3-cyano-N-(5-fluoropyridin-2-yl)-4-[2-(1H-pyrazol-4-yl)-4-(trifluoromethyl)phenoxy]benzenesulfonamide | 504 [MH]+ |
| 316 | 3-cyano-4-{4-[1-ethyl-4-(trifluoromethyl)-1H-imidazol-2-yl]phenoxy}-N-1,3-thiazol-2-ylbenzenesulfonamide | 520 [MH]+ |
| 317 | 3-cyano-4-[4-(4-methyl-1,3-oxazol-2-yl)phenoxy]-N-1,3-thiazol-2-ylbenzenesulfonamide | 439 [MH]+ |
| 318 | 4-[4-chloro-2-(4-methyl-1,3-oxazol-2-yl)phenoxy]-3-cyano-N-1,3-thiazol-2-ylbenzenesulfonamide | 473 [M$^{35}$ClH]+ |
| 319 | 3-cyano-4-[3-(1H-pyrazol-1-yl)phenoxy]-N-1,3-thiazol-2-ylbenzenesulfonamide | 424 [MH]+ |
| 320 | 3-cyano-4-{4-[1-methyl-4-(trifluoromethyl)-1H-imidazol-2-yl]phenoxy}-N-1,3-thiazol-2-ylbenzenesulfonamide | 506 [MH]+ |
| 321 | 4-[4-chloro-2-(2H-1,2,3-triazol-2-yl)phenoxy]-3-cyano-N-1,3-thiazol-2-ylbenzenesulfonamide | 459 [M$^{35}$ClH]+ |
| 322 | 4-[4-chloro-2-(1H-1,2,3-triazol-1-yl)phenoxy]-3-cyano-N-1,3-thiazol-2-ylbenzenesulfonamide | 459 [M$^{35}$ClH]+ |
| 323 | 4-{4-chloro-2-[1-(ethoxymethyl)-1H-1,2,3-triazol-5-yl]phenoxy}-3-cyano-N-1,3-thiazol-2-ylbenzenesulfonamide | 515 [M$^{35}$ClH]− |
| 324 | 3-cyano-4-{4-[1-ethyl-5-(trifluoromethyl)-1H-pyrazol-3-yl]-2-fluorophenoxy}-N-1,3-thiazol-2-ylbenzenesulfonamide | 538 [MH]+ |
| 325 | 4-[4-chloro-2-(1-methyl-1H-1,2,4-triazol-3-yl)phenoxy]-3-cyano-N-1,3-thiazol-2-ylbenzenesulfonamide | 473 [M$^{35}$ClH]+ |
| 326 | 4-[4-chloro-2-(1-methyl-1H-1,2,4-triazol-5-yl)phenoxy]-3-cyano-N-1,3-thiazol-2-ylbenzenesulfonamide | 473 [M$^{35}$ClH]+ |
| 327 | 3-cyano-4-{4-[1-ethyl-3-(trifluoromethyl)-1H-pyrazol-5-yl]-3-fluorophenoxy}-N-1,3-thiazol-2-ylbenzenesulfonamide | 538 [MH]+ |
| 328 | 3-cyano-4-{4-[1-ethyl-3-(trifluoromethyl)-1H-pyrazol-5-yl]-2-fluorophenoxy}-N-1,3-thiazol-2-ylbenzenesulfonamide | 538 [MH]+ |
| 329 | 3-cyano-4-{3-fluoro-4-[1-methyl-3-(trifluoromethyl)-1H-pyrazol-5-yl]phenoxy}-N-1,3-thiazol-2-ylbenzenesulfonamide | 524 [MH]+ |
| 330 | 3-cyano-4-{2-fluoro-4-[1-methyl-3-(trifluoromethyl)-1H-pyrazol-5-yl]phenoxy}-N-1,3-thiazol-2-ylbenzenesulfonamide | 524 [MH]+ |
| 331 | 4-{[1-(4-chlorobenzyl)-1H-pyrazol-4-yl]oxy}-3-cyano-N-1,3-thiazol-2-ylbenzenesulfonamide | 472 [M$^{35}$ClH]+ |
| 332 | 4-{[1-(4-chlorophenyl)-1H-pyrazol-4-yl]oxy}-3-cyano-N-1,3-thiazol-2-ylbenzenesulfonamide | 458 [M$^{35}$ClH]+ |
| 333 | 3-cyano-4-{[1-(2,4-dichlorophenyl)-1H-pyrazol-4-yl]oxy}-N-1,3-thiazol-2-ylbenzenesulfonamide | 492 [M$^{35}$ClH]+ |
| 334 | 3-cyano-N-1,3-thiazol-2-yl-4-({1-[3-(trifluoromethyl)phenyl]-1H-pyrazol-4-yl}oxy)benzenesulfonamide | 492 [MH]+ |
| 335 | 4-{2-chloro-4-[1-methyl-3-(trifluoromethyl)-1H-pyrazol-5-yl]phenoxy}-3-cyano-N-1,3-thiazol-2-ylbenzenesulfonamide | 540 [M$^{35}$ClH]+ |
| 336 | 4-[4-chloro-3-(1H-1,2,4-triazol-1-ylmethyl)phenoxy]-3-cyano-N-1,3-thiazol-2-ylbenzenesulfonamide | 473 [M$^{35}$ClH]+ |
| 337 | 3-cyano-4-{4-[1-ethyl-3-(trifluoromethyl)-1H-pyrazol-5-yl]phenoxy}-N-isoxazol-3-ylbenzenesulfonamide | 504 [MH]+ |
| 338 | 3-cyano-4-{4-[1-ethyl-3-(trifluoromethyl)-1H-pyrazol-5-yl]phenoxy}-N-(5-fluoropyrimidin-2-yl)benzenesulfonamide | 533 [MH]+ |
| 339 | N-(3-chloropyridin-2-yl)-3-cyano-4-{4-[1-ethyl-3-(trifluoromethyl)-1H-pyrazol-5-yl]phenoxy}benzenesulfonamide | 548 [M$^{35}$ClH]+ |
| 340 | 3-cyano-4-{4-[1-ethyl-3-(trifluoromethyl)-1H-pyrazol-5-yl]phenoxy}-N-[5-(trifluoromethyl)pyridin-2-yl]benzenesulfonamide | 582 [MH]+ |
| 341 | 3-cyano-4-{4-[1-ethyl-3-(trifluoromethyl)-1H-pyrazol-5-yl]phenoxy}-N-1,2,5-thiadiazol-3-ylbenzenesulfonamide | 521 [MH]+ |
| 342 | 3-cyano-N-(4-cyanopyridin-2-yl)-4-{4-[1-ethyl-3-(trifluoromethyl)-1H-pyrazol-5-yl]phenoxy}benzenesulfonamide | 539 [MH]+ |

| Eg No | Name | MS m/z (unless otherwise indicated) |
|---|---|---|
| 343 | 3-cyano-N-(5-cyanopyridin-2-yl)-4-{4-[1-ethyl-3-(trifluoromethyl)-1H-pyrazol-5-yl]phenoxy}benzenesulfonamide | 539 [MH]+ |
| 344 | 3-cyano-4-{4-[1-ethyl-3-(trifluoromethyl)-1H-pyrazol-5-yl]phenoxy}-N-pyrimidin-2-ylbenzenesulfonamide | 513 [MH]− |
| 345 | 3-cyano-4-{4-[1-ethyl-3-(trifluoromethyl)-1H-pyrazol-5-yl]phenoxy}-N-(3-fluoropyridin-2-yl)benzenesulfonamide | 530 [MH]− |
| 346 | 3-cyano-4-{4-[1-ethyl-3-(trifluoromethyl)-1H-pyrazol-5-yl]phenoxy}-N-1,3,4-thiadiazol-2-ylbenzenesulfonamide | 519 [MH]− |
| 347 | 3-fluoro-4-[4-fluoro-2-(1-methyl-1H-pyrazol-5-yl)phenoxy]-N-(5-fluoro-1,3-thiazol-2-yl)benzenesulfonamide | 467 [MH]+ |
| 348 | 4-{4-[1-ethyl-3-(trifluoromethyl)-1H-pyrazol-5-yl]phenoxy}-3-fluoro-N-(5-fluoro-1,3-thiazol-2-yl)benzenesulfonamide | 529 [MH]− |
| 349 | 4-[4-chloro-2-(1-methyl-1H-1,2,4-triazol-5-yl)phenoxy]-3-fluoro-N-(5-fluoro-1,3-thiazol-2-yl)benzenesulfonamide | 484 [M$^{35}$ClH]+ |
| 350 | 3-cyano-4-[4-ethyl-2-(1-methyl-1H-pyrazol-5-yl)phenoxy]-N-1,3-thiazol-2-ylbenzenesulfonamide | 466 [MH]+ |
| 351 | 3-cyano-4-[4-isopropyl-2-(1-methyl-1H-pyrazol-5-yl)phenoxy]-N-1,3-thiazol-2-ylbenzenesulfonamide | 480 [MH]+ |
| 352 | 3-cyano-4-{2-isopropyl-4-[3-(trifluoromethyl)-1H-pyrazol-1-yl]phenoxy}-N-1,3-thiazol-2-ylbenzenesulfonamide | 534 [MH]+ |
| 353 | 4-[4-chloro-1H-pyrazol-1-yl)-2-isopropylphenoxy]-3-cyano-N-1,3-thiazol-2-ylbenzenesulfonamide | 500 [M$^{35}$ClH]+ |
| 354 | 3-cyano-4-{2-isopropyl-4-[1-methyl-3-(trifluoromethyl)-1H-pyrazol-5-yl]phenoxy}-N-1,3-thiazol-2-ylbenzenesulfonamide | 548 [MH]+ |
| 355 | 4-[4-bromo-2-(pyrrolidin-1-ylmethyl)phenoxy]-3-cyano-N-1,3-thiazol-2-ylbenzenesulfonamide | 519 [M$^{79}$BrH]+ |
| 356 | 3-cyano-4-{2-isopropyl-4-[5-methyl-3-(trifluoromethyl)-1H-pyrazol-1-yl]phenoxy}-N-1,3-thiazol-2-ylbenzenesulfonamide | 548 [MH]+ |
| 357 | 4-{4-chloro-2-[(3-hydroxypyrrolidin-1-yl)methyl]phenoxy}-3-cyano-N-1,3-thiazol-2-ylbenzenesulfonamide | 491 [M$^{35}$ClH]+ |
| 358 | 4-{4-chloro-2-[(4,4-difluoropiperidin-1-yl)methyl]phenoxy}-3-cyano-N-1,3-thiazol-2-ylbenzenesulfonamide | 525 [M$^{35}$ClH]+ |
| 359 | 3-cyano-4-[5-iodo-2-(1-methyl-1H-pyrazol-5-yl)phenoxy]-N-1,3-thiazol-2-ylbenzenesulfonamide | 564 [MH]+ |
| 360 | 4-{4-chloro-2-[(3,3-difluoropyrrolidin-1-yl)methyl]phenoxy}-3-cyano-N-1,3-thiazol-2-ylbenzenesulfonamide | 511 [M$^{35}$ClH]+ |
| 361 | 4-[4-chloro-2-(1-methyl-1H-pyrazol-5-yl)phenoxy]-3-cyano-N-pyrimidin-4-ylbenzenesulfonamide | 467 [M$^{35}$ClH]+ |
| 362 | 4-[4-chloro-2-(1-methyl-1H-pyrazol-5-yl)phenoxy]-3-cyano-N-isoxazol-3-ylbenzenesulfonamide | 454 [M$^{35}$ClH]− |
| 363 | 4-[4-chloro-2-(1-methyl-1H-pyrazol-5-yl)phenoxy]-3-cyano-N-1,3,4-thiadiazol-2-ylbenzenesulfonamide | 473 [M$^{35}$ClH]+ |
| 364 | 5-chloro-2-fluoro-4-(4-fluoro-2-(1-methyl-1H-pyrazol-5-yl)phenoxy)-N-(1,2,3-thiadiazol-4-yl)benzenesulfonamide | 484 [M$^{35}$ClH]+ |
| 365 | 3-fluoro-4-[2-(1-methyl-1H-pyrazol-5-yl)-4-(trifluoromethoxy)phenoxy]-N-1,3-thiazol-2-ylbenzenesulfonamide | 515 [MH]+ |
| 366 | 4-(biphenyl-2-yloxy)-3-cyano-N-(5-fluoropyridin-2-yl)benzenesulfonamide | 446 [MH]+ |
| 367 | 3-cyano-4-{4-[1-ethyl-3-(trifluoromethyl)-1H-pyrazol-5-yl]phenoxy}-N-(5-fluoropyridin-2-yl)benzenesulfonamide | 532 [MH]+ |
| 368 | 3-cyano-4-{3-[1-ethyl-3-(trifluoromethyl)-1H-pyrazol-5-yl]phenoxy}-N-(5-fluoropyridin-2-yl)benzenesulfonamide | 532 [MH]+ |
| 369 | 3-cyano-4-[4-(3-cyclopropyl-1-ethyl-1H-pyrazol-5-yl)phenoxy]-N-1,3-thiazol-2-ylbenzenesulfonamid | 492 [MH]+ |
| 370 | 3-cyano-4-[4-(3-cyclopropyl-1H-pyrazol-1-yl)phenoxy]-N-1,3-thiazol-2-ylbenzenesulfonamide | 464 [MH]+ |
| 371 | 3-cyano-4-{4-[1-methyl-5-(trifluoromethyl)-1H-pyrazol-3-yl]phenoxy}-N-1,3-thiazol-2-ylbenzenesulfonamide | 506 [MH]+ |
| 372 | 3-cyano-4-[4-(5-cyclopropyl-1-ethyl-1H-pyrazol-3-yl)phenoxy]-N-1,3-thiazol-2-ylbenzenesulfonamide | 492 [MH]+ |
| 373 | 4-[3-chloro-4-(3-cyclopropyl-1H-pyrazol-5-yl)phenoxy]-3-cyano-N-1,3-thiazol-2-ylbenzenesulfonamide | 498 [M$^{35}$ClH]+ |
| 374 | 3-cyano-4-{4-[1-(2-hydroxyethyl)-3-methyl-1H-pyrazol-5-yl]phenoxy}-N-1,3-thiazol-2-ylbenzenesulfonamide | 482 [MH]+ |
| 375 | 1-(4-{2-cyano-4-[(1,3-thiazol-2-ylamino)sulfonyl]phenoxy}phenyl)-N,N-dimethyl-1H-pyrazole-4-carboxamide | 495 [MH]+ |
| 376 | 3-cyano-4-{4-[4-(methoxymethyl)-1H-pyrazol-1-yl]phenoxy}-N-1,3-thiazol-2-ylbenzenesulfonamide | 468 [MH]+ |
| 377 | 3-cyano-4-(4-{4-[(dimethylamino)methyl]-1H-pyrazol-1-yl}phenoxy)-N-1,3-thiazol-2-ylbenzenesulfonamide | 481 [MH]+ |
| 378 | N-tert-butyl-1-(4-{2-cyano-4-[(1,3-thiazol-2-ylamino)sulfonyl]phenoxy}phenyl)-1H-pyrazole-4-carboxamide | 523 [MH]+ |
| 379 | 1-(4-{2-cyano-4-[(1,3-thiazol-2-ylamino)sulfonyl]phenoxy}phenyl)-1H-pyrazole-4-carboxamide | 467 [MH]+ |
| 380 | 4-{3-chloro-4-[3-(trifluoromethyl)-1H-pyrazol-1-yl]phenoxy}-3-cyano-N-1,3-thiazol-2-ylbenzenesulfonamide | 526 [M$^{35}$ClH]+ |
| 381 | 3-cyano-4-{3-fluoro-4-[3-(trifluoromethyl)-1H-pyrazol-1-yl]phenoxy}-N-1,3-thiazol-2-ylbenzenesulfonamide | 510 [MH]+ |
| 382 | 3-cyano-4-{4-[1-(2-hydroxyethyl)-3-(trifluoromethyl)-1H-pyrazol-5-yl]phenoxy}-N-1,3-thiazol-2-ylbenzenesulfonamide | 536 [MH]+ |
| 383 | 3-cyano-4-{4-[3-(difluoromethyl)-1-methyl-1H-pyrazol-5-yl]phenoxy}-N-1,3-thiazol-2-ylbenzenesulfonamide | 488 [MH]+ |
| 284 | 4-[3-chloro-4-(4-chloro-1H-pyrazol-1-yl)phenoxy]-3-cyano-N-1,3-thiazol-2-ylbenzenesulfonamide | 492 [M$^{35}$ClH]+ |
| 385 | 4-(2-(1H-pyrazol-4-yl)phenoxy)-3-cyano-N-(1,2,4-thiadiazol-5-yl)benzenesulfonamide | 425 [MH]+ |
| 386 | 3-cyano-4-[4-fluoro-2-(1-methyl-1H-pyrazol-5-yl)phenoxy]-N-(5-fluoro-1,3-thiazol-2-yl)benzenesulfonamide | 474 [MH]+ |
| 387 | 3-cyano-N-(5-fluoro-1,3-thiazol-2-yl)-4-{4-[1-methyl-3-(trifluoromethyl)-1H-pyrazol-5-yl]phenoxy}benzenesulfonamide | 524 [MH]+ |
| 388 | 3-cyano-4-[4-(1-ethyl-3-methyl-1H-pyrazol-5-yl)phenoxy]-N-1,3-thiazol-2-ylbenzenesulfonamide | 466 [MH]+ |
| 389 | 3-cyano-4-[4-(1,3-dimethyl-1H-pyrazol-4-yl)phenoxy]-N-1,3-thiazol-2-ylbenzenesulfonamide | 452 [MH]+ |
| 390 | 3-cyano-4-{3-[3-(difluoromethyl)-5-(hydroxymethyl)-1H-pyrazol-1-yl]phenoxy}-N-1,3-thiazol-2-ylbenzenesulfonamide | 504 [MH]+ |
| 391 | 3-cyano-4-[4-iodo-2-(1H-pyrazol-5-yl)phenoxy]-N-1,3-thiazol-2-ylbenzenesulfonamide | 550 [MH]+ |
| 392 | 4-[2-(2-aminopyridin-4-yl)-4-chlorophenoxy]-3-cyano-N-1,3-thiazol-4-ylbenzenesulfonamide | 484 [M$^{35}$ClH]+ |
| 393 | 4-[2-(5-amino-1H-pyrazol-4-yl)-4-chlorophenoxy]-3-cyano-N-1,3-thiazol-4-ylbenzenesulfonamide | 473 [M$^{35}$ClH]+ |
| 394 | 4-{4-chloro-2-[1-(difluoromethyl)-1H-pyrazol-4-yl]phenoxy}-3-cyano-N-1,3-thiazol-4-ylbenzenesulfonamide | 508 [M$^{35}$ClH]+ |
| 395 | 4-{4-chloro-2-[1-methyl-3-(trifluoromethyl)-1H-pyrazol-5-yl]phenoxy}-3-cyano-N-1,3-thiazol-4-ylbenzenesulfonamide | 540 [M$^{35}$ClH]+ |
| 396 | 3-cyano-4-[4-fluoro-2-(3-isopropoxy-1-methyl-1H-pyrazol-5-yl)phenoxy]-N-1,3-thiazol-4-ylbenzenesulfonamide | 514 [MH]+ |
| 397 | 4-{4-chloro-2-[4-(trifluoromethyl)-1H-imidazol-1-yl]phenoxy}-3-cyano-N-1,3-thiazol-4-ylbenzenesulfonamide | 526 [M$^{35}$ClH]+ |
| 398 | 4-{4-chloro-2-[1-(trifluoromethyl)-1H-pyrazol-3-yl]phenoxy}-3-cyano-N-1,3-thiazol-4-ylbenzenesulfonamide | 526 [M$^{35}$ClH]+ |

| Eg No | Name | MS m/z (unless otherwise incidated) |
|---|---|---|
| 399 | 4-{4-chloro-2-[1-(trifluoromethyl)-1H-pyrazol-5-yl]phenoxy}-3-cyano-N-1,3-thiazol-4-ylbenzenesulfonamide | 526 [M$^{35}$ClH]+ |
| 400 | 3-cyano-4-[2-(1-methyl-1H-pyrazol-5-yl)phenoxy]-N-1,3-thiazol-4-ylbenzenesulfonamide | 438 [MH]+ |
| 401 | 3-cyano-4-{4-[1-ethyl-3-(trifluoromethyl)-1H-pyrazol-5-yl]phenoxy}-N-1,3-thiazol-4-ylbenzenesulfonamide | 520 [MH]+ |
| 402 | 4-{4-chloro-2-[1-(difluoromethyl)-1H-pyrazol-5-yl]phenoxy}-3-cyano-N-1,3-thiazol-4-ylbenzenesulfonamide | 508 [M$^{35}$ClH]+ |
| 403 | 4-[2-(6-aminopyridin-2-yl)-4-chlorophenoxy]-5-chloro-2-fluoro-N-1,2,4-thiadiazol-5-ylbenzenesulfonamide | 512 [M$^{35}$ClH]+ |
| 404 | 5-chloro-4-{4-[1-ethyl-3-(trifluoromethyl)-1H-pyrazol-5-yl]phenoxy}-2-fluoro-N-(5-fluoropyridin-2-yl)benzenesulfonamide | 559 [M$^{35}$ClH]+ |
| 405 | 4-[2-(2-aminopyridin-4-yl)-4-fluorophenoxy]-5-chloro-2-fluoro-N-1,2,4-thiadiazol-5-ylbenzenesulfonamide | 496 [M$^{35}$ClH]+ |
| 406 | 4-[4-chloro-2-(1-methyl-1H-1,2,4-triazol-5-yl)phenoxy]-3-fluoro-N-1,3-thiazol-2-ylbenzenesulfonamide | 466 [M$^{35}$ClH]+ |
| 407 | 4-[2-(6-aminopyridin-2-yl)-4-fluorophenoxy]-2,5-difluoro-N-1,2,4-thiadiazol-5-ylbenzenesulfonamide | 480 [MH]+ |
| 408 | 4-{4-[1-ethyl-3-(trifluoromethyl)-1H-pyrazol-5-yl]phenoxy}-3-fluoro-N-1,3-thiazol-2-ylbenzenesulfonamide | 513 [MH]+ |
| 409 | 4-[2-(6-aminopyridin-2-yl)-4-chlorophenoxy]-2,5-difluoro-N-1,2,4-thiadiazol-5-ylbenzenesulfonamide | 496 [M$^{35}$ClH]+ |
| 410 | 4-[2-(6-aminopyridin-3-yl)-4-chlorophenoxy]-2,5-difluoro-N-1,2,4-thiadiazol-5-ylbenzenesulfonamide | 496 [M$^{35}$ClH]+ |
| 411 | 4-[2-(5-aminopyridin-2-yl)-4-chlorophenoxy]-2,5-difluoro-N-1,2,4-thiadiazol-5-ylbenzenesulfonamide | 496 [M$^{35}$ClH]+ |
| 412 | 5-chloro-4-[4-(difluoromethoxy)-2-piperidin-4-ylphenoxy]-2-fluoro-N-1,2,4-thiadiazol-5-ylbenzenesulfonamide | 535.0 [M$^{35}$ClH]+ |
| 413 | 4-[4-chloro-2-(1-methyl-1H-pyrazol-5-yl)phenoxy]-N-(5-chloro-1,3-thiazol-4-yl)-3-cyanobenzenesulfonamide | 506 [M$^{35}$ClH]+ |
| 414 | 4-[4-chloro-2-(1-methyl-1H-pyrazol-4-yl)phenoxy]-3-cyano-N-1,3-thiazol-4-ylbenzenesulfonamide | 472 [M$^{35}$ClH]+ |
| 415 | 4-{4-fluoro-2-[1-(2,2,2-trifluoroethyl)-1H-pyrazol-4-yl]phenoxy}-3-cyano-N-1,3-thiazol-4-ylbenzenesulfonamide | 524 [MH]+ |
| 416 | 4-(4-chloro-2-(1H-tetrazol-1-yl)phenoxy)-3-cyano-N-(thiazol-2-yl)benzenesulfonamide | 460 [M$^{35}$ClH]+ |
| 417 | 4-[2-(2-aminopyridin-4-yl)-4-chlorophenoxy]-3-cyano-N-1,2,4-thiadiazol-5-ylbenzenesulfonamide | 485 [M$^{35}$ClH]+ 487 [M$^{37}$ClH]+ |
| 418 | 4-[4-chloro-3-(1H-imidazol-1-ylmethyl)phenoxy]-3-cyano-N-1,3-thiazol-4-ylbenzenesulfonamide | 472 [M$^{35}$ClH]+ |
| 419 | 4-{3-[(1-tert-butyl-1H-pyrazol-4-yl)methyl]phenoxy}-3-cyano-N-1,3-thiazol-4-ylbenzenesulfonamide | 494 [MH]+ |
| 420 | 4-(biphenyl-2-yloxy)-3-cyano-N-(3-fluoropyridin-2-yl)benzenesulfonamide | 446 [MH]+ |
| 421 | 4-(biphenyl-2-yloxy)-3-cyano-N-(6-cyanopyridin-2-yl)benzenesulfonamide | 453 [MH]+ |
| 422 | 4-(biphenyl-2-yloxy)-3-cyano-N-(4-cyanopyridin-2-yl)benzenesulfonamide | 453 [MH]+ |
| 423 | 4-(biphenyl-2-yloxy)-3-cyano-N-(5-cyanopyridin-2-yl)benzenesulfonamide | 451 [MH]− |
| 424 | 4-(biphenyl-2-yloxy)-3-cyano-N-(5-methylpyridin-2-yl)benzenesulfonamide | 442 [MH]+ |
| 425 | 4-(biphenyl-2-yloxy)-3-cyano-N-(4-methylpyrimidin-2-yl)benzenesulfonamide | 443 [MH]+ |
| 426 | 4-(biphenyl-2-yloxy)-N-(2-chloropyrimidin-5-yl)-3-cyanobenzenesulfonamide | 463 [M$^{35}$ClH]+ |
| 427 | 4-(biphenyl-2-yloxy)-3-cyano-N-(5-fluoropyrimidin-2-yl)benzenesulfonamide | 447 [MH]+ |
| 428 | 4-(biphenyl-2-yloxy)-3-cyano-N-(5-methylpyrimidin-4-yl)benzenesulfonamide | 443 [MH]+ |
| 429 | 4-(biphenyl-2-yloxy)-3-cyano-N-(5-methylpyrimidin-2-yl)benzenesulfonamide | 443 [MH]+ |
| 430 | 4-(biphenyl-2-yloxy)-N-(5-chloropyrimidin-2-yl)-3-cyanobenzenesulfonamide | 463 [M$^{35}$ClH]+ |
| 431 | 4-(biphenyl-2-yloxy)-3-cyano-N-1H-1,2,4-triazol-5-ylbenzenesulfonamide | 418 [MH]+ |
| 432 | 4-(biphenyl-2-yloxy)-3-cyano-N-(5-cyanopyrimidin-2-yl)benzenesulfonamide | 452 [MH]− |
| 433 | 4-(biphenyl-2-yloxy)-3-cyano-N-(4-cyanopyrimidin-2-yl)benzenesulfonamide | 454 [MH]+ |
| 434 | 4-(biphenyl-2-yloxy)-3-cyano-N-[4-(trifluoromethyl)pyrimidin-2-yl]benzenesulfonamide | 497 [MH]+ |
| 435 | 4-[2-fluoro-4-(3-methoxy-1-methyl-1H-pyrazol-5-yl)phenoxy]-N-1,3-thiazol-2-ylbenzenesulfonamide | 486 [MH]+ |
| 436 | 3-cyano-4-[4-(1-methyl-1H-pyrazol-5-yl)phenoxy]-N-1,3-thiazol-2-ylbenzenesulfonamide | 438 [MH]+ |
| 437 | 3-cyano-4-[2-(1-methyl-1H-pyrazol-5-yl)-4-(trifluoromethyl)phenoxy]-N-1,2,4-thiadiazol-5-ylbenzenesulfonamide | 507 [MH]+ |
| 438 | 3-cyano-4-[2-(1H-pyrazol-4-yl)-4-(trifluoromethyl)phenoxy]-N-1,2,4-thiadiazol-5-ylbenzenesulfonamide | 493 [MH]+ |
| 439 | 4-[4-chloro-2-(3-methoxy-1-methyl-1H-pyrazol-5-yl)phenoxy]-3-cyano-N-1,3-thiazol-2-ylbenzenesulfonamide | 502 [M$^{35}$ClH]+ |
| 440 | 3-cyano-4-[2-(1-methyl-1H-pyrazol-5-yl)-4-(trifluoromethyl)phenoxy]-N-1,3-thiazol-2-ylbenzenesulfonamide | 506 [MH]+ |
| 441 | N-(5-chloro-1,3-thiazol-2-yl)-4-[4-cyano-2-(1-methyl-1H-pyrazol-5-yl)phenoxy]-2,5-difluorobenzenesulfonamide | 508 [M$^{35}$ClH]+ |
| 442 | 4-[4-chloro-2-(1-methyl-1H-pyrazol-5-yl)phenoxy]-3-cyano-N-pyridin-2-ylbenzenesulfonamide | 466 [M$^{35}$ClH]+ |
| 443 | 4-[3-chloro-4-(1-methyl-1H-pyrazol-5-yl)phenoxy]-3-cyano-N-1,3-thiazol-2-ylbenzenesulfonamide | 472 [M$^{35}$ClH]+ |
| 444 | 3-cyano-4-[3-(1H-pyrazol-5-yl)phenoxy]-N-1,3-thiazol-2-ylbenzenesulfonamide | 424 [MH]+ |
| 445 | 3-cyano-4-[3-(1-methyl-1H-pyrazol-5-yl)phenoxy]-N-1,3-thiazol-2-ylbenzenesulfonamide | 438 [MH]+ |
| 446 | 4-[4-chloro-3-(1H-pyrazol-5-yl)phenoxy]-3-cyano-N-1,3-thiazol-2-ylbenzenesulfonamide | 458 [M$^{35}$ClH]+ |
| 447 | 3-cyano-N-1,3-thiazol-2-yl-4-{3-[4-(trifluoromethyl)pyridin-2-yl]phenoxy}benzenesulfonamide | 503 [MH]+ |
| 448 | 3-cyano-N-1,3-thiazol-2-yl-4-{3-[6-(trifluoromethyl)pyridin-2-yl]phenoxy}benzenesulfonamide | 503 [MH]+ |
| 449 | 3-cyano-4-(3-pyridin-2-ylphenoxy)-N-1,3-thiazol-2-ylbenzenesulfonamide | 435 [MH]+ |
| 450 | 3-cyano-4-[4-(4-methylpyridin-2-yl)phenoxy]-N-1,3-thiazol-2-ylbenzenesulfonamide | 449 [MH]+ |
| 451 | 3-cyano-4-[4-(6-methoxypyridin-2-yl)phenoxy]-N-1,3-thiazol-2-ylbenzenesulfonamide | 465 [MH]+ |
| 452 | 3-cyano-N-1,3-thiazol-2-yl-4-{4-[5-(trifluoromethyl)pyridin-2-yl]phenoxy}benzenesulfonamide | 501 [MH]− |
| 453 | 3-cyano-N-1,3-thiazol-2-yl-4-{4-[6-(trifluoromethyl)pyridin-2-yl]phenoxy}benzenesulfonamide | 503 [MH]+ |
| 454 | 3-cyano-N-1,3-thiazol-2-yl-4-{4-[4-(trifluoromethyl)pyrimidin-2-yl]phenoxy}benzenesulfonamide | 504 [MH]+ |
| 455 | 3-cyano-4-[4-(3-methylpyridin-2-yl)phenoxy]-N-1,3-thiazol-2-ylbenzenesulfonamide | 449 [MH]+ |
| 456 | 4-[4-(3-chloropyridin-2-yl)phenoxy]-3-cyano-N-1,3-thiazol-2-ylbenzenesulfonamide | 469 [M$^{35}$ClH]+ |
| 457 | 3-cyano-N-1,3-thiazol-2-yl-4-{4-[3-(trifluoromethyl)pyridin-2-yl]phenoxy}benzenesulfonamide | 503 [MH]+ |
| 458 | 3-cyano-5-fluoro-4-[4-fluoro-2-(1H-pyrazol-4-yl)phenoxy]-N-1,2,4-thiadiazol-5-ylbenzenesulfonamide | 459 [MH]− |
| 459 | 3-cyano-5-fluoro-4-[4-fluoro-2-(1H-pyrazol-5-yl)phenoxy]-N-1,2,4-thiadiazol-5-ylbenzenesulfonamide | 461 [MH]+ |
| 460 | 4-(2-(1H-pyrazol-4-yl)-4-(trifluoromethyl)phenoxy)-3-cyano-N-(thiazol-2-yl)benzenesulfonamide | 492 [MH]+ |
| 461 | 4-[4-bromo-2-(1H-pyrazol-5-yl)phenoxy]-3-cyano-N-1,3-thiazol-2-ylbenzenesulfonamide | 502 [M$^{79}$BrH]+ |
| 462 | 4-[4-chloro-2-(1-methyl-1H-pyrazol-5-yl)phenoxy]-3-cyano-N-[5-(trifluoromethyl)pyrimidin-2-yl]benzenesulfonamide | 535 [M$^{35}$ClH]+ |

| Eg No | Name | MS m/z (unless otherwise incidated) |
|---|---|---|
| 463 | 4-[4-chloro-2-(1-methyl-1H-pyrazol-5-yl)phenoxy]-3-cyano-N-(5-cyanopyrimidin-2-yl)benzenesulfonamide | 492 [M$^{35}$ClH]+ |
| 464 | 4-[4-chloro-2-(1-methyl-1H-pyrazol-5-yl)phenoxy]-N-(5-chloropyrimidin-2-yl)-3-cyanobenzenesulfonamide | 503 [M$^{35}$ClH]+ |
| 465 | 4-[4-chloro-2-(1-methyl-1H-pyrazol-5-yl)phenoxy]-3-cyano-N-(5-fluoropyrimidin-2-yl)benzenesulfonamide | 485 [M$^{35}$ClH]+ |
| 466 | 4-[4-chloro-2-(1-methyl-1H-pyrazol-5-yl)phenoxy]-3-cyano-N-(5-cyanopyridin-2-yl)benzenesulfonamide | 491 [M$^{35}$ClH]+ |
| 467 | 4-[2-(5-amino-1H-pyrazol-4-yl)-4-chlorophenoxy]-N-(5-chloro-1,3-thiazol-2-yl)-2,5-difluorobenzenesulfonamide | 518 [M$^{35}$ClH]+ |
| 468 | 2,5-difluoro-4-[2-(1-methyl-1H-pyrazol-5-yl)-4-(trifluoromethyl)phenoxy]-N-1,2,4-thiadiazol-5-ylbenzenesulfonamide | 518 [MH]+ |
| 469 | 3-cyano-4-[4-(1H-pyrazol-1-yl)phenoxy]-N-1,3-thiazol-2-ylbenzenesulfonamide | 424 [MH]+ |
| 470 | 3-cyano-4-[4-(1,4-dimethyl-1H-pyrazol-3-yl)phenoxy]-N-1,3-thiazol-2-ylbenzenesulfonamide | 452 [MH]+ |
| 471 | 3-cyano-4-{4-[1-(difluoromethyl)-4-methyl-1H-pyrazol-3-yl]phenoxy}-N-1,3-thiazol-2-ylbenzenesulfonamide | 488 [MH]+ |
| 472 | 3-cyano-4-{2,3-difluoro-5-[1-methyl-3-(trifluoromethyl)-1H-pyrazol-5-yl]phenoxy}-N-1,3-thiazol-2-ylbenzenesulfonamide | 542 [MH]+ |
| 473 | 3-chloro-4-{4-[1-ethyl-3-(trifluoromethyl)-1H-pyrazol-5-yl]phenoxy}-N-1,2,4-thiadiazol-5-ylbenzenesulfonamide | 530 [M$^{35}$ClH]+ |
| 474 | 4-[2-(1-tert-butyl-1H-pyrazol-5-yl)-4-chlorophenoxy]-3-chloro-N-1,2,4-thiadiazol-5-ylbenzenesulfonamide | 524 [M$^{35}$ClH]+ |
| 475 | 3-chloro-4-[4-chloro-2-(1H-pyrazol-5-yl)phenoxy]-N-1,2,4-thiadiazol-5-ylbenzenesulfonamide | 468 [M$^{35}$ClH]+ |
| 476 | 4-[2-(1-tert-butyl-1H-pyrazol-5-yl)-4-fluorophenoxy]-3-chloro-N-1,2,4-thiadiazol-5-ylbenzenesulfonamide | 508 [M$^{35}$ClH]+ |
| 477 | 3-chloro-4-(4-chloro-2-piperidin-4-ylphenoxy)-N-1,2,4-thiadiazol-5-ylbenzenesulfonamide | 485 [M$^{35}$ClH]+ |
| 478 | 3-chloro-4-[4-fluoro-2-(1H-pyrazol-5-yl)phenoxy]-N-1,2,4-thiadiazol-5-ylbenzenesulfonamide | 452 [M$^{35}$ClH]+ |
| 479 | 3-cyano-4-{3-[1-ethyl-3-(trifluoromethyl)-1H-pyrazol-5-yl]phenoxy}-N-(5-fluoro-1,3-thiazol-2-yl)benzenesulfonamide | 538 [MH]+ |
| 480 | 3-cyano-4-{2-fluoro-4-[1-(3-fluoropropyl)-5-(trifluoromethyl)-1H-pyrazol-3-yl]phenoxy}-N-1,3-thiazol-2-ylbenzenesulfonamide | 570 [MH]+ |
| 481 | 3-cyano-4-(3-{1-[2-(dimethylamino)ethyl]-3-methyl-1H-pyrazol-5-yl}phenoxy)-N-1,3-thiazol-2-ylbenzenesulfonamide | 509 [MH]+ |
| 482 | 4-{4-[3-amino-1-(2,2,2-trifluoroethyl)-1H-pyrazol-4-yl]phenoxy}-3-cyano-N-1,3-thiazol-2-ylbenzenesulfonamide | 521 [MH]+ |
| 483 | 4-[4-(3-amino-1-methyl-1H-pyrazol-4-yl)phenoxy]-3-cyano-N-1,3-thiazol-2-ylbenzenesulfonamide | 453 [MH]+ |
| 484 | 3-cyano-4-[4-(4-methyl-2-oxoimidazolidin-1-yl)phenoxy]-N-1,3-thiazol-2-ylbenzenesulfonamide | 456 [MH]+ |
| 485 | 3-cyano-4-[4-(4-isopropyl-2-oxoimidazolidin-1-yl)phenoxy]-N-1,3-thiazol-2-ylbenzenesulfonamide | 484 [MH]+ |
| 486 | 3-cyano-4-[4-(2-oxoimidazolidin-1-yl)phenoxy]-N-1,3-thiazol-2-ylbenzenesulfonamide | 442 [MH]+ |
| 487 | 3-cyano-4-[4-(3-methyl-2-oxoimidazolidin-1-yl)phenoxy]-N-1,3-thiazol-2-ylbenzenesulfonamide | 456 [MH]+ |
| 488 | 3-cyano-4-[4-(2-oxopyrrolidin-1-yl)phenoxy]-N-1,3-thiazol-2-ylbenzenesulfonamide | 441 [MH]+ |
| 489 | 3-cyano-4-[2-ethyl-4-(1H-pyrazol-1-yl)phenoxy]-N-1,3-thiazol-2-ylbenzenesulfonamide | 452 [MH]+ |
| 490 | 3-cyano-4-{2-ethyl-4-[3-(trifluoromethyl)-1H-pyrazol-1-yl]phenoxy}-N-1,3-thiazol-2-ylbenzenesulfonamide | 520 [MH]+ |
| 491 | 3-cyano-4-[4-(1H-pyrazol-1-yl)-2-(trifluoromethyl)phenoxy]-N-1,3-thiazol-2-ylbenzenesulfonamide | 492 [MH]+ |
| 492 | 3-cyano-N-1,3-thiazol-2-yl-4-{2-(trifluoromethyl)-4-[3-(trifluoromethyl)-1H-pyrazol-1-yl]phenoxy}benzenesulfonamide | 560 [MH]+ |
| 493 | 4-[4-chloro-2-(morpholin-4-ylmethyl)phenoxy]-3-cyano-N-1,3-thiazol-2-ylbenzenesulfonamide | 491 [M$^{35}$ClH]+ |
| 494 | 3-cyano-4-[5-fluoro-2-(1-methyl-1H-pyrazol-3-yl)phenoxy]-N-1,3-thiazol-2-ylbenzenesulfonamide | 456 [MH]+ |
| 495 | methyl 2-(4-chloro-1H-pyrazol-1-yl)-5-{2-cyano-4-[(1,3-thiazol-2-ylamino)sulfonyl]phenoxy}benzoate | 516 [M$^{35}$ClH]+ |
| 496 | 4-[4-(4-chloro-1H-pyrazol-1-yl)-3-(methoxymethyl)phenoxy]-3-cyano-N-1,3-thiazol-2-ylbenzenesulfonamide | 502 [M$^{35}$ClH]+ |
| 497 | 2-(4-chloro-1H-pyrazol-1-yl)-5-{2-cyano-4-[(1,3-thiazol-2-ylamino)sulfonyl]phenoxy}benzoic acid | 502 [M$^{35}$ClH]+ |
| 498 | 4-[4-chloro-2-(1H-pyrazol-5-yl)phenoxy]-3-cyano-N-1,2,4-thiadiazol-5-ylbenzenesulfonamide | 459 [MH]+ |
| 499 | 3-cyano-4-[2-fluoro-4-(1H-pyrazol-5-yl)phenoxy]-N-1,2,4-thiadiazol-5-ylbenzenesulfonamide | 443 [MH]+ |
| 500 | 3-cyano-4-{4-[1-ethyl-3-(trifluoromethyl)-1H-pyrazol-5-yl]phenoxy}-N-1,2,4-thiadiazol-5-ylbenzenesulfonamide | 521 [MH]+ |
| 501 | 4-[4-bromo-2-(1-methyl-1H-pyrazol-5-yl)phenoxy]-3-cyano-N-1,2,4-thiadiazol-5-ylbenzenesulfonamide | 517 [M$^{79}$BrH]+ |
| 502 | 3-cyano-4-[2-(1H-pyrazol-4-yl)-4-(trifluoromethoxy)phenoxy]-N-1,2,4-thiadiazol-5-ylbenzenesulfonamide | 509 [MH]+ |
| 503 | 4-[Bromo-2-(1H-pyrazol-4-yl)phenoxy]-3-cyano-N-1,2,4-thiadiazol-5-ylbenzenesulfonamide | 503 [M$^{79}$BrH]+<br>505 [M$^{81}$BrH]+ |
| 504 | 4-[(3'-acetyl-5-chlorobiphenyl-2-yl)oxy]-3-cyano-N-1,2,4-thiadiazol-5-ylbenzenesulfonamide | 511 [M$^{35}$ClH]+ |
| 505 | 4-(4-chloro-2-piperidin-4-ylphenoxy)-3-cyano-N-1,2,4-thiadiazol-5-ylbenzenesulfonamide | 476 [M$^{35}$ClH]+ |
| 506 | 3-cyano-4-[4-iodo-2-(1H-pyrazol-5-yl)phenoxy]-N-1,2,4-thiadiazol-5-ylbenzenesulfonamide | 551 [MH]+ |
| 507 | 3-cyano-4-[5-iodo-2-(1-methyl-1H-pyrazol-5-yl)phenoxy]-N-1,2,4-thiadiazol-5-ylbenzenesulfonamide | 565 [MH]+ |
| 508 | 3-cyano-4-[2-(2-methylpyridin-4-yl)-4-(trifluoromethyl)phenoxy]-N-1,2,4-thiadiazol-5-ylbenzenesulfonamide | 518 [MH]+ |
| 509 | 3-cyano-4-{[3'-cyano-5-(trifluoromethyl)biphenyl-2-yl]oxy}-N-1,2,4-thiadiazol-5-ylbenzenesulfonamide | 528 [MH]+ |
| 510 | 4-{4-chloro-2-[1-(difluoromethyl)-1H-pyrazol-5-yl]phenoxy}-3-cyano-N-1,2,4-thiadiazol-5-ylbenzenesulfonamide | 509 [M$^{35}$ClH]+ |
| 511 | 4-{[3'-(aminomethyl)-5-chlorobiphenyl-2-yl]oxy}-3-cyano-N-1,2,4-thiadiazol-5-ylbenzenesulfonamide | 498 [M$^{35}$ClH]+ |
| 512 | N-(5-Bromo-1,3-thiazol-2-yl)-3-cyano-4-[(3,5-dibromobiphenyl-2-yl)oxy]benzenesulfonamide | 668 [M$^{79}$BrH]+ |
| 513 | 4-[4-chloro-2-(1-methyl-1H-pyrazol-5-yl)phenoxy]-3-fluoro-N-1,2,4-thiadiazol-5-ylbenzenesulfonamide | 466 [M$^{35}$ClH]+ |
| 514 | 4-[4-chloro-2-(1-methyl-1H-pyrazol-5-yl)phenoxy]-3-fluoro-N-(5-fluoropyridin-2-yl)benzenesulfonamide | 477 [M$^{35}$ClH]+ |
| 515 | 4-[4-chloro-2-(1-methyl-1H-pyrazol-5-yl)phenoxy]-3-fluoro-N-(3-methyl-1,2,4-thiadiazol-5-yl)benzenesulfonamide | 480 [M$^{35}$ClH]+ |
| 516 | tert-Butyl [(5-chloro-2,4-difluorophenyl)sulfonyl](5-cyano-1,3-thiazol-4-yl)carbamate | 508 [M$^{35}$ClH]+ |
| 517 | 5-chloro-2-fluoro-4-{4-fluoro-2-[1-(2-hydroxyethyl)-1H-pyrazol-5-yl]phenoxy}-N-1,3-thiazol-4-ylbenzenesulfonamide | 513 [M$^{35}$ClH]+ |
| 518 | 5-chloro-2-fluoro-4-[2-pyrimidin-5-yl-5-(trifluoromethyl)phenoxy]-N-1,3-thiazol-4-ylbenzenesulfonamide | 531 [M$^{35}$ClH]+ |
| 519 | 4-[2-(1-tert-butyl-1H-pyrazol-5-yl)-4-fluorophenoxy]-5-chloro-2-fluoro-N-1,3-thiazol-4-ylbenzenesulfonamide | 525 [M$^{35}$ClH]+ |
| 520 | 4-[2-(1-tert-butyl-1H-pyrazol-3-yl)-4-fluorophenoxy]-5-chloro-2-fluoro-N-1,3-thiazol-4-ylbenzenesulfonamide | 525 [M$^{35}$ClH]+ |
| 521 | 5-chloro-2-fluoro-4-[4-fluoro-2-(1H-1,2,3-triazol-4-yl)phenoxy]-N-1,3-thiazol-4-ylbenzenesulfonamide | 470 [M$^{35}$ClH]+ |

| Eg No | Name | MS m/z (unless otherwise indicated) |
|---|---|---|
| 522 | 5-chloro-2-fluoro-4-[4-fluoro-2-(1-methyl-1H-pyrazol-3-yl)phenoxy]-N-1,3-thiazol-4-ylbenzenesulfonamide | 483 [M$^{35}$ClH]+ |
| 523 | 5-chloro-2-fluoro-4-[4-fluoro-2-(1-methyl-1H-1,2,3-triazol-5-yl)phenoxy]-N-1,3-thiazol-4-ylbenzenesulfonamide | 484 [M$^{35}$ClH]+ |
| 524 | 5-chloro-4-{2-cyano-4-[1-methyl-3-(trifluoromethyl)-1H-pyrazol-5-yl]phenoxy}-2-fluoro-N-1,3-thiazol-4-ylbenzenesulfonamide | 558 [M$^{35}$ClH]+ |
| 525 | 3-cyano-N-1,3-thiazol-2-yl-4-{4-[4-(trifluoromethyl)pyridin-2-yl]phenoxy}benzenesulfonamide | 501 [MH]− |
| 526 | 3-cyano-4-[4,5-difluoro-2-(1-methyl-1H-pyrazol-5-yl)phenoxy]-N-1,3-thiazol-2-ylbenzenesulfonamide | 474 [MH]+ |
| 527 | 3-cyano-4-{2-fluoro-3-[1-methyl-3-(trifluoromethyl)-1H-pyrazol-5-yl]phenoxy}-N-1,3-thiazol-2-ylbenzenesulfonamide | 524 [MH]+ |
| 528 | 3-fluoro-4-[4-fluoro-2-(1-methyl-1H-pyrazol-5-yl)phenoxy]-N-pyrimidin-4-ylbenzenesulfonamide | 444 [MH]+ |
| 529 | 4-(Biphenyl-2-yloxy)-3-cyano-N-(5-fluoro-1,3-thiazol-2-yl)benzenesulfonamide | 450 [MH]− |
| 530 | 4-[4-chloro-3-(1H-imidazol-1-ylmethyl)phenoxy]-3-cyano-N-(5-fluoro-1,3-thiazol-2-yl)benzenesulfonamide | 490 [M$^{35}$ClH]+ |
| 531 | 4-[(6-chloro-3'-methoxybiphenyl-3-yl)oxy]-3-cyano-N-(5-fluoro-1,3-thiazol-2-yl)benzenesulfonamide | 516 [M$^{35}$ClH]+ |
| 532 | 4-{[6-chloro-3'-(methoxymethyl)biphenyl-3-yl]oxy}-3-cyano-N-(5-fluoro-1,3-thiazol-2-yl)benzenesulfonamide | 530 [M$^{35}$ClH]+ |
| 533 | 4-[4-chloro-3-(1H-1,2,3-triazol-1-ylmethyl)phenoxy]-3-cyano-N-(5-fluoro-1,3-thiazol-2-yl)benzenesulfonamide | 491 [M$^{35}$ClH]+ |
| 534 | 4-[4-chloro-3-(1H-pyrazol-1-ylmethyl)phenoxy]-3-cyano-N-(5-fluoro-1,3-thiazol-2-yl)benzenesulfonamide | 490 [M$^{35}$ClH]+ |
| 535 | 3-cyano-4-{2-fluoro-4-[1-methyl-3-(trifluoromethyl)-1H-pyrazol-5-yl]phenoxy}-N-(5-fluoro-1,3-thiazol-2-yl)benzenesulfonamide | 542 [MH]+ |
| 536 | 3-cyano-4-{4-[1-ethyl-3-(trifluoromethyl)-1H-pyrazol-5-yl]-3-fluorophenoxy}-N-(5-fluoro-1,3-thiazol-2-yl)benzenesulfonamide | 556 [MH]+ |
| 537 | 3-cyano-4-{4-[1-ethyl-3-(trifluoromethyl)-1H-pyrazol-5-yl]-2-fluorophenoxy}-N-(5-fluoro-1,3-thiazol-2-yl)benzenesulfonamide | 556 [MH]+ |
| 538 | 3-cyano-4-[2-cyano-4-(1-methyl-1H-pyrazol-5-yl)phenoxy]-N-(5-fluoro-1,3-thiazol-2-yl)benzenesulfonamide | 481 [MH]+ |
| 539 | 3-cyano-N-(5-fluoro-1,3-thiazol-2-yl)-4-[2-methyl-4-(1-methyl-1H-pyrazol-5-yl)phenoxy]benzenesulfonamide | 468 [MH]− |
| 540 | 3-cyano-4-{4-[1-ethyl-5-(trifluoromethyl)-1H-pyrazol-3-yl]-2-fluorophenoxy}-N-(5-fluoro-1,3-thiazol-2-yl)benzenesulfonamide | 556 [MH]+ |
| 541 | 3-cyano-4-[5-methoxy-2-(1-methyl-1H-pyrazol-5-yl)phenoxy]-N-1,3-thiazol-2-ylbenzenesulfonamide | 468 [MH]+ |
| 542 | 3-cyano-4-[5-fluoro-2-(1-methyl-1H-pyrazol-5-yl)phenoxy]-N-1,3-thiazol-2-ylbenzenesulfonamide | 456 [MH]+ |
| 543 | 3-cyano-4-[5-methyl-2-(1-methyl-1H-pyrazol-5-yl)phenoxy]-N-1,3-thiazol-2-ylbenzenesulfonamide | 452 [MH]+ |
| 544 | 4-[5-chloro-2-(1-methyl-1H-pyrazol-5-yl)phenoxy]-3-cyano-N-1,3-thiazol-2-ylbenzenesulfonamide | 472 [M$^{35}$ClH]+ |
| 545 | 3-cyano-4-[4-cyclopropyl-2-(1-methyl-1H-pyrazol-5-yl)phenoxy]-N-1,3-thiazol-2-ylbenzenesulfonamide | 478 [MH]+ |
| 546 | 4-[4-chloro-2-(5-methyl-1H-pyrazol-4-yl)phenoxy]-3-cyano-N-1,3-thiazol-2-ylbenzenesulfonamide | 472 [M$^{35}$ClH]+ |
| 547 | 3-cyano-4-{3-[1-ethyl-3-(trifluoromethyl)-1H-pyrazol-5-yl]phenoxy}-N-1,3-thiazol-2-ylbenzenesulfonamide | 520 [MH]+ |
| 548 | 3-cyano-4-{4-[3-(1-cyano-1-methylethyl)-1-ethyl-1H-pyrazol-5-yl]phenoxy}-N-1,3-thiazol-2-ylbenzenesulfonamide | 519 [MH]+ |
| 549 | 3-cyano-4-{3-[1-(2-hydroxyethyl)-3-(trifluoromethyl)-1H-pyrazol-5-yl]phenoxy}-N-1,3-thiazol-2-ylbenzenesulfonamide | 536 [MH]+ |
| 550 | 3-cyano-4-(3-{1-[2-(dimethylamino)ethyl]-3-(trifluoromethyl)-1H-pyrazol-5-yl}phenoxy)-N-1,3-thiazol-2-ylbenzenesulfonamide | 563 [MH]+ |
| 551 | 3-cyano-4-{2-fluoro-4-[1-(3-fluoropropyl)-3-(trifluoromethyl)-1H-pyrazol-5-yl]phenoxy}-N-1,3-thiazol-2-ylbenzenesulfonamide | 570 [MH]+ |
| 552 | 4-[2-(2-aminopyridin-4-yl)-4-(trifluoromethoxy)phenoxy]-2,5-difluoro-N-1,2,4-thiadiazol-5-ylbenzenesulfonamide | 547 [MH]+ |
| 553 | 4-[2-(2-aminopyridin-4-yl)-4-(trifluoromethoxy)phenoxy]-5-chloro-2-fluoro-N-1,2,4-thiadiazol-5-ylbenzenesulfonamide | 562 [M$^{35}$ClH]+ |
| 554 | 4-[2-(4-aminopyridin-2-yl)-4-chlorophenoxy]-5-chloro-2-fluoro-N-1,2,4-thiadiazol-5-ylbenzenesulfonamide | 512 [M$^{35}$ClH]+ |
| 555 | 4-[2-(6-aminopyridin-2-yl)-4-(trifluoromethyl)phenoxy]-2,5-difluoro-N-1,2,4-thiadiazol-5-ylbenzenesulfonamide | 530 [MH]+ |
| 556 | 4-[2-(2-aminopyridin-4-yl)-4-(trifluoromethyl)phenoxy]-2,5-difluoro-N-1,2,4-thiadiazol-5-ylbenzenesulfonamide | 530 [MH]+ |
| 557 | 4-[2-(2-aminopyridin-4-yl)-4-(trifluoromethyl)phenoxy]-5-chloro-2-fluoro-N-1,2,4-thiadiazol-5-ylbenzenesulfonamide | 546 [M$^{35}$ClH]+ |
| 558 | 4-{4-[1-azetidin-3-yl-3-(trifluoromethyl)-1H-pyrazol-5-yl]phenoxy}-3-cyano-N-1,3-thiazol-2-ylbenzenesulfonamide | 547 [MH]+ |
| 559 | 4-[2-(1-azetidin-3-yl-1H-pyrazol-5-yl)-4-chlorophenoxy]-N-(5-fluoro-1,3-thiazol-2-yl)-3-cyanobenzenesulfonamide | 547 [M$^{35}$ClH]+ |
| 560 | 5-chloro-4-(4-chloro-2-piperidin-4-ylphenoxy)-2-fluoro-N-pyrimidin-4-ylbenzenesulfonamide | 497 [M$^{35}$ClH]+ |
| 561 | 4-(4-chloro-2-piperidin-4-ylphenoxy)-2,5-difluoro-N-(5-fluoropyridin-2-yl)benzenesulfonamide | 498 [M$^{35}$ClH]+ |
| 562 | 4-{4-chloro-2-[1-(2-methoxyethyl)-1H-pyrazol-5-yl]phenoxy}-3-cyano-N-1,2,4-thiadiazol-5-ylbenzenesulfonamide | 517 [M$^{35}$ClH]+ 519 [M$^{37}$ClH]+ |
| 563 | 5-chloro-4-{4-chloro-2-[1-(2-methoxyethyl)-1H-pyrazol-5-yl]phenoxy}-2-fluoro-N-1,3,4-thiadiazol-2-ylbenzenesulfonamide | 544 [M$^{35}$ClH]+ 546 [M$^{37}$ClH]+ |
| 564 | 5-chloro-4-[4-chloro-2-(1H-pyrazol-4-yl)phenoxy]-2-fluoro-N-1,3,4-thiadiazol-2-ylbenzenesulfonamide | 486 [M$^{35}$ClH]+ 488 [M$^{37}$ClH]+ |
| 565 | 3-cyano-N-(5-fluoropyridin-2-yl)-4-{4-[(1,3,5-trimethyl-1H-pyrazol-4-yl)methyl]phenoxy}benzenesulfonamide | 492 [MH]+ |
| 566 | 4-[4-(azetidin-1-ylmethyl)-3-fluorophenoxy]-3-cyano-N-(5-fluoropyridin-2-yl)benzenesulfonamide | 457 [MH]+ |
| 567 | 3-cyano-N-(5-fluoropyridin-2-yl)-4-[4-(pyridin-3-ylmethyl)phenoxy]benzenesulfonamide | 461 [MH]+ |
| 568 | 3-cyano-4-[4-(3-ethyl-5-methyl-4H-1,2,4-triazol-4-yl)phenoxy]-N-(5-fluoropyridin-2-yl)benzenesulfonamide | 479 [MH]+ |
| 569 | 3-cyano-N-(5-fluoropyridin-2-yl)-4-[4-(1H-imidazol-1-yl)phenoxy]benzenesulfonamide | 436 [MH]+ |
| 570 | 3'-(2-cyano-4-{[(5-fluoropyridin-2-yl)amino]sulfonyl}phenoxy)-N-ethylbiphenyl-4-carboxamide | 517 [MH]+ |
| 571 | 3-cyano-N-(5-fluoropyridin-2-yl)-4-[2-(3-methyl-isothiazol-5-yl)phenoxy]benzenesulfonamide | 467 [MH]+ |
| 572 | 3-cyano-N-(5-fluoropyridin-2-yl)-4-[2-(2-methyl-1,3-thiazol-4-yl)phenoxy]benzenesulfonamide | 467 [MH]+ |
| 573 | 3-cyano-N-(5-fluoropyridin-2-yl)-4-[3-(1-methylpiperidin-4-yl)phenoxy]benzenesulfonamide | 467 [MH]+ |
| 574 | 3-cyano-N-(5-fluoropyridin-2-yl)-4-[3-(5-methyl-1,2,4-oxadiazol-3-yl)phenoxy]benzenesulfonamide | 452 [MH]+ |
| 575 | 3-cyano-N-(5-fluoropyridin-2-yl)-4-[3-methoxy-4-(4-methyl-1H-imidazol-1-yl)phenoxy]benzenesulfonamide | 480 [MH]+ |
| 576 | 3-cyano-N-(5-fluoropyridin-2-yl)-4-[4-(5-methyl-1,3,4-oxadiazol-2-yl)phenoxy]benzenesulfonamide | 452 [MH]+ |
| 577 | 3-cyano-N-(5-fluoropyridin-2-yl)-4-[2-(4-methyl-isothiazol-5-yl)phenoxy]benzenesulfonamide | 467 [MH]+ |
| 578 | 3-cyano-N-(5-fluoropyridin-2-yl)-4-[3-methoxy-4-(2-methyl-1H-imidazol-1-yl)phenoxy]benzenesulfonamide | 480 [MH]+ |

| Eg No | Name | MS m/z (unless otherwise incidated) |
|---|---|---|
| 579 | 3-cyano-N-(5-fluoropyridin-2-yl)-4-[3-methoxy-4-(1H-pyrazol-1-yl)phenoxy]benzenesulfonamide | 466 [MH]+ |
| 580 | 3-cyano-N-(5-fluoropyridin-2-yl)-4-[2-(1,3,4-oxadiazol-2-yl)phenoxy]benzenesulfonamide | 438 [MH]+ |
| 581 | 3-cyano-N-(5-fluoropyridin-2-yl)-4-[4-(1,3-oxazol-4-yl)phenoxy]benzenesulfonamide | 437 [MH]+ |
| 582 | 4-[4-Chloro-2-(1H-pyrazol-4-yl)phenoxy]-3-cyano-N-(5-iodo-1,3-thiazol-2-yl)benzenesulfonamide | 584 [M$^{35}$ClH]+ |
| 583 | 4-[2-(5-Amino-1H-pyrazol-4-yl)-4-chlorophenoxy]-N-(5-chloro-1,3-thiazol-2-yl)-3-cyanobenzenesulfonamide | 507 [M$^{35}$ClH]+ |
| 584 | 4-[2-(2-Aminopyridin-4-yl)-4-fluorophenoxy]-N-(5-chloro-1,3-thiazol-2-yl)-3-cyanobenzenesulfonamide | 502 [M$^{35}$ClH]+ |
| 585 | 4-[2-(2-Aminopyridin-4-yl)-4-chlorophenoxy]-N-(5-chloro-1,3-thiazol-2-yl)-3-cyanobenzenesulfonamide | 516 [M$^{35}$ClH]− |
| 586 | 4-{4-Chloro-2-[2-(hydroxymethyl)pyridin-4-yl]phenoxy}-N-(5-chloro-1,3-thiazol-2-yl)-3-cyanobenzenesulfonamide | 533.0 [M$^{35}$ClH]+ |
| 587 | 4-[2-(6-Aminopyridin-3-yl)-4-fluorophenoxy]-N-(5-chloro-1,3-thiazol-2-yl)-3-cyanobenzenesulfonamide | 502 [M$^{35}$ClH]+ |
| 588 | 4-(4-Chloro-2-oxetan-3-ylphenoxy)-N-(5-chloro-1,3-thiazol-2-yl)-3-cyanobenzenesulfonamide | 482 [M$^{35}$ClH]+ |
| 589 | N-(5-Chloro-1,3-thiazol-2-yl)-3-cyano-4-[4-fluoro-2-(1H-pyrazol-5-yl)phenoxy]benzenesulfonamide | 476 [M$^{35}$ClH]+ |
| 590 | N-(5-Chloro-1,3-thiazol-2-yl)-3-cyano-4-[2-(1H-pyrazol-4-yl)-4-(trifluoromethyl)phenoxy]benzenesulfonamide | 526 [M$^{35}$ClH]+ |
| 591 | N-(5-Chloro-1,3-thiazol-2-yl)-3-cyano-4-[2-(1H-pyrazol-4-yl)-4-(trifluoromethoxy)phenoxy]benzenesulfonamide | 542 [M$^{35}$ClH]+ |
| 592 | N-(5-Chloro-1,3-thiazol-2-yl)-3-cyano-4-{[4-(1-methyl-1H-pyrazol-5-yl)-6-(trifluoromethyl)pyridin-3-yl]oxy}benzenesulfonamide | 540 [M$^{35}$ClH]+ |
| 593 | 4-(4-Chloro-2-piperidin-4-ylphenoxy)-N-(5-chloro-1,3-thiazol-2-yl)-3-cyanobenzenesulfonamide | 509 [M$^{35}$ClH]+ |
| 594 | 4-(2-Azetidin-3-yl-4-chlorophenoxy)-N-(5-chloro-1,3-thiazol-2-yl)-3-cyanobenzenesulfonamide | 481 [M$^{35}$ClH]+ |
| 595 | 4-{4-Chloro-2-[1-(difluoromethyl)-1H-pyrazol-5-yl]phenoxy}-N-(5-chloro-1,3-thiazol-2-yl)-3-cyanobenzenesulfonamide | 542.0 [M$^{35}$ClH]+ |
| 596 | N-(5-Chloro-1,3-thiazol-2-yl)-3-cyano-4-[4-fluoro-2-(1-methyl-1H-pyrazol-5-yl)phenoxy]benzenesulfonamide | 490 [M$^{35}$ClH]+ |
| 597 | 4-[4-Chloro-2-(1-methyl-1H-pyrazol-5-yl)phenoxy]-N-(5-chloro-1,3-thiazol-2-yl)-3-cyanobenzenesulfonamide | 506 [M$^{35}$ClH]+ |
| 598 | 3-cyano-4-[2-(1H-pyrazol-4-yl)-4-(trifluoromethyl)phenoxy]-N-1,3-thiazol-4-ylbenzenesulfonamide | 492 [MH]+ |
| 599 | 3-cyano-4-[2-(1H-pyrazol-4-yl)-4-(trifluoromethoxy)phenoxy]-N-1,3-thiazol-4-ylbenzenesulfonamide | 508 [MH]+ |
| 600 | 4-(biphenyl-2-yloxy)-3-cyano-N-(5-methyl-1,3-thiazol-4-yl)benzenesulfonamide | 448 [MH]+ |
| 601 | 3-cyano-4-{[4-(1-methyl-1H-pyrazol-5-yl)-6-(trifluoromethyl)pyridin-3-yl]oxy}-N-1,3-thiazol-4-ylbenzenesulfonamide | 507.0 [MH]+ |
| 602 | 4-[4-chloro-2-(1-methyl-1H-pyrazol-5-yl)phenoxy]-3-cyano-N-(5-fluoro-1,3-thiazol-4-yl)benzenesulfonamide | 490 [M$^{35}$ClH]+ |
| 603 | 4-(biphenyl-2-yloxy)-3-cyano-N-1,2,4-thiadiazol-3-ylbenzenesulfonamide | 433 [MH]− |
| 604 | 4-(2-azetidin-3-yl-4-chlorophenoxy)-2,5-difluoro-N-1,3-thiazol-4-ylbenzenesulfonamide | 458 [M$^{35}$ClH]+ |
| 605 | 4-[4-chloro-2-(1H-pyrazol-4-yl)phenoxy]-2,5-difluoro-N-1,3-thiazol-4-ylbenzenesulfonamide | 469 [M$^{35}$ClH]+ |
| 606 | 4-[4-chloro-2-(1-methyl-1H-pyrazol-5-yl)phenoxy]-2,5-difluoro-N-1,3-thiazol-4-ylbenzenesulfonamide | 483 [M$^{35}$ClH]+ |
| 607 | 2,5-difluoro-4-[2-(1H-pyrazol-4-yl)-4-(trifluoromethoxy)phenoxy]-N-1,3-thiazol-4-ylbenzenesulfonamide | 533 [MH]+ |
| 608 | 4-[4-chloro-2-(1-methyl-1H-pyrazol-5-yl)phenoxy]-3-cyano-N-(5-fluoropyridin-2-yl)benzenesulfonamide | 484 [M$^{35}$ClH]+ |
| 609 | 3-fluoro-N-(5-fluoro-1,3-thiazol-2-yl)-4-{4-[1-methyl-3-(trifluoromethyl)-1H-pyrazol-5-yl]phenoxy}benzenesulfonamide | 517 [MH]+ |
| 610 | 4-[4-(3,5-Dimethyl-1H-pyrazol-1-yl)phenoxy]-2-fluoro-N-1,3-thiazol-2-ylbenzenesulfonamide | 445 [MH]+ |
| 611 | 4-[4-chloro-2-(1H-pyrazol-4-yl)phenoxy]-3-fluoro-N-1,3-thiazol-4-ylbenzenesulfonamide | 451 [M$^{35}$ClH]+ |
| 612 | 3-fluoro-4-[2-(1H-pyrazol-4-yl)-4-(trifluoromethoxy)phenoxy]-N-1,3-thiazol-4-ylbenzenesulfonamide | 501 [MH]+ |
| 613 | N-(5-chloro-1,3-thiazol-2-yl)-2,5-difluoro-4-[4-fluoro-2-(1-methyl-1H-pyrazol-5-yl)phenoxy]benzenesulfonamide | 501 [M$^{35}$ClH]+ |
| 614 | N-(5-chloro-1,3-thiazol-2-yl)-2,5-difluoro-4-[4-fluoro-2-(1H-pyrazol-4-yl)phenoxy]benzenesulfonamide | 487 [M$^{35}$ClH]+ |
| 615 | N-(5-chloro-1,3-thiazol-2-yl)-4-[5-cyano-2-(1-methyl-1H-pyrazol-5-yl)phenoxy]-2,5-difluorobenzenesulfonamide | 508 [M$^{35}$ClH]+ |
| 616 | 5-chloro-4-[2-(5-cyanopyridin-3-yl)-4-(trifluoromethyl)phenoxy]-2-fluoro-N-1,2,4-thiadiazol-5-ylbenzenesulfonamide | 556 [M$^{35}$ClH]+ |
| 617 | 4-[2-(6-aminopyridin-2-yl)-4-fluorophenoxy]-5-chloro-2-fluoro-N-1,2,4-thiadiazol-5-ylbenzenesulfonamide | 496 [M$^{35}$ClH]+ |
| 618 | 4-[2-(2-aminopyridin-3-yl)-4-chlorophenoxy]-5-chloro-2-fluoro-N-1,2,4-thiadiazol-5-ylbenzenesulfonamide | 512 [M$^{35}$ClH]+ |
| 619 | 4-(2-azetidin-3-yl-4-chlorophenoxy)-5-chloro-2-fluoro-N-1,2,4-thiadiazol-5-ylbenzenesulfonamide | 475 [M$^{35}$ClH]+ |
| 620 | 5-chloro-2-fluoro-4-[4-fluoro-2-(1H-pyrazol-5-yl)phenoxy]-N-1,2,4-thiadiazol-5-ylbenzenesulfonamide | 470 [M$^{35}$ClH]+ |
| 621 | 5-chloro-2-fluoro-4-(4-fluoro-2-(1-methyl-1H-pyrazol-5-yl)phenoxy)-N-(1,2,4-thiadiazol-5-yl)benzenesulfonamide | 484 [M$^{35}$ClH]+ |
| 622 | 4-[2-(2-aminopyrimidin-4-yl)-4-fluorophenoxy]-N-(5-chloro-1,3-thiazol-2-yl)-2,5-difluorobenzenesulfonamide | 514 [M$^{35}$ClH]+ |
| 623 | 5-chloro-4-(4-chloro-2-piperidin-4-ylphenoxy)-2-fluoro-N-(5-fluoropyridin-2-yl)benzenesulfonamide | 514 [M$^{35}$ClH]+ |
| 624 | 5-chloro-4-[4-chloro-2-(1-methyl-1H-pyrazol-5-yl)phenoxy]-2-fluoro-N-(5-fluoropyridin-2-yl)benzenesulfonamide | 509 [M$^{35}$ClH]+ |
| 625 | 5-bromo-2-fluoro-4-[4-fluoro-2-(1-methyl-1H-pyrazol-5-yl)phenoxy]-N-1,3-thiazol-4-ylbenzenesulfonamide | 527 [M$^{79}$BrH]+ |
| 626 | 2-fluoro-4-[4-fluoro-2-(1-methyl-1H-pyrazol-5-yl)phenoxy]-5-methyl-N-1,3-thiazol-4-ylbenzenesulfonamide | 463 [MH]+ |
| 627 | 5-ethyl-2-fluoro-4-[4-fluoro-2-(1-methyl-1H-pyrazol-5-yl)phenoxy]-N-1,3-thiazol-4-ylbenzenesulfonamide | 477 [MH]+ |
| 628 | 3-methyl-4-[2-(1-methyl-1H-pyrazol-5-yl)phenoxy]-N-1,3-thiazol-4-ylbenzenesulfonamide | 427 [MH]+ |
| 629 | 3-iodo-4-[2-(1-methyl-1H-pyrazol-5-yl)phenoxy]-N-1,3-thiazol-4-ylbenzenesulfonamide | 539 [MH]+ |
| 630 | 5-chloro-2-fluoro-4-(4-fluoro-2-(1-methyl-1H-pyrazol-5-yl)phenoxy)-N-(5-methylthiazol-4-yl)benzenesulfonamide | 497 [M$^{35}$ClH]+ |
| 631 | 5-chloro-6-(4-chloro-2-(1-methyl-1H-pyrazol-5-yl)phenoxy)-N-(thiazol-4-yl)pyridine-3-sulfonamide | 482 [M$^{35}$ClH]+ |
| 632 | 2,5-difluoro-4-[2-pyrazin-2-yl-4-(trifluoromethyl)phenoxy]-N-1,2,4-thiadiazol-5-ylbenzenesulfonamide | 516 [MH]+ |
| 633 | 2,5-difluoro-4-[2-(tetrahydro-2H-pyran-4-yl)-4-(trifluoromethyl)phenoxy]-N-1,2,4-thiadiazol-5-ylbenzenesulfonamide | 522 [MH]+ |
| 634 | 4-[2-(2-aminopyridin-4-yl)-4-fluorophenoxy]-2,5-difluoro-N-1,2,4-thiadiazol-5-ylbenzenesulfonamide | 480 [MH]+ |
| 635 | 4-[4-chloro-2-(5-methyl-1H-pyrazol-4-yl)phenoxy]-2,5-difluoro-N-1,2,4-thiadiazol-5-ylbenzenesulfonamide | 484 [M$^{35}$ClH]+ |
| 636 | 4-(4-chloro-2-piperidin-4-ylphenoxy)-2,5-difluoro-N-1,2,4-thiadiazol-5-ylbenzenesulfonamide | 470 [M$^{35}$ClH]+ |

| Eg No | Name | MS m/z (unless otherwise incidated) |
|---|---|---|
| 637 | 4-[4-Chloro-2-(1H-pyrazol-5-yl)phenoxy]-2,5-difluoro-N-1,2,4-thiadiazol-5-ylbenzenesulfonamide | 470 [MH]+ |
| 638 | 4-(4-chloro-2-(1-methyl-1H-pyrazol-5-yl)phenoxy)-2,5-difluoro-N-(1,2,4-thiadiazol-5-yl)benzenesulfonamide | 484.0 [M$^{35}$ClH]+ |
| 639 | 4-[3-(6-aminopyridin-2-yl)phenoxy]-3-cyano-N-1,3-thiazol-2-ylbenzenesulfonamide | 450 [MH]+ |
| 640 | 4-[2-(1-acetylazetidin-3-yl)-4-chlorophenoxy]-3-cyano-N-1,3-thiazol-2-ylbenzenesulfonamide | 489 [M$^{35}$ClH]+ |
| 641 | 3-cyano-4-{4-fluoro-2-[1-(2,2,2-trifluoroethyl)-1H-pyrazol-4-yl]phenoxy}-N-1,3-thiazol-2-ylbenzenesulfonamide | 524 [MH]+ |
| 642 | 3-cyano-4-[2-fluoro-4-(1H-pyrazol-1-ylmethyl)phenoxy]-N-1,3-azol-2-ylbenzenesulfonamide | 456 [MH]+ |
| 643 | 3-cyano-N-1,3-thiazol-2-yl-4-({6-[3-(trifluoromethyl)-1H-pyrazol-1-yl]pyridin-3-yl}oxy)benzenesulfonamide | 493 [MH]+ |
| 644 | 3-cyano-4-[(6-phenoxypyridin-3-yl)oxy]-N-1,3-thiazol-2-ylbenzenesulfonamide | 451 [MH]+ |
| 645 | 3-cyano-4-{[6-(1-methyl-1H-pyrazol-5-yl)pyridin-3-yl]oxy}-N-1,3-thiazol-2-ylbenzenesulfonamide | 439 [MH]+ |
| 646 | 3-cyano-4-[(6-phenylpyridin-3-yl)oxy]-N-1,3-thiazol-2-ylbenzenesulfonamide | 435 [MH]+ |
| 647 | 3-cyano-4-({6-[1-methyl-3-(trifluoromethyl)-1H-pyrazol-5-yl]pyridin-3-yl}oxy)-N-1,3-thiazol-2-ylbenzenesulfonamide | 507 [MH]+ |
| 648 | 4-[4-chloro-3-(1-methyl-1H-pyrazol-5-yl)phenoxy]-3-cyano-N-1,3-thiazol-2-ylbenzenesulfonamide | 472 [M$^{35}$ClH]+ |
| 649 | 3-cyano-N-1,3-thiazol-2-yl-4-{3-[3-(trifluoromethyl)-1H-pyrazol-1-yl]phenoxy}benzenesulfonamide | 490 [MH]− |
| 650 | 3-cyano-4-{3-[5-methyl-3-(trifluoromethyl)-1H-pyrazol-1-yl]phenoxy}-N-1,3-thiazol-2-ylbenzenesulfonamide | 506 [MH]+ |
| 651 | 4-[4-chloro-2-(1-methyl-1H-imidazol-2-yl)phenoxy]-3-cyano-N-1,3-thiazol-2-ylbenzenesulfonamide | 472 [M$^{35}$ClH]+ |
| 652 | 4-(4-chloro-2-pyrazin-2-ylphenoxy)-3-cyano-N-1,3-thiazol-2-ylbenzenesulfonamide | 470 [M$^{35}$ClH]+ |
| 653 | 3-cyano-4-{3-fluoro-5-[1-methyl-3-(trifluoromethyl)-1H-pyrazol-5-yl]phenoxy}-N-1,3-thiazol-2-ylbenzenesulfonamide | 524 [MH]+ |
| 654 | 3-cyano-4-{3-[3-(difluoromethyl)-5-(methoxymethyl)-1H-pyrazol-1-yl]phenoxy}-N-1,3-thiazol-2-ylbenzenesulfonamide | 518 [MH]+ |
| 655 | 5-chloro-4-(4-chloro-2-piperidin-4-ylphenoxy)-2-fluoro-N-1,3-thiazol-4-ylbenzenesulfonamide | 502 [M$^{35}$ClH]+ |
| 656 | 5-chloro-2-fluoro-4-{[2-(1-methyl-1H-pyrazol-5-yl)-6-(trifluoromethyl)pyridin-3-yl]oxy}-N-1,3-thiazol-4-ylbenzenesulfonamide | 534 [M$^{35}$ClH]+ |
| 657 | 5-chloro-2-fluoro-4-[4-fluoro-2-(1-methyl-1H-pyrazol-5-yl)phenoxy]-N-1,3-thiazol-4-ylbenzenesulfonamide | 483 [M$^{35}$ClH]+ |
| 658 | 5-chloro-2-fluoro-4-[4-fluoro-2-(1H-pyrazol-5-yl)phenoxy]-N-1,3-thiazol-4-ylbenzenesulfonamide | 469 [M$^{35}$ClH]+ |
| 659 | 5-chloro-2-fluoro-4-[2-(1H-pyrazol-4-yl)-4-(trifluoromethyl)phenoxy]-N-1,3-thiazol-4-ylbenzenesulfonamide | 519 [M$^{35}$ClH]+ |
| 660 | 5-chloro-4-[4-chloro-2-(1-methyl-1H-pyrazol-5-yl)phenoxy]-2-fluoro-N-1,3-thiazol-4-ylbenzenesulfonamide | 499 [M$^{35}$ClH]+ |
| 661 | 5-chloro-4-[4-chloro-2-(1H-pyrazol-4-yl)phenoxy]-2-fluoro-N-1,3-thiazol-4-ylbenzenesulfonamide | 485 [M$^{35}$ClH]+ |
| 662 | 5-chloro-4-[4-chloro-2-(3-methyl-1H-pyrazol-4-yl)phenoxy]-2-fluoro-N-1,3-thiazol-4-ylbenzenesulfonamide | 499 [M$^{35}$ClH]+ |
| 663 | 5-chloro-2-fluoro-4-{[3'-(hydroxymethyl)-4-(trifluoromethyl)biphenyl-2-yl]oxy}-N-1,3-thiazol-4-ylbenzenesulfonamide | 559 [[M$^{35}$ClH]+ |
| 664 | 5-chloro-2-fluoro-4-[2-(1H-pyrazol-4-yl)-5-(trifluoromethyl)phenoxy]-N-1,3-thiazol-4-ylbenzenesulfonamide | 518 [M$^{35}$ClH]+ 520 [M$^{37}$ClH]+ |
| 665 | 3-Cyano-4-{4-[4-(hydroxymethyl)-1,3-oxazol-2-yl]phenoxy}-N-1,2,4-thiadiazol-5-ylbenzenesulfonamide | 456 [MH]+ |
| 666 | 2,5-Difluoro-N-(5-fluoropyridin-2-yl)-4-[2-piperidin-4-yl-4-(trifluoromethyl)phenoxy]benzenesulfonamide | 532 [MH]+ |
| 667 | 4-[4-chloro-2-(1-methyl-1H-pyrazol-5-yl)phenoxy]-N-(3,5-difluoropyridin-2-yl)-3-fluorobenzenesulfonamide | 495 [M$^{35}$ClH]+ |
| 668 | 3-Chloro-4-[4-chloro-2-(1-methyl-1H-pyrazol-5-yl)phenoxy]-N-pyrimidin-4-ylbenzenesulfonamide | 476 [M$^{35}$ClH]+ |
| 669 | 3-Chloro-4-[4-fluoro-2-(1-methyl-1H-pyrazol-5-yl)phenoxy]-N-pyrimidin-4-ylbenzenesulfonamide | 460 [M$^{35}$ClH]+ |
| 670 | 4-[4-Chloro-2-(1-methyl-1H-pyrazol-5-yl)phenoxy]-3-fluoro-N-pyrimidin-4-ylbenzenesulfonamide | 460 [M$^{35}$ClH]+ |
| 671 | 3-cyano-4-[2-pyrazin-2-yl-4-(trifluoromethyl)phenoxy]-N-1,2,4-thiadiazol-5-ylbenzenesulfonamide | 505 [MH]+ |
| 672 | 4-[4-chloro-2-(1H-pyrazol-4-yl)phenoxy]-N-1,3-thiazol-4-ylbenzenesulfonamide | 433 [M$^{35}$ClH]+ |
| 673 | 3-chloro-4-[4-chloro-2-(1H-pyrazol-4-yl)phenoxy]-N-1,3-thiazol-4-ylbenzenesulfonamide | 467 [M$^{35}$ClH]+ |
| 674 | 4-[4-chloro-2-(1H-pyrazol-4-yl)phenoxy]-3-fluoro-N-(5-fluoro-1,3-thiazol-2-yl)benzenesulfonamide | 469 [M$^{35}$ClH]+ |
| 675 | 3-cyano-5-fluoro-4-[4-fluoro-2-(1-methyl-1H-pyrazol-5-yl)phenoxy]-N-1,2,4-thiadiazol-5-ylbenzenesulfonamide | 475 [MH]+ |
| 676 | 4-[4-chloro-2-(1H-pyrazol-4-yl)phenoxy]-3-cyano-5-fluoro-N-1,2,4-thiadiazol-5-ylbenzenesulfonamide | 477 [M$^{35}$ClH]+ |
| 677 | 2,5-difluoro-4-[2-(1H-pyrazol-4-yl)-4-(trifluoromethoxy)phenoxy]-N-1,3-thiazol-2-ylbenzenesulfonamide | 519 [MH]+ |
| 678 | 2,5-difluoro-4-{4-[1-methyl-3-(trifluoromethyl)-1H-pyrazol-5-yl]phenoxy}-N-1,3-thiazol-2-ylbenzenesulfonamide | 517 [MH]+ |
| 679 | 4-[4-chloro-2-(1H-pyrazol-4-yl)phenoxy]-2,5-difluoro-N-1,3-thiazol-2-ylbenzenesulfonamide | 469 [M$^{35}$ClH]+ |
| 680 | 4-[4-chloro-2-(1H-pyrazol-4-yl)phenoxy]-2-fluoro-N-1,3-thiazol-4-ylbenzenesulfonamide | 451 [M$^{35}$ClH]+ |
| 681 | 4-[4-chloro-2-(1-methyl-1H-pyrazol-5-yl)phenoxy]-2-fluoro-N-1,3-thiazol-4-ylbenzenesulfonamide | 465 [M$^{35}$ClH]+ |
| 682 | 2,5-difluoro-N-(5-fluoro-1,3-thiazol-2-yl)-4-{4-[1-methyl-3-(trifluoromethyl)-1H-pyrazol-5-yl]phenoxy}benzenesulfonamide | 535 [MH]+ |
| 683 | 4-[4-chloro-2-(1H-pyrazol-4-yl)phenoxy]-2,5-difluoro-N-(5-fluoro-1,3-thiazol-2-yl)benzenesulfonamide | 487 [M$^{35}$ClH]+ |
| 684 | 3-fluoro-4-{4-[1-methyl-3-(trifluoromethyl)-1H-pyrazol-5-yl]phenoxy}-N-1,3-thiazol-2-ylbenzenesulfonamide | 499 [MH]+ |
| 685 | 4-[4-chloro-2-(1H-pyrazol-4-yl)phenoxy]-3-fluoro-N-1,3-thiazol-2-ylbenzenesulfonamide | 451 [M$^{35}$ClH]+ |
| 686 | 3-fluoro-4-[4-fluoro-2-(1H-pyrazol-4-yl)phenoxy]-N-1,3-thiazol-2-ylbenzenesulfonamide | 435 [MH]+ |
| 687 | 3-fluoro-4-[2-(1H-pyrazol-4-yl)-4-(trifluoromethoxy)phenoxy]-N-1,3-thiazol-2-ylbenzenesulfonamide | 501 [MH]+ |
| 688 | 5-Chloro-2-fluoro-4-[4-fluoro-2-(3-methoxy-1-methyl-1H-pyrazol-5-yl)-phenoxy]-N-1,3-thiazol-4-yl-benzenesulfonamide | 513 [M$^{35}$ClH]+ |
| 689 | 5-Chloro-2-fluoro-4-{2-[5-(hydroxymethyl)pyridin-3-yl]-4-(trifluoromethyl)phenoxy}-N-1,3-thiazol-4-ylbenzenesulfonamide | 560 [M$^{35}$ClH]+ |
| 690 | 4-(2-azetidin-3-yl-4-chlorophenoxy)-3-cyano-N-1,3-thiazol-2-ylbenzenesulfonamide | 447 [M$^{35}$ClH]+ |
| 691 | 4-{4-chloro-2-[3-(trifluoromethyl)-1H-pyrazol-4-yl]phenoxy}-3-cyano-N-1,3-thiazol-2-ylbenzenesulfonamide | 524 [M$^{35}$ClH]− |
| 692 | 4-[(5-chloro-2'-methylbiphenyl-2-yl)oxy]-3-cyano-N-1,3-thiazol-2-ylbenzenesulfonamide | 482 [M$^{35}$ClH]+ |
| 693 | 4-[4-chloro-2-(1-methyl-1H-pyrazol-4-yl)phenoxy]-3-cyano-N-1,3-thiazol-2-ylbenzenesulfonamide | 472 [M$^{35}$ClH]+ |
| 694 | 4-[4-chloro-2-(1H-1,2,3-triazol-5-yl)phenoxy]-3-cyano-N-1,3-thiazol-2-ylbenzenesulfonamide | 459 [M$^{35}$ClH]+ |
| 695 | 4-{4-[4-chloro-1-ethyl-3-(trifluoromethyl)-1H-pyrazol-5-yl]phenoxy}-3-cyano-N-1,3-thiazol-2-ylbenzenesulfonamide | 554 [M$^{35}$ClH]+ |

| Eg No | Name | MS m/z (unless otherwise indicated) |
|---|---|---|
| 696 | 3-cyano-4-[4-iodo-2-(1H-pyrazol-4-yl)phenoxy]-N-1,3-thiazol-2-ylbenzenesulfonamide | 550 [MH]+ |
| 697 | 4-[4-Bromo-2-(1H-pyrazol-4-yl)phenoxy]-3-cyano-N-1,3-thiazol-2-ylbenzenesulfonamide | 502 [M$^{79}$BrH]+ |
| 698 | 4-[4-chloro-2-(4-methyl-1,3-thiazol-5-yl)phenoxy]-3-cyano-N-1,3-thiazol-2-ylbenzenesulfonamide | 489 [M$^{35}$ClH]+ |
| 699 | 3-cyano-4-[2-(1-methyl-1H-pyrazol-5-yl)-5-(trifluoromethyl)phenoxy]-N-1,3-thiazol-2-ylbenzenesulfonamide | 506 [MH]+ |
| 700 | 4-(4-chloro-2-pyridin-3-ylphenoxy)-3-cyano-N-1,3-thiazol-2-ylbenzenesulfonamide | 469 [M$^{35}$ClH]+ |
| 701 | 4-(4-chloro-2-pyrimidin-5-ylphenoxy)-3-cyano-N-1,3-thiazol-2-ylbenzenesulfonamide | 470 [M$^{35}$ClH]+ |
| 702 | 3-cyano-4-[4-fluoro-2-(6-fluoropyridin-3-yl)phenoxy]-N-1,3-thiazol-2-ylbenzenesulfonamide | 469 [MH]− |
| 703 | 3-cyano-4-[(4'-cyano-3'-methoxybiphenyl-2-yl)oxy]-N-1,3-thiazol-2-ylbenzenesulfonamide | 489 [MH]+ |
| 704 | 3-cyano-4-[2-(1H-pyrazol-4-yl)-4-(trifluoromethoxy)phenoxy]-N-1,3-thiazol-2-ylbenzenesulfonamide | 508 [MH]+ |
| 705 | 4-[4-bromo-2-(1-methyl-1H-pyrazol-5-yl)phenoxy]-3-cyano-N-1,3-thiazol-2-ylbenzenesulfonamide | 516 [M$^{79}$BrH]+ |
| 706 | 4-[2-(3-amino-1H-pyrazol-4-yl)-4-chlorophenoxy]-3-cyano-N-1,3-thiazol-2-ylbenzenesulfonamide | 473 [M$^{35}$ClH]+ |
| 707 | 4-[2-(5-amino-1H-pyrazol-4-yl)phenoxy]-3-cyano-N-1,3-thiazol-2-ylbenzenesulfonamide | 439 [MH]+ |
| 708 | 3-cyano-4-{4-[3-(difluoromethyl)-5-(hydroxymethyl)-1H-pyrazol-1-yl]phenoxy}-N-1,3-thiazol-2-ylbenzenesulfonamide | 504 [MH]+ |
| 709 | 4-[4-chloro-2-(1H-pyrazol-5-yl)phenoxy]-3-cyano-N-1,3-thiazol-2-ylbenzenesulfonamide | 458 [M$^{35}$ClH]+ |
| 710 | 4-[4-chloro-2-(4-fluoro-1H-pyrazol-5-yl)phenoxy]-3-cyano-N-1,3-thiazol-2-ylbenzenesulfonamide | 476 [M$^{35}$ClH]+ |
| 711 | 4-[5-chloro-2-(1H-pyrazol-5-yl)phenoxy]-3-cyano-N-1,3-thiazol-2-ylbenzenesulfonamide | 458 [M$^{35}$ClH]+ |
| 712 | 4-(biphenyl-2-yloxy)-3-cyano-N-(5-fluoro-4-methyl-1,3-thiazol-2-yl)benzenesulfonamide | 466 [MH]+ |
| 713 | 3-Cyano-N-(5-fluoro-1,3-thiazol-2-yl)-4-[4-iodo-2-(1H-pyrazol-5-yl)phenoxy]benzenesulfonamide | 568 [MH]+ |
| 714 | 3-cyano-N-(5-fluoro-1,3-thiazol-2-yl)-4-[4-(3-hydroxypropyl)-2-(1H-pyrazol-4-yl)phenoxy]benzenesulfonamide | 500 [MH]+ |
| 715 | 3-cyano-N-(5-fluoro-1,3-thiazol-2-yl)-4-[4-(3-hydroxypropyl)-2-(1-methyl-1H-pyrazol-5-yl)phenoxy]benzenesulfonamide | 514 [MH]+ |
| 716 | 3-cyano-N-(5-fluoro-1,3-thiazol-2-yl)-4-[4-(2-hydroxyethyl)-2-(1-methyl-1H-pyrazol-5-yl)phenoxy]benzenesulfonamide | 500 [MH]+ |
| 717 | 4-[4-chloro-2-(1-methyl-1H-1,2,4-triazol-5-yl)phenoxy]-3-cyano-N-(5-fluoro-1,3-thiazol-2-yl)benzenesulfonamide | 491 [M$^{35}$ClH]+ |
| 718 | 3-cyano-N-(5-fluoro-1,3-thiazol-2-yl)-4-[2-(1-methyl-1H-pyrazol-5-yl)-4-(trifluoromethyl)phenoxy]benzenesulfonamide | 524 [MH]+ |
| 719 | 3-cyano-4-{3-fluoro-4-[1-methyl-3-(trifluoromethyl)-1H-pyrazol-5-yl]phenoxy}-N-(5-fluoro-1,3-thiazol-2-yl)benzenesulfonamide | 542 [MH]+ |
| 720 | 4-{2-chloro-4-[1-methyl-3-(trifluoromethyl)-1H-pyrazol-5-yl]phenoxy}-3-cyano-N-(5-fluoro-1,3-thiazol-2-yl)benzenesulfonamide | 558 [M$^{35}$ClH]+ |
| 721 | 4-[4-Cyano-2-(1-methyl-1H-pyrazol-5-yl)phenoxy]-3-fluoro-N-1,3-thiazol-2-ylbenzenesulfonamide | 456 [MH]+ |
| 722 | 4-[5-Chloro-2-(1H-pyrazol-5-yl)phenoxy]-3-fluoro-N-1,3-thiazol-2-ylbenzenesulfonamide | 451 [M$^{35}$ClH]+ |
| 723 | 3-Fluoro-4-[4-isobutyl-2-(1-methyl-1H-pyrazol-5-yl)phenoxy]-N-1,3-thiazol-2-ylbenzenesulfonamide | 487 [MH]+ |
| 724 | 3-chloro-4-[4-chloro-2-(1H-pyrazol-4-yl)phenoxy]-N-1,2,4-thiadiazol-5-ylbenzenesulfonamide | 468 [M$^{35}$ClH]+ / 470 [M$^{37}$ClH]+ |
| 725 | 4-{4-chloro-2-[1-(1-methylpiperidin-4-yl)-1H-pyrazol-5-yl]phenoxy}-3-cyano-N-1,2,4-thiadiazol-5-ylbenzenesulfonamide | 556 [M$^{35}$ClH]+ |
| 726 | 4-[2-(1-azetidin-3-yl-1H-pyrazol-5-yl)-4-chlorophenoxy]-5-chloro-2-fluoro-N-1,3-thiazol-4-ylbenzenesulfonamide | 540 [M$^{35}$ClH]+ |
| 727 | 4-[2-(1-azetidin-3-yl-1H-pyrazol-4-yl)-4-(trifluoromethyl)phenoxy]-3-cyano-N-1,3-thiazol-4-ylbenzenesulfonamide | 547 [MH]+ |
| 728 | 4-[2-(1-azetidin-3-yl-1H-pyrazol-5-yl)-4-chlorophenoxy]-3-cyano-N-1,2,4-thiadiazol-5-ylbenzenesulfonamide | 514 [M$^{35}$ClH]+ / 516 [M$^{37}$ClH]+ |
| 729 | 4-{4-chloro-2-[1-(1-methylazetidin-3-yl)-1H-pyrazol-5-yl]phenoxy}-3-cyano-N-1,3-thiazol-4-ylbenzenesulfonamide | 527 [M$^{35}$ClH]+ |
| 730 | 5-chloro-4-{4-chloro-2-[1-(1-methylazetidin-3-yl)-1H-pyrazol-5-yl]phenoxy}-2-fluoro-N-1,3-thiazol-4-ylbenzenesulfonamide | 554 [M$^{35}$ClH]+ / 556 [M$^{37}$ClH]+ |
| 731 | 4-{4-chloro-2-[1-(1-methylazetidin-3-yl)-1H-pyrazol-5-yl]phenoxy}-2,5-difluoro-N-1,3-thiazol-4-ylbenzenesulfonamide | 538 [M$^{35}$ClH]+ |
| 732 | 4-[2-(2-aminopyridin-4-yl)-4-chlorophenoxy]-5-chloro-2-fluoro-N-1,2,4-thiadiazol-5-ylbenzenesulfonamide | 512 [M$^{35}$ClH]+ |
| 733 | 2,5-difluoro-4-[2-(1,2,3,6-tetrahydropyridin-4-yl)-4-(trifluoromethyl)phenoxy]-N-1,2,4-thiadiazol-5-ylbenzenesulfonamide | 519 [MH]+ |
| 734 | 4-[4-chloro-2-(1-methylpiperidin-4-yl)phenoxy]-2,5-difluoro-N-1,2,4-thiadiazol-5-ylbenzenesulfonamide | 501 [M$^{35}$ClH]+ |
| 735 | 2-[4-bromo-2-(1-methyl-1H-pyrazol-5-yl)phenoxy]-5-[(1,2,4-thiadiazol-5-ylamino)sulfonyl]benzamide | 535 [M$^{79}$BrH]+ / 537 [M$^{81}$BrH]+ |
| 736 | 4-[4-chloro-2-(2-piperazin-1-ylpyridin-4-yl)phenoxy]-3-cyano-N-1,2,4-thiadiazol-5-ylbenzenesulfonamide | 554 [MH]+ |
| 737 | 4-[4-chloro-2-(1H-pyrazol-4-yl)phenoxy]-3-fluoro-N-1,2,4-thiadiazol-5-ylbenzenesulfonamide | 452 [M$^{35}$ClH]+ / 454 [M$^{37}$ClH]+ / 450 [M$^{35}$ClH]− / 452 [M$^{37}$ClH]− |
| 738 | 4-[4-chloro-2-(1H-pyrazol-4-yl)phenoxy]-2,5-difluoro-N-1,2,4-thiadiazol-5-ylbenzenesulfonamide | 470 [M$^{35}$ClH]+ / 472 [M$^{37}$ClH]+ / 468 [M$^{35}$ClH]− / 470 [M$^{37}$ClH]− |
| 739 | 6-[4-chloro-2-(1-methyl-1H-pyrazol-5-yl)phenoxy]-5-cyano-N-1,3-azol-2-ylpyridine-3-sulfonamide | 473 [MH]+ / 471 [MH]− |
| 740 | 5-cyano-6-{4-[1-ethyl-3-(trifluoromethyl)-1H-pyrazol-5-yl]phenoxy}-N-1,3-thiazol-2-ylpyridine-3-sulfonamide | 521 [MH]+ / 519 [MH]− |
| 741 | 3-cyano-4-[2-(1H-pyrazol-5-yl)-4-(trifluoromethyl)phenoxy]-N-1,2,4-thiadiazol-5-ylbenzenesulfonamide | 493 [MH]+ / 491 [MH]− |
| 742 | 4-[2-(3-amino-1H-pyrazol-4-yl)-4-chlorophenoxy]-2,5-difluoro-N-1,2,4-thiadiazol-5-ylbenzenesulfonamide | 485 [M$^{35}$ClH]+ / 487 [M$^{37}$ClH]+ |
| 743 | 4-[4-chloro-2-(2-chloropyridin-4-yl)phenoxy]-3-cyano-N-1,2,4-thiadiazol-5-ylbenzenesulfonamide | 504 [M$^{35}$ClH]+ |
| 744 | 3-chloro-4-(4-chloro-2-piperidin-4-ylphenoxy)-N-pyrimidin-4-ylbenzenesulfonamide | 479 [M$^{35}$ClH]+ |
| 745 | 3-chloro-4-[4-chloro-2-(1-methyl-1H-pyrazol-5-yl)phenoxy]-N-(5-fluoropyridin-2-yl)benzenesulfonamide | 493 [M$^{35}$ClH]+ |
| 746 | 3-chloro-4-[4-chloro-2-(1H-pyrazol-5-yl)phenoxy]-N-pyrimidin-4-ylbenzenesulfonamide | 462 [M$^{35}$ClH]+ |
| 747 | 3-chloro-4-[4-chloro-2-(1H-pyrazol-5-yl)phenoxy]-N-1,2,4-adiazol-2-ylbenzenesulfonamide | 468 [M$^{35}$ClH]+ |
| 748 | 5-chloro-4-{4-chloro-2-[1-(2-hydroxyethyl)-1H-pyrazol-5-yl]phenoxy}-2-fluoro-N-1,3,4-thiadiazol-2-ylbenzenesulfonamide | 530 [M$^{35}$ClH]+ |
| 749 | 4-[4-chloro-2-(3-methyl-1H-pyrazol-4-yl)phenoxy]-3-fluoro-N-1,3-thiazol-2-ylbenzenesulfonamide | 465 [M$^{35}$ClH]+ |
| 750 | 2,5-difluoro-4-[2-(1H-pyrazol-4-yl)-4-(trifluoromethoxy)phenoxy]-N-1,3-thiazol-4-ylbenzenesulfonamide | 519 [MH]+ |
| 751 | 4-[5-chloro-4-fluoro-2-(1H-pyrazol-5-yl)phenoxy]-3-cyano-N-1,2,4-thiadiazol-5-ylbenzenesulfonamide | 477 [M$^{35}$ClH]+ |
| 752 | 4-[5-chloro-4-fluoro-2-(1H-pyrazol-5-yl)phenoxy]-N-1,2,4-thiadiazol-5-ylbenzenesulfonamide | 488 [M$^{35}$ClH]+ |
| 753 | 4-[5-chloro-4-fluoro-2-(1H-pyrazol-5-yl)phenoxy]-2,5-difluoro-N-1,2,4-thiadiazol-5-ylbenzenesulfonamide | 488 [M$^{35}$ClH]+ |

| Eg No | Name | MS m/z (unless otherwise incidated) |
|---|---|---|
| 754 | 4-[5-chloro-4-fluoro-2-(1H-pyrazol-4-yl)phenoxy]-3-cyano-N-1,2,4-thiadiazol-5-ylbenzenesulfonamide | 477 [M$^{35}$ClH]+ |
| 755 | 5-chloro-2-fluoro-4-[4-fluoro-2-(1H-pyrazol-4-yl)phenoxy]-N-1,2,4-thiadiazol-5-ylbenzenesulfonamide | 470 [M$^{35}$ClH]+ |
| 756 | 2,5-difluoro-4-[4-fluoro-2-(1H-pyrazol-4-yl)phenoxy]-N-1,2,4-thiadiazol-5-ylbenzenesulfonamide | 454 [MH]+ |
| 757 | 4-[4-chloro-5-fluoro-2-(1H-pyrazol-4-yl)phenoxy]-2,5-difluoro-N-1,2,4-thiadiazol-5-ylbenzenesulfonamide | 488 [M$^{35}$ClH]+ |
| 758 | 5-chloro-6-{4-[1-ethyl-3-(trifluoromethyl)-1H-pyrazol-5-yl]phenoxy}-N-1,3-thiazol-2-ylpyridine-3-sulfonamide | 530 [M$^{35}$ClH]+ |
| 759 | 5-chloro-6-[4-chloro-2-(1-methyl-1H-pyrazol-5-yl)phenoxy]-N-1,3-thiazol-2-ylpyridine-3-sulfonamide | 482 [M$^{35}$ClH]+ |
| 760 | 4-[4-chloro-2-(1-piperidin-4-yl-1H-pyrazol-5-yl)phenoxy]-3-cyano-N-1,3-thiazol-4-ylbenzenesulfonamide | 541 [M$^{35}$ClH]+ |
| 761 | 4-[4-chloro-2-(1-piperidin-4-yl-1H-pyrazol-3-yl)phenoxy]-3-cyano-N-1,3-thiazol-4-ylbenzenesulfonamide | 541 [M$^{35}$ClH]+ |
| 762 | 4-[4-chloro-5-fluoro-2-(1H-pyrazol-5-yl)phenoxy]-2,5-difluoro-N-1,2,4-thiadiazol-5-ylbenzenesulfonamide | 488 [M$^{35}$ClH]+ |
| 763 | 4-[4-chloro-5-fluoro-2-(1H-pyrazol-5-yl)phenoxy]-3-cyano-N-1,2,4-thiadiazol-5-ylbenzenesulfonamide | 477 [M$^{35}$ClH]+ |
| 764 | 5-chloro-2-fluoro-4-[2-(1H-pyrazol-4-yl)-4-(trifluoromethyl)phenoxy]-N-1,3,4-thiadiazol-2-ylbenzenesulfonamide | 520 [M$^{35}$ClH]+ |
| 765 | 5-chloro-4-(4-chloro-2-piperidin-4-ylphenoxy)-2-fluoro-N-1,3,4-thiadiazol-2-ylbenzenesulfonamide | 503 [M$^{35}$ClH]+ |
| 766 | 4-[2-(6-aminopyridin-2-yl)-4-chlorophenoxy]-3-cyano-N-1,3-thiazol-4-ylbenzenesulfonamide | 484 [M$^{35}$ClH]+ |
| 767 | 4-[4-chloro-2-(1H-pyrazol-4-yl)phenoxy]-3-cyano-N-1,3-thiazol-4-ylbenzenesulfonamide | 458 [M$^{35}$ClH]+ |
| 768 | 3-cyano-4-[3-(1H-pyrazol-3-ylmethyl)phenoxy]-N-1,3-thiazol-4-ylbenzenesulfonamide | 438 [MH]+ |
| 769 | 4-{3-[(1-tert-butyl-1H-pyrazol-3-yl)methyl]phenoxy}-3-cyano-N-1,3-thiazol-4-ylbenzenesulfonamide | 494 [MH]+ |
| 770 | 4-(biphenyl-2-yloxy)-3-cyano-N-[5-(trifluoromethyl)pyridin-2-yl]benzenesulfonamide | 496 [MH]+ |
| 771 | N-(5-chloro-1,3-thiazol-2-yl)-4-[4-cyano-2-(1H-pyrazol-4-yl)phenoxy]-2,5-difluorobenzenesulfonamide | 494 [M$^{35}$ClH]+ |
| 772 | 4-[4-chloro-2-(1-methyl-1H-pyrazol-5-yl)phenoxy]-3-cyano-N-[5-(trifluoromethyl)pyridin-2-yl]benzenesulfonamide | 534 [M$^{35}$ClH]+ |
| 773 | 5-chloro-2-fluoro-4-[5-fluoro-2-(1H-pyrazol-5-yl)phenoxy]-N-1,2,4-thiadiazol-5-ylbenzenesulfonamide | 470 [M$^{35}$ClH]+ |
| 774 | 3-cyano-4-[4-(4-fluoro-1H-pyrazol-1-yl)phenoxy]-N-1,3-thiazol-2-ylbenzenesulfonamide | 442 [MH]+ |
| 775 | 4-[2-(1-tert-butyl-1H-pyrazol-5-yl)-4-chlorophenoxy]-3-cyano-N-1,2,4-thiadiazol-5-ylbenzenesulfonamide | 515 [M$^{35}$ClH]+ |
| 776 | 4-[4-chloro-2-(1-methyl-1H-pyrazol-5-yl)phenoxy]-3-fluoro-N-(5-methyl-1,3,4-thiadiazol-2-yl)benzenesulfonamide | 480 [M$^{35}$ClH]+ |
| 777 | 5-chloro-4-[4-chloro-2-(1H-1,2,3-triazol-5-yl)phenoxy]-2-fluoro-N--thiazol-4-ylbenzenesulfonamide | 486 [M$^{35}$ClH]+ |
| 778 | 4-(biphenyl-3-yloxy)-3-cyano-N-1,3-thiazol-2-ylbenzenesulfonamide | 434 [MH]+ |
| 779 | 3-cyano-4-{2-fluoro-5-[1-methyl-3-(trifluoromethyl)-1H-pyrazol-5-yl]phenoxy}-N-1,3-thiazol-2-ylbenzenesulfonamide | 524 [MH]+ |
| 780 | 3-cyano-N-(5-fluoro-1,3-thiazol-2-yl)-4-[5-iodo-2-(1-methyl-1H-pyrazol-5-yl)phenoxy]benzenesulfonamide | 582 [MH]+ |
| 781 | 2,5-difluoro-4-[4-fluoro-2-(1H-pyrazol-5-yl)phenoxy]-N-1,2,4-thiadiazol-5-ylbenzenesulfonamide | 454 [MH]+ |

Example 587

4-[2-(6-Aminopyridin-3-yl)-4-fluorophenoxyl-N-(5-chloro-1,3-thiazol-2-yl)-3-cyanobenzenesulfonamide

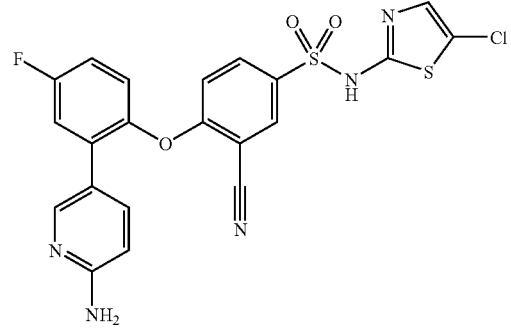

Example 587 from above can be prepared as follows.

N-(5-Chloro-1,3-thiazol-2-yl)-3-cyano-N-(2,4-dimethoxybenzyl)-4-(4-fluoro-2-iodophenoxy)benzenesulfonamide (Preparation 217, 100 mg, 0.146 mmol), 2-aminopyridine-5-boronic acid pinacol ester (35.4 mg, 0.161 mmol), palladium (0) tetrakis(triphenylphoshine) (17.3 mg, 0.015 mmol) and caesium carbonate (143 mg, 0.438 mmol) were charged to a 25 ml round-bottomed flask and purged with nitrogen (×3). To this was added fresh degassed 1,4-dioxane (4 ml) and fresh degassed water (1 ml) and the vessel was heated to 60° C. and stirred for 16 hours. The solvent was removed in vacuo and the residue was dissolved in methanol (2 ml) before loading on to a ISOLUTE™ SCX-2 cartridge (2 g). The cartridge was washed with methanol (50 ml) followed by ammonia (2 M in methanol, 50 ml). The basic washes were concentrated in vacuo and the residue was dissolved in dichloromethane (10 ml). To this solution was added trifluoroacetic acid (1 ml) and the solution stirred at room temperature for 18 hours before concentrating in vacuo. The residue was dissolved in methanol (2 ml) and loaded on to a ISOLUTE™ PE-AX cartridge (5 g). The cartridge was washed with methanol (3 column volumes) followed by formic acid (2% solution in methanol, 3 column volumes). The acidic washes were concentrated in vacuo to afford a sticky yellow solid which was triturated in dichloromethane to afford the title compound as a white solid.

Yield 28 mg, 38%.

LCMS $R_t$=2.04 minutes. MS m/z 502 [M$^{35}$ClH]+

$^1$HNMR (d$_6$-DMSO): δ 6.35 (b s, 2H), 6.45 (m, 1H), 6.75 (m, 1H), 7.32 (m, 1H), 7.48 (m, 3H), 7.55 (m, 1H), 7.9 (m, 1H), 8.0 (m, 1H), 8.1 (m, 1H).

Example 655

5-chloro-4-(4-chloro-2-piperidin-4-ylphenoxy)-2-fluoro-N-1,3-thiazol-4-ylbenzenesulfonamide

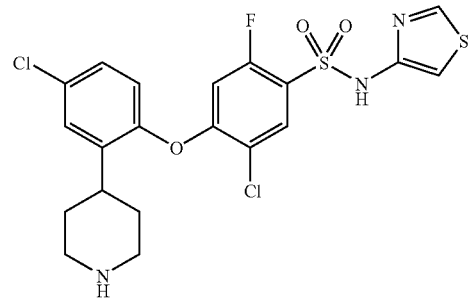

Example 655 from above can be made as follows. To a solution of tert-butyl 4-(5-chloro-2-hydroxyphenyl)piperidine-1-carboxylate (Preparation 231, 38 mg, 0.122 mmol) and potassium carbonate (50.6 mg, 0.366 mmol) in dimethyl sulfoxide (1 mL) was added tert-butyl [(5-chloro-2,4-difluorophenyl)sulfonyl]1,3-thiazol-4-ylcarbamate (Preparation 453, 50 mg, 0.122 mmol). The mixture was stirred at room temperature for 16 hours before diluting with ethyl acetate (10 mL) and water (10 mL). The aqueous phase was acidified to pH 4 with saturated citric acid solution (aqueous) and extracted with ethyl acetate (3×10 mL). The combined organic layers were washed with saturated aqueous sodium chloride solution (30 mL), dried over sodium sulphate, filtered and concentrated in vacuo to afford tert-butyl 4-[2-(4-{[(tert-butoxycarbonyl)(1,3-thiazol-4-yl)amino]sulfonyl}-2-chloro-5-fluorophenoxy)-5-chlorophenyl]piperidine-1-carboxylate as a white foam. This was dissolved in dichloromethane (1 mL), trifluoroacetic acid added (200 μL) and reaction stirred for 16 hours at room temperature before concentrating in vacuo. Purification by preparative HPLC afforded the title compound.

LCMS Rt=1.05 minutes. MS m/z 502 [M$^{35}$ClH]+

Example 782

4-[4-Chloro-2-(1H-pyrazol-4-yl)phenoxy]-3-cyano-N-1,3-thiazol-2-ylbenzenesulfonamide

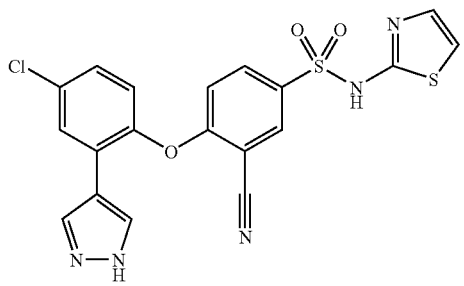

tert-Butyl 4-(5-chloro-2-hydroxyphenyl)-1H-pyrazole-1-carboxylate (Preparation 205, 624 mg, 2.12 mmol), 3-cyano-4-fluoro-N-1,3-thiazol-2-ylbenzenesulfonamide (Preparation 46, 500 mg, 1.76 mmol) and potassium carbonate (732 mg, 5.30 mmol) were stirred in dimethyl sulphoxide (10 ml) at 50° C. for 2 hours. The reaction was cooled to room temperature and the mixture poured dropwise into hydrochloric acid (2M aqueous, 100 ml). The mixture was stirred at room temperature for 18 hours. The precipitate was filtered and suspended in methanol (10 ml). The mixture was treated with hydrogen chloride (4M in dioxane, 2 ml). The mixture was then stirred at room temperature over for 60 hours. The mixture was evaporated in vacuo. The residue was dissolved in methanol (5 ml). The black solution was passed through an ISOLUTE™ SCX cartridge. The cartridge was eluted with methanol (100 ml) followed by ammonia (2M in methanol). The dark ammonia solution was evaporated in vacuo. The residue was dissolved in dichloromethane/methanol (95/5, 5 ml) and passed through a pad of silica. The solution was evaporated in vacuo. The residue was purified using a silica gel column chromatography eluting with dichloromethane:ethyl acetate (gradient 1:0 to 1:9, by volume). Concentration in vacuo afforded the title compound as a white solid. Yield 427 mg, 53%

LCMS Rt=2.26 minutes, MS m/z 458 [M$^{35}$ClH]+

$^1$H NMR (d$_6$-DMSO): δ 6.87 (m, 2 H), 7.28 (d, 1 H), 7.32-7.41 (m, 3 H), 7.87 (m, 3 H), 8.12 (br. s, 1 H), 8.23 (d, 1 H), 12.83 (br. s, 1 H), 13.08 (br. s, 1 H).

Example 783

3-cyano-4-[2-(1-methyl-1H-pyrazol-5-yl)-4-(trifluoromethoxy)phenoxy]-N-1,3-thiazol-2-ylbenzenesulfonamide

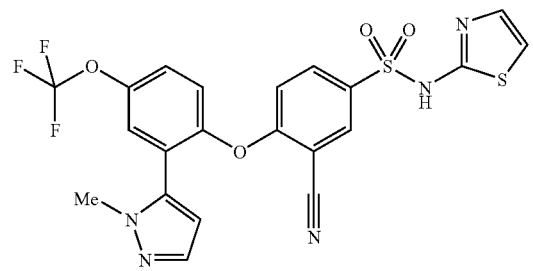

2-(1-methyl-1H-pyrazol-5-yl)-4-(trifluoromethoxy)phenol (Preparation 533, 50.0 mg, 0.20 mmol) and 3-cyano-4-fluoro-N-(1,3-thiazol-2-yl)benzenesulfonamide (Preparation 46, 57 mg, 0.20 mmol) were used to prepare the title compound using Method F above. The product was purified by flash column chromatography (SiO$_2$) eluting with dichloromethane:ethyl acetate (gradient 8:2 to 2:8, by volume) to afford the title compound, 98 mg, 97% yield.

LCMS Rt=1.47 minutes. MS m/z 522 [MH]+

$^1$H NMR (400 MHz, CDCl$_3$): δ 3.86 (s, 3H), 6.21 (d, 1H), 6.58 (d, 1H), 6.66 (d, 1H), 7.10 (d, 1H), 7.24 (d, 1H), 7.33 (d, 1H), 7.36-7.42 (m, 2H), 7.91 (dd, 1H), 8.09 (d, 1H), 11.64 (br. s, 1H) ppm.

$^{19}$F NMR (376 MHz, CDCl$_3$): δ −58.52 (s) ppm.

Example 784

4-(2-azetidin-3-yl-4-chlorophenoxy)-5-chloro-N-(5-chloro-1,3-thiazol-2-yl)-2-fluorobenzenesulfonamide

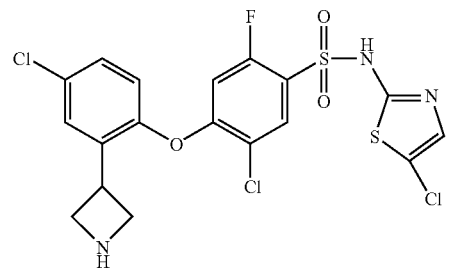

5-Chloro-N-(5-chloro-1,3-thiazol-2-yl)-N-(2,4-dimethoxybenzyl)-2,4-difluorobenzenesulfonamide (Preparation 655) and tert-butyl 3-(5-chloro-2-hydroxyphenyl)azetidine-1-carboxylate (Preparation 237) were stirred in dichloromethane (2 ml) and trifluoroacetic acid (1 ml) to prepare the title compound using Method F above but where the N,N-dimethylformamide was replaced with dimethyl sulphoxide. The crude product was concentrated in vacuo and purified by preparative HPLC to afford the title compound.
LCMS Rt=2.47 minutes MS m/z 509 [M$^{35}$ClH]+

Example 785

N-(5-Chloro-1,3-thiazol-2-yl)-3-cyano-4-[4-fluoro-2-(1H-pyrazol-4-yl)phenoxy]benzenesulfonamide

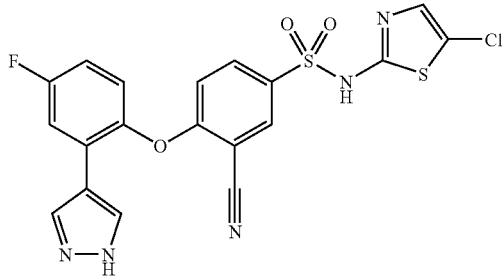

N-(5-Chloro-1,3-thiazol-2-yl)-3-cyano-4-(4-fluoro-2-iodophenoxy)benzenesulfonamide (Preparation 240, 50 mg, 0.09 mmol), 4-(4,4,5,5-tetramethyl-1,3,2-dioxaborolan-2-yl)-1H-pyrazole (27 mg, 0.14 mmol) palladium (0) tetrakis (triphenylphosphine) (10 mg, 0.009 mmol) and sodium carbonate (30 mg, 0.28 mmol) were dissolved in dimethylformamide:water (2:1, 1.5 ml.) and heated to 90° C. for 18 hours. The reaction was partitioned between ethyl acetate and saturated aqueous sodium chloride solution. The organic layer was separated, dried over sodium sulfate and evaporated in vacuo to afford a brown oil. Purification by preparative HPLC afforded the title compound. Yield 12.5 mg 30%.
LCMS=Rt 2.50 minutes. MS m/z 476 [M$^{35}$ClH]+

Example 786

N-(5-Chloro-1,3-thiazol-2-yl)-3-cyano-4-[4-chloro-2-(1H-pyrazol-4-yl)phenoxy]benzenesulfonamide

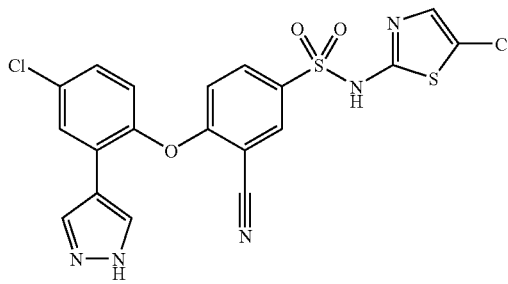

The title compound was prepared according to the same method as that used for Example 785 above using 4-(4-chloro-2-iodophenoxy)-N-(5-chloro-1,3-thiazol-2-yl)-3-cyanobenzenesulfonamide (Preparation 219) and 4-(4,4,5,5-tetramethyl-1,3,2-dioxaborolan-2-yl)-1H-pyrazole as starting materials. Purification by preparative HPLC afforded the title compound. Yield 7.8 mg 17%.

LCMS=Rt 2.45 minutes. MS m/z 492 [M$^{35}$ClH]+
$^1$HNMR (400 MHz; CDCl$_3$): δ 6.63 (s, 1H), 7.05 (d, 1H), 7.22 (m, 1H), 7.60 (s, 1H), 7.80 (m, 3H), 8.15 (s, 1H)

Example 787

4-[2-(2-aminopyridin-4-yl)-4-chlorophenoxy]-2,5-difluoro-N-1,2,4-thiadiazol-5-ylbenzenesulfonamide

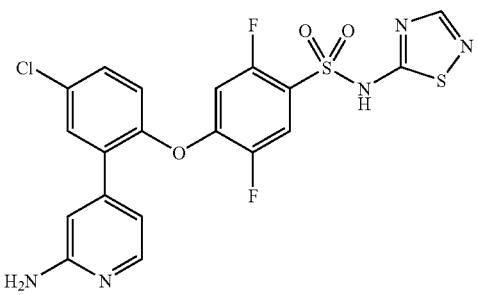

A suspension of N-(2,4-dimethoxybenzyl)-2,4,5-trifluoro-N-1,2,4-thiadiazol-5-ylbenzenesulfonamide (Preparation 647, 10 g, 22.45 mmol), 2-(2-aminopyridin-4-yl)-4-chlorophenol (Preparation 258, 5 g, 22.67 mmol) and potassium carbonate (3.72 g, 26.94 mmol) in dimethyl sulfoxide (150 mL) was stirred at room temperature for 2 hours. The reaction was partitioned between ethyl acetate (150 mL) and saturated aqueous sodium chloride solution (150 mL). The organic layer was collected and concentrated in vacuo to afford an orange residue. This was dissolved in dichloromethane (145 mL) and trifluoroacetic acid (8.48 mL) was added. The reaction was stirred at room temperature for 24 hours before concentrating in vacuo to afford a pink residue. This was taken up in ethyl acetate (200 mL) to form a white slurry that was washed with saturated sodium bicarbonate solution (200 mL). Filtration yielded a white solid that was dried in vacuo, slurried in water and hydrochloric acid (1 N aqueous solution, 1.05 eq) and extracted with ethyl acetate. The organic layer was collected and concentrated in vacuo to yield the title compound.
LCMS Rt=1.92 minutes. MS m/z 496 [M$^{35}$ClH]+
1H NMR (d$_6$-DMSO): δ 6.95 (m, 1H), 7.05 (s, 1H), 7.20-7.30 (m, 2H), 7.55 (d, 1H), 7.65 (s, 1H), 7.75 (m, 1H), 7.95-8.05 (m, 3H), 8.40 (s, 1H).

Example 788

4-[2-(5-amino-1H-pyrazol-4-yl)-4-chlorophenoxy]-5-chloro-2-fluoro-N-1,3-thiazol-4-ylbenzenesulfonamide To a suspension of sodium hydride (29 mg, 1.2 mmol) in dimethylformamide (1 mL) was added N-(1-tert-butyl-4-(5-chloro-2-hydroxyphenyl)-1H-pyrazol-5-yl)-2,2,2-trifluoroacetamide (Preparation 209, 239 mg, 0.661 mmol) and stirred for 30 minutes. To this was added tert-butyl 5-chloro-2,4-difluorophenylsulfonyl(thiazol-4-yl)carbamate (Preparation 453, 206 mg, 0.501 mmol) and stirred for 24 hours. After this time only a small amount of product was observed, so potassium carbonate (40 mg, 0.3 mmol) was added and the reaction heated at 55° C. for 3 days. The reaction was cooled, diluted with ethyl acetate and the organic extract washed with water and saturated aqueous sodium chloride solution, dried over magnesium sulfate, filtered and concentrated in vacuo. Purification by automated flash column chromatography eluting with ethyl acetate:hexanes (gradient 0:1 to 1:0, by volume) afforded fully protected product. This residue was dissolved in methanol (1 mL) and sodium carbonate solution (2 M aqueous, 0.08 mL, 0.2 mmol) and water (0.2 mL) added. The reaction was stirred at room temperature for 6 hours and then heated at 55° C. for 16 hours before concentrating in vacuo and passing through a short silica gel column eluting with methanol:dichloromethane (gradient 0:1 to 1:9, by volume). All product related fractions were combined, concentrated in vacuo, dissolved in methanol (saturated in gaseous hydrogen chloride) and heated at 50° C. for 16 hours. Purification by preparative HPLC afforded the title compound as a white solid, 31 mg, 12% yield.

LCMS Rt=1.72 minutes. MS m/z 500 [M$^{35}$ClH]+

$^1$H NMR (300 MHz, d$_6$-DMSO): δ 6.85 (d, 1H), 7.11 (m, 1H), 7.24 (m, 1H), 7.41 (dd, 1H), 7.71 (m, 2H), 7.93 (d, 1H), 8.93 (m, 1H), 11.45 (br s, 1H).

Example 789

2,5-difluoro-4-[2-(1H-pyrazol-5-yl)-4-(trifluoromethyl)phenoxy]-N-1,2,4-thiadiazol-5-ylbenzenesulfonamide

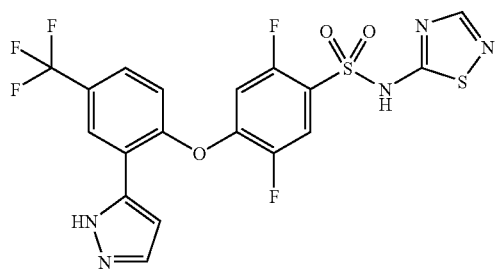

A suspension of N-(2,4-dimethoxybenzyl)-2,5-difluoro-4-[2-iodo-4-(trifluoromethyl)phenoxy]-N-1,2,4-thiadiazol-5-ylbenzenesulfonamide (Preparation 363, 100 mg, 0.14 mmol), potassium carbonate (48 mg, 1.12 mmol) and 1-(ethoxymethyl)-5-(4,4,5,5-tetramethyl-1,3,2-dioxaborolan-2-yl)-1H-pyrazole (Preparation 337, 70 mg, 0.28 mmol) in 1,4-dioxane (5 mL) and water (2 mL) was degassed and palladium tetrakis (16 mg, 0.014 mmol) added before heating at 80° C. for 16 hours. Dicholoromethane (20 mL) and water (10 mL) were added and the organics separated and evaporated in vacuo to afford the crude product. Dicholoromethane (10 mL) and trifluoroacetic acid (5 mL) were added and the reaction mixture was stirred at room temperature for 16 hours before concentrating in vacuo. Hydrochloric acid (4 M in 1,4-dioxane, 10 mL) was added and the reaction mixture was stirred for 16 hours before concentrating in vacuo. The residue was purified by reverse phase chromatography to afford the desired product, 6 mg, 9% yield.

LCMS Rt=4.23 minutes. MS m/z 504 [MH]+

$^1$H NMR (CD$_3$OD): δ 8.05 (m, 1H), 8.30 (m, 1H), 8.70 (m, 1H), 8.95-9.10 (m, 3H), 9.70 (m, 2H).

Example 790

2,5-difluoro-4-[2-(1H-pyrazol-4-yl)-4-(trifluoromethyl)phenoxy]-N-1,2,4-thiadiazol-5-ylbenzenesulfonamide

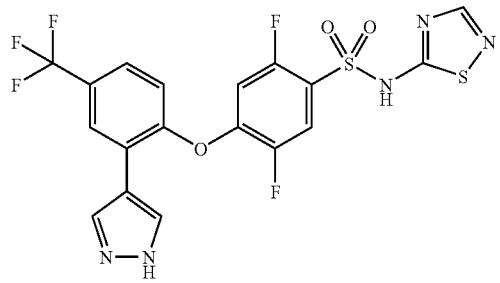

The title compound was prepared according to the same method as that used for Example 789 above using N-(2,4-dimethoxybenzyl)-2,5-difluoro-4-[2-iodo-4-(trifluoromethyl)phenoxy]-N-1,2,4-thiadiazol-5-ylbenzenesulfonamide (Preparation 363) and the boronic ester tert-butyl 4-(4,4,5,5-tetramethyl-1,3,2-dioxaborolan-2-yl)-1H-pyrazole-1-carboxylate. Purificiation using reverse phase chromatography afforded the title compound.

LCMS Rt=3.98 minutes. MS m/z 504 [MH]+

$^1$H NMR (CD$_3$OD): δ 8.30 (m, 1H), 8.60 (m, 1H), 8.85 (m, 1H), 9.05 (m, 1H), 9.35-9.45 (m, 3H), 10.65 (s, 1H).

Example 791

4-(4-chloro-2-(1H-pyrazol-4-yl)phenoxy)-3-cyano-N-(1,2,4-thiadiazol-5-yl)benzenesulfonamide

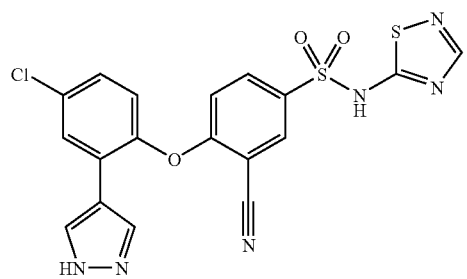

The title compound was prepared from 4-(4-chloro-2-iodophenoxy)-3-cyano-N-(1,2,4-thiadiazol-5-yl)benzenesulfonamide (Preparation 355) and (4,4,5,5-tetramethyl-1,3,2-dioxaborolan-2-yl)-1H-pyrazole using Method E above with microwave irradiation for 1 hour at 85° C.

LCMS Rt=3.24 minutes MS m/z 457 [M$^{35}$ClH]−

$^1$HNMR (400 MHz, d$_6$-DMSO): δ 6.85 (d, 1H), 7.30-7.40 (m, 2H), 7.95 (m, 2H), 8.00 (s, 2H), 8.25 (s, 1H), 8.45 (s, 1H)

Example 792

4-[2-(5-amino-1H-pyrazol-4-yl)-4-chlorophenoxy]-3-cyano-N-1,2,4-thiadiazol-5-ylbenzenesulfonamide

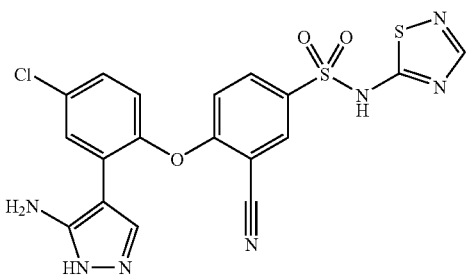

To a solution of the N-{1-tert-butyl-4-[5-chloro-2-(2-cyano-4-{[(2,4-dimethoxybenzyl)(1,2,4-thiadiazol-5-yl)amino]sulfonyl}phenoxy)phenyl]-1H-pyrazol-5-yl}-2,2,2-trifluoroacetamide (Preparation 419, 157 mg, 0.20 mmol) in methanol (15 ml) was added hydrogen chloride (4 M in 1,4-dioxane, 3 ml). The resulting yellow solution was stirred and heated at 60° C. for 48 hours. The solvent removed in vacuo to afford a pale yellow residue. The material was purified by column chromatography (80 g silica gel column) eluting with methanol:dichloromethane (5:95, by volume) to afford the title compound as a yellow oily solid, 56 mg, 59% yield.

LCMS Rt=3.09 minutes. MS m/z 474 [M$^{35}$ClH]+

$^1$H NMR (CD$_3$OD):δ 6.64-6.70 (m, 1H), 7.19-7.22 (m, 1H), 7.31-7.38 (m, 1H), 7.50 (br-s, 1H), 7.64 (br-s, 1H), 7.86-7.90 (m, 2H), 8.10 (s, 1H).

Example 793

3-cyano-4-[2-(1H-pyrazol-5-yl)-4-(trifluoromethoxy)phenoxy]-N-1,2,4-thiadiazol-5-ylbenzenesulfonamide

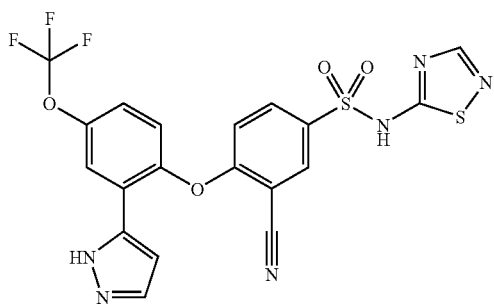

3-cyano-N-(1,2,4-thiadiazol-5-yl)-4-[2-iodo-4-(trifluoromethoxy)phenoxy]benzenesulfonamide (Preparation 760, 500 mg, 0.88 mmol), 1-(ethoxymethyl)-5-(4,4,5,5-tetramethyl-1,3,2-dioxaborolan-2-yl)-1H-pyrazole (Preparation 337, 600 mg, 1.4 mmol), palladium (0) tetrakis triphenylphosphine (78 mg, 0.067 mmol) and sodium carbonate (420 mg, 3.963 mmol) were dissolved in a mixture of water (4 mL) and 1,4-dioxane (12 mL) and heated to 85° C. under N$_2$ for 7 hours. Further 1-(ethoxymethyl)-5-(4,4,5,5-tetramethyl-1,3,2-dioxaborolan-2-yl)-1H-pyrazole (100 mg 0.23 mmol) and palladium (0) tetrakis triphenylphosphine (10 mg, 0.008 mmol) were added and the reaction stirred at 85° C. under N$_2$ for 18 hours. The reaction was quenched by the addition of ethyl acetate (20 mL) and saturated aqueous brine solution (20 mL). The organic layer was collected, dried over sodium sulphate and concentrated in vacuo before purification using silica gel column chromatography (dichloromethane:methanol:acetic acid v/v/v 100:0:0 to 95:5:0.5) to afford a white solid. This was dissolved in 4M HCl in 1,4-dioxane (5 mL) and stirred at room temperature for 4 hours before concentration in vacuo and purification using silica gel column chromatography (v/v/v dichloromethane:methanol:acetic acid 100:0:0 to 90:10:1 to afford a residue that was triturated in dichloromethane (5 mL) to afford 210 mg of the title compound as a white solid as the HCl salt.

LCMS Rt=1.56 minutes. MS m/z 509 [MH]+

$^1$H NMR (d$_6$-DMSO): δ 6.55 (s, 1H), 6.85 (d, 1H), 7.45-7.50 (m, 2H), 7.75 (s, 1H), 7.90-8.00 (m, 2H), 8.25 (s, 1H), 8.45 (s, 1H)

Example 794

4-[2-(5-amino-1H-pyrazol-4-yl)-4-chlorophenoxy]-5-chloro-2-fluoro-N-1,2,4-thiadiazol-5-ylbenzenesulfonamide

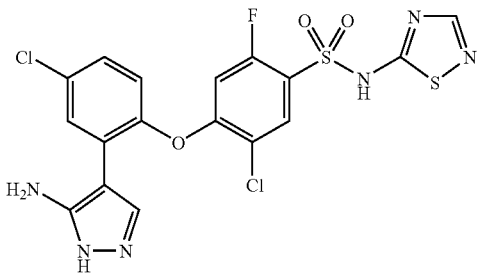

Dimethyl sulfoxide (5.0 mL) was added to a flask containing N-[1-tert-butyl-4-(5-chloro-2-hydroxyphenyl)-1H-pyrazol-5-yl]-2,2,2-trifluoroacetamide (Preparation 209, 0.100 g, 0.000276 mol), 5-chloro-N-(2,4-dimethoxybenzyl)-2,4-difluoro-N-1,2,4-thiadiazol-5-ylbenzenesulfonamide (Preparation 333, 0.116 g, 0.000251 mol) and potassium carbonate (0.104 g, 0.000753 mol) and the reaction mixture was stirred at room temperature under nitrogen for 16 hours. The reaction mixture was poured into water (50.0 mL) and the aqueous extracted with ethyl acetate (4×30.0 mL). The combined organics were washed with saturated aqueous sodium chloride solution (30 mL), dried over magnesium sulfate, filtered and concentrated in vacuo. The residue was dissolved in methanol (5.0 mL) and hydrochloric acid (4 M in 1,4-dioxane, 5.0 mL, 0.020 mol) and stirred at 100° C. under nitrogen for 16 hours. The mixture was concentrated in vacuo and the residue was purified by reverse phase chromatography eluting with water:acetonitrile:trifluoroacetic acid (gradient 95:5:0.1 to 30:70:0.1, by volume) to afford a colourless gum.

This was triturated with heptane to afford the title compound as a white powder, 0.030 g, 22% yield.

LCMS R$_f$=3.40 minutes. MS m/z 501 [M$^{35}$Cl$^{35}$ClH]+

$^1$H NMR (400 MHz, d$_6$-DMSO): δ 6.75 (m, 1H), 7.2 (m, 1H), 7.35 (m, 1H), 7.55 (s, 1H), 7.65 (m, 1H), 7.85 (m, 1H), 8.4 (s, 1H).

Example 795

3-cyano-4-[2-(1-methyl-1H-pyrazol-5-yl)-4-(trifluoromethoxy)phenoxy]-N-1,2,4-thiadiazol-5-ylbenzenesulfonamide

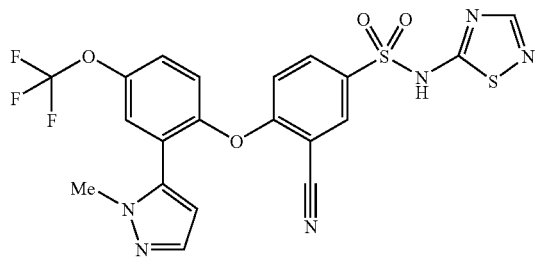

The title compound was prepared from 3-cyano-N-(2,4-dimethoxybenzyl)-4-[2-iodo-4-(trifluoromethoxy)phenoxy]-N-1,2,4-thiadiazol-5-ylbenzenesulfonamide (Preparation 497) and 1-methyl-1H-pyrazole-5-boronic acid pinacol ester using Method E above. Purification afforded the title compound.

LCMS R$_f$=3.96 minutes. MS m/z 523 [MH]+

$^1$H NMR (CDCl$_3$): δ 3.9 (s, 3H), 6.25 (m, 1H), 6.7 (m, 1H), 7.3-7.45 (m, 3H), 7.9 (m, 1H), 8.05 (m, 3H).

Example 796

5-chloro-4-(4-chloro-2-piperidin-4-ylphenoxy)-2-fluoro-N-1,2,4-thiadiazol-5-ylbenzenesulfonamide

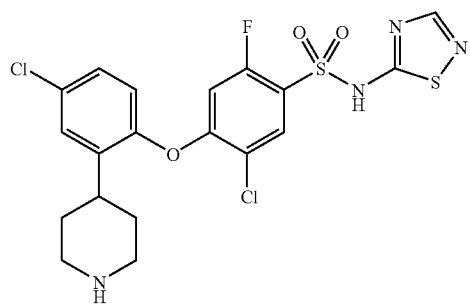

To a solution of tert-butyl 4-(5-chloro-2-hydroxyphenyl)piperidine-1-carboxylate (Preparation 231, 0.500 g, 0.0014 mol) and potassium carbonate (0.579 g, 0.00419 mol) in dimethyl sulfoxide (5.0 mL) was added 5-chloro-N-(2,4-dimethoxybenzyl)-2,4-difluoro-N-1,2,4-thiadiazol-5-ylbenzenesulfonamide (Preparation 333, 0.644 g, 0.0014 mol). The mixture was stirred at room temperature under nitrogen for 1.5 hours before diluting with ethyl acetate (10.0 mL) and water (10.0 mL). The aqueous layer was extracted with ethyl acetate (3×10.0 mL). The combined organic extracts were washed with saturated aqueous sodium chloride solution (30 mL), dried over sodium sulfate, filtered and concentrated in vacuo. The residue was purified by column chromatography (40 g silica gel column) eluting with ethyl acetate:heptane (gradient 0:1 to 35:65, by volume) to afford 1.03 g of tert-butyl 4-[5-chloro-2-(2-chloro-4-{[(2,4-dimethoxybenzyl)(1,2,4-thiadiazol-5-yl)amino]sulfonyl}-5-fluorophenoxy)phenyl]piperidine-1-carboxylate as a white solid. This material was dissolved in dichloromethane (5.0 mL), trifluoroacetic acid (1.0 mL) added and reaction stirred for 16 hours at room temperature under nitrogen. Methanol (5.0 mL) was added to afford a white precipitate. This suspension mixture was filtered through a Celite™ pad and washed with methanol. The filtrate was concentrated in vacuo and the residue was diluted with methanol (2.0 mL), dichloromethane (2.0 mL) and saturated aqueous sodium bicarbonate (4.0 mL) and stirred for 1 hour at room temperature to afford a white solid. The suspension was filtered and the solid washed with water and diethyl ether. The collected solid was recrystallised from hot acetonitrile and ethanol (1:1 v/v) to afford the title compound as a white solid, 0.1929 mg, 27% yield.

$^1$HNMR (400 MHz, d$_6$-DMSO): δ 1.83 (m, 2H), 1.95 (m, 2H), 3.02 (m, 3H), 3.33 (d, 2H), 6.90 (d, 1H), 7.00 (dd, 1H), 7.33 (m, 2H), 7.85 (d, 1H), 7.90 (s, 1H), 8.29 (br. s., 2H)

Anal. Calcd for C$_{19}$H$_{17}$Cl$_2$FN$_4$O$_3$S$_2$.0.12C$_4$H$_{10}$: C, 45.41; H, 3.51; N, 11.01. Found: C, 45.19; H, 3.49; N, 11.02.

Example 797

3-cyano-4-[2-(5-methyl-1H-pyrazol-4-yl)-4-(trifluoromethyl)phenoxy]-N-1,2,4-thiadiazol-5-ylbenzenesulfonamide

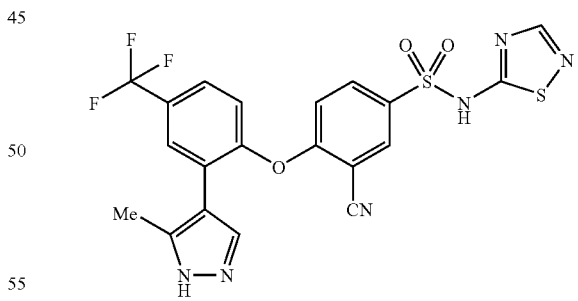

3-cyano-4-[2-(5-methyl-1-trityl-1H-pyrazol-4-yl)-4-(trifluoromethyl)phenoxy]-N-1,2,4-thiadiazol-5-ylbenzenesulfonamide (Preparation 428, 345 mg, 0.46 mmol) was dissolved in 4N HCl in 1,4-dioxane (5 ml) and stirred at room temperature for 3 hours before concentrating in vacuo. The residue obtained was purified using an ISCO™ (12 g SiO$_2$) eluting with methanol:dichloromethane (gradient 0:1 to 1:9, by volume). The purified compound was triturated with dichloromethane (10 mL) to afford the title compound as a white solid (148 mg, 34%—isolated as the hydrochloride salt).

LCMS Rt=1.84 minutes. MS m/z 507 [MH]+

$^1$H NMR (400 MHz, d$_6$-DMSO): δ 2.25 (s, 3H), 6.85 (d, 1H), 7.50 (d, 1H), 7.60 (d, 1H), 7.80 (s, 2H), 7.90 (d, 1H), 8.20 (s, 1H), 8.45 (s, 1H).

Example 798

4-{2-[2-(aminomethyl)pyridin-4-yl]-4-chlorophenoxy}-5-chloro-2-fluoro-N-1,2,4-thiadiazol-5-ylbenzenesulfonamide

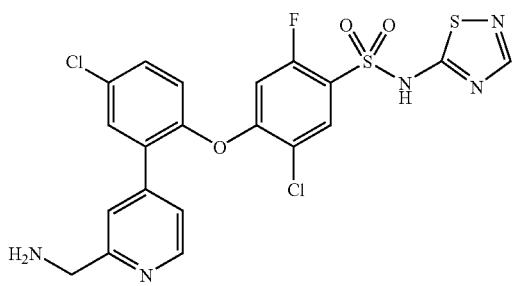

5-chloro-4-[4-chloro-2-(2-cyanopyridin-4-yl)phenoxy]-N-(2,4-dimethoxybenzyl)-2-fluoro-N-1,2,4-thiadiazol-5-yl-benzenesulfonamide (Preparation 340, 0.04 g, 0.00006 mol) was partially dissolved in methanol (5.0 mL) and 1,4-dioxane (5.0 mL). The solution was passed through an H-Cube™ at 70° C. with Raney nickel catalyst (30 mm cartridge) 3 times eluting with methanol to get complete conversion. Concentration in vacuo afforded the title compound as a colourless solid, 0.004 g, 10% yield.

LCMS Rt=1.13 minutes. MS m/z 527.0 [M$^{35}$ClH]+

$^1$H NMR (400 MHz, CD$_3$OD): δ 4.11(s, 2H), 6.52(m 1H), 6.97(m 1H), 7.24(m, 1H), 7.55(m, 4H), 7.85(s 1H), 8.59 (m, 1H)

Example 799

3-Cyano-4-[2-(tetrahydro-2H-pyran-4-yl)-4-(trifluoromethyl)phenoxy]-N-1,2,4-thiadiazol-5-ylbenzenesulfonamide

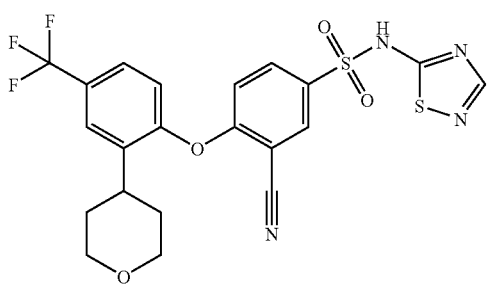

To a suspension of zinc dust (458 mg, 7.00 mmol) and lithium chloride (212 mg, 5.00 mmol) in tetrahydrofuran was added dibromoethane (0.043 mL, 0.50 mmol) under nitrogen. The mixture was heated at 70° C. for 10 minutes before cooling and adding chlorotrimethlsilane (0.013 mL, 0.10 mmol). The reaction mixture was stirred for 1 hour then 4-iodotetrahydro-2H-pyran (1060 mg, 5.00 mmol) was added and stirring continued for 18 hours. This mixture was added to a pre-stirred (10 minutes) suspension of 3-cyano-N-(2,4-dimethoxybenzyl)-4-[2-iodo-4-(trifluoromethyl)phenoxy]-N-1,2,4-thiadiazol-5-ylbenzenesulfonamide (Preparation 429, 11 mg, 0.3 mmol), palladium(II) acetate (6.7 mg, 0.03 mmol) and dicyclohexyl(2',6'-dimethoxybiphenyl-2-yl)phosphine (24.6 mg, 0.06 mmol) in tetrahydrofuran (0.5 mL). The reaction mixture was stirred at room temperature for 2 hours before pouring into saturated aqueous ammonium chloride solution (10 mL). The aqueous layer was extracted with ethyl acetate (3×10 mL). The combined organic layers were dried over magnesium sulfate and concentrated in vacuo to obtain a residue that was purified using an ISCO™ system eluting with heptane:ethyl acetate (1:0 to 4:6, by volume). The residue was dissolved in dichloromethane (3 mL) and trifluoroacetic acid (3 mL) was added. After stirring for 1 hour at room temperature, methanol (20 mL) was added and the resulting precipitate was filtered and the filtrate concentrated in vacuo. The crude material was purified using preparative HPLC to afford the title compound.

LCMS Rt=2.51 minutes. MS m/z 509 [MH]−

Example 800

5-Chloro-2-fluoro-N-(5-fluoropyridin-2-yl)-4-[2-piperidin-4-yl-4-(trifluoromethyl)phenoxy]benzenesulfonamide

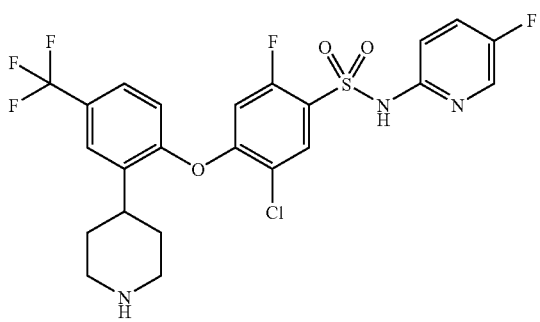

A mixture of tert-butyl 4-[2-hydroxy-5-(trifluoromethyl)phenyl]piperidine-1-carboxylate (Preparation 317, 51 mg, 0.15 mmol), 5-chloro-2,4-difluoro-N-(5-fluoropyridin-2-yl)-N-(methoxymethyl)benzenesulfonamide (Preparation 349, 50 mg, 0.1 mmol) and potassium carbonate (28 mg, 0.20 mmol) in anhydrous dimethyl sulfoxide (2 mL) was heated at 50° C. for 30 minutes. The reaction mixture was cooled to room temperature and diluted with ethyl acetate and water. The layers were separated and the aqueous layer extracted with ethyl acetate. The combined extracts were washed with saturated aqueous sodium chloride solution, water, dried over magnesium sulfate and concentrated in vacuo to afford the title compound as a light yellow thick oil, which was used in the next step without further purification. The residue was diluted with dichloromethane (2 mL), trifluoroacetic acid (210 uL, 2.7 mmol) was added and solution stirred at room temperature for 18 hours. The reaction solution was concentrated in vacuo and purified by preparative HPLC to afford the title compound as a white powder, 55.3 mg (as the trifluoroacetic acid salt)

LCMS Rt=1.54 minutes. MS m/z 548 [M$^{35}$ClH]+

$^1$H NMR (CD$_3$OD): δ 1.94-2.32 (m, 5H), 3.09-3.28 (m, 2H), 3.47-3.63 (m, 2H), 6.97-7.31 (m, 3H), 7.72-7.55 (m, 2H), 7.74 (s, 1H), 8.12 (m, 1H), 8.21(m, 1H)

Example 801

4-[2-(1-azetidin-3-yl-1H-pyrazol-5-yl)-4-chlorophenoxy]-2,5-difluoro-N-1,2,4-thiadiazol-5-ylbenzenesulfonamide

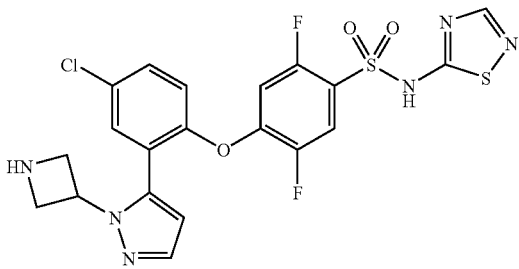

4-(4-chloro-2-{1-[1-(diphenylmethyl)azetidin-3-yl]-1H-pyrazol-5-yl}phenoxy)-N-(2,4-dimethoxybenzyl)-2,5-difluoro-N-1,2,4-thiadiazol-5-ylbenzenesulfonamide (Preparation 688, 270 mg, 0.321 mmol) was dissolved in dichloromethane (15 ml) and N,N,N',N'-tetramethylnaphthalene-1,8-diamine (85 mg, 0.40 mmol) was added followed by 1-chloroethyl chloroformate (0.07 ml, 0.65 mmol) and the solution was stirred at room temperature for 4 hours. The solution was concentrated in vacuo and the residue was partitioned between ethyl acetate (40 ml) and 1M aqueous citric acid solution (20 ml), the ethyl acetate was washed with water, dried over anhydrous sodium sulphate, evaporated and the solvents removed in vacuo to give an oil. The oil was dissolved in methanol (15 ml) and refluxed for 5 hours. Some of the methanol was removed in vacuo to leave about 5 ml, the precipitated solid was removed by filtration and the filtrate was adsorbed onto silica gel (5 g) and dried prior to purification by column chromatography on silica gel using 10-25% v/v methanol (containing 10% v/v 0.880 aqueous ammonia) in dichloromethane. This afforded the title compound as a pinkish solid, 80 mg.

LCMS Rt=1.10 minutes, m/z=525 [M$^{35}$ClH]+; 527 [M$^{37}$ClH]+

$^1$HNMR (d$_6$-DMSO): δ 3.20 (brs, 3H), 4.22-4.28 (m, 4H), 5.14-5.21 (m, 1H), 6.45 (d, 1H), 7.03-7.09 (m, 1H), 7.23 (d, 1H), 7.52-7.61 (m, 3H), 7.72 (d, 1H), 7.89 (s, 1H), 8.75 (brs, 1H)

CHN analysis. Required for mono hydrate: C, 44.24; H, 3.16; N, 15.48. Found: C, 44.33/44.19; H, 3.22/3.22; N, 15.66/15.68

Example 801

Trifluoroacetic Acid Salt

4-[2-(1-Azetidin-3-yl-1H-pyrazol-5-yl)-4-chlorophenoxy]-2,5-difluoro-N-1,2,4-thiadiazol-5-ylbenzenesulfonamide

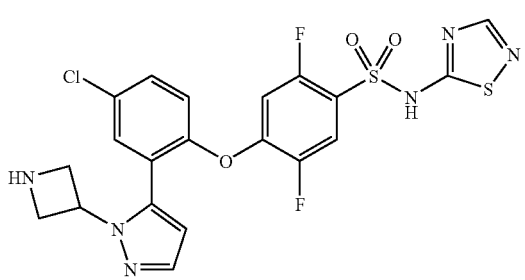

An alternative method to the trifluoroacetic acid salt of Example 801 is provided below:

Tert-butyl 3-{5-[5-chloro-2-(4-{[(2,4-dimethoxybenzyl) (1,2,4-thiadiazol-5-yl)amino]sulfonyl}-2,5-difluorophenoxy)phenyl]-1H-pyrazol-1-yl}azetidine-1-carboxylate, (Preparation 850, 145.47 g, 0.1455 mol) was dissolved in dichloromethane (1450 mL) and then trifluoroacetic acid (354.7 mL, 4.69 mol) was added slowly over 30 minutes. The pink mixture was stirred at room temperature for 2 hours and then methanol (1450 mL) was added to give a white precipitate. The solid was filtered off and the filtrate was concentrated in vacuo to give an oil. The oil was dissolved in a small volume of methanol and tert-butylmethyl ether was added very slowly with stirring to give an oily dispersion which would not crystallize. The solvents were removed in vacuo and the residue was dissolved in methanol and evaporated, this was repeated a further two times to give a foam. The foam was triturated with tert-butylmethyl ether, filtered off and dried to give the title compound as the trifluoroacetate salt which was a pale yellow powder, (120 g).

HPLC Rt=2.22 minutes

¹HNMR (CD₃OD) δ 4.50-4.55 (m, 4H), 5.19-5.28 (m, 1H), 6.39 (d, 1H), 6.76-6.82 (m, 1H), 7.27 (d, 1H), 7.54 (d, 1H), 7.60-7.64 (m, 1H), 7.68-7.74 (m, 2H), 8.24 (s, 1H).

Example 802

3-cyano-4-[2-pyridazin-4-yl-4-(trifluoromethyl)phenoxy]-N-1,2,4-thiadiazol-5-ylbenzenesulfonamide

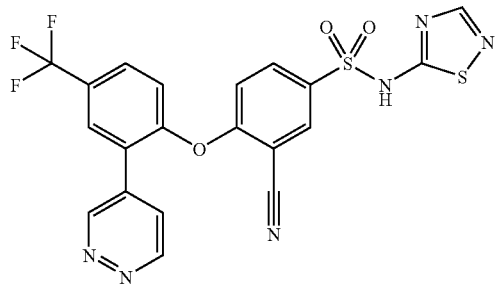

To a solution of 3-cyano-N-(2,4-dimethoxybenzyl)-4-[2-pyridazin-4-yl-4-(trifluoromethyl)phenoxy]-N-1,2,4-thiadiazol-5-ylbenzenesulfonamide, (Preparation 711, 59.7 mg, 0.091 mmol) in dichloromethane (3 mL) was added trifluoroacetic acid (0.33 mL) The mixture was stirred overnight at room temperature under nitrogen. The reaction mixture was concentrated in vacuo. The purple residue was partitioned between dichloromethane (10 mL) and water (10 mL). The aqueous layer was extracted with dichloromethane (3×10 mL) and the combined organic layers were washed with saturated aqueous sodium chloride solution (10 mL), dried over anhydrous sodium sulfate, filtered and the solvent removed in vacuo to afford a brown solid (30.7 mg, 67%).

LCMS Rt=3.81 minutes, MS m/z 505 [MH]+

¹HNMR (d₆-DMSO): δ 7.28 (m, 1H), 7.56 (m, 1H), 7.91 (m, 1H), 7.98 (m, 1H), 8.02 (m, 1H), 8.18 (m, 1H), 8.27 (m, 1H), 8.44 (s, 1H), 9.31 (m, 1H), 9.45 (m, 1H).

Method 2

The sodium salt of Example 802 can also be prepared as follows.

To a solution of 3-cyano-N-(2,4-dimethoxybenzyl)-4-[2-pyridazin-4-yl-4-(trifluoromethyl)phenoxy]-N-1,2,4-thiadiazol-5-ylbenzenesulfonamide, (Preparation 711, 18.2 g, 0.028 mol) in dichloromethane (182 mL) was added trifluoroacetic acid (91 mL) dropwise over 3 minutes. The mixture was stirred for 45 minutes before addition of water (200 mL) and methanol (200 mL). The resulting slurry was stirred at room temperature for 18 hours before filtration through a short pad of silica (9 cm diameter×2 cm deep). The filtrate was concentrated in vacuo to remove organics before addition of a saturated aqueous solution of sodium bicarbonate (91 mL) and dichloromethane (150 mL) with vigourous stirring for 30 minutes. The aqueous layer was extracted with methyl ethyl ketone (3×100 mL) and solid sodium bicarbonate (20 g) added to improve separation of aqueous/organic layers. The combined organic extracts were washed with brine (150 mL), dried over sodium sulfate before addition of toluene (180 mL) and concentration/drying in vacuo at 50° C. The resulting pale orange solid (14.7 g) was slurried in water (120 mL) at room temperature for 100 minutes before filtration and drying in vacuo to provide sodium salt of the title compound as a cream coloured solid (9.6 g).

¹⁹FNMR (d₆-DMSO): δ −60.5 ppm (s).

¹HNMR (d₆-DMSO): δ 7.22 (d, 1H), 7.43 (d, 1H), 7.80-8.00 (m, 4H), 8.04 (s, 1H), 8.13 (s, 1H), 9.28 (s, 1H), 9.45 (s, 1H).

Example 803

4-[2-(5-amino-1H-pyrazol-4-yl)-4-chlorophenoxy]-5-chloro-2-fluoro-N-1,3,4-thiadiazol-2-ylbenzenesulfonamide

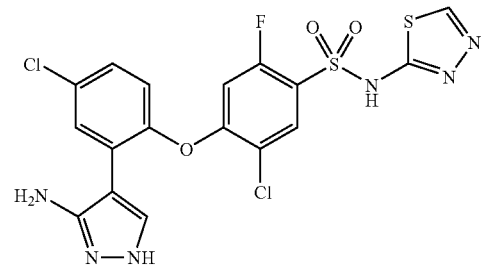

The title compound was prepared from N-[1-tert-Butyl-4-(5-chloro-2-hydroxyphenyl)-1H-pyrazol-3-yl]-2,2,2-trifluoroacetamide (Preparation 209) and 5-chloro-N-(2,4-dimethoxybenzyl)-2,4-difluoro-N-1,3,4-thiadiazol-2-ylbenzenesulfonamide (Preparation 247) using Method B above with the exception that heating at 55° C. in HCl (gas) saturated methanol for 16 hours was used to remove the protecting groups. Purification by preparative HPLC afforded the title compound.

LCMS Rt=1.61 minutes

MS m/z 503 [M³⁷ClH]+, 501 [M³⁵ClH]+

¹HNMR (d₆-DMSO): δ 4.50 (br s, 2H), 6.89 (m, 1H), 7.21 (m, 1H), 7.37 (m, 1H), 7.66 (m, 1H), 7.70 (m, 1H), 7.89 (m, 1H), 8.81 (d, 1H).

Example 804

4-[4-chloro-5-fluoro-2-(1H-pyrazol-4-yl)phenoxy]-3-cyano-N-1,2,4-thiadiazol-5-ylbenzenesulfonamide

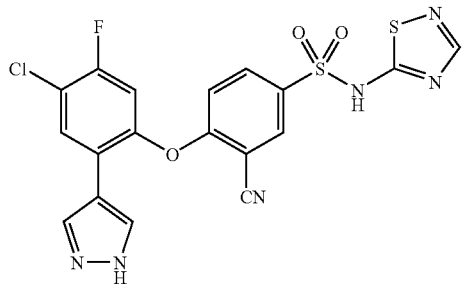

To a solution of tert-butyl 4-[5-chloro-2-(2-cyano-4-{[(2,4-dimethoxybenzyl)(1,2,4-thiadiazol-5-yl)amino]sulfonyl}phenoxy)-4-fluorophenyl]-1H-pyrazole-1-carboxylate (Preparation 728, 190 mg, 0.26 mmol) in dichloromethane (5 mL) was added trifluoroacetic acid (0.3 mL, 3.65 mmol) and the reaction mixture was left to stir at room temperature for 16 hours. The reaction was quenched by addition of water (10 mL) and the resulting mixture left to stir for 20 minutes. Then the layers were separated, the organic phase was washed with saturated aqueous sodium chloride solution (5 mL), dried over anhydrous magnesium sulphate, filtered and concentrated in vacuo. The crude oil was purified using ISCO ™ (5 g cartridge) 1-20% v/v gradient of methanol in dichloromethane as the eluent. The title compound was obtained as a white solid (61 mg. 50%).

LCMS Rt=4.51 minutes, MS m/z 477 [M$^{35}$ClH]+

$^1$HNMR (d$_6$-DMSO): δ 6.95 (m, 1H), 7.10 (m, 1H), 7.55 (m, 1H), 7.80-8.01 (m, 2H), 8.10 (m, 2H), 13.0 (brs, 1H).

Example 805

2,5-difluoro-4-[2-pyridazin-4-yl-4-(trifluoromethyl)phenoxy]-N-1,2,4-thiadiazol-5-ylbenzenesulfonamide

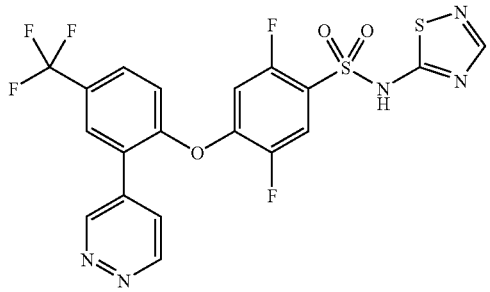

The mixture of N-(2,4-dimethoxybenzyl)-2,4,5-trifluoro-N-1,2,4-thiadiazol-5-ylbenzenesulfonamide (Preparation 647, 44 mg, 0.10 mmol), 2-pyridazin-4-yl-4-(trifluoromethyl)phenol (Preparation 712, 34 mg, 0.10 mmol), and potassium carbonate (55 mg, 0.40 mmol) in N,N-dimethylformamide (1.0 ml) was stirred at room temperature for 24 hours. The reaction mixture was poured into aqueous 2 M hydrochloric acid solution (5.0 ml) and filtered to give a solid. The solid was dissolved in dichloromethane (1.0 ml) and trifluoroacetic acid (1.0 ml) was added to the solution. The resulting solution was stirred for 16 hours. Methanol (5.0 ml) was added to the reaction mixture and filtered off polymeric solid. The filtrate was concentrated in vacuo to give a residue. The residue was passed through a 5 g SCX™ column with 1:1 dichloromethane:methanol solution and then 1:0.75:0.25 dichloromethane:methanol:7N ammonia solution in methanol. The filtrate was concentrated in vacuo and purified by HPLC. Yield 7.3 mg, 14%.

LCMS Rt=2.44 minutes MS m/z 516 [MH]+

$^1$HNMR (400 MHz, CD$_3$OD): δ 7.25 (m, 1H), 7.30 (d-d, 1H), 7.80-7.85 (m, 2H), 8.00 (d, 1H), 8.05 (d-d, 1H), 8.25 (s, 1H), 9.30 (d, 1H), 9.50 (s, 1H)

Example 806

5-Chloro-2-fluoro-4-{4-fluoro-2-[1-(1-methylazetidin-3-yl)-1H-pyrazol-5-yl]phenoxy)-N-1,2,4-thiadiazol-5-ylbenzenesulfonamide

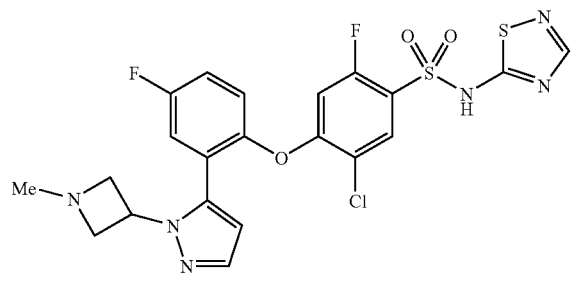

The title compound was prepared by analogy with Example 807 below using 4-[2-(1-azetidin-3-yl-1H-pyrazol-5-yl)-4-fluorophenoxy]-5-chloro-2-fluoro-N-1,2,4-thiadiazol-5-ylbenzenesulfonamide (Example 810, 45 mg, 0.08 mmol).

Yield 14.5 mg 34%.

LCMS Rt=2.49 minutes, m/z 539 [M$^{35}$ClH]+

TLC Rf=0.5 (methyl isobutyl ketone:acetic acid:water 2:1:1)

$^1$HNMR (d$_6$-DMSO): δ 2.94 (s, 3H), 4.13-4.58 (m, 4H), 5.20 (m, 1H), 6.43 (s, 1H), 6.81 (d, 1H), 7.26-7.34 (m, 1H), 7.39-7.48 (m, 2H), 7.67-7.74 (m, 2H), 7.91 (s, 1H)

Example 807

5-Chloro-2-fluoro-4-{4-fluoro-2-[1-(1-methylazetidin-3-yl)-1H-pyrazol-5-yl]phenoxy}-N-1,3-thiazol-4-ylbenzenesulfonamide

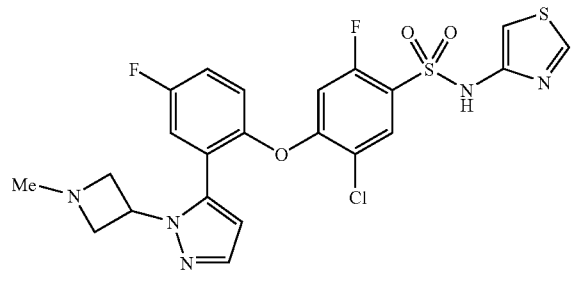

4-[2-(1-Azetidin-3-yl-1H-pyrazol-5-yl)-4-fluorophenoxy]-5-chloro-2-flouro-N-1,3-thiazol-4-ylbenzenesulfonamide (Example 808, 29 mg, 0.052 mmol) was stirred in dichloromethane (2 ml), methanol (0.2 ml), aqueous formaldehyde (0.015 ml of 37% wt/vol) added and the reaction stirred at room temperature for a further 30 minutes. Sodium triacetoxyborohydride (37 mg, 0.172 mmol) was added and the solution stirred for 3 hours. The solvents were removed in vacuo and the residue dissolved in ethyl acetate and extracted with saturated aqueous sodium hydrogencarbonate solution (2×10 ml) and brine (2×10 ml). The organic layer was separated, dried over sodium sulphate, filtered and evaporated to give a solid. The compound was purified using preparative HPLC to afford the title compound. Yield 15.9 mg 57%.

LCMS Rt=2.38 minutes, m/z 538 [M$^{35}$ClH]+

$^1$HNMR (CD$_3$OD): δ 4.25 (m, 4H), 5.25 (m, 1H), 6.34 (s, 1H), 6.92 (d, 1H) 7.08 (s, 1H), 7.45 (m, 3H), 7.66 (s, 1H), 7.79 (d, 1H), 8.92 (s, 1H), 9.17 (brs, 1H), 11.32 (brs, 1H).

Example 808

4-[2-(1-Azetidin-3-yl-1H-pyrazol-5-yl)-4-fluorophenoxy]-5-chloro-2-fluoro-N-1,3-thiazol-4-ylbenzenesulfonamide

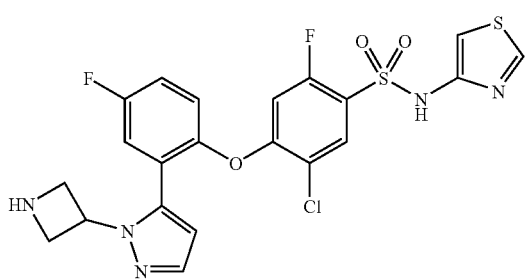

The title compound was prepared by analogy with Example 809, below, from tert-butyl {[5-chloro-4-(2-{1-[1-(diphenylmethyl)azetidin-3-yl]-1H-pyrazol-5-yl}-4-fluorophenoxy)-2-fluorophenyl]sulfonyl}1,3-thiazol-4-ylcarbamate (Preparation 683, 140 mg, 0.177 mmol). Yield 42 mg 42%.

LCMS Rt=1.04 minutes, m/z 524 [M$^{35}$ClH]+

$^1$HNMR (CD$_3$OD): δ 4.25 (m, 4H), 5.25 (m, 1H), 6.34 (s, 1H), 6.92 (d, 1H) 7.08 (s, 1H), 7.45 (m, 3H), 7.66 (s, 1H), 7.79 (d, 1H), 8.92 (s, 1H), 9.17 (brs, 1H), 11.32 (brs, 1H).

Example 809

4-[2-(1-azetidin-3-yl-1H-pyrazol-5-yl)-4-chlorophenoxy]-3-cyano-N-1,3-thiazol-4-ylbenzenesulfonamide

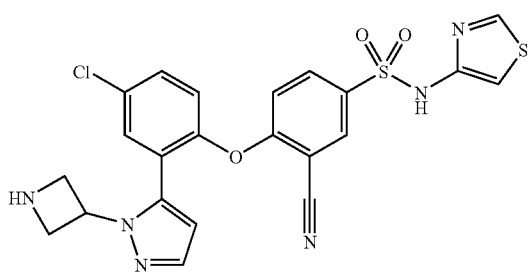

tert-butyl ({4-[2-(1-azetidin-3-yl-1H-pyrazol-5-yl)-4-chlorophenoxy]-3-cyanophenyl}sulfonyl)1,3-thiazol-4-ylcarbamate (Preparation 679, 200 mg, 0.326 mmol) was stirred in 4M hydrogen chloride solution in 1,4-dioxan (10 ml) at room temperature for 2 hours. The reaction mixture was concentrated in vacuo and the residue was partitioned between methyl-t-butyl ether (80 ml) and water (40 ml). The aqueous layer was neutralized to pH=7 by adding sodium hydrogen carbonate and was then concentrated in vacuo. The crude product was purified by column chromatography on silica gel using dichloromethane:methanol:0.880 aqueous ammonia, 90:10:1 to 70:30:3. This gave a buff powder (65 mg) which was triturated with methyl tert-butyl ether to give the title compound as a buff powder, 55 mg.

LCMS Rt=1.26 minutes, m/z 513 [M$^{35}$ClH]+; 515 [M$^{37}$ClH]+

NMR (d$_6$-DMSO) δ 3.31 (bs, 2H) 4.04-4.14 (m, 4H), 5.05-5.14 (m, 1H), 6.30 (s, 1H), 6.38 (bs, 1H), 6.86 (d, 1H), 7.43 (d, 1H), 7.61 (m, 2H), 7.68 (m, 1H), 7.84 (m, 1H), 8.01 (s, 1H), 8.67 (s, 1H).

Example 810

4-[2-(1-azetidin-3-yl-1H-pyrazol-5-yl)-4-fluorophenoxy[-5-chloro-2-fluoro-N-1,2,4-thiadiazol-5-ylbenzenesulfonamide

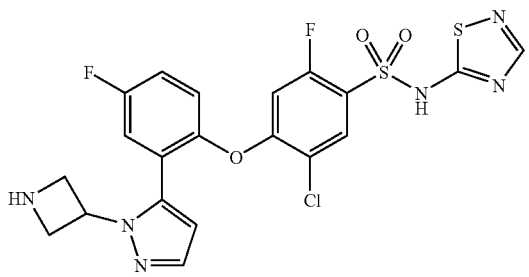

The title compound was prepared by analogy with Example 809, above, from 5-chloro-N-(2,4-dimethoxybenzyl)-4-(2-(1-[1-(diphenylmethyl)azetidin-3-yl]-1H-pyrazol-5-yl}-4-fluorophenoxy)-2-fluoro-N-1,2,4-thiadiazol-5-yl-benzenesulfonamide (Preparation 681, 500 mg, 0.594 mmol). Final purification was achieved by suspending the solid in methanol and the mixture filtered through Celite™ (insoluble purple solid discarded). The colourless filtrate was evaporated and the residue triturated with diethyl ether and the off-white solid filtered off and dried at 60° C. in vacuo to give the title compound. Yield 113 mg 34%.

LCMS Rt=1.10 minutes, m/z 525 [M$^{35}$ClH]+

$^1$HNMR (d$_6$-DMSO): δ 4.27 (m, 4H), 5.23 (m, 1H), 6.40 (s, 1H), 6.92 (d, 1H) 7.34 (m, 1H), 7.45 (m, 2H), 7.69 (s, 1H), 7.79 (d, 1H), 8.35 (s, 1H), 8.72 (brs, 1H), 9.10 (brs, 1H).

$^{19}$FNMR (d$_6$-DMSO) δ 74.39 (s, 3F) 106.9 (s, 1F) 116.7 (s, 1F).

TLC Rf=0.5 (methyl isobutyl ketone:acetic acid:water 2:1:1)

Example 811

4-{4-Chloro-2-[1-(1-methylazetidin-3-yl)-1H-pyrazol-5-yl]phenoxy}-2,5-difluoro-N-1,2,4-thiadiazol-5-ylbenzenesulfonamide

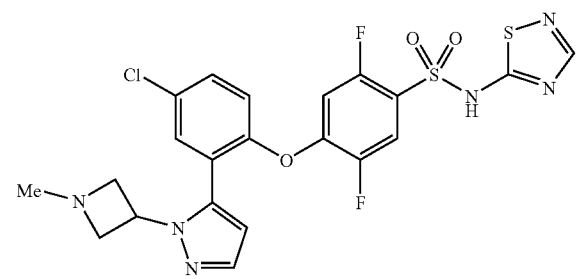

4-[2-(1-azetidin-3-yl-1H-pyrazol-5-yl)-4-chlorophenoxy]-2,5-difluoro-N-1,2,4-thiadiazol-5-ylbenzenesulfonamide (Example 801, 54 mg, 0.1 mmol) was stirred with dichloromethane (2 mL) methanol (0.2 mL) and 37% w/v aqueous formaldehyde solution (0.025 mL, 0.34 mmol) at room temperature for 15 minutes. Sodium triacetoxyborohydride (68 mg, 0.32 mmol) was added at the reaction stirred at room temperature for 18 hours. 37% wt/vol aqueous formaldehyde solution (0.025 mL, 0.34 mmol) was added and the reaction stirred for 15 minutes then sodium triacetoxyborohydride (68 mg, 0.32 mmol) was added at the reaction stirred at room temperature for 3 hours. The mixture was evaporated and the residue dissolved in ethyl acetate (20 mL) and washed with saturated aqueous sodium bicarbonate solution (2×10 ml) and saturated aqueous sodium chloride solution (2×10 ml). The organic layer was separated, dried over sodium sulphate, filtered and evaporated to give a solid. The solid was suspended in methyl isobutyl ketone:acetic acid:water 2:1:1 and eluted through a silica column (5 g) with methyl isobutyl ketone:acetic acid:water 2:1:1. The appropriate fractions were combined and concentrated in vacuo to give a film. This was scratched with ethyl acetate then diethyl ether and dried in vacuo to give the title compound as a white solid. Yield 30 mg. 54%.

LCMS Rt=1.11 minutes, m/z 539 [M$^{35}$ClH]+

$^1$HNMR (d$_6$-DMSO): δ 2.80 (s, 3H), 4.10(m 2H) 4.24(m 2H) 5.05(m 1H) 6.43(d 1H) 7.07(m 1H) 7.22(d 1H) 7.57 (m, 3H) 7.69(s 1H) 7.89(s, 1H),

TLC Rf=0.5 (methyl isobutyl ketone:acetic acid:water 2:1:1)

Example 811

Sodium Salt

4-{4-Chloro-2-[1-(1-methylazetidin-3-yl)-1H-pyrazol-5-yl]phenoxy)-2,5-difluoro-N-1,2,4-thiadiazol-5-ylbenzenesulfonamide sodium salt The sodium salt of Example 811 was prepared as follows:
4-{4-Chloro-2-[1-(1-methylazetidin-3-yl)-1H-pyrazol-5-yl]phenoxy}-2,5-difluoro-N-1,2,4-thiadiazol-5-ylbenzenesulfonamide, (Example 811, 35.0 g, 0.06494 mol) was suspended in water (210 mL) and a solution of sodium hydroxide (2.47 g, 0.06169 mol) in water (210 mL) was added dropwise over 10 minutes. The resulting cloudy solution was filtered and the water removed in vacuo to give a white foam. The foam was triturated with tert-butylmethyl ether and the white solid filtered off and dried to give the title compound as a white powder, (28.85 g).

$^1$HNMR (d$_6$-DMSO) δ 2.27 (s, 3H), 3.29-3.35 (m, 2H), 3.54-3.59 (m, 2H), 4.70-4.79 (m, 1H), 6.34 (d, 1H), 7.04-7.10 (m, 1H), 7.18-7.21 (d, 1H), 7.49 (d, 1H), 7.53-7.60 (m, 3H), 7.90 (s, 1H).

Example 811

4-{4-Chloro-2-[1-(1-methylazetidin-3-yl)-1H-pyrazol-5-yl]phenoxy}-2,5-difluoro-N-1,2,4-thiadiazol-5-ylbenzenesulfonamide

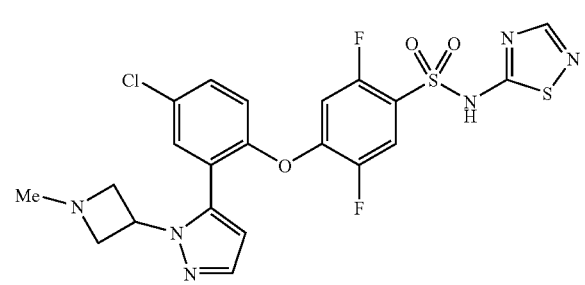

An alternative method of preparing Example 811 is as follows:

4-[2-(1-Azetidin-3-yl-1H-pyrazol-5-yl)-4-chlorophenoxy]-2,5-difluoro-N-1,2,4-thiadiazol-5-ylbenzenesulfonamide trifluoroacetate salt, (Example 801, 110.45 g, 0.1558 mol) was dissolved in dichloromethane (1050 mL) and methanol (110.45 mL). Acetic acid (17.86 mL, 2.73 mol) was added followed by aqueous formaldehyde solution (58.54 mL of 37 wt % in water, 0.779 mol), stirred at room temperature for 30 minutes. The solution was then cooled in an ice bath and sodium triacetoxyborohydride (82.56 g, 0.3895 mol) was added, stirred whilst warming to room temperature over 1.5 hours. Aqueous formaldehyde solution (29.27 mL of 37 wt % in water, 0.3895 mol) was added, stirred for 30 minutes then sodium triacetoxyborohydride (82.56 g, 0.3895 mol) was added and stirred at room temperature for 1.5 hours. The reaction was quenched by adding water (552.25 mL) and stirred for 30 minutes then 0.880 aqueous ammonia solution (100 mL) was added in two equal portions and stirred for a further 30 minutes. The resulting solid was filtered off and dried to give the crude title compound as a white solid, (135 g). The crude product was suspended in ethanol (405 mL) and heated to reflux for 1 hour then water (405 mL) was added and the resulting slurry was stirred at 90° C. for 30 minutes before being allowed to cool to 35° C. The solid was filtered off and dried to give the title compound as a white solid, (67.5 g).

HPLC Rt=2.43 minutes

LCMS Rt=2.11 minutes, m/z=539 [M$^{35}$ClH]+$^1$HNMR (d$_6$-DMSO) δ 2.96 (s, 3H), 4.28-4.35 (m, 2H), 4.42-4.51 (m, 2H), 5.11-5.21 (m, 1H), 6.47 (d, 1H), 7.04-7.10 (m, 1H), 7.24-7.26 (m, 1H), 7.55-7.62 (m, 3H), 7.73 (d, 1H), 7.92 (s, 1H).

Example 812

4-[2-(2-aminopyridin-4-yl)-4-chlorophenoxy]-5-chloro-2-fluoro-N-pyrimidin-4-ylbenzenesulfonamide

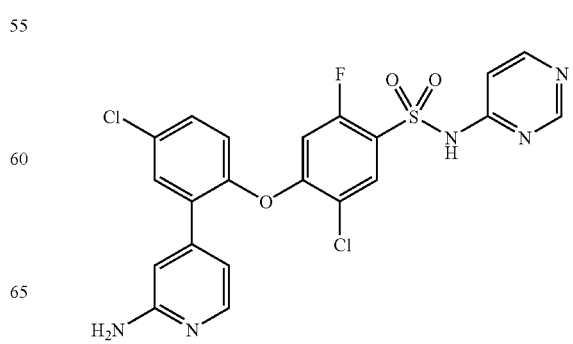

The title compound was prepared by analogy with the method used for Example 813 below using 5-chloro-N-(ethoxymethyl)-2,4-difluoro-N-pyrimidin-4-ylbenzene-sulfonamide, 5-chloro-N-[(4E)-1-(ethoxymethyl)pyrimidin-4(1H)-ylidene]-2,4-difluorobenzenesulfonamide and 5-chloro-N-[(4E)-1-(ethoxymethyl)pyrimidin-4(1H)-ylidene]-2,4-difluorobenzenesulfonamide, (Preparation 719) used as a mixture of three regioisomers and 2-(2-aminopyridin-4-yl)-4-chlorophenol (Preparation 721).

LCMS Rt=1.39 minutes, MS m/z 506 [MH]+
$^1$HNMR (d$_6$-DMSO): δ 6.90-7.02 (m, 2 H), 7.05 (s, 1 H), 7.21-7.29 (m, 2 H), 7.66 (dd, 1 H), 7.77 (d, 1 H), 7.90-8.30 (m, 4 H), 8.62 (s, 1 H).

Example 813

5-chloro-4-[4-chloro-2-(1-methyl-1H-pyrazol-5-yl)phenoxy]-2-fluoro-N-pyrimidin-4-ylbenzenesulfonamide

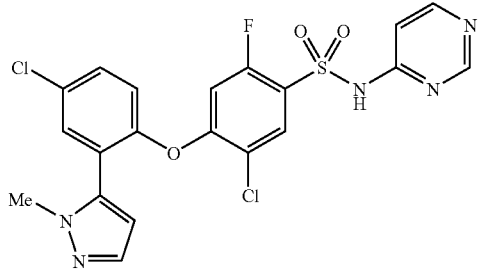

A suspension of 5-chloro-N-(ethoxymethyl)-2,4-difluoro-N-pyrimidin-4-ylbenzenesulfonamide and 5-chloro-N-[(4E)-1-(ethoxymethyl)pyrimidin-4(1H)-ylidene]-2,4-difluorobenzenesulfonamide and 5-chloro-N-[(4E)-1-(ethoxymethyl)pyrimidin-4(1H)-ylidene]-2,4-difluorobenzenesulfonamide (Preparation 719) used as a mixture of three regioisomers, (64 mg, 0.18 mmol), 4-chloro-2-(1-methyl-1H-pyrazol-5-yl)phenol (Preparation 89) (37 mg, 0.18 mmol) and potassium carbonate (37 mg, 0.26 mmol) in dimethyl sulfoxide (1 mL) was stirred at room temperature for 19 hours then diluted with ethyl acetate (30 mL), washed with 1M aqueous sodium hydroxide, water, saturated aqueous sodium chloride solution, dried over anhydrous sodium sulfate and concentrated in vacuo. The residue was taken up in trifluoroacetic acid (1 mL) and stirred for 3 hours then concentrated in vacuo. The residue was purified by reverse phase HPLC to give 29 mg (27%) of the desired product as a white solid.

LCMS Rt=1.67 minutes MS m/z 494 [MH]+
$^1$HNMR (d$_6$-DMSO): δ 3.77 (s, 3 H), 6.33 (d, 1 H), 6.96-7.02 (m, 2 H), 7.32 (d, 1 H), 7.41 (d, 1 H), 7.55-7.65 (m, 2 H), 7.96 (d, 1 H), 8.25 (d, 1 H), 8.60 (s, 1 H).

Example 814

4-[2-(2-aminopyridin-4-yl)-4-chlorophenoxy]-5-chloro-2-fluoro-N-1,3,4-thiadiazol-2-ylbenzene-sulfonamide

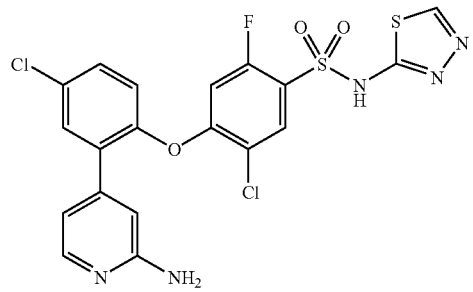

The title compound was prepared from 2-(2-aminopyridin-4-yl)-4-chlorophenol, (Preparation 721) and 5-chloro-N-(2,4-dimethoxybenzyl)-2,4-difluoro-N-1,3,4-thiadiazol-2-yl-benzenesulfonamide (Preparation 247) using a method analogous to that used in Preparation 669. Purification by semi-preparative HPLC using 15-100% MeOH/H$_2$O yielded the title compound.

LCMS Rt=1.47 minutes, MS m/z 512 [MH]+
$^1$HNMR (d$_6$-DMSO): δ 6.96 (m, 1H), 7.04 (m, 1H), 7.23 (m, 2H), 7.60 (m, 1H), 7.73 (d, 1H), 7.91 (m, 2H), 8.83 (m, 1H).

Yet further examples of the present invention were prepared, again using methods analogous to the General Schemes described above, Library Protocols 1 and 2 described above, and Methods A-M as described for Examples 1-6, 95-99, 134, 170, and 279 above, or any of the other fully written up experimental conditions provided, substituting appropriate starting materials where necessary and making appropriate changes to experimental conditions informed by the schemes and conditions provided and common general knowledge. Purification was performed either by silica gel column chromatography, trituration or preparative HPLC.

| Eg No | Name | MS m/z Unless otherwise stated |
|---|---|---|
| 815 | 4-{[3'-(azetidin-1-ylmethyl)-5-iodobiphenyl-2-yl]oxy}-3-cyano-N-1,2,4-thiadiazol-5-ylbenzenesulfonamide | 630 [MH]+ |
| 816 | 5-chloro-4-[4-chloro-2-(5-methyl-1H-pyrazol-4-yl)phenoxy]-2-fluoro-N-1,3,4-thiadiazol-2-ylbenzenesulfonamide | 500 [M$^{35}$ClH]+ |
| 817 | 5-chloro-4-[4-chloro-2-(1-methyl-1H-pyrazol-5-yl)phenoxy]-2-fluoro-N-(5-methyl-1,3,4-thiadiazol-2-yl)benzenesulfonamide | 514 [M$^{35}$ClH]+ |
| 818 | 4-[2-(2-aminopyridin-4-yl)-4-chlorophenoxy]-3-cyano-N-1,3,4-thiadiazol-2-ylbenzenesulfonamide | 485 [MH]+ |
| 819 | 5-chloro-4-{4-chloro-2-[1-(2-methoxyethyl)-1H-pyrazol-3-yl]phenoxy}-2-fluoro-N-1,3,4-thiadiazol-2-ylbenzenesulfonamide | 544 [M$^{35}$ClH]+ |

-continued

| Eg No | Name | MS m/z Unless otherwise stated |
|---|---|---|
| 820 | 4-[2-(2-aminopyridin-4-yl)-4-chlorophenoxy]-2,5-difluoro-N-1,3,4-thiadiazol-2-ylbenzenesulfonamide | 496 [MH]+ |
| 821 | 4-[4-chloro-2-(1H-pyrazol-4-yl)phenoxy]-2,5-difluoro-N-1,3,4-thiadiazol-2-ylbenzenesulfonamide | 470 [M$^{35}$ClH]+ |
| 822 | 4-{[3'-(azetidin-1-ylmethyl)-5-chlorobiphenyl-2-yl]oxy}-5-chloro-2-fluoro-N-1,3,4-thiadiazol-2-ylbenzenesulfonamide | 565 [M$^{35}$ClH]+ |
| 823 | 4-{[3'-(azetidin-1-ylcarbonyl)-5-chlorobiphenyl-2-yl]oxy}-5-chloro-2-fluoro-N-1,2,4-thiadiazol-5-ylbenzenesulfonamide | 579 [M$^{35}$ClH]+ |
| 824 | 5-chloro-4-({5-chloro-3'-[(3-hydroxyazetidin-1-yl)carbonyl]biphenyl-2-yl}oxy)-2-fluoro-N-1,2,4-thiadiazol-5-ylbenzenesulfonamide | 595 [M$^{35}$ClH]+ |
| 825 | 4-[4-chloro-2-(tetrahydro-2H-pyran-4-yl)phenoxy]-3-fluoro-N-1,2,4-thiadiazol-5-ylbenzenesulfonamide | 470 [M$^{35}$ClH]+ |
| 826 | 4-[2-(3-amino-1H-pyrazol-5-yl)-4-fluorophenoxy]-3-cyano-N-1,2,4-thiadiazol-5-ylbenzenesulfonamide | 458 [MH]+ |
| 827 | 4-[4-chloro-2-(1-cyclopropyl-1H-pyrazol-5-yl)phenoxy]-3-cyano-N-1,2,4-thiadiazol-5-ylbenzenesulfonamide | 498 [MH]− |
| 828 | 4-[4-chloro-2-(1-cyclobutyl-1H-pyrazol-5-yl)phenoxy]-3-cyano-N-1,2,4-thiadiazol-5-ylbenzenesulfonamide | 512 [MH]− |
| 829 | 3-fluoro-4-[2-(1H-pyrazol-5-yl)-4-(trifluoromethoxy)phenoxy]-N-1,2,4-thiadiazol-5-ylbenzenesulfonamide | 502 [MH]+ |
| 830 | 4-[2-(6-aminopyridin-2-yl)-4-(trifluoromethoxy)phenoxy]-2,5-difluoro-N-1,2,4-thiadiazol-5-ylbenzenesulfonamide | 546 [MH]+ |

| Eg No | Name | MS m/z Unless otherwise stated |
|---|---|---|
| 831 | 4-{2-[6-(azetidin-1-ylmethyl)pyridin-2-yl]-4-chlorophenoxy}-5-chloro-2-fluoro-N-1,3,4-thiadiazol-2-ylbenzenesulfonamide | 566 [MH]+ |
| 832 | 4-(4-chloro-2-pyridazin-4-ylphenoxy)-3-cyano-N-1,3,4-thiadiazol-2-ylbenzenesulfonamide | 471 [MH]+ |
| 833 | 4-[4-chloro-2-(2-piperazin-1-ylpyridin-4-yl)phenoxy]-2,5-difluoro-N-1,3,4-thiadiazol-2-ylbenzenesulfonamide | 565 [M$^{35}$ClH]+ |
| 834 | 4-[4-chloro-2-(2-piperazin-1-ylpyridin-4-yl)phenoxy]-3-cyano-N-1,3-thiazol-4-ylbenzenesulfonamide | 553 [M$^{35}$ClH]+ |
| 835 | 4-[4-chloro-2-(2-piperazin-1-ylpyridin-4-yl)phenoxy]-3-cyano-N-1,3,4-thiadiazol-2-ylbenzenesulfonamide | 554 [M$^{35}$ClH]+ |
| 836 | 4-[4-chloro-2-(tetrahydro-2H-pyran-4-yl)phenoxy]-3-cyano-N-1,2,4-thiadiazol-5-ylbenzenesulfonamide | 477 [M$^{35}$ClH]+ |
| 837 | 4-[4-(difluoromethoxy)-2-(1H-pyrazol-4-yl)phenoxy]-2,5-difluoro-N-1,2,4-thiadiazol-5-ylbenzenesulfonamide | 502 [MH]+ |
| 838 | 4-{2-[2-(azetidin-1-ylmethyl)pyridin-4-yl]-4-chlorophenoxy}-2,5-difluoro-N-1,2,4-thiadiazol-5-ylbenzenesulfonamide | 550 [M$^{35}$ClH]+ |
| 839 | 4-[4-chloro-2-(1H-pyrazol-4-yl)phenoxy]-3-cyano-N-1,3,4-thiadiazol-2-ylbenzenesulfonamide | 459 [M$^{35}$ClH]+ |
| 840 | 4-[2-(3-amino-1H-pyrazol-5-yl)-4-fluorophenoxy]-5-chloro-2-fluoro-N-1,2,4-thiadiazol-5-ylbenzenesulfonamide | 485 [M$^{35}$ClH]+ |
| 841 | 4-[2-(1-azetidin-3-yl-1H-pyrazol-5-yl)-4-(trifluoromethyl)phenoxy]-2,5-difluoro-N-1,3-thiazol-4-ylbenzenesulfonamide | 558 [MH]+ |
| 842 | 3-cyano-4-[4-fluoro-2-(tetrahydro-2H-pyran-4-yl)phenoxy]-N-1,2,4-thiadiazol-5-ylbenzenesulfonamide | 461 [MH]+ |
| 843 | 5-chloro-4-(4-chloro-2-pyridazin-4-ylphenoxy)-2-fluoro-N-1,3,4-thiadiazol-2-ylbenzenesulfonamide | 498 [MH]+ |
| 844 | 4-{4-chloro-2-[1-(1-methylazetidin-3-yl)-1H-pyrazol-5-yl]phenoxy}-2,5-difluoro-N-1,3-thiazol-4-ylbenzenesulfonamide | 539 [MH]+ |
| 845 | 5-chloro-4-(4-chloro-2-pyridazin-4-ylphenoxy)-2-fluoro-N-1,3-thiazol-4-ylbenzenesulfonamide | 497 [MH]+ |
| 846 | 4-(4-chloro-2-pyridazin-4-ylphenoxy)-2,5-difluoro-N-(5-fluoropyridin-2-yl)benzenesulfonamide | 493 [M$^{35}$ClH]+ |
| 847 | 3-chloro-4-(4-chloro-2-pyridazin-4-ylphenoxy)-N-pyrimidin-4-ylbenzenesulfonamide | 474 [M$^{35}$ClH]+ |
| 848 | 5-chloro-4-{2-[1-(1-ethylazetidin-3-yl)-1H-pyrazol-5-yl]-4-fluorophenoxy}-2-fluoro-N-1,2,4-thiadiazol-5-ylbenzenesulfonamide | 553 [M$^{35}$ClH]+ |
| 849 | 4-[2-(2-aminopyrimidin-4-yl)-4-chlorophenoxy]-2,5-difluoro-N-1,2,4-thiadiazol-5-ylbenzenesulfonamide | 497 [M$^{35}$ClH]+ |
| 850 | 5-chloro-4-[4-cyano-2-(1H-pyrazol-4-yl)phenoxy]-2-fluoro-N-1,2,4-thiadiazol-5-ylbenzenesulfonamide | 477 [M$^{35}$ClH]+ |

-continued

| Eg No | Name | MS m/z Unless otherwise stated |
|---|---|---|
| 851 | 4-{4-chloro-2-[1-(1-ethylazetidin-3-yl)-1H-pyrazol-5-yl]phenoxy}-2,5-difluoro-N-1,3-thiazol-4-ylbenzenesulfonamide | 552 [MH]+ |
| 852 | 4-{[3'-(azetidin-1-ylmethyl)-5-chlorobiphenyl-2-yl]oxy}-3-cyano-N-1,2,4-thiadiazol-5-ylbenzenesulfonamide | 538 [MH]+ |
| 853 | 4-[4-chloro-2-(5-cyanopyridin-2-yl)phenoxy]-3-cyano-N-1,2,4-thiadiazol-5-ylbenzenesulfonamide | 495 [M$^{35}$ClH]+ |
| 854 | 4-{[3'-(azetidin-1-ylcarbonyl)-5-chlorobiphenyl-2-yl]oxy}-3-cyano-N-1,2,4-thiadiazol-5-ylbenzenesulfonamide | 552 [M$^{35}$ClH]+ |
| 855 | 4-{[3'-(azetidin-1-ylcarbonyl)-5-chlorobiphenyl-2-yl]oxy}-2,5-difluoro-N-1,2,4-thiadiazol-5-ylbenzenesulfonamide | 563 [M$^{35}$ClH]+ |
| 856 | 4-{[3'-(azetidin-1-ylcarbonyl)-5-chlorobiphenyl-2-yl]oxy}-5-chloro-2-fluoro-N-1,3-thiazol-4-ylbenzenesulfonamide | 578 [M$^{35}$ClH]+ |
| 857 | 4-{[3'-(azetidin-1-ylcarbonyl)-5-chlorobiphenyl-2-yl]oxy}-5-chloro-2-fluoro-N-1,3,4-thiadiazol-2-ylbenzenesulfonamide | 579 [M$^{35}$ClH]+ |
| 858 | 4-{[3'-(azetidin-1-ylcarbonyl)-5-chlorobiphenyl-2-yl]oxy}-3-chloro-N-pyrimidin-4-ylbenzenesulfonamide | 555 [M$^{35}$ClH]+ |
| 859 | 4-{2-[6-(azetidin-1-ylcarbonyl)pyridin-2-yl]-4-chlorophenoxy}-5-chloro-2-fluoro-N-1,2,4-thiadiazol-5-ylbenzenesulfonamide | 580 [M$^{35}$ClH]+ |
| 860 | 5-chloro-4-{4-chloro-2-[3-(dimethylamino)-1H-pyrazol-4-yl]phenoxy}-2-fluoro-N-1,3-thiazol-4-ylbenzenesulfonamide | 528 [M$^{35}$ClH]+ |
| 861 | 4-{4-chloro-2-[1-(1-isopropylazetidin-3-yl)-1H-pyrazol-5-yl]phenoxy}-3-cyano-N-1,3-thiazol-4-ylbenzenesulfonamide | 555 [MH]+ |
| 862 | 3-chloro-4-[4-chloro-2-(1-methyl-1H-pyrazol-5-yl)phenoxy]-N-pyridazin-3-ylbenzenesulfonamide | 476 [M$^{35}$ClH]+ |
| 863 | 4-[4-chloro-5-fluoro-2-(5-methyl-1H-pyrazol-4-yl)phenoxy]-3-cyano-N-1,2,4-thiadiazol-5-ylbenzenesulfonamide | 491 [M$^{35}$ClH]+ |
| 864 | 5'-chloro-2'-{2-cyano-4-[(1,2,4-thiadiazol-5-ylamino)sulfonyl]phenoxy}-N-cyclopropylbiphenyl-3-carboxamide | 552 [MH]+ |
| 865 | 4-[4-chloro-2-(5-methyl-1H-pyrazol-4-yl)phenoxy]-3-cyano-N-1,2,4-thiadiazol-5-ylbenzenesulfonamide | 473 [M$^{35}$ClH]+ |
| 866 | 4-{4-chloro-2-[1-(1,1-dioxidotetrahydro-3-thienyl)-1H-pyrazol-5-yl]phenoxy}-2,5-difluoro-N-1,2,4-thiadiazol-5-ylbenzenesulfonamide | 588 [M$^{35}$ClH]+ |
| 867 | 4-[(3'-{[3,3-bis(hydroxymethyl)azetidin-1-yl]methyl}-5-chlorobiphenyl-2-yl)oxy]-3-cyano-N-1,2,4-thiadiazol-5-ylbenzenesulfonamide | 598 [MH]+ |
| 868 | 4-(4-chloro-2-pyridazin-4-ylphenoxy)-3-cyano-N-1,2,4-thiadiazol-5-ylbenzenesulfonamide | 471 [M$^{35}$ClH]+ |
| 869 | 3-chloro-4-(4-chloro-2-pyridazin-4-ylphenoxy)-N-pyridazin-3-ylbenzenesulfonamide | 474 [M$^{35}$ClH]+ |
| 870 | 5-chloro-4-{4-chloro-2-[3-(dimethylamino)-1H-pyrazol-4-yl]phenoxy}-2-fluoro-N-1,3,4-thiadiazol-2-ylbenzenesulfonamide | 529 [M$^{35}$ClH]+ |
| 871 | 5-chloro-2-fluoro-N-(3-methyl-1,2,4-thiadiazol-5-yl)-4-[2-pyridazin-4-yl-4-(trifluoromethyl)phenoxy]benzenesulfonamide | 546 [M$^{35}$ClH]+ |
| 872 | 4-[2-(3-amino-1H-pyrazol-4-yl)-4-chlorophenoxy]-5-chloro-2-fluoro-N-(3-methyl-1,2,4-thiadiazol-5-yl)benzenesulfonamide | 515 [M$^{35}$ClH]+ |
| 873 | 4-[4-chloro-2-(6-morpholin-4-ylpyrimidin-4-yl)phenoxy]-2,5-difluoro-N-1,3,4-thiadiazol-2-ylbenzenesulfonamide | 567 [M$^{35}$ClH]+ |
| 874 | 4-(4-chloro-2-{6-[(3,3-difluoroazetidin-1-yl)methyl]pyridin-2-yl}phenoxy)-3-cyano-N-1,2,4-thiadiazol-5-ylbenzenesulfonamide | 575 [MH]+ |
| 875 | 4-[4-chloro-2-(6-piperazin-1-ylpyrimidin-4-yl)phenoxy]-3-cyano-N-1,2,4-thiadiazol-5-ylbenzenesulfonamide | 555 [M$^{35}$ClH]+ |
| 876 | 4-[4-chloro-2-(6-morpholin-4-ylpyrimidin-4-yl)phenoxy]-3-cyano-N-1,3,4-thiadiazol-2-ylbenzenesulfonamide | 556 [M$^{35}$ClH]+ |
| 877 | 4-[2-(6-azetidin-1-ylpyrimidin-4-yl)-4-chlorophenoxy]-3-cyano-N-1,2,4-thiadiazol-5-ylbenzenesulfonamide | 526 [M$^{35}$ClH]+ |
| 878 | 3-cyano-4-[2-pyridazin-4-yl-4-(trifluoromethoxy)phenoxy]-N-1,2,4-thiadiazol-5-ylbenzenesulfonamide | 521 [MH]+ |
| 879 | 4-(4-chloro-2-pyridazin-4-ylphenoxy)-2,5-difluoro-N-1,2,4-thiadiazol-5-ylbenzenesulfonamide | 482 [M$^{35}$ClH]+ |
| 880 | 4-(4-chloro-2-isoxazol-3-ylphenoxy)-3-cyano-N-1,2,4-thiadiazol-5-ylbenzenesulfonamide | 460 [M$^{35}$ClH]+ |
| 881 | 4-[4-chloro-2-(1-methyl-1H-pyrazol-5-yl)phenoxy]-3-cyano-N-pyrimidin-2-ylbenzenesulfonamide | 467 [M$^{35}$ClH]+ |
| 882 | 4-{4-chloro-2-[1-(tetrahydrofuran-3-yl)-1H-pyrazol-5-yl]phenoxy}-3-cyano-N-1,2,4-thiadiazol-5-ylbenzenesulfonamide | 529 [M$^{35}$ClH]+ |
| 883 | 4-[4-chloro-2-(1-methyl-1H-pyrazol-5-yl)phenoxy]-3-cyano-N-(5-methylisoxazol-3-yl)benzenesulfonamide | 470 [M$^{35}$ClH]+ |

-continued

| Eg No | Name | MS m/z Unless otherwise stated |
|---|---|---|
| 884 | 5-chloro-4-{4-chloro-2-[1-(1-methylazetidin-3-yl)-1H-pyrazol-5-yl]phenoxy}-2-fluoro-N-1,3,4-thiadiazol-2-ylbenzenesulfonamide | 555 [M$^{35}$ClH]+ |
| 885 | 4-[4-chloro-2-(1-methyl-1H-pyrazol-5-yl)phenoxy]-3-cyano-N-pyrazin-2-ylbenzenesulfonamide | 467 [M$^{35}$ClH]+ |
| 886 | 4-[4-chloro-2-(1-methyl-1H-pyrazol-5-yl)phenoxy]-3-cyano-N-(5-ethoxy-1,3,4-thiadiazol-2-yl)benzenesulfonamide | 517 [M$^{35}$ClH]+ |
| 887 | 4-[4-chloro-2-(1-methyl-1H-pyrazol-5-yl)phenoxy]-3-cyano-N-(1-methyl-1H-pyrazol-3-yl)benzenesulfonamide | 469 [M$^{35}$ClH]+ |
| 888 | 4-[4-chloro-2-(1-methyl-1H-pyrazol-5-yl)phenoxy]-3-cyano-N-(5-methyl-1,3,4-thiadiazol-2-yl)benzenesulfonamide | 487 [M$^{35}$ClH]+ |
| 889 | 3-cyano-4-[4-fluoro-2-(1,3-oxazol-4-yl)phenoxy]-N-1,2,4-thiadiazol-5-ylbenzenesulfonamide | 444 [MH]+ |
| 890 | 5-chloro-4-[4-cyano-2-(1H-pyrazol-5-yl)phenoxy]-2-fluoro-N-1,2,4-thiadiazol-5-ylbenzenesulfonamide | 475 [M$^{35}$ClH]− |
| 891 | 4-[4-chloro-2-(1-methyl-1H-pyrazol-5-yl)phenoxy]-3-cyano-N-[5-(methylthio)-1,3,4-thiadiazol-2-yl]benzenesulfonamide | 519 [M$^{35}$ClH]+ |
| 892 | 4-[4-chloro-2-(1-methyl-1H-pyrazol-5-yl)phenoxy]-3-cyano-N-(5-methylpyrazin-2-yl)benzenesulfonamide | 481 [M$^{35}$ClH]+ |
| 893 | 4-[4-chloro-2-(1-methyl-1H-pyrazol-5-yl)phenoxy]-3-cyano-N-[5-(methylthio)-1,2,4-thiadiazol-3-yl]benzenesulfonamide | 519 [M$^{35}$ClH]+ |
| 894 | 4-[4-chloro-2-(1-methyl-1H-pyrazol-5-yl)phenoxy]-3-cyano-N-(1-methyl-1H-pyrazol-5-yl)benzenesulfonamide | 469 [M$^{35}$ClH]+ |
| 895 | 4-[4-chloro-2-(1-methyl-1H-pyrazol-5-yl)phenoxy]-3-cyano-N-pyrimidin-5-ylbenzenesulfonamide | 467 [M$^{35}$ClH]+ |
| 896 | 4-[4-chloro-2-(6-morpholin-4-ylpyrimidin-4-yl)phenoxy]-3-cyano-N-1,2,4-thiadiazol-5-ylbenzenesulfonamide | 556 [M$^{35}$ClH]+ |
| 897 | 2,5-difluoro-4-[2-pyridazin-4-yl-4-(trifluoromethoxy)phenoxy]-N-1,2,4-thiadiazol-5-ylbenzenesulfonamide | 532 [MH]+ |
| 898 | 3-chloro-4-(4-chloro-2-pyridazin-4-ylphenoxy)-N-1,2,4-thiadiazol-5-ylbenzenesulfonamide | 480 [M$^{35}$ClH]+ |
| 899 | 4-[4-chloro-2-(2-morpholin-4-ylpyridin-4-yl)phenoxy]-3-cyano-N-1,3,4-thiadiazol-2-ylbenzenesulfonamide | 555 [M$^{35}$ClH]+ |
| 900 | 3-chloro-4-[2-pyridazin-4-yl-4-(trifluoromethoxy)phenoxy]-N-1,2,4-thiadiazol-5-ylbenzenesulfonamide | 530 [M$^{35}$ClH]+ |
| 901 | 3-cyano-4-[2-pyridazin-3-yl-4-(trifluoromethyl)phenoxy]-N-1,2,4-thiadiazol-5-ylbenzenesulfonamide | 505 [MH]+ |
| 902 | 4-{4-chloro-2-[2-(cyclobutylamino)pyridin-4-yl]phenoxy}-3-cyano-N-1,2,4-thiadiazol-5-ylbenzenesulfonamide | 539, 541 [MH]+ |
| 903 | 3-cyano-4-[2-pyrimidin-4-yl-4-(trifluoromethyl)phenoxy]-N-1,2,4-thiadiazol-5-ylbenzenesulfonamide | 505 [MH]+ |
| 904 | 4-[2-(6-chloropyridazin-3-yl)-4-(trifluoromethyl)phenoxy]-2,5-difluoro-N-1,2,4-thiadiazol-5-ylbenzenesulfonamide | 550 [M$^{35}$ClH]+ |
| 905 | 4-(4-chloro-2-isothiazol-3-ylphenoxy)-3-cyano-N-1,2,4-thiadiazol-5-ylbenzenesulfonamide | 476 [M$^{35}$ClH]+ |
| 906 | 4-(2-azetidin-3-yl-4-chlorophenoxy)-3-cyano-N-1,2,4-thiadiazol-5-ylbenzenesulfonamide | 448 [M$^{35}$ClH]+ |
| 907 | 4-[4-chloro-2-(1-methyl-1H-pyrazol-5-yl)phenoxy]-3-cyano-N-(4-methyl-1,2,5-oxadiazol-3-yl)benzenesulfonamide | 471 [M$^{35}$ClH]+ |
| 908 | 4-[4-chloro-2-(1-methyl-6-oxo-1,6-dihydropyridin-3-yl)phenoxy]-3-cyano-N-1,2,4-thiadiazol-5-ylbenzenesulfonamide | 500 [MH]+ |
| 909 | 5-chloro-2-fluoro-4-[2-pyridazin-4-yl-4-(trifluoromethoxy)phenoxy]-N-1,2,4-thiadiazol-5-ylbenzenesulfonamide | 548 [M$^{35}$ClH]+ |
| 910 | 5-chloro-4-(4-chloro-2-pyridazin-4-ylphenoxy)-2-fluoro-N-1,2,4-thiadiazol-5-ylbenzenesulfonamide | 498 [M$^{35}$ClH]+ |
| 911 | 3-chloro-4-[4-chloro-2-(1H-pyrazol-5-yl)phenoxy]-N-1,3-thiazol-4-ylbenzenesulfonamide | 467 [M$^{35}$ClH]+ |
| 912 | 4-[2-(5-amino-1H-pyrazol-4-yl)-4-chlorophenoxy]-3-chloro-N-1,3-thiazol-4-ylbenzenesulfonamide | 482 [M$^{35}$ClH]+ |
| 913 | 4-[2-(5-amino-1H-pyrazol-4-yl)-4-chlorophenoxy]-3-chloro-N-1,2,4-thiadiazol-5-ylbenzenesulfonamide | 483 [M$^{35}$ClH]+ |
| 914 | 4-[4-chloro-2-(5-methylpyridazin-4-yl)phenoxy]-3-cyano-N-1,2,4-thiadiazol-5-ylbenzenesulfonamide | 485 [M$^{35}$ClH]+ |
| 915 | 4-[4-chloro-2-(1-methyl-1H-pyrazol-5-yl)phenoxy]-3-cyano-N-pyridazin-3-ylbenzenesulfonamide | 467 [M$^{35}$ClH]+ |
| 916 | 4-[4-chloro-2-(1-methyl-1H-pyrazol-5-yl)phenoxy]-3-cyano-N-(3-methoxypyrazin-2-yl)benzenesulfonamide | 497 [M$^{35}$ClH]+ |
| 917 | 2,5-difluoro-4-[2-pyridazin-4-yl-4-(trifluoromethyl)phenoxy]-N-1,3,4-thiadiazol-2-ylbenzenesulfonamide | 516 [MH]+ |
| 918 | 4-[2-(2-aminopyridin-4-yl)-4-chlorophenoxy]-5-chloro-2-fluoro-N-pyrazin-2-ylbenzenesulfonamide | 506 [M$^{35}$ClH]+ |
| 919 | 4-[2-(2-azetidin-1-ylpyridin-4-yl)-4-chlorophenoxy]-3-cyano-N-1,3,4-thiadiazol-2-ylbenzenesulfonamide | 525 [M$^{35}$ClH]+ |

| Eg No | Name | MS m/z Unless otherwise stated |
|---|---|---|
| 920 | 2,5-difluoro-4-[2-pyridazin-3-yl-4-(trifluoromethyl)phenoxy]-N-1,2,4-thiadiazol-5-ylbenzenesulfonamide | 516 [MH]+ |
| 921 | 4-[4-chloro-2-(1-methyl-1H-pyrazol-5-yl)phenoxy]-3-cyano-N-1,2,5-thiadiazol-3-ylbenzenesulfonamide | 473 [M$^{35}$ClH]+ |
| 922 | 4-[4-chloro-2-(1-methyl-1H-pyrazol-5-yl)phenoxy]-3-cyano-N-1H-pyrazol-3-ylbenzenesulfonamide | 455 [M$^{35}$ClH]+ |
| 923 | 4-[4-chloro-2-(1-methyl-1H-pyrazol-5-yl)phenoxy]-3-cyano-N-pyridin-3-ylbenzenesulfonamide | 466 [M$^{35}$ClH]+ |
| 924 | 4-(4-chloro-5-fluoro-2-pyridazin-4-ylphenoxy)-3-cyano-N-1,2,4-thiadiazol-5-ylbenzenesulfonamide | 489 [M$^{35}$ClH]+ |
| 925 | 5-chloro-4-(4-cyano-2-pyridazin-4-ylphenoxy)-2-fluoro-N-1,3,4-thiadiazol-2-ylbenzenesulfonamide | 489 [M$^{35}$ClH]+ |
| 926 | 4-[2-(2-aminopyridin-4-yl)-4-chlorophenoxy]-5-chloro-2-fluoro-N-pyrimidin-2-ylbenzenesulfonamide | 506 [M$^{35}$ClH]+ |
| 927 | 5-chloro-6-[4-chloro-2-(1-methyl-1H-pyrazol-5-yl)phenoxy]-N-1,2,4-thiadiazol-5-ylpyridine-3-sulfonamide | 483 [M$^{35}$ClH]+ |
| 928 | 3-chloro-4-[2-pyridazin-4-yl-4-(trifluoromethyl)phenoxy]-N-1,2,4-thiadiazol-5-ylbenzenesulfonamide | 514 [MH]+ |
| 929 | 3-fluoro-4-[2-pyridazin-4-yl-4-(trifluoromethyl)phenoxy]-N-1,2,4-thiadiazol-5-ylbenzenesulfonamide | 498 [MH]+ |
| 930 | 4-(4-chloro-5-fluoro-2-pyridazin-4-ylphenoxy)-3-fluoro-N-1,2,4-thiadiazol-5-ylbenzenesulfonamide | NMR data was: 1H NMR (CD$_3$OD): δ 6.95 (1H, m), 7.25 (1H, m), 7.73 (2H, m), 7.85 (1H, m), 7.96 (2H, m), 9.20 (1H, m), 9.42 (1H, m). |
| 931 | 2,5-difluoro-4-(4-fluoro-2-pyridazin-4-ylphenoxy)-N-1,2,4-thiadiazol-5-ylbenzenesulfonamide | 466 [MH]+ |
| 932 | 5-chloro-2-fluoro-4-[2-pyridazin-4-yl-4-(trifluoromethoxy)phenoxy]-N-1,3,4-thiadiazol-2-ylbenzenesulfonamide | 548 [M$^{35}$ClH]+ |
| 933 | 3-cyano-4-[2-pyridazin-4-yl-4-(trifluoromethoxy)phenoxy]-N-1,3,4-thiadiazol-2-ylbenzenesulfonamide | 521 [MH]+ |
| 934 | 4-(5-chloro-4-fluoro-2-pyridazin-4-ylphenoxy)-3-fluoro-N-1,2,4-thiadiazol-5-ylbenzenesulfonamide | 482 [M$^{35}$ClH]+ |
| 935 | 4-[2-(1-azetidin-3-yl-1H-pyrazol-5-yl)-4-(trifluoromethyl)phenoxy]-3-cyano-N-1,2,4-thiadiazol-5-ylbenzenesulfonamide | 548 [MH]+ |
| 936 | 4-(4-chloro-5-fluoro-2-pyridazin-4-ylphenoxy)-2,5-difluoro-N-1,2,4-thiadiazol-5-ylbenzenesulfonamide | 500 [M$^{35}$ClH]+ |
| 937 | 4-(5-chloro-4-fluoro-2-pyridazin-4-ylphenoxy)-2,5-difluoro-N-1,2,4-thiadiazol-5-ylbenzenesulfonamide | 500 [M$^{35}$ClH]+ |
| 938 | 4-(5-chloro-4-fluoro-2-pyridazin-4-ylphenoxy)-3-cyano-N-1,2,4-thiadiazol-5-ylbenzenesulfonamide | 489 [M$^{35}$ClH]+ |
| 939 | 5-chloro-2-fluoro-4-[2-pyridazin-4-yl-5-(trifluoromethyl)phenoxy]-N-1,3,4-thiadiazol-2-ylbenzenesulfonamide | 532 [M$^{35}$ClH]+ |
| 940 | 3-cyano-4-[2-pyridazin-4-yl-5-(trifluoromethyl)phenoxy]-N-1,2,4-thiadiazol-5-ylbenzenesulfonamide | 505 [MH]+ |
| 941 | 5-chloro-4-(4-chloro-2-pyridazin-4-ylphenoxy)-2-fluoro-N-pyrimidin-2-ylbenzenesulfonamide | 492 [M$^{35}$ClH]+ |
| 942 | 3-chloro-4-[2-pyridazin-4-yl-4-(trifluoromethoxy)phenoxy]-N-1,3,4-thiadiazol-2-ylbenzenesulfonamide | 530 [M$^{35}$ClH]+ |
| 943 | 4-(4-chloro-2-pyridazin-4-ylphenoxy)-2-fluoro-5-methyl-N-1,3,4-thiadiazol-2-ylbenzenesulfonamide | 478 [M$^{35}$ClH]+ |
| 944 | 4-[2-(2-aminopyridin-4-yl)-4-chlorophenoxy]-3-chloro-N-pyrimidin-4-ylbenzenesulfonamide | 488 [M$^{35}$ClH]+ |
| 945 | 5-chloro-2-fluoro-4-[2-pyridazin-4-yl-4-(trifluoromethoxy)phenoxy]-N-pyrimidin-2-ylbenzenesulfonamide | 542 [M$^{35}$ClH]+ |
| 946 | 3-cyano-4-[2-pyridazin-4-yl-4-(trifluoromethyl)phenoxy]-N-1,3,4-thiadiazol-2-ylbenzenesulfonamide | 505 [MH]+ |
| 947 | 5-chloro-2-fluoro-4-[4-fluoro-2-pyridazin-4-yl-5-(trifluoromethyl)phenoxy]-N-1,3,4-thiadiazol-2-ylbenzenesulfonamide | 550 [M$^{35}$ClH]+ |
| 948 | 3-cyano-4-[4-fluoro-2-pyridazin-4-yl-5-(trifluoromethyl)phenoxy]-N-1,2,4-thiadiazol-5-ylbenzenesulfonamide | 523 [MH]+ |
| 949 | 4-[2-(2-aminopyridin-4-yl)-4-fluorophenoxy]-5-chloro-2-fluoro-N-pyrimidin-2-ylbenzenesulfonamide | 490 [M$^{35}$ClH]+ |
| 950 | 6-[4-chloro-2-(1-methyl-1H-pyrazol-5-yl)phenoxy]-N-1,2,4-thiadiazol-5-ylpyridine-3-sulfonamide | 449 [M$^{35}$ClH]+ |

| Eg No | Name | MS m/z Unless otherwise stated |
|---|---|---|
| 951 | 5-chloro-4-(5-cyano-2-pyridazin-4-ylphenoxy)-2-fluoro-N-1,2,4-thiadiazol-5-ylbenzenesulfonamide | 489 [M$^{35}$ClH]+ |
| 952 | 5-chloro-2-fluoro-4-[2-pyridazin-4-yl-4-(trifluoromethyl)phenoxy]-N-1,3-thiazol-4-ylbenzenesulfonamide | 531 [MH]+ |
| 953 | 3-cyano-4-[2-pyridazin-4-yl-4-(trifluoromethyl)phenoxy]-N-1,3-thiazol-4-ylbenzenesulfonamide | 504 [MH]+ |
| 954 | 2,5-difluoro-4-[2-pyridazin-4-yl-4-(trifluoromethyl)phenoxy]-N-1,3-thiazol-4-ylbenzenesulfonamide | 515 [MH]+ |
| 955 | 3-chloro-4-[4-chloro-2-(1-methyl-1H-pyrazol-5-yl)phenoxy]-N-pyrimidin-2-ylbenzenesulfonamide | 476 [M$^{35}$ClH]+ |
| 956 | 5-chloro-4-(4-chloro-3-fluoro-2-pyridazin-4-ylphenoxy)-2-fluoro-N-1,3,4-thiadiazol-2-ylbenzenesulfonamide | 516 [MH]+ |
| 957 | 3-cyano-4-[2-pyridazin-4-yl-5-(trifluoromethoxy)phenoxy]-N-1,2,4-thiadiazol-5-ylbenzenesulfonamide | 521 [MH]+ |
| 958 | 3-cyano-4-[5-fluoro-2-pyridazin-4-yl-4-(trifluoromethoxy)phenoxy]-N-1,2,4-thiadiazol-5-ylbenzenesulfonamide | 539 [MH]+ |
| 959 | 3-cyano-4-{2-[1-(1-ethylazetidin-3-yl)-1H-pyrazol-5-yl]-4-(trifluoromethyl)phenoxy}-N-1,3-thiazol-4-ylbenzenesulfonamide | 573 [MH]− |
| 960 | 3-cyano-4-[2-pyridin-4-yl-4-(trifluoromethyl)phenoxy]-N-1,2,4-thiadiazol-5-ylbenzenesulfonamide | 504 [MH]+ |
| 961 | 4-[4-chloro-2-(3-methylisoxazol-4-yl)phenoxy]-3-cyano-N-1,2,4-thiadiazol-5-ylbenzenesulfonamide | 474 [M$^{35}$ClH]+ |
| 962 | 4-[2-(1-azetidin-3-yl-1H-pyrazol-5-yl)-4-(trifluoromethoxy)phenoxy]-3-cyano-N-1,3-thiazol-4-ylbenzenesulfonamide | 563 [MH]+ |
| 963 | 5-chloro-2-fluoro-4-[5-fluoro-2-pyridazin-4-yl-4-(trifluoromethoxy)phenoxy]-N-1,3,4-thiadiazol-2-ylbenzenesulfonamide | 566 [M$^{35}$ClH]+ |
| 964 | 3-cyano-4-[4-fluoro-2-pyridazin-4-yl-5-(trifluoromethoxy)phenoxy]-N-1,2,4-thiadiazol-5-ylbenzenesulfonamide | 539 [MH]+ |
| 965 | 5-chloro-2-fluoro-4-[4-fluoro-2-pyridazin-4-yl-5-(trifluoromethoxy)phenoxy]-N-1,3,4-thiadiazol-2-ylbenzenesulfonamide | 566 [M$^{35}$ClH]+ |
| 966 | 5-chloro-2-fluoro-4-[2-pyridazin-4-yl-5-(trifluoromethoxy)phenoxy]-N-1,3,4-thiadiazol-2-ylbenzenesulfonamide | 548 [M$^{35}$ClH]+ |
| 967 | 4-[4-chloro-2-(1,3-oxazol-5-yl)phenoxy]-3-cyano-N-1,2,4-thiadiazol-5-ylbenzenesulfonamide | 460 [M$^{35}$ClH]+ |
| 968 | 5-chloro-6-{4-chloro-2-[1-(1-methylazetidin-3-yl)-1H-pyrazol-5-yl]phenoxy}-N-1,2,4-thiadiazol-5-ylpyridine-3-sulfonamide | 538 [M$^{35}$ClH]+ |
| 969 | 4-[2-(1-azetidin-3-yl-1H-pyrazol-5-yl)-4-(trifluoromethyl)phenoxy]-3-cyano-N-1,3-thiazol-4-ylbenzenesulfonamide | 547 [MH]+ |
| 970 | 4-[4-chloro-2-(1,3-oxazol-5-yl)phenoxy]-2,5-difluoro-N-1,2,4-thiadiazol-5-ylbenzenesulfonamide | 471 [M$^{35}$ClH]+ |
| 971 | 3-cyano-4-(4,5-dichloro-2-pyridazin-4-ylphenoxy)-N-1,2,4-thiadiazol-5-ylbenzenesulfonamide | 505 [M$^{35}$ClH]+ |
| 972 | 4-[2-(2-aminopyridin-4-yl)-4-fluorophenoxy]-5-chloro-2-fluoro-N-pyrimidin-4-ylbenzenesulfonamide | 490 [M$^{35}$ClH]+ |
| 973 | 4-[2-(3-amino-1H-pyrazol-4-yl)-4-chlorophenoxy]-3-chloro-N-pyrimidin-4-ylbenzenesulfonamide | 477 [M$^{35}$ClH]+ |
| 974 | 5-chloro-6-[2-pyridazin-4-yl-4-(trifluoromethyl)phenoxy]-N-1,2,4-thiadiazol-5-ylpyridine-3-sulfonamide | 515 [M$^{35}$ClH]+ |
| 975 | 4-{4-chloro-2-[1-(1-ethylazetidin-3-yl)-1H-pyrazol-5-yl]phenoxy}-2,5-difluoro-N-1,2,4-thiadiazol-5-ylbenzenesulfonamide | 553 [MH]+ |
| 976 | 4-[2-pyridazin-4-yl-4-(trifluoromethyl)phenoxy]-N-1,2,4-thiadiazol-5-yl-3-(trifluoromethyl)benzenesulfonamide | 548 [MH]+ |
| 977 | 3-cyano-4-[2-pyridin-3-yl-4-(trifluoromethyl)phenoxy]-N-1,2,4-thiadiazol-5-ylbenzenesulfonamide | 502 [MH]− |
| 978 | 2-fluoro-5-methyl-4-[2-pyridazin-4-yl-4-(trifluoromethyl)phenoxy]-N-1,2,4-thiadiazol-5-ylbenzenesulfonamide | 512 [MH]+ |
| 979 | 3-cyano-4-[2-(1-oxidopyridin-3-yl)-4-(trifluoromethyl)phenoxy]-N-1,2,4-thiadiazol-5-ylbenzenesulfonamide | 520 [MH]+ |
| 980 | 4-[2-(1-azetidin-3-yl-1H-pyrazol-5-yl)-4-chlorophenoxy]-2,5-difluoro-N-1,3-thiazol-4-ylbenzenesulfonamide | 524, 526 [MH]+ |
| 981 | 3-cyano-4-[2-(3-furyl)-4-(trifluoromethyl)phenoxy]-N-1,2,4-thiadiazol-5-ylbenzenesulfonamide | 493 [MH]+ |

| Eg No | Name | MS m/z Unless otherwise stated |
|---|---|---|
| 982 | 4-[2-(1-tert-butyl-3-methyl-1H-pyrazol-4-yl)-4-chlorophenoxy]-5-chloro-2-fluoro-N-1,3,4-thiadiazol-2-ylbenzenesulfonamide | 556 [MCl35H]+ |
| 983 | 2-[2-(3-methyl-1H-pyrazol-4-yl)phenoxy]-5-[(1,3-thiazol-2-ylamino)sulfonyl]benzamide | 456 [MH]+ |
| 984 | 4-[4-chloro-2-(3-ethoxy-1H-pyrazol-4-yl)phenoxy]-2,5-difluoro-N-1,3-thiazol-4-ylbenzenesulfonamide | 513 [M$^{35}$ClH]+ |
| 985 | 3-cyano-4-(2-pyrimidin-5-ylphenoxy)-N-1,3-thiazol-2-ylbenzenesulfonamide | 436 [MH]+ |
| 986 | 4-{4-[5-amino-1-(2,2,2-trifluoroethyl)-1H-pyrazol-4-yl]phenoxy}-3-cyano-N-1,3-thiazol-2-ylbenzenesulfonamide | 521 [MH]+ |
| 987 | 3-cyano-4-{3'-{[(3R)-3-hydroxypyrrolidin-1-yl]methyl}-5-(trifluoromethyl)biphenyl-2-yl]oxy}-N-1,2,4-thiadiazol-5-ylbenzenesulfonamide | 602 [MH]+ |
| 988 | 4-{[3'-(azetidin-1-ylmethyl)-5-(trifluoromethyl)biphenyl-2-yl]oxy}-3-cyano-N-1,2,4-thiadiazol-5-ylbenzenesulfonamide | 572 [MH]+ |
| 989 | 4-{2-[1-(1-acetylazetidin-3-yl)-1H-pyrazol-5-yl]-4-fluorophenoxy}-5-chloro-2-fluoro-N-1,3-thiazol-4-ylbenzenesulfonamide | 566 [M$^{35}$ClH]+ |
| 990 | 4-(4-chloro-2-isoxazol-3-ylphenoxy)-N-(5-chloro-1,3-thiazol-2-yl)-3-cyanobenzenesulfonamide | 493 [M$^{35}$ClH]+ |
| 991 | 4-[2-(6-aminopyridin-2-yl)-4-fluorophenoxy]-N-(5-chloro-1,3-thiazol-2-yl)-3-cyanobenzenesulfonamide | 502 [M$^{35}$ClH]+ |
| 992 | N-(5-chloro-1,3-thiazol-2-yl)-3-cyano-4-[5-fluoro-2-(1H-pyrazol-5-yl)phenoxy]benzenesulfonamide | 476 [M$^{35}$ClH]+ |
| 993 | tert-butyl 4-(5-chloro-2-{2-cyano-4-[(1,2,4-thiadiazol-5-ylamino)sulfonyl]phenoxy}phenyl)piperidine-1-carboxylate | 476 [M − Boc + H]+, 574 [MH]− |
| 994 | 3-cyano-4-[4-(4-cyano-1H-pyrazol-1-yl)phenoxy]-N-1,3-thiazol-2-ylbenzenesulfonamide | 449 [MH]+ |
| 995 | methyl 3-(5-chloro-2-{2-cyano-4-[(1,3-thiazol-2-ylamino)sulfonyl]phenoxy}phenyl)azetidine-1-carboxylate | 505 [M$^{35}$ClH]+ |
| 996 | ethyl 1-(4-{2-cyano-4-[(1,3-thiazol-2-ylamino)sulfonyl]phenoxy}phenyl)-1H-pyrazole-4-carboxylate | 496 [MH]+ |
| 997 | tert-butyl 4-[5-chloro-2-(2,5-difluoro-4-{[(5-fluoro-1,3-thiazol-2-yl)amino]sulfonyl}phenoxy)phenyl]-1H-pyrazole-1-carboxylate | 487 [M − Boc$^{35}$ClH]+ |
| 998 | tert-butyl 4-(5-chloro-2-{2,5-difluoro-4-[(1,3-thiazol-2-ylamino)sulfonyl]phenoxy}phenyl)-1H-pyrazole-1-carboxylate | 469 [M − Boc$^{35}$ClH]+ |
| 999 | 5'-chloro-2'-{2-cyano-4-[(1,2,4-thiadiazol-5-ylamino)sulfonyl]phenoxy}biphenyl-4-carboxylic acid | 513 [M$^{35}$ClH]+ |
| 1000 | (5'-chloro-2'-{2-cyano-4-[(1,2,4-thiadiazol-5-ylamino)sulfonyl]phenoxy}biphenyl-3-yl)acetic acid | 527 [M$^{35}$ClH]+ |
| 1001 | (5'-chloro-2'-{2-cyano-4-[(1,2,4-thiadiazol-5-ylamino)sulfonyl]phenoxy}biphenyl-4-yl)acetic acid | 527 [M$^{35}$ClH]+ |
| 1002 | 5'-chloro-2'-{2-cyano-4-[(1,2,4-thiadiazol-5-ylamino)sulfonyl]phenoxy}biphenyl-3-carboxylic acid | 513 [M$^{35}$ClH]+ |
| 1003 | methyl 5'-chloro-2'-{2-cyano-4-[(1,2,4-thiadiazol-5-ylamino)sulfonyl]phenoxy}biphenyl-3-carboxylate | 527 [M$^{35}$ClH]+ |
| 1004 | 3-cyano-4-(2-cyclopropyl-4-fluorophenoxy)-N-(5-fluoropyridin-2-yl)benzenesulfonamide | 428 [MH]+ |
| 1005 | 3-cyano-N-(5-fluoropyridin-2-yl)-4-[2-(tetrahydro-2H-pyran-2-yl)phenoxy]benzenesulfonamide | 454 [MH]+ |
| 1006 | 3-cyano-4-{[6-(3-methoxyphenyl)pyridin-3-yl]oxy}-N-1,3-thiazol-2-ylbenzenesulfonamide | 465 [MH]+ |
| 1007 | 4-(biphenyl-2-yloxy)-3-cyano-N-2-thienylbenzenesulfonamide | 433 [MH]+ |
| 1008 | 2-{2-cyano-4-[(1,2,4-thiadiazol-5-ylamino)sulfonyl]phenoxy}-N,N-dimethylbiphenyl-3-carboxamide | 506 [MH]+ |
| 1009 | 4-[4-chloro-2-(2-methylpyridin-3-yl)phenoxy]-3-cyano-N-1,2,4-thiadiazol-5-ylbenzenesulfonamide | 484 [M$^{35}$ClH]+ |
| 1010 | 4-[4-chloro-2-(3-methylpyrazin-2-yl)phenoxy]-3-cyano-N-1,2,4-thiadiazol-5-ylbenzenesulfonamide | 485 [M$^{35}$ClH]+ |
| 1011 | 4-[4-chloro-2-(3-methylpyridin-4-yl)phenoxy]-3-cyano-N-1,2,4-thiadiazol-5-ylbenzenesulfonamide | 484 [M$^{35}$ClH]+ |
| 1012 | 5-chloro-4-{4-chloro-2-[1-(1-methylazetidin-3-yl)-1H-pyrazol-5-yl]phenoxy}-2-fluoro-N-pyrimidin-2-ylbenzenesulfonamide | 549 [M$^{35}$ClH]+ |
| 1013 | 4-[2-(2-aminopyridin-4-yl)-4-(trifluoromethyl)phenoxy]-3-chloro-N-pyrimidin-4-ylbenzenesulfonamide | 522 [M$^{35}$ClH]+ |
| 1014 | 4-[2-(2-aminopyridin-4-yl)-4-chlorophenoxy]-3-chloro-N-pyridazin-3-ylbenzenesulfonamide | 488 [M$^{35}$ClH]+ |
| 1015 | ethyl {5-[2-{2-cyano-4-[(1,2,4-thiadiazol-5-ylamino)sulfonyl]phenoxy}-5-(trifluoromethyl)phenyl]-1H-pyrazol-1-yl}acetate | 579 [MH]+ |

-continued

| Eg No | Name | MS m/z Unless otherwise stated |
|---|---|---|
| 1016 | {5-[2-{2-cyano-4-[(1,2,4-thiadiazol-5-ylamino)sulfonyl]phenoxy}-5-(trifluoromethyl)phenyl]-1H-pyrazol-1-yl}acetic acid | 551 [MH]+ |
| 1017 | 5-chloro-2-fluoro-4-{2-[1-(1-methylazetidin-3-yl)-1H-pyrazol-5-yl]-4-(trifluoromethoxy)phenoxy}-N-1,3,4-thiadiazol-2-ylbenzenesulfonamide | 605 [M$^{35}$ClH]+ |
| 1018 | 4-(4-chloro-2-pyridazin-4-ylphenoxy)-N-1,3,4-thiadiazol-2-yl-3-(trifluoromethyl)benzenesulfonamide | 514 [M$^{35}$ClH]+ |
| 1019 | 4-[2-(3-amino-1H-pyrazol-4-yl)-4-chlorophenoxy]-5-chloro-2-fluoro-N-pyrimidin-2-ylbenzenesulfonamide | 495 [MH]+ |
| 1020 | 4-[2-(2-aminopyridin-4-yl)-4-chlorophenoxy]-2,5-difluoro-N-1,3-thiazol-4-ylbenzenesulfonamide | 495 [M$^{35}$ClH]+ |
| 1021 | 5-chloro-4-[4-(1-cyano-1-methylethyl)-2-pyridazin-4-ylphenoxy]-2-fluoro-N-1,3,4-thiadiazol-2-ylbenzenesulfonamide | 531 [M$^{35}$ClH]+ |

Example 878

3-cyano-4-[2-pyridazin-4-yl-4-(trifluoromethoxy)phenoxy]-N-1,2,4-thiadiazol-5-ylbenzenesulfonamide

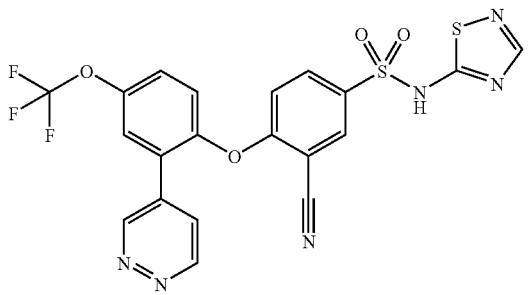

Example 878 from above can be prepared as follows.

2-pyridazin-4-yl-4-(trifluoromethoxy)phenol (Preparation 888, 1.03 g, 4.02 mmol) was taken up in dimethyl sulfoxide (50 mL, 600 mmol) and potassium carbonate (1.03 g, 7.45 mmol) added, followed by 3-cyano-N-(2,4-dimethoxybenzyl)-4-fluoro-N-(1,2,4-thiadiazol-5-yl)benzenesulfonamide (Preparation 68, 1.74 g, 4.00 mmol). The reaction mixture was stirred at 23° C. for 18 hours. The reaction mixture was diluted with water and extracted two times with ethyl ether. The combined organic phase was washed successively with water and brine. The organic phase was dried over magnesium sulfate, then treated with activated carbon and filtered through a pad of diatomaceous earth. The solvent was removed in vacuo. The residue was dissolved in methylene chloride (100 mL, 2000 mmol) and trifluoroacetic acid (2.0 mL, 26 mmol) was added. The solution was stirred for 2 hours then concentrated in vacuo. The residue was purified by column chromatography (40 g silica gel column, 0 to 10% methanol in dichloromethane gradient elution). The product fractions were combined and concentrated in vacuo to a residue. The residue was triturated with ethyl ether and the solid collected by filtration. Vacuum drying gave 1.35 g of product as a white solid.

LCMS Rt=1.67 min, MS m/z 521 [MH]+
$^1$HNMR (300 MHz, d$_6$-DMSO): δ 7.14 (d, 1H), 7.57 (d, 1H), 7.68 (m, 1H), 7.85 (dd, 1H), 7.89 (d, 1H), 7.98 (dd, 1H), 8.25 (d, 1H), 8.49 (s, 1H), 9.29 (dd, 1H), 9.40 (dd, 1H).

Example 1022

4-{4-Chloro-2-[2-(dimethylamino)pyridin-4-yl]phenoxy}-3-cyano-N-1,2,4-thiadiazol-5-ylbenzenesulfonamide

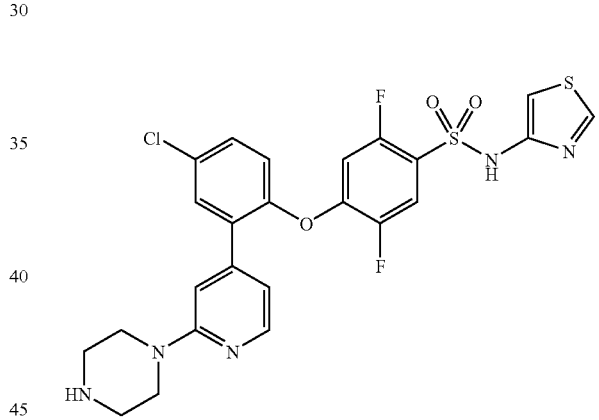

A solution of lithium hexamethyldisilazide (1.0 M in tetrahydrofuran, 272 uL, 0.272 mmol) was added to a solution of tert-butyl 4-(4-(5-chloro-2-hydroxyphenyl)pyridin-2-yl)piperazine-1-carboxylate (Preparation 853, 100.0 mg, 0.2180 mmol) in N,N-dimethylformamide (3 mL, 40 mmol). After stirring 5 minutes, tert-butyl [(2,4,5-trifluorophenyl)sulfonyl]1,3-thiazol-4-ylcarbamate (Preparation 854, 72 mg, 0.18 mmol) was added as a solid. The reaction mixture was stirred at ambient temperature. After 2 hours, the reaction mixture was diluted with water, neutralized with saturated aqueous ammonium chloride, and extracted with ethyl acetate (3×). The combined organic layers were washed with brine, dried over sodium sulfate, filtered, and concentrated onto diatomaceous earth. The residue was purified by automated flash chromatography (24 g SiO2, hexanes to ethyl acetate) to afford the intermediate.

LC/MS Rt=1.96 minutes, MS m/z 764 [M$^{35}$ClH]+
$^1$H NMR (d$_6$-DMSO): δ 9.11 (d, 1H), 8.10 (d, 1H), 7.98 (m, 1H), 7.91 (d, 1H), 7.72 (d, 1H), 7.62 (m, 1H), 7.40 (d, 1H), 7.12 (m, 1H), 6.93 (br s, 1H), 6.76 (m, 1H), 3.48 (m, 4H), 3.40 (m, 4H), 1.41 (s, 9H), 1.22 (s, 9H).

Trifluoroacetic acid (500 μL, 7 mmol) was added to a solution of tert-butyl 4-{4-[2-(4-{[tert-butoxycarbonyl)(1,3-thiazol-4-yl)amino]sulfonyl}-2,5-difluorophenoxy)-5-chlorophenyl]pyridin-2-yl}piperazine-1-carboxylate in 5 mL of methylene chloride. After stirring 3 hours at ambient temperature, the reaction mixture was concentrated in vacuo. The residue was taken up in 2 mL of dimethyl sulfoxide, filtered through a plug of cotton, and purified by reverse-phase HPLC. The product-containing fractions were concentrated in vacuo, and the residual solution was diluted with water and lyophilized to afford an off white powder (85.0 mg, 83%).

LC/MS Rt=1.43 minutes, MS m/z 564 [M$^{35}$ClH]+

$^1$H NMR (d$_6$-DMSO): δ 11.42 (s, 1H), 8.91 (d, 1H), 8.13 (d, 1H), 7.75 (m, 1H), 7.68 (d, 1H), 7.57 (m, 1H), 7.31 (d, 1H), 7.13 (m, 1H), 7.06 (d, 1H), 7.01 (br s, 1H), 6.82 (m, 1H), 3.72 (m, 4H), 3.18 (m, 4H).

Example 1023

2,5-Difluoro-4-{2-[1-(1-methylazetidin-3-yl)-1H-pyrazol-5-yl]-4-(trifluoromethyl)phenoxy}-N-1,3-thiazol-4-ylbenzenesulfonamide

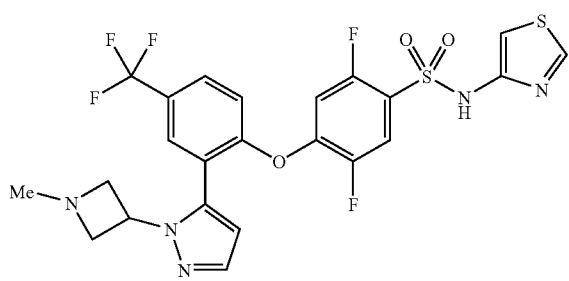

2-[1-(1-Methylazetidin-3-yl)-1H-pyrazol-5-yl]-4-(trifluoromethyl)phenol, (Preparation 855, 137 mg, 0.00046 mol) was dissolved in acetonitrile (10 mL) and treated with potassium tert-butoxide (57 mg, 0.0005 mol) and stirred under nitrogen for 30 minutes. Tert-butyl 1,3-thiazol-4-yl[(2,4,5-trifluorophenyl)sulfonyl]carbamate, (Preparation 297, 182 mg, 0.00046 mol) was added and the solution stirred for 2 hours. Water (0.2 mL) was added and the solution evaporated. The residue was suspended in water and extracted with ethyl acetate (1×20 mL). The organic layer was separated and washed with brine (2×20 mL). The organic layer was separated, dried over anhydrous sodium sulphate, filtered and evaporated to give a foam. The foam was purified using an ISCO™ Companion (4 g. silica gel, eluting with dichloromethane:acetic acid 99.5:0.5 to dichloromethane:methanol:acetic acid 95:5:0.5). The appropriate fractions were evaporated to give a film. The film was triturated with diethyl ether to give the title compound as a white solid (11 mg).

LCMS Rt=1.19 minutes, MS m/z=572 [MH]+

TLC dichloromethane:methanol:acetic acid 95:5:0.5, Rf=0.5

$^1$HNMR (CDCl$_3$) δ 3.15 (s, 3H) 4.24-4.34 (m, 2H) 4.83-4.87 (m, 2H) 5.41-5.49 (m, 1H) 6.42 (s, 1H) 6.47 (s, 1H) 6.82 (d, 1H) 7.27 (s, 1H) 7.61 (d, 1H) 7.67 (s, 1H) 7.77 (s, 1H) 7.91-7.95 (m, 1H) 8.21 (s, 1H).

Example 1024

4-{4-Chloro-2-[1-(1-ethylazetidin-3-yl)-1H-pyrazol-5-yl]phenoxy}-3-cyano-N-1,3-thiazol-4-ylbenzenesulfonamide

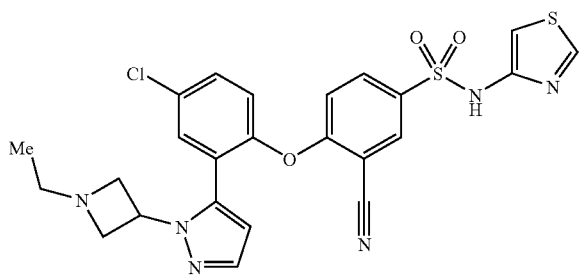

To a suspension of 4-[2-(1-azetidin-3-yl-1H-pyrazol-5-yl)-4-chlorophenoxy]-3-cyano-N-1,3-thiazol-4-ylbenzenesulfonamide, Example 809 (500 mg, 0.000797 mol) in methanol (4 mL) and dichloromethane (4 mL) was added triethylamine (161 mg, 0.00159 mol) and the reaction cooled to 0° C. in an ice/water bath. To the suspension was added sodium triacetoxyborohydride (422 mg, 0.00199 mol) and the reaction was then stirred at 0° C. for 10 minutes. Acetaldehyde (105 mg, 0.00239 mol) was added dropwise and the reaction stirred at 0° C. for 1.5 hours. The solvent was removed in vacuo to give an orange oil which was partitioned between dichloromethane (25 mL) and water (25 mL). The organic layer was separated and the aqueous layer was extracted with dichloromethane (2×20 mL). The combined organic layers were washed with saturated aqueous sodium chloride solution (20 mL) and filtered through a phase separator. The solvent was removed in vacuo to give a pink solid which was triturated in hot ethyl acetate (10.0 mL), allowed to cool to room temperature and then filtered to give the title compound as a white solid, (431 mg).

LCMS Rt=1.95 minutes, MS m/z=541 [MH]+

$^1$HNMR (d$_6$-DMSO) δ 1.11 (t, 3H), 3.26 (q, 2H), 4.16 (brs, 2H), 4.42 (brs., 2H), 5.14 (brs., 1H), 6.30 (d, 1H), 6.99 (d, 1H), 7.11 (d, 1H), 7.53 (d, 1H), 7.63 (d, 1H), 7.72-7.77 (m, 2H), 7.89 (dd, 1H), 8.14 (d, 1H), 8.92 (d, 1H).

Example 1025

4-{4-Chloro-2-[2-(cyclobutyloxy)pyridin-4-yl]phenoxy}-3-cyano-N-1,2,4-thiadiazol-5-ylbenzenesulfonamide

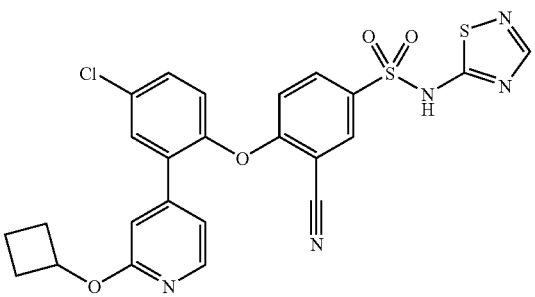

4-{4-chloro-2-[2-(cyclobutyloxy)pyridin-4-yl]phenoxy}-3-cyano-N-(2,4-dimethoxybenzyl)-N-1,2,4-thiadiazol-5-yl-benzenesulfonamide, (Preparation 861, 40 mg, 0.000058 mol) was dissolved in dichloromethane (1 mL) and cooled to 0° C. Trifluoroacetic acid (0.2 mL, 0.00261 mol) was added and the reaction stirred for 1 hour warming slowly to room temperature. The solvent was removed in vacuo and the residue redissolved in dichloromethane (1 mL). Once again the solvent was removed in vacuo to give a purple residue (154 mg). The material was suspended in methanol (3 mL) and filtered through Celite™. The solvent was removed in vacuo to obtain the title compound as an off white solid (15.5 mg).

LCMS Rt=1.83 minutes, MS m/z=540 [M$^{35}$ClH]+
$^1$HNMR (CD$_3$OD) δ 1.62-1.74 (m, 1H), 1.79-1.88 (m, 1H), 2.04-2.14 (m, 2H), 2.38-2.45 (m, 2H), 5.03-5.11 (m, 1H), 6.87-6.90 (m, 2H), 7.08-7.09 (m, 1H), 7.33 (d, 1H), 7.57-7.60 (dd, 1H), 7.63 (d, 1H), 7.93 (dd, 1H), 8.07-8.09 (m, 1H), 8.12 (d, 1H), 8.20 (s, 1H).

Example 1026

4-{4-Chloro-2-[2-(dimethylamino)pyridin-4-yl]phenoxy}-3-cyano-N-1,2,4-thiadiazol-5-ylbenzenesulfonamide

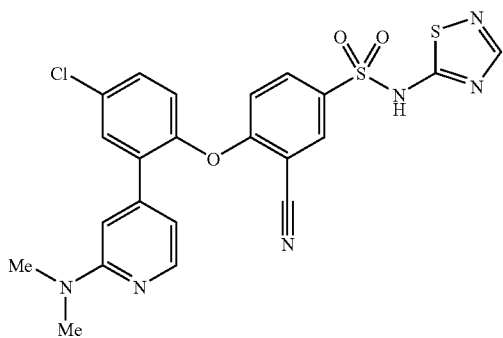

3-Cyano-4-fluoro-N-(1,2,4-thiadiazol-5-yl)benzenesulfonamide (Preparation 65, 40 mg, 0.14 mmol), 4-chloro-2-[2-(dimethylamino)pyridin-4-yl]phenol (Preparation 865, 35.0 mg, 0.141 mmol) and potassium carbonate (58 mg, 0.42 mmol) in dimethyl sulfoxide (1 mL, 20 mmol) was stirred at 150° C. for 16 hours. The reaction mixture was cooled to ambient temperature and poured into saturated aqueous ammonium chloride. The aqueous layer was extracted with ethyl acetate (3×). The combined organic layers were washed with brine, dried over sodium sulfate, filtered, and concentrated in vacuo. The residue was taken up in methylene chloride, concentrated onto diatomaceous earth, and purified by automated flash chromatography (12 g SiO2, hexanes to 20% methanol in ethyl acetate). The product-containing fractions were concentrated in vacuo then lyophilized from water and minimal acetonitrile to afford the product as a light yellow powder (40 mg, 60%).

LC/MS Rt=1.40 minutes, MS m/z 513 [M$^{35}$ClH]+
$^1$H NMR (d$_6$-DMSO): δ 8.03 (m, 2H), 7.94 (s, 1H), 7.86 (m, 1H), 7.68 (d, 1H), 7.60 (m, 1H), 7.41 (d, 1H), 6.89 (d, 1H), 6.60 (m, 2H), 2.95 (s, 6H).

Example 1027

5-Chloro-2-fluoro-4-[2-pyridazin-4-yl-4-(trifluoromethyl)phenoxy]-N-1,3,4-thiadiazol-2-ylbenzenesulfonamide

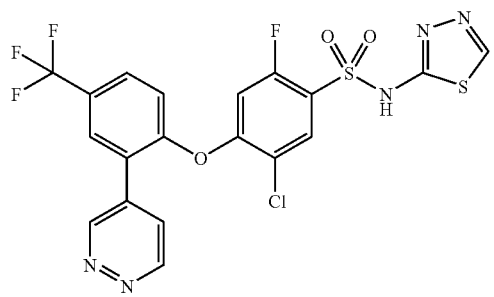

To a stirred solution of 5-Chloro-N-(2,4-dimethoxybenzyl)-2-fluoro-4-[2-pyridazin-4-yl-4-(trifluoromethyl)phenoxy]-N-1,3,4-thiadiazol-2-ylbenzenesulfonamide (Preparation 900, 30.3 g, 44.4 mmol) in 1,4-dioxane (250 mL) at room temperature was added a 4M solution of HCl in 1,4-dioxane (300 mL) dropwise over 30 minutes. The resulting suspension was left to stir at room temperature for 3 hours before concentration in vacuo. The residue was azeotroped with diethyl ether (3×300 mL) followed by a diethyl ether trituration (200 mL) to provide crude material as a fawn coloured solid. This material was suspended in methanol (200 mL) and filtered through Celite, washed with methanol (400 mL) and the resulting filtrate concentrated in vacuo to give a sand coloured solid. This material was suspended in water (100 mL) and treated with 880 ammonia (60 mL) portionwise until pH 9-10 was achieved. The resulting solution was washed with diethyl ether (3×75 mL) and the aqueous layer acidified to pH=5 with citric acid. The mixture was then extracted with ethyl acetate (3×200 mL) and brine (100 mL) added to aid separation. The combined organic layers were washed with water (200 mL), dried over MgSO$_4$ and concentrated in vacuo to approximately 100 mL whereby a precipitate was observed. This mixture was allowed to cool for 18 hours and the resulting solid filtered and washed with cold ethyl acetate (10 mL) and dried in vacuo at 60° C. to provide the title compound as a sand coloured crystalline solid (17.5 g) containing 8.2% by weight ethyl acetate solvate.

LCMS Rt=1.58 minutes. MS m/z 532 [M$^{35}$ClH]+
$^1$HNMR (d$_6$-DMSO): δ7.30 (d, 1H), 7.50 (d, 1H), 7.83-7.85 (m, 1H), 7.92-7.98 (m, 2H), 8.08-8.13 (m, 1H), 8.81 (s, 1H), 9.32 (d, 1H), 9.51 (s, 1H).

Microanalysis: $C_{19}H_{10}ClF_4N_5O_3S_2 \cdot 0.55$ EtOAc required C, 43.91; H, 2.48; N, 12.08; Cl, 6.13%. Found C, 43.90; H, 2.42; N, 12.04; Cl, 6.14%.

Example 1028

4-[2-(3-amino-1H-pyrazol-4-yl)-4-(trifluoromethyl)phenoxy]-5-chloro-2-fluoro-N-1,3,4-thiadiazol-2-ylbenzenesulfonamide

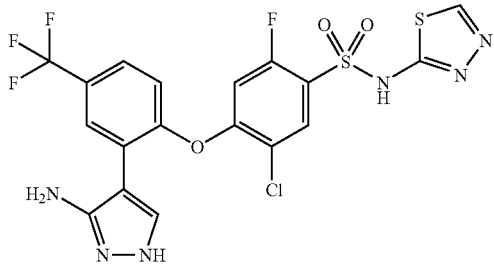

To a solution of 5-chloro-N-(2,4-dimethoxybenzyl)-2-fluoro-4-{2-[3-nitro-1-(tetrahydro-2H-pyran-2-yl)-1H-pyrazol-4-yl]-4-(trifluoromethyl)phenoxy}-N-1,3,4-thiadiazol-2-ylbenzenesulfonamide (Preparation 867, 3.20 g, 4.00 mmol) in ethanol (200 mL) was added saturated aqueous ammonium chloride solution (50 mL) and iron (5.66 g, 101 mmol). The reaction solution was heated at 80° C. for 15 minutes. The solution was cooled, filtered and adjusted to pH=9 with saturated aqueous sodium bicarbonate solution. The mixture was filtered and then concentrated to remove most of the ethanol. The resulting slurry was extracted with dichloromethane (3×). The organic extracts were combined, dried over anhydrous magnesium sulfate, filtered, and concentrated. This provided the aminopyrazole as a yellow foam. To this was added an HCl(g) saturated methanol solution (200 mL) and the mixture heated at 60° C. for two hours. The reaction solution was cooled, concentrated, and purified by automated flash column chromatography using a 0-10% methanol/dichloromethane gradient. Additional purification by prep HPLC provided the TFA salt. The resulting white solid was redissolved in a HCl(g) saturated methanol solution and concentrated (3×) in order to isolate the HCl salt of the title compound (1.20 g, 53%) as a white solid.

LC/MS Rt=1.67 minutes
MS m/z 535 [M$^{35}$ClH]+
$^1$H NMR (d$_6$-DMSO): δ 7.25 (d, 1H), 7.32 (d, 1H), 7.73 (m, 1H), 7.96 (d, 1H), 7.99 (m, 1H), 8.09 (s, 1H), 8.86 (s, 1H).

Example 1029

4-[2-(3-amino-1H-pyrazol-4-yl)-4-(trifluoromethyl)phenoxy]-5-chloro-2-fluoro-N-1,3-thiazol-4-ylbenzenesulfonamide

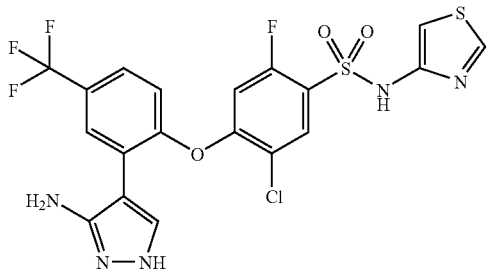

To a solution of tert-butyl [(5-chloro-2-fluoro-4-{2-[3-nitro-1-(tetrahydro-2H-pyran-2-yl)-1H-pyrazol-4-yl]-4-(trifluoromethyl)phenoxy}phenyl)sulfonyl]1,3-thiazol-4-ylcarbamate (Preparation 872, 55 g, 74 mmol) in ethanol (800 mL) was added saturated aqueous ammonium chloride solution (200 mL, 3000 mmol) and iron (65 g, 1200 mmol). The reaction solution was heated at 80° C. for two hours at which point iron (10 g, 185 mmol) was added and the mixture heated for an additional hour. The solution was cooled, filtered and adjusted to pH=9 with saturated aqueous sodium bicarbonate solution. The mixture was filtered and then concentrated to remove most of the ethanol. The resulting slurry was extracted with dichloromethane (4×). The organic extracts were combined, dried over anhydrous magnesium sulfate, filtered, and concentrated to provide the free amine as an orange oil. Purification by manual flash column chromatography using 40% then 75% ethyl acetate/hexanes and a 5×31 cm column provided a mix of Boc protected sulphonamide and non-Boc protected sulphonamide free amine as an orange oil. To this mixture was added an HCl(g) saturated methanol solution (400 mL) and the mixture heated at 60° C. for 7 hours. The reaction solution was cooled and concentrated to give a white solid. The solid was redissolved in methanol, heated to reflux and ethyl acetate added until just before a precipitate formed. It was then cooled, washed with ethyl acetate and dichloromethane to provide the title compound as a white solid. This was repeated until no more clean product was obtained. The impure filtrate was purified by prep HPLC, the product fractions concentrated and the TFA salt exchanged for an HCl salt. All product was combined, dissolved in methanol, filtered, concentrated and isolated as a white solid with 1.5 eq of HCl present (30.3 g, 70%) via trituration with dichloromethane.

LC/MS Rt=1.73 minutes MS m/z 534 [M$^{35}$ClH]+
$^1$H NMR (d$_6$-DMSO): δ 7.00 (d, 1H), 7.10 (d, 1H), 7.30 (m, 1H), 7.53 (m, 1H), 7.61 (m, 1H), 7.93 (d, 1H), 7.97 (s, 1H), 8.91 (d, 1H).

Example 1030

4-[4-Chloro-2-(2-piperazin-1-ylpyrimidin-4-yl)phenoxy]-3-cyano-N-1,2,4-thiadiazol-5-ylbenzenesulfonamide

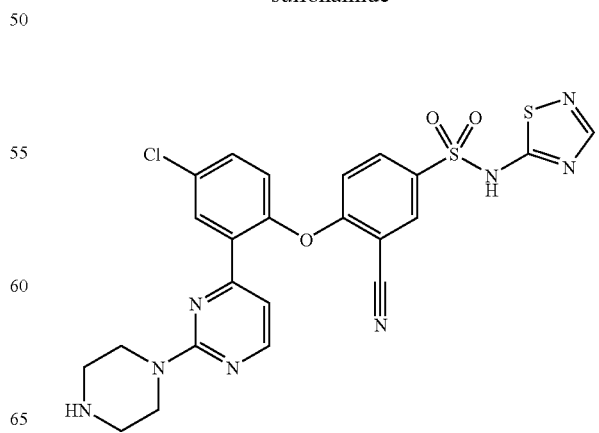

3-Cyano-4-fluoro-N-(1,2,4-thiadiazol-5-yl)benzenesulfonamide (Preparation 65, 43.6 mg, 0.154 mmol), tert-butyl 4-[4-(5-chloro-2-hydroxyphenyl)pyrimidin-2-yl]piperazine-1-carboxylate (Preparation 873, 50.0 mg, 0.128 mmol) and potassium carbonate (53 mg, 0.38 mmol) in dimethyl sulfoxide (1 mL, 10 mmol) was stirred at 100° C. for 16 hours. The reaction mixture was cooled to ambient temperature and poured into saturated aqueous ammonium chloride. The aqueous layer was extracted with ethyl acetate (3×). The combined organic layers were washed with brine, dried over sodium sulfate, filtered, and concentrated in vacuo to afford the crude intermediate, tert-butyl 4-[4-(5-chloro-2-{2-cyano-4-[(1,2,4-thiadiazol-5-ylamino)sulfonyl]phenoxy}phenyl)pyrimidin-2-yl]piperazine-1-carboxylate, as a yellow solid. Trifluoroacetic acid (300 uL, 4 mmol) was added to a solution of tert-butyl 4-[4-(5-chloro-2-{2-cyano-4-[(1,2,4-thiadiazol-5-ylamino)sulfonyl]phenoxy}phenyl)pyrimidin-2-yl]piperazine-1-carboxylate (83 mg, 0.154 mmol) in methylene chloride (2.9 mL, 46 mmol). After 1 hour, the reaction mixture was concentrated in vacuo. The residue was purified by reverse-phase HPLC to afford the product as a white solid (trifluoroacetic acid salt, 36 mg, 51%).

LC/MS Rt=1.52 minutes, MS m/z 555 [M$^{35}$ClH]+

$^1$H NMR (d$_6$-DMSO): δ 8.49 (d, 1H), 8.38 (s, 1H), 8.23 (d, 1H), 7.97 (m, 2H), 7.72 (m, 1H), 7.49 (d, 1H), 7.04 (d, 1H), 6.99 (d, 1H), 3.73 (m, 4H), 3.08 (m, 4H).

Example 1031

4-[2-(2-aminopyridin-4-yl)-4-chlorophenoxy]-5-chloro-2-fluoro-N-pyridazin-3-ylbenzenesulfonamide

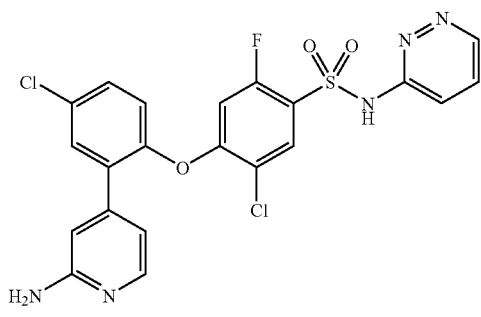

4-[2-(2-aminopyridin-4-yl)-4-chlorophenoxy]-5-chloro-2-fluoro-N-(methoxymethyl)-N-pyridazin-3-ylbenzenesulfonamide and 4-[2-(2-aminopyridin-4-yl)-4-chlorophenoxy]-5-chloro-2-fluoro-N-[(3E)-2-(methoxymethyl)pyridazin-3(2H)-ylidene]benzenesulfonamide, (Preparation 875, 93 mg, 0.17 mmol) in trifluoroacetic acid (1 mL, 10 mmol) was stirred for 24 hours. The reaction mixture was concentrated and the residue was taken in methanol (1 mL, 20 mmol) and 2 M of hydrogen chloride in water (1 mL, 2 mmol). After stirring for two days, the reaction mixture was concentrated and the residue liophilized from acetonitrile-water to give 76 mg of product as a hydrochloride salt.

LCMS Rt=1.36 min MS m/z 506 [MH]+

$^1$H NMR (300 MHz, d$_6$-DMSO): δ 6.99 (dd, 1 H), 7.12 (d, 1 H), 7.21 (d, 1 H), 7.24 (s, 1 H), 7.62 (dd, 1 H), 7.73 (d, 1 H), 7.78 (dd, 1 H), 7.96-8.02 (m, 3H), 8.17 (bs, 2H), 8.40 (dd, 1H), 13.8 (bs, 1H).

Example 1032

4-{2-[2-(Azetidin-1-ylmethyl)pyridin-4-yl]-4-chlorophenoxy}-2,5-difluoro-N-1,3-thiazol-4-ylbenzenesulfonamide

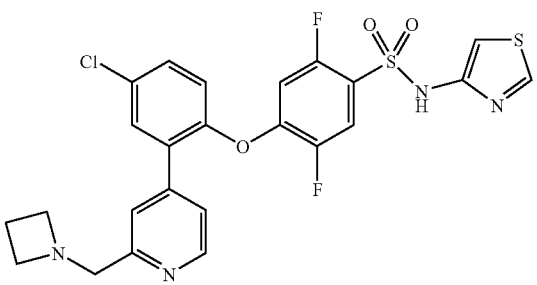

tert-Butyl [(4-{2-[2-(azetidin-1-ylmethyl)pyridin-4-yl]-4-chlorophenoxy}-2,5-difluorophenyl)sulfonyl]1,3-thiazol-4-ylcarbamate, (Preparation 878, 0.325 g, 0.0005 mol) was dissolved in dichloromethane (3 mL) then 4 molar hydrogen chloride in 1,4-dioxane (3 mL) was added. The reaction was stirred at room temperature for 18 hours. The reaction was concentrated in vacuo and the crude product purified by preparative HPLC to give the title compound.

LCMS Rt=1.07 minutes, MS m/z=549 [M$^{35}$ClH]+

Example 1033

3-Cyano-4-{2-[1-(1-ethylazetidin-3-yl)-1H-pyrazol-5-yl]-4-(trifluoromethyl)phenoxy}-N-1,2,4-thiadiazol-5-ylbenzenesulfonamide

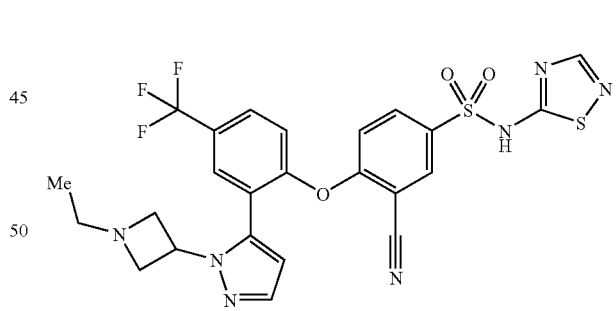

4-[2-(1-Azetidin-3-yl-1H-pyrazol-5-yl)-4-(trifluoromethyl)phenoxy]-3-cyano-N-1,2,4-thiadiazol-5-ylbenzenesulfonamide, (Preparation 881, 2.90 g, 0.00529 mol) was dissolved in acetic acid (6 mL) with warming and then dichloromethane (50 ml) was added. The solution was stirred under nitrogen and cooled in an ice/acetone bath. Sodium triacetoxyborohydride (5.0 g, 0.0236 mol) was added, stirred with cooling for 15 minutes and then a solution of acetaldehyde (1.2 mL, 0.021 mol) in dichloromethane (10 mL) was added dropwise over 45 minutes. The reaction mixture was stirred with cooling for 1 hour and then allowed to warm to room temperature and stirred for a further 45 minutes. LCMS indicated that a small amount of starting material remained so the mixture was cooled again in ice and a further portion of sodium triacetoxyborohydride (0.50 g, 0.00236 mol) was added, followed by acetaldehyde (0.10 mL, 0.00178 mol). The reaction mixture was stirred whilst warming to room temperature over 1 hour. Water (5.0 mL) was added to quench the reaction and the mixture was stirred at room temperature for 15 minutes and the solvents were then removed in vacuo. The residue was partitioned between ethyl acetate (150 mL) and water (50 mL) with 0.880 aqueous ammonia (20 mL) added. The organic layer was washed with water (2×50 mL), dried over anhydrous sodium sulphate, filtered and the solvents removed in vacuo to give the crude product as a pale yellow foam (2.30 g). A further batch was obtained by re-extracting the combined aqueous layers with ethyl acetate (80 mL) to give a pale yellow foam (700 mg). The two batches were combined and re-crystallized from ethyl acetate (25 mL) to give the title compound as a white powder (1.84 g). 300 mg of this material was re-crystallized from water/ethanol to give the pure title compound (215 mg).

LCMS Rt=11.40 minutes, MS m/z=576 [MH]+

$^1$HNMR (d$_6$-DMSO) δ 1.09 (t, 3H), 3.32 (brm, 2H), 4.23-4.49 (brm, 4H), 5.13 (m, 1H), 6.47 (s, 1H), 7.05 (d, 1H), 7.53 (d, 1H), 7.73 (s, 1H), 7.88-8.00 (m, 4H), 8.04 (d, 1H).

The remaining material (1.53 g, 0.00266 mol) was added to a solution sodium hydroxide (97 mg, 0,00243 mol) in water (15 mL) and warmed to give a slightly cloudy solution which was filtered whilst still hot and the water was then removed in vacuo to give a gum. The gum was treated with tert-butylmethylether (50 mL) for 3 days and then the solvent was removed in vacuo to give the sodium salt of the title compound as a foam (1.20 g).

LCMS Rt=1.28 minutes, MS m/z=576 [MH]+

$^1$HNMR (d$_6$-DMSO) δ 0.85 (t, 3H), 2.41 (q, 2H), 3.24 (m, 2H), 3.52 (m, 2H), 4.74 (m, 1H), 6.33 (s, 1H), 7.07 (d, 1H), 7.48-7.56 (m, 2H), 7.81-8.03 (m, 5H).

Example 1034

5-Chloro-2-fluoro-4-[5-fluoro-2-pyridazin-4-yl-4-(trifluoromethyl)phenoxy]-N-1,3,4-thiadiazol-2-ylbenzenesulfonamide

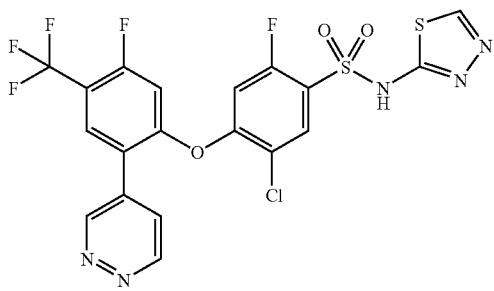

5-Chloro-N-(2,4-dimethoxybenzyl)-2,4-difluoro-N-1,3,4-thiadiazol-2-ylbenzenesulfonamide (Preparation 247, 63 mg, 0.14 mmol) was added to a mixture of 5-fluoro-2-pyridazin-4-yl-4-(trifluoromethyl)phenol (Preparation 884, 35 mg, 0.14 mmol) and potassium carbonate (22 mg, 0.16 mmol) in dimethyl sulfoxide (2 mL, 30 mmol). The reaction mixture was stirred at ambient temperature. After 3 hours the reaction mixture was diluted with water and saturated aqueous ammonium chloride and extracted with ethyl acetate (3×). The combined organic layers were washed with water then brine, dried over sodium sulfate, filtered, and concentrated in vacuo. The residue was taken up in methylene chloride, concentrated onto diatomaceous earth, and purified by automated flash chromatography (12 g SiO$_2$, hexanes to ethyl acetate) to afford the intermediate 5-chloro-N-(2,4-dimethoxybenzyl)-2-fluoro-4-[5-fluoro-2-pyridazin-4-yl-4-(trifluoromethyl)phenoxy]-N-1,3,4-thiadiazol-2-ylbenzenesulfonamide as a glass (22 mg, 23%).

LC/MS Rt=1.88 minutes, MS m/z 700 [M$^{35}$ClH]+

Trifluoroacetic acid (500 uL, 6 mmol) was added to a solution of 5-chloro-N-(2,4-dimethoxybenzyl)-2-fluoro-4-[5-fluoro-2-pyridazin-4-yl-4-(trifluoromethyl)phenoxy]-N-1,3,4-thiadiazol-2-ylbenzenesulfonamide (22 mg) in methylene chloride (5 mL, 70 mmol). After stirring 20 min, the reaction mixture was concentrated onto diatomaceous earth and purified by automated flash chromatography (4 g SiO2, methylene chloride to 9:1 methylene chloride-methanol) to afford the product as a tan solid (6 mg, 9%).

LC/MS Rt=1.72 minutes, MS m/z 550 [M$^{35}$ClH]+

$^1$H NMR (d$_6$-DMSO): δ 9.50 (m, 1H), 9.33 (m, 1H), 8.83 (s, 1H), 8.16 (d, 1H), 7.95 (m, 2H), 7.62 (d, 1H), 7.52 (d, 1H).

Example 1035

3-Cyano-4-[5-fluoro-2-pyridazin-4-yl-4-(trifluoromethyl)phenoxy]-N-1,2,4-thiodiazol-5-ylbenzenesulfonamide

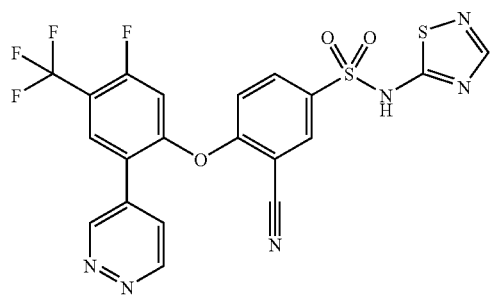

3-Cyano-N-(2,4-dimethoxybenzyl)-4-fluoro-N-(1,2,4-thiadiazol-5-yl)benzenesulfonamide (Preparation 68, 59 mg, 0.14 mmol) was added to a mixture of 5-fluoro-2-pyridazin-4-yl-4-(trifluoromethyl)phenol (Preparation 884, 35 mg, 0.14 mmol) and potassium carbonate (22 mg, 0.16 mmol) in dimethyl sulfoxide (2 mL, 30 mmol). The reaction mixture was stirred at ambient temperature. After 3 hours the reaction mixture was diluted with water and saturated aqueous ammonium chloride and extracted with ethyl acetate (3×). The combined organic layers were washed with water then brine, dried over sodium sulfate, filtered, and concentrated in vacuo. The residue was taken up in methylene chloride, concentrated onto diatomaceous earth, and purified by automated flash chromatography (12 g SiO2, hexanes to ethyl acetate) to afford the intermediate as a glass (63 mg, 69%).

LC/MS Rt=1.88 minutes, MS m/z 673 [MH]+

Trifluoroacetic acid (500 uL, 6 mmol) was added to a solution of 3-cyano-N-(2,4-dimethoxybenzyl)-4-[5-fluoro-2-pyridazin-4-yl-4-(trifluoromethyl)phenoxy]-N-1,2,4-thiadiazol-5-ylbenzenesulfonamide (63 mg) in methylene chloride (5 mL, 70 mmol). After stirring 20 minutes, the reaction mixture was concentrated onto diatomaceous earth and purified by automated flash chromatography (12 g SiO2, methylene chloride to 9:1 methylene chloride-methanol) to afford the product as a light yellow solid (38 mg, 54%).

LC/MS Rt=1.66 minutes, MS m/z 523 [MH]+
¹H NMR (d₆-DMSO): δ 9.45 (m, 1H), 9.31 (m, 1H), 8.48 (s, 1H), 8.30 (d, 1H), 8.23 (d, 1H), 8.04 (m, 1H), 7.90 (m, 1H), 7.75 (d, 1H), 7.44 (d, 1H).

Example 1036

4-[2-(3-amino-1H-pyrazol-4-yl)-4-chlorophenoxy]-5-chloro-2-fluoro-N-pyrimidin-4-ylbenzenesulfonamide

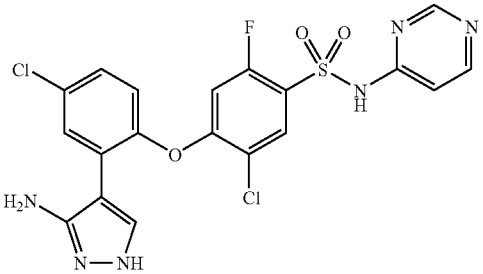

4-{2-[3-amino-1-(tetrahydro-2H-pyran-2-yl)-1H-pyrazol-4-yl]-4-chlorophenoxy}-5-chloro-2-fluoro-N-(methoxymethyl)-N-pyrimidin-4-ylbenzenesulfonamide (Preparation 887, 58 mg, 0.093 mmol) in methanol (1 mL, 20 mmol) and 2 M of hydrogen chloride in water (1 mL, 2 mmol) was heated at 60° C. for 2 hours then concentrated. The residue was liophilized from acetonitrile-water to give 50 mg of a white solid.

LCMS Rt=1.64 min, MS m/z 495 [MH]+
¹HNMR (d₆-DMSO): δ 6.93 (m, 2H), 7.18 (d, 1H), 7.46 (dd, 1H), 7.72 (d, 1H), 7.97 (m, 2H), 8.21 (d, 1H), 8.58 (s, 1H).

Example 1037

2-fluoro-5-methyl-4-[2-pyridazin-4-yl-4-(trifluoromethoxy)phenoxy]-N-1,3,4-thiadiazol-2-ylbenzenesulfonamide

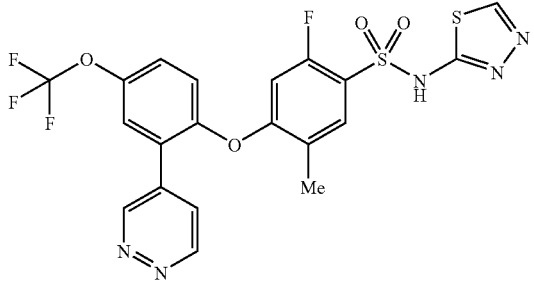

2-pyridazin-4-yl-4-(trifluoromethoxy)phenol (Preparation 888, 30 mg, 0.12 mmol) was taken up in dimethyl sulfoxide (1 mL, 20 mmol) and potassium carbonate (30 mg, 0.22 mmol) added, followed by N-(2,4-dimethoxybenzyl)-2,4-difluoro-5-methyl-N-1,3,4-thiadiazol-2-ylbenzenesulfonamide (Preparation 889, 51.7 mg, 0.117 mmol). The reaction was heated at 60° C. for 72 hours. The reaction was cooled and diluted with 1N HCl. The resulting precipitate was collected by filtration. The solid was dissolved in methylene chloride (1.0 mL, 16 mmol) and dried over magneisum sulfate. The solution was then treated with trifluoroacetic acid (45 uL, 0.58 mmol) and stirred for 2 hours. The reaction mixture was concentrated in vacuo. The residue was purified by reverse phase HPLC. Product fractions were combined and the solvent removed in vacuo to give a residue. The product was purified a second time by column chromatography (4 g silica gel column, 0 to 10% methanol in methylene chloride gradient elution). Product fractions were combined and concentrated in vacuo to give 11.2 mg of colorless glass.

LCMS Rt=1.67 min, MS m/z 528 [MH]+
¹HNMR (300 MHz, d₆-DMSO): δ 2.20 (s, 3H), 6.94 (d, 1H), 7.23 (d, 1H), 7.54 (m, 1H), 7.75 (d, 1H), 7.81 (d, 1H), 7.90 (dd, 1H), 8.78 (s, 1H), 9.29 (dd, 1H), 9.45 (dd, 1H).

Example 1038

4-[2-(3-amino-1H-pyrazol-4-yl)-4-chlorophenoxy]-5-chloro-2-fluoro-N-pyridazin-3-ylbenzenesulfonamide

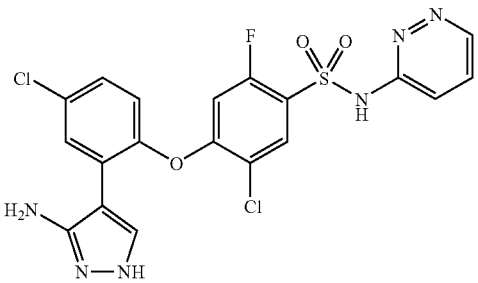

The title compound was prepared according to the procedure in Example 1036 using 4-{2-[3-amino-1-(tetrahydro-2H-pyran-2-yl)-1H-pyrazol-4-yl]-4-chlorophenoxy}-5-chloro-2-fluoro-N-(methoxymethyl)-N-pyridazin-3-ylbenzenesulfonamide and 4-{2-[3-amino-1-(tetrahydro-2H-pyran-2-yl)-1H-pyrazol-4-yl]-4-chlorophenoxy}-5-chloro-2-fluoro-N-[(3E)-2-(methoxymethyl)pyridazin-3(2H)-ylidene]benzenesulfonamide (Preparation 891).

LCMS Rt=1.62 min, MS m/z 495 [MH]+
¹HNMR (d₆-DMSO): δ 6.94 (d, 1H), 7.17 (d, 1H), 7.44 (dd, 1H), 7.71 (d, 1H), 7.76 (dd, 1H), 7.97 (m, 3H), 8.38 (dd, 1H).

Example 1039

[(2Z)-2-[({4-[4-Chloro-2-(1-methyl-1H-pyrazol-5-yl)phenoxy]-3-cyanophenyl}sulfonyl)imino]-1,3-thiazol-3(2H)-yl]methyl dihydrogen phosphate

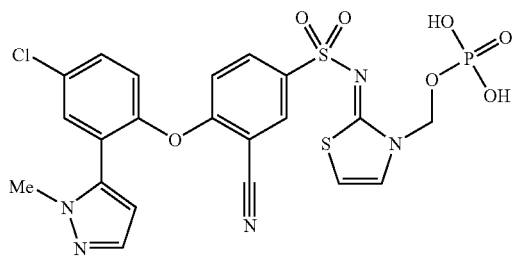

Di-tert-butyl [(2Z)-2-[({4-[4-chloro-2-(1-methyl-1H-pyrazol-5-yl)phenoxy]-3-cyanophenyl}sulfonyl)imino]-1,3-thiazol-3(2H)-yl]methyl phosphate, (Example 1040, 250 mg, 0.00036 mol) was dissolved in ethyl acetate (10 mL) and then trifluoroacetic acid (1 mL) was added. The solution was stirred at room temperature for 3 hours, then a further portion of trifluoroacetic acid (2 mL) was added and stirred at room temperature for 18 hours. The solvents were removed in vacuo and the residue was partitioned between tert-butylmethyl ether (30 mL) and water (40 mL) and a few drops of aqueous sodium hydroxide solution (2 molar). The aqueous layer was then acidified to pH 1-2 with aqueous hydrochloric acid (2 molar) to give a sticky cream precipitate which was dissolved in a mixture of dichloromethane, ethanol and methanol. This organic layer was dried over anhydrous sodium sulphate, filtered and the solvents removed in vacuo to give the crude product which was triturated with ethyl acetate to give the title compound as a buff powder, (85 mg).

MS m/z=582 [M$^{35}$ClH]+

$^1$HNMR (d$_6$-DMSO) δ 3.73 (s, 3H), 5.60 (d, 2H), 6.22 (d, 1H), 6.90-6.96 (m, 2H), 7.34 (s, 1H), 7.41 (d, 1H), 7.47-7.51 (m, 1H), 7.66-7.71 (m, 2H), 7.92-7.97 (m, 1H), 8.18 (d, 1H).

Example 1040

Di-tert-butyl [(2Z)-2-[({4-[4-chloro-2-(1-methyl-1H-pyrazol-5-yl)phenoxy]-3-cyanophenyl}sulfonyl)imino]-1,3-thiazol-3(2H)-yl]methyl phosphate

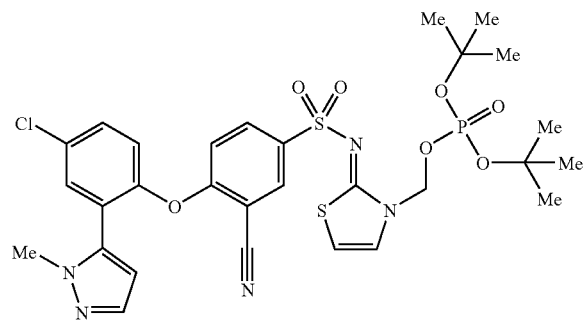

4-[4-Chloro-2-(1-methyl-1H-pyrazol-5-yl)phenoxy]-3-cyano-N-1,3-thiazol-2-ylbenzenesulfonamide, (Example 170, 200 mg, 0.000424 mol), di-tert-butyl chloromethyl phosphate (J. Med. Chem. 51 (2008) p 1111-1114, supplimentary data) (160 mg, 0.000619 mol) and cesium carbonate (420 mg, 0.00129 mol) were stirred in dimethylformamide (2 mL) at 60° C. for 18 hours. The mixture was cooled then partitioned between tert-butylmethyl ether (80 mL) and water (40 mL), the organic layer was dried over anhydrous sodium sulphate, filtered and the solvent removed in vacuo to give the title compound as a pale yellow gum, (250 mg).

LCMS=1.63 minutes, MS m/z=694 [M$^{35}$ClH]+

$^1$HNMR (CDCl$_3$) δ 1.42 (s, 9H), 1.51 (s, 9H), 3.87 (s, 3H), 5.68 (d, 2H), 6.21 (s, 1H), 6.50 (d, 1H), 6.66 (d, 1H), 7.13 (d, 1H), 7.23 (d, 1H), 7.39 (s, 1H), 7.46 (s, 1H), 7.48-7.53 (m, 1H), 7.94-7.99 (m, 1H), 8.15 (s, 1H).

Preparations

The following Preparations illustrate the preparation of certain intermediates used to prepare the Examples above.

Preparation 14

(2,4-dimethoxy-benzyl)-[1,2,4]thiadiazol-5-yl-amine/N-(2,4-dimethoxybenzyl)-1,2,4-thiadiazol-5-amine

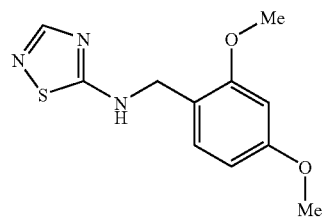

A mixture of 5-amino-1,2,4-thiadiazole (1 g; 9.89 mmol) and 2,4-dimethoxybenzaldehyde (1.81 g; 10.9 mmol) in toluene (30 ml) was refluxed under Dean and Stark conditions for 2 hours. The reaction mixture was evaporated, the residue taken up in methanol (25 ml), NaBH$_4$ (600 mg; 15.9 mmol) added carefully in small portions (vigorous effervescence after each addition), and the reaction was left stirring overnight at ambient temperature. Aqueous HCl (2M, 1 ml) was added followed by aqueous NaOH (2M, 10 ml). The bulk of the methanol was evaporated, water (20 ml) added and extracted with ethyl acetate (2×30 ml). The combined organic was washed brine (20 ml), dried, and evaporated. The residue was purified by silica gel column chromatography (ISCO™ column 120 g; ethyl acetate:heptane 25:75 to 60:40) to furnish a semi-solid residue that was re-evaporated from heptane. 2-3 ml tBuOMe was added, then 2-3 ml heptane, the solid filtered off, washed with heptane and dried to afford 1.22 g of the title compound.

$^1$HNMR (d$_6$-DMSO): δ 3.73 (s, 3 H), 3.78 (s, 3 H), 4.36 (d, J=5.46 Hz, 2 H), 6.47 (dd, J=8.58, 2.34 Hz, 1 H), 6.56 (d, J=2.34 Hz, 1 H), 7.15 (d, J=8.19 Hz, 1 H), 7.88 (s, 1 H), 8.65 (br. S., 1 H)

Preparation 37

4'-isopropoxy-2'-methylbiphenyl-2-ol

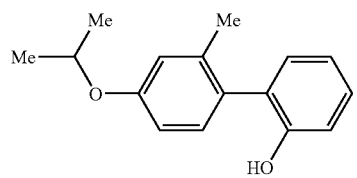

2-Iodophenol (1.54 g, 7.00 mmol) was combined with 2-(4-isopropoxy-2-methyl-phenyl)-4,4,5,5-tetramethyl-[1,3,2]dioxaborolane (Preparation 38, 2.00 g, 7.24 mmol), cesium carbonate (4.56 g, 13.99 mmol) and palladium tetrakis(triphenylphosphine) (0.24 g, 0.21 mmol) in 1,2-dimethoxyethane (40 mL). The reaction mixture was heated to reflux for 18 hours. The reaction mixture was cooled to room temperature and then acidified with a 1 N aqueous HCl solution. The organics were extracted 3 times with diethylether. The organic layers were combined, washed with brine, dried over magnesium sulphate and concentrated in vacuo. The residue was purified by column chromatography using as eluant a mixture heptane/ethyl acetate to afford 543 mg (31% yield) of 4'-isopropoxy-2'-methylbiphenyl-2-ol as a pale yellow oil.

MS m/z 243 [MH]+

$^1$HNMR (CDCl$_3$): δ 1.37 (d, 6H), 2.12 (s, 3H), 4.56-4.62 (m, 1H), 6.80 (dd, 1H), 6.85 (d, 1H), 6.93-7.01 (m, 2H), 7.10-7.14 (m, 2H), 7.23-7.28 (m, 1H).

Preparation 38

2-(4-isopropoxy-2-methyl-phenyl)-4,4,5,5-tetramethyl-[1,3,2]dioxaborolane

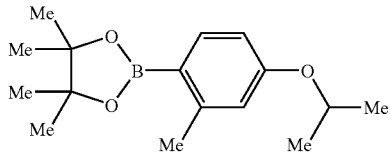

In a flame-dried flask under nitrogen, 3-methyl-4-(4,4,5,5-tetramethyl-1,3,2-dioxaborolan-2-yl)phenol (see WO2007092751A, 2.30 g, 9.82 mmol) was dissolved in dimethylformamide (40 mL). Sodium hydride 60% dispersion in mineral oil (0.48 g, 12 mmol) was added to the mixture. The reaction mixture was stirred at room temperature under nitrogen for 30 minutes. 2-Iodopropane (2.55 g, 15.00 mmol) was added and the reaction mixture was stirred at 70° C. for 18 hours. The reaction mixture was quenched with water. The organics were extracted 3 times with diethylether. The organic layers were combined, dried over magnesium sulphate and concentrated in vacuo. The residue was purified by column chromatography, using as eluant a mixture of heptane/ethyl acetate, to afford 2.02 g (73% yield) of 2-(4-isopropoxy-2-methyl-phenyl)-4,4,5,5-tetramethyl-[1,3,2]dioxaborolane as a yellow oil. MS m/z 277 [MH]+

$^1$HNMR (CDCl$_3$): 1-1.32 (m, 18H), 2.50 (s, 3H), 4.50-4.60 (m, 1H), 6.67-6.69 (m, 2H), 7.69 (d, 1H).

Preparation 42

4-(4-fluorophenyl)-2-(methylamino)pyrimidin-5-ol

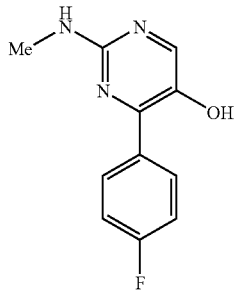

(2-Amino-1,3-oxazol-5-yl)(4-fluorophenyl)methanone (US2005032859, 1 g, 4.85 mmol) and 40% methyl amine water in excess (50 mL) were combined in tert-butanol (50 mL). The mixture was stirred at 50° C. under nitrogen for 2 hours. The mixture was concentrated in vacuo. The residue was filtered through a pad of silica gel using neat ethyl acetate as eluant. The solution was concentrated in vacuo to afford 0.73 g (66%) of 4-(4-fluorophenyl)-2-(methylamino)pyrimidin-5-ol as a crystalline brown solid. MS m/z 220 [M]+

1H NMR CDCl$_3$/CD$_3$OD: δ 2.94 (s, 3H), 6.90-7.20 (m, 2H), 7.95 (s, 1H), 8.00-8.30 (m, 2H).

Preparation 44

4-(2-bromo-4-fluoro-phenoxy)-3-cyano-N-[1,2,4]thiadiazol-5-ylbenzenesulfonamide

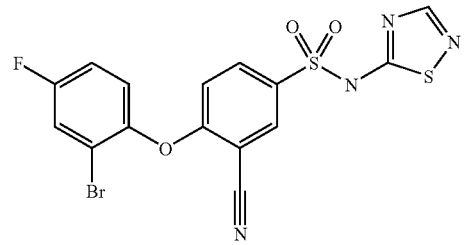

Prepared according to the process of Preparation 51, using 2-bromo-4-fluorophenol and 3-cyano-4-fluoro-N-(1,2,4-thiadiazol-5-yl)benzenesulfonamide (Preparation 65). LCMS Rt=3.01 min MS m/z 284 [MH]+ $^1$HNMR (d$_6$-DMSO): δ 6.8 (m, 1H), 7.4 (m, 1H), 7.6 (m, 1H), 7.8 (m, 1H), 8.0 (m, 1H), 8.3 (m, 1H), 8.5 (s, 1H).

Preparation 46

3-cyano-4-fluoro-N-(thiazol-2-yl)benzenesulfonamide

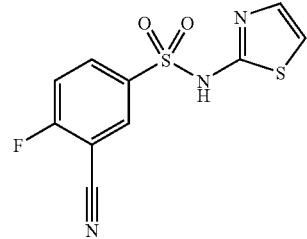

To 2-aminothiazole (12.55 g, 125.3 mmol) was added pyridine (46 ml) and dichloromethane (75 mL) and the mixture stirred to give a solution. A solution of 3-cyano-4-fluorobenzenesulfonyl chloride (25 g, 114 mmol) in dichloromethane (50 ml) was added over approx 20 minutes at room temperature. The reaction was stirred at this temperature for 2 days before decanting the supernatant and concentrating in vacuo to furnish a dark oil. 2M HCl (200 ml) was added and the mixture triturated until solidification occurred. A brick red solid was filtered off, washed with water and dried to furnish 21.5 g of the title product. $^1$HNMR (d$_6$-DMSO): δ 6.9(d, 1H), 7.3 (m, 1H), 7.6 (m, 1H), 8.15 (m, 1H), 8.3 (d, 1H), 12.9 (br s 1H). LCMS Rt=2.34 min MS m/z 284 [MH]+.

Preparation 50

3-cyano-4-(2-iodo-phenoxy)-N-[1,2,4]thiadiazol-5-yl-benzenesulfonamide

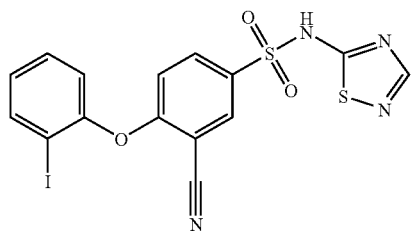

To a solution of 2-iodophenol (6.0 mmol, 1320 mg) and $K_2CO_3$ (10.5 mmol, 1450 mg) in DMF (15.0 mL) was added 3-cyano-4-fluoro-N-(1,2,4-thiadiazol-5-yl)benzenesulfonamide (Preparation 65, 4.5 mmol, 1280 mg). The reaction mixture was heated at 80° C. for 24 hours. The reaction was cooled to room temperature and the mixture was poured into 1 N aqueous HCl (100 mL) to obtain a white solid. The afforded solid was washed with heptane and the solid was dried in vacuo to furnish 1.932 g of the title compound. LCMS Rt=1.67 minutes MS m/z 485 [MH]+

$^1$HNMR (d$_6$-DMSO): δ 6.78 (d, 1H), 7.14-7.22 (m, 1H), 7.39-7.44 (m, 1H), 7.52-7.58 (m, 1H), 7.99-8.05 (m, 2H), 8.33 (d, 1H), 8.52 (s, 1H).

Preparation 51

3-cyano-4-(2-bromo-6-methyl-phenoxy)-N-[1,2,4]thiadiazol-5-yl-benzenesulfonamide

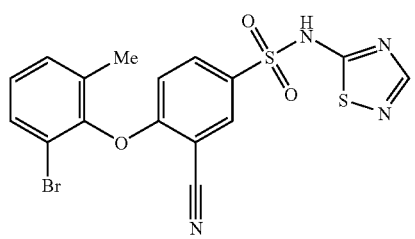

To a solution of 2-bromo-6-methylphenol (6.0 mmol, 1120 mg) and $K_2CO_3$ (10.5 mmol, 1450 mg) in DMF (15.0 mL) was added 3-cyano-4-fluoro-N-(1,2,4-thiadiazol-5-yl)benzenesulfonamide (Preparation 65, 4.5 mmol, 1280 mg). The reaction mixture was heated at 80° C. After stirring for overnight at 80° C., the reaction was cooled to room temperature and poured into 1 N aqueous HCl (100 mL) to precipitate which was filtered to obtain solid. The solid was washed with water (100 mL) and heptane (100 mL) and the solid was dried under vacuum to furnish the title compound. LCMS Rt=3.05 minutes MS m/z 451 [M(79Br)H]+, 453 [M(81Br)H]+

$^1$HNMR (d$_6$-DMSO): δ 2.17 (s, 3H), 6.70 (d, 1H), 7.25-7.31 (m, 1H), 7.44-7.48 (m, 1H), 7.64-7.69 (m, 1H), 8.01 (dd, 1H), 8.34 (d, 1H), 8.52 (s, 1H).

Preparation 52

N-(5-chloro-thiazol-2-yl)-3-cyano-4-fluorobenzenesulfonamide

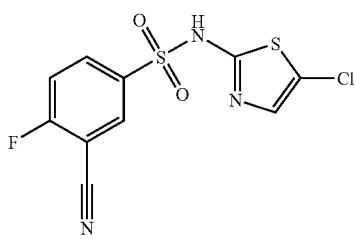

To a stirred mixture of 2-amino-5-chlorothiazole-hydrochloride (3.76 g, 22.0 mmol) in dichloromethane (20 ml) was added pyridine (8.09 ml, 100 mmol). 3-cyano-4-fluorobenzenesulfonyl chloride (4.39 g, 20 mmol) dissolved in dichloromethane (5 mL) and was added to the reaction mixture dropwise at room temperature. After stirring for 48 hours at room temperature, 1 N HCl (100 mL) was poured into the reaction and the mixture was extracted with dichloromethane/methanol (v/v=95/5, 100 ml) three times. The collected organic layer was evaporated in vacuo and dried over $MgSO_4$ to obtain the crude residue. The crude residue was washed with dichloromethane (10 mL) and filtered to afford pale yellow solid as the title compound. LCMS Rt=1.39 minutes MS m/z 318 [M$^{35}$ClH]+, 320 [M$^{37}$ClH]+ $^1$HNMR (d$_6$-DMSO): δ7.59 (s, 1H), 7.66-7.73 (m, 1H), 8.15-8.21 (m, 1H), 8.33-8.37 (m, 1H).

Preparation 55

4-(biphenyl-2-yloxy)-3-cyanobenzenesulfonyl chloride

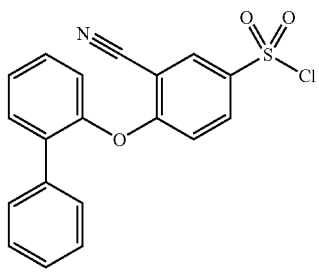

A mixture of 5-benzylsulfamyl-2-(biphenyl-2-yloxy)-benzonitrile (Preparation 56, 6.06 g, 15.4 mmol), dichloromethane and aq HCl was stirred vigorously with cooling (ice bath). Sodium hypochlorite was added dropwise over 30 minutes and stirring continued with cooling for 1 hour. The layers were separated, the aqueous extracted with dichloromethane (2×100ml), and the organic collected, dried ($MgSO_4$) and concentrated in vacuo. The residue was purified using silica gel column chromatography (ethyl acetate:Heptane 10/90 to 20/80) to furnish 4.58 g of the title compound.

1HNMR (CDCl3): δ 6.7 (m, 1H), 7.2-7.6 (m, 9H), 7.85 (m, 1H), 8.15 (m, 1H).

Preparation 56

5-benzylsulfamyl-2-(biphenyl-2-yloxy)-benzonitrile

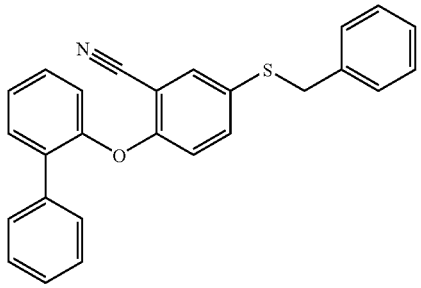

To a stirred mixture of 2-(biphenyl-2-yloxy)-5-bromo-benzonitrile (Preparation 57, 10.1 g, 28 8 mmol), Pd$_2$dba$_3$ (1.32 g, 1.44 mmol), and xantphos (1.67 g, 2.88 mmol) in diisopropylether (10 ml) and 1,4-dioxane (100 ml) was added benzyl mercaptan (3.58 g, 28 8 mmol) and the reaction heated at gentle reflux for 4 to 5 hours, then stirred at ambient temperature for 30 hours. The reaction mixture was evaporated and the residue purified using silica gel column chromatography, eluting with dichloromethane/heptane (30/70, then 50/50, then 60/40), to furnish 6.08 gm pale yellow solid as the title compound. LCMS Rt=1.88 minutes MS m/z 394 [MH]+ 1HNMR (CDCl3): δ 3.93 (s, 2 H) 6.46 (d, J=8.58 Hz, 1 H) 7.06-7.18 (m, 4 H) 7.21-7.30 (m, 4 H) 7.31-7.43 (m, 5 H) 7.45-7.55 (m, 3 H)

Preparation 57

2-(biphenyl-2-yloxy)-5-bromo-benzonitrile

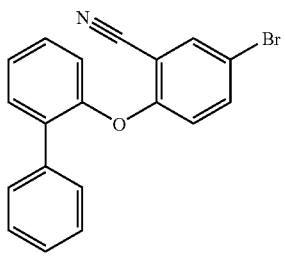

A suspension of 5-bromo-2-fluorobenzonitrile (6.48 g, 32.4 mmol), 2-phenylphenol (5.79 g, 34 mmol) and potassium carbonate (4.92 g, 35.6 mmol) in DMF (50 ml) was heated at 70° C. for 3 hours. The reaction was cooled and quenched by the addition of water (200 ml) followed by extraction with tBuOMe. The organic layer was dried (MgSO$_4$) and concentrated in vacuo. The residue was purified using silica gel column chromatography (ethyl acetate:Heptane 5:95 to 15:85) to furnish 10.1 g of the desired compound.

LCMS Rt=1.78 min MS m/z 349 [M]+ 1HNMR (d$_6$-DMSO): δ 6.6 (m, 1H), 7.2-7.6 (m, 9H), 7.65 (m, 1H), 8.0 (m, 1H).

Preparation 58

4-(biphenyl-2-yloxy)-3-cyano-benzenesulfonic acid pentafluorophenyl ester

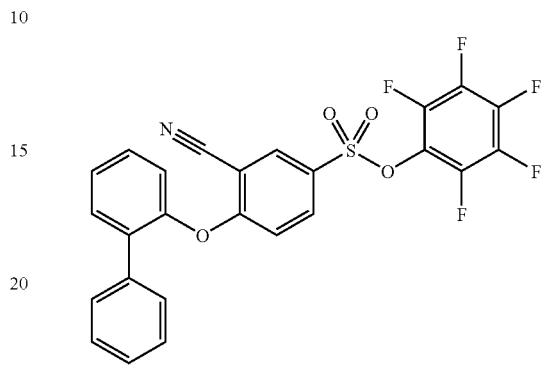

A solution of 4-(biphenyl-2-yloxy)-3-cyano-benzenesulfonyl chloride (Preparation 55, 500 mg, 1.35 mmol) in dichloromethane (5 ml) was added slowly to pentafluorophenol (249 mg, 1.35 mmol) and Et$_3$N (137 mg, 1.35 mmol) in dichloromethane (5 ml) and stirring continued overnight at ambient temperature. The reaction was concentrated in vacuo and purified using silica gel column chromatography (dichloromethane/heptane 40/60, then 60/40, then 80/20, then dichloromethane) to furnish the title compound. LCMS Rt=1.92 minutes $^1$H NMR (400 MHz; CDCl$_3$) δ (ppm): 6.69 (d, J=8.98 Hz, 1 H) 7.21-7.30 (m, 2 H) 7.31-7.38 (m, 2 H) 7.43-7.53 (m, 4 H) 7.53-7.58 (m, 1 H) 7.79 (dd, J=8.98, 2.34 Hz, 1 H) 8.06 (d, J=2.34 Hz, 1 H) $^{19}$F NMR (376 MHz, CDCl$_3$) δ (ppm): 160.82 (t, J=19.50 Hz) −154.87 (t, J=21.80 Hz) −151.09 (d, J=17.21 Hz)

Preparation 60

N-tert-butyl-3,4-difluoro-N-(thiazol-2-yl)benzenesulfonamide and N-[3-tert-butyl-3H-thiazol-(2Z)-ylidene]-3,4-difluorobenzenesulfonamide or (Z)-N-(3-tert-butylthiazol-2(3H)-ylidene)-3,4-difluorobenzenesulfonamide

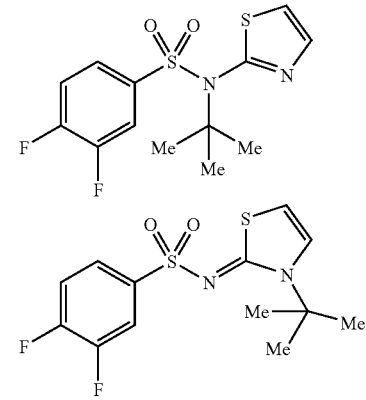

To a solution of 3,4-difluoro-N-(thiazol-2-yl)benzenesulfonamide (Preparation 61, 50 g, 0.2 mol) in tetrahydrofuran (500 mL) was added 4-dimethylaminopyridine (22 g, 0.18 mol) and di-tert-butyldicarbonate (200 g, 0.9 mol) and the mixture was heated to 50° C. for 4 days. The di-tert-butyldicarbonate was added portionwise every few hours, usually in conjunction with a precipitate that would form and then go back into solution after the addition. After cooling to room temperature the reaction was concentrated and absorbed onto silica gel and purified by flash column chromatography (ethyl acetate:Hexanes 0-100% ethyl acetate). This provided the two products in a 4:1 A:B ratio.

A=N-tert-butyl-3,4-difluoro-N-thiadiazol-2-yl-benzenesulfonamide:
LCMS Rt=1.66 minutes MS m/z 333 [MH]+ $^1$H NMR (CDCl$_3$) δ 8.02 (m, 1H), 7.89 (m, 1H), 7.73 (d, 1H), 7.45 (d, 1H), 7.33 (m, 1H), 1.43 (s, 9H).

B=N-[3-tert-butyl-3H-thiazol-(2Z)-ylidene]-3,4-difluorobenzenesulfonamide:
LCMS Rt=1.51 minutes MS m/z 333 [MH]+ $^1$H NMR (CDCl$_3$) δ 7.69 (m, 2H), 7.20 (m, 1H), 7.07 (d, 1H), 6.42 (d, 1H), 1.57 (s, 9H).

Preparation 61

3,4-difluoro-N-(thiazol-2-yl)benzenesulfonamide

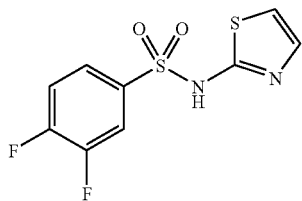

To a slurry of 2-aminothiazole (23.88 g, 0.2384 mol) in methylene chloride (150 mL) and pyridine (38.0 mL, 0.470 mol) was added dropwise a solution of 3,4-difluorobenzenesulphonyl chloride (25.0 g, 0.118 mol) in 10 mL of methylene chloride. After stirring for 48 hours the reaction was diluted with more dichloromethane and extracted with 1N HCl. The organic layer was dried over sodium sulfate, filtered, and concentrated. The residue was purified by flash column chromatography to give 3,4-difluoro-N-(thiazol-2-yl)benzenesulfonamide as a white solid. LCMS Rt=1.24 minutes MS m/z 277 [MH]+

Preparation 62

N-tert-butyl-2,4-difluoro-(N-thiazol-2-yl)benzenesulfonamide and N-[3-tert-butyl-3H-thiazol-(2Z)-ylidene]-2,4-difluorobenzenesulfonamide

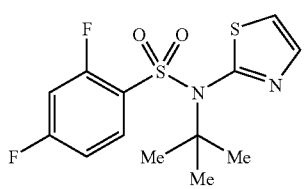

-continued

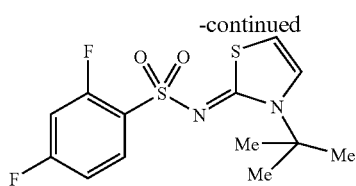

To a solution of 2,4-difluoro-N-(thiazol-2-yl)benzenesulfonamide (Preparation 63, 11.3 g, 0.0409 mol) in tetrahydrofuran (200 mL) was added 4-dimethylaminopyridine (5.0 g, 0.041 mol) and di-tert-butyldicarbonate (26.8 g, 0.123 mol) and heated to 40° C. for 3 days. The di-tert-butyldicarbonate was added portion-wise every few hours, usually in conjunction with a precipitate that would form and then go back into solution after the addition. After cooling to room temperature the reaction was concentrated and absorbed onto silica gel and purified by flash column chromatography. This provided the two products in a 5.5:1 A:B ratio.

A=N-tert-butyl-2,4-difluoro-N-thiadiazol-2-yl-benzenesulfonamide:
LCMS Rt=1.92 minutes MS m/z 333 [MH]+ $^1$H NMR (CDCl$_3$) δ 8.03 (m, 1H), 7.67 (d, 1H), 7.42 (d, 1H), 6.96 (m, 2H), 1.49 (s, 9H).

B=N-[3-tert-butyl-3H-thiazol-(2Z)-ylidene]-2,4-difluorobenzenesulfonamide:
LCMS Rt=1.54 minutes MS m/z 333 [MH]+ $^1$H NMR (CDCl$_3$) δ 8.07 (m, 1H), 7.12 (d, 1H), 6.95 (m, 2H), 6.47 (d, 1H), 1.70 (s, 9H).

Preparation 63

2,4-difluoro-N-(thiazol-2-yl)benzenesulfonamide

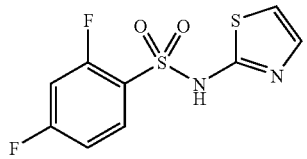

To a slurry of 2-aminothiazole (15.08 g, 0.1506 mol) in methylene chloride (100 mL) and pyridine (24 mL, 0.30 mol) was added dropwise over 20 minutes a solution of 2,4-difluorobenzenesulfonyl chloride (10 mL, 0.07 mol) in 10 mL of methylene chloride. After stirring at room temperature for 48 hours the reaction was concentrated and purified by flash column chromatography eluting with hexane/ethyl acetate. LCMS Rt=1.21 minutes
MS m/z 277 [MH]+

Preparation 65

3-cyano-4-fluoro-N-(1,2,4-thiadiazol-5-yl)benzenesulfonamide

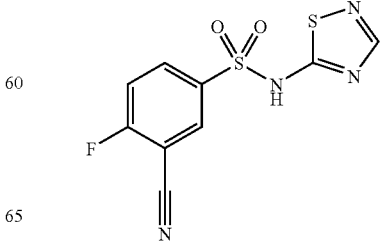

Sodium hydroxide (5.08 g, 0.127 mol) was dissolved in water (60 mL) and 1,4-1,4-dioxane (300 mL). 1,2,4-Thiadiazol-5-amine (10 g, 0.1 mol) was added and the reaction stirred for 5 minutes. 3-Cyano-4-fluorobenzene-1-sulfonyl chloride (8.25 g, 0.0376 mol) was added and the reaction was allowed to stir for 3 hours at 20° C. After this time, the reaction was poured into 150 mL of 1N HCl. This solution was extracted with ethyl acetate (3×50 mL). The combined organics were dried over sodium sulfate, filtered and concentrated to give the title compound as a brown solid. LCMS Rt=1.22 minutes MS m/z 283 [MH]+ $^1$H NMR (d$_6$-DMSO) δ 8.54 (s, 1H), 8.39 (dd, 1H), 8.19 (m, 1H), 7.71 (m, 1H).

Preparation 68

3-cyano-N-(2,4-dimethoxybenzyl)-4-fluoro-N-(1,2,4-thiadiazol-5-yl)benzenesulfonamide

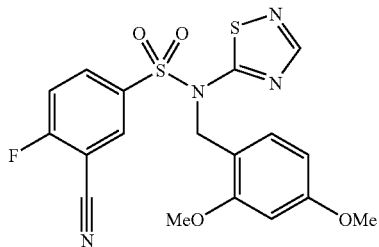

(2,4-Dimethoxy-benzyl)-(1,2,4)thiadiazol-5-yl-amine (Preparation 14, 8.010 g, 0.03200 mol) was dissolved in tetrahydrofuran (100 mL, 1.3 mol) and cooled to −78° C. 1.0 M of Lithium hexamethyldisilazide in tetrahydrofuran (35.2 mL) was added dropwise to the reaction mixture. The cooling bath was removed and the reaction was allowed to stir for 30 minutes. The reaction was cooled back to −78° C. and a solution of 3-cyano-4-fluorobenzenesulfonyl chloride (7.028 g, 0.03200 mol) in tetrahydrofuran (80 mL, 0.99 mol) was added dropwise to the reaction. The reaction was allowed to stir for 30 minutes at −78° C. The reaction was poured into saturated aqueous ammonium chloride. The aqueous phase was extracted with ethyl acetate (three times). The combined organic phase was washed twice with 10% citric acid solution, water and brine. The organic phase was dried over magnesium sulfate and evaporated to a residue. The residue was purified by column chromatography (120 g silica gel column, Hexanes to ethyl acetate gradient elution). Product fractions were combined and evaporated to a residue. The residue was triturated with 10% t-butyl methyl ether in hexanes and the resulting off-white solid collected by filtration and rinsed with hexanes. Vacuum drying gave 3.58 g of the title compound. LCMS Rt=1.66 minutes MS m/z 457 [MNa]+.

MS m/z 151 [MH]+ 2,4-Dimethoxybenzyl $^1$H NMR (d$_6$-DMSO) δ 8.44 (s, 1H), 8.33 (dd, 1H), 8.25 (m, 1H), 7.72 (t, 1H), 7.03 (d, 1H), 6.43 (m, 2H), 5.23 (s, 2H), 3.73 (s, 3H), 3.64 (s, 3H).

Preparation 72 thiazole-4-yl-carbamic acid tert-butyl ester

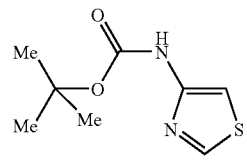

Thiazole-4-carboxylic acid (6.46 g, 50.0 mmol) was slurried in tert-butyl alcohol (280 mL, 2900 mmol). Triethylamine (7.68 mL, 55.1 mmol) and diphenylphosphonic azide (11.9 mL, 55.1 mmol) were added and the reaction was heated at reflux for 18 hours. The reaction was evaporated to a residue. The residue was dissolved in ethyl acetate and washed with water, 5% citric acid (aqueous), water, saturated aqueous sodium bicarbonate and brine. The organic phase was dried over magnesium sulfate and evaporated to a residue. The residue was purified by silica gel chromatography (80 g ISCO™ column, hexanes to ethyl acetate gradient elution). Product fractions were combined and evaporated to a residue. The residue was triturated with 20% methyl t-butyl ether in hexanes. The solid was collected by filtration. Vacuum drying gave 6.48 g of product as a white solid. LCMS Rt=1.46 minutes MS m/z 201 [MH]+

Preparation 88

4-fluoro-2-(1-methyl-1H-pyrazol-5-yl)phenol and 4-fluoro-2-(1-methyl-1H-pyrazol-3-yl)phenol

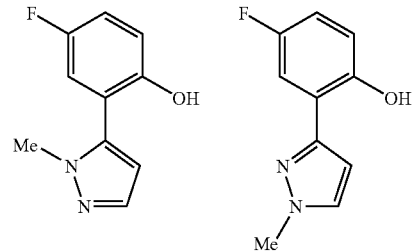

To a suspension of 6-fluorochromone (2.01 g, 0.0122 mol) in ethanol (40 mL) was added methylhydrazine sulfate (1.91 g, 0.0132 mol) and triethylamine (2.2 mL, 0.016 mol). The reaction was heated to reflux for 18 hours. After cooling, the reaction was concentrated in vacuo and the residue purified by flash column chromatography eluting with hexane/ethyl acetate. Two regioisomeric products in a 1:2 A:B ratio were obtained with the major being the less polar and the minor being more polar.

A=4-fluoro-2-(1-methyl-1H-pyrazol-5-yl)phenol

LCMS Rt=1.28 minutes MS m/z 193 [MH]+

1H NMR (CDCl$_3$) δ 7.54 (d, 1H), 7.07-6.91 (m, 4H), 6.33 (d, 1H), 3.78 (s, 3H).

B=4-fluoro-2-(1-methyl-1H-pyrazol-3-yl)phenol
LCMS Rt=1.43 minutes MS m/z 193 [MH]+
1H NMR (CDCl$_3$) δ 10.64 (s, 1H), 7.44 (d, 1H), 7.27 (dd, 1H), 6.97 (m, 2H), 6.59 (d, 1H), 3.99 (s, 3H).

Preparation 89

4-chloro-2-(1-methyl-1H-pyrazol-5yl)phenol and 4-chloro-2-(1-methyl-1H-pyrazol-3-yl)phenol

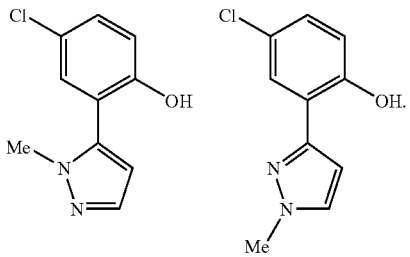

To a suspension of 6-chlorochromone (2.00 g, 0.0111 mol) in ethanol (35 mL) was added methylhydrazine sulfate (1.85 g, 0.0128 mol) and triethylamine (2.0 mL, 0.014 mol). The reaction was heated to reflux for 18 hours. After cooling, the reaction was concentrated in vacuo and the residue purified by flash column chromatography eluting with 0-100% hexane/ethyl acetate gradient. Two regioisomeric products in a 1:4 A:B ratio were obtained with the major being the less polar and the minor being more polar.

A=4-chloro-2-(1-methyl-1H-pyrazol-5-yl)phenol
LCMS Rt=1.43 minutes MS m/z 209 [MH]+
1H NMR (CDCl$_3$) δ 7.65 (d, 1H), 7.34 (dd, 1H), 7.22 (d, 1H), 6.99 (d, 1H), 6.40 (d, 1H), 5.52 (m, 1H), 2.96 (s, 3H).

B=4-chloro-2-(1-methyl-1H-pyrazol-3-yl)phenol
LCMS Rt=1.58 minutes MS m/z 209 [MH]+
1H NMR (CDCl$_3$) δ 10.85 (s, 1H), 7.54 (d, 1H), 7.44 (d, 1H), 7.17 (dd, 1H), 7.00 (d, 1H), 6.61 (d, 1H), 3.98 (s, 3H).

Preparation 92

2-(1-methyl-1H-pyrazol-5-yl)phenol and 2-(1-methyl-1H-pyrazol-3-yl)phenol

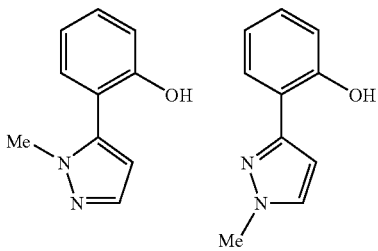

Prepared by the process described by J. Catalan et. al in JACS, 1992, 114, 5039. Two regioisomeric products in a 1:1 A:B ratio were obtained.

A=2-(1-methyl-1H-pyrazol-5-yl)phenol
LCMS Rt=1.31 minutes MS m/z 175 [MH]+
¹H NMR (CDCl$_3$) δ 7.62 (d, 1H), 7.39 (m, 1H), 7.26 (dd, 1H), 7.06 (m, 2H), 6.39 (d, 1H), 6.34 (m, 1H), 3.83 (s, 3H).

B=2-(1-methyl-1H-pyrazol-3-yl)phenol
LCMS Rt=1.45 minutes MS m/z 175 [MH]+
¹H NMR (CDCl$_3$) δ 10.94 (s, 1H), 7.62 (dd, 1H), 7.42 (d, 1H), 7.25 (m, 1H), 7.08 (dd, 1H), 6.95 (m, 1H), 6.64 (d, 1H), 3.98 (s, 3H).

Preparation 190

4-(2-tert-butyl-5-trifluoromethyl-2H-pyrazol-3-yl)-phenol

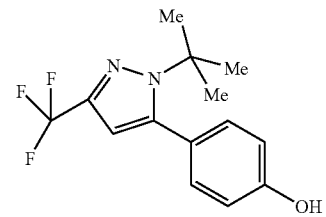

A mixture of 4,4,4-trifluoro-1-(4-hydroxyphenyl)butane-1,3-dione (500 mg, 0.002 mol) and tert-butylhydrazine hydrochloride(270 mg, 0.0022 mol) in ethanol (12 mL, 0.21 mol) was heated at 150° C. in microwave for 1 h. Solvent was removed and the residue was purified via automated flash chromatography (silica gel, 0% to 30% ethyl acetate in hexanes) to give the product as an off-white solid (0.36 g, 60%).
LCMS Rt=1.75 minutes
MS m/z 285 [MH]+

Preparation 205 tert-butyl 4-(5-chloro-2-hydroxyphenyl)-1H-pyrazole-1-carboxylate

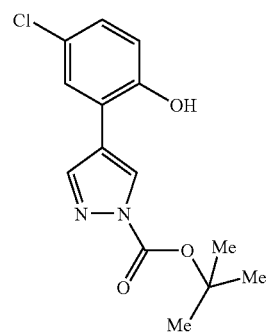

A suspension of 4-chloro-2-iodophenol (200 mg, 0.78 mmol) and potassium carbonate (434 mg, 3.14 mmol) in 1,4-dioxane (3 mL) and water (1 mL) was degassed and heated for 1 hour at 50° C. tert-butyl 4-(4,4,5,5-tetramethyl-1,3,2-dioxaborolan-2-yl)-1H-pyrazole-1-carboxylate (347 mg, 1.18 mmol) and palladium (0) tetrakis(triphenylphoshine) (91 mg, 0.08 mmol) were added and the mixture heated at 50° C. for 5 hours. Dichloromethane (20 ml) and water (10 ml) were added and the organics separated and evaporated in vacuo. The residue was purified by column chromatography (silica gel) eluting with ethyl acetate:heptane (2:8 to 1:0, by volume) to afford the title product as a white solid, 155 mg, 66% yield.

LCMS Rt 3.03 minutes. MS m/z 195 [M$^{35}$Cl(-BOC)H]+
$^1$HNMR (d$_6$-DMSO): δ 1.60 (s, 9H), 6.90 (m, 1H), 7.15 (m, 1H), 7.80 (m, 1H), 8.40 (m, 1H), 8.65 (m, 1H), 10.40 (s, 1H).

Preparation 207

N-(5-Chloro-1,3-thiazol-2-yl)-3-cyano-N-(2,4-dimethoxybenzyl)-4-fluorobenzenesulfonamide

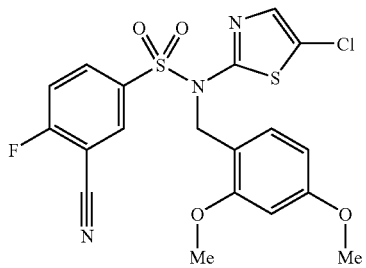

Under an atmosphere of nitrogen, 5-chloro-N-(2,4-dimethoxybenzyl)-1,3-thiazol-2-amine (Preparation 208, 3.0 g 10.5 mmol) was dissolved in tetrahydrofuran (20 ml) and cooled to −70° C. Lithium hexamethyldisilazane (1 M in tetrahydrofuran, 12.6 ml, 12.6 mmol) was added dropwise, keeping the temperature below −60° C. After 5 minutes, the cooling bath was removed and the reaction warmed to room temperature, stirred for a further 5 minutes then cooled back to −70° C. 3-Cyano-4-fluorobenzenesulfonyl chloride (2.54 g, 11.6 mmol) in tetrahydrofuran (10 ml) was added dropwise keeping the temperature below −60° C. and the reaction mixture was warmed to room temperature. Saturated aqueous ammonium chloride solution (50 ml) was added followed by water to dissolve the solid which had precipitated out. The aqueous layer was extracted with ethyl acetate (50 ml) and the organic extracts dried over magnesium sulphate and decolourising charcoal, filtered through Celite™ and the filtrate evaporated in vacuo. The resulting gum was purified using a short column (silica gel, 150 g) eluting with ethyl acetate: heptane (1:1, by volume) affording a gum which was triturated with tert-butyl ether, filtered, washed with heptane and dried in vacuo to give the title compound as a buff solid, 2.84 g, 57% yield.

LCMS Rt=4.65 minutes. MS m/z 468
$^1$HNMR (CDCl$_3$): δ 3.68 (s, 3 H), 3.80 (s, 3 H), 4.99 (s, 2 H), 6.34 (d, 1 H), 6.39 (dd, 1 H), 7.12 (d, 1 H), 7.28 (s, 1 H), 7.31 (t, 1 H), 7.98 (dd, 1 H), 8.05 (m, 1 H). $^{19}$FNMR (CDCl$_3$): δ −98.51 (m, 1 F)

Preparation 208

5-Chloro-N-(2,4-dimethoxybenzyl)-1,3-thiazol-2-amine

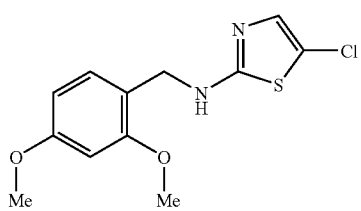

Nitrogen was bubbled through a suspension of 2-amino-5-chlorothiazole hydrochloride (25.0 g, 146 mmol) in dichloromethane (1000 ml) for 10 minutes before the addition of piperidine (13.0 g, 15.0 ml, 150 mmol) via syringe. 2,4-Dimethoxybenzaldehyde (22.1 g, 133 mmol) was added followed by freshly dried 3 Å molecular sieves (ca. 40 g). The mixture was stirred at 45° C. under nitrogen fro 16 hours. Upon cooling to room temperature the mixture was filtered through a pad of Celite™, washing with dichloromethane (2000 ml) before concentrating in vacuo to give a yellow solid, 58.2 g. This residue was dissolved in methanol (1250 ml) and sodium borohydride (13.0 g, 340 mmol) was added portionwise. Upon complete addition the mixture was heated to 50° C. for 30 minutes before cooling to room temperature and stirring under nitrogen for 16 hours. The solvent was concentrated in vacuo and the residue partitioned between ethyl acetate (300 ml) and water (500 ml). The layers were separated and the aqueous was extracted with ethyl acetate (3×300 ml). The combined organics were washed with water (300 ml), saturated aqueous sodium chloride solution (300 ml), dried over magnesium sulphate, filtered and concentrated in vacuo to give a red-brown solid, 41.6 g. This residue was dissolved in ethyl acetate and passed through a plug of silica. Concentration in vacuo afforded a red-brown solid, 39.3 g, which was subsequently triturated with diethyl ether (ca. 500 ml) and stirred for 60 hours. The solid was filtered and air-dried to give the title compound as a white solid, 12.1 g, 32% yield. The mother liquor was concentrated in vacuo to give a brown solid, 25 g, which was stirred in diethyl ether: heptane (2:3, 500 ml). The solid material was filtered and air-dried to give the title compound as an off-white solid, 13.2 g, 35% yield.

$^1$HNMR (d$_6$-DMSO): δ 3.65 (s, 3H), 3.75 (s, 3H), 4.2 (m, 2H), 6.4 (m, 1H), 6.5 (s, 1H), 6.9 (s, 1H), 7.1 (m, 1H), 7.9 (m, 1H).

Preparation 209

N-[1-tert-butyl-4-(5-chloro-2-hydroxyphenyl)-1H-pyrazol-5-yl]-2,2,2-trifluoroacetamide

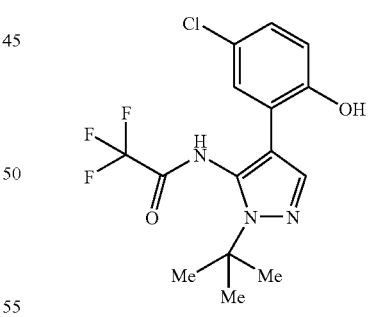

To a solution of (5-chloro-2-methoxy-phenyl)acetonitrile (Preparation 210, 2.154 g, 11.86 mmol) in ethyl formate (20 ml) was added sodium (605 mg, 26.3 mmol). The reaction was heated at a gentle reflux for 16 hours. After cooling to room temperature, water and dichloromethane were added and the solution adjusted to pH 3 with hydrochloric acid (6 M aqueous solution). The layers were separated and the aqueous layer extracted with dichloromethane (2×50 ml). The combined organics were washed with saturated aqueous sodium chloride solution, dried over magnesium sulphate, filtered and evaporated in vacuo. Purification by flash column chromatography eluting with ethyl acetate:hexanes (gradient 0:1 to 1:1, by volume) gave a white solid which was dissolved in ethanol (50 ml), tert-butylhydrazine hydrochloride (1.77 g, 14.2 mmol) added and solution heated to reflux for 24 hours. The reaction was cooled and evaporated in vacuo to give a brown oil. This oil was dissolved in dichloromethane (50 ml) and triethylamine (4.2 ml, 30 mmol) and trifluoroacetic anhydride (4.2 ml, 30 mmol) were added. After stirring for 16 hours, the reaction was washed with potassium hydrogen sulphate (1 N aqueous solution), sodium bicarbonate (1 N aqueous solution) and saturated aqueous sodium chloride solution. The organic layer was separated, dried over magnesium sulphate, filtered and concentrated in vacuo to give a brown oil. This oil was dissolved in dichloromethane (20 ml) and cooled over an ice water bath before the addition of boron tribromide (1 M in dichloromethane, 22 ml, 22 mmol). After stirring for 45 minutes the reaction was added to ice water. The layers were separated and the aqueous layer washed with dichloromethane (2×20 ml). The combined organics were dried over magnesium sulfate, filtered and concentrated in vacuo to give a brown oil. Purification by flash column chromatography eluting with ethyl acetate:hexane (gradient 0:1 to 1:0, by volume) to afford the title compound as a brown oil that solidified to a tan solid upon standing, 2.82 g, 66% yield.

LCMS Rt 1.61 minutes. MS m/z 362 [MH]+

$^1$HNMR (CDCl$_3$): δ 1.69 (s, 9H), 6.87 (m, 1H), 7.16 (m, 2H), 7.64 (s, 1H), 8.74 (s, 1H).

Preparation 210

(5-Chloro-2-methoxy-phenyl)acetonitrile

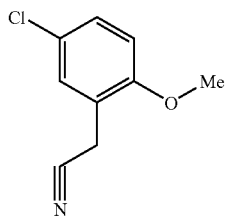

To a solution of methyl 5-chloro-2-methoxybenzoate (25.4 g, 127 mmol) in ether (200 ml), cooled in an ice water bath, was added dropwise lithium tetrahydroaluminate (1 M in diethyl ether, 110 ml, 110 mmol). After 2 hours the reaction was quenched with water and then acidified to pH 3 with hydrochloric acid (6 M aqueous solution). The layers were separated and the organic layer dried over magnesium sulfate, filtered and concentrated in vacuo to give a white solid. The solid was dissolved dichloromethane (200 ml) and treated with thionyl chloride (25 ml, 340 mmol). After heating at reflux for 2 hours, the reaction was cooled to room temperature and water added. The layers were separated and the aqueous layer extracted with dichloromethane (2×50 ml). The combined organics were dried over magnesium sulfate, filtered and concentrated in vacuo to give an orange solid. This solid was dissolved dimethyl sulphoxide (175 ml), sodium cyanide (12.75 g, 260.2 mmol) added and solution heated to 80° C. for 3 hours. After cooling to room temperature, water was added and a solid formed that was filtered and washed with water to provide the title compound as an off white solid, 20.8 g, 91% yield.

LCMS Rt 1.55 minutes.

$^1$HNMR (CDCl$_3$): δ3.70 (s, 2H), 3.90 (s, 3H), 6.84 (d, 1H), 7.30 (m, 1H), 7.39 (m, 1H).

Preparation 211 tert-Butyl [4-(5-fluoro-2-hydroxyphenyl)pyridin-2-yl]carbamate

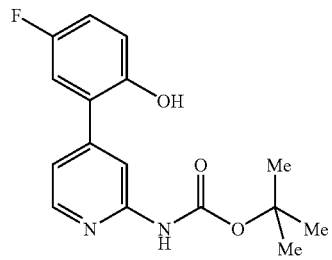

4-Fluoro-2-(4,4,5,5-tetramethyl-1,3,2-dioxaborolan-2-yl)phenol (Preparation 212, 0.082 g, 0.000386 mol), tert-butyl (4-chloropyridin-2-yl)carbamate (0.0588 g, 0.000257 mol), anhydrous sodium carbonate (0.070 g, 0.000660 mol) and palladium (0) tetrakis(triphenylphosphine) (0.029 mg, 0.000025 mol) were suspended in 1,4-dioxane (3.0 ml) and water (1.0 ml). The suspension was stirred at 85° C. for 16 hours before cooling to room temperature. The reaction was diluted with ethyl acetate (10 ml) and organic phase was washed with saturated aqueous sodium bicarbonate solution (2×10.0 ml), dried over sodium sulphate, filtered and concentrated in vacuo. Purification by ISCO™ (12 g SiO$_2$) eluting with ethyl acetate:heptane (gradient 0:1 to 3:7, by volume) afforded the title compound as a solid, 41 mg, 54%.

LCMS Rt=1.40 minutes MS m/z 303 [MH]+

$^1$H NMR (400 MHz, d$_6$-DMSO): δ 1.45 (s, 9H), 6.95 (m, 1H), 7.05 (m, 1H), 7.15 (m, 1H), 7.20 (d, 1H), 8.00 (s, 1H), 8.25 (d, 1H), 9.65 (s, 1H), 9.75 (s, 1H)

Preparation 212

4-Fluoro-2-(4,4,5,5-tetramethyl-1,3,2-dioxaborolan-2-yl)phenol

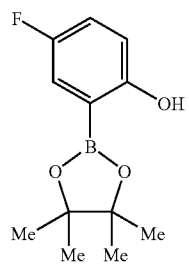

To a suspension of (5-fluoro-2-hydroxyphenyl)boronic acid (1.000 g, 0.00641 mol) in toluene (3.0 ml) was added pinacol (0.875 g, 0.007404 mol). This was heated to reflux using a Dean-Stark apparatus for 24 hours before concentrating in vacuo. The residue was suspended in tert-butyl-methyl ether (10.0 ml) and organic layer was washed with saturated aqueous sodium chloride solution (2×10.0 ml), dried over sodium sulphate, filtered and concentrated in vacuo to afford the title compound as a translucent oil, 1.4 g, 92% yield.

1HNMR (CDCl3): δ 1.35 (s, 12 H), 6.80 (dd, 1 H), 7.05 (dt, 1 H), 7.35 (dd, 1 H), 7.60 (s, 1 H).

Preparation 217

N-(5-Chloro-1,3-thiazol-2-yl)-3-cyano-N-(2,4-dimethoxybenzyl)-4-(4-fluoro-2-iodophenoxy)benzenesulfonamide

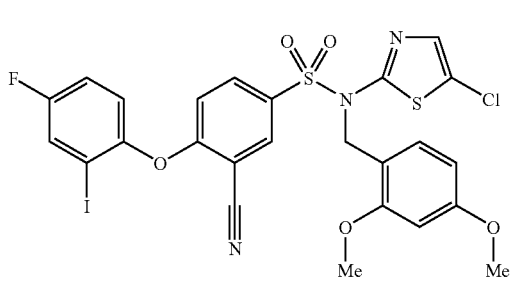

N-(5-Chloro-1,3-thiazol-2-yl)-3-cyano-N-(2,4-dimethoxybenzyl)-4-fluorobenzenesulfonamide (Preparation 207, 410 mg, 0.876 mmol), 2-iodo-4-fluorophenol (Preparation 218, 229 mg, 0.964 mmol) and potassium carbonate (363 mg, 2.63 mmol) in dimethyl sulphoxide (20 ml) were stirred at room temperature under nitrogen for 18 hours. The reaction mixture was poured into water (50 ml) and extracted with ethyl acetate (3×30 ml). The combined organics were washed with saturated aqueous sodium chloride solution (30 ml), dried over magnesium sulfate, filtered and concentrated in vacuo to give the title compound as an off-white solid, 670 mg, quantitative yield.

LCMS $R_t$ 3.50 minutes.

1HNMR (d6-DMSO): δ 3.6 (s, 3H), 3.7 (s, 3H), 4.9 (s, 2H), 6.4 (m, 2H), 6.8 (m, 1H), 7.0 (m, 1H), −7.4 (m, 2H), 7.55 (s, 1H), 7.9 (m, 1H), 8.0 (m, 1H), 8.35 (m, 1H).

Preparation 218

4-Fluoro-2-iodophenol

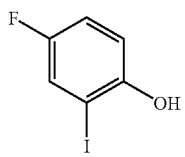

N-Iodosuccinimide (10 g, 45.0 mmol) and 4-fluoro-phenol (5.00 g, 40.0 mmol) were suspended in acetic acid (39 ml, 649.0 mmol) and stirred for 5 minutes before addition of concentrated sulphuric acid (0.79 ml, 13.4 mmol). The reaction mixture was stirred for 18 hours at room temperature before diluting with water (100 ml). The aqueous layer was extracted with dichloromethane (2×30 ml). The combined organic extracts were washed with sodium thiosulphate solution (20% aqueous, wt:v), water, dried over sodium sulfate, filtered and concentrated in vacuo. The crude residue was purified by column chromatography (silica gel) eluting with toluene to afford the title compound as an off white solid, 4.5 g, 40% yield.

LCMS Rt=1.33 minutes. MS m/z 237 [MH]−
1H NMR (400 MHz, CDCl3) δ: 5.22 (s, 1H), 6.99 (m, 2H), 7.42 (dd, 1H) ppm.

Preparation 219

4-(4-Chloro-2-iodophenoxy)-N-(5-chloro-1,3-thiazol-2-yl)-3-cyanobenzenesulfonamide

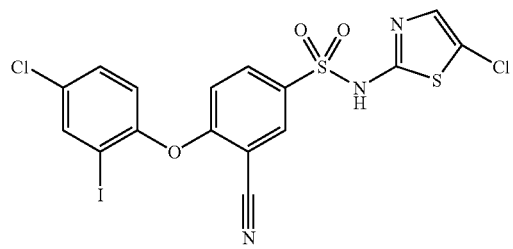

To a stirred suspension of 4-chloro-2-iodophenol (305 mg, 1.20 mmol) and potassium carbonate (207 mg, 1.5 mmol) in dimethyl sulphoxide (5.0 ml) was added N-(5-chloro-1,3-thiazol-2-yl)-3-cyano-N-(2,4-dimethoxybenzyl)-4-fluorobenzenesulfonamide (Preparation 207, 468 mg, 1.00 mmol). Suspension stirred at room temperature for 18 hours. The reaction mixture was poured into ethyl acetate (20 ml) and saturated aqueous ammonium chloride solution (20 ml) and the aqueous layer extracted with ethyl acetate (3×20 ml). Combined organic layers were dried over magnesium sulfate and concentrated in vacuo. The crude residue was dissolved in dichloromethane (5 ml), trifluoroacetic acid (5 ml) was added and the reaction mixture was stirred at room temperature for 2 hours. The solvent was concentrated in vacuo and purified by ISCO™ preparative system eluting with dichloromethane:ethyl acetate (gradient 1:0 to 6:4, by volume) to afford the title compound as a solid, 396 mg, 72% yield.

LCMS Rt 3.43 minutes. MS m/z 552 $[M^{35}ClH]^+$
1HNMR (d6-DMSO): δ 6.86 (d, 1H), 7.43 (d, 1H), 7.55 (s, 1H), 7.62 (dd, 1H), 7.99 (dd, 1H), 8.09 (d, 1H), 8.29 (d, 1H).

Preparation 221

(2E)-3-(Dimethylamino)-1-(5-fluoro-2-hydroxyphenyl)prop-2-en-1-one

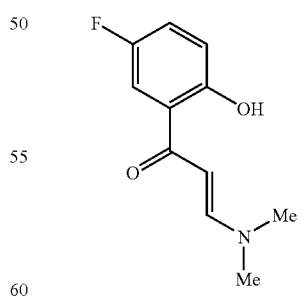

To a solution of 4-fluoro-2-hydroxyacetophenone (13.0 g, 84.4 mmol) in isopropanol (150 ml), was added dimethylformamide dimethylacetal (20.1 g, 169 mmol). The resulting yellow solution was heated at 45° C. without stirring for 18 hours before cooling to room temperature. The resulting crystalline yellow solid was isolated by filtration and washed with

Preparation 224

2-Iodo-4-(trifluoromethyl)phenol

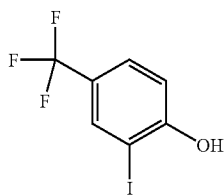

To a suspension of N-iodosuccinimide (11.10 g, 49.5 mmol) in glacial acetic acid (40 ml) was added 4-trifluoromethyl phenol (8.02 g, 49.5 mmol) and, after 5 minutes, concentrated sulphuric acid (0.87 ml, 14.8 mmol). The pale brown/red suspension was stirred at room temperature under nitrogen for 48 hours before diluting with water and extracting with dichloromethane. The organic extract was washed with water, saturated aqueous sodium thiosulphate solution, water, dried over magnesium sulphate before decolourising charcoal added. The suspension was left to stand for 10 minutes before filtering through a short pad of silica gel eluting with dichloromethane. The solvent was evaporated in vacuo to give an oil which was purified by flash column chromatography on silica eluting with dichloromethane to give the title compound as a pale yellow oil, 9.017 g, 63% yield.

LCMS Rt=1.53 minutes. MS m/z 287 [MH]⁻

$^1$H NMR (400 MHz, CDCl$_3$): δ 5.79 (br s, 1H), 7.05 (d, 1H), 7.51 (dd, 1H), 7.93 (d, 1H) ppm.

Method 2

Preparation 224 can also be prepared as follows.

N-iodosuccinimide (69.5 g, 0.309 moles) was suspended in acetic acid (257 mL) and cooled to 0° C. 4-Trifluoromethylphenol (50.0 g, 0.310 moles) was added followed by sulphuric acid (5.44 mL) dropwise over 5 minutes. The orange-brown suspension was stirred whist warming slowly to room temperature over 18 hours. A further portion of N-iodosuccinimide (2.5 g, 0.011 moles) was added and the mixture was stirred at room temperature for 24 hours. The reaction was quenched by adding water (150 mL) and extracted with dichloromethane (2×100 mL). The combined organics were washed with a saturated aqueous solution of sodium metabisulphite (2×50 mL) and then with saturated aqueous sodium chloride solution (50 mL). The organics were dried over anhydrous magnesium sulphate, filtered and the solvents removed in vacuo to give the crude title product as a light yellow oil. This batch was combined with the products from two further identical reactions and purified by distillation in vacuo. The product was collected boiling at approximately 45° C. at 2mBar to give the title compound as a pink-orange semi-solid (216 g).

LCMS Rt=2.89 minutes. MS m/z=287 [M−H]−

$^1$HNMR (CDCl$_3$): δ5.62 (br s, 1H), 7.03 (d, 1H), 7.51 (d, 1H), 7.92 (s, 1H).

Preparation 226

2-Iodo-4-(trifluoromethoxy)phenol

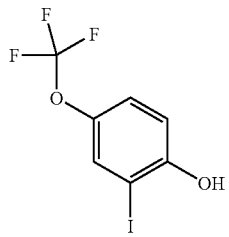

To a suspension of N-iodosuccinimide (6.95 g, 31 mmol) in glacial acetic acid (2 ml) was added 4-trifluoromethoxy phenol (4.0 ml, 31 mmol) and, after 5 minutes, concentrated sulphuric acid (0.5 ml, 9 mmol). The pale brown suspension was stirred at room temperature under nitrogen for 48 hours before diluting with water and extracting with dichloromethane. Organic extract was washed with water, saturated aqueous sodium thiosulphate solution, water, dried over magnesium sulfate and decolourising charcoal added. The resulting suspension was left to stand for 30 minutes before filtering through a short pad of silica gel eluting with dichloromethane. The solvent was evaporated in vacuo to give the title compound as an oil, 8.78 g, 94% yield.

LCMS Rt=1.51 minutes. MS m/z 303 [MH]−

$^1$H NMR (400 MHz, CDCl$_3$): δ 5.49 (br s, 1H), 6.99 (d, 1H), 7.15 (dd, 1H), 7.55 (d, 1H) ppm.

Preparation 231 tert-Butyl 4-(5-chloro-2-hydroxyphenyl)piperidine-1-carboxylate

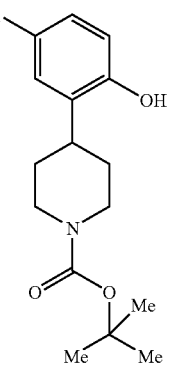

To a suspension of 4-chloro-2-piperidin-4-ylphenol hydrobromide (Preparation 232, 100 mg, 0.342 mmol) and N-ethyl-N-isopropylpropan-2-amine (65.5 μl, 0.376 mmol) in dichloromethane (5 ml) at 0° C. was added dropwise a solution of di-tert-butyl dicarbonate (82.9 mg, 0.376 mmol) in dichloromethane (1 ml). The resulting mixture was warmed to room temperature and stirred for 16 hours. Water (1 ml) was added and stirred for 5 minutes before filtering through a phase separating cartridge. The organics were evaporated in vacuo to afford the title compound as a pale cream solid, 110 mg, 100% yield.

LCMS Rt 1.64 minutes. MS m/z 310 [MH]−

$^1$HNMR (CDCl$_3$): δ 1.51 (m, 9H), 1.61 (m, 2H), 1.82 (d, 2H), 2.83 (t, 2H), 3.0 (m, 1H), 4.25 (d, 2H), 6.69 (d, 1H), 7.04 (dd, 1H), 7.10 (d, 1H).

Preparation 232

4-Chloro-2-piperidin-4-ylphenol hydrobromide

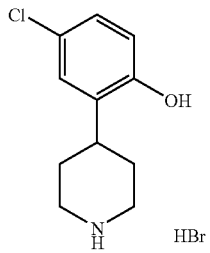

To 4-(5-chloro-2-methoxyphenyl)piperidine (Preparation 233, 40 g, 0.177 mol) was added hydrogen bromide (48% in water, 100 ml) and refluxed for 24 hours before concentrating in vacuo. 1,4-Dioxane was added and solution concentrated in vacuo. The resulting crystals were washed with diethyl ether and dried in vacuo to give the title compound as white crystals, 53 g, 97% yield.

LCMS (7.5 minute acid run) ESI m/z 212 [M$^{35}$ClH]$^+$ Rt 2.25 minutes.

$^1$HNMR (d$_6$-DMSO): δ 1.80 (m, 4H), 3.10 (m, 3H), 3.35 (m, 2H), 6.84 (d, 1H), 7.02 (m, 1H), 7.11 (m, 1H), 8.30 (brs, 1H), 8.62 (brs, 1H), 9.80 (s, 1H).

Preparation 233

4-(5-Chloro-2-methoxyphenyl)piperidine

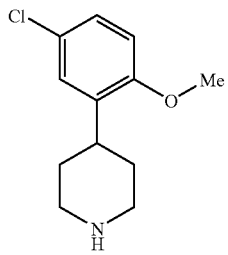

A solution of benzyl 4-(5-chloro-2-methoxyphenyl)piperidine-1-carboxylate (Preparation 234, 73 g, 0.2 mol) in concentrated hydrochloric acid (200 ml) was refluxed with stirring for 2 hours before concentrating in vacuo. Water (100 ml), sodium hydroxide (10 M aqueous solution, 20 ml) and chloroform (200 ml) were added to the residue. The aqueous layer was extracted with chloroform (2×200 ml). The combined organic layers were washed with water (200 ml), saturated aqueous sodium chloride solution (200 ml), dried over sodium sulphate, filtered through silica gel (100 g, 40/63 μm) and evaporated in vacuo to afford the title compound as white crystals, 40 g, 89% yield.

Preparation 234

Benzyl 4-(5-chloro-2-methoxyphenyl)piperidine-1-carboxylate

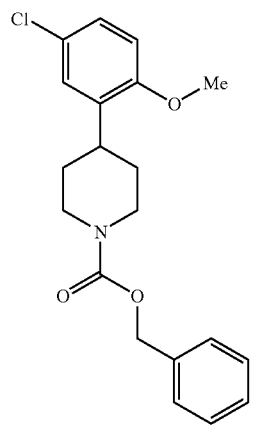

To a solution of tert-butyl 4-(5-chloro-2-methoxyphenyl)-4-hydroxypiperidine-1-carboxylate (Preparation 235, 90 g, 0.263 mol) in 1,4-dioxane (200 ml) was added hydrogen chloride (4 M in dioxane, 150 ml, 0.6 mol) under argon. The mixture was stirred for 24 hours and evaporated in vacuo. Diethyl ether was added before concentrating in vacuo. Water (300 ml) and diethyl ether (500 ml) were added to this residue before the addition of sodium carbonate (32 g, 0.3 mol) under vigorous stirring. Mixture cooled over an ice bath before the dropwise addition of benzyl chlorocarbonate (43 ml, 0.3 mol). The bath was removed and the mixture stirred for 1 hour. The aqueous layer was extracted with ether (2×200 ml). The combined organic layers were washed with water (200 ml), saturated aqueous sodium chloride solution (200 ml), dried over sodium sulfate, filtered through silica gel (100 g, 40/63 μm) and evaporated in vacuo. 1,4-Dioxane was added and concentrated in vacuo before diluting with dichloromethane (300 ml). Triethylsilane (132 ml, 0.828 mol) and trifluoroacetic acid (96 ml, 1.24 mol) were added under argon and the mixture was stirred for 20 hours before concentrating in vacuo. To this residue were added saturated aqueous potassium carbonate solution to basify the solution to pH 10. Water (200 ml) was added and the aqueous layer was extracted with diethyl ether. The combined organic fractions were washed with water (2×200 ml), saturated aqueous sodium chloride solution (200 ml), dried over sodium sulphate, filtered through silica gel (100 g, 40/63 μm) and evaporated in vacuo. 1,4-dioxane was added to this residue before concentrating in vacuo. To a solution of this residue in tetrahydrofuran (300 ml), cooled over an ice bath in an atmosphere of argon, was added borane (1 M in tetrahydrofuran, 260 ml). The mixture was stirred at room temperature for 2 hours before cooling over an ice bath in argon and adding acetic acid (260 ml). The mixture was stirred for 24 hours before evaporating in vacuo. To this residue were added saturated aqueous potassium carbonate solution to basify the solution to pH 10. Water (200 ml) was added and the aqueous layer was extracted with diethyl ether. The organic fractions were washed with water (2×200 ml), saturated aqueous sodium chloride solution (200 ml), dried over sodium sulfate and evaporated in vacuo. The residue was purified on silica gel (500 g, 60/100 μm) eluting with carbon tetrachloride:ethyl acetate (gradient 1:0 to 10:1, by volume) to give the title compound as a yellow oil, 73 g, 77% yield.

Preparation 235 tert-Butyl 4-(5-chloro-2-methoxyphenyl)-4-hydroxypiperidine-1-carboxylate

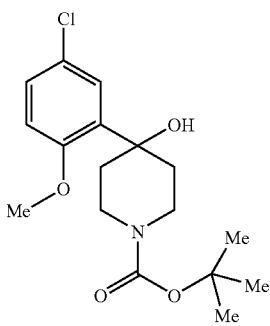

To a stirred solution of 2-bromo-4-chloroanisole (164 g, 0.74 mol) in tetrahydrofuran (1 L), cooled at −70° C. and under an atmosphere of argon, was added butyl lithium (2.7 M in heptane, 280 ml) over a period of 1 hour. The mixture was stirred for 30 minutes, maintaining the temperature at −70° C., before the addition of N-boc-4-piperidone (145 g, 0.73 mol) in tetrahydrofuran (250 ml) over a period of 1 hour. The reaction temperature was warmed to −40° C. over 2 hours before the addition of sodium hydrogen sulphate (5M aqueous, 160 ml), sodium sulphate (300 g) and hexane (500 ml). The mixture was stirred for 10 hours. The organic layer was decanted, filtered through silica gel (300 g, 63/100 μm) washing with ethyl acetate:hexane (4:6, by volume, 2×400 ml). The filtrate was evaporated in vacuo and the residue recrystallized from ethyl acetate:hexane to afford the title compound as white crystals, 100 g, 39% yield.

Preparation 237 tert-Butyl 3-(5-chloro-2-hydroxyphenyl)azetidine-1-carboxylate

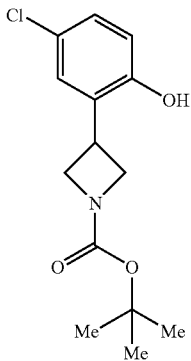

To a solution of tert-Butyl 3-(2-{[tert-butyl(dimethyl)silyl]oxy}-5-chlorophenyl)azetidine-1-carboxylate (Preparation 238, 3.1 g, 7.79 mmol) in tetrahydrofuran (80 ml) was added tetramethylammonium fluoride (1.0 g, 10.74 mmol). The mixture was stirred at room temperature for 18 hours before concentrating in vacuo. The residue was partitioned between tert-butyl methyl ether (100 ml) and aqueous sodium hydroxide solution. The organics were dried over sodium sulfate, filtered and evaporated in vacuo to give a reddish brown oil, 2.33 g. This was purified by column chromatography (100 g of silica) eluting with heptane:ethyl acetate (6:4, by volume) to afford the title compound as a reddish brown gum, 850 mg, 38% yield.

LCMS Rt 1.52 minutes. MS m/z 282 $[M^{35}ClH]^+$.
$^1$HNMR (CDCl$_3$): δ1.44 (s, 9H), 3.93 (m, 1H), 4.04 (m, 2H), 4.28 (m, 2H), 6.72 (d, 1H), 7.05 (m, 2H).

Preparation 238 tert-Butyl 3-(2-{[tert-butyl(dimethyl)silyl]oxy}-5-chlorophenyl)azetidine-1-carboxylate

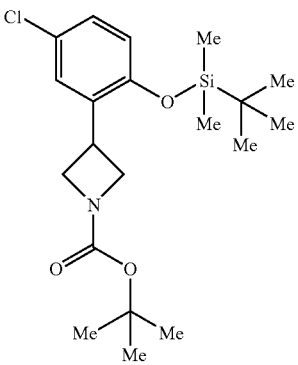

Zinc powder (700 mg, 10.7 mmol) was suspended in N,N-dimethylformamide (20 ml) under nitrogen. 1,2-dibromoethane (120 ul) was added and suspension heated to 60° C. for 10 minutes before cooling to room temperature. Chlorotrimethylsilane (180 ul) was added and the mixture heated to 60° C. for 10 minutes then cooled to room temperature. tert-Butyl 3-iodoazetidine-1-carboxylate (3.0 g, 10.6 mmol) was added with a slight-exotherm observed. The mixture was stirred at room temperature for 1 hour before the addition of tert-butyl (4-chloro-2-iodophenoxy)dimethylsilane (Preparation 239, 2.2 g, 5.97 mmol) followed immediately by tri-2-furylphosphine (250 mg, 1.08 mmol) and (1E, 4E)-1,5-diphenylpenta-1,4-dien-3-one-palladium (2:1) (300 mg, 0.52 mmol). The mixture was stirred at room temperature for 30 minutes then heated at 70° C. for 5 hours before concentration in vacuo. The residue was partitioned between ethyl acetate (100 ml) and aqueous sodium carbonate solution (50 ml). The organic extract was dried over sodium sulphate, filtered and evaporated in vacuo to afford the title compound as a brown oil, 3.2 g, LCMS Rt 1.68 minutes. MS m/z 795 $[M^{35}ClH]+$

Preparation 239 tert-Butyl(4-chloro-2-iodophenoxy)dimethylsilane

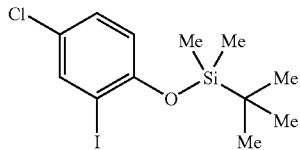

To a solution of 4-chloro-2-iodophenol (1.587 g, 6.238 mmol) in dichloromethane (10 ml) was added 1H-imidazole (1.01 g, 14.3 mmol) followed by a solution of tert-butyl (chloro)dimethylsilane (2.63 ml, 13.7 mmol) in dichloromethane (10 ml) dropwise. The resulting white suspension was stirred for 16 hours at room temperature before concentrating in vacuo. The residue was diluted with ethyl acetate (20 ml) and water (20 ml). The aqueous phase was acidified with hydrochloric acid (2 M aqueous solution) and extracted with ethyl acetate. The combined organic layers were washed with hydrochloric acid (2 M aqueous solution), saturated aqueous sodium chloride solution, dried over sodium sulfate, filtered and concentrated in vacuo. The residue was purified by column chromatography (40 g silica gel column) eluting with ethyl acetate:heptane (gradient 0:1 to 3:7, by volume) to afford the title compound as pale yellow oil, 2.2 g, 95% yield.

$^1$HNMR (CDCl$_3$): δ 0.28 (s, 6H), 1.07 (s, 9H), 6.74 (d, 1H), 7.18 (dd, 1H), 7.74 (dd).

Preparation 240

N-(5-Chloro-1,3-thiazol-2-yl)-3-cyano-4-(4-fluoro-2-iodophenoxy)benzenesulfonamide

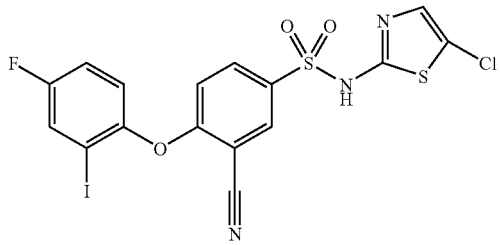

To a solution of N-(5-Chloro-1,3-thiazol-2-yl)-3-cyano-4-fluorobenzenesulfonamide (Preparation 52, 100 mg, 0.32 mmol) and potassium carbonate (109 mg, 0.8 mmol) in dimethylformamide (3 ml) was added 4-fluoro-2-iodophenol (Preparation 218, 0.32 mmol) and the reaction heated at 80° C. for 24 hours. The solution was added dropwise into rapidly stirring hydrochloric acid (2M aqueous solution). The fine dark precipitate was filtered and dried in vacuo to afford the title product as a brown solid, 100 mg, 59% yield.

LCMS Rt 1.59 minutes. (ESI) m/z 536 [M$^{35}$ClH]$^+$.
$^1$HNMR (d$_6$-DMSO): δ6.81 (d, 1H), 7.46 (m, 2H), 7.57 (s, 1H), 7.92 (m, 1H), 8.00 (m, 1H), 8.29 (s, 1H), 13.03 (brs, 1H).

Preparation 247

5-Chloro-N-(2,4-dimethoxybenzyl)-2,4-difluoro-N-1,3,4-thiadiazol-2-ylbenzenesulfonamide

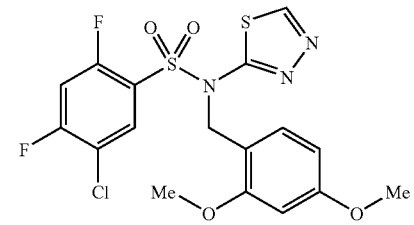

To a solution of N-(2,4-dimethoxybenzyl)-1,3,4-thiadiazol-2-amine (Preparation 248, 899 mg, 3.58 mmol) in tetrahydrofuran (6.0 mL), cooled to −78° C., was added lithium hexamethyldisilazide (1.0 M in tetrahydrofuran, 4.3 mL) dropwise. The reaction was stirred for 35 minutes at room temperature, cooled to −78° C. before the dropwise addition of 5-chloro-2,4-difluorobenzenesulfonyl chloride (850 mg, 0.0034 mol). The reaction mixture was stirred at −78° C. for 1 hour then at room temperature for 4 hours. The reaction mixture was poured into saturated aqueous ammonium chloride solution and extracted with dichloromethane. The combined organic layers were washed with saturated aqueous sodium chloride solution, dried over magnesium sulfate, filtered and concentrated in vacuo. The residue was purified by automated flash chromatography eluting with ethyl acetate: hexanes (gradient 0:1 to 1:0, by volume) to afford the title compound as a white solid, 1.16 g, 73% yield.

LCMS Rt=1.76 minutes. MS m/z 484 [M$^{35}$ClNa]+
$^1$HNMR (CDCl$_3$): δ3.71 (s, 3H), 3.78 (s, 3H), 5.35 (m, 2H), 6.26 (m, 1H), 6.38 (m, 1H), 6.99 (m, 1H), 7.27 (m, 1H), 7.83 (m, 1H), 8.87 (m, 1H).
Method 2

Preparation 247 can also be prepared as follows.
N-(2,4-Dimethoxybenzyl)-1,3,4-thiadiazol-2-amine (Preparation 248, 203.4 g, 0.809 moles) was dissolved in 2-methyltetrahydrofuran (1.63 L) and the yellow suspension was cooled to −38° C. to −45° C. Lithium bis(trimethylsilyl) amide (890 mL of 1 molar solution in tetrahydrofuran, 0.890 moles) was added slowly over 15 minutes keeping the temperature between −38° C. and −45° C. to give an orange suspension. This orange suspension was stirred at −38° C. to −45° C. for 45 minutes and then a solution of 5-chloro-2,4-difluorobenzenesulfonyl chloride, (200 g, 0.809 moles) in 2-methyltetrahydrofuran (407 mL) was added slowly over 20 minutes keeping the temperature between −38° C. and −45° C. to give an orange suspension. The mixture was stirred whist warming to 15° C. over 1 hour. The reaction was quenched by adding a solution of, ammonium chloride (203.4 g, 3.80 moles) in water (1.02 L) and stirred vigorously for 5 minutes. The stirring was stopped and the phases allowed to separate. The lower layer was removed and the organic layer was washed with water (813.6 mL). The organic layer was concentrated in vacuo to give an orange solid which was triturated with isopropyl acetate (1.22 L) to give the title compound as a yellow-orange solid (218.6 g).

LC Rt=1.76 minutes. MS m/z 484 [M$^{35}$ClNa]+

$^1$HNMR (CDCl$_3$): δ3.71 (s, 3H), 3.78 (s, 3H), 5.35 (m, 2H), 6.26 (m, 1H), 6.38 (m, 1H), 6.99 (m, 1H), 7.27 (m, 1H), 7.83 (m, 1H), 8.87 (m, 1H).

Preparation 248

N-(2,4-Dimethoxybenzyl)-1,3,4-thiadiazol-2-amine

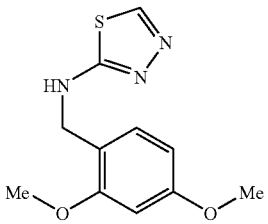

To a solution of 2-amino-1,3,4-thiadiazole (3.05 g, 0.0302 mol) and 2,4-dimethoxy-benzaldehyde (4.55 g, 0.0274 mol) in dichloromethane (125 mL) was added chlorotriisopropoxytitanium (16 mL, 0.067 mol) portionwise over 5 minutes. After stirring for 1 hour, sodium triacetoxyborohydride (11.72 g, 0.05530 mol) was added portion wise and stirred for 24 hours. The reaction was quenched with saturated aqueous sodium bicarbonate solution and adjusted to pH 9 with sodium hydroxide (6 N aqueous solution) and extracted with dichloromethane. The combined organic extracts were dried over magnesium sulfate, filtered and concentrated in vacuo. The residue was purified by flash column chromatography eluting with methanol:dichloromethane (gradient 0:1 to 1:9, by volume) to afford the title compound as a white solid, 590 mg, 45% yield.

LCMS Rt=1.36 minutes. MS m/z 252 [MNa]+

$^1$HNMR (CDCl$_3$): δ3.86 (s, 3H), 3.90 (s, 3H), 4.49 (m, 2H), 6.08 (br s, 1H), 6.47 (m, 2H), 7.27 (m, 1H), 8.39 (s, 1H).

Method 2

Preparation 248 can also be prepared as follows.

2,4-Dimethoxybenzaldehyde (771.37 g, 4.64 moles) was added to a suspension of 2-amino-1,3,4-thiadiazole (391.2 g, 3.87 moles) in xylene (5.87 L) and heated to reflux. Dean-Stark apparatus was used to remove the water and the reaction was stirred overnight. After cooling to room temperature, the reaction was further cooled to 5° C. and diluted with 2-methyltetrahydrofuran (2.93 L). Sodium tetrahydroborate (73.17 g, 1.93 moles) was added as a single portion. Methanol (782.8 mL) was then added slowly over 30 minutes, maintaining the temperature below 15° C. After a further 30 minutes water (1 L) was added followed by saturated aqueous sodium hydrogencarbonate solution (1 L) and the mixture stirred at room temperature overnight. The biphasic mixture was diluted with 2-methyltetrahydrofuran and heated to 43° C. to aid dissolution. The layers were separated and the organic layer washed with water (3 L) before concentrating in vacuo. The resulting solid was slurried in heptanes (2.5 L), homogenised, filtered, washed with tert-butylmethyl ether and dried to afford 715 g of the title compound.

LC Rt=1.36 minutes. MS m/z 252 [MNa]+

$^1$HNMR (d$_6$-DMSO): δ3.75 (s, 3H), 3.80 (s, 3H), 4.37 (d, 2H), 6.49 (m, 1H), 6.58 (s, 1H), 7.19 (d, 1H), 7.97 (m, 1H), 8.59 (s, 1H).

Preparation 250 tert-Butyl [(3-cyano-4-fluorophenyl)sulfonyl]1,3-thiazol-4-ylcarbamate

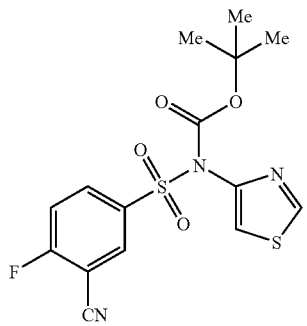

To a stirred solution of tert-butyl 1,3-thiazol-4-ylcarbamate (Preparation 72, 0.500 g, 0.002497 mol) in tetrahydrofuran (10.0 mL) was added lithium 1,1,1,3,3,3-hexamethyldisilazan-2-ide (1.0 M solution in tetrahydrofuran, 2.50 mL, 0.0025 mol) at 0° C. under nitrogen. After stirring for 1 hour at 0° C. the reaction mixture was cooled to −78° C. and 3-cyano-4-fluorobenzenesulfonyl chloride (0.453 g, 0.002063 mol) in tetrahydrofuran (5.0 mL) was added. The mixture was warmed to room temperature for 16 hours. Saturated aqueous ammonium chloride solution (20.0 mL) was added and the aqueous layer was extracted with ethyl acetate (3×20.0 mL). Combined organic layers were dried over sodium sulfate and concentrated in vacuo. This crude residue was purified using ISCO™ (12 g SiO$_2$) eluting with ethyl acetate:dichloromethane (gradient 0:1 to 3:7, by volume) to afford the title compound as a white solid, 426 mg, 54% yield.

LCMS Rt=1.53 minutes MS m/z 284 [MH(-Boc)]+

$^1$H NMR (400 MHz, d$_6$-DMSO): δ 1.25 (s, 9H), 7.90 (t, 1H), 8.15 (s, 1H), 8.40 (m, 1H), 8.55 (d, 1H), 9.15 (s, 1H)

Preparation 255 tert-Butyl {[4-(4-chloro-2-iodophenoxy)-3-cyanophenyl]sulfonyl}1,3-thiazol-4-ylcarbamate

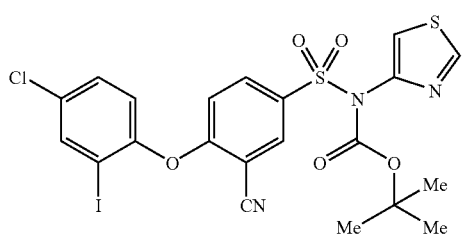

To a suspension of potassium carbonate (0.0549 g, 0.000397 mol) in N,N-dimethylformamide (3.0 mL) was added tert-butyl [(3-cyano-4-fluorophenyl)sulfonyl]1,3-thiazol-4-ylcarbamate (Preparation 250, 0.1004 g, 0.000167 mol) and stirred at room temperature under nitrogen for 10 minutes. 4-chloro-2-iodophenol (0.067 g, 0.000263 mol) was added and stirred at room temperature for 16 hours. The reaction was diluted with ethyl acetate (10.0 mL). The organic phase was washed saturated aqueous sodium chloride solution (2×10.0 mL), dried over sodium sulfate, filtered and concentrated in vacuo to afford the title compound as a yellow oil, 162 mg, 100% yield.

LCMS Rt=1.78 minutes MS m/z 618 [M$^{35}$ClH]+

$^1$H NMR (400 MHz, d$_6$-DMSO): δ 1.25 (s, 9H), 7.00 (d, 1H), 7.50 (d, 1H), 7.65 (d, 1H), 7.90 (s, 1H), 8.10 (s, 1H), 8.20 (d, 1H), 8.55 (s, 1H), 9.15 (s, 1H)

Preparation 258

2-(2-aminopyridin-4-yl)-4-chlorophenol

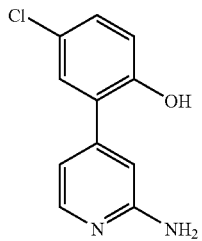

A suspension of 2-amino-4-chloropyridine (13 g, 101.12 mmol), (5-chloro-2-hydroxy)benzeneboronic acid (20.9 g, 121 mmol), tetrakis triphenylphosphine palladium (11.7 g, 10.1 mmol) and sodium carbonate (42.9 g, 404 mmol) in water (120 mL) and 1,4-dioxane (360 mL) was heated to 90° C. under nitrogen for 24 hours. The reaction was cooled, concentrated in vacuo and the residue was extracted into ethyl acetate (500 mL) before filtration. The filtrate was washed with 2N HCl (aqueous, 500 mL) and water (700 mL). The combined aqueous layer was basified with saturated aqueous sodium bicarbonate solution (1500 mL) before extracting into ethyl acetate twice (2×800 mL). The organic layer was dried over sodium sulphate and concentrated in vacuo. The residue was purified using silica gel column chromatography (2-12% methanol in dichloromethane) to afford the title compound as a yellow solid, 11.13 g, 50%.

LCMS Rt=1.58 minutes. MS m/z 221 [M$^{35}$ClH]+

$^1$H NMR (400 MHz, d$_6$-DMSO): δ 5.80 (br s, 2H), 6.60 (m, 2H), 6.95 (m, 1H), 7.20 (m, 1H), 7.90 (m, 1H), 9.95 (m, 1H).

Preparation 297 tert-Butyl 1,3-thiazol-4-yl[(2,4,5-trifluorophenyl)sulfonyl]carbamate

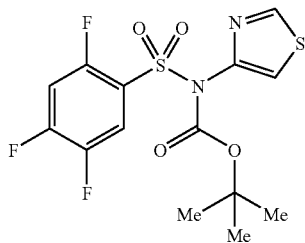

To a solution of tert-butyl 1,3-thiazol-4-ylcarbamate (Preparation 72, 28.94 g, 144.55 mmol) in anhydrous tetrahydrofuran (600 ml), cooled to −70° C., under nitrogen was added lithium 1,1,1,3,3,3-hexamethyldisilazan-2-ide (1 M in tetrahydrofuran, 144.55 ml, 144.55 mmol) dropwise. The reaction mixture was warmed to room temperature and stirred for 1 hour before cooling −70° C. 2,4,5-trifluro benzenesulfonyl chloride (40 g, 173.46 mmol) in tetrahydrofuran (80 ml) was added dropwise and then the reaction mixture was slowly warmed to room temperature and stirred for 2 hours. The reaction mixture was quenched with saturated aqueous ammonium chloride solution and extracted with ethyl acetate. Organic layer was washed with water and saturated aqueous sodium chloride solution before concentrating in vacuo. The crude residue was purified by column chromatography eluting with ethyl acetate:hexane (gradient 1:19 to 3:17, by volume) to afford the title compound as white solid, 37 g, 64% yield.

LCMS Rt=3.46 minutes MS m/z 395 [MH]+

$^1$H NMR (400 MHz, CDCl$_3$): δ 1.35 (s, 9H), 7.07-7.13 (m, 1H), 7.52 (s, 1H), 8.00-8.06 (m, 1H), 8.78 (s, 1H).

Preparation 301

3-Cyano-4-fluoro-N-(5-fluoropyridin-2-yl)benzenesulfonamide

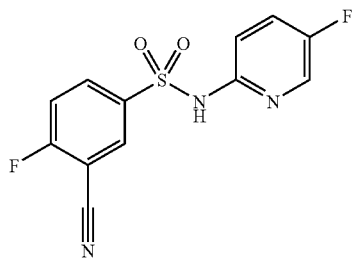

3-Cyano-4-fluorobenzenesulfonyl chloride (5 g, 20 mmol), 5-fluoropyridin-2-amine (3.37 g, 30 mmol) and pyridine (4.87 mL, 60 mmol) in dichloromethane (100 mL) were stirred at room temperature for 2 hours before concentrating in vacuo. The residue was triturated in hydrochloric acid (2 N aqueous solution, 100 mL) for 16 hours. The precipitate was filtered to afford the title compound as a pale pink solid, 6.1 g.

LCMS Rt=2.61 minutes, MS m/z 296 [MH]+.

$^1$H NMR (400 MHz, d$_6$-DMSO): δ ppm 7.12 (dd, 1 H), 7.62-7.79 (m, 2 H), 8.19 (d, 1 H), 8.24-8.32 (m, 1 H), 8.45 (dd, 1 H), 11.42 (br. s., 1 H).

Preparation 317 tert-Butyl 4-[2-hydroxy-5-(trifluoromethyl)phenyl]piperidine-1-carboxylate

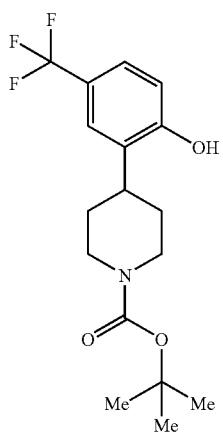

Boron tribromide (1 M in dichloromethane, 2.8 mL) was added to a solution of tert-butyl 4-[2-methoxy-5-(trifluoromethyl)phenyl]piperidine-1-carboxylate (Preparation 318, 503 mg, 1.40 mmol) in dichloromethane (2 mL) at 0° C. and stirred for 1 hour at 0° C. and then at room temperature for 1 hour. The reaction mixture was quenched with cold water and basified to pH 9 with saturated aqueous sodium bicarbonate solution. The aqueous layer was extracted with ethyl acetate and organic extracts dried over sodium sulfate, filtered and concentrated in vacuo to afford the intermediate as a light yellow solid.

LCMS Rt=1.23 minutes MS m/z 246 [MH]+

To the above crude intermediate (270 mg, 1.1 mmol) in acetonitrile (2.8 mL) was added di-tert-butyldicarbonate (240 mg, 1.1 mmol) and stirred 18 hours at room temperature before concentrating in vacuo. The residue was purified via automated flash chromatography eluting with ethyl acetate: hexanes (gradient 2:8 to 1:0, by volume) to afford the title compound as a white solid, 127 mg.

LCMS Rt=1.90 minutes MS m/z 246 [MH]+

Preparation 318 tert-Butyl 4-[2-methoxy-5-(trifluoromethyl)phenyl]piperidine-1-carboxylate

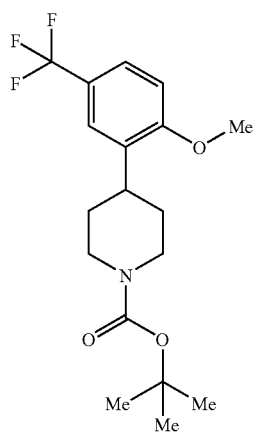

tert-Butyl 4-[2-methoxy-5-(trifluoromethyl)phenyl]-3,6-dihydropyridine-1(2H)-carboxylate (Preparation 319, 512 mg, 1.43 mmol) was hydrogenated for 16 hours over palladium (10 wt. % on activated carbon, 10 mg, 0.009 mmol) at a pressure of 40 psi. The reaction mixture was filtered through Celite™ and concentrated in vacuo to afford the title compound as a white solid, 503 mg.

LCMS Rt=2.03 minutes MS m/z 260 [MH]+

Preparation 319 tert-Butyl 4-[2-methoxy-5-(trifluoromethyl)phenyl]-3,6-dihydropyridine-1(2H)-carboxylate

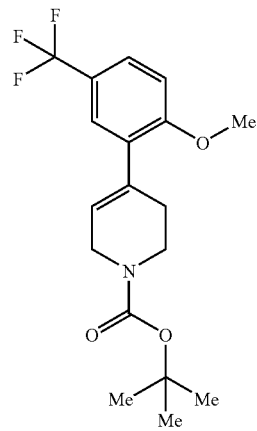

A suspension of 2-bromo-1-methoxy-4-(trifluoromethyl)benzene (825 mg, 3.23 mmol), tert-butyl 4-(4,4,5,5-tetramethyl-1,3,2-dioxaborolan-2-yl)-3,6-dihydropyridine-1(2H)-carboxylate (1.00 g, 3.23 mmol), potassium carbonate (1.34 g, 9.697 mmol) and [1,1'-bis(diphenylphosphino)ferrocene]dichloro-palladium(II) complex with dichloromethane (1:1) (158 mg, 0.193 mmol) in N,N-dimethylformamide (19 mL) was purged with argon. After 30 minutes, the reaction mixture was heated at 90° C. and stirred for 22 hours before cooling to room temperature and filtering through Celite™, washing with ethyl acetate. The filtrate was concentrated in vacuo to quarter and partitioned between water (100 mL) and ethyl acetate (75 mL). The aqueous layer was extracted with ethyl acetate (2×75 mL). Combined organic layers were washed with water, aqueous lithium chloride solution, saturated aqueous sodium chloride solution, dried over sodium sulfate, filtered and concentrated in vacuo. The residue was purified by automated flash chromatography (24 g silica gel) eluting with hexanes:ethyl acetate (gradient 1:0 to 3:1, by volume) to afford the title compound as a clear oil, 1.1 g.

LCMS Rt=1.71 minutes MS m/z 258 [MH]+

Preparation 322

N-(5-Chloro-1,3-thiazol-2-yl)-4-(4-cyano-2-iodophenoxy)-2,5-difluorobenzenesulfonamide

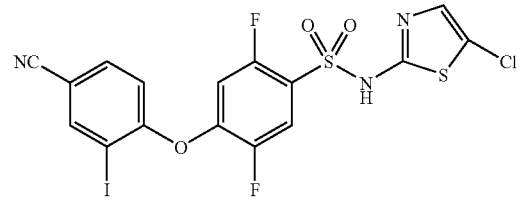

To a suspension of potassium carbonate (0.068 g, 0.000492 mol) and N-(5-chloro-1,3-thiazol-2-yl)-N-(2,4-dimethoxybenzyl)-2,4,5-trifluorobenzenesulfonamide (Preparation 334, 0.200 g, 0.000418 mol) in dimethyl sulfoxide (3.0 mL) was added 4-hydroxy-3-iodobenzonitrile (Preparation 342, 0.108 g, 0.000441 mol) and was stirred at 65° C. under nitrogen for 16 hours. The reaction was diluted with ethyl acetate (10.0 mL). The organic phase was washed with saturated aqueous sodium chloride solution (2×10.0 mL), dried over sodium sulfate, filtered and concentrated in vacuo. The crude was dissolved in dichloromethane (1.5 mL), treated with trifluoroacetic acid (1.5 mL) and stirred at room temperature under nitrogen for 16 hours. Reaction was concentrated in vacuo and residue dissolved in ethyl acetate (10.0 mL). The organic extract was washed with saturated aqueous sodium bicarbonate solution (2×10.0 mL), dried over sodium sulphate, filtered and concentrated in vacuo. The resulting residue was purified using ISCO™ (12 g SiO$_2$) eluting with methanol:dichloromethane (gradient 0:1 to 1:39, by volume) to afford the title compound as an orange solid, 165 mg, 35% yield.

LCMS Rt=1.60 minutes. MS m/z 552 [M$^{35}$ClH]+

Preparation 333

5-Chloro-N-(2,4-dimethoxybenzyl)-2,4-difluoro-N-1,2,4-thiadiazol-5-ylbenzenesulfonamide

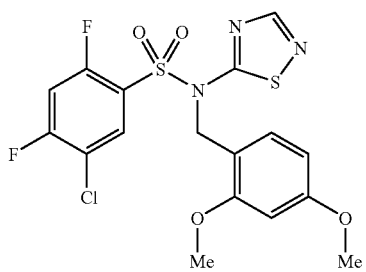

To a solution of (N-(2,4-dimethoxybenzyl)-1,2,4-thiadiazol-5-amine (Preparation 14, 40.6 g, 0.1619 mol) in anhydrous tetrahydrofuran (600 mL), cooled to −70° C., under nitrogen was added lithium 1,1,1,3,3,3-hexamethyldisilazan-2-ide (1 M in tetrahydrofuran, 161.9 mL, 0.161.9 mol) drop wise. The reaction mixture was warmed to room temperature and stirred for 1 hour before cooling to −70° C. A solution of 5-chloro-2,4-difluorobenzenesulfonyl chloride (40 g, 0.1619 mol) in tetrahydrofuran (200.0 mL) was added dropwise. After complete addition, the reaction mixture was gradually warmed to room temperature and stirred for 1 hour. Reaction mixture was quenched with saturated aqueous ammonium chloride solution and extracted with ethyl acetate. Organic layer was washed with water and saturated aqueous sodium chloride solution. Crude residue was purified by column chromatography eluting with ethyl acetate:hexane (gradient 1:19 to 3:17, by volume) to afford the title compound as a white solid, 46 g.

LCMS Rt=3.88 minutes. MS m/z 462 [M$^{35}$ClH]+

$^1$H NMR (400 MHz, CDCl$_3$): δ 3.66 (s, 3H), 3.74 (s, 3H), 5.34 (s, 2H), 6.14-6.15 (m, 2H), 6.34 (dd, 1H), 6.86 (t, 1H), 7.19 (d, 1H), 7.73 (t, 1H), 8.21(s, 1H)

Preparation 334

N-(5-Chloro-1,3-thiazol-2-yl)-N-(2,4-dimethoxybenzyl)-2,4,5-trifluorobenzenesulfonamide

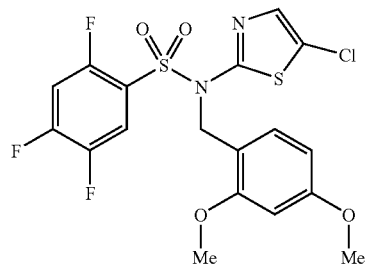

Prepared according to Preparation 333 using 5-chloro-N-(2,4-dimethoxybenzyl)-1,3-thiazol-2-amine (Preparation 208) and 2,4,5-trifluorobenzenesulfonyl chloride. Purification using ISCO™ (12 g SiO$_2$) eluting with ethyl acetate:heptane (gradient 0:1 to 3:7, by volume) afforded the title compound as an orange solid.

LCMS Rt=1.80 minutes. MS m/z 479 [M$^{35}$ClH]+

$^1$H NMR (400 MHz, CDCl$_3$): δ 3.70 (s, 3H), 3.75 (s, 3H), 5.15 (s, 2H), 6.18 (d, 1H), 6.35 (m, 1H), 6.87 (m, 1H), 7.20 (d, 1H), 7.77 (m, 1H), 8.22 (s, 1H)

Preparation 337

1-(Ethoxymethyl)-5-(4,4,5,5-tetramethyl-1,3,2-dioxaborolan-2-yl)-1H-pyrazole

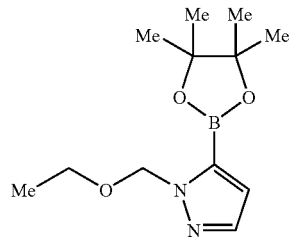

Butyl lithium (2.5 M in hexanes, 32.4 mL, 0.0811 mol) was added slowly via syringe to a solution of 1-(ethoxymethyl)-1H-pyrazole (Preparation 338, 9.3 g, 0.074 mol) in anhydrous tetrahydrofuran (100.0 mL) at 0° C. and stirred under nitrogen for 15 minutes and then at room temperature for 30 minutes. The mixture was cooled to −78° C. and 2-isopropoxy-4,4,5,5-tetramethyl-1,3,2-dioxaborolane (16.5 mL, 0.0811 mol) was added via syringe. The mixture was warmed to room temperature and stirred under nitrogen for 60 hours. Saturated aqueous ammonium chloride solution (50.0 mL) was added followed by water (150.0 mL). The mixture was poured into tert-butylmethylether (200.0 mL) and the biphasic mixture stirred vigorously for 30 minutes. The aqueous layer was acidified to pH 6 with hydrochloric acid (6.0 M aqueous solution) and extracted with tert-butylmethylether (3×200.0 mL). The combined organics were washed with saturated aqueous sodium chloride solution (100.0 mL) and then stirred with activated charcoal (1 g) for 30 minutes. Magnesium sulphate was added and the mixture filtered through a pad of Celite™, washing with tert-butylmethylether (1 L). Concentration in vacuo afforded the title compound as a brown oil, 14.5 g, 78% yield.

$^1$H NMR (400 MHz, CDCl$_3$): δ 1.14 (t, 3H) 1.34 (s, 12H) 3.52 (q, 2H) 5.71 (s, 2H) 6.78 (d, 1H) 7.58 (d, 1H).

Preparation 338

1-(Ethoxymethyl)-1H-pyrazole

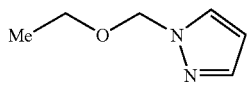

To a mixture of pyrazole (10 g, 0.150 mol) and potassium carbonate (22.3 g, 0.162 mol) in acetone (200.0 mL), cooled to 0° C. under nitrogen, was added chloromethyl ethyl ether (15.0 mL, 0.162 mol) via syringe over a period of 20 minutes. The reaction was stirred for 30 minutes at 0° C. and then for 2 hours at room temperature. The mixture was filtered, washing the solid with acetone (200.0 mL). The filtrate was carefully concentrated in vacuo (at 400 mbar). The crude material was purified by flash column chromatography eluting with pentane:diethylether (1:1, by volume) to afford the title compound as a colourless oil, 9.3 g, 50% yield.

$^1$H NMR (400 MHz, CDCl$_3$): δ 1.18 (t, 3 H) 3.54 (q, 2 H) 5.47 (s, 2 H) 6.35 (t, 1 H) 7.57 (d, 1 H) 7.59 (d, 1 H).

Preparation 339

4-(5-Chloro-2-hydroxyphenyl)pyridine-2-carbonitrile

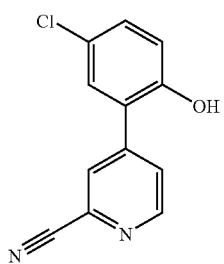

(5-Chloro-2-hydroxyphenyl)boronic acid (2.0 g, 0.012 mol), 4-chloropyridine-2-carbonitrile (1.61 g, 0.012 mol), (1,1'-bis(diphenylphosphino)ferrocene)dichloropalladium (II) (0.424 g, 0.00058 mol) and sodium carbonate (3.7 g, 0.035 mol) in 1,4-dioxane (20.0 mL) and deionised water (1.0 mL) were degassed with nitrogen (×3) before heating at 100° C. for 18 hours under nitrogen. The reaction was cooled and hydrochloric acid (2.0 M aqueous solution, 30.0 mL) added. Reaction was filtered, washing with ethyl acetate (50.0 mL). The organic layer was concentrated in vacuo and purified by flash column chromatography on the ISCO™ (40 g SiO$_2$) eluting with ethyl acetate:heptane (gradient 0:1 to 7:3, by volume) to afford the title compound as a yellow solid, 0.23 g, 8.6% yield.

LCMS Rt=1.42 minutes. MS m/z 231.0 [M$^{35}$ClH]+

$^1$H NMR (400 MHz, d$_6$-DMSO): δ 7.01 (d, 1H), 7.33 (dd, 1H), 7.54 (d, 1H), 7.97 (dd, 1H), 8.23 (m, 1H), 8.74 (m, 1H)

Preparation 340

5-Chloro-4-[4-chloro-2-(2-cyanopyridin-4-yl)phenoxy]-N-(2,4-dimethoxybenzyl)-2-fluoro-N-1,2,4-thiadiazol-5-ylbenzenesulfonamide

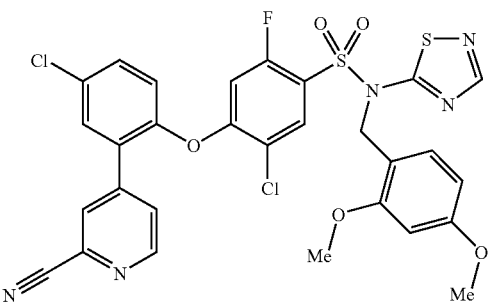

Prepared according to Preparation 255 using 4-(5-chloro-2-hydroxyphenyl)pyridine-2-carbonitrile (Preparation 339, 0.23 g, 0.001 mol) and 5-chloro-N-(2,4-dimethoxybenzyl)-2,4-difluoro-N-1,2,4-thiadiazol-5-ylbenzenesulfonamide (Preparation 333, 461 mg, 0.998 mmol). Saturated aqueous sodium chloride solution (20.0 mL) was added to the reaction resulting in the formation of a white precipitate. This was filtered and washed with water (20.0 mL) and heptane (20.0 mL) before being dried in vacuo for 2 hours to afford the title compound as a white solid, 0.67 g, 100% yield.

LCMS Rt=3.87 minutes. MS m/z 694.0 [M$^{35}$ClH]+

$^1$H NMR (400 MHz, d$_6$-DMSO): δ 3.58 (s, 3H), 3.66 (s, 3H), 5.20 (s, 2H), 6.20 (m, 1H), 6.40 (m, 1H), 7.05(m, 2H), 7.22 (m, 1H), 7.65 (m, 2H), 7.82 (d, 1H), 7.85 (dd, 1H), 8.20 (dd, 1H), 8.42 (d, 1H), 8.77 (dd, 1H)

Preparation 341

4-(Difluoromethoxy)-2-iodophenol

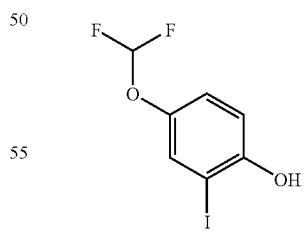

To a suspension of N-iodosuccinimide (1.12 g, 0.005 mol) in acetic acid (15.0 mL) was added 4-(difluoromethoxy)phenol (0.8 g, 0.005 mol) under nitrogen. Sulfuric acid (0.147 g, 0.0015 mol) was added and the resulting dark brown suspension was stirred at room temperature for 4 hours before the addition of N-iodosuccinimide (0.6 g, 0.0025 mol). The mixture was stirred for 16 hours before diluting with citric acid (1.0 M aqueous solution, 20.0 mL) and water (20.0 mL). The aqueous layer was extracted with dichloromethane (2×30.0 mL). Combined organic layers were dried over sodium sulphate, filtered and concentrated in vacuo to afford a dark purple oil. This was concentrated in vacuo from toluene (3×20.0 mL) to afford a brown oil. The aqueous layer was concentrated in vacuo. Both organic and aqueous crude residues were purified by flash column chromatography on the ISCO™ (40 g SiO₂) eluting with ethyl acetate:heptane (gradient 0:1 to 1:1, by volume) to afford the title compound as a yellow oil, 0.604 g, 42% yield.

LCMS Rt=1.44 minutes. MS m/z 285.0 [MH]−

$^1$H NMR (400 MHz, CDCl₃): δ 6.40 (t, 1H), 6.97 (d, 1H), 7.07 (dd, 1H), 7.46 (d, 1H)

Preparation 342

4-Hydroxy-3-iodobenzonitrile

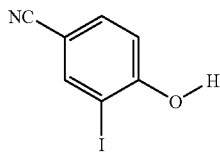

4-Hydroxy-3-iodobenzonitrile was prepared by the method analogous to Preparation 341 above using N-iodosuccinimide, acetic acid, sulfuric acid and 4-Hydroxybenzonitrile. Purified by ISCO™ (80 g SiO₂) eluting with ethyl acetate:heptane (gradient 0:1 to 3:7, by volume) to yield the title compound.

LCMS Rt=1.28 minutes
MS m/z 244 [MH]−
$^1$H NMR (400 MHz, d₆-DMSO): δ 6.95 (d, 1H), 7.65 (d, 1H), 8.15 (s, 1H), 11.50 (s, 1H)

Preparation 349

5-Chloro-2,4-difluoro-N-(5-fluoropyridin-2-yl)-N-(methoxymethyl)benzenesulfonamide

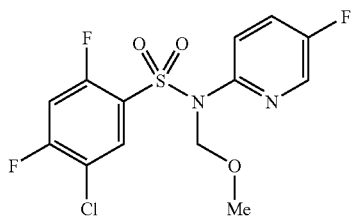

5-Chloro-2,4-difluorobenzenesulfonyl chloride (1 g, 4 mmol) in dichloromethane (7.6 mL) was added portion-wise to a solution of 2-amino-5-fluoropyridine (498 mg, 4.44 mmol) in pyridine (7.6 mL, 94 mmol) cooled to 0° C. After addition was complete, the reaction mixture was warmed to room temperature. After 16 hours, the reaction mixture was diluted with dichloromethane and hydrochloric acid (1 N aqueous solution). The aqueous layer was extracted with dichloromethane. The combined organic layers were washed with water, diluted with ethyl acetate, dried over sodium sulfate, filtered and concentrated in vacuo. The residue was dissolved in dichloromethane (8.0 mL) and N,N-diisopropylethylamine (0.776 mL, 4.45 mmol) added. The mixture was cooled to 0° C. and chloromethyl methyl ether (0.338 mL, 4.45 mmol) was added dropwise by syringe. The reaction mixture was warmed to room temperature and after stirring for 6 hours, the reaction mixture was diluted with dichloromethane and washed with saturated aqueous sodium bicarbonate solution. The organic layer was dried over sodium sulfate, filtered and concentrated in vacuo onto Celite™. The residue was purified by automated flash chromatography (24 g silica gel column) eluting with ethyl acetate:hexanes (gradient 0:1 to 1:0, by volume) to afford the title compound, 363 mg.

LCMS Rt=1.78 minutes. MS m/z 367 [MH]+

Preparation 355

4-(4-Chloro-2-iodophenoxy)-3-cyano-N-(1,2,4-thiadiazol-5-yl)benzenesulfonamide

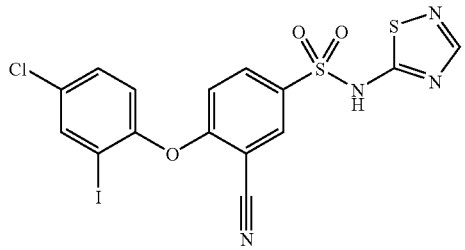

Prepared according to Preparation 50 using 4-chloro-2-iodophenol.

1H NMR (400 MHz, d₆-DMSO) δ 6.86 (d, 1 H), 7.42 (d, 1 H), 7.61 (dd, 1 H), 7.99 (dd, 1 H) 8.08 (d, 1 H) 8.31 (d, 1 H) 8.48 (s, 1 H) ppm.

Preparation 363

N-(2,4-Dimethoxybenzyl)-2,5-difluoro-4-[2-iodo-4-(trifluoromethyl)phenoxy]-N-1,2,4-thiadiazol-5-ylbenzenesulfonamide

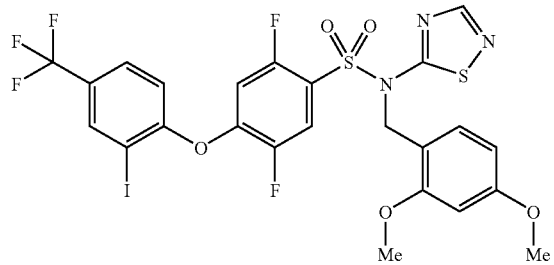

Prepared according to Preparation 255 using N-(2,4-dimethoxybenzyl)-2,4,5-trifluoro-N-1,2,4-thiadiazol-5-ylbenzenesulfonamide (Preparation 647, 1000 mg, 2.26 mmol) and 2-iodo-4-(trifluoromethyl)phenol (Preparation 224, 975 mg, 3.38 mmol) to afford the title compound, 1080 mg, 67% yield.

LCMS Rt=4.14 minutes.

$^1$H NMR (d$_6$-DMSO): δ 3.60 (s, 3H), 3.70 (s, 3H), 5.20 (s, 2H), 6.40 (m, 2H), 7.05 (m, 1H), 7.30 (m, 2H), 7.80 (m, 2H), 8.30 (s, 1H), 8.45 (s, 1H).

Preparation 369

3-Methyl-4-(4,4,5,5-tetramethyl-1,3,2-dioxaborolan-2-yl)-1-trityl-1H-pyrazole

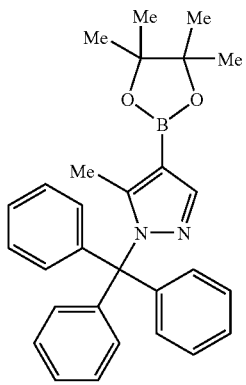

3-Methyl-4-(4,4,5,5-tetramethyl-1,3,2-dioxaborolan-2-yl)-1H-pyrazole (7.4 g, 0.0356 mol), 1,1',1''-(chloromethane-triyl)tribenzene (9.9 g, 0.0356 mol) and triethylamine (7.2 g, 0.0712 mol) were suspended in N,N-dimethylformamide (70.0 mL) and stirred at room temperature for 16 hours. The reaction mixture was quenched by addition of water (30.0 mL) and extracted with ethyl acetate (3×30.0 mL). The combined organic layers were washed with saturated aqueous sodium chloride solution (40.0 mL), dried over sodium sulfate and concentrated in vacuo. This crude residue was initially purified via column chromatography eluting with petroleum ether:ethyl acetate (10:1, by volume) and then purified by preparative HPLC to yield title compound as a white solid.

$^1$H NMR (400 MHz, CDCl$_3$): δ 1.25 (s, 12H), 2.32 (s, 3H), 7.06 (m, 6H), 7.20 (m, 9H), 7.52 (s, 1H).

Preparation 403

(1-Methyl-1H-pyrazol-5-yl)boronic acid

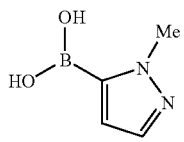

To a stirred solution of 1-methyl-1H-pyrazole (2.49 mL, 30 mmol) in tetrahydrofuran (100 mL) was added butyllithium (2.5 M in hexane, 15.6 mL, 39 mmol) at −78° C. dropwise. After stirring for 1 hour, triisopropyl borate (27.6 mL, 120 mmol) was added and the reaction mixture was gradually warmed to room temperature for 16 hours. Hydrochloric acid (1 N aqueous solution) was added to the reaction mixture until pH 7 achieved. The mixture was extracted with dichloromethane:methanol (9:1, 5×200 mL). Combined organic extracts were dried over magnesium sulphate and concentrated in vacuo to obtain crude residue. Purification was undertaken by flash column chromatography (ISCO™) eluting with dichloromethane:methanol (7:3, by volume) to afford the title compound as a white solid, 1258 mg, 33% yield.

$^1$H NMR (400 MHz, CD$_3$OD): δ 3.99 (s, 3H), 6.66 (d, 1H), 7.42-7.51 (m, 1H) ppm.

Preparation 408

3-Cyano-4-[2-iodo-4-(trifluoromethyl)phenoxy]-N-1,2,4-thiadiazol-5-ylbenzenesulfonamide

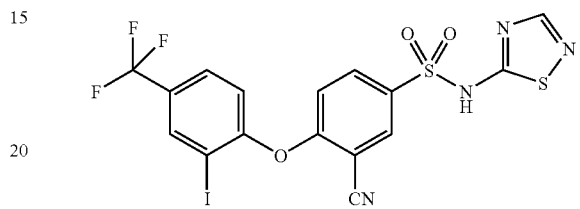

To a suspension of potassium carbonate (0.850 g, 0.006150 mol) and 3-cyano-4-fluoro-N-1,2,4-thiadiazol-5-ylbenzenesulfonamide (Preparation 65, 0.500 g, 0.001759 mol) in dimethyl sulfoxide (5.0 mL) was added 2-iodo-4-(trifluoromethyl)phenol (Preparation 224, 0.595 g, 0.002066 mol) and stirred at 80° C. under nitrogen for 16 hours. The reaction mixture was diluted with ethyl acetate (10.0 mL) and the organic phase was washed with saturated aqueous sodium chloride solution (2×10.0 mL), dried over sodium sulphate, filtered and concentrated in vacuo. The residue was triturated in ethyl acetate (5.0 mL) to yield title compound as a white solid, 560 mg, 58% yield.

LCMS Rt=1.75 minutes MS m/z 553 [MH]+

$^1$H NMR (400 MHz, d$_6$-DMSO): δ 6.90 (d, 1H), 7.45 (d, 1H), 7.85 (m, 2H), 7.95 (d, 1H), 8.10 (s, 1H), 8.30 (s, 1H)

Preparation 419

N-{1-tert-Butyl-4-[5-chloro-2-(2-cyano-4-{[(2,4-dimethoxybenzyl)(1,2,4-thiadiazol-5-yl)amino]sulfonyl}phenoxy)phenyl]-1H-pyrazol-5-yl}-2,2,2-trifluoroacetamide

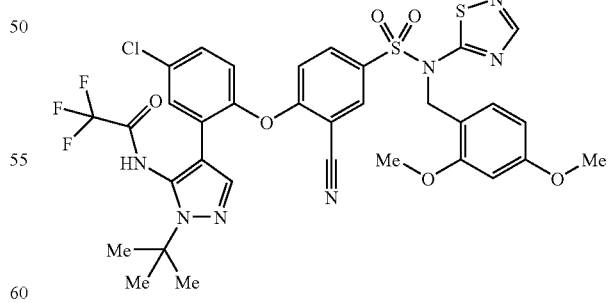

To a solution of 3-cyano-N-(2,4-dimethoxybenzyl)-4-fluoro-N-1,2,4-thiadiazol-5-ylbenzenesulfonamide (Preparation 68, 150 mg, 0.35 mmol) in dimethyl sulfoxide (10 ml) was added N-[1-tert-butyl-4-(5-chloro-2-hydroxyphenyl)-1H-pyrazol-5-yl]-2,2,2-trifluoroacetamide (Preparation 209, 131 mg, 0.36 mmol) and potassium carbonate (135 mg, 0.86 mmol) and the flask was purged with nitrogen (×3). The resulting suspension was stirred at room temperature for 18 hours before pouring into sodium hydroxide (1 M aqueous solution) and extracting with dichloromethane. The combined organic phase was dried over magnesium sulfate, filtered and concentrated in vacuo to afford a pale yellow oil. This was purified by column chromatography (80 g silica gel column) eluting with ethyl acetate:heptane (1:1, by volume) to furnish the title compound as a pale yellow oil, 157 mg, 59% yield.

LCMS Rt=4.88 minutes.

$^1$H NMR (CDCl$_3$, 400 MHz): δ 1.63 (s, 9H), 3.52 (s, 3H), 3.80 (s, 3H), 5.26 (s, 2H), 6.12 (s, 1H), 6.33-6.38 (m, 1H), 6.54-6.59 (m, 1H), 7.04-7.10 (m, 2H), 7.37-7.42 (m, 1H), 7.45 (s, 1H), 7.49 (s, 1H), 7.66-7.72 (m, 2H), 8.18 (s, 1H), 8.30 (s, 1H).

Preparation 424

3-Cyano-N-(2,4-dimethoxybenzyl)-4-{2-[1-(ethoxymethyl)-1H-pyrazol-5-yl]-4-(trifluoromethoxy)phenoxy}-N-1,2,4-thiadiazol-5-ylbenzenesulfonamide

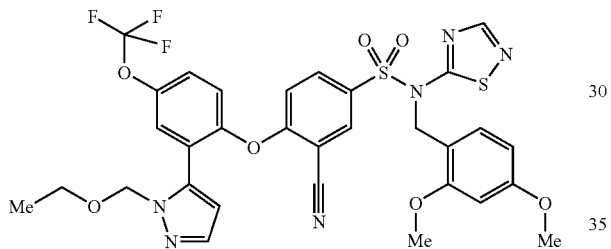

Prepared according to Method U (below) using 1-(ethoxymethyl)-5-(4,4,5,5-tetramethyl-1,3,2-dioxaborolan-2-yl)-1H-pyrazole (Preparation 337, 197 mg, 0.714 mmol), and 3-cyano-N-(2,4-dimethoxybenzyl)-4-[2-iodo-4-(trifluoromethoxy)phenoxy]-N-1,2,4-thiadiazol-5-ylbenzenesulfonamide (Preparation 497, 210 mg, 0.42 mmol). The material was purified by column chromatography eluting with ethyl acetate:heptane (1:1, by volume) to furnish the title compound as a white solid, 70 mg, 29% yield.

LCMS Rt=3.71 minutes $^1$H NMR (d$_6$-DMSO): δ 1.00 (m, 3H), 3.40 (m, 2H), 3.80 (m, 6H), 5.05 (s, 2H), 5.40 (s, 2H), 6.40 (m, 2H), 6.50 (m, 1H), 6.80 (m, 1H), 7.20 (m, 1H), 7.40 (m, 2H), 7.60 (m, 1H), 7.70 (m, 1H), 7.80 (m, 1H), 8.00 (m, 1H), 8.35 (m, 1H).

Method U

Example 771 was prepared using Method U below.

To a solution of N-(5-chloro-1,3-thiazol-2-yl)-4-(4-cyano-2-iodophenoxy)-2,5-difluorobenzenesulfonamide (Preparation 322, 0.160 g, 0.000200 mol) in 1,4 dioxane (3.0 mL) and water (1.0 mL) was added caesium carbonate (0.165 g, 0.000506 mol), palladium tetrakis triphenylphosphine (0.0023 g, 0.000020 mol) and 4-(4,4,5,5-tetramethyl-1,3,2-dioxaborolan-2-yl)-1H-pyrazole (0.0784 g, 0.000404 mol) and stirred at 85° C. under nitrogen for 16 hours. The reaction was diluted with ethyl acetate (10.0 mL) and the organic phase washed saturated aqueous sodium chloride solution (2×10.0 mL), dried over sodium sulphate, filtered and concentrated in vacuo. Purification by preparative HPLC afforded the title compound.

LCMS Rt=3.18 minutes MS m/z 494 [M$^{35}$ClH]+

Preparation 426

3-Chloro-4-fluoro-N-pyrimidin-4-ylbenzenesulfonamide

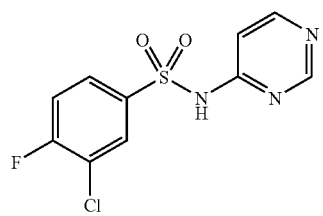

4-Aminopyrimidine (1.0 g, 10.5 mmol) and DABCO™ (1.18 g, 10.5 mmol) were added concurrently to a solution of 3-chloro-4-fluorobenzenesulfonyl chloride (1.25 mL, 10.0 mmol) in anhydrous acetonitrile (49 mL). The reaction mixture immediately turned yellow and a precipitate was formed. After stirring for 16 hours, the mixture was concentrated in vacuo. The crude material was suspended in ethyl acetate (75 mL) and water (75 mL) and stirred for 15 minutes. The resulting solid was filtered and dried in vacuo to afford the title compound, 0.83 g, 27% yield.

LCMS Rt=1.31 minutes MS m/z 288 [MH]+

$^1$HNMR (300 MHz, d$_6$-DMSO): δ6.90-7.00 (1 H, m), 7.63 (1 H, t), 7.91-7.96 (1 H, m), 8.28 (1 H, s), 8.07-88.10 (1 H, m), 8.64 (1 H, s), 13.05 (1 H, br s).

Preparation 428

3-Cyano-4-[2-(5-methyl-1-trityl-1H-pyrazol-4-yl)-4-(trifluoromethyl)phenoxy]-N-1,2,4-thiadiazol-5-ylbenzenesulfonamide

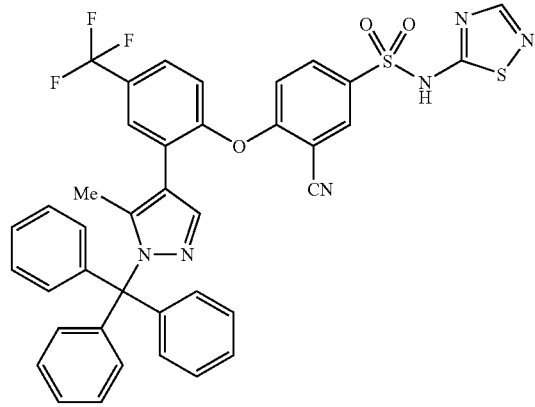

Prepared according to Preparation 211 using 3-cyano-4-[2-iodo-4-(trifluoromethyl)phenoxy]-N-1,2,4-thiadiazol-5-ylbenzenesulfonamide (Preparation 408) and 3-methyl-4-(4,4,5,5-tetramethyl-1,3,2-dioxaborolan-2-yl)-1-trityl-1H-pyrazole (Preparation 369). Purified by silica gel chromatography (ISCO™ 12 g SiO$_2$) eluting with dichloromethane:(methanol:acetic acid 10:1, by volume) (gradient 1:0 to 95:5, by volume) to afford the title compound.

LCMS Rt=4.91 minutes $^1$H NMR (400 MHz, $d_6$-DMSO): δ 2.20 (s, 3H), 6.75 (d, 1H), 6.90 (m, 6H), 7.20 (d, 1H), 7.25-7.30 (m, 9H), 7.55 (d, 1H), 7.80-7.90 (m, 3H), 8.20 (d, 1H), 8.45 (s, 1H)

Preparation 429

3-Cyano-N-(2,4-dimethoxybenzyl)-4-[2-iodo-4-(trifluoromethyl)phenoxy]-N-1,2,4-thiadiazol-5-ylbenzenesulfonamide

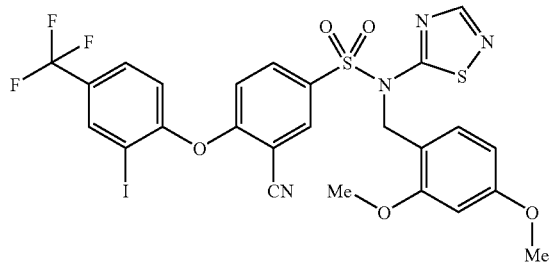

Prepared according to Method O (below) at room temperature using 3-cyano-N-(2,4-dimethoxybenzyl)-4-fluoro-N-1,2,4-thiadiazol-5-ylbenzenesulfonamide (Preparation 68) and 2-iodo-4-(trifluoromethyl)phenol (Preparation 224). The title compound was isolated as a white solid.

$^1$HNMR (400 MHz, $d_6$-DMSO): δ 3.60 (s, 3H), 3.75 (s, 3H), 5.20 (s, 2H), 6.45 (m, 2H), 6.90 (d, 1H), 7.05 (d, 1H), 7.55 (d, 1H), 7.90 (d, 1H), 8.05 (d, 1H), 8.25 (s, 1H), 8.35 (s, 1H), 8.40 (s, 1H)

Method O

Example 765 was prepared as follows.

To a solution of tert-butyl 4-(5-chloro-2-hydroxyphenyl)piperidine-1-carboxylate (Preparation 231, 37.1 mg, 0.119 mmol) in dimethyl sulfoxide (2 mL) was added potassium carbonate (22.4 mg, 0.162 mmol) and 5-chloro-N-(2,4-dimethoxybenzyl)-2,4-difluoro-N-(1,3,4-thiadiazol-2-yl)benzenesulfonamide (Preparation 247, 50.0 mg, 0.108 mmol). The resulting mixture was heated to 50° C. for 30 minutes. After cooling, the reaction was diluted with ethyl acetate and water. The layers were separated and the aqueous layer extracted with ethyl acetate. The combined organic extracts were washed with saturated aqueous sodium chloride solution and water, dried over magnesium sulphate and concentrated in vacuo. The residue was purified by automated flash column chromatography using an ISCO™ (12 g column) eluting with ethyl acetate:hexanes (gradient 0:1 to 1:1, by volume). The fully protected intermediate was taken up in dichloromethane (2 mL) and trifluoroacetic acid (83.4 uL, 1.08 mmol) was added. The resulting mixture was stirred at room temperature. After 16 hours, the reaction was concentrated in vacuo and purified by preparative HPLC eluting with acetonitrile:water (gradient 15:85 to 1:0, by volume) to afford the trifluoroacetic acid salt of the title compound as a white solid, 26 mg, 39% yield.

LCMS Rt=1.47 minutes. MS m/z 503 [M$^{35}$ClH]+

$^1$H NMR ($d_6$-DMSO): δ 1.80 (m, 4H), 2.94 (m, 3H), 3.31 (m, 2H), 7.03 (m, 2H), 7.35 (m, 2H), 7.96 (d, 1H), 8.83 (s, 1H).

Method 2

Preparation 429 can also be prepared as follows.

To a solution of 3-cyano-N-(2,4-dimethoxybenzyl)-4-fluoro-N-1,2,4-thiadiazol-5-ylbenzenesulfonamide (Preparation 68, 25 g, 57.5 mmol) in DMSO (125 mL) was added potassium carbonate (20.4 g, 148 mmol) followed by dropwise addition of the 2-iodo-4-(trifluoromethyl)phenol (Preparation 224, 17.4 g, 60.6 mmol). The reaction was stirred at room temperature for 2 hours. The reaction was poured into water (1 L) and extracted with ethyl acetate (3×300 mL). The organic layers were combined and washed with water (2×250 mL), dried over sodium sulfate and concentrated in vacuo. The residue was slurried in methanol (150 mL) for 1 hour before filtering and drying under vacuum to afford 33.92 g of the title compound as a white solid (83%).

$^1$HNMR (400 MHz, $d_6$-DMSO): δ 3.60 (s, 3H), 3.75 (s, 3H), 5.20 (s, 2H), 6.45 (m, 2H), 6.90 (d, 1H), 7.05 (d, 1H), 7.55 (d, 1H), 7.90 (d, 1H), 8.05 (d, 1H), 8.25 (s, 1H), 8.35 (s, 1H), 8.40 (s, 1H).

Preparation 453 tert-Butyl [(5-chloro-2,4-difluorophenyl)sulfonyl]1,3-thiazol-4-ylcarbamate

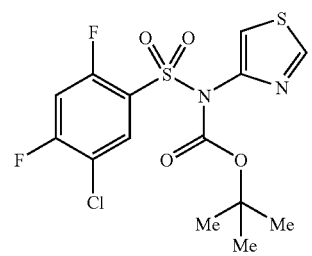

To a solution of thiazol-4-yl-carbamic acid tert-butyl ester (Preparation 72, 503 mg, 0.00251 mol) in tetrahydrofuran (5.0 mL) cooled to −78° C. was added lithium hexamethyldisilazide (1.0 M in tetrahydrofuran, 2.76 mL, 0.00276 mol). The reaction was stirred for 30 minutes at room temperature and then cooled to −78° C. A solution of 5-chloro-2,4-difluorobenzenesulfonyl chloride (620.5 mg, 0.002512 mol) in tetrahydrofuran (5.0 mL) was added slowly via syringe. After addition was complete, the reaction mixture remained immersed in the cooling bath; the temperature of the dry ice bath was not maintained, allowing the reaction mixture to slowly warm to room temperature. After 24 hours, the reaction mixture was poured into saturated aqueous ammonium chloride solution and extracted with ethyl acetate. The combined organic extracts were dried over magnesium sulfate, filtered and concentrated in vacuo onto Celite™. The residue was purified by automated flash chromatography (40 g SiO$_2$) eluting with ethyl acetate:dichloromethane (gradient 0:1 to 5:95, by volume) to afford the title compound as a white solid, 733 mg, 71% yield.

LCMS Rt=1.70 minutes. MS m/z 311 [M$^{35}$Cl(-Boc)H]$^+$ $^1$H NMR (300 MHz, $d_6$-DMSO): δ1.40 (s, 9H), 7.10 (m, 1H), 7.52 (m, 1H), 8.25 (t, 1H), 8.80 (m, 1H) ppm.

Preparation 497

3-cyano-N-(2,4-dimethoxybenzyl)-4-[2-iodo-4-(trifluoromethoxy)phenoxy]-N-1,2,4-thiadiazol-5-ylbenzenesulfonamide

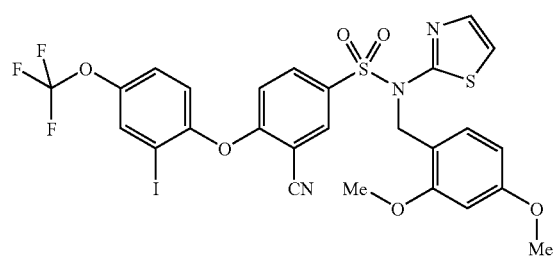

The title compound was prepared according to Preparation 255 using 2-iodo-4-(trifluoromethoxy)phenol (Preparation 226) and 3-cyano-N-(2,4-dimethoxybenzyl)-4-fluoro-N-1,2,4-thiadiazol-5-ylbenzene sulfonamide (Preparation 68).

¹HNMR (CDCl₃): δ 3.65 (s, 1H), 3.80 (s, 3H), 5.38 (s, 2H), 6.25 (m, 1H), 6.37 (m, 1H), 6.50 (m, 1H), 7.10 (m, 2H), 7.35 (m, 1H), 7.8 (m, 3H), 8.2 (s, 1H).

Preparation 533

2-(1-Methyl-1H-pyrazol-5-yl)-4-(trifluoromethoxy)phenol

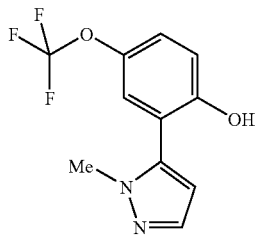

A solution of 5-[2-(benzyloxy)-5-(trifluoromethoxy)phenyl]-1-methyl-1H-pyrazole (Preparation 534, 2.3 g, 6.6 mmol) in methanol (25 mL) was degassed with argon before the addition of palladium on carbon (10%, 230 mg). Reaction mixture was stirred at room temperature under hydrogen atmosphere (using a balloon) for 16 hours. After filtration through Celite™, filtrate was concentrated in vacuo to afford the title compound as a white solid, 1.6 g, 94% yield.

¹H NMR (400 MHz, d₆-DMSO): δ 3.68 (s, 3H), 6.28 (d, 1H), 7.04 (d, 1H), 7.18 (s, 1H), 7.28-7.30 (m, 1H), 7.44 (d, 1H), 10.36 (br s, 1H) ppm.

Preparation 534

5-[2-(Benzyloxy)-5-(trifluoromethoxy)phenyl]-1-methyl-1H-pyrazole

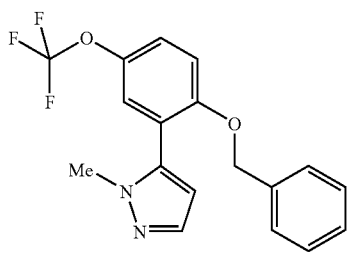

A solution of 1-(benzyloxy)-2-bromo-4-(trifluoromethoxy)benzene (Preparation 535, 3.3 g, 9.5 mmol) and (1-methyl-1H-pyrazol-5-yl)boronic acid (Preparation 403, 1.2 g, 9.5 mmol) 1,4-in dioxane (25 mL) was degassed under argon for 30 minutes. Under argon, (1E,4E)-1,5-Diphenyl-penta-1,4-dien-3-one-palladium (3:2) (348 mg, 0.38 mmol) and tricyclohexylphosphine (213 mg, 0.76 mmol) were added followed by the dropwise addition of a degassed solution of tripotassium phosphate (4 g, 19 mmol) in water (12.6 mL). Reaction mixture was refluxed for 16 hours before cooling to room temperature and filtering through Celite™. The filtrate was concentrated in vacuo and the residue was diluted with ethyl acetate (100 mL). The organic extract was washed with water, saturated aqueous sodium chloride solution, dried over sodium sulfate and concentrated in vacuo. Purification by silica gel column chromatography eluting with ethyl acetate:hexane (1:9, by volume) afforded the title compound, 2.3 g, 70% yield.

¹H NMR (400 MHz, d₆-DMSO): δ 3.64 (s, 3H), 5.18 (s, 2H), 6.33 (s, 1H), 7.32-7.51 (m, 9H) ppm.

Preparation 535

1-(Benzyloxy)-2-bromo-4-(trifluoromethoxy)benzene

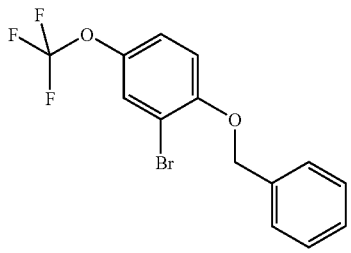

To a suspension of 2-bromo-4-(trifluoromethoxy)phenol (3 g, 11.7 mmol) and potassium carbonate (3.23 g, 23.4 mmol) in N,N-dimethylformamide (35 mL) was added benzyl bromide (2.1 mL, 17.5 mmol) dropwise and stirred at room temperature for 16 hours. Reaction mixture was diluted with ethyl acetate and washed with water, saturated aqueous sodium chloride solution, dried over sodium sulfate, filtered and concentrated in vacuo. Purification by silica gel column chromatography eluting with ethyl acetate:hexane (2:98, by volume) afforded the title compound, 3.3 g, 81% yield.

¹H NMR (400 MHz, CDCl₃): δ 5.14 (s, 2H), 6.90 (d, 1H), 7.10 (d, 1H), 7.31-7.46 (m, 6H) ppm.

Preparation 647

N-(2,4-dimethoxybenzyl)-2,4,5-trifluoro-N-1,2,4-thiadiazol-5-ylbenzenesulfonamide

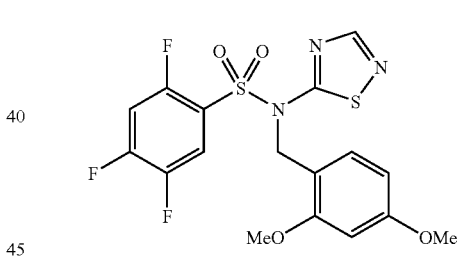

To a solution of (N-(2,4-dimethoxybenzyl)-1,2,4-thiadiazol-5-amine (Preparation 14, 13 g, 51.73 mmol) in dry tetrahydrofuran (150 ml) at −70° C. under argon atmosphere was added 1 M lithium 1,1,1,3,3,3-hexamethyldisilazan-2-ide in tetrahydrofuran (56.9 ml, 56.9 mmol) dropwise. The reaction mixture was allowed to warm up to room temperature and stirred for 1 h. It was again cooled to −70° C. and a tetrahydrofuran (50 ml) solution of 2,4,5-trifluorobenzenesulfonyl chloride (11.9 g, 51.73 mmol) was added dropwise to it at this temperature. After complete addition, reaction mixture was gradually allowed to warm up to room temperature and stirred for 1 hour. The reaction mixture was quenched with saturated aqueous ammonium chloride solution and extracted with ethyl acetate. The organic layer was washed with water and saturated aqueous sodium chloride solution. Crude product was purified over 100-200 silica gel using 5-15% v/v ethyl acetate in hexane to give 17 g (75%) of the title compound as a white solid.

LCMS Rt=3.85 minutes MS m/z 446 [MH]+

¹HNMR (CDCl₃): δ 3.68 (s, 3H), 3.74 (s, 3H), 5.32 (s, 2H), 6.20 (m, 1H), 6.34 (m 1H), 6.90 (m, 1H), 7.17 (d, 1H), 7.56-7.62 (m, 1H), 8.19 (s, 1H).

Preparation 653

3-chloro-N-(2,4-dimethoxybenzyl)-4-fluoro-N-1,2,4-thiadiazol-5-ylbenzenesulfonamide

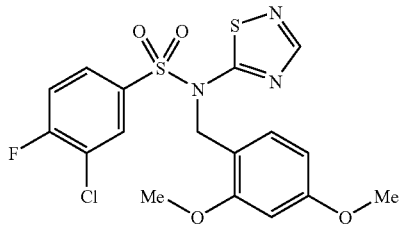

Prepared according to Preparation 207 using (2,4-dimethoxybenzyl)-[1,2,4]thiadiazol-5-yl-amine (Preparation 14) and 3-chloro-4-fluorobenzenesulfonyl chloride.

$^1$HNMR (d$_6$-DMSO): δ 3.63 (s, 3H), 3.71 (s, 3H), 5.21 (s, 2H), 6.38-6.44 (m, 2H), 7.00 (m, 1H), 7.61 (m, 1H) 7.85-7.93 (m, 2H), 8.41 (s, 1H).

Preparation 655

5-chloro-N-(5-chloro-1,3-thiazol-2-yl)-N-(2,4-dimethoxybenzyl)-2,4-difluorobenzenesulfonamide

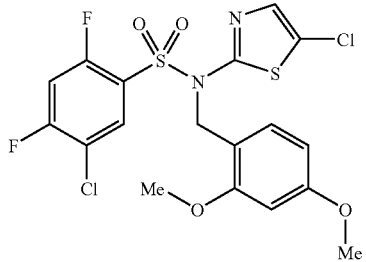

Prepared according to Preparation 207 using 5-chloro-N-(2,4-dimethoxybenzyl)-1,3-thiazol-2-amine (Preparation 208) and 5-chloro-2,4-difluorobenzenesulfonyl chloride.
LCMS Rt=1.84 minutes MS m/z 495 [M$^{35}$ClH]+

Preparation 669 tert-butyl 4-[5-chloro-2-(2-chloro-4-{[(2,4-dimethoxybenzyl)(1,2,4-thiadiazol-5-yl)amino]sulfonyl}phenoxy)phenyl]-1H-pyrazole-1-carboxylate

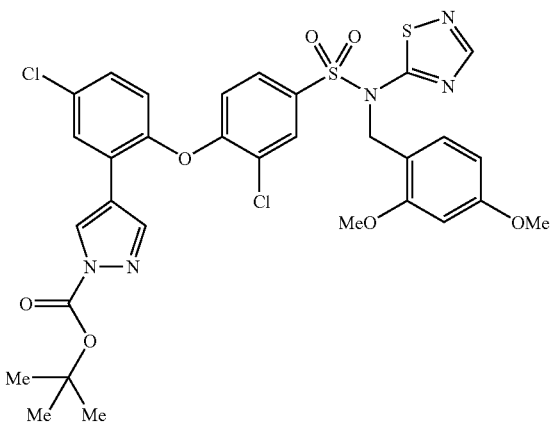

tert-butyl 4-(5-chloro-2-hydroxyphenyl)-1H-pyrazole-1-carboxylate (Preparation 205, 99.6 mg, 0.338 mmol), 3-chloro-N-(2,4-dimethoxybenzyl)-4-fluoro-N-1,2,4-thiadiazol-5-ylbenzenesulfonamide (Preparation 653, 153 mg, 0.345 mmol) and potassium carbonate (59.8 mg, 0.433 mmol) were stirred in dimethylsulphoxide (5 ml) at room temperature for 16 hours. The mixture was diluted with saturated aqueous sodium chloride solution (40 ml) and extracted with ethyl acetate (3×40 ml). The combined organics were dried over anhydrous magnesium sulphate, filtered and the solvents removed in vacuo to give the crude product which was purified by column chromatography using the ISCO® (using a gradient of 0-40% v/v ethyl acetate in heptane, 12 g SiO$_2$) to give the title compound as a white solid (121 mg)
LCMS Rt=1.94 minutes, MS m/z 616 [$^{35}$ClM-BocH]$^-$ and 618 [$^{37}$ClMH-Boc]$^-$
$^1$HNMR (CDCl$_3$): δ 1.65 (s, 9H), 3.67 (s, 3H), 3.76 (s, 3H), 5.27 (s, 2H), 6.28 (s, 1H), 6.35 (d, 1H), 6.60 (d, 1H), 6.94 (d, 1H), 7.08 (d, 1H), 7.31 (dd, 1H), 7.48 (dd, 1H), 7.64 (s, 1H), 7.75 (s, 1H), 8.03 (s, 1H), 8.18 (s, 1H), 8.44 (s, 1H)

Preparation 679 tert-butyl ({4-[2-(1-azetidin-3-yl-1H-pyrazol-5-yl)-4-chlorophenoxy]-3-cyanophenyl}sulfonyl)1,3-thiazol-4-ylcarbamate

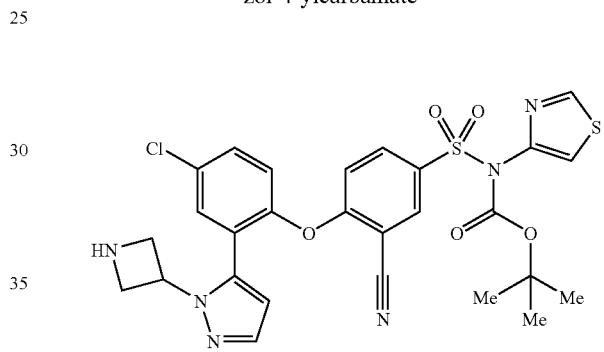

tert-butyl {[4-(4-chloro-2-{1-[1-(diphenylmethyl)azetidin-3-yl]-1H-pyrazol-5-yl}phenoxy)-3-cyanophenyl]sulfonyl}1,3-thiazol-4-ylcarbamate, (Preparation 680, 224 mg, 0.287 mmol) was dissolved in dichloromethane (10 ml) and N,N,N',N'-tetramethylnaphthalene-1,8-diamine (150 mg, 0.70 mmol) was added, followed by 1-chloroethyl chloroformate (0.07 ml, 0.65 mmol) and the solution was stirred at room temperature for 3.5 hours. Concentrated in vacuo and the residue was dissolved in methanol (10 ml) and refluxed for 4 hours. Concentrated in vacuo to give the crude title compound as a brown gum, 200 mg. This material was used without purification in Example 815.

Preparation 680 tert-Butyl {[4-(4-chloro-2-{1-[1-(diphenylmethyl)azetidin-3-yl]-1H-pyrazol-5-yl}phenoxy)-3-cyanophenyl]sulfonyl}1,3-thiazol-4-ylcarbamate

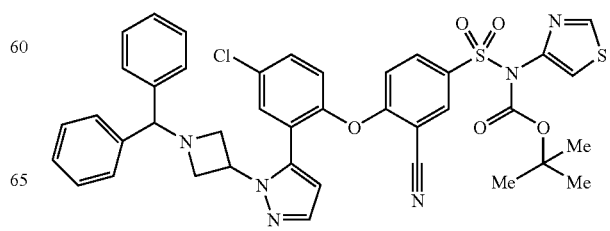

4-chloro-2-{1-[1-(diphenylmethyl)azetidin-3-yl]-1H-pyrazol-5-yl}phenol, (Preparation 689, 75 mg, 0.18 mmol), tert-butyl [(3-cyano-4-fluorophenyl)sulfonyl]1,3-thiazol-4-ylcarbamate (Preparation 250, 69 mg, 0.18 mmol), potassium carbonate (62 mg, 0.45 mmol) and dimethyl sulphoxide (4 ml) were combined and stirred at room temperature under nitrogen for 4 hours. Saturated aqueous ammonium chloride solution (20 ml) was added and the mixture extracted with ethyl acetate (1×20 ml). The organic layer was separated and back-washed with saturated aqueous sodium chloride solution (2×20 ml). The organic layer was separated, dried over sodium sulphate, filtered and evaporated to give an oil. The oil was purified using an ISCO® Companion (4 g. silica gel, gradient from dichloromethane to dichloromethane:methanol 98:2). The appropriate fractions were combined and solvents removed in vacuo to give the title compound as a glass. Yield 33 mg. 24%.

LCMS Rt=1.48 minutes, m/z 779 [M$^{35}$ClH]+

$^1$HNMR (CDCl$_3$): δ 1.32 (s, 9H), 3.59 (m, 2H), 3.67 (m, 2H), 4.57 (s, 1H) 4.90 (m, 1H), 6.21 (s, 1H) 6.87 (d, 1H) 7.35 (m, 15H), 8.10 (d, 1H), 8.31 (s, 1H), 8.59 (s, 1H).

TLC Rf=0.5 (dichloromethane:methanol 98:2)

Preparation 681

5-chloro-N(2,4-dimethoxybenzyl)-4-(2-{1-[1-(diphenylmethyl)azetidin-3-yl]-1H-pyrazol-5-yl}-4-fluorophenoxy)-2-fluoro-N-1,2,4-thiadiazol-5-ylbenzenesulfonamide

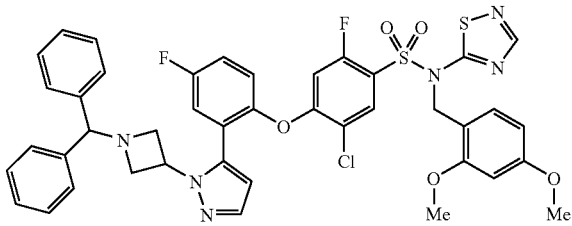

Prepared by analogy to Preparation 680 from 2-{1-[1-(diphenylmethyl)azetidin-3-yl]-1H-pyrazol-5-yl}-4-fluorophenol (Preparation 682, 249 mg, 0.623 mmol) and 5-chloro-N-(2,4-dimethoxybenzyl)-2,4-difluoro-N-1,2,4-thiadiazol-5-ylbenzenesulfonamide (Preparation 333, 288 mg, 0.623 mmol) and was used without further purification. Yield 500 mg 95%.

LCMS Rt=1.58 minutes, m/z 841 [M$^{35}$ClH]+
TLC Rf=0.6 (ethyl acetate:heptane 1:1)

Preparation 682

2-{1-[1-(Diphenylmethyl)azetidin-3-yl]-1H-pyrazol-5-yl}-4-fluorophenol

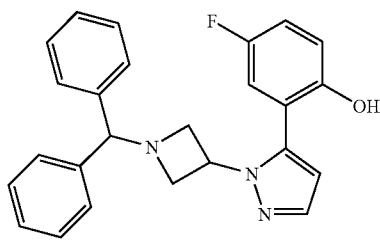

1-(diphenylmethyl)-3-hydrazinoazetidine dihydrochloride (Preparation 690, 1.25 g, 4.30 mmol) was stirred in ethanol (20 ml) and acetic acid (8 ml) for 30 minutes with ice cooling to give a suspension. To this cold suspension was added (2E)-3-(dimethylamino)-1-(5-fluoro-2-hydroxyphenyl)prop-2-en-1-one (Preparation 221, 900 mg, 4.3 mmol), stirred at 0° C. for 1 hour then allowed to warm up to room temperature over 18 hours. The reaction mixture was evaporated and then partitioned between ethyl acetate (100 ml), water (50 ml) and saturated aqueous sodium hydrogencarbonate solution (30 ml). The organic layer was separated and back-washed with saturated aqueous sodium chloride solution (2×20 ml), dried over sodium sulphate, filtered and evaporated. The solid was triturated with diethyl ether and the off-white solid filtered. The solid was crystallized from ethyl acetate:hexane (1:4) to give the title compound as colourless crystals were. Yield 490 mg 29%.

LCMS Rt=1.36 minutes m/z 400 [MH]+

$^1$HNMR (CDCl$_3$): δ 3.61 (m, 4H), 4.60 (s, 1H), 4.88 (m, 1H), 5.2 (brs, 1H), 6.80 (m, 1H) 6.89 (m, 1H), 7.03 (m, 1H), 7.16 (m, 2H), 7.26 (m, 4H), 7.42 (m, 4H), 7.71 (s, 1H).

TLC Rf=0.6 (ethyl acetate:heptane 1:1)

Preparation 683 tert-Butyl {[5-chloro-4-(2-{1-[1-(diphenylmethyl) azetidin-3-yl]-1H-pyrazol-5-yl}-4-fluorophenoxy)-2-fluorophenyl]sulfonyl}1,3-thiazol-4-ylcarbamate

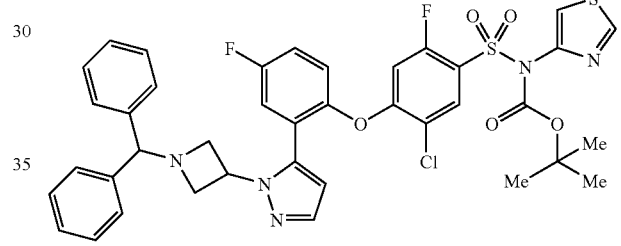

Prepared by analogy to Preparation 680 from 2-{1-[1-(diphenylmethyl)azetidin-3-yl]-1H-pyrazol-5-yl}-4-fluorophenol (Preparation 682, 97.1 mg, 0.243 mmol) and tert-butyl [(5-chloro-2,4-difluorophenyl)sulfonyl]1,3-thiazol-4-ylcarbamate (Preparation 453, 100 mg, 0.243 mmol). Yield 145 mg 76%.

LCMS Rt=1.58 minutes, m/z 790 [M$^{35}$ClH]+

$^1$HNMR (CD$_3$OD): δ 1.31 (s, 9H), 3.55 (m, 4H), 4.60 (s, 1H), 4.97 (m, 1H), 6.31 (s, 1H), 6.58 (d, 1H), 7.17 (m, 2H), 7.26 (m, 5H), 7.39 (m, 6H), 7.51 (d, 1H), 7.55 (d, 1H), 8.00 (d, 1H), 8.87 (d, 1H).

TLC Rf=0.7 (ethyl acetate:heptane 1:1)

Preparation 688

4-(4-chloro-2-{1-[1-(diphenylmethyl)azetidin-3-yl]-1H-pyrazol-5-yl}phenoxy)-N-(2,4-dimethoxybenzyl)-2,5-difluoro-N-1,2,4-thiadiazol-5-ylbenzenesulfonamide

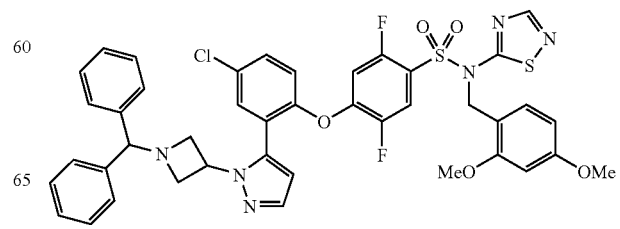

N-(2,4-dimethoxybenzyl)-2,4,5-trifluoro-N-1,2,4-thiadiazol-5-ylbenzenesulfonamide (Preparation 647, 157 mg, 0.353 mmol), 4-chloro-2-{1-[1-(diphenylmethyl)azetidin-3-yl]-1H-pyrazol-5-yl}phenol (Preparation 689, 147 mg, 0.353 mmol) and potassium carbonate (147 mg, 1.06 mmol) were stirred in dimethyl sulphoxide (1.0 ml) for 18 hours. The mixture was partitioned between methyl-t-butyl ether (40 ml) and water (20 ml), the organic layer was dried over anhydrous sodium sulphate, filtered and evaporated to give the title compound as a glass, 270 mg.

LCMS Rt=1.60 minutes, m/z=841 [M$^{35}$ClH]+

$^1$HNMR (CDCl$_3$): δ 3.56-3.66 (m, 7H), 3.70 (s, 3H), 4.61 (s, 1H), 4.79-4.88 (m 1H), 5.27 (s, 2H), 6.14-6.19 (m, 1H), 6.25-6.35 (m, 2H), 7.00 (d, 1H), 7.13-7.21 (m, 3H), 7.24-7.35 (m, 6H), 7.40-7.50 (m, 6H), 7.54 (s, 1H), 8.18 (s, 1H).

Preparation 689

4-chloro-2-{1-[1-(diphenylmethyl)azetidin-3-yl]-1H-pyrazol-5-yl}phenol

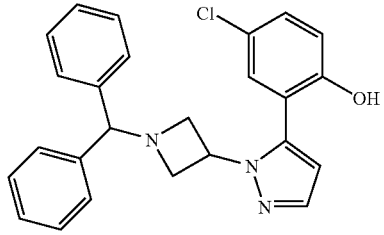

1-(diphenylmethyl)-3-hydrazinoazetidine dihydrochloride (Preparation 690, 1.00 g, 3.06 mmol) was added to an ice cold, stirred suspension of (2E)-1-(5-chloro-2-hydroxyphenyl)-3-(dimethylamino)prop-2-en-1-one (Preparation 759, 700 mg, 3.1 mmol) in ethanol (5 ml) and acetic acid (5 ml), stirred at 0° C. for 2 hours then allowed to warm up to room temperature over 2 hours. The solvents were removed in vacuo and the residue partitioned between ethyl acetate (80 ml) and saturated aqueous sodium hydrogencarbonate solution (50 ml). The organic layer was separated and dried over sodium sulphate, filtered and the solvents removed in vacuo to give a yellow gum. This was dissolved in warm methyl-t-butyl ether (20 ml) and allowed to crystallize to give the title compound as a pale yellow powder, 541 mg, yield 42%.

LCMS Rt=1.30 minutes, m/z 416 [M$^{35}$ClH]$^+$ $^1$HNMR (CDCl$_3$): δ 3.59-3.67 (m, 4H), 4.61 (s, 1H), 4.81-4.91 (m, 1H), 6.33 (s, 1H), 6.90 (d, 1H) 7.08 (d, 1H), 7.16-7.22 (m, 2H), 7.23-7.31 (m, 5H), 7.40-7.45 (m, 4H), 7.70 (m, 1H).

The title compound can also be made using the following method:

1-(diphenylmethyl)azetidin-3-yl methanesulfonate (0.1 g, 0.000315 mol) was suspended in hydrazine hydrate (0.61 mL, 0.0126 mol) and the reaction heated to 70° C. for 6 hours under nitrogen. The reaction was cooled, solvent was removed in vacuo then left under vacuum to dry for 18 hours. The resulting solid was suspended in ethanol (10 mL) and acetic acid (3 mL), (2E)-1-(5-chloro-2-hydroxyphenyl)-3-(dimethylamino)prop-2-en-1-one (Preparation 759, 0.09 g, 0.0004 mol) was added and the reaction stirred at room temperature for 2 hours. Solvent removed in vacuo and crude purified by ISCO® (using 0-30% ethyl acetate in heptane, 12 g SiO$_2$) to recover the title compound as a pale yellow solid, 43 mg, yield=33%.

LCMS Rt=1.29 minutes, MS m/z 416 [M$^{35}$ClH]+

$^1$HNMR (CDCl$_3$): δ 3.64 (m, 4H), 4.66 (s, 1H), 4.89(m, 1H), 6.33 (s, 1H), 6.90 (d, 1H) 7.08 (d, 1H), 7.19 (m, 2H), 7.28 (m, 5H), 7.42 (m, 4H), 7.70 (m, 1H).

Preparation 690

1-(diphenylmethyl)-3-hydrazinoazetidine dihydrochloride

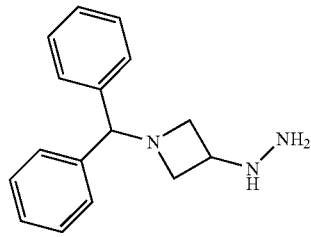

To a stirred suspension of tert-butyl 2-[1-(diphenylmethyl)azetidin-3-yl]hydrazinecarboxylate (Preparation 691, 19.3 g, 54.6 mmol) in 1,4-dioxane (64 ml) was added 4M hydrogen chloride in 1,4-dioxane (290 ml) at 0° C. and stirred at room temperature for 4 hours. Then the reaction mixture was concentrated in vacuo and the residue was triturated with diethyl ether to give 15 g (85%) of the title compound as a white solid.

TLC Rf=0.2 (dichloromethane:methanol, 95:5)

$^1$HNMR (d$_6$-DMSO): δ 3.90-4.20 (m, 5H), 5.90-6.06 (m, 1H), 7.36-7.45 (m 6H), 7.60-7.76 (m 4H), 9.55 (br, 3H), 12.70 (br, 1H).

Preparation 691 tert-butyl 2-[1-(diphenylmethyl)azetidin-3-yl]hydrazinecarboxylate

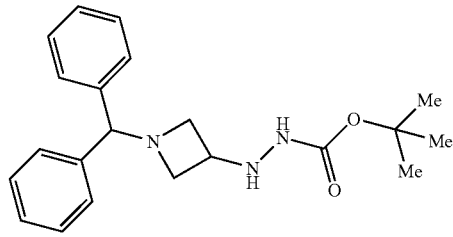

To a stirred solution of tert-butyl 2-[1-(diphenylmethyl)azetidin-3-ylidene]hydrazinecarboxylate (Preparation 692, 15.8 g, 45 mmol) in acetic acid (126 ml) was added sodium cyanoborohydride (2.82 g, 45 mmol) portionwise at room temperature and stirred at room temperature for 4 hours. Then the reaction mixture was concentrated in vacuo. The pH was adjusted to 8-10 with 1M aqueous sodium hydroxide solution and extracted with dichloromethane (3×200 ml). The combined organic layer was washed with water (3×150 ml), saturated aqueous sodium chloride solution (150 ml), dried over anhydrous sodium sulphate and concentrated in vacuo. The crude product was triturated with diethyl ether to get 15 g (94%) of the title compound as a white solid.

TLC Rf=0.3 (ethyl acetate:hexane, 1:1)

¹HNMR (CDCl₃): δ 1.43 (s, 9H), 3.27 (brs, 2H), 3.68 (brs, 2H), 3.90 (brs, 1H), 4.67 (brs, 1H), 6.21 (brs, 1H), 7.21-7.25 (m, 2H), 7.28-7.32 (m, 4H), 7.43-745 (m, 4H).

Preparation 692 tert-butyl 2-[1-(diphenylmethyl)azetidin-3-ylidene]hydrazinecarboxylate

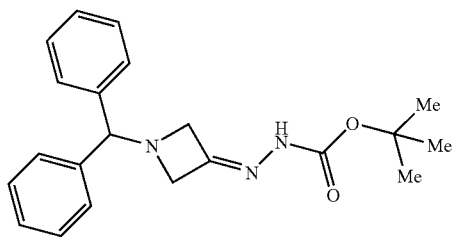

To a stirred solution of 1-(diphenylmethyl)azetidin-3-one (Preparation 693, 11.4 g, 48 mmol) and tert-butyl hydrazinecarboxylate (6.3 g, 48 mmol) in methanol (110 ml) at 0° C. was added acetic acid (5.56 ml, 96 mmol) dropwise and stirred at room temperature for 18 hours. Then the reaction mixture was concentrated in vacuo and the residue was dissolved in dichloromethane (500 ml). The organic layer was washed with 1M aqueous sodium hydroxide solution (2×150 ml), water (3×150 ml), saturated aqueous sodium chloride solution (150 ml), dried over anhydrous sodium sulphate and concentrated in vacuo. The crude product was triturated with diethyl ether to get 15.8 g (94%) of the title compound as a white solid.

TLC Rf=0.25 (ethyl acetate:hexane, 1:4)

¹HNMR (CDCl₃): δ 1.45 (s, 9H), 3.85 (s, 2H), 3.97 (s, 2H), 4.51 (s, 1H), 7.12-7.21 (m, 2H), 7.25-7.29 (m, 4H), 7.40-7.42 (m, 4H).

Preparation 693

1-(diphenylmethyl)azetidin-3-one

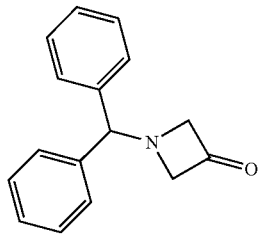

To a stirred solution of 1-(diphenylmethyl)azetidin-3-ol hydrochloride salt, (20 g, 72.5 mmol) in tetrahydrofuran (69 ml) and DMSO (173 ml) was added triethylamine (50.5 ml, 362.6 mmol) at 0° C. Then sulphur trioxide:pyridine complex (69 g, 433 mmol) was added portionwise to the reaction mixture over 10 minutes. The resulting yellow solution was stirred at room temperature for 2 hours. Then the reaction mixture was poured in to cold water (173 ml) and extracted with (1:1) ethyl acetate:hexane (5×200 ml). The combined organic layer was washed with water (200 ml), saturated aqueous sodium chloride solution (200 ml), dried over anhydrous sodium sulphate and concentrated in vacuo. Crude product was purified over 100-200 silica gel using 5% v/v ethyl acetate in hexane to get 11.4 g (67%) of the title compound as a white solid.

TLC Rf=0.8 (ethyl acetate:hexane, 3:7)

¹HNMR (CDCl₃): δ 3.99 (s, 4H), 4.58 (s, 1H), 7.19-7.22 (m, 2H), 7.27-7.31 (m, 4H), 7.46-7.48 (m, 4H).

Preparation 696 tert-butyl 3-hydrazinoazetidine-1-carboxylate

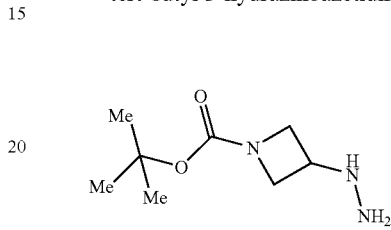

tert-butyl 3-iodoazetidine-1-carboxylate (2 g, 0.007 mol) and hydrazine hydrate (3.44 mL, 0.07 mol) were combined and the reaction heated to 80° C. for 18 hours under nitrogen. The reaction was cooled and reaction partitioned between ethyl acetate (30 mL) and water (30 mL). The aqueous layer was extracted a further 3 times with dichloromethane (3×30 mL). The organic extracts were combined and solvent removed in vacuo to give a clear oil (0.87 g) which was a 2:1 mix of title product to di-tert-butyl 3,3'-hydrazine-1,2-diyl-diazetidine-1-carboxylate LCMS Rt=0.28 minutes MS m/z no mass ion detected ¹HNMR (CDCl₃) δ 1.42 (s, 9H), 2.36 (m, 3H), 4.01 (m, 2H).

Preparation 711

3-cyano-N-(2,4-dimethoxybenzyl)-4-[2-pyridazin-4-yl-4-(trifluoromethyl)phenoxyl]-N-1,2,4-thiadiazol-5-ylbenzenesulfonamide

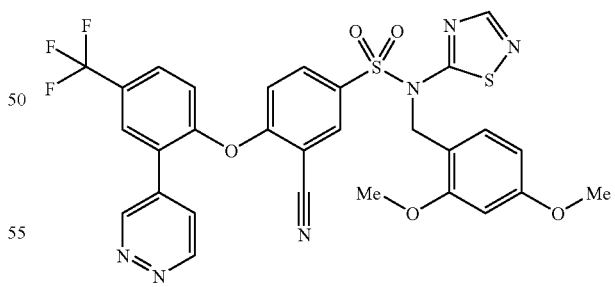

To a solution of 2-pyridazin-4-yl-4-(trifluoromethyl)phenol (Preparation 712, 60.6 mg, 0.25 mmol) in dimethylsulfoxide (2.5 mL) was added 3-cyano-N-(2,4-dimethoxybenzyl)-4-fluoro-N-1,2,4-thiadiazol-5-ylbenzenesulfonamide (Preparation 68, 109.2 mg, 0.25 mmol) followed by potassium carbonate (101.7 mg, 0.74 mmol). The resulting mixture was stirred overnight at room temperature under nitrogen. The reaction mixture was poured into water (125 mL), and extracted with ethyl acetate (3×25 mL). The combined organic extract was washed successively with aqueous sodium hydroxide solution (1M, 15 mL) and saturated aqueous sodium chloride solution (4×25 mL), dried over anhydrous sodium sulfate, filtered and the solvent removed in vacuo. The resulting residue was purified by column chromatography using a gradient of 25-40% v/v ethyl acetate in heptane to give the title compound as a white foam (59.7 mg, 36%).

LCMS Rt=3.47 minutes, MS m/z 655 [MH]+

$^1$HNMR (CDCl$_3$): δ 3.56 (s, 3H), 3.80 (s, 3H), 5.33 (s, 2H), 6.17 (m, 1H), 6.34-6.37 (m, 1H), 6.73-6.76 (m, 1H), 7.10 (m, 1H), 7.20 (m, 1H), 7.76 (m, 2H), 7.81-7.86 (m, 3H), 8.22 (s, 1H), 9.34 (m, 1H), 9.38 (m, 1H).

Method 2

An alternative method of preparing Preparation 711 is as follows.

A mixture of 3-Cyano-N-(2,4-dimethoxybenzyl)-4-[2-iodo-4-(trifluoromethyl)phenoxy]-N-1,2,4-thiadiazol-5-yl-benzenesulfonamide (Preparation 429, 33.07 g, 47.08 mmol) in dimethylformamide (140 mL) was treated with copper (I) iodide (1830 mg, 9.60 mmol) and cesium fluoride (14.4 g, 94.2 mmol). The mixture was sparged with nitrogen for 15 minutes. Then 4-(tributylstannyl)pyridazine (19.1 g, 51.8 mmol) dissolved in dimethylformamide (10 mL) was added and the reaction heated to 30° C. The reaction was cooled, poured onto water (1 L) and extracted with diethylether (4×450 mL). The combined extracts were washed with water (6×500 mL), dried over magnesium sulfate and evaporated to furnish an orange foam. This residue was purified using column chromatography (using a gradient of 100% heptane with 2% triethylamine to 40:60 ethylacetate:heptane with 2% triethylamine) to furnish the title compound as an off-white solid.

Preparation 712

2-pyridazin-4-yl-4-(trifluoromethyl)phenol

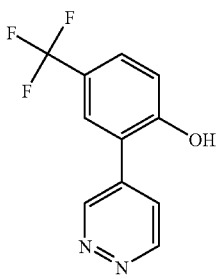

Method 1

To a solution of 2-iodo-4-trifluoromethylphenol (360 mg, 1.25 mmol), 4-(tributylstannyl)pyridazine (485.2 mg, 1.31 mmol) and cesium fluoride (376.5 mg, 2.47 mmol) in N,N-dimethylformide (2.90 mL) was added the tetrakis(triphenylphosphine)palladium(0) (70.9 mg, 0.061 mmol) and copper(I) iodide (25.2 mg, 0.13 mmol). The resulting mixture was evacuated and refilled with nitrogen five times and stirred at 45° C. for 21 hours under nitrogen. The reaction was concentrated in vacuo and the residue partitioned between ethyl acetate (20 mL) and water (20 mL). The aqueous layer was extracted with ethyl acetate (3×20 mL) and the combined organic extracts were washed with water (3×20 mL) and saturated aqueous sodium chloride solution (20 mL). The organics were dried over anhydrous sodium sulfate, filtered and concentrated in vacuo. The resulting residue was purified by column chromatography using a gradient of 25-60% v/v ethyl acetate in dichloromethane to give the title compound as a yellow-orange solid (150.3 mg, 50%).

LCMS Rt=2.42 minutes, MS m/z 241 [MH]+

$^1$HNMR (CDCl$_3$): δ 7.33 (m, 1H), 7.64 (m, 1H), 7.68 (m, 1H), 7.79 (m, 1H), 9.31 (m, 1H), 9.74 (m, 1H).

Method 2

An alternative method of preparing Preparation 712 is as follows.

To a suspension of 4-(5-trifluoro-2-methoxyphenyl)pyridazine (Preparation 896, 0.045 g, 0.00177 mol) in dichloromethane (5.0 mL) at 0° C. under nitrogen was added tribromoborane in dichloromethane (1.0 M solution, 0.53 mL, 0.00053 mol). This was stirred at room temperature under nitrogen for 18 hours. The reaction was diluted in water (10.0 mL) and stirred at room temperature for 10 minutes before adding a solution of aqueous saturated ammonium chloride (10.0 mL) and a 2M (aq) HCl solution (10.0 mL). Dichloromethane was added (10.0 mL) and the organic layer was discarded. The aqueous layer was brought to neutral pH adding a saturated aqueous solution of sodium hydrogen carbonate followed by extraction with dichloromethane (15 mL). The organic layer was dried over sodium sulphate, filtered, and concentrated in vacuo. The residue was triturated in dichloromethane (5.0 mL) and the title compound was isolated as a pale yellow solid.

LCMS Rt=1.44 minutes MS m/z 241 [MH]+

$^1$H NMR (400 MHz, d$_6$-DMSO): δ 7.20 (d, 1H), 7.65 (d-d, 1H), 7.80 (s, 1H), 7.90 (m, 1H), 9.25 (d, 1H), 9.50 (s, 1H), 11.10 (s, 1H)

Method 3

A further alternative method of preparing Preparation 712 is as follows.

To a 5 L jacketed vessel was added acetonitrile (9 L) and the solvent was sparged with nitrogen for 2 hours. To the solvent was added cesium fluoride (335.8 g, 2.21 moles), 4-(tributylstannyl)pyridazine (408 g, 1.11 moles), 4-trifluoromethyl-6-iodophenol (318.33 g, 1.11 moles), palladium tetrakis triphenylphosphine (61.31 g, 53.05 mmole) and copper (I) iodide (40 g, 210 mmol) at 20° C. The resulting orange suspension was heated to 45-50° C. for 2 hours. The reaction was cooled and partitioned between tert-butylmethylether (2×5 L) and 2N (aq) HCl (2×5 L). The resulting biphasic solution was filtered and the layers separated. The aqueous phases were combined and basified with 4M (aq) sodium hydroxide solution (6 L) to obtain a pH=4-5. The resulting suspension was extracted into ethyl acetate (10 L) and the organic layer concentrated to dryness to afford an orange solid as the title compound (60%).

Method 4

Yet another alternative method for the preparation of Preparation 712 is as follows.

2-(3-furyl)-4-(trifluoromethyl)phenyl acetate (Preparation 899, 0.44 g, 0.0018 mol) was dissolved in dichloromethane (10 mL) then zinc triflate (0.03 g, 0.00008 mol) added. The reaction was heated to 40 degrees Celsius and di-tert butyl azodicarboxylate (0.45 g, 0.002 mol) added portionwise over 2 hours. The reaction was then stirred at 45 degrees celsius for 72 hours. Acetic acid (0.5 mL) was then added and the reaction stirred at 45 degrees celsius for 48 hours. The reaction was cooled to room temperature and 2M aqueous sodium hydroxide (30 mL) added. The resultant solution was stirred vigorously for 30 minutes. The aqueous layer was then separated, acidified to pH=1 with concentrated aqueous hydrogen chloride and washed with dichloromethane (10 mL). The reaction was brought to pH=6 with sodium bicarbonate and extracted with ethyl acetate (2×50 ml). The organics were combined and concentrated in vacuo to give the title compound as a brown solid (0.29 g, 64% yield) LCMS Rt=1.46 min; MS m/z 241 [MH]+

$^1$H NMR (400 MHz, d$_6$-DMSO): δ 7.17(d 1H) 7.66(dd 1H) 7.81 (d 1H), 7.92(dd 1H), 9.25(dd, 1H), 9.49(m 1H) 11.09(s 1H)

Preparation 716

3-chloro-4-fluoro-N-(methoxymethyl)-N-pyrimidin-4-ylbenzenesulfonamide and 3-chloro-4-fluoro-N-[(4E)-3-(methoxymethyl)pyrimidin-4(3H)-ylidene]benzenesulfonamide and 3-chloro-4-fluoro-N-[(4E)-1-(methoxymethyl)pyrimidin-4(1H)-ylidene]benzenesulfonamide

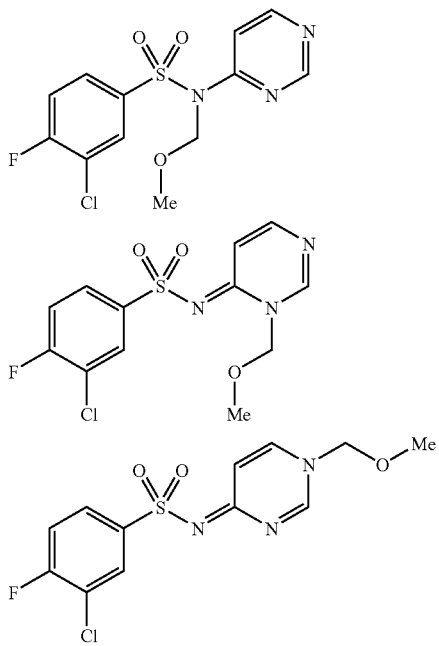

To 3-chloro-4-fluoro-N-pyrimidin-4-ylbenzenesulfonamide (Preparation 426, 73 mg, 0.25 mmol) in methylene chloride (2 mL) cooled at 0° C. was added N,N-diisopropylethylamine (0.066 mL, 0.38 mmol) and chloromethyl methyl ether (0.025 mL, 0.28 mmol). After stirring at room temperature for 18 hours, the reaction mixture was diluted with ethyl acetate, washed successively with 1N aqueous sodium hydroxide, water, saturated aqueous sodium chloride solution, dried over anhydrous sodium sulfate and concentrated to give 76 mg (90%) of the title compound as an orange oil and a mixture of three regioisomers that were not separated.

LCMS Rt=1.64 (major), 1.33 & 1.46 minutes, MS m/z 332 [MH]+.

Preparation 719

5-chloro-N-(ethoxymethyl)-2,4-difluoro-N-pyrimidin-4-ylbenzenesulfonamide and 5-chloro-N-[(4E)-1-(ethoxymethyl)pyrimidin-4(1H)-ylidene]-2,4-difluorobenzenesulfonamide and 5-chloro-N-[(4E)-1-(ethoxymethyl)pyrimidin-4(1H)-ylidene]-2,4-difluorobenzenesulfonamide

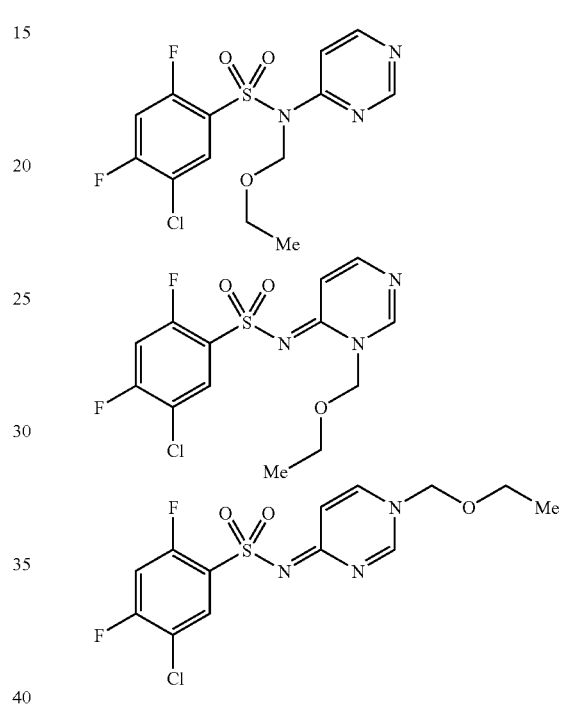

Prepared according to the process of Preparation 716 using 5-chloro-2,4-difluoro-N-pyrimidin-4-ylbenzenesulfonamide, Preparation 723 and chloromethyl ethyl ether. The product was a mixture of three regioisomers that were not separated and used in subsequent reactions as a mixture.

LCMS Rt=1.71 (major), 1.41 & 1.55 (minor) minutes, MS m/z 364 [MH]+.

Preparation 721

2-(2-aminopyridin-4-yl)-4-chlorophenol

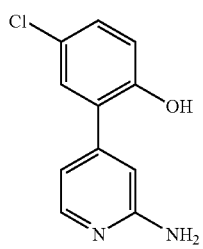

5-chloro-2-hydroxyphenylboronic acid (200 mg, 1 mmol), 2-amino-4-bromopyridine (220 mg, 1.3 mmol), sodium carbonate (490 mg, 4.6 mmol), and tetrakis(triphenylphosphine) palladium (0) (130 mg, 0.12 mmol) were all placed in a round bottom flask and 1,4-dioxane (3 mL) and water (1 mL) were added. The mixture was heated to 85° C. for 2 hours. The mixture was cooled to room temperature and diluted with ethyl acetate and water. The layers were separated and the aqueous layer was extracted with ethyl acetate (1×). The combined extracts were dried over anhydrous magnesium sulfate and concentrated in vacuo. The residue was purified by column chromatography (12 g silica gel column, 0-100% v/v ethyl acetate/hexanes gradient elution) to afford the title compound (242 mg).

LCMS Rt=1.05 minutes, MS m/z 221 [MH]+

$^1$HNMR (d$_6$-DMSO): δ 5.87 (m, 2H), 6.63 (m, 2H), 6.93 (m, 1H), 7.22 (m, 2H), 7.90 (d, 1H), 9.98 (bs, 1H).

Preparation 723

5-chloro-2,4-difluoro-N-pyrimidin-4-ylbenzene-sulfonamide

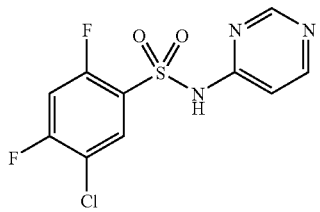

A mixture of 4-aminopyrimidine (1.30 g, 13.7 mmol) and 1,4-diazabicyclo[2.2.2]octane (1.54 g, 13.7 mmol) were added concurrently to a solution of 5-chloro-2,4-difluorobenzenesulfonyl chloride (3.4 g, 14 mmol) in anhydrous acetonitrile (63 mL). The reaction mixture immediately turned yellow and a precipitate formed. The reaction mixture was stirred under argon. After 72 hours, the reaction mixture was filtered and the filtrate was concentrated in vacuo to give a residue. The residue was partitioned between 1M hydrochloric acid and ethyl acetate. The organic phase was separated, dried over anhydrous magnesium sulfate and concentrated in vacuo. The residue was partially purified by automated flash column chromatography using an 80 g silica gel ISCO™ column using hexanes to 1% v/v acetic acid in ethyl acetate gradient elution. The product was purified a second time by reverse phase HPLC to give the title compound (193 mg, 5%) as a white solid.

LCMS Rt=1.22 minutes, MS m/z 307 [M$^{37}$ClH]+, 305 [M$^{35}$ClH]+

$^1$HNMR (d$_6$-DMSO): δ 6.93 (m, 1H), 7.72 (m, 1H), 8.04 (m, 1H), 8.20 (m, 1H), 8.56 (s, 1H), 13.53 (br s, 1H).

Preparation 728 tert-butyl 4-[5-chloro-2-(2-cyano-4-{[(2,4-dimethoxybenzyl)(1,2,4-thiadiazol-5-yl)amino]sulfonyl}phenoxy)-4-fluorophenyl]-1H-pyrazole-1-carboxylate

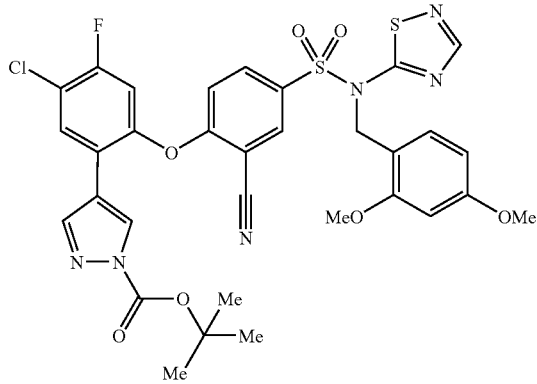

The title compound was prepared using a method analogous to that for Preparation 733 below, using 3-cyano-N-(2,4-dimethoxybenzyl)-4-fluoro-N-1,2,4-thiadiazol-5-ylbenzenesulfonamide (Preparation 68) and tert-butyl 4-(5-chloro-4-fluoro-2-hydroxyphenyl)-1H-pyrazole-1-carboxylate (Preparation 743). Purification was by column chromatography (silica, heptane-ethyl acetate 10-60% v/v).

LCMS Rt=4.39 minutes MS m/z=728 [M$^{35}$ClH]+

$^1$HNMR (d$_6$-DMSO): δ 1.55 (s, 9H), 3.6 (s, 3H), 3.75 (s, 3H), 5.20 (s, 2H), 6.4 (m, 2H), 6.95-7.10 (m, 2H), 7.70 (m, 2H), 7.95 (m, 1H), 8.2 (s, 1H), 8.30 (d, 1H), 8.40 (m, 1H), 8.55 (s, 1H).

Preparation 733

4-(5-chloro-4-fluoro-2-iodophenoxy)-3-cyano-N-(2,4-dimethoxybenzyl)-N-1,2,4-thiadiazol-5-ylbenzene-sulfonamide

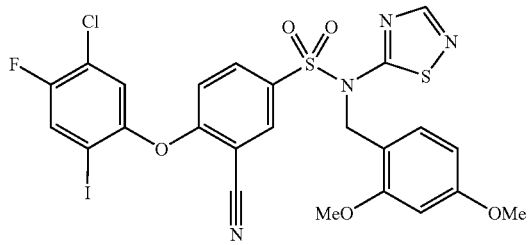

To a solution of 3-cyano-N-(2,4-dimethoxybenzyl)-4-fluoro-N-1,2,4-thiadiazol-5-ylbenzenesulfonamide (Preparation 68, 335 mg, 0.77 mmol) in dimethylsulfoxide (10 ml), was added 5-chloro-4-fluoro-2-iodophenol (Preparation 734, 200 mg, 0.73 mmol) and potassium carbonate (229 mg, 1.47 mmol). The flask was purged with nitrogen (3×). The resulting suspension was allowed to stir at room temperature for 18 hours. The reaction was poured into a 1M aqueous solution of sodium hydroxide, and extracted with dichloromethane (3×). The combined organic phase was then dried over anhydrous magnesium sulfate, filtered and the solvent removed in vacuo to leave the desired product as an off white solid (504 mg, 100%).

LCMS Rt=4.70 minutes, no mass ion observed.

$^1$HNMR (CDCl$_3$): δ 3.62 (s, 3H), 3.80 (s, 3H), 5.35 (s, 2H), 6.26 (s, 1H), 6.34-6.38 (m, 1H), 6.49-6.55 (m, 1H), 7.04-7.09 (m, 1H), 7.18-7.22 (m, 1H), 7.67-7.71 (m, 1H), 7.77-7.83 (m, 2H), 8.22 (s, 1H).

Preparation 734

5-chloro-4-fluoro-2-iodophenol

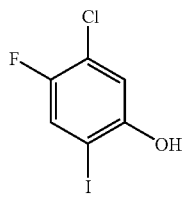

N-iodosuccinimide (4.61 g, 20.5 mmol), was suspended in glacial acetic acid (20 ml). To this suspension was added 3-chloro-4-fluorophenol (3.0 g, 20.0 mmol) and then concentrated sulphuric acid (0.36 ml, 6.14 mmol) was added dropwise over 5 minutes. The resulting brown/orange suspension was stirred at room temperature for 18 hours. The mixture was concentrated in vacuo and the residue was partitioned between water and dichloromethane, the dichloromethane was dried over anhydrous magnesium sulphate, filtered and concentrated in vacuo to give an orange/red oil. The crude product was purified by column chromatography on silica gel using 1:1 ethyl acetate:heptane to give the title compound as a pale orange/brown solid (3.50 g, 60% yield)

LCMS Rt=2.83 minutes, m/z=271 [M$^{35}$ClH]–; 273 [M$^{37}$ClH]–

$^1$HNMR (CDCl$_3$): δ 5.33 (s, 1H), 7.02 (d, 1H), 7.43 (d, 1H)

Preparation 743 tert-butyl 4-(5-chloro-4-fluoro-2-hydroxyphenyl)-1H-pyrazole-1-carboxylate

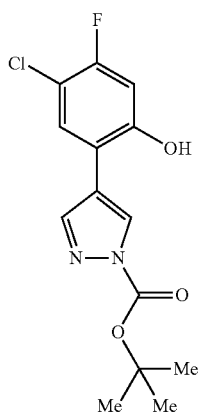

Prepared using the method of Example 587 using 4-chloro-5-fluoro-2-iodophenol (Preparation 744, 386 mg, 1.42 mmol) and tert-butyl 4-(4,4,5,5-tetramethyl-1,3,2-dioxaborolan-2-yl)-1H-pyrazole-1-carboxylate (500 mg, 1.70 mmol) gave the title compound as a white solid (200 mg, 38%).

LCMS Rt=3.43 minutes, MS m/z 312 [M$^{35}$ClH]+

$^1$HNMR (d$_6$-DMSO): δ 1.60 (s, 9H), 6.90 (m, 1H), 7.90 (m, 1H), 8.40 (s, 1H), 8.60 (s, 1H).

Preparation 744

4-chloro-5-fluoro-2-iodophenol

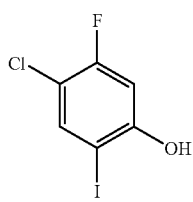

To a suspension of N-iodosuccinamide (6.1 g, 27.3 mmol) in glacial acetic acid (23 mL) was added 4-chloro-3-fluorophenol (4.0 g, 27.3 mmol) and after 5 minutes sulphuric acid was added (0.5 mL, 8.2 mmol) and the reaction mixture was left to stir at room temperature for 16 hours. The reaction was quenched by addition of water (30 mL) and the compound was extracted into dichloromethane (3×30 mL). The combined organic layers were washed with 10% sodium metabisulphite aqueous solution (2×20 mL), then saturated aqueous sodium chloride solution, dried over anhydrous magnesium sulphate, filtered and evaporated in vacuo. The crude material was purified by flash column chromatography (silica, toluene) to afford the desired product as an oil (4.0 g, 54%).

LCMS=3.10 minutes, MS m/z=270 [M$^{35}$ClH]–

$^1$HNMR (d$_6$-DMSO): δ 6.80 (m, 1H), 7.85 (d, 1H), 11.1 (s, 1H).

Preparation 759

(2E)-1-(5-chloro-2-hydroxyphenyl)-3-(dimethylamino)prop-2-en-1-one

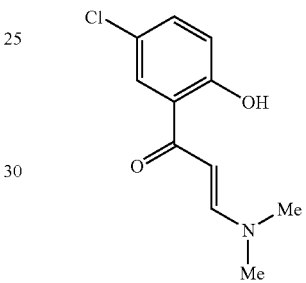

To a solution of 1-(5-chloro-2-hydroxyphenyl)ethanone (17.2 g, 100.8 mmol) in propan-2-ol (100 ml) was added 1,1-dimethoxy-N,N-dimethylmethanamine (27 ml, 200 mmol) dropwise and the reaction mixture was warmed to 45° C. and stirred for 24 hours. The resulting suspension was cooled in ice, filtered and washed with propan-2-ol then tert-butyl methyl ether. The solid was dried in vacuo to give the title compound as a bright yellow solid, 16.39 g, 72% yield.

LCMS Rt=1.48 minutes, MS m/z 226 [M$^{35}$ClH]+; 228 [M$^{37}$ClH]+

$^1$HNMR (d$_6$-DMSO): δ 3.00 (s, 3H), 3.19 (s, 3H), 6.00 (d, 1H), 6.79 (d, 1H), 7.35 (m, 1H), 7.92 (d, 1H), 8.00 (s, 1H).

Preparation 760

3-cyano-N-(1,2,4-thiadiazol-5-yl)-4-[2-iodo-4-(trifluoromethoxy)phenoxy]benzenesulfonamide

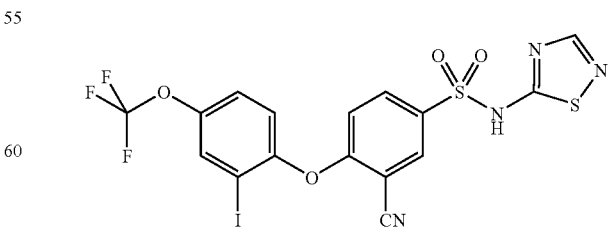

To a suspension of 2-iodo-4-(trifluoromethoxy)phenol (Preparation 226, 600 mg, 1.97 mmol) and potassium carbonate (1125 mg, 8.14 mmol) in Dimethylsulfoxide (10 mL) was added 3-cyano-4-fluoro-N-[1,2,4]thiadiazol-5-yl-benzenesulfonamide (Preparation 65). The reaction was heated to 80° C. under $N_2$ for 7 hours before the addition of ethyl acetate (20 mL) and 3M aqueous HCl solution (30 mL). The organic layer was collected, washed with brine (20 mL), dried over sodium sulphate and concentrated in vacuo. The residue was triturated in dichloromethane and filtered to afford 965 mg of the title compound.

LCMS Rt=1.90 minutes. MS m/z 569 [MH]+
$^1$H NMR ($d_6$-DMSO): δ 6.90 (d, 1H), 7.55-7.760 (m, 2H), 8.00 (m, 2 H), 8.35 (s, 1H), 8.45 (s, 1H)

Preparation 850

Tert-butyl 3-{5-[5-chloro-2-(4-{[(2,4-dimethoxybenzyl)(1,2,4-thiadiazol-5-yl)amino]sulfonyl}-2,5-difluorophenoxy)phenyl]-1H-pyrazol-1-yl}azetidine-1-carboxylate

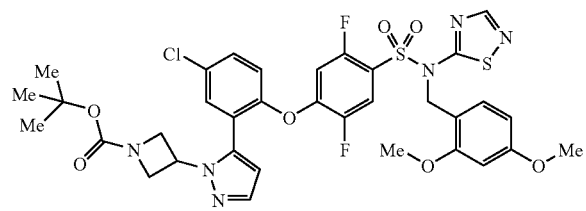

Tert-butyl 3-[5-(5-chloro-2-hydroxyphenyl)-1H-pyrazol-1-yl]azetidine-1-carboxylate (Preparation 851, 80.0 g, 0.2287 mol) and potassium carbonate (94.82 g, 0.686 mol) were combined in dimethylsulphoxide (600 mL). To this slurry was added N-(2,4-dimethoxybenzyl)-2,4,5-trifluoro-N-1,2,4-thiadiazol-5-ylbenzenesulfonamide, (Preparation 647, 101.87 g, 0.2287 mol) and stirred at room temperature for 4.5 hours. Ethyl acetate (1600 mL) and water (1000 mL) were added and the layers separated. The ethyl acetate was washed with water (2×800 mL), then saturated aqueous sodium chloride solution (200 mL) and then dried over anhydrous magnesium sulphate. To this suspension, tert-butylmethyl ether (250 mL) was added and the mixture was washed with dilute aqueous sodium chloride solution (1000 mL), the organics were dried over magnesium sulphate, filtered and the solvents removed in-vacuo to give a pale yellow solid. This solid was dissolved in dichloromethane (500 mL) and tert-butylmethyl ether was added gradually whilst evaporating the dichloromethane in vacuo to give a white precipitate which was filtered off and washed with a little tert-butylmethyl ether to give the title compound as a white solid, (145.47 g).

HPLC Rt=4.04 minutes
$^1$HNMR (CDCl$_3$) δ 1.47 (s, 9H), 3.65 (s, 3H), 3.78 (s, 3H), 4.30 (m, 2H), 4.42 (m, 2H), 4.84-4.91 (m, 1H), 5.31 (s, 2H), 6.17 (d, 1H), 6.22 (d, 1H), 6.26-6.31 (m, 1H), 6.35-6.37 (m, 1H), 7.02 (d, 1H), 7.19 (d, 1H), 7.41 (d, 1H), 7.45-7.50 (m, 1H), 7.51-7.53 (m, 1H), 7.62 (d, 1H), 8.21 (s, 1H).

Preparation 851

Tert-butyl 3-[5-(5-chloro-2-hydroxyphenyl)-1H-pyrazol-1-yl]azetidine-1-carboxylate

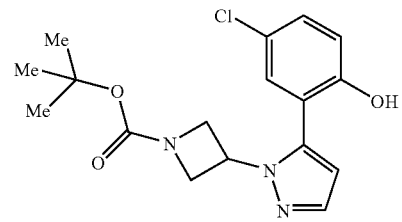

Tert-butyl 3-hydrazinoazetidine-1-carboxylate, (Preparation 696, 88.37 g, 0.4247 mol) was dissolved in ethanol (883.7 mL) and the solution was cooled to 0° C. in an ice bath. Acetic acid (97.36 mL, 1.70 mol) was added followed by (2E)-1-(5-chloro-2-hydroxyphenyl)-3-(dimethylamino) prop-2-en-1-one, (Preparation 852, 95.86 g, 0.4247 mol) and the resulting slurry was allowed to warm to room temperature then stirred at room temperature for 2 days. The resulting suspension was cooled to 0° C. and the solid was filtered off, washed with cold ethanol (2×40 mL) and dried to give the title compound as a white granular solid, (83.23 g).

HPLC Rt=3.12 minutes
$^1$HNMR (d$_6$-DMSO): δ 1.39 (s, 9H), 4.10-4.24 (m, 4H), 4.80-4.89 (m, 1H), 6.29 (s, 1H), 6.97 (d, 1H), 7.20 (s, 1H), 7.33 (dd, 1H), 7.63 (s, 1H).

Preparation 852

(2E)-1-(5-Chloro-2-hydroxyphenyl)-3-(dimethylamino)prop-2-en-1-one

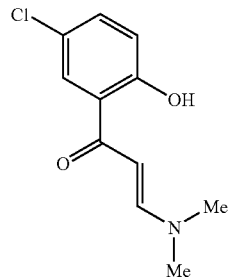

1-(5-chloro-2-hydroxyphenyl)ethanone, (165 g, 0.967 mol) was slurried in 2-propanol (1000 mL) then 1,1-dimethoxy-N,N-dimethylmethanamine (258.28 mL, 1.93 mol) was added and the resulting yellow solution was stirred at 45° C. for 18 hours. The resulting suspension was cooled to room temperature and stirred for a further 48 hours. The solid was filtered off, washed with 2-propanol (2×200 mL) and then tert-butylmethyl ether (200 mL) then dried to give the title compound as a bright yellow solid, (204.59 g).

HPLC Rt=5.25 minutes
$^1$HNMR (CDCl$_3$) δ 2.99 (s, 3H), 3.21 (s, 3H), 5.67 (d, 1H), 6.88 (d, 1H), 7.29 (dd, 1H), 7.63 (d, 1H), 7.89 (d, 1H), 13.97 (s, 1H).

Preparation 853 tert-Butyl 4-(4-(5-chloro-2-hydroxyphenyl)pyridin-2-yl)piperazine-1-carboxylate

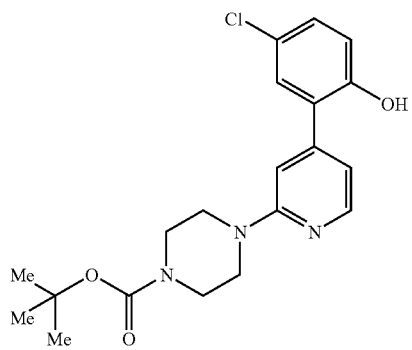

A mixture of 4-chloro-2-iodophenol (367 mg, 1.44 mmol), tert-butyl 4-(4-(4,4,5,5-tetramethyl-1,3,2-dioxaborolan-2-yl)pyridin-2-yl)piperazine-1-carboxylate (707.5 mg, 1.817 mmol), and sodium carbonate (615.0 mg, 5.802 mmol) in 1,4-dioxane (6.0 mL, 77 mmol) and water (2.0 mL, 110 mmol) was sparged 5 minutes with argon. Tetrakis(triphenylphosphine)palladium(0) (100.0 mg, 0.08654 mmol) was added, the vial was capped, and the reaction mixture was heated at 90° C. After 4 hours, the reaction mixture was cooled to ambient temperature and poured into water. Saturated aqueous ammonium chloride was added, and the mixture was extracted with ethyl acetate (3×). The combined organic layers were washed with brine, dried over sodium sulfate, filtered, and concentrated onto diatomaceous earth. The residue was purified by automated flash chromatography (24 g SiO2, hexanes to ethyl acetate) to afford the product as an amber oil that solidified on standing (491 mg, 74%).

LC/MS Rt=1.66 minutes, MS m/z 390 [M$^{35}$ClH]+

$^1$H NMR (d$_6$-DMSO): δ 10.01 (s, 1H), 8.12 (d, 1H), 7.35 (d, 1H), 7.25 (m, 1H), 6.94 (m, 2H), 6.88 (m, 1H), 3.51 (m, 4H), 3.43 (m, 4H), 1.42 (s, 9H).

Preparation 854 tert-Butyl [(2,4,5-trifluorophenyl)sulfonyl]1,3-thiazol-4-ylcarbamate

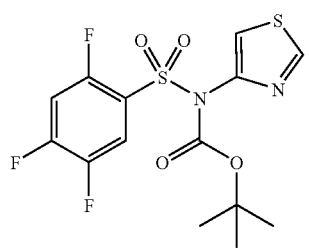

The above titled compound was prepared from 2,4,5-trifluorobenzenesulfonyl chloride (5.0 g, 0.022 mol) and thiazole-4-yl-carbamic acid tert-butyl ester (Preparation 72, 4.3 g, 0.022 mol) using the method of Preparation 453 to afford the product as a white solid (6.84 g, 80%).

LC/MS Rt=1.65 minutes, MS m/z 395 [MH]+

$^1$H NMR (d$_6$-DMSO): δ 9.14 (d, 1H), 8.19 (m, 1H), 8.03 (m, 2H), 1.28 (s, 9H).

Preparation 855

2-[1-(1-Methylazetidin-3-yl)-1H-pyrazol-5-yl]-4-(trifluoromethyl)phenol

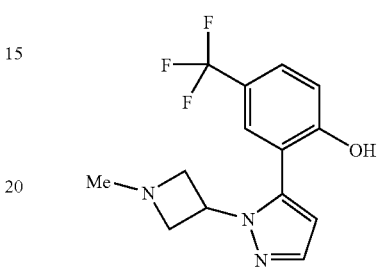

2-(1-Azetidin-3-yl-1H-pyrazol-5-yl)-4-(trifluoromethyl)phenol, (Preparation 856, 190 mg, 0.00067 mol) was stirred in dichloromethane (5 mL), methanol (0.5 mL) and acetic acid (0.1 mL). Aqueous formaldehyde (0.25 mL of 37% wt/vol, 0.00336 mol) was added and the reaction stirred at room temperature for 15 minutes. Sodium triacetoxyborohydride (711 mg, 0.00336 mol) was added and the reaction stirred at room temperature for 4 hours. The solvents were removed in vacuo and the residue dissolved in water. Aqueous ammonium hydroxide (7.5 molar) was added to pH 10 to give a white precipitate. The mixture was extracted with ethyl acetate (1×20 mL). The organic layer was separated and washed with saturated aqueous sodium chloride solution (2×10 mL). The organic layer was separated, dried over anhydrous sodium sulphate, filtered and the solvents removed in vacuo to give the title compound as a foam. (140 mg).

LCMS Rt=0.97 minutes, MS m/z=298 [MH]+

TLC dichloromethane:methanol:acetic acid 95:5:0.5, Rf=0.4

$^1$HNMR (CDCl$_3$) δ 2.64 (s, 3H) 3.92-4.04 (m, 4H) 5.05-5.12 (m, 1H) 6.28 (s, 1H) 6.76 (d, 1H) 7.49-7.52 (m, 2H) 7.68 (s, 1H).

Preparation 856

2-(1-Azetidin-3-yl-1H-pyrazol-5-yl)-4-(trifluoromethyl)phenol

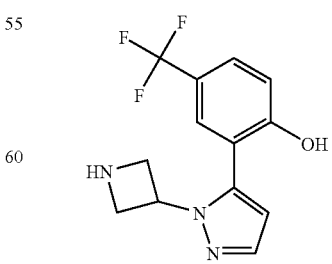

Trifluoroacetic acid (4 mL) was added to a stirred solution of tert-butyl 3-{5-[2-hydroxy-5-(trifluoromethyl)phenyl]-

1H-pyrazol-1-yl}azetidine-1-carboxylate, (Preparation 857, 375 mg, 0.001 mol) in dichloromethane (10 mL) under nitrogen and the solution was stirred for 3 hours. The pink solution was evaporated and the residue dissolved in methanol and then the solvents were removed in vacuo. This was repeated a further two times. The residue was then suspended in diethyl ether and the solvents removed in vacuo to give an off-white foam. The foam was dissolved in water and treated with aqueous ammonia solution (7.5 molar) until pH10 to give a white precipitate. The mixture was extracted with ethyl acetate (6×30 mL). The combined organic layers were washed with saturated aqueous sodium chloride solution (2×20 mL), dried over anhydrous sodium sulphate, filtered and the solvents removed in vacuo to give a solid. The solid was triturated with diethyl ether to give the title compound as a white solid (200 mg).

LCMS Rt=0.97 minutes, MS m/z=284 [MH]+

TLC dichloromethane:methanol:formic acid 100:10:0.1, Rf=0.3.

$^1$HNMR (d$_6$-DMSO) δ 3.62-3.66 (m, 2H) 4.01-4.05 (m, 2H) 4.87-4.94 (m, 1H) 6.29 (s, 1H) 7.05 (d, 1H) 7.40 (s, 1H) 7.57-7.60 (m, 2H).

Preparation 857 tert-Butyl 3-{5-[2-hydroxy-5-(trifluoromethyl)phenyl]-1H-pyrazol-1-yl}azetidine-1-carboxylate

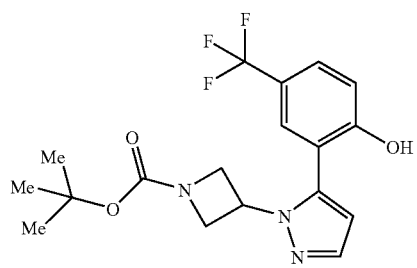

To a stirred solution of crude tert-butyl 3-hydrazinoazetidine-1-carboxylate, (Preparation 858, 5.7 g, 0.030 mol) in ethanol (66 mL) at 0° C. was added acetic acid (6.6 mL) dropwise. Then (2E)-3-(dimethylamino)-1-[2-hydroxy-5-(trifluoromethyl)phenyl]prop-2-en-1-one, (Preparation 859, 6.4 g, 24.68 m mol) was added portionwise and allowed to stir at room temperature for 20 hours. The reaction mixture was concentrated in vacuo and neutralised with aqueous sodium hydrogencarbonate solution. The mixture was extracted with ethyl acetate (150 mL). The combined organic layer was washed with water (100 mL), saturated aqueous sodium chloride solution (50 mL) and dried over anhydrous sodium sulphate. After concentration of organic layer in vacuo, the crude product was washed with 20% v/v ethyl acetate in hexane to get the title compound as a white solid (7.4 g).

LCMS Rt=3.52 minutes, MS m/z=384 [MH]+

$^1$HNMR (CDCl$_3$) δ1.45 (s, 9H), 4.27-4.37 (m, 3H), 4.70 (brs, 1H), 4.79-4.83 (m, 1H), 6.25 (s, 1H), 7.16 (d, 1H), 7.46 (s, 1H), 7.55 (d, 1H), 7.66 (s, 1H), 9.64 (s, 1H).

HPLC Purity: 99.84%

Preparation 858

Tert-butyl 3-hydrazinoazetidine-1-carboxylate

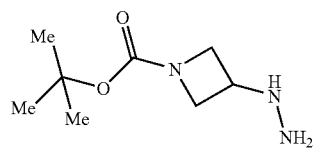

Tert-butyl 3-iodoazetidine-1-carboxylate (142 g, 0.5016 mol) and hydrazine hydrate (245.21 mL, 5.02 mol) were mixed in ethanol (284 mL) and the reaction was heated to 85° C. for 48 hours under nitrogen. The reaction was cooled and the ethanol was removed in vacuo. The residue was partitioned between water (200 mL) and dichloromethane (300 mL), the water layer was re-extracted with dichloromethane (2×200 mL), the combined organics were dried over anhydrous magnesium sulphate, filtered and concentrated in vacuo to give the title compound as a colourless oil, (88.37 g). This compound was used immediately in the next step.

$^1$HNMR (CDCl$_3$) δ 1.44 (s, 9H), 3.05 (br s, 3H) 3.65-3.76 (m, 3H), 4.00-4.07 (m, 2H).

Preparation 859

(2E)-3-(Dimethylamino)-1-[2-hydroxy-5-(trifluoromethyl)phenyl]prop-2-en-1-one

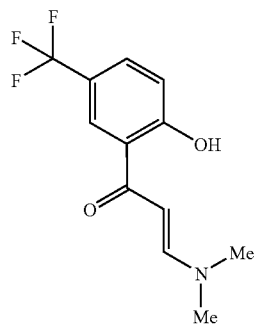

1-[2-Hydroxy-5-(trifluoromethyl)phenyl]ethanone, (Preparation 860, 7.0 g, 0.0343 mol) was taken in dimethylformamide dimethylacetal (18.2 mL, 0.137 mol) at room temperature and then heated at 110° C. for 30 min. The reaction mixture was concentrated in vacuo and the crude product was crystallised from 2-propanol to give the title compound as bright yellow solid (6.4 g).

LCMS Rt=1.61 minutes, MS m/z=260 [MH]+

$^1$HNMR (CDCl$_3$) δ3.02 (s, 3H) 3.22 (s, 3H), 5.72 (d, 1H), 6.99 (d, 1H), 7.55 (d 1H), 7.89-7.94 (m, 2H), 14.45 (s, 1H).

Preparation 860

1-[2-Hydroxy-5-(trifluoromethyl)phenyl]ethanone

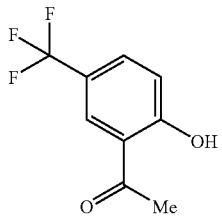

To a stirred solution of 1-[2-methoxy-5-(trifluoromethyl)phenyl]ethanone (35 g, 0.160 mol) in dry dichloromethane (400 mL) at 0° C. was added solid tetrabutylammonium iodide (2.96 g, 0.008 mol) followed by boron tribromide (33.96 mL, 0.353 mol) dropwise. After addition, the reaction mixture was stirred at room temperature for 90 minutes. The reaction mixture was cooled to 0° C. and quenched with ice. The mixture was extracted with diethyl ether (1000 mL). The organic layer was washed with water (2000 mL) and then saturated aqueous sodium chloride (1000 mL). After concentration of the organic layer at room temperature in vacuo, the crude product was purified by column chromatography (100-200 silica gel, 2% v/v diethyl ether in hexane) to give 11.5 g (35%) of the title compound as a colourless oil.

GCMS Rt=5.59 minutes, MS m/z=204 [MH]+
$^1$HNMR (CDCl$_3$) δ2.68 (s, 3H) 7.07 (d, 1H), 7.69 (d, 1H), 7.98 (s, 1H), 12.53 (s, 1H).

Preparation 861

4-{4-Chloro-2-[2-(cyclobutyloxy)pyridin-4-yl]phenoxy}-3-cyano-N-(2,4-dimethoxybenzyl)-N-1,2,4-thiadiazol-5-ylbenzenesulfonamide

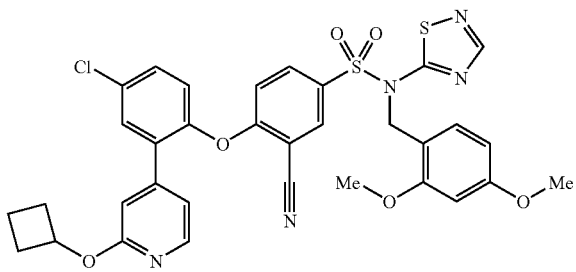

4-Chloro-2-[2-(cyclobutyloxy)pyridin-4-yl]phenol, (Preparation 862, 20.5 mg, 0.000074 mol) was dissolved in dimethylsulphoxide (1 mL). Potassium carbonate (24.6 mg, 0.00018 mol) was added and the reaction stirred for 10 minutes at room temperature. 3-cyano-N-(2,4-dimethoxybenzyl)-4-fluoro-N-1,2,4-thiadiazol-5-ylbenzenesulfonamide, (Preparation 68, 32.2 mg, 0.000074 mol) was added and the reaction was stirred at room temperature for 15 hours under nitrogen. The reaction was partitioned between a saturated aqueous sodium chloride solution (10 mL) and ethyl acetate (10 mL), the organic layer was washed with water (30 mL). The organic extracts were dried over anhydrous magnesium sulphate, filtered and the solvent removed in vacuo to give a colourless foam (56 mg). The material was purified using an ISCO™ companion (4 g column, eluting with 100% heptane to 7:3 heptane/ethyl acetate). Fractions containing product were combined and concentrated in vacuo to obtain the title compound as a colourless oil (45 mg).

LCMS Rt=1.98 minutes MS m/z=690 [M$^{35}$ClH]+
$^1$HNMR (CDCl$_3$) δ 1.61-1.73 (m, 1H), 1.79-1.88 (m, 1H), 2,06-2.18 (m, 2H), 2.40-2.49 (m, 2H), 3.45 (s, 3H), 3.82 (s, 3H), 5.14-5.21 (m, 1H), 5.29 (s, 2H), 6.11 (d, 1H), 6.35 (dd, 1H), 6.49 (d, 1H), 6.73 (m, 1H), 7.00-7.02 (m, 1H), 7.07-7.10 (m, 2H), 7.47 (dd, 1H), 7.52 (d, 1H), 7.61 (d, 1H), 7.68 (dd, 1H), 8.15 (d, 1H), 8.20 (s, 1H).

Preparation 862

4-Chloro-2-[2-(cyclobutyloxy)pyridin-4-yl]phenol

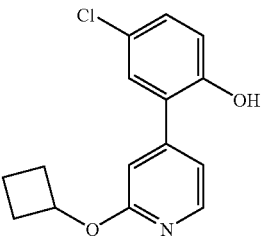

4-(5-Chloro-2-methoxyphenyl)-2-(cyclobutyloxy)pyridine, (Preparation 863, 88 mg, 0.00030 mol) was dissolved in anhydrous dichloromethane (1 mL) and cooled to 0° C. Boron tribromide (152 mg, 0.00061 mol) was added and the solution stirred for 90 minutes, warming slowly to room temperature. The reaction was cooled to 0° C. and water (2 mL) added. The reaction was partitioned between ethyl acetate (300 mL) and water (50 mL). The organics were dried over anhydrous magnesium sulphate, filtered and the solvents removed in vacuo to give an off white residue (54 mg). The material was purified using an ISCO™ companion (4 g column, eluting with 100% dichloromethane to 95:5:0.5 dichloromethane/methanol/0.880 aqueous ammonia solution). Fractions containing product were combined and concentrated in vacuo to obtain the title compound as a yellow residue (20 mg).

LCMS Rt=1.72 minutes, MS m/z=276 [M$^{35}$ClH]+
$^1$HNMR (CDCl$_3$) δ 1.64-1.76 (m, 1H), 1.82-1.91 (m, 1H), 2.13-2.23 (m, 2H), 2.45-2.54 (m, 2H), 5.18-5.25 (m, 1H), 5.64 (s, 1H), 6.83 (m, 1H), 6.90-6.94 (m, 1H), 6.98 (dd, 1H), 7.23-7.26 (m, 2H), 8.22 (dd, 1H).

Preparation 863

4-(5-Chloro-2-methoxyphenyl)-2-(cyclobutyloxy)pyridine

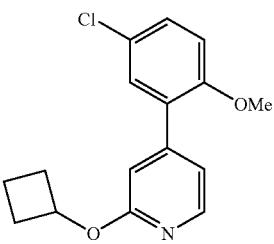

2-Chloro-4-(5-chloro-2-methoxyphenyl)pyridine (Preparation 864, 150 mg, 0.00059 mol) and cyclobutanol (76.6 mg, 0.00106 mol) were dissolved in 1,4-dioxane (2 mL). Potassium Pert-butoxide (132 mg, 0.00118 mol) was added and the solution stirred at 101° C. for 15 hours. The reaction was partitioned between ethyl acetate (15 mL) and a 10% aqueous solution of citric acid (10 mL). The organic layer was washed with water (10 mL) followed by a saturated aqueous sodium chloride solution (10 mL). The organics were dried over anhydrous magnesium sulphate, filtered and the solvents removed in vacuo to give a yellow oil (195 mg). The material was purified using an ISCO™ companion (12 g column, eluting with 100% heptane to 7:3 heptane/ethyl acetate). Fractions containing product were combined and concentrated in vacuo to obtain the title compound as a colourless oil (84 mg).

LCMS Rt=1.92 minutes, MS m/z=290 [M$^{35}$ClH]$^+$ $^1$HNMR (CDCl$_3$) δ 1.64-1.76 (m, 1H), 1.81-1.90 (m, 1H), 2.12-2.23 (m, 2H), 2.45-2.53 (m, 2H), 3.82 (s, 3H), 5.19-5.26 (m, 1H), 6.84-6.85 (m, 1H), 6.90-6.94 (m, 1H), 7.00 (dd, 1H), 7.30-7.33 (m, 2H), 8.15 (dd, 1H).

Preparation 864

2-Chloro-4-(5-chloro-2-methoxyphenyl)pyridine

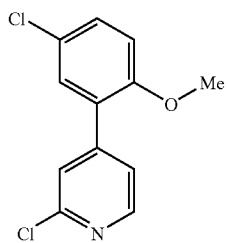

To a nitrogen purged aqueous solution of sodium carbonate (2M, 14 mL) and ethylene glycol dimethyl ether (25 mL) was added 4-chloro-2-iodoanisole (2.50 g, 0.00931 mol), 2-chloropyridine-4-boronic acid (1.61 g, 0.0102 mol) and bis(triphenylphosphine)palladium (II) dichloride (327 mg, 0.00047 mol). The reaction mixture was warmed to 50° C. and stirred for 5 hours. Following LCMS analysis the reaction was warmed to 75° C. and stirred for 5 hours before cooling to room temperature. The reaction was partitioned between ethyl acetate (100 mL) and a 10% w/v aqueous solution of citric acid (50 mL). The organic layer was washed with water (50 mL), dried over anhydrous magnesium sulphate, filtered and the solvents removed in vacuo to give the crude product as an orange oil (2.95 g). The material was purified using an ISCO™ companion (120 g column, eluting with 100% heptane to 7:3 heptane/ethyl acetate). Fractions containing product were combined and concentrated in vacuo to obtain the title compound as an off white solid (1.10 g).

LCMS Rt=1.74 minutes, MS m/z=254 [M$^{35}$ClH]$^+$ $^1$HNMR (CDCl$_3$) δ 3.84 (s, 3H), 6.95 (d, 1H), 7.31 (d, 1H), 7.35-7.38 (m, 2H), 7.49-7.50 (m, 1H), 8.41 (d, 1H).

Preparation 865

4-Chloro-2-[2-(dimethylamino)pyridin-4-yl]phenol

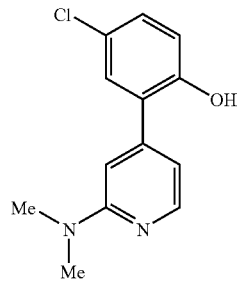

A mixture of 2-chloro-4-(5-chloro-2-methoxyphenyl)pyridine (Preparation 866, 157 mg, 0.618 mmol), azetidine hydrochloride (120 mg, 1.2 mmol), and N,N-diisopropylethylamine (220 uL, 1.2 mmol) in N,N-dimethylacetamide (4.1 mL, 44 mmol) was heated 20 minutes at 170° C. under microwave irradiation. The reaction mixture was poured into water and saturated aqueous ammonium chloride and extracted with ethyl acetate (3×). The combined organic layers were washed with water then brine, dried over sodium sulfate, filtered and concentrated in vacuo. The residue was taken up in methylene chloride, concentrated onto diatomaceous earth, and purified by automated flash chromatography (12 g SiO2, hexanes to 9:1 ethyl acetate-methanol). A single peak containing the major products eluted from the column. The appropriate fractions were concentrated in vacuo. The residue was dissolved in 1 mL of dimethylsulfoxide, filtered through a plug of cotton, and purified by reverse-phase HPLC to afford 4-chloro-2-[2-(dimethylamino)pyridin-4-yl]phenol as a tan solid (50 mg, 33%) followed by 4-chloro-2-(2-chloropyridin-4-yl)phenol as a light pink solid (24 mg, 16%). Unexpectedly 4-chloro-2-[2-(dimethylamino)pyridin-4-yl]phenol was isolated as the main product and none of the intended product was isolated. This presumably occurred due to decomposition of the dimethylacetamide to provide dimethylamine which reacted preferentially to give 4-chloro-2-[2-(dimethylamino)pyridin-4-yl]phenol 4-chloro-2-[2-(dimethylamino)pyridin-4-yl]phenol:
LC/MS Rt=1.16 minutes, MS m/z 249 [M$^{35}$ClH]+
$^1$H NMR (d$_6$-DMSO): δ 10.49 (s, 1H), 7.98 (d, 1H), 7.55 (d, 1H), 7.38 (m, 1H), 7.26 (br s, 1H), 7.14 (d, 1H), 7.02 (d, 1H), 3.23 (s, 6H).
4-chloro-2-(2-chloropyridin-4-yl)phenol:
LC/MS Rt=1.46 minutes, MS m/z 240 [M$^{35}$ClH]+

217

¹H NMR (d₆-DMSO): δ 10.36 (s, 1H), 8.43 (m, 1H), 7.72 (m, 1H), 7.64 (m, 1H), 7.48 (d, 1H), 7.33 (m, 1H), 7.01 (d, 1H).

Preparation 866

2-Chloro-4-(5-chloro-2-methoxyphenyl)pyridine

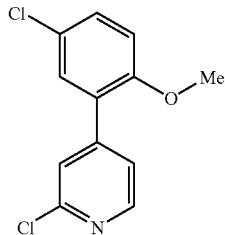

A mixture of 4-chloro-2-iodo-1-methoxybenzene (542 mg, 2.02 mmol), (2-chloropyridin-4-yl)boronic acid (400 mg, 2 mmol), and sodium carbonate (860.2 mg, 8.116 mmol) in 1,4-dioxane (8.4 mL, 110 mmol) and water (2.8 mL, 160 mmol) was sparged 5 minutes with argon. Tetrakis(triphenylphosphine)palladium(0) (139.9 mg, 0.1210 mmol) was added and the reaction vial was capped. The reaction mixture was heated at 90° C. After 3 hours, the reaction mixture was cooled to ambient temperature and poured into water. The mixture was extracted with ethyl acetate (3×). The combined organic layers were washed with brine, dried over sodium sulfate, filtered and concentrated in vacuo. The residue was taken up in methylene chloride, concentrated onto diatomaceous earth, and purified by automated flash chromatography (24 g SiO2, hexanes to 3:1 hexanes-ethyl acetate) to afford the product as a light yellow powder.

LC/MS Rt=1.78 minutes, MS m/z 254 [M³⁵ClH]+

Preparation 867

5-chloro-N-(2,4-dimethoxybenzyl)-2-fluoro-4-{2-[3-nitro-1-(tetrahydro-2H-pyran-2-yl)-1H-pyrazol-4-yl]-4-(trifluoromethyl)phenoxy}-N-1,3,4-thiadiazol-2-ylbenzenesulfonamide

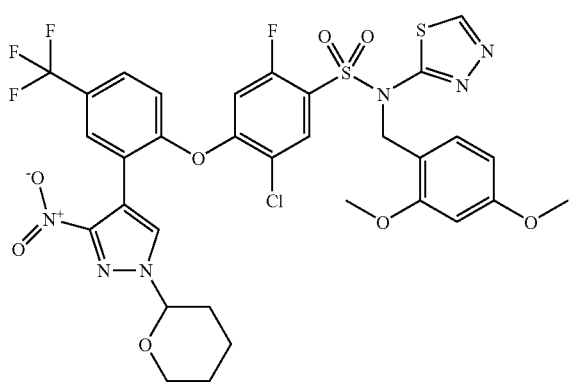

To a solution of 2-[3-nitro-1-(tetrahydro-2H-pyran-2-yl)-1H-pyrazol-4-yl]-4-(trifluoromethyl)phenol (Preparation 868, 2.069 g, 5.791 mmol) in dimethyl sulfoxide (34 mL) was added potassium carbonate (1.66 g, 12.0 mmol). After stirring

218 for 10 minutes, 5-chloro-N-(2,4-dimethoxybenzyl)-2,4-difluoro-N-1,3,4-thiadiazol-2-ylbenzenesulfonamide (Preparation 247, 2.67 g, 5.78 mmol) was added. After stirring at room temperature for 16 hours, the reaction solution was diluted with ethyl acetate and washed with water and brine. The organic layer was dried over anhydrous magnesium sulfate, filtered, and concentrated. Purification by automated flash column chromatography using a 0-100% ethyl acetate/hexanes gradient and a 40 g column gave the title compound (3.20 g, 69%) as a clear oil.

LC/MS Rt=1.98 minutes
MS m/z 647 [M³⁵Cl-DMB]⁻.

Preparation 868

2-[3-Nitro-1-(tetrahydro-2H-pyran-2-yl)-1H-pyrazol-4-yl]-4-(trifluoromethyl)phenol

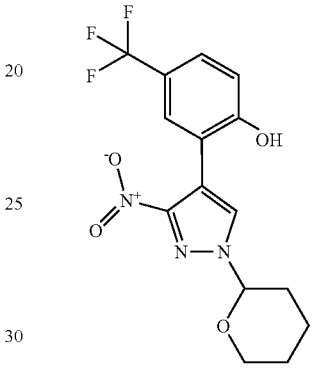

To a solution of 4-bromo-3-nitro-1-(tetrahydro-2H-pyran-2-yl)-1H-pyrazole (Preparation 869, 18.95 g, 0.06864 mol) in 1,2-dimethoxyethane (175 mL) was added aqueous potassium carbonate (2M in water, 68.0 mL, 0.123 mol) and tetrakis(triphenylphosphine)palladium(0) (6.34 g, 0.00549 mol). The reaction was sparged 3 times with Argon and heated to 75° C. To this, [2-hydroxy-5-(trifluoromethyl)phenyl]boronic acid (Preparation 871, 21.22 g, 0.103 mol) was added in four portions over six hours. The reaction solution was heated for an additional 12 hours and then allowed to cool. The mixture was diluted with ethyl acetate, washed with water and brine, dried over anhydrous magnesium sulfate, filtered, and concentrated. Purification by automated flash column chromatography using a 0-50% ethyl acetate/hexanes gradient and a 80 g column gave the title compound (13.2 g, 54%) as a yellow oil.

LC/MS Rt=1.71 minutes MS m/z 356 [M]−

¹H NMR (CDCl3): δ 1.70 (m, 3H), 2.03 (m, 2H), 2.20 (m, 1H), 3.70 (m, 1H), 4.11 (m, 1H), 5.44 (m, 1H), 6.80 (br s, 1H), 6.97 (m, 1H), 7.49 (m, 2H), 7.79 (s, 1H).

Preparation 869

4-bromo-3-nitro-1-(tetrahydro-2H-pyran-2-yl)-1H-pyrazole or 4-bromo-5-nitro-1-(tetrahydro-2H-pyran-2-yl)-1H-pyrazole

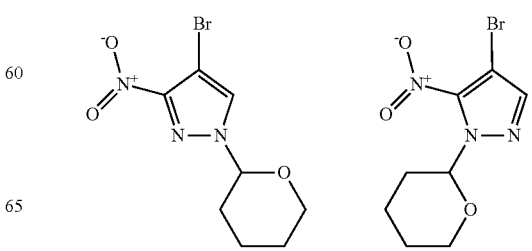

A 5 L 3-neck flask, charged with 4-bromo-3-nitro-1H-pyrazole (Preparation 870, 136 g, 708 mmol), toluene (1100 mL), and trifluoroacetic acid (2.63 mL, 34.1 mind) was equipped with a mechanical stirrer, temperature probe, and an addition funnel. The reaction mixture was heated to 80° C. Dihydropyran (71.4 mL, 783 mmol) was added over 30 minutes via addition funnel. The reaction mixture became more homogeneous over the course of addition of dihydropyran. Within 30 minutes after addition was complete, the reaction mixture was homogeneous. The addition funnel was replaced with a condenser, and the temperature was increased to 110° C. After 21 hours, the reaction mixture was cooled and concentrated in vacuo to a brown solid. The residue was taken up in 1.5 L of ethyl acetate and washed successively with water (200 mL), saturated aqueous sodium bicarbonate (200 mL), and brine (2×200 mL). The organic layer was dried over magnesium sulfate and concentrated in vacuo to half the initial volume. The solution was treated with activated charcoal, filtered through diatomaceous earth, and concentrated in vacuo to about half the volume with the bath temperature set at about 40° C. The solution was transferred to a 1 L Erlenmeyer flask, seeded with crystals from a previous batch, and cooled in the freezer. After 45 hours, the crystals were collected by filtration, washed sparingly with cold ethyl acetate, and dried in vacuo to afford a light tan powder (73.03 g, 37%). The filtrate was concentrated to ~100 mL, transferred to a 500 mL Erlenmeyer flask, seeded with crystals from a previous batch, and cooled in the freezer. After 3 days, the crystals were collected by filtration, washed sparingly with ethyl acetate then hexanes, and dried in vacuo to afford a second crop of product as a light tan powder (67.41 g, 35%). Only one regioisomeric product was obtained as indicated by $^1$H NMR analysis, but the regioisomer was not determined.

LC/MS Rt=1.51 minutes MS m/z no molecular ion observed $^1$H NMR (d$_6$-DMSO): δ 8.55 (s, 1H), 5.56 (m, 1H), 3.92 (m, 1H), 3.67 (m, 1H), 1.99 (m, 3H), 1.68 (m, 1H), 1.56 (m, 2H).

Preparation 870

4-bromo-3-nitro-1H-pyrazole

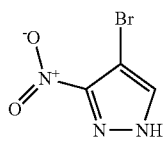

A 1 L 3-neck flask equipped with a stir bar was charged with 3-nitro-1H-pyrazole (41.3 g, 365 mmol), sodium acetate (36.0 g, 438 mmol), and acetic acid (260 mL). The flask was fitted with a septum, addition funnel, and a temperature probe. Bromine (23 mL, 450 mmol) was added over 30 minutes via addition funnel to the reaction mixture; the temperature increased to 40° C. over the course of bromine addition. The heterogeneous reaction mixture became homogeneous as the reaction progressed, with the exception of a few chunks of solid. As the temperature of the reaction mixture fell, a precipitate formed. The reaction mixture was poured into 1.2 L of ice and water and stirred vigorously. After 15 minutes, the solids were collected by filtration and washed with several portions of water (500 mL total). The solids were dried under vacuum to afford the product as a tan powder (49.67 g, 71%).

LC/MS Rt=1.10 minutes MS m/z 190 [M–H]–
$^1$H NMR (d$_6$-DMSO): δ 8.35 (s, 1H).
Reference for synthesis of 3-nitro-1H-pyrazole: Klebe, K. J.; Habraken, C. L. *Synthesis*, 1973, 294.

Preparation 871

[2-hydroxy-5-(trifluoromethyl)phenyl]boronic acid

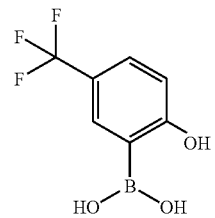

To a suspension of 2-methoxy-5-(trifluoromethyl)phenylboronic acid (24.93 g, 0.1133 mol) in dichloromethane (150 mL) cooled to 0° C. was added dropwise boron tribromide (11.0 mL, 0.116 mol) over 30 minutes. After stirring for 5 hours, more boron tribromide (2.0 mL, 0.021 mol) was added. After stirring for 2 more hours, the reaction mixture was added to ice water and stirred for 20 minutes. The resulting white precipitate was filtered and washed with water to give a white solid that contained product. The layers of the filtrate were separated and extracted with dichloromethane (2×). The combined organics were dried over anhydrous magnesium sulfate, filtered, and concentrated to give a white solid which also contained product. It was determined by NMR that there was some methyl ether remaining, so all the material recovered was suspended in dichloromethane (100 mL) and cooled to 0° C. To this was added boron tribromide (7.0 mL, 0.074 mol) dropwise over 10 minutes and then boron tribromide (1M in dichloromethane, 11.0 mL, 0.0110 mol) dropwise over 10 minutes. After stirring for 5 hours, the reaction was complete as indicated by TLC. The reaction mixture was added to ice water, filtered, and washed with water to provide product (15.24 g, 65%) as a white solid. The layers of the filtrate were separated and extracted with dichloromethane (2×) and 4:1 dichloromethane:isopropyl alcohol. The combined organics were dried over anhydrous magnesium sulfate, filtered, and concentrated to give additional product (5.7 g, 24%) as a white solid.

LCMS Rt=1.55 minutes, MS m/z 205 [M]$^-$
$^1$HNMR (d$_6$-DMSO): δ 6.61 (d, 1H), 7.41 (m, 1H), 7.72 (m, 1H).

Preparation 872 tert-butyl [(5-chloro-2-fluoro-4-{2-[3-nitro-1-(tetrahydro-2H-pyran-2-yl)-1H-pyrazol-4-yl]-4-(trifluoromethyl)phenoxy}phenyl)sulfonyl]1,3-thiazol-4-ylcarbamate

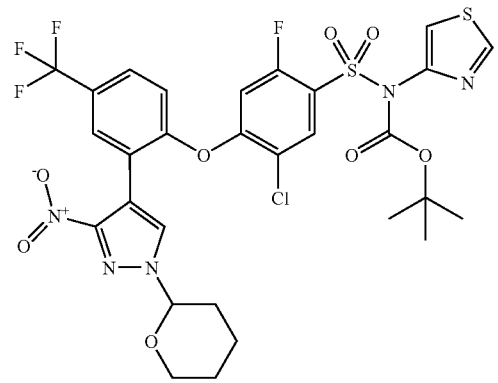

To a solution of 2-[3-nitro-1-(tetrahydro-2H-pyran-2-yl)-1H-pyrazol-4-yl]-4-(trifluoromethyl)phenol (Preparation 868, 28.73 g, 80.41 mmol) in dimethyl sulfoxide (175 mL) was added potassium carbonate (22.3 g, 161 mmol). After stirring for 10 minutes, tert-butyl [(5-chloro-2,4-difluorophenyl)sulfonyl]1,3-thiazol-4-ylcarbamate (Preparation 453, 33.02 g, 80.37 mmol) was added. After stirring for 14 hours at room temperature, additional potassium carbonate (4.7 g, 34 mmol) and tert-butyl [(5-chloro-2,4-difluorophenyl)sulfonyl]1,3-thiazol-4-ylcarbamate (1.25 g, 3.0 mmol) were added and the reaction mixture heated at 45° C. for 7 hours. The mixture was allowed to cool, diluted with ethyl acetate, and washed with water and brine. The organic layer was dried over anhydrous magnesium sulfate, filtered, and concentrated. Purification by manual flash column chromatography using 25% ethyl acetate/hexanes and an 8×46 cm column provided product as a yellow oil (40 g, 70%).

LC/MS Rt=1.90 minutes MS m/z 770 [M$^{35}$Cl+Na]$^+$.

Preparation 873 tert-Butyl 4-[4-(5-chloro-2-hydroxyphenyl)pyrimidin-2-yl]piperazine-1-carboxylate

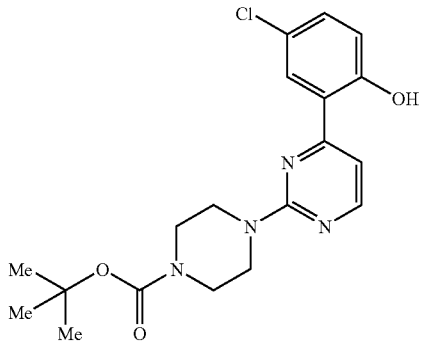

tert-Butyl piperazine-1-carboxylate (24.0 mg, 0.125 mmol) was added to a mixture of 4-chloro-2-(2-chloropyrimidin-4-yl)phenol (Preparation 874, 30.1 mg, 0.125 mmol), and triethylamine (61.2 uL, 0.437 mmol) in isopropyl alcohol (0.2 mL, 3 mmol). The reaction mixture was stirred at ambient temperature. After 18 hours, LC/MS analysis indicated the reaction was not complete. The reaction mixture was heated 30 minutes at 70° C. then cooled to ambient temperature. The reaction mixture was diluted with ethyl acetate, washed with water then brine, dried over sodium sulfate, filtered, and concentrated to give the product as a light brown paste (50 mg, 100%).

LC/MS Rt=2.02 minutes, MS m/z 391 [M$^{35}$ClH]+

$^1$H NMR (d$_6$-DMSO): δ 8.52 (d, 1H), 8.03 (d, 1H), 7.46 (d, 1H), 7.40 (m, 1H), 6.98 (d, 1H), 3.73 (m, 4H), 3.47 (m, 4H), 1.43 (s, 9H).

Preparation 874

4-Chloro-2-(2-chloropyrimidin-4-yl)phenol

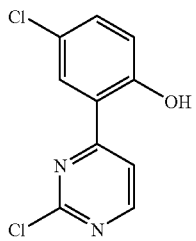

A mixture of 2,4-dichloropyrimidine (0.765 g, 5.03 mmol), (5-chloro-2-hydroxyphenyl)boronic acid (0.568 g, 3.30 mmol), 2.0 M aqueous sodium carbonate (2.82 mL, 5.64 mmol), and 1,2-dimethoxyethane (8 mL, 80 mmol) was sparged for 10 minutes with argon. Tetrakis(triphenylphosphine)palladium(0) (0.217 g, 0.188 mmol) was added, and the resultant mixture was heated 4 hours at 85° C. The reaction mixture was cooled to 0° C., quenched with saturated aqueous ammonium chloride solution, and extracted with methylene chloride (3×). The combined organic layers were washed with brine, dried over sodium sulfate, filtered, and concentrated in vacuo. The residue was purified by automated flash chromatography (12 g silica gel, hexanes to ethyl acetate) to afford the product as a yellow solid (61.5 mg, 7%). Additional 4-chloro-2-(2-chloropyrimidin-4-yl)phenol was isolated as a mixture of the desired product and unreacted 2,4-dichloropyrimidine (62 mg, 50% purity by LC/MS).

LC/MS Rt=1.74 minutes, MS m/z 241 [M$^{35}$ClH]+

$^1$H NMR (d$_6$-DMSO): δ 11.21 (s, 1H), 8.81 (d, 1H), 8.28 (d, 1H), 8.00 (d, 1H), 7.45 (m, 1H), 7.06 (d, 1H).

Preparation 875

4-[2-(2-aminopyridin-4-yl)-4-chlorophenoxy]-5-chloro-2-fluoro-N-(methoxymethyl)-N-pyridazin-3-ylbenzenesulfonamide and 4-[2-2-aminopyridin-4-yl)-4-chlorophenoxy]-5-chloro-2-fluoro-N-[(3E)-2-(methoxymethyl)pyridazin-3(2H)-ylidene]benzenesulfonamide

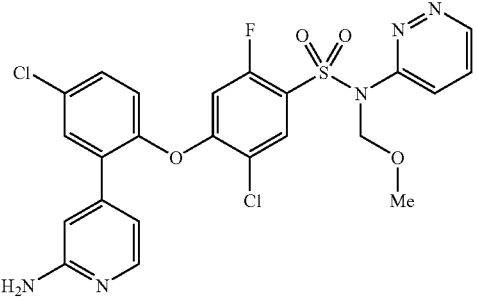

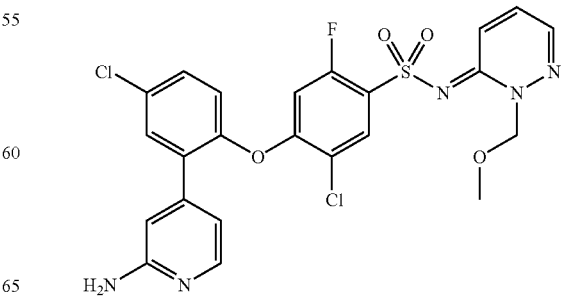

The title compound was prepared by analogy with the method used for Example 815 using 5-chloro-2,4-difluoro-N-(methoxymethyl)-N-pyridazin-3-ylbenzenesulfonamide and 5-chloro-2,4-difluoro-N-[(3E)-2-(methoxymethyl)pyridazin-3(2H)-ylidene]benzenesulfonamide (Preparation 876) used as a mixture of two regioisomers and 2-(2-aminopyridin-4-yl)-4-chlorophenol (Preparation 721). The product was purified on silica gel (chloroform to 100% of 10% methanol in chloroform) to give the desired product as an inseparable mixture of isomers (3:1 ratio).

Product LCMS Rt=1.39 (minor) & 1.43 min MS m/z 550 [MH]+

Preparation 876

5-chloro-2,4-difluoro-N-(methoxymethyl)-N-pyridazin-3-ylbenzenesulfonamide and 5-chloro-2,4-difluoro-N-[(3E)-2-(methoxymethyl)pyridazin-3(2H)-ylidene]benzenesulfonamide

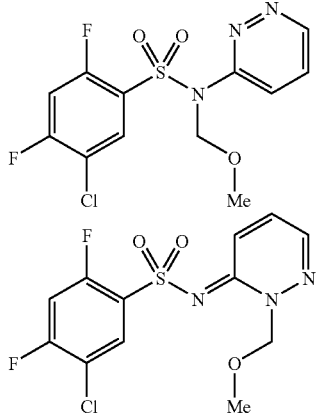

Prepared according to the process of Preparation 716 using 5-chloro-2,4-difluoro-N-pyridazin-3-ylbenzenesulfonamide (Preparation 877). The reaction was purified on silica gel (hexane to 50% hexane-ethyl acetate) to give the desired product as a mixture of isomer (3:2 ratio) which were used as a mixture in subsequent reactions.

LCMS Rt=1.49 & 1.55 min MS m/z 350 [MH]+

Preparation 877

5-chloro-2,4-difluoro-N-pyridazin-3-ylbenzenesulfonamide

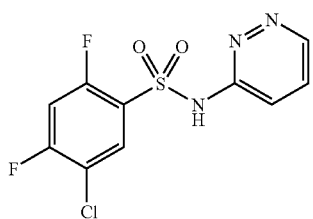

Pyridazin-3-amine (1.00 g, 10.5 mmol) and triethylenediamine (1.18 g, 10.5 mmol) was added concurrently to a solution of 5-chloro-2,4-difluorobenzenesulfonyl chloride (2.60 g, 10.5 mmol) in acetonitrile (50 mL, 1000 mmol). The reaction mixture was stirred for 18 h then concentrated. The residue was dissolved in ethyl acetate (30 mL), washed with water, brine, dried over sodium sulfate and concentrated. The residue was purified on automated silica gel chromatography (chloroform to 50% of 10% methanol in chloroform) to give 800 mg of the desired product as a yellow solid.

LCMS Rt=1.46 min, MS m/z 306 [MH]+

Preparation 878 tert-Butyl [(4-{2-[2-(azetidin-1-ylmethyl)pyridin-4-yl]-4-chlorophenoxy}-2,5-difluorophenyl)sulfonyl]1,3-thiazol-4-ylcarbamate

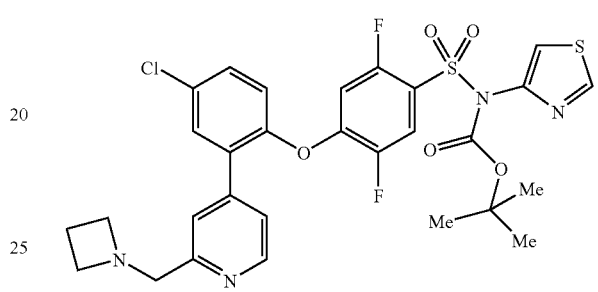

tert-Butyl ({4-[4-chloro-2-(2-formylpyridin-4-yl)phenoxy]-2,5-difluorophenyl}sulfonyl)1,3-thiazol-4-ylcarbamate, (Preparation 879, 0.36 g, 0.00059 mol) was dissolved in dichloromethane (3 mL) then azetidine hydrochloride (0.083 g, 0.00089 mol) was added and reaction allowed to stir at room temperature for 30 minutes. Sodium triacetoxyborohydride (0.144 g, 0.00068 mol) was added and the reaction stirred at room temperature for 18 hours. Saturated aqueous sodium bicarbonate solution (5 mL) was added and the reaction stirred for 30 minutes. The reaction was then passed through a phase separation cartridge and the isolated dichloromethane layer concentrated in vacuo to give the desired product as an orange foam (0.325 g).

LCMS Rt=1.16 minutes, MS m/z=649 [M$^{35}$ClH]+.

$^1$HNMR (CDCl$_3$) δ 1.32 (s, 9H), 2.12 (m, 2H), 3.30 (m, 4H), 3.75 (s, 2H), 6.51 (m, 1H), 7.09 (d, 1H), 7.28 (dd, 1H), 7.46 (m, 3H), 7.53 (d, 1H), 7.88 (m, 1H), 8.55 (d, 1H), 8.76 (d, 1H).

Preparation 879 tert-Butyl ({4-[4-chloro-2-(2-formylpyridin-4-yl)phenoxy]-2,5-difluorophenyl}sulfonyl)1,3-thiazol-4-ylcarbamate

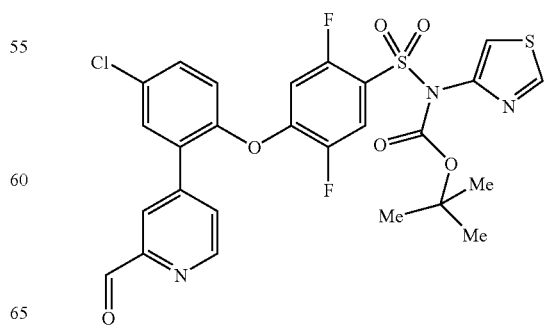

4-(5-Chloro-2-hydroxyphenyl)pyridine-2-carbaldehyde, (Preparation 880, 0.3 g, 0.0013 mol) and tert-butyl 1,3-thiazol-4-yl[(2,4,5-trifluorophenyl)sulfonyl]carbamate, (Preparation 297, 0.456 g, 0.0012 mol) were dissolved in dimethyl sulfoxide (5 mL) and potassium carbonate (0.355 g, 0.0026 mol) was added and reaction allowed to stir at room temperature for 2 hours. Water (10 mL) was added to the reaction, the resultant white precipitate was filtered off and dried in vacuo to give the title compound as a white solid (0.658 g).

LCMS Rt=1.73 minutes, MS m/z=608 [M$^{35}$ClH]$^+$ $^1$HNMR (CD$_3$OD) δ 1.30 (s, 9H), 6.70 (m, 1H), 7.22 (d, 1H), 7.52 (m, 2H), 7.60 (d, 1H), 7.61 (d, 1H), 7.76 (d, 1H), 7.85 (m, 1H), 8.51 (d, 1H), 8.89 (d, 1H), 10.02 (s, 1H).

Preparation 880

4-(5-Chloro-2-hydroxyphenyl)pyridine-2-carbaldehyde

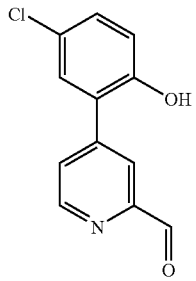

(5-Chloro-2-hydroxyphenyl)boronic acid (1.58 g, 0.00914 mol) was combined with 4-bromopyridine-2-carbaldehyde (1.70 g, 0.0091 mol), bis(triphenylphosphine)palladium (II) chloride (0.321 g, 0.00046 mol) and potassium carbonate (3.16 g, 0.0228 mol) in a 5 mL microwave vial. 1,4-dioxane (3 mL) and water (0.2 mL) were added and heated to 100° C. for 50 minutes in the microwave. The reaction was diluted with ethyl acetate (30 mL) and water (20 mL), filtered, the organic phase was separated then dried over anhydrous sodium sulphate, concentrated in vacuo and purified by flash column chromatography, ISCO™ (80 g column, eluting with 100% heptane to 50% v/v ethyl acetate in heptane) to give the title compound as a beige solid (0.47 g).

LCMS Rt=1.39 minutes, MS m/z=234 [M$^{35}$ClH]$^+$.

$^1$HNMR (CD$_3$OD) δ 6.92 (d, 1H), 7.23 (dd, 1H), 7.37 (d, 1H), 7.88 (dd, 1H), 8.22 (d, 1H), 8.75 (d, 1H), 10.05 (s 1H).

Preparation 881

4-[2-(1-Azetidin-3-yl-1H-pyrazol-5-yl)-4-(trifluoromethyl)phenoxy]-3-cyano-N-1,2,4-thiadiazol-5-ylbenzenesulfonamide

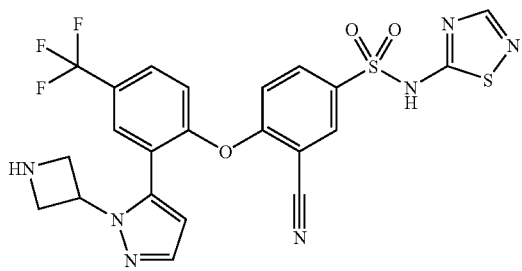

tert-Butyl 3-{5-[2-(2-cyano-4-{[(2,4-dimethoxybenzyl)(1,2,4-thiadiazol-5-yl)amino]sulfonyl}phenoxy)-5-(trifluoromethyl)phenyl]-1H-pyrazol-1-yl}azetidine-1-carboxylate, (Preparation 882, 4.76 g, 0.00597 mol) was dissolved in dichloromethane (80 mL) and cooled in ice. Trifluoroacetic acid (10 mL) was added and the solution was stirred whilst warming to room temperature over 18 hours. The solvents were removed in vacuo and the residue was slurried in methanol (80 mL) and then the methanol was removed in vacuo. This was repeated two more times. Finally the residue was again slurried in methanol (80 mL) and the solid was removed by filtration. The filtrate was evaporated in vacuo to give a yellowish foam. Water (50 mL) was added, then 0.880 aqueous ammonia (5 mL) to give a white solid which was filtered off, washed with a little tert-butylmethylether and dried in vacuo to give the title compound as a white solid (3.02 g).

LCMS Rt=1.28 minutes, MS m/z=548 [MH]+

$^1$HNMR (d$_6$-DMSO) δ 4.17-4.31 (m, 4H), 5.13 (m, 1H), 6.44 (s, 1H), 7.05 (d, 1H), 7.54 (d, 1H), 7.72 (s, 1H), 7.86-8.05 (m, 5H).

Preparation 882 tert-Butyl 3-{5-[2-(2-cyano-4-{[(2,4-dimethoxybenzyl)(1,2,4-thiadiazol-5-yl)amino]sulfonyl}phenoxy)-5-(trifluoromethyl)phenyl]-1H-pyrazol-1-yl}azetidine-1-carboxylate

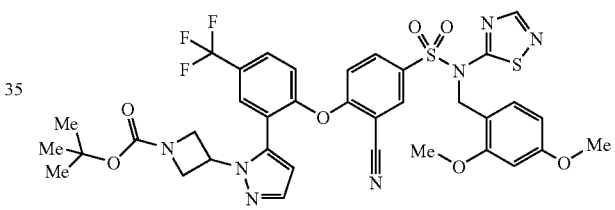

tert-Butyl 3-{5-[2-hydroxy-5-(trifluoromethyl)phenyl]-1H-pyrazol-1-yl}azetidine-1-carboxylate, (Preparation 883, 2.20 g, 0.00574 mol), potassium carbonate (1.60 g, 0.0116 mol) and 3-cyano-N-(2,4-dimethoxybenzyl)-4-fluoro-N-1,2,4-thiadiazol-5-ylbenzenesulfonamide, (Preparation 68, 2.50 g, 0.00575 mol) were combined in a 50 mL round bottomed flask and the flask was cooled in ice. Dimethylsulphoxide (15 mL) was added and after a few minutes the ice bath was removed and the reaction was stirred at room temperature for 3 hours under nitrogen. The reaction was diluted with water (50 mL) and extracted with tert-butylmethylether (100 mL) and the organic layer was washed with water (30 mL). The organic extracts were dried over anhydrous sodium sulphate, filtered and the solvent removed in vacuo to give the title compound as a white foam (4.76 g).

LCMS Rt=1.90 minutes, MS m/z=698 [M-BocH]$^+$ $^1$HNMR (CDCl$_3$) δ 1.45 (s, 9H), 3.52 (s, 3H), 3.82 (s, 3H), 4.28-4.48 (m, 4H), 4.92 (m, 1H), 5.32 (s, 2H), 6.13 (m, 1H), 6.27 (m, 1H), 6.35 (m, 1H), 6.52 (d, 1H), 7.08 (d, 1H), 7.19 (d, 1H), 7.63 (m, 2H), 7.69 (m, 1H), 7.77 (d, 1H), 7.83 (m, 1H), 8.21 (s, 1H).

Preparation 883 tert-Butyl 3-{5-[2-hydroxy-5-(trifluoromethyl)phenyl]-1H-pyrazol-1-yl}azetidine-1-carboxylate

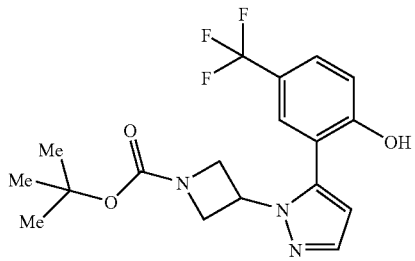

To a stirred solution of crude tert-butyl 3-hydrazinoazetidine-1-carboxylate, (Preparation 696, 5.7 g, 0.030 mol) in ethanol (66 mL) at 0° C. was added acetic acid (6.6 mL) dropwise. Then (2E)-3-(dimethylamino)-1-[2-hydroxy-5-(trifluoromethyl)phenyl]prop-2-en-1-one, (Preparation 859, 6.4 g, 24.68 m mol) was added portionwise and allowed to stir at room temperature for 20 hours. The reaction mixture was concentrated in vacuo and neutralised with aqueous sodium hydrogencarbonate solution. The mixture was extracted with ethyl acetate (150 mL). The combined organic layer was washed with water (100 mL), saturated aqueous sodium chloride solution (50 mL) and dried over anhydrous sodium sulphate. After concentration of organic layer in vacuo, the crude product was washed with 20% v/v ethyl acetate in hexane to get the title compound as a white solid (7.4 g)

LCMS Rt=3.52 minutes, MS m/z=384 [MH]$^+$ $^1$HNMR (CDCl$_3$) δ1.45 (s, 9H), 4.27-4.37 (m, 3H), 4.70 (brs, 1H), 4.79-4.83 (m, 1H), 6.25 (s, 1H), 7.16 (d, 1H), 7.46 (s, 1H), 7.55 (d, 1H), 7.66 (s, 1H), 9.64 (s, 1H).

HPLC Purity: 99.84%

Preparation 884

5-Fluoro-2-pyridazin-4-yl-4-(trifluoromethyl)phenol

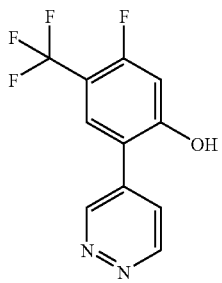

Cesium fluoride (570 mg, 3.8 mmol), tetrakis(triphenylphosphine)palladium(0) (220 mg, 0.19 mmol), and copper(I) iodide (72 mg, 0.38 mmol) were added to a solution of 5-fluoro-2-iodo-4-(trifluoromethyl)phenol (Preparation 885, 579 mg, 1.89 mmol) and 4-(tributylstannyl)pyridazine (770 mg, 2.1 mmol) in N,N-dimethylformamide (4 mL, 50 mmol).

The sides of the flask were washed down with N,N-dimethylformamide (3 mL, 40 mmol). The flask was capped with a septum then evacuated and back-filled with argon (5 cycles). The reaction mixture was heated at 45° C. After 90 min, the reaction mixture was cooled to ambient temperature, diluted with ethyl acetate and water, and filtered through diatomaceous earth. The solids were washed with additional ethyl acetate. The layers were separated, and the organic layer was washed successively with water, aqueous lithium chloride, and brine. The organic layer was then dried over sodium sulfate, filtered, and concentrated in vacuo. The residue was taken up in methylene chloride, concentrated onto diatomaceous earth, and purified by automated flash chromatography (24 g SiO2, methylene chloride to 9:1 methylene chloride-methanol) to afford the product as a tan solid (305 mg, 62%).

LC/MS Rt=1.57 minutes, MS m/z 259 [MH]+

$^1$H NMR (d$_6$-DMSO): δ 11.74 (s, 1H), 9.49 (m, 1H), 9.26 (m, 1H), 7.93 (m, 1H), 7.87 (d, 1H), 6.99 (d, 1H).

Preparation 885

5-Fluoro-2-iodo-4-(trifluoromethyl)phenol

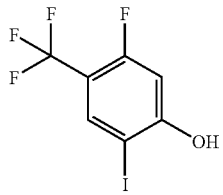

A solution of iodine (0.874 g, 3.44 mmol) in chloroform (17.1 mL, 214 mmol) was added over a period of 1.5 hours dropwise via addition funnel to a mixture of 3-fluoro-4-(trifluoromethyl)phenol (Preparation 886, 620 mg, 3.4 mmol) and silver trifluoroacetate (0.760 g, 3.44 mmol) in chloroform (3.4 mL, 43 mmol). After addition was complete, the reaction mixture was stirred an additional 1 hour. The reaction mixture was filtered through diatomaceous earth, and the filtrate was washed successively with 10% aqueous sodium thiosulfate (w/v), half-saturated aqueous sodium bicarbonate, water and brine. The organic phase was dried over sodium sulfate, filtered, and concentrated onto diatomaceous earth. The residue was purified by automated flash chromatography (24 g SiO$_2$, hexanes to 1:1 methylene chloride-hexanes gradient elution). The initial product-containing fraction contained predominantly diiodinated material (by mass) with some monoiododinated material. The remaining fractions were concentrated in vacuo to afford the product as a light yellow oil (579 mg, 54%). The product was not dried under vacuum due to volatility.

LC/MS Rt=1.79 minutes, MS m/z 305 [MH]–

$^1$H NMR (d$_6$-DMSO): δ 11.81 (s, 1H), 7.97 (d, 1H), 6.85 (d, 1H).

Preparation 886

3-Fluoro-4-(trifluoromethyl)phenol

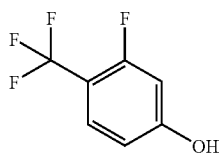

A solution of OXONE® (1.50 g, 2.45 mmol) in water (7.8 mL, 430 mmol) was added over about 4 minutes dropwise to a solution of 2-[3-fluoro-4-(trifluoromethyl)phenyl]-4,4,5,5-tetramethyl-1,3,2-dioxaborolane (710 mg, 2.4 mmol) in acetone (7.8 mL, 110 mmol). A precipitate formed during addition of the OXONE®. The reaction mixture was stirred vigorously for 15 minutes after addition was complete then quenched with 20 mL of a 10% aqueous solution of sodium metabisulfite (w/v). The aqueous layer was extracted with methylene chloride (3×), dried over sodium sulfate, filtered, and concentrated in vacuo to a light yellow oil. The product was advanced to the iodination reaction without purification; 100% conversion to the phenol was assumed.

LC/MS Rt=1.65 minutes, MS m/z 179 [MH]−

Preparation 887

4-{2-[3-amino-1-(tetrahydro-2H-pyran-2-yl)-1H-pyrazol-4-yl]-4-chlorophenoxy}-5-chloro-2-fluoro-N-(methoxymethyl)-N-pyrimidin-4-ylbenzenesulfonamide

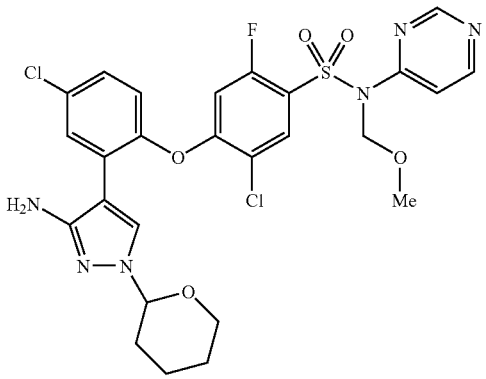

To a solution of 5-chloro-4-(4-chloro-2-(3-nitro-1-(tetrahydro-2H-pyran-2-yl)-1H-pyrazol-4-yl)phenoxy)-2-fluoro-N-(methoxymethyl)-N-(pyrimidin-4-yl)benzenesulfonamide (80 mg, 0.1 mmol) in ethanol (4 mL, 70 mmol) was added saturated aqueous ammonium chloride solution (0.4 mL, 6 mmol) and iron (328 mg, 5.87 mmol). The reaction solution was heated at 80° C. for 20 minutes then filtered. Saturated aqueous sodium bicarbonate was added until the pH was 9. The mixture was concentrated in vacuo to remove the ethanol. Water was added and the mixture was extracted three times with dichloromethane. The combined organic phase was dried over anhydrous sodium sulfate, filtered, and concentrated in vacuo. The residue was purified on silica gel (hexane to 100% ethyl acetate gradient) to give 61 mg of a colorless oil.

LCMS Rt=1.97 min MS m/z 623 [MH]+

Preparation 888

2-pyridazin-4-yl-4-(trifluoromethoxy)phenol

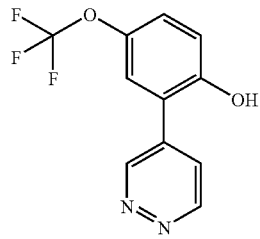

The title compound was prepared according to the process of Preparation 712 using 2-iodo-4-(trifluoromethoxy)phenol (Preparation 226).

LCMS Rt=1.62 minutes, MS m/z 257 [MH]+
$^1$HNMR (300 MHz, $d_6$-DMSO): δ 7.09 (d, 1H), 7.34 (m, 1H), 7.56 (d, 1H), 7.92 (dd, 1H), 9.26 (dd, 1H), 9.49 (dd, 1H), 10.64 (s, 1H).

Preparation 889

N-(2,4-dimethoxybenzyl)-2,4-difluoro-5-methyl-N-1,3,4-thiadiazol-2-ylbenzenesulfonamide

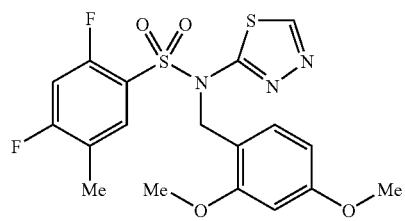

The title compound was prepared according to the process of Preparation 247 using 2,4-difluoro-5-methylbenzenesulfonyl chloride (Preparation 890).

LCMS Rt=1.76 min, MS m/z 464 [MNa]+
$^1$HNMR (300 MHz, CDCl$_3$): δ 2.23 (s, 3H), 3.71 (s, 3H), 3.75 (s, 3H), 5.30 (s, 2H), 6.28 (d, 1H), 6.35 (dd, 1H), 6.83 (t, 1H), 7.23 (d, 1H), 7.62 (t, 1H), 8.80 (s, 1H)

Preparation 890

2,4-difluoro-5-methylbenzenesulfonyl chloride

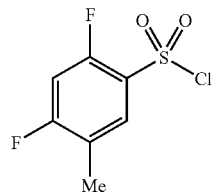

Chlorosulfonic acid (5.2 mL, 0.078 mol) was added dropwise to a solution of 2,4-difluorotoluene (4.00 g, 0.0312 mol)

in chloroform (75 mL, 0.94 mol). The reaction was stirred 2 hours. Additional chlorosulfonic acid (3.1 mL, 0.047 mol) was added and stirring was continued for 18 hours. The reaction was evaporated to an oil and poured onto ice. The mixture was extracted two times with ethyl ether. The combined organic phase was dried over magnesium sulfate and treated with activated carbon. The mixture was filtered through diatomaceous earth and the filtrate was evaporated to give 5.31 g of light brown oil.

LCMS Rt=1.67 minutes, MS m/z not observed.

$^1$HNMR (300 MHz, CDCl$_3$): δ 2.34 (s, 3H), 7.02 (t, 1H), 7.23 (m, 2H), 7.84 (t, 1H).

Preparation 891

4-{2-[3-amino-1-(tetrahydro-2H-pyran-2-yl)-1H-pyrazol-4-yl]-4-chlorophenoxy}-5-chloro-2-fluoro-N-(methoxymethyl)-N-pyridazin-3-ylbenzene-sulfonamide and 4-{2-[3-amino-1-(tetrahydro-2H-pyran-2-yl)-1H-pyrazol-4-yl]-4-chlorophenoxy}-5-chloro-2-fluoro-N-[(3E)-2-(methoxymethyl)pyridazin-3(2H)-ylidene]benzenesulfonamide

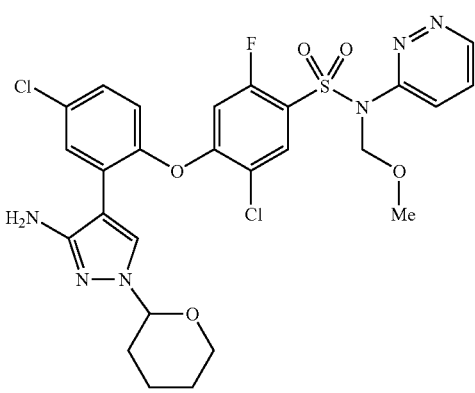

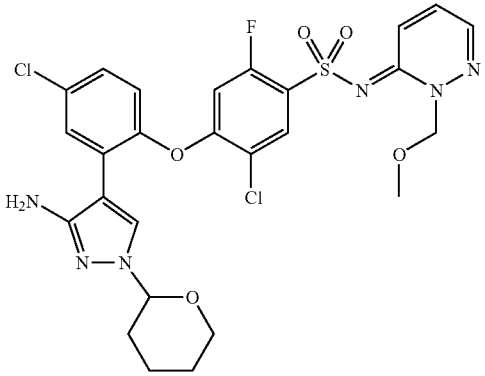

The title compound was prepared using the method described in Preparation 887 using 5-chloro-4-{4-chloro-2-[3-nitro-1-(tetrahydro-2H-pyran-2-yl)-1H-pyrazol-4-yl]phenoxy}-2-fluoro-N-(methoxymethyl)-N-pyridazin-3-yl-benzenesulfonamide and 5-chloro-4-{4-chloro-2-[3-nitro-1-(tetrahydro-2H-pyran-2-yl)-1H-pyrazol-4-yl]phenoxy}-2-fluoro-N-[(3E)-2-(methoxymethyl)pyridazin-3(2H)-ylidene]benzenesulfonamide (Preparation 892). The product was a mixture of isomers.

LCMS Rt=1.84 min MS m/z 623 [MH]+

Preparation 892

5-chloro-4-{4-chloro-2-[3-nitro-1-(tetrahydro-2H-pyran-2-yl)-1H-pyrazol-4-yl]phenoxy}-2-fluoro-N-(methoxymethyl)-N-pyridazin-3-ylbenzenesulfonamide and 5-chloro-4-{4-chloro-2-[3-nitro-1-(tetrahydro-2H-pyran-2-yl)-1H-pyrazol-4-yl]phenoxy}-2-fluoro-N-[(3E)-2-(methoxymethyl)pyridazin-3(2H)-ylidene]benzenesulfonamide

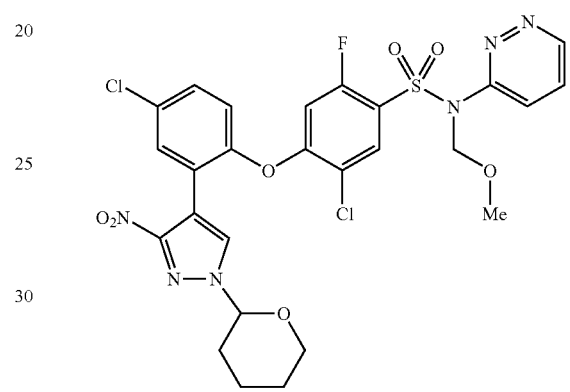

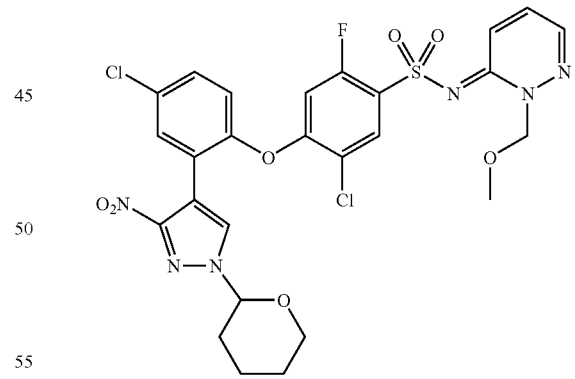

The title compound was prepared using the method described in Preparation 893 using 5-chloro-2,4-difluoro-N-(methoxymethyl)-N-pyridazin-3-ylbenzenesulfonamide and 5-chloro-2,4-difluoro-N-[(3E)-2-(methoxymethyl)pyridazin-3(2H)-ylidene]benzenesulfonamide (Preparation 876) and 4-chloro-2-[3-nitro-1-(tetrahydro-2H-pyran-2-yl)-1H-pyrazol-4-yl]phenol (Preparation 894). A mixture of isomers was present.

LCMS Rt=1.85 min MS m/z 653 [MH]+

Preparation 893

5-chloro-4-{4-chloro-2-[3-nitro-1-(tetrahydro-2H-pyran-2-yl)-1H-pyrazol-4-yl]phenoxy}-2-fluoro-N-(methoxymethyl)-N-pyrimidin-4-ylbenzenesulfonamide

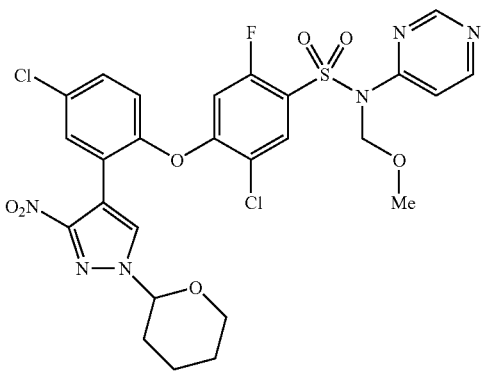

The title compound was prepared using the method described in Preparation 872 using 5-chloro-2,4-difluoro-N-(methoxymethyl)-N-pyrimidin-4-ylbenzenesulfonamide (Preparation 895) and 4-chloro-2-[3-nitro-1-(tetrahydro-2H-pyran-2-yl)-1H-pyrazol-4-yl]phenol (Preparation 894). The product was purified on silica gel (hexane to 50% of 60% ethyl acetate gradient) to provide 82 mg of a colorless oil.

LCMS Rt=1.92 min MS m/z 653 [MH]+
$^1$HNMR ($d_6$-DMSO): δ 1.45-1.73 (m, 3H), 1.76-2.06 (m, 3H), 3.35 (3H, s), 3.63 (m, 1H), 3.81 (m, 1H), 5.42 (s, 2H), 5.52 (dd, 1H), 6.83 (d, 1H), 7.37 (m, 2H), 7.59 (dd, 1H), 7.71 (d, 1H), 8.07 (d, 1H), 8.28 (s, 1H), 8.69 (d, 1H), 8.80 (s, 1H).

Preparation 894

4-chloro-2-[3-nitro-1-(tetrahydro-2H-pyran-2-yl)-1H-pyrazol-4-yl]phenol

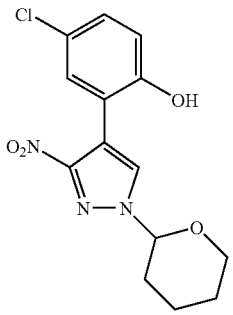

(5-chloro-2-hydroxyphenyl)boronic acid (16.10 g, 93.38 mmol) and 4-bromo-3-nitro-1-(tetrahydro-2H-pyran-2-yl)-1H-pyrazole or 4-bromo-5-nitro-1-(tetrahydro-2H-pyran-2-yl)-1H-pyrazole (Preparation 869, 22.95 g, 83.12 mmol) in 1,2-dimethoxyethane (300 mL, 3000 mmol) and 2 M of potassium carbonate in water (116 mL, 2.10E2 mmol) was added tetrakis(triphenylphosphine)palladium(0) (5.0 g, 4.3 mmol). The solution was sparged 3 times with Ar and heated at 80° C. for 4 hours. Additional (5-chloro-2-hydroxyphenyl) boronic acid (2.866 g, 16.62 mmol) was added to the reaction. The reaction was heated at 80° C. for another 18 hours. The cooled reaction was poured into a separatory funnel and the phases separated. The aqueous phase was washed two times with dichloromethane (250 mL). The combined organic phase was washed with brine then dried over anhydrous magnesium sulfate and treated with activated carbon. The mixture was filtered through diatomacious earth and the filtrate evaporated to a residue. The crude product was separated into two portions and each purified by column chromatography (80 g silica gel column, hexanes to 20% ethyl acetate gradient elution). Product fractions were combined and evaporated to give a thick oil which formed a waxy solid upon standing. The solid was triturated with hexanes and filtered to give 17.71 g of tan powder after vacuum drying.

LCMS Rt=1.46 min MS m/z 322 [MH]–
$^1$HNMR ($d_6$-DMSO): δ 1.58-1.75 (m, 3H), 1.91-2.16 (m, 3H), 3.69 (m, 1H), 3.95 (m, 1H), 5.55 (dd, 2H), 6.87 (d, 1H), 7.24 (dd, 1H), 7.34 (d, 1H), 8.32 (s, 1H), 10.06 (s, 1H).

Preparation 895

5-chloro-2,4-difluoro-N-(methoxymethyl)-N-pyrimidin-4-ylbenzenesulfonamide and 5-chloro-2,4-difluoro-N-[(4E)-3-(methoxymethyl)pyrimidin-4(3H)-ylidene]benzenesulfonamide and 5-chloro-2,4-difluoro-N-[(4E)-1-(methoxymethyl)pyrimidin-4(1H)-ylidene]benzenesulfonamide

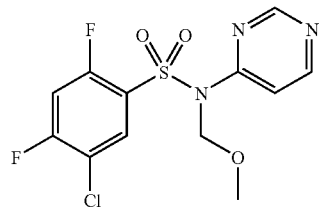

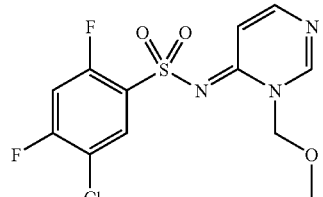

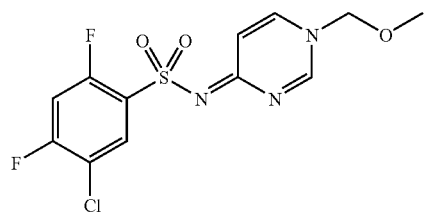

5-chloro-2,4-difluoro-N-pyrimidin-4-ylbenzenesulfonamide (Preparation 723, 0.80 g, 2.6 mmol) and N,N-diisopropylethylamine (0.68 mL, 3.9 mmol) in methylene chloride (20 mL, 300 mmol) at −78° C. was added Chloromethyl Methyl Ether (0.26 mL, 2.9 mmol). After stirring from −78° C. to room temperature for 20 hours, the reaction mixture was diluted with ethyl acetate, washed with 1N NaOH, water, brine, dried over anhydrous sodium sulfate, filtered and concentrated. The residue was purified on silica gel (hexane to 100% ethyl acetate) to give three isomers.

Isomer A: 467 mg

LCMS Rt=1.66 min MS m/z 350 [MH]+

$^1$HNMR (d$_6$-DMSO): δ 3.38 (s, 3H), 5.47 (s, 2H), 7.41 (dd, 1H), 7.88 (t, 1H), 8.27 (t, 1H), 8.71 (d, 1H), 8.81 (s, 1H).

Isomer B: 187 mg

LCMS Rt=1.50 min MS m/z 350 [MH]+

$^1$HNMR (d$_6$-DMSO): δ 3.33 (s, 3H), 5.43 (s, 2H), 7.47 (d, 1H), 7.79 (t, 1H), 8.09 (t, 1H), 8.30 (d, 1H), 8.89 (s, 1H).

Isomer C: 132 mg

LCMS Rt=1.12 min MS m/z 350 [MH]+

$^1$HNMR (d$_6$-DMSO): δ 3.28 (s, 3H), 5.26 (s, 2H), 6.77 (d, 1H), 7.69 (t, 1H), 8.01 (t, 1H), 8.15 (dd, 1H), 8.69 (d, 1H).

Preparation 896

4-(5-trifluoro-2-methoxyphenyl)pyridazine

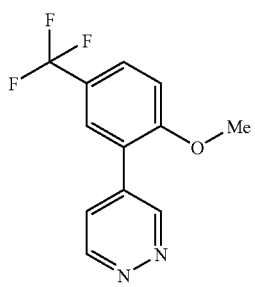

Method 1

4-(5-trifluoro-2-methoxyphenyl)pyridazine was prepared using a method analogous to that below for Preparation 897 using 4-bromopyridazine hydrobromide (Preparation 898) and the appropriate boronic acid, namely (5-trifluoro-2-methoxyphenyl)boronic acid. Purification using ISCO™ (using a gradient of 0-80% ethyl acetate in heptane, 12 g SiO$_2$) afforded the title compound.

LCMS Rt=1.46 min MS m/z 255 [MH]+

$^1$H NMR (400 MHz, d$_6$-DMSO): δ 3.90 (s, 3H), 7.70 (m, 1H), 7.85 (m, 3H), 9.30 (m, 1H), 9.45 (s, 1H)

Method 2

4-(5-trifluoro-2-methoxyphenyl)pyridazine can also be prepared according to the following procedure:

To a solution of acetic anhydride (1 mL) and acetic acid (2 mL) was added potassium acetate (517 mg, 5.28 mmol) and the mixture stirred until dissolution. The solution was then cooled to 0° C. using an ice bath and bromine (68 μL, 1.32 mmol) added followed by the bromofuran (194 mg, 1.32 mmol). The reaction turned pale yellow and was allowed to stir at 0° C. for 30 minutes before warming to room temperature. The reaction was concentrated in vacuo, azeotroping with toluene (2×5 mL). The resulting solid was slurried in 1,4-dioxane (5 mL) and hydrazine hydrate (320 μL, 6.60 mmol) was added. The reaction was stirred at room temperature for 1 hour before the addition of cesium carbonate (860 mg, 2.64 mmol), (5-trifluoro-2-methoxyphenyl)boronic acid (290 mg, 1.32 mmol) and palladium tetrakistriphenylphosphine (152 mg, 0.132 mmol). The reaction was heated to 70° C. under nitrogen for 3 hours. The reaction was cooled and concentrated in vacuo to afford the crude title compound.

LCMS Rt=1.46 min MS m/z 255 [MH]+

Preparation 897

4-[2-(benzyloxy)-5-(trifluoromethyl)phenyl]pyridazine

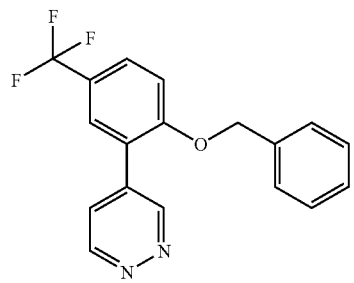

([2-(benzyloxy)-5-(trifluoromethyl)phenyl]boronic acid (3.72 g, 0.0126 mol) and caesium carbonate (8.9 g, 0.0273 mol) were suspended in 1,4 dioxane (40.0 mL) and water (20.0 mL). The reaction was degassed twice before being brought to 80° C. under nitrogen. Then 4-bromopyridazine hydrobromide (Preparation see above, 2.52 g, 0.0105 mol) and palladium tetrakistriphenylphosphine (0.62 g, 0.000537 mol) were added to the reaction and it was stirred for three hours. The reaction was concentrated in vacuo to 20.0 mL, and partitioned between ethyl acetate (70.0 mL) and saturated aqueous brine (50.0 mL). The two layers were filtered over arbocel™ to remove a fine black solid. Then the organic layer was washed with more saturated aqueous brine (2×50.0 mL) and it was dried over sodium sulphate. The solvents were concentrated in vacuo and crude was purified using ISCO™ (using a gradient of 0-50% ethyl acetate in heptane, 80 g SiO$_2$) to afford the title compound as a light orange solid.

LCMS Rt=1.67 minutes

MS m/z 331 [MH]+

$^1$H NMR (400 MHz, d$_6$-DMSO): δ 5.25 (s, 2H), 7.35-7.45 (m, 5H), 7.50 (d, 1H), 7.85 (m, 1H), 7.90 (t, 1H), 9.25 (d, 1H), 9.45 (s, 1H)

Preparation 898

4-bromopyridazine hydrobromide

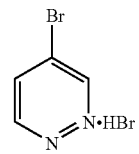

3-Bromofuran (5.0 g, 0.034 mol) and potassium acetate (9.2 g, 0.0937 mol) were suspended in acetic acid (30.0 mL). Bromine (1.75 mL, 0.0342 mol) in acetic acid (10.0 mL) was then added drop wise and the reaction stirred for one hour. The reaction was filtered and the filtrate concentrated in vacuo. The residue was dissolved in ethanol (50.0 mL) and hydrazine hydrate (5.0 mL, 0.103 mol) was added drop wise to the solution, which was stirred at room temperature for two hours. The reaction was diluted in ethyl acetate (100.0 mL) and washed with a solution of saturated aqueous brine (100.0 mL). The organic layer was collected and washed once more with a solution of saturated aqueous brine (100.0 mL). The aqueous layer was extracted with ethyl acetate (50.0 mL) and the organic layers were combined, then dried over sodium sulfate, filtered, and concentrated in vacuo. The resulting residue was dissolved in 1,4-dioxane (25 mL) and hydrobromic acid in acetic acid (5 mL) was added drop wise. The resulting brown solid was filtered, then suspended in acetone (25 mL), subjected to a sonication bath and finally filtered again. Title compound was isolated as a brown solid (5.95 g, 73% yield).

LCMS Rt=0.75 minutes MS m/z 159 [M$^{79}$BrH]+

$^1$H NMR (400 MHz, d$_6$-DMSO): δ 8.10 (m, 1H), 7.80-8.80 (br s, 1H), 9.10 (d, 1H), 9.45 (s, 1H)

Preparation 899

2-(3-Furyl)-4-(trifluoromethyl)phenyl acetate

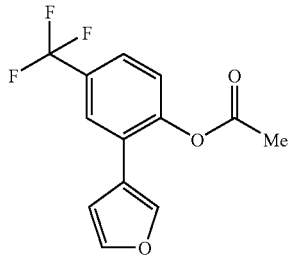

2-Iodo-4-(trifluoromethyl)phenol (9.9 g, 0.0344 mol) was dissolved in 2-methyl tetrahydrofuran (100 mL) then potassium acetate (11.8 g, 0.12 mol) and 3-furylboronic acid (5.0 g, 0.0447 mol) was added and the reaction degasses 3 times before bis(tri-tert-butylphosphine)palladium (0) (1.0 g, 0.00196 mol) was added and the reaction degassed 3 more times. The reaction was then stirred at 90° C. under nitrogen for 18 hours. The reaction was then cooled and partitioned between EtOAc (50 mL) and water (50 mL), the organic layer was separated and dried in vacuo to give a brown oil. This was dissolved in tert-butyl methyl ether (50 mL), triethylamine (7.2 mL, 0.051 mol) added then acetic anhydride (4.7 mL, 0.051 mol) and stirred for 2 hours at room temperature. The reaction was then partitioned between EtOAc (30 ml) and water (30 ml) then organic layer was dried in vacuo to give a brown oil which crystallised upon standing. This was triturated with heptane to give the title product as a pale brown solid (8.04 g, 86.6%). LCMS Rt=1.70 min. $^1$H NMR (400 MHz, CDCl$_3$): δ 2.34(s, 3H), 6.67(s, 1H) 7.26(m, 1H) 7.51 (s, 1H), 7.57(d, 1H), 7.76(m 2H)

Preparation 900

5-Chloro-N-(2,4-dimethoxybenzyl)-2-fluoro-4-[2-pyridazin-4-yl-4-(trifluoromethyl)phenoxy]-N-1,3,4-thiadiazol-2-ylbenzenesulfonamide

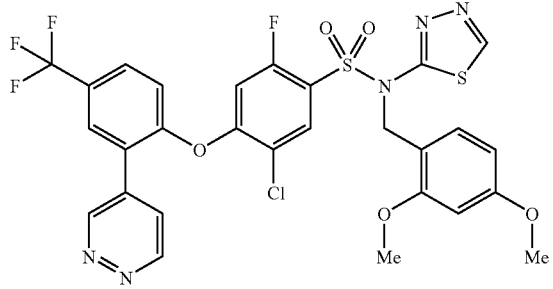

5-Chloro-N-(2,4-dimethoxybenzyl)-2,4-difluoro-N-1,3,4-thiadiazol-2-ylbenzenesulfonamide (Preparation 247, 378.0 g, 0.761 moles) was dissolved in dimethylsulphoxide (1.9 L). Potassium carbonate (117.8 g, 0.8524 moles) was added and stirred to give a suspension to which was added 2-pyridazin-4-yl-4-(trifluoromethyl)phenol (Preparation 712, 182.8 g, 0.761 moles) in one portion. The reaction mixture was stirred at room temperature for 18 hours. The reaction mixture was partitioned between ethyl acetate (2.7 L) and aqueous sodium hydroxide solution (2.5 L of 1 molar). The organic phase was washed with water (2×2 L) and then saturated aqueous sodium chloride solution (250 mL). The solution was concentrated in vacuo to give the crude title product. The crude product was purified by column chromatography on silica gel (2 Kg) eluting with ethyl acetate/heptane (3:1). The cleanest fractions were combined and the solvents removed in vacuo to give the title compound as a dark red foam, (440 g). This material was dried in vacuo at 45° C. for 48 hours to give the title compound as a red solid (400 g).

LCMS Rt=1.81 minutes. MS m/z 682 [MH]+ and 704 [M+Na]+

$^1$HNMR (d$_6$-DMSO): δ 3.65 (s, 3H), 3.70 (s, 3H), 5.14 (s, 2H), 6.41-6.45 (m, 2H), 7.10 (d, 1H), 7.37 (d, 1H), 7.54 (d, 1H), 7.88-7.99 (m, 3H), 8.17 (s, 1H), 9.83 (s, 1H), 9.86 (d, 1H), 9.51 (m, 1H).

The ability of the compounds of the formula (I) to block the Nav1.7 (or SCN9A) channel were measured using the assay described below.

Cell Line Construction and Maintenance

Human Embryonic Kidney (HEK) cells were transfected with an hSCN9A construct using lipofectamine reagent (Invitrogen), using standard techniques. Cells stably expressing the hSCN9A constructs were identified by their resistance to G-418 (400 µg/ml). Clones were screened for expression using the whole-cell voltage-clamp technique.

Cell Culture

HEK cells stably transfected with hSCN9A were maintained in DMEM medium supplemented with 10% heat-inactivated fetal bovine serum and 400 µg/ml G-418 in an incubator at 37° C. with a humidified atmosphere of 10% CO$_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and re-plated at low density onto glass cover slips. Cells were typically used for electrophysiological experiments within 24 to 72 hours after plating.

Electrophysiological Recording

Cover slips containing HEK cells expressing hSCN9A were placed in a bath on the stage of an inverted microscope and perfused (approximately 1 ml/minutes) with extracellular solution of the following composition: 138 mM NaCl, 2 mM CaCl$_2$, 5.4 mM KCl, 1 mM MgCl$_2$, 10 mM glucose, and 10 mM HEPES, pH 7.4, with NaOH. Pipettes were filled with an intracellular solution of the following composition: 135 mM CsF, 5 mM CsCl, 2 mM MgCl$_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hSCN9A currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN9A sodium currents.

The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or V½). Compounds were tested for their ability to inhibit hSCN9A sodium channels by activating the channel with a 20 msec voltage step to 0 mV following an 8 second conditioning prepulse to the empirically determined V½. Compound effect (% inhibition) was determined by difference in current amplitude before and after application of test compounds. For ease of comparison, "estimated IC-50" values were calculated from single point electrophysiology data by the following equation, (tested concentration, uM)×(100-% inhibition/% inhibition). Inhibition values <20% and >80% were excluded from the calculation.

In some cases electrophysiological assays were conducted with PatchXpress 7000 hardware and associated software (Molecular Devices Corp). All assay buffers and solutions were identical to those used in conventional whole-cell voltage clamp experiments described above. hSCN9A cells were grown as above to 50%-80% confluency and harvested by trypsinization. Trypsinized cells were washed and resuspended in extracellular buffer at a concentration of $1\times10^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined V½ and current was activated by a 20 msec voltage step to 0 mV.

Electrophysiological assays were also conducted using the Ionworks Quattro automated electrophysiological platform (Molecular Devices Corp). Intracellular and extracellular solutions were as described above with the following changes, 100 μg/ml amphotericin was added to the intracellular solution to perforate the membrane and allow electrical access to the cells. hSCN9A cells were grown and harvested as for PatchXpress and cells were resuspended in extracellular solution at a concentration of $3-4\times10^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans. The ability of the compounds of the formula (I) to block the Nav1.5 (or SCN5A) channel can also be measured using an assay analogous to that described above but replacing the SCN9A gene with the SCN5A gene. All other conditions remain the same including the same cell line and conditions for cell growth. The estimated IC50s are determined at the half inactivation for Nav1.5. These results can be compared to the $EIC_{50}$ value at the Nav1.7 channel to determine the selectivity of a given compound for Nav1.7 vs Nav1.5.

Compounds of the Examples were tested in the assay described above using the PatchXpress platform and found to have the $EIC_{50}$ values specified in the table below.

| Eg No | SCN9A EIC50 (μM) |
|---|---|
| 1 | 0.09 |
| 2 | 0.81 |
| 3 | 0.10 |
| 4 | 1.71 |
| 5 | 0.07 |
| 6 | >1 |
| 7 | 35.92 |
| 8 | 0.45 |
| 9 | 3.50 |
| 10 | 0.63 |
| 11 | 0.43 |
| 12 | 0.72 |
| 13 | 0.17 |
| 14 | 4.30 |
| 15 | 0.84 |
| 16 | 12.51 |
| 17 | 25.49 |
| 18 | >10 |
| 19 | 0.72 |
| 20 | >10 |
| 21 | >10 |
| 22 | 3.14 |
| 23 | 2.03 |
| 24 | 0.11 |
| 25 | 0.02 |
| 26 | 0.45 |
| 27 | 0.78 |
| 28 | 2.98 |
| 29 | 0.23 |
| 30 | 0.30 |
| 31 | 16.21 |
| 32 | 3.38 |
| 33 | 0.38 |
| 34 | 0.09 |
| 35 | 12.71 |
| 36 | 1.29 |
| 37 | 30.90 |
| 38 | 15.53 |
| 39 | 2.03 |
| 40 | 5.74 |
| 41 | 10.87 |
| 42 | 1.73 |
| 43 | 21.70 |
| 44 | 5.93 |
| 45 | 30.44 |
| 46 | 0.21 |
| 47 | 0.67 |
| 48 | 0.90 |
| 49 | 0.16 |
| 50 | 0.84 |
| 51 | 0.33 |
| 52 | 0.36 |
| 53 | 3.54 |
| 54 | 0.26 |
| 55 | 0.92 |
| 56 | 0.38 |
| 57 | 0.66 |

| Eg No | SCN9A EIC50 (μM) |
|---|---|
| 58 | 0.34 |
| 59 | 2.28 |
| 60 | 2.79 |
| 61 | 25.70 |
| 62 | 3.98 |
| 63 | 2.35 |
| 64 | 0.78 |
| 65 | 12.21 |
| 66 | 2.66 |
| 67 | 4.22 |
| 68 | 0.77 |
| 69 | 36.08 |
| 70 | 0.11 |
| 71 | 12.46 |
| 72 | >0.3 |
| 73 | 23.43 |
| 74 | 1.11 |
| 75 | 3.34 |
| 76 | >10 |
| 77 | 0.36 |
| 78 | 0.60 |
| 79 | 0.45 |
| 80 | >0.3 |
| 81 | 0.51 |
| 82 | 37.19 |
| 83 | 2.45 |
| 84 | >10 |
| 85 | 1.43 |
| 86 | 1.88 |
| 87 | 1.60 |
| 88 | 0.27 |
| 89 | 0.68 |
| 90 | 0.10 |
| 91 | 1.12 |
| 92 | 1.81 |
| 93 | 1.57 |
| 94 | 2.18 |
| 95 | >10 |
| 96 | 12.54 |
| 97 | 2.32 |
| 99 | >10 |
| 99 | 24.94 |
| 100 | 3.17 |
| 101 | 1.58 |
| 102 | >10 |
| 103 | 1.30 |
| 104 | 2.25 |
| 105 | 2.67 |
| 106 | 4.16 |
| 107 | 12.21 |
| 108 | >10 |
| 109 | 5.68 |
| 110 | 4.27 |
| 111 | >3 |
| 112 | 33.74 |
| 113 | 12.86 |
| 114 | >10 |
| 115 | >10 |
| 116 | 3.11 |
| 117 | 19.23 |
| 118 | 18.45 |
| 119 | 17.67 |
| 120 | 37.35 |
| 121 | 32.32 |
| 122 | 4.54 |
| 123 | 9.20 |
| 124 | 15.06 |
| 125 | 22.96 |
| 126 | 11.49 |
| 127 | >10 |
| 128 | 3.11 |
| 129 | 0.70 |
| 130 | 9.19 |
| 131 | 12.12 |
| 132 | 17.28 |
| 133 | 11.59 |
| 134 | 3.77 |
| 135 | 0.73 |
| 136 | 2.70 |
| 137 | 2.59 |
| 138 | 38.71 |
| 139 | 5.00 |
| 140 | 3.41 |
| 141 | 1.23 |
| 142 | 2.62 |
| 143 | >10 |
| 144 | 1.39 |
| 145 | 2.00 |
| 146 | 0.89 |
| 147 | 1.51 |
| 148 | 2.53 |
| 149 | 0.92 |
| 150 | 0.19 |
| 151 | 0.05 |
| 152 | 0.08 |
| 153 | 0.06 |
| 154 | 0.13 |
| 155 | 0.85 |
| 156 | 0.03 |
| 157 | 0.45 |
| 158 | 0.31 |
| 159 | 0.08 |
| 160 | 0.06 |
| 161 | 0.07 |
| 162 | 0.42 |
| 163 | 0.41 |
| 164 | 0.58 |
| 165 | 0.05 |
| 166 | 1.81 |
| 167 | 0.75 |
| 168 | 0.07 |
| 169 | 0.05 |
| 170 | 0.01 |
| 171 | 0.11 |
| 172 | 0.07 |
| 173 | 2.09 |
| 174 | >10 |
| 175 | 0.54 |
| 176 | 8.87 |
| 177 | 0.10 |
| 178 | 3.08 |
| 179 | 2.19 |
| 180 | 0.09 |
| 181 | >10 |
| 182 | 0.93 |
| 183 | 0.99 |
| 184 | 9.17 |
| 185 | 32.99 |
| 186 | 1.05 |
| 187 | 1.67 |
| 188 | 9.42 |
| 189 | 2.80 |
| 190 | 7.71 |
| 191 | >10 |
| 192 | 2.05 |
| 193 | 1.23 |
| 194 | 36.85 |
| 195 | 1.08 |
| 196 | 0.03 |
| 197 | 1.13 |
| 198 | 2.47 |
| 199 | 0.11 |
| 200 | 0.10 |
| 201 | 0.42 |
| 202 | 0.60 |
| 203 | 7.48 |
| 204 | 3.14 |
| 205 | 0.33 |
| 206 | 1.19 |
| 207 | 1.03 |
| 208 | 0.13 |
| 209 | 0.59 |
| 210 | 1.37 |
| 211 | 0.11 |

| Eg No | SCN9A EIC50 (µM) |
|---|---|
| 212 | 15.41 |
| 213 | 1.60 |
| 214 | 2.41 |
| 215 | 6.44 |
| 216 | 0.91 |
| 217 | 0.51 |
| 218 | 0.23 |
| 219 | 0.02 |
| 220 | 0.15 |
| 221 | 0.45 |
| 222 | 0.06 |
| 223 | 1.51 |
| 224 | 0.77 |
| 225 | 0.43 |
| 226 | 0.03 |
| 227 | 0.03 |
| 228 | 0.57 |
| 229 | 0.12 |
| 230 | 0.71 |
| 231 | 0.47 |
| 232 | 1.87 |
| 233 | 3.49 |
| 234 | 0.09 |
| 235 | 0.76 |
| 236 | 13.93 |
| 237 | 0.21 |
| 238 | 2.21 |
| 239 | 1.90 |
| 240 | 1.98 |
| 241 | 1.47 |
| 242 | 0.12 |
| 243 | 3.86 |
| 244 | 1.79 |
| 245 | 1.04 |
| 246 | 3.76 |
| 247 | 2.95 |
| 248 | 2.78 |
| 249 | 2.40 |
| 250 | 1.85 |
| 251 | 2.54 |
| 252 | 24.47 |
| 253 | 0.63 |
| 254 | 0.34 |
| 255 | 0.49 |
| 256 | 0.22 |
| 257 | 2.20 |
| 258 | 1.02 |
| 259 | 16.53 |
| 260 | 15.88 |
| 261 | 0.47 |
| 262 | 1.32 |
| 263 | 1.44 |
| 264 | 2.38 |
| 265 | 38.90 |
| 266 | 0.10 |
| 267 | 0.19 |
| 268 | 3.06 |
| 269 | 0.48 |
| 270 | 0.03 |
| 271 | 1.15 |
| 272 | 0.81 |
| 273 | 2.17 |
| 274 | >10 |
| 275 | 0.07 |
| 276 | 0.55 |
| 277 | 1.11 |
| 278 | 2.66 |
| 279 | 0.07 |
| 280 | 0.09 |
| 281 | 0.12 |
| 282 | 0.18 |

Yet further compounds of the Examples were also tested as described above and found to have the $EIC_{50}$ values specified in the table below.

| Eg No | SCN9A EIC50 (µM) |
|---|---|
| 283 | 0.58 |
| 284 | 1.6 |
| 285 | 0.62 |
| 286 | 0.53 |
| 287 | >1 |
| 288 | >1 |
| 289 | 0.39 |
| 290 | 2.0 |
| 291 | 2.5 |
| 292 | 0.044 |
| 293 | 0.093 |
| 294 | 0.034 |
| 295 | 0.13 |
| 296 | 0.025 |
| 297 | 1.0 |
| 298 | 0.14 |
| 299 | 0.020 |
| 300 | 0.039 |
| 301 | 0.28 |
| 302 | 0.16 |
| 303 | 0.43 |
| 304 | 0.025 |
| 305 | 0.097 |
| 306 | >1 |
| 307 | 0.81 |
| 308 | 0.98 |
| 309 | 0.025 |
| 310 | >1 |
| 311 | 4.9 |
| 312 | 0.017 |
| 313 | 0.47 |
| 314 | 0.73 |
| 315 | 1.2 |
| 316 | 0.74 |
| 317 | 2.2 |
| 318 | 1.3 |
| 319 | 2.5 |
| 320 | 3.3 |
| 321 | 0.77 |
| 322 | 0.55 |
| 323 | >0.30 |
| 324 | >1 |
| 325 | >0.30 |
| 326 | 2.1 |
| 327 | 0.37 |
| 328 | 0.081 |
| 329 | 0.34 |
| 330 | 0.25 |
| 331 | 2.0 |
| 332 | >1 |
| 333 | >1 |
| 334 | 3.4 |
| 335 | 0.032 |

-continued

| Eg No | SCN9A EIC50 (μM) |
|---|---|
| 336 | 2.2 |
| 337 | 2.5 |
| 338 | 1.8 |
| 339 | 15 |
| 340 | 34 |
| 341 | 3.6 |
| 342 | 18 |
| 343 | >10 |
| 344 | 1.0 |
| 345 | 14 |
| 346 | 0.77 |
| 347 | 0.30 |
| 348 | 0.82 |
| 349 | >1 |
| 350 | 0.015 |
| 351 | 0.018 |
| 352 | 0.19 |
| 353 | 0.22 |
| 354 | 0.18 |
| 355 | 0.40 |
| 356 | 0.12 |
| 357 | 0.39 |
| 358 | 0.36 |
| 359 | 0.011 |
| 360 | 0.33 |
| 361 | 0.48 |
| 362 | 1.5 |
| 363 | 0.24 |
| 364 | 0.48 |
| 365 | 0.069 |
| 366 | 4.8 |
| 367 | 2.4 |
| 368 | >1 |
| 369 | 0.49 |
| 370 | 1.6 |
| 371 | 1.8 |
| 372 | 2.6 |
| 373 | >1 |
| 374 | 1.9 |
| 375 | >1 |
| 376 | >1 |
| 377 | >1 |
| 378 | >1 |
| 379 | >1 |
| 380 | 0.20 |
| 381 | 0.47 |
| 382 | 0.050 |
| 383 | 0.31 |
| 384 | 0.35 |
| 385 | 0.067 |
| 386 | 0.091 |
| 387 | 0.14 |
| 388 | 0.74 |
| 389 | 1.1 |
| 390 | 0.30 |
| 391 | 0.0025 |
| 392 | 0.14 |
| 393 | 0.99 |
| 394 | 2.9 |
| 395 | 1.8 |
| 396 | >3 |
| 397 | >1 |
| 398 | >1 |
| 399 | 1.2 |
| 400 | 1.2 |
| 401 | 2.7 |
| 402 | 0.25 |
| 403 | 0.0045 |
| 404 | 1.2 |
| 405 | 0.0027 |
| 406 | 3.0 |
| 407 | 0.19 |
| 408 | 0.30 |
| 409 | 0.019 |
| 410 | 0.029 |
| 411 | 0.54 |
| 412 | 0.0025 |

-continued

| Eg No | SCN9A EIC50 (μM) |
|---|---|
| 413 | 12 |
| 414 | 1.0 |
| 415 | >1 |
| 416 | 1.6 |
| 417 | 0.0085 |
| 418 | 2.3 |
| 419 | 2.1 |
| 420 | 24 |
| 421 | 12 |
| 422 | >1 |
| 423 | 25 |
| 424 | >3 |
| 425 | 11 |
| 426 | 36 |
| 427 | 4.3 |
| 428 | >10 |
| 429 | >10 |
| 430 | 12 |
| 431 | 11 |
| 432 | >10 |
| 433 | 15 |
| 434 | 18 |
| 435 | 2.7 |
| 436 | 1.3 |
| 437 | 0.056 |
| 438 | 0.017 |
| 439 | 0.49 |
| 440 | 0.017 |
| 441 | 0.96 |
| 442 | 1.3 |
| 443 | 1.8 |
| 444 | 9.9 |
| 445 | >1 |
| 446 | 2.3 |
| 447 | 1.8 |
| 448 | 2.0 |
| 449 | 3.1 |
| 450 | 3.4 |
| 451 | >1 |
| 452 | 3.3 |
| 453 | 1.7 |
| 454 | >1 |
| 455 | 2.3 |
| 456 | 1.9 |
| 457 | 2.0 |
| 458 | 0.74 |
| 459 | 0.84 |
| 460 | 0.015 |
| 461 | 0.020 |
| 462 | 51 |
| 463 | 22 |
| 464 | 6.0 |
| 465 | 1.0 |
| 466 | 36 |
| 467 | 0.0096 |
| 468 | 0.029 |
| 469 | 3.3 |
| 470 | 3.4 |
| 471 | 2.7 |
| 472 | 0.97 |
| 473 | 0.072 |
| 474 | 0.044 |
| 475 | 0.0075 |
| 476 | 0.17 |
| 477 | 0.016 |
| 478 | 0.044 |
| 479 | 0.23 |
| 480 | >1 |
| 481 | 1.7 |
| 482 | >1 |
| 483 | >1 |
| 484 | >1 |
| 485 | >1 |
| 486 | >1 |
| 487 | >1 |
| 488 | >1 |
| 489 | 1.2 |

| Eg No | SCN9A EIC50 (μM) |
|---|---|
| 490 | 0.66 |
| 491 | >1 |
| 492 | 1.5 |
| 493 | 0.58 |
| 494 | 2.5 |
| 495 | >1 |
| 496 | 3.8 |
| 497 | >1 |
| 498 | 0.030 |
| 499 | 0.19 |
| 500 | 0.088 |
| 501 | 0.040 |
| 502 | 0.022 |
| 503 | 0.007 |
| 504 | 0.0049 |
| 505 | 0.050 |
| 506 | 0.011 |
| 507 | 0.011 |
| 508 | 0.020 |
| 509 | 0.031 |
| 510 | 0.077 |
| 511 | 0.0084 |
| 512 | 3.4 |
| 513 | 0.036 |
| 514 | 1.1 |
| 515 | 1.9 |
| 516 | 10 |
| 517 | 2.2 |
| 518 | >1 |
| 519 | 1.2 |
| 520 | >1 |
| 521 | 2.9 |
| 522 | 7.3 |
| 523 | 2.6 |
| 524 | 0.58 |
| 525 | 0.37 |
| 526 | 0.16 |
| 527 | 0.14 |
| 528 | 0.74 |
| 529 | 0.53 |
| 530 | 0.23 |
| 531 | 1.1 |
| 532 | 2.9 |
| 533 | 0.78 |
| 534 | 0.50 |
| 535 | 0.17 |
| 536 | 0.22 |
| 537 | 0.025 |
| 538 | 3.4 |
| 539 | 1.1 |
| 540 | 4.0 |
| 541 | 0.14 |
| 542 | 0.066 |
| 543 | 0.066 |
| 544 | 0.022 |
| 545 | 0.023 |
| 546 | 0.020 |
| 547 | 0.12 |
| 548 | 0.41 |
| 549 | 0.16 |
| 550 | 0.20 |
| 551 | 0.071 |
| 552 | 0.0024 |
| 553 | 0.0017 |
| 554 | 0.12 |
| 555 | 0.014 |
| 556 | 0.0023 |
| 557 | 0.0008 |
| 558 | 0.039 |
| 559 | 0.0007 |
| 560 | 0.078 |
| 561 | 0.38 |
| 562 | 0.017 |
| 563 | 0.13 |
| 564 | 0.0092 |
| 565 | 54 |
| 566 | >30 |

| Eg No | SCN9A EIC50 (μM) |
|---|---|
| 567 | No data |
| 568 | >3 |
| 569 | >3 |
| 570 | 8.6 |
| 571 | 10 |
| 572 | >30 |
| 573 | 7.3 |
| 574 | >3 |
| 575 | >30 |
| 576 | >3 |
| 577 | 11 |
| 578 | 5.5 |
| 579 | >3 |
| 580 | 6.9 |
| 581 | >3 |
| 582 | 0.034 |
| 583 | 0.013 |
| 584 | 0.097 |
| 585 | 0.097 |
| 586 | 0.14 |
| 587 | 0.20 |
| 588 | 0.12 |
| 589 | 0.51 |
| 590 | 0.053 |
| 591 | 0.073 |
| 592 | 0.22 |
| 593 | 0.035 |
| 594 | 0.16 |
| 595 | 0.080 |
| 596 | 0.079 |
| 597 | 0.020 |
| 598 | 0.23 |
| 599 | 0.30 |
| 600 | 15 |
| 601 | 0.94 |
| 602 | 1.5 |
| 603 | 4.6 |
| 604 | 0.82 |
| 605 | 0.10 |
| 606 | 0.13 |
| 607 | 2.8 |
| 608 | 0.40 |
| 609 | 1.7 |
| 610 | >1 |
| 611 | 0.52 |
| 612 | 0.54 |
| 613 | 0.11 |
| 614 | 0.18 |
| 615 | 2.0 |
| 616 | 0.28 |
| 617 | 0.030 |
| 618 | 0.011 |
| 619 | 0.045 |
| 620 | 0.0048 |
| 621 | 0.075 |
| 622 | >1 |
| 623 | 0.046 |
| 624 | 0.057 |
| 625 | 0.018 |
| 626 | 0.12 |
| 627 | 0.16 |
| 628 | 1.0 |
| 629 | 0.24 |
| 630 | >1 |
| 631 | 3.3 |
| 632 | 0.10 |
| 633 | 0.027 |
| 634 | 0.011 |
| 635 | 0.0063 |
| 636 | 0.0084 |
| 637 | 0.016 |
| 638 | 0.0048 |
| 639 | 6.9 |
| 640 | 1.00 |
| 641 | 1.3 |
| 642 | 2.6 |
| 643 | 2.1 |

| Eg No | SCN9A EIC50 (μM) |
|---|---|
| 644 | 2.6 |
| 645 | >1 |
| 646 | 2.8 |
| 647 | 2.9 |
| 648 | 1.6 |
| 649 | 0.93 |
| 650 | 1.6 |
| 651 | 1 |
| 652 | 0.90 |
| 653 | 1.1 |
| 654 | 1.1 |
| 655 | 0.049 |
| 656 | 0.27 |
| 657 | 0.083 |
| 658 | 0.25 |
| 659 | 0.091 |
| 660 | 0.034 |
| 661 | 0.077 |
| 662 | 0.033 |
| 663 | 0.13 |
| 664 | 0.26 |
| 665 | >1 |
| 666 | 0.27 |
| 667 | 3.1 |
| 668 | 0.053 |
| 669 | 0.20 |
| 670 | 0.35 |
| 671 | 0.26 |
| 672 | 2.5 |
| 673 | 0.69 |
| 674 | 0.088 |
| 675 | 0.37 |
| 676 | 0.19 |
| 677 | 0.012 |
| 678 | 0.26 |
| 679 | 0.031 |
| 680 | 1.0 |
| 681 | 1.2 |
| 682 | 0.71 |
| 683 | 0.022 |
| 684 | 1.0 |
| 685 | 0.13 |
| 686 | 0.33 |
| 687 | 0.080 |
| 688 | 5.1 |
| 689 | >0.30 |
| 690 | 0.11 |
| 691 | 0.43 |
| 692 | 0.11 |
| 693 | 0.081 |
| 694 | 0.48 |
| 695 | 0.34 |
| 696 | 0.078 |
| 697 | 0.0014 |
| 698 | 0.096 |
| 699 | 0.14 |
| 700 | 0.057 |
| 701 | 0.30 |
| 702 | 0.23 |
| 703 | 0.19 |
| 704 | 0.011 |
| 705 | 0.015 |
| 706 | 0.026 |
| 707 | 0.12 |
| 708 | 0.40 |
| 709 | 0.014 |
| 710 | 0.088 |
| 711 | 0.040 |
| 712 | 1.2 |
| 713 | 0.0024 |
| 714 | 0.19 |
| 715 | 0.21 |
| 716 | 0.43 |
| 717 | >0.30 |
| 718 | 0.033 |
| 719 | 0.16 |
| 720 | 0.056 |
| 721 | 0.16 |
| 722 | 0.14 |
| 723 | 0.064 |
| 724 | 0.0017 |
| 725 | 0.020 |
| 726 | 0.0058 |
| 727 | 1.9 |
| 728 | 0.0048 |
| 729 | 0.022 |
| 730 | 0.0099 |
| 731 | 0.0073 |
| 732 | 0.0035 |
| 733 | 0.010 |
| 734 | 0.053 |
| 735 | 1.00 |
| 736 | 0.0027 |
| 737 | 0.017 |
| 738 | 0.0014 |
| 739 | 0.15 |
| 740 | 0.40 |
| 741 | 0.0078 |
| 742 | 0.0036 |
| 743 | 0.012 |
| 744 | 0.17 |
| 745 | 0.12 |
| 746 | 0.095 |
| 747 | 0.050 |
| 748 | 0.17 |
| 749 | 0.045 |
| 750 | 0.21 |
| 751 | 0.013 |
| 752 | 0.0021 |
| 753 | 0.0052 |
| 754 | 0.0053 |
| 755 | 0.0024 |
| 756 | 0.011 |
| 757 | 0.0009 |
| 758 | 0.21 |
| 759 | 0.25 |
| 760 | 0.088 |
| 761 | 5.4 |
| 762 | 0.0042 |
| 763 | 0.034 |
| 764 | 0.030 |
| 765 | 0.11 |
| 766 | 0.50 |
| 767 | 0.24 |
| 768 | 11 |
| 769 | 8.7 |
| 770 | 24 |
| 771 | 0.24 |
| 772 | 31 |
| 773 | 0.0069 |
| 774 | >1 |
| 775 | 0.088 |
| 776 | 2.5 |
| 777 | 1.3 |
| 778 | 0.47 |
| 779 | 0.21 |
| 780 | 0.032 |
| 781 | 0.022 |
| 782 | 0.009 |
| 783 | 0.0078 |
| 784 | 0.010 |
| 785 | 0.040 |
| 786 | 0.0076 |
| 787 | 0.0072 |
| 788 | 0.0086 |
| 789 | 0.0021 |
| 790 | 0.0012 |
| 791 | 0.0037 |
| 792 | 0.011 |
| 793 | 0.0031 |
| 794 | 0.0048 |
| 795 | 0.0046 |
| 796 | 0.0021 |
| 797 | 0.0024 |

| Eg No | SCN9A EIC50 (μM) |
|---|---|
| 798 | 0.0049 |
| 799 | 0.0088 |
| 800 | 0.052 |
| 801 | 0.0013 |
| 802 | 0.0098 |
| 803 | 0.0048 |
| 804 | 0.0012 |
| 805 | 0.0062 |
| 806 | 0.0054 |
| 807 | 0.015 |
| 808 | 0.007 |
| 809 | 0.038 |
| 810 | 0.0038 |
| 811 | 0.0026 |
| 812 | 0.0051 |
| 813 | 0.030 |
| 814 | 0.0062 |

Even further compounds of the Examples were also tested as described above and found to have the $EIC_{50}$ values specified in the table below.

| Eg No | SCN9A EIC50 (μM) |
|---|---|
| 815 | 0.0006 |
| 816 | 0.011 |
| 817 | 0.3 |
| 818 | 0.32 |
| 819 | 2.4 |
| 820 | 0.23 |
| 821 | 0.1 |
| 822 | 0.0078 |
| 823 | 0.0074 |
| 824 | 0.0047 |
| 825 | 0.19 |
| 826 | 0.3 |
| 827 | 0.017 |
| 828 | 0.012 |
| 829 | 0.034 |
| 830 | 0.023 |
| 831 | 0.063 |
| 832 | 0.42 |
| 833 | 0.0059 |
| 834 | 0.0039 |
| 835 | 0.0021 |
| 836 | 0.04 |
| 837 | 0.0058 |
| 838 | 0.0018 |
| 839 | 0.13 |
| 840 | 0.052 |
| 841 | 0.011 |
| 842 | 0.096 |
| 843 | 0.034 |
| 844 | 0.0073 |
| 845 | 0.041 |
| 846 | 0.23 |
| 847 | 0.13 |
| 848 | 0.0051 |
| 849 | 0.12 |
| 850 | 0.0032 |
| 851 | 0.0097 |
| 852 | 0.0016 |
| 853 | 0.74 |
| 854 | 0.0064 |
| 855 | 0.0042 |
| 856 | 0.022 |
| 857 | 0.014 |
| 858 | 0.017 |
| 859 | 0.0044 |
| 860 | 0.17 |
| 861 | 0.014 |
| 862 | 0.24 |
| 863 | 0.0031 |
| 864 | 0.0044 |
| 865 | 0.0044 |
| 866 | 0.014 |
| 867 | 0.0014 |
| 868 | 0.015 |
| 869 | 0.54 |
| 870 | 0.14 |
| 871 | 0.025 |
| 872 | 0.012 |
| 873 | 3.9 |
| 874 | 0.35 |
| 875 | 0.05 |
| 876 | >1 |
| 877 | 0.47 |
| 878 | 0.0058 |
| 879 | 0.007 |
| 880 | 0.11 |
| 881 | 0.26 |
| 882 | 0.04 |
| 883 | 14 |
| 884 | 0.036 |
| 885 | 6.3 |
| 886 | 6.2 |
| 887 | 9 |
| 888 | 0.92 |
| 889 | 0.67 |
| 890 | 0.0094 |
| 891 | 0.78 |
| 892 | >10 |
| 893 | 3.8 |
| 894 | >10 |
| 895 | >30 |
| 896 | 0.34 |
| 897 | 0.0058 |
| 898 | 0.0051 |
| 899 | 0.018 |
| 900 | 0.0028 |
| 901 | 0.32 |
| 902 | 0.0023 |
| 903 | 0.32 |
| 904 | 0.39 |
| 905 | 0.19 |
| 906 | 0.057 |
| 907 | >10 |
| 908 | 0.78 |
| 909 | 0.0021 |
| 910 | 0.012 |
| 911 | 0.17 |
| 912 | 0.014 |
| 913 | 0.0009 |
| 914 | 0.18 |
| 915 | 1.6 |
| 916 | >10 |
| 917 | 0.24 |
| 918 | 0.14 |
| 919 | 0.024 |

| Eg No | SCN9A EIC50 (μM) |
|---|---|
| 920 | 0.31 |
| 921 | 3.9 |
| 922 | >10 |
| 923 | >10 |
| 924 | 0.019 |
| 925 | 0.66 |
| 926 | 0.067 |
| 927 | 0.12 |
| 928 | 0.0036 |
| 929 | 0.1 |
| 930 | 0.23 |
| 931 | 0.14 |
| 932 | 0.075 |
| 933 | >0.1 |
| 934 | 0.053 |
| 935 | 0.0038 |
| 936 | 0.008 |
| 937 | 0.019 |
| 938 | 0.025 |
| 939 | 0.048 |
| 940 | 0.031 |
| 941 | 0.072 |
| 942 | 0.035 |
| 943 | 0.077 |
| 944 | 0.031 |
| 945 | 0.099 |
| 946 | 0.23 |
| 947 | 0.023 |
| 948 | 0.011 |
| 949 | 0.087 |
| 950 | 2.7 |
| 951 | 0.04 |
| 952 | 0.032 |
| 953 | 0.11 |
| 954 | 0.24 |
| 955 | 0.076 |
| 956 | 0.13 |
| 957 | 0.022 |
| 958 | 0.0059 |
| 959 | 0.022 |
| 960 | 0.004 |
| 961 | 0.0079 |
| 962 | 0.0099 |
| 963 | 0.015 |
| 964 | 0.021 |
| 965 | 0.025 |
| 966 | 0.04 |
| 967 | 0.027 |
| 968 | 2 |
| 969 | 0.0041 |
| 970 | 0.017 |
| 971 | 0.0085 |
| 972 | 0.025 |
| 973 | 0.025 |
| 974 | 0.074 |
| 975 | 0.0015 |
| 976 | 0.0025 |
| 977 | 0.012 |
| 978 | 0.0046 |
| 979 | 0.11 |
| 980 | No data |
| 981 | No data |
| 982 | >0.3 |
| 983 | 2.7 |
| 984 | 0.56 |
| 985 | 2.3 |
| 986 | >10 |
| 987 | 0.0011 |
| 988 | 0.0007 |
| 989 | 0.95 |
| 990 | 0.31 |
| 991 | >0.01 |
| 992 | 0.54 |
| 993 | 0.35 |
| 994 | 9.5 |
| 995 | 1.3 |
| 996 | 0.76 |
| 997 | 0.025 |
| 998 | 0.056 |
| 999 | 3.3 |
| 1000 | 0.13 |
| 1001 | 0.82 |
| 1002 | 0.14 |
| 1003 | 0.02 |
| 1004 | 7.1 |
| 1005 | >3 |
| 1006 | No data |
| 1007 | 3.3 |
| 1008 | 0.74 |
| 1009 | 0.021 |
| 1010 | 0.82 |
| 1011 | 0.028 |
| 1012 | 0.27 |
| 1013 | 0.0048 |
| 1014 | 0.01 |
| 1015 | No data |
| 1016 | No data |
| 1017 | 0.0021 |
| 1018 | 0.23 |
| 1019 | 0.022 |
| 1020 | 0.019 |
| 1021 | 1.3 |
| 1022 | 0.0037 |
| 1023 | 0.004 |
| 1024 | 0.019 |
| 1025 | 0.0041 |
| 1026 | 0.0016 |
| 1027 | 0.013 |
| 1028 | 0.0031 |
| 1029 | 0.005 |
| 1030 | 0.0007 |
| 1031 | 0.029 |
| 1032 | 0.013 |
| 1033 | 0.0035 |
| 1034 | 0.011 |
| 1035 | 0.0038 |
| 1036 | 0.021 |
| 1037 | 0.012 |
| 1038 | 0.034 |
| 1039 | 0.31 |
| 1040 | No data |

The invention claimed is:

1. 4-[2-(5-amino-1H-pyrazol-4-yl)-4-chlorophenoxy]-5-chloro-2-fluoro-N-1,3-thiazol-4-ylbenzenesulfonamide, or a pharmaceutically acceptable salt thereof.

2. A pharmaceutical composition comprising a compound of claim 1, and one or more pharmaceutically acceptable excipients.

3. A pharmaceutical composition as claimed in claim 2 comprising one or more additional therapeutic agents.

4. A method of treating pain in a mammal comprising administering to a mammal requiring such treatment an effective amount of a compound of claim 1.

5. The method according to claim 4 in which said pain is nociceptive.

6. The method according to claim 4 in which said pain is inflammatory.

* * * * *